US008843356B2

(12) United States Patent
Schadt et al.

(10) Patent No.: US 8,843,356 B2
(45) Date of Patent: Sep. 23, 2014

(54) COMPUTER SYSTEMS AND METHODS FOR ASSOCIATING GENES WITH TRAITS USING CROSS SPECIES DATA

(75) Inventors: Eric E. Schadt, Kirkland, WA (US); John Lamb, Shoreline, WA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1900 days.

(21) Appl. No.: 10/540,405

(22) PCT Filed: Dec. 24, 2003

(86) PCT No.: PCT/US03/41613
§ 371 (c)(1),
(2), (4) Date: Jun. 30, 2006

(87) PCT Pub. No.: WO2004/061616
PCT Pub. Date: Jul. 22, 2004

(65) Prior Publication Data
US 2007/0166707 A1    Jul. 19, 2007

Related U.S. Application Data

(60) Provisional application No. 60/436,684, filed on Dec. 27, 2002, provisional application No. 60/460,343, filed on Apr. 2, 2003.

(51) Int. Cl.
G06G 7/58    (2006.01)
G01N 33/48   (2006.01)
G01N 33/50   (2006.01)
G01N 31/00   (2006.01)

(52) U.S. Cl.
USPC ................ 703/11; 702/19; 702/20; 702/27

(58) Field of Classification Search
None
See application file for complete search history.

(56) References Cited

U.S. PATENT DOCUMENTS

| | | | |
|---|---|---|---|
| 5,075,217 A | 12/1991 | Weber | |
| 5,324,631 A | 6/1994 | Helentjaris et al. | |
| 5,510,270 A | 4/1996 | Fodor et al. | |
| 5,569,588 A | 10/1996 | Ashby et al. | |
| 5,578,832 A | 11/1996 | Trulson et al. | |
| 5,965,352 A | 10/1999 | Stoughton et al. | |
| 6,132,969 A | 10/2000 | Stoughton et al. | |
| 6,132,997 A | 10/2000 | Shannon | |
| 6,165,709 A | 12/2000 | Friend et al. | |
| 6,218,122 B1 | 4/2001 | Friend et al. | |
| 6,271,002 B1 | 8/2001 | Linsley et al. | |
| 6,324,479 B1 | 11/2001 | Friend et al. | |
| 6,368,806 B1 | 4/2002 | Openshaw et al. | |
| 2003/0180761 A1 | 9/2003 | Castonguay et al. | |
| 2003/0224394 A1 | 12/2003 | Schadt et al. | |
| 2006/0122816 A1 | 6/2006 | Schadt et al. | |

FOREIGN PATENT DOCUMENTS

| | | |
|---|---|---|
| WO | WO 9913107 | 3/1999 |
| WO | PCT/US03/03100 | 2/2003 |
| WO | PCT/US03/15768 | 5/2003 |
| WO | PCT/US03/023976 | 8/2003 |
| WO | WO 03065282 | 8/2003 |
| WO | PCT/US03/41613 | 12/2003 |
| WO | WO 03100557 | 12/2003 |
| WO | WO 2004013727 | 2/2004 |
| WO | PCT/US04/16917 | 5/2004 |
| WO | WO 2004 061616 | 7/2004 |
| WO | WO 2004 109447 | 12/2004 |
| WO | WO 2005 017652 | 2/2005 |
| WO | PCT/US05/15419 | 5/2005 |
| WO | WO 2005 107412 | 11/2005 |

OTHER PUBLICATIONS

U.S. Appl. No. 10/558,928, filed Nov. 30, 2005, Schadt et al.
U.S. Appl. No. 10/540,143, filed Feb. 12, 2004, Schadt et al.
U.S. Appl. No. 10/515,804, filed May 28, 2004, Schadt et al.
Aitman et al., 1999, "Identification of Cd36 (Fat) as an insulin-resistance gene causing defective fatty acid and glucose metabolism in hypertensive rats," Nature Genetics 21: 76-83.
Akagi et al., 1996, "Microsatellite DNA markers for rice chromosomes," Theor. Appl. Genet. 93:1071-1077.
Allison et al., 1998, "Multiple phenotype modeling in gene-mapping studies of quantitative traits: power advantages," Am. J. Hum. Genet. 63:1190-1201.
Amos et al., 1990, "A multivariate method for detecting genetic linkage, with application to a pedigree with an adverse lipoprotein phenotype," Am. J. Hum. Genet. 47:247-254.
Barbosa et al., 1976, "The genetic heterogeneity of diabetes : histocompatibility antigens (HLA) in families with maturity-onset type diabetes of the young (MODY) and juvenile, insulin-dependent diabetes (HD) [proceedings]," Diabete. Metab. 2:160.
Blanchard et al., 1996, "Sequence to array: Probing the genome's secrets," Nature Biotechnology 14:1649.
Blanchard et al., 1996, "High-density oligonucleotide arrays," Biosensors & Bioelectronics 11: 687-690.
Bligh et al, 1995, "A microsatellite sequence closely linked to the Waxy gene of *Oryza sativa*," Euphytica 86:83-85.

(Continued)

*Primary Examiner* — Eric S Dejong
(74) *Attorney, Agent, or Firm* — Christensen O'Connor Johnson Kindness PLLC

(57) ABSTRACT

A method for confirming the association of a query QTL or a query gene in the genome of a second species with a clinical trait T exhibited by the second species. A first QTL or a first gene in a first species that is linked to a trait T' is found. The trait T' is indicative of trait T. A region of the genome of the first species that comprises the first QTL or the first gene is mapped to a particular region of the genome of the second species. A query QTL or a query gene in the second species that is potentially associated with the trait T is found. The potential association of the query QTL or the query gene with the clinical trait T is confirmed when the query QTL or the query gene is in the particular region of the genome of the second species.

24 Claims, 91 Drawing Sheets

(56) References Cited

OTHER PUBLICATIONS

Bochner et al., 2001, "Phenotype microarrays for high-throughput phenotypic testing and assay of gene function," Genome Res. 11:1246-1255.

Börjeson, 1976, "The aetiology of obesity in children," Acta. Paediar. Scand. 65:279-287.

Bray, 1989, "1989 McCollum Award Lecture. Genetic and hypothalamic mechanisms for obesity-finding the needle in the haystack," Am. J. Clin. Nutr. 50:891-902.

Bray, 1992, "Genetic, hypothalamic and endocrine features of clinical and experimental obesity," Progress in Brain Research 93:333-341.

Brem et al., 2002, "Genetic Dissection of Transcriptional Regulation in Budding Yeast," Science 296:752-755.

Brown et al., 2000, "Knowledge-based analysis of microarray gene expression data by using support vector machines," Proc. Natl. Acad. Sci. USA 97:262-267.

Cheung et al., 2002, "The genetics of variation in gene expression," Nature Genetics Supplement 32: 522-525.

Cheung et al., 2003, "Natural variation in human gene expression assessed in lymphoblastoid cells," Nature Genetics 33: 422-425.

Chirgwin et al., 1979, "Isolation of biologically active ribonucleic acid from sources enriched in ribionuclease," Biochemistry 18:5294-5299.

Cohen et al., 2000, "A computational analysis of whole-genome expression data reveals chromosomal domains of gene expression," Nature Genetics 26:183-186.

Corder et al., 1993, "Gene dose of apolipoprotein E type 4 allele and the risk of Alzheimer's disease in late onset families," Science 261:921-923.

Cox et al., 1999, "Loci on chromosomes 2 (NIDDMI) and 15 interact to increase susceptibility to diabetes in Mexican Americans," Nature Genetics 21:213-215.

DeRisi et al., 1996, "Use of a cDNA microarray to analyse gene expression patterns in human cancer," Nature Genetics 14:457-460.

Doerge, 2002, "Mapping and analysis of quantitative trait loci in experimental populations," Nature Reviews 3:43-52.

Draghici, 2003, "Data Analysis Tools for DNA Microarrays," Chapman & Hall, p. 1-478.

Duda et al., 2001, Pattern Classification, John Wiley & Sons, New York, NY, p. 521-530.

Duda et al., 2001, Pattern Classification, John Wiley & Sons, New York, NY, p. 550-557.

Easton et al., 1993, "Inherited susceptibility to breast cancer," Cancer Surv. 18:95-113.

Eaves et al., 2002, "Combining Mouse Congenic Strains and Microarray Gene Expression Analyses to Study a Complex Trait: The NOD Model of Type 1 Diabetes," Genome Research 12: 232-243.

Egholm et al., 1993, "PNA hybridizes to complementary oligonucleotides obeying the Watson-Crick hydrogen-bonding rules," Nature 365:566-568.

Elowitz et al., 2002, "Stochastic Gene Expression in a Single Cell," Science 297:1183-1186.

Falk et al., 1987, "Haplotype relative risks: an easy reliable way to construct a proper control sample for risk calculations," Ann. Hum. Genet. 51 ( Pt 3):227-233.

Ferguson et al., 1996, "A fiber-optic DNA biosensor microarray for the analysis of gene expression," Nature Biotechnology 14:1681-1684.

Fiehn et al., 2000, "Metabolite profiling for plant functional genomics," Nature Biotech. 18:1157-1161.

Fishel et al., 1993, "The human mutator gene homolog MSH2 and its association with hereditary nonpolyposis colon cancer," Cell 75:1027-1038.

Fodor et al., 1991, "Light-directed, spatially addressable parallel chemical synthesis," Science 251:767-773.

Ford et al., 1994, "Risks of cancer in BRCA1-mutation carriers. Breast Cancer Linkage Consortium," Lancet 343:692-695.

Friedman et al., 1991, "Molecular mapping of obesity genes," Mammalian Genome 1:130-144.

Friedman et al., 1992, "Tackling a weighty problem," Cell 69:217-220.

Froehler et al., 1986, "Synthesis of DNA via deoxynucleoside H-phosphonate intermediates," Nucleic Acids Research 14:5399-5407.

Fulker et al., 1999, "Combined Linkage and Association Sib-Pair Analysis for Quantitative Traits," Am. J. Hum. Genet. 64:259-267.

Fullerton et al., 2000, "Apolipoprotein E variation at the sequence haplotype level: implications for the origin and maintenance of a major human polymorphism," Am. J. Hum. Genet. 67:881-900.

Gaasterland et al., 2000, "Making the most of microarray data," Nature Genetics 24:204-206.

Goffeau et al., 1996, "Life with 6000 genes," Science 274:546-567.

Grunau et al., 2001, "MethDB-a public database for DNA methylation data," Nucelic Acids Research, 29: 270-274.

Grundy et al., 1990, "Metabolic and health complications of obesity," Dis. Mon. 36:641-731.

Haley et al., 1992, "A simple regression method for mapping quantitative trait loci in line crosses using flanking markers," The Genetical Society of Great Britain 69:315-324.

Hayashi et al., 1994, "Detection of additive and dominance effects of QTLs in interval mapping of F2 RFLP data," Theor. Appl. Genet. 87:1021-1027.

Helentjaris et al., 1985, "Restriction fragment polymorphisms as probes for plant diversity and their development as tools for applied plant breeding," Plant Molecular Biology 5:109-118.

Helm et al., 1991, "Classification and identification of bacteria by Fourier-transform infrared spectroscopy," Journal of General Microbiology 137: 69-79.

Hu et al., 1991, "Identification of broccoli and cauliflower cultivars with RPD markers," Plant Cell Reports 10:505-511.

Hughes et al., 2000, "Functional Discovery via a Compendium of Expression Profiles," Cell 102:109-126.

International Human Genome Consortium, 2001, "Initial sequencing and analysis of the human genome," Nature 409:860-921.

James et al., 1998, "Non-alcoholic steatohepatitis (NASH): a disease of emerging identity and importance," Journal of Hepatology 29: 495-501.

Jansen, 1993, "Interval mapping of multiple quantitative trait loci," Genetics 135:205-211.

Jansen, 1994, "Controlling the type I and type II errors in mapping quantitative trait loci," Genetics 138:871-881.

Jansen et al., 2001, "Genetical genomics: the added value from segregation," Trends in Genetics 17:388-391.

Jarvis et al., 1973, "Clustering using a similarity measure based on shared near neighbors," IEEE Transactions on computers C-22:1025-1034.

Jaspers et al., 1982, "Genetic heterogeneity in ataxia-telangiectasia studied by cell fusion," Proc. Natl. Acad. 79: 2641-2644.

Jiang et al., 1995, "Multiple trait analysis of genetic mapping for quantitative trait loci," Genetics 140:1111-1127.

Jin et al., 2001, "The contributions of sex, genotype and age to transcriptional variance in *Drosophila melanogaster*," Nature Genetics 29: 389-395.

Kajiwara et al., 1994, "Digenic Retinitis Pigmentosa Due to Mutations at the Unlinked Peripherin/RDS and ROM1 Loci," Science 264: 1604-1608.

Karp et al., 2000, "Identification of complement factor 5 as a susceptibility locus for experimental allergic asthma," Nature Immunology, vol. 1, No. 3: 221-226.

Kearsey et al., 1994, "QTL analysis: a simple 'marker-regression' approach," Theor. Appl. Genet. 89:698-702.

Knapp et al., 1993, "The haplotype-relative-risk (HRR) method for analysis of association in nuclear families," Am. J. Hum. Genet. 52:1085-1093.

Knoll et al., 1993, "Cytogeneitc and Molecular Studies in the Prader-Willi and Angelman Syndromes: An Overview," Amer. Journal of Medical Genetics 46: 2-6.

Kruglyak et al., 1996, "Parametric and nonparametric linkage analysis: a unified multipoint approach," Am. J. Hum. Genet. 58:1347-1363.

Kruglyak et al., 1998, "Faster multipoint linkage analysis using Fourier transforms," J. Comput. Biol. 5:1-7.

(56) References Cited

OTHER PUBLICATIONS

Kruglyak et al., 2001, "Variation is the spice of life," Nature Genetics 27:234-236.
Lan et al., 2006, "Combined Expression Trait correlations and Expression Quantitative Trait Locus Mapping," PLoS Genetics 2: 55-61.
Lance et al., 1967, "A general theory of classificatory sorting strategies," Computer Journal 9:373-380.
Lander et al., 1989, "Mapping Mendelian factors underlying quantitative traits using RFLP linkage maps," Genetics 121:185-199.
Lander et al., 1994, "Genetic dissection of complex traits," Science 265:2037-2048.
Lander, 1996, "The new genomics: Global views of biology," Science 274:536-539.
Levsky et al., 2002, "Single-Cell gene expression profiling," Science 297:836-840.
Lockhart et al., 1996, "Expression monitoring by hybridization to high-density oligonucleotide arrays," Nature Biotechnology 14:1675-1680.
Lynch et al., 1998, "Genetics and Analysis of Quantitative Traits," Sinauer Associates, Inc.: Chapters 15 and 16 pp. 431-532.
Machleder et al., 1997, "Complex Genetic Control of HDL Levels in Mice in Response to an Atherogenic Diet," J. Clin. Invest. 99:1406-1419.
Manley et al., 1999, "Overview of QTL mapping software and introduction to Map Manager QT," Mammalian Genome 10:327-334.
Martinez et al., 1994, "Missing markets when estimating quantitative trait loci using regression mapping," The Genetical Society of Great Britain 73:198-206.
Maskos et al., 1992, "Oligonucleotide hybridisations on glass supports: a novel linker for oligonucleotide synthesis and hybridisation properties of oligonucleotides synthesised in situ," Nucleic Acids Research 20: 1679-1684.
McBride et al., 1983, "An Investigation of Several Deoxynucleoside Phosphoramidites Useful for Sythesizing Deoxyoligonucleotides," Tetrahedron Letters 24: 245-248.
Moll et al., 1991, "The Genetic and Environmental Sources of Body Mass Index Variability: Te Muscatine Ponderosity Family Study," Am. J. Hum. Genet. 49: 1243-1255.
Mount, 2001, "Genome Analysis," Bioinformatics Sequence and Genome Analysis Chapter 10, p. 479-531.
Naumann et al., 1991, "Microbiological characterizations by FT-IR spectroscopy," Nature 351: 81-82.
Nguyen et al., 1995, "Differential gene expression in the murine thymus assayed by quantitative hybridization of arrayed cDNA clones," Genomics 29:207-216.
Nishina et al., 1994, "Atherosclerosis in genetically obese mice: the mutants obese, diabetes, fat, tubby, and lethal yellow," Metabolism 43:554-558.
Olson et al., 1999, "Tutorial in biostatistics genetic mapping of complex traits," Statistics in Medicine 18:2961-2981.
Patil et al., 2001, "Blocks of limited haplotype diversity revealed by high-resolution scanning of human chromosome 21," Science 294:1719-1723.
Pericak-Vance et al., 1991, "Linkae Studies in Familial Alzheimer Disease: Evidence for Chromosome 19 Linkage," Am. J. Hum. Genet. 48: 1034-1050.
Prashar et al., 1996, "Analysis of differential gene expression by display of 3' end restriction fragments of cDNAs," Proc. Natl. Acad. Sci. USA 93:659-663.
Reeders et al., 1987, "A study of genetic linkage heterogeneity in adult polycystic kidney disease," Hum. Genet. 76:348-351.
Roberts et al., 2000, "Signaling and Circuitry of Multiple MAPK Pathways Revealed by a Matrix of Global Gene Expression Profiles," Science 287: 873-880.
Sagliocco et al., 1996, "Identification of Proteins of the Yeast Protein Map using Genetically Manipulated Strains and Peptide-Mass Fingerprinting," Yeast 12: 1519-1533.
Sandberg et al., 2000, "Regional and strain-specific gene expression mapping in the adult mouse brain," PNAS 97: 11038-11043.
Schadt et al., 2003, "Genetics of gene expression surveyed in maize, mouse and man," Nature 422:297-302.
Schadt et al., 2003, "A new paradigm for drug discovery: integrating clinical genetic, genomic and molecular phenotype data to identify drug targets," Biochemical Society 31:437-443.
Schena et al., 1996, "Parallel human genome analysis; microarray-based expression of 1000 genes," Proc. Natl. Acad. Sci. USA 93:10614-10619.
Schena et al., 1995, "Quantitative Monitoring of Gene Expression Patterns with a Complementary DNA Microarray," Science 270: 467-470.
Shalon et al., 1996, "A DNA microarray system for analyzing complex DNA samples using two-color fluorescent probe hybridization," Genome Research 6:639-645.
Spielman et al., 1989, "Genetic Analysis of IDDM: Summary of GAW5 IDDM Results," Genetic Analysis of complex Traits, Part I: 43.-58.
Steinmetz et al., 2002, "Dissecting the architecture of a quantitative trait locus in yeast," Nature 416: 326-330.
St. George-Hyslop et al., 1990, "Genetic linkage studies suggest that Alzheimer's disease is not a single homogeneous disorder. FAD Collaborative Study Group," Nature 347:194-197.
Struss et al., 1998, "The use of microsatellite markers for detection of genetic diversity in barley populations," Theor. Appl. Genet. 97:308-315.
Stover, et al., 2001, "Characterization of Gene Expression Profiles in Peripheral Blood Mononuclear Cells and Bone Marrow of Normal Human Volunteers," FASEB Journal, 534.9: A696.
Stunkard et al., 1990, "The Body-Mass Index of Twins Who Have Been Reared Apart," New England Journal of Medicine 322: 1483-1487.
Tamayo et al., 1999, "Interpreting patterns of gene expression with self-organizing maps: Methods and application to hematopoietic differentiation," Proc. Natl. Acad. Sci. USA 96:2907-2912.
Terwilliger et al., 1992, "A haplotype-based 'haplotype relative risk' approach to detecting allelic associations," Hum. Hered. 42:337-346.
Twine et al., 2003, "Disease-associated Expression Profiles in Peripheral Blood Mononuclear Cells from Patients with Advanced Renal Cell Carcinoma," Cancer Research 63: 6069-6075.
Velculescu et al., 1995, "Serial Analysis of Gene Expression," Science 270: 484-487.
Venter et al., 2001, "The Sequence of the Human Genome," Science 291: 1304-1351.
Weisblum et al., 1972, "Genetic Heterogeneity of Xeroderma Pigmentosum demonstrated by Somatic Cell Hybridization," Nature New Biology 238: 80-83.
Welsh et al., 1990, "Fingerprinting genomes using PCR with arbitrary primers," Nucleic Acids Research 18: 7213-7218.
Williams et al., 1999, "Joint multipoint linkage analysis of multivariate qualitative and quantitative traits," Am. J. Hum. Genet. 6:1134-1147.
Wu et al., 1993, "Abundance, polymorphism and genetic mapping of microsatellites in rice," Mol. Gen. Genet. 241:225-235.
Younossi et al., 2002, "Perspectives in Clinical Hepatology: Nonalcoholic Fatty Liver Disease: An Agenda for Clinical Research," Hepatology: 746-752.
Zeng, 1993, "Theoretical basis for separation of multiple linked gene effects in mapping quantitative trait loci," Proc. Natl. Acad. Sci. USA 90:10972-10976.
Zeng, 1994, "Precision mapping of quantitative trait loci," Genetics 136:1457-1468.

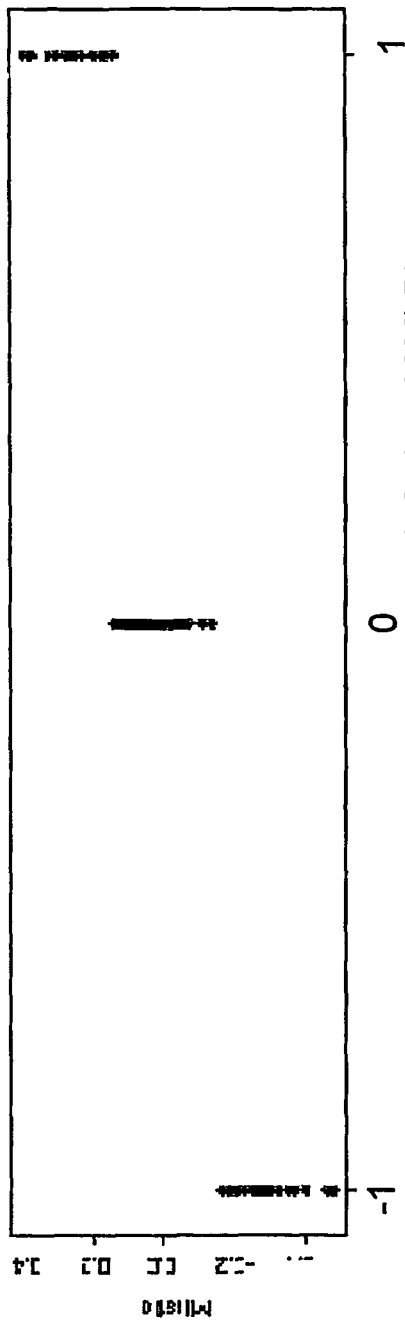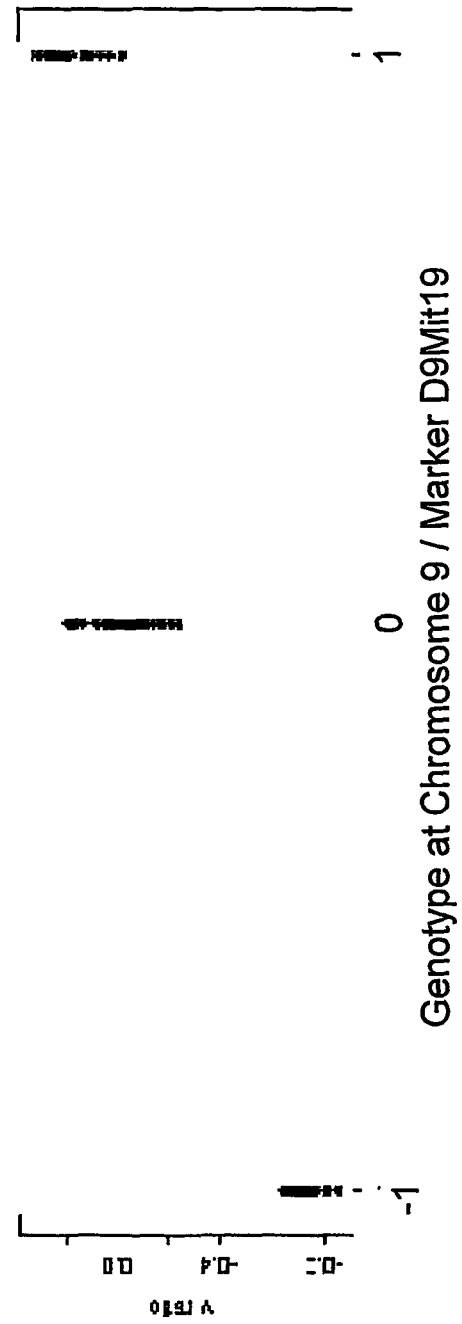
FIG. 7

 nicotinamide nucleotide transhydrogenase
 9530010C24Rik
 ectonucleotide pyrophosphatase
 EST AW456442
 5' nucleotidase
 EST AW540195
 purine-nucleoside phosphorylase
 N-terminal Asn amidase
 nicotinamide N-methyltransferase
 aldehyde oxidase 1
(PRIOR ART)
FIG. 12

```
   1 GAGCTATTCG GCCTCTCTAG GCCGGCGGGT CCTCCGCTCC ATGGTCCTGT CTGTCAGCGC
  61 TGTGTCAGGA GGCCAGTGCC GAGGTCCGGT CGCGCTCCGA CGCTTCGACC CTCGAGCCGG
 121 TCGCGGGTAT CCCGGCGGCC GCGGGACGAT GGCGTGGTGG CACTGACAGG CGCGGGCGGC
 181 TGCCGAGCCC CGCGGCCGGC ATGGCGGGCC AGTTCCGCAG CTACGTGTGG GACCCGTTGC
 241 TAATCCTGTC GCAGATCGTA CTCATGCAGA CCGTCTACTA TGGCTCTCTG GGCCTGTGGC
 301 TGGCGCTGGT GGACGCGCTG GTGCGCAAGC CCGTCCCTGG ACCAGATGTT CGACGCGGAG
 361 ATCCTGGGCT TCTCCACCCC TCCAGGCCGG CTCTCAATGA TGTCCTTCGT CCTCAACGCC
 421 CTCACCTGTG CCCTGGGCTT GCTGTACTTC ATCCGGCGAG GGAAGCAGTG CCTGGATTTC
 481 ACTGTCACTG TGCATTTCTT TCACCTCCTG GCTGCTGGC TCTACAGCTC CCGTTTCCCC
 541 TCGGCGCTGA CCTGGTGGCT GGTCCAGGCT GTGTGCATTG CACTCATGGC CGTCATCGGG
 601 GAGTACCTGT GCATGCGGAC GGAGCTCAAG GAGATCCCCC TCAGCTCAGC CCCTAAGTCC
 661 AATGTCTAGA GTTGGGCCCT TTGGACACTC TGCTGGCACT TGGGCCCCAT CACCTTGGGC
 721 TGCTCAGACC TCCAGATGGG GTCTGGCCCA AGTCTGAGCA GAACCCTGGA AATGTGAAGT
 781 CTGTTGGTGG AGAGATAATG AGGTCCCATC ATAAAGGCAG GTAGCAGCCA TGATCACAGA
 841 TGTAAGAATG GCCTCTGTCT GCCAAAGCCT TGATATCTGG AGGCCAGTAA GGGACCTCAT
 901 GGAGGGTAGT GGCAGATTTG GAACCATGTC ACATGAGCCA TCATACTGTC ACCAGCCTGT
 961 TATTTTAAAA AGAAAAAAAA AAAATCAAGG ATATCTGATT GGAATAAACC ACTCTTCTCG
1021 TTGTCTGTCT TATGCCCATG ACAGCCAGTA CCTTTGCTGT GTTGCCAAAC CACAGGGATT
1081 CTCTGTGGAG AAATACCTGA TTTCTGGGTC CATAGCCACA GAAAAGATG TAGGTACAGA
1141 GTGCTAGGCT GCTGACAGGA CGTCGAGGGG AGGAGGCATC AAGCACAAGA AAAATGCATG
1201 GCCGTGCCGT TAGACACACA CACACACTTT TGTGTGTGTC CAGGACCCAT GACTGTCTCC
1261 CTCCAGTTCC CTGTATGGAC TCTGCCTTGC TGTTGTCACT CAGCACAGCC AGAGACAGGA
1321 CCCAGAGAAA ACCCCAGCAT CCCTCCCAGC CTTCCCTTCA TAATAAAAGC CATTGTCTGC
1381 TCTCTGGAAG TGAGCAGGCA GCCAGCTTCT ACTGGACCTC AACTGTGGCA GGAGTTTCTG
1441 TTTGCTGTCT TTTGAGTTCT GTGATAGGGA GGGTGTACTA AAGGTGCTGG AGGCTCACCC
1501 TGCTAAGCTT TCTTCCAAGT GGTTTCCTCA GGAAGGGCTG GCAGCTGTCC TTCCTAGGTA
1561 CATAAATACA CTATTTTCCA ATC
```

Figure 27

```
TCTAGGCCGGCAGCGCCTCTCCTCCATGGTCCTGTCTGTCAGCGCTGTTTTGGGAGCCCGCCGGTGAGGC
CGGGCCACGCTCAGACACTTCGATCGTCGAGTCTGTCACTGGGCATGGCGGGTCAGTTCCGCAGCTACGT
GTGGGACCCGCTGCTGATCCTGTCGCAGATCGTCCTCATGCAGACCGTGTATTACGGCTCGCTGGGCCTG
TGGCTGGCGCTGGTGGACGGGCTAGTGCGACAGCCCCTCGCTGGACCAGATGTTCGACGCCGAGATCCTG
GGCTTTTCCACCCCTCCAGGCCGGCTCTCCATGATGTCCTTCATCCTCAACGCCCTCACCTGTGCCCTGG
GCTTGCTGTACTTCATCCGGCGAGGAAAGCAGTGTCTGGATTTCACTGTCACTGTCCATTTCTTTCACCT
CCTGGGCTGCTGGTTCTACAGCTCCCGTTTCCCCTCGGCGCTGACCTGGTGGCTGGTCCAAGCCGTGTGC
ATTGCACTCATGGCTGTCATCGGGGAGTACCTGTGCATGCGGACGGAGCTCAAGGAGATACCCCTCAACT
CAGCCCCTAAATCCAATGTCTAGAATCAGGCCCTTTGGACATCCTGCTGACACTTGGGCCCCTTAACACC
TTGGGCTGCTCAGACCCTCCAGATGAGGTCCAGCCCAGATCTGAGAGGAACCCTGGAAATGTGAAGTCTC
TGTTGGTTTGGGAGAGATAGTGAGGGCCTGTCAAAGAAGGCAGGTAGCAGTCAGCATGACAGCTGCAAGA
ATGACCTCTGTCTGTTGAAGCCTTGGTATCTGAGAGGTCAGGAAGGGGACCTCTTTGAGGGTAATAACAG
AATTGGAACCATGCCACTCTTGAGCCACAATACCTGTCACCAGCCTGTTGTTTTAAGAGAGAAAAAAAAT
CAAGGATATCTGATTGGAGCAAACCACTTCTTTAGTCATCTGTCTTACCCCCCTGGGACAGCTGTTACCT
TTGCAGTGTTGCCGAATCACAGCAGTTACCTTTGCAGTGTTGCCGAATCACAGCAGTTCTGTTGGAGAAA
CGCTTGGTTTCCGGATCCAGAGCCACAGAAAGAAATGTAGGTGTGAAGTATTAGGCTGCTGTCAGGGAGA
GGATGGCAGATGGAGGCATCAAGCACAAGGAAAATGCACAACCTGTGCCCTGTTATACACACGTTCATGT
GCACCCAAGAACCTATGACTTTCTTCCAGTTCCTTCTACCAGGTCCCCATCCTGCTGCCAGCTCTCAACA
TAGCAGGCCATAGGACCCAGAGAAGAATCCCAGCGTTGCTCAAAGTCTAACCATCATAAAGACACTGCCT
GTCTTCTAGGAATGACCAGGCACCCAGCTCCCACTGGACTCCAATTTTTTTCCTGCCTTATTTAGAATT
CTTTGGCGGGAAGGGTATGATGGGTTCCCAGAGACAAGAAGCCCAACCTTCTGGCCTGGGCTGTGCTGAT
AGTGCTGAGGGAGATAGGAATTTGCTGCTAAGATTTTCTTTGGGGTGGAGTTTCCTCTGTGAGGGCTT
GCAGCTATCCTTCCTGTGTATACAAATACAGTATTTTCCATGGTTCTGCCTGCACTTACTTTGTAATGCC
ACGGTTGAGATTGAGAGAGATCAGCGCAGCCAGGCAAGGGAACTTTAAAGAATTATTAGGCCACCTTCTC
CCTTTCCTGGACCCCAGAGTCATTCCTCCATTTGGTTAAAATACTCAGTGCAGGGAACTCTTACATCCTG
TCTCCTTCACTTGCAGCGTCCCCTGCTATGCCTCAGGTGAACCACATAATTCTTGGGTTTCCGTTCCTAC
TTGCTAGTGATTTCTGAACATGTTCAATGGAGCGGCACACAGTCTAGACCCACTTCCGCATTGAAACCTT
CACTGTTCCTCTTTGGTTTCTTCAGAGCTTTCCCAAGAGAGCTGTCAGTTTTCAGCTGTCAGTAACACAA
ATGAGTTTATGGTAACACAAATGAGTTTTGCTATCTCTGAGAAGCTCATCTGACCTCCTGACTCTCAG
CCCTACAGAGTAGGGAGTTGATGCTGACAGGATGAAGATTTAGGAATAAATATGCCTGGGAAGAGACTGG
GAAGGTTCTAGGGTGAGGCACCTCAGTAACTCATGGTACCTTGGCCAAGTTGGAAGGAAGCAGTTTGTTA
ATGAGGCACAGTAATCCTGGCTGCAGGGTCTAGGAGGTAAGACCAGCTGGGATGACCTTCCCTGGGTTAA
TCAATTTCCCTCTAGACAACACAAACTGCAGGCATGTGACTAACTTTGAAAGAACACCCATCATGTGGCT
GCTGTCACCCTTGACCAGCCGTGGTGGTGGTTACTCCATCTGTGGTTGGAGCGCCTCTTTGGGATTCACT
TCAAGGTCTTGTGCCTATTTTTCTGCATATCTTCTGTGATGACAAATCTCTGTCCCCTGAGTGTTAATTT
GATTTTTAGAAATGGCCAAAAGTCACGTGATCCAAACTTTTTTTCAGTAATATGGAGACTGAGCTGCATG
GTAGTTGGGGATCAAAAATATGTGACCTTAATGAGATTTTTATGATTTCTAAAGTAACAATAAAAGCAGT
TTTTAGAGTTGAGTTCCAGAGAGGGCAGGGCAATGGCAGTGACATGTTTGTCATTTTAATAATAAATAAC
ATCTATTGAGTGCTTAA
```

Figure 28

```
ATGGCGGGTCAGTTCCGCAGCTACGTGTGGGACCCGCTGCTGATCCTGTCGCAGATCGTCCTCATGCAGA
CCGTGTATTACGGCTCGCTGGGCCTGTGGCTGGCGCTGGTGGACGGGCTAGTGCGACAGCCCCTCGCTGG
ACCAGATGTTCGACGCCGAGATCCTGGGCTTTTCCACCCCTCCAGGCCGGCTCTCCATGATGTCCTTCAT
CCTCAACGCCCTCACCTGTGCCCTGGGCTTGCTGTACTTCATCCGGCGAGGAAAGCAGTGTCTGGATTTC
ACTGTCACTGTCCATTTCTTTCACCTCCTGGGCTGCTGGTTCTACAGCTCCCGTTTCCCCTCGGCGCTGA
CCTGGTGGCTGGTCCAAGCCGTGTGCATTGCACTCATGGCTGTCATCGGGGAGTACCTGTGCATGCGGAC
GGAGCTCAAGGAGATACCCCTCAACTCAGCCCC
```

Figure 29

```
MAGQFRSYVW DPLLILSQIV LMQTVYYGSL GLWLALVDAL VRSSPSLDQM FDAEILGFST
PPGRLSMMSF VLNALTCALG LLYFIRRGKQ CLDFTVTVHF FHLLGCWLYS SRFPSALTWW
LVQAVCIALM AVIGEYLCMR TELKEIPLSS APKSNV
```

Figure 30A

```
MALWACGWRW WTRWCAQPVP GPDVRRGDPG LLHPSRPALN DVLRPQRPHL CPGLAVLHPA
REAVPGFHCH CAFLSPPGLL ALQLPFPLGA DLVAGPGCVH CTHGRHRGVP VHADGAQGDP
PQLSP
```

Figure 30B

```
MAGQFRSYVW DPLLILSQIV LMQTVYYGSL GLWLALVDAL VRKPVPGPDV RRGDPGLLHP
SRPALNDVLR PQRPHLCPGL AVLHPAREAV PGFHCHCAFL SPPGLLALQL PFPLGADLVA
GPGCVHCTHG RHRGVPVHAD GAQGDPPQLS P
```

Figure 30C

```
MAGQFRSYVW DPLLILSQIV LMQTVYYGSL GLWLALVDAL VRSSPSLDQM FDAEILGFST
PPGRLSMMSF VLNALTCALG LLYFIRRGKQ CLDFTVTVHF FHLLGCWLYS SRFPSALTWW
LVQAVCIALM AVIGEYLCMR TELKEVPLSS APKSNV
```

Figure 30D

PFPGSRGPQL FGLSRPAGPP LHGPVCQRCV RRPVPRSGRA PTLRPSSRSR VSRRPRDDGV
VALTGAGGCR APRAGMAGQF RSYVWDPLLI LSQIVLMQTV YYGSLGLWWR WWTRWCAQPV
PGPDVRRGDP GLLHPSRPAL NDVLRPQRPH LCPGLAVLHP AREAVPGFHC HCAFLSPPGL
LALQLPFPLG ADLVAGPGCV HCTHGRHRGV PVHADGAQGD PPQLSP

Figure 30E

MAGQFRSYVW DPLLILSQIV LMQTVYYGSL GLWLALVDAL VRKPVPGPDV RRGDPGLLHP
SRPALNDVLR PQRPHLCPGL AVLHPAREAV PGFHCHCAFL SPPGLLALQL PFPLGADLVA
GPGCVHCTHG RHRGVPVHAD GAQGDPPQLS P

Figure 30F

MAGQFRSYVW DPLLILSQIV LMQTVYYGSL GLWLALVDGL VRQPLAGDPV RRRDPGLFHP
SRPALHDVLH PQRPHLCPGL AVLHPARKAV SGFHCHCPFL SPPGLLVLQL PFPLGADLVA
GPSRVHCTHG CHRGVPVHAD GAQGDTPQLS P

Figure 31

```
   1 GCACGAGGGC GGGCGCGCGC GTGGGCGCAG CGCGGAGCGG GGCCCATGGT GCGGCCGTGT
  61 CCGTCGGTCG GGCCGCGCGG GCGGCTCCGC GCGTGGCCCG GCGCTCGCGA CCTCGCCCCT
 121 GCGCTGCGGG CCCGGCCCGC CCGCTGCCGG CGCCTCCTCC CCCTGCCCCG GGGCGGCGCG
 181 GAGGCCGCGG GGAGCGCAGG GGGCGCGGCG GGCGGCGACA TGACGGACAG CATCCCGCTG
 241 CAGCCCGTGC GCCACAAGAA GCGGGTGGAC AGTAGGCCGC GCGCGGGGTG CTGTGAGTGG
 301 CTGAGATGTT GCGGTGGAGG GGAGCCCAGG CCCCGTACTG TCTGGTTGGG ACACCCCGAG
 361 AAGAGGGACC AGCGGTACCC TCGAAATGTC ATCAACAACC AGAAGTACAA TTTCTTCACA
 421 TTTCTTCCTG GGGTGTTGTT CAGCCAGTTC AGATACTTCT TCAACTTCTA CTTCCTGCTT
 481 CTCGCCTGCT CGCAGTTCGT CCCAGAGATG AGGCTTGGCG CCCTGTACAC CTACTGGGTT
 541 CCTCTGGGCT TCGTGCTGGC TGTCACCATC ATCCGTGAGG CAGTAGAGGA GATCCGATGT
 601 TATGTGCGTG ACAAGGAGAT GAACTCCCAG GTCTACAGCC GGCTCACGTC ACGAGGGACC
 661 GTGAAGGTGA AGAGTTCAAA CATCCAGGTG GGAGACCTCA TCCTTGTGGA AAAGAACCAG
 721 CGGGTCCCTG CTGACATGAT CTTCCTGAGG ACGTCAGAGA AAAACGGCTC TTGCTTCTTG
 781 CGCACGGATC AGCTGGATGG AGAGACAGAC TGGAAGCTTC GGCTCCCGGT GGCCTGCACA
 841 CAGAGGCTTC CCACGGCTGC TGACCTCCTG CAGATTCGGT CCTATGTGTA CGCTGAAAAA
 901 CCCAACATCG ACATTCACAA CTTCCTGGGG ACTTTCACCA GGGAAAACAG TGACCCTCCG
 961 ATCAGTGAGA GTCTGAGCAT TGAGAACACG CTGTGGGCCG GCACCGTCAT AGCATCAGGC
1021 ACTGTTGTAG GCGTTGTTCT CTACACTGGC AGAAAACTGC GGAGTGTCAT GAATACTTCC
1081 GACCCCAGAA GTAAGATTGG CCTGTTCGAC CTGGAGGTGA ACTGCCTCAC CAAAATCCTG
1141 TTTGGTGCGC TGGTGGTGGT GTCCCTGGTC ATGGTGGCCC TGCAGCACTT TGCCGGCCGC
1201 TGGTACCTGC AGATCATCCG CTTCCTGCTC CTGTTTTCCA ACATCATTCC TATCAGCTTG
1261 CGTGTGAACT TGGACATGGG CAAGATCGTG TACAGCTGGG TGATCCGCAG GGATTCCAAA
1321 ATCCCCGGGA CCGTGGTTCG TTCCAGCACA ATTCCTGAGC AGCTGGGCAG GATTTCGTAC
1381 TTGCTCACAG ACAAGACAGG AACCCTGACC CAGAATGAGA TGGTGTTCAA GCGGCTGCAC
1441 CTGGGTACGG TGGCCTACGG CCTGGACTCC ATGGACGAAG TGCAGAGTCA CATCTTCAGC
1501 ATTTACACCC AGCAATCCCA GGATCCACCT GCTCAGAAGG CCCCACGGT CACCACCAAG
1561 GTCCGGAGGA CCATGAGCAG CCGTGTCCAC GAGGCTGTGA AGGCCATTGC ACTCTGCCAC
1621 AACGTGACAC CCGTGTACGA GTCCAATGGT GTGACGGACC AGGCTGAGGC TGAGAAGCAG
1681 TTTGAGGACT CCTGCCGAGT GTACCAGGCA TCCAGCCCGG ATGAGGTGGC TCTGGTCCAG
1741 TGGACAGAAA GTGTGGGACT GACGCTGGTG GGTCGAGACC AGTCCTCCAT GCAGCTGAGG
1801 ACCCCTGGTG ACCAGGTCCT GAATCTCACC ATCCTTCAGG TCTTCCCGTT CACCTATGAG
1861 AGCAAGCGGA TGGGCATCAT CGTGCGGGAT GAGTCCACGG GGGAAATCAC GTTCTACATG
1921 AAGGGAGCAG ACGTCGTCAT GGCTGGCATT GTCCAGTACA ACGACTGGCT GGAGGAGGAG
1981 TGTGGCAACA TGGCCCGGGA GGGACTACGT GTGCTGGTGG TAGCCAAGAA GTCCCTCACA
2041 GAGGAGCAGT ACCAACACTT TGAAGCCCGC TACGTCCAGG CTAAGCTGAG TGTGCATGAC
2101 CGCTCGCTGA AGGTGGCCAC GGTGATCGAG AGCTTGGAGA TGGAGATGGA GCTGCTGTGC
2161 CTGACTGGTG TGGAGGACCA GCTGCAGGCA GATGTCAGGC CCACGCTGGA GACGCTGCGC
2221 AACGCTGGCA TCAAGGTTTG GATGCTAACA GGGGACAAGC TGGAGACAGC CACGTGCACA
2281 GCCAAGAACG CACATCTGGT GACCAGAAAC CAAGATATCC ATGTTTTCCG ACTGGTGACC
2341 AACCGCGGGG AGGCCCACCT GGAGCTGAAT GCCTTCCGTA GGAAGCATGA CTGTGCCCTG
2401 GTCATCTCTG GAGACTCCCT GGAGGTTTGC CTCAAATACT ATGAGTACGA GTTCATGGAA
2461 CTGGCCTGCC AGTGCCCGGC TGTGGTGTGC TGCCGCTGTG CCCCAACCCA GAAGGCCCAG
2521 ATTGTTCGGC TGCTCCAAGA ACGCACCGGG AAACTCACCT GTGCAGTATG GGACGGAGGC
2581 AATGACGTCA GCATGATCCA GGAATCCGAC TGCGGCGTGG GCGTGGAGGG CAAGGAAGGG
2641 AAGCAGGCCT CGCTGGCAGC GGACTTCTCC ATCACCCAGT TCAAGCATCT CGGCCGCTTG
2701 CTCATGGTGC ACGGTCGGAA CAGCTACAAG CGCTCGGCGG CCCTCAGTCA GTTTGTGATC
2761 CACAGGAGCC TCTGCATCAG CACCATGCAG GCTGTCTTCT CGTCTGTGTT CTACTTTGCA
```

Figure 32A

```
2821 TCCGTTCCTC TCTACCAAGG CTTCCTGATC ATTGGGTATT CTACCATCTA CACGATGTTT
2881 CCCGTGTTCT CCCTGGTTTT GGACAAAGAC GTGAAGTCGG AAGTCGCCAT GTTGTATCCT
2941 GAGCTCTACA AGGACCTGCT TAAGGGGCGG CCACTGTCCT ACAAGACGTT CTTAATTTGG
3001 GTGTTAATCA GCATCTATCA AGGGAGCACC ATCATGTACG GGCGCTGCT GCTGTTCGAG
3061 TCGGAGTTTG TACACATCGT GGCAATCTCC TTCACATCCC TCATCCTCAC TGAGCTACTG
3121 ATGGTGGCGC TCACCATCCA GACGTGGCAC TGGCTCATGA CAGTGGCCGA GCTACTCAGC
3181 CTGGCCTGCT ACATTGCCTC CCTGGTGTTC CTCCATGAGT TCATCGATGT CTACTTCATT
3241 GCCACCCTGT CATTCCTCTG GAAGGTGTCC GTCATCACCT TGGTCAGCTG TCTCCCCCTC
3301 TATGTCCTCA GTACCTGCG GAGACGGTTC TCCCCACCCA GCTACTCGAA GCTCACTTCC
3361 TAAGCTGCAG GGCTGCCTCG GGCAGGGCCT CCGGCCTCCG GCGCTNTCCC CAGGAGGAGG
3421 TCAAGTTCCA CACGCACGAG CCGCCTCTGC TGGACGGTGC AGTCATGGCT GGCACATGAG
3481 GCTTCGCTGA GGCGACACTG GCACCTAAT GGGGATGGAA CATTGGTGGA ACCGGAGGGA
3541 GGGACCTGAG AGCTGTACCT ATCAGAACCT TGGGTGCTAA GCTGTGCTGA GGGGGAAGAC
3601 GTGGGACCGG ATGGCCCGTC TGAGGTTTGT GGGGTCACTG TGCAAGCTTC CCTTATGGTT
3661 TGAACCTCTT GCCTGCAGCC CGGGG
```

Figure 32B

Symbol and Name (MGI)

Atp9a: ATPase, class II, type 9A
LocusID: 11981

Overview

| | |
|---|---|
| Locus Type: | gene with protein product, function known or inferred |
| Product: | ATPase, class 2 |
| Alternate Symbols: | IIa |
| Alias: | Class II<br>ATPase, class 2<br>ATPase 9A, p type<br>ATPase 9A, class II |

Function — SubmitGeneRIF

Gene Ontology™:

| Term | Evidence | Source | Pub |
|---|---|---|---|
| • membrane | IEA | MGD | |
| • hydrolase | IEA | MGD | |
| • metabolism | IEA | MGD | |
| • ATP binding | IEA | MGD | |
| • cation transport | IEA | MGD | |
| • magnesium binding | IEA | MGD | |
| • integral membrane protein | IEA | MGD | |
| • plasma membrane cation-transporting ATPase | IEA | MGD | |

Relationships

Human Homology Maps:
NCBI vs. MGD          20q13.11-13.2  ATP9A Hs
UCSC vs. MGD          20q13.11-13.2  ATP9A Hs

| LocusID | Org | Symbol | Description |
|---|---|---|---|
| ☐ 11981 | Mm | Atp9a | ATPase, class II, type 9A |
| More | Mm | | ATPase, class 2;<br>ATPase 9A, p type;<br>Class II; ATPase 9A, class II |

Figure 33

NCBI Reference Sequences (RefSeq)
Category: NCBI Genome Annotation

| | | gb sv mv ev mm |
|---|---|---|
| Genomic Contig: | NT_011362 | |
| Annotated transcripts/proteins for this locus: | | |
| Evidence: | supported by alignment with both mRNA and ESTs (27) | |
| Model mRNA: | XM_030577 | |
| Model Protein: | XP_030577 | BL |

GenBank Sequences

| Nucleotide | Type | Protein | |
|---|---|---|---|
| AB014511 | m | BAA31586 | BL |
| AK025559 | m | | |
| AK026513 | m | | |
| BC016044 | m | AAH16044 | BL |

Figure 34

```
   1 MTDSIPLQPV RHKKRVDSRP RAGCCEWLRC CGGGEPRPRT VWLGHPEKRD QRYPRNVINN
  61 QKYNFFTFLP GVLFSQFRYF FNFYFLLLAC SQFVPEMRLG ALYTYWVPLG FVLAVTIIRE
 121 AVEEIRCYVR DKEMNSQVYS RLTSRGTVKV KSSNIQVGDL ILVEKNQRVP ADMIFLRTSE
 181 KNGSCFLRTD QLDGETDWKL RLPVACTQRL PTAADLLQIR SYVYAEKPNI DIHNFLGTFT
 241 RENSDPPISE SLSIENTLWA GTVIASGTVV GVVLYTGRKL RSVMNTSDPR SKIGLFDLEV
 301 NCLTKILFGA LVVVSLVMVA LQHFAGRWYL QIIRFLLLFS NIIPISLRVN LDMGKIVYSW
 361 VIRRDSKIPG TVVRSSTIPE QLGRISYLLT DKTGTLTQNE MVFKRLHLGT VAYGLDSMDE
 421 VQSHIFSIYT QQSQDPPAQK GPTVTTKVRR TMSSRVHEAV KAIALCHNVT PVYESNGVTD
 481 QAEAEKQFED SCRVYQASSP DEVALVQWTE SVGLTLVGRD QSSMQLRTPG DQVLNLTILQ
 541 VFPFTYESKR MGIIVRDEST GEITFYMKGA DVVMAGIVQY NDWLEEECGN MAREGLRVLV
 601 VAKKSLTEEQ YQHFEARYVQ AKLSVHDRSL KVATVIESLE MEMELLCLTG VEDQLQADVR
 661 PTLETLRNAG IKVWMLTGDK LETATCTAKN AHLVTRNQDI HVFRLVTNRG EAHLELNAFR
 721 RKHDCALVIS GDSLEVCLKY YEYEFMELAC QCPAVVCCRC APTQKAQIVR LLQERTGKLT
 781 CAVWDGGNDV SMIQESDCGV GVEGKEGKQA SLAADFSITQ FKHLGRLLMV HGRNSYKRSA
 841 ALSQFVIHRS LCISTMQAVF SSVFYFASVP LYQGFLIIGY STIYTMFPVF SLVLDKDVKS
 901 EVAMLYPELY KDLLKGRPLS YKTFLIWVLI SIYQGSTIMY GALLLFESEF VHIVAISFTS
 961 LILTELLMVA LTIQTWHWLM TVAELLSLAC YIASLVFLHE FIDVYFIATL SFLWKVSVIT
1021 LVSCLPLYVL KYLRRRFSPP SYSKLTS
```

Figure 35

```
   1 MTDNIPLQPV RQKKRMDSRP RAGCCEWLRC CGGGEARPRT VWLGHPEKRD QRYPRNVINN
  61 QKYNFFTFLP GVLFNQFKYF FNLYFLLLAC SQFVPEMRLG ALYTYWVPLG FVLAVTVIRE
 121 AVEEIRCYVR DKEVNSQVYS RLTARGTVKV KSSNIQVGDL IIVEKNQRVP ADMIFLRTSE
 181 KNGSCFLRTD QLDGETDWKL RLPVACTQRL PTAADLLQIR SYVYAEEPNI DIHNFVGTFT
 241 REDSDPPISE SLSIENTLWA GTVVASGTVV GVVLYTGREL RSVMNTSNPR SKIGLFDLEV
 301 NCLTKILFGA LVVVSLVMVA LQHFAGRWYL QIIRFLLLFS NIIPISLRVN LDMGKIVYSW
 361 VIRRDSKIPG TVVRSSTIPE QLGRISYLLT DKTGTLTQNE MIFKRLHLGT VAYGLDSMDE
 421 VQSHIFSIYT QQSQDPPAQK GPTLTTKVRR TMSSRVHEAV KAIALCHNVT PVYESNGVTD
 481 QAEAEKQYED SCRVYQASSP DEVALVQWTE SVGLTLVGRD QSSMQLRTPG DQILNFTILQ
 541 IFPFTYESKR MGIIVRDEST GEITFYMKGA DVVMAGIVQY NDWLEEECGN MAREGLRVLV
 601 VAKKSLAEEQ YQDFEARYVQ AKLSVHDRSL KVATVIESLE MEMELLCLTG VEDQLQADVR
 661 PTLETLRNAG IKVWMLTGDK LETATCTAKN AHLVTRNQDI HVFRLVTNRG EAHLELNAFR
 721 RKHDCALVIS GDSLEVCLKY YEYEFMELAC QCPAVVCCRC APTQKAQIVR LLQERTGKLT
 781 CAVGDGGNDV SMIQESDCGV GVEGKEGKQA SLAADFSITQ FKHLGRLLMV HGRNSYKRSA
 841 ALSQFVIHRS LCISTMQAVF SSVFYFASVP LYQGFLIIGY STIYTMFPVF SLVLDKDVKS
 901 EVAMLYPELY KDLLKGRPLS YKTFLIWVLI SIYQGSTIMY GALLLFESEF VHIVAISFTS
 961 LILTELLMVA LTIQTWHWLM TVAELLSLAC YIASLVFLHE FIDVYFIATL SFLWKVSVIT
1021 LVSCLPLYVL KYLRRRFSPP SYSKLTS
```

Figure 36

```
ATGACGGACAACATCCCGCTGCAGCCGGTGCGCCAGAAGAAGCGGATGGACAGCAGGCCC
CGCGCCGGGTGCTGCGAGTGGCTGAGATGCTGCGGTGGAGGGGAGGCCAGGCCCCGCACT
GTCTGGCTGGGGCACCCCGAGAAGAGAGACCAGAGGTATCCTCGGAATGTCATCAACAAT
CAGAAGTACAATTTCTTCACCTTTCTTCCTGGGGTGCTGTTCAACCAGTTCAAATACTTT
TTCAACCTCTATTTCTTACTTCTTGCCTGCTCTCAGTTTGTTCCCGAAATGAGACTTGGT
GCACTCTATACCTACTGGGTTCCCCTGGGCTTCGTGCTGGCCGTCACTGTCATCCGTGAG
GCGGTGGAGGAGATCCGATGCTACGTGCGGGACAAGGAAGTCAACTCCCAGGTCTACAGC
CGGCTCACAGCACGAGGCACAGTGAAGGTGAAGAGTTCTAACATCCAAGTTGGAGACCTT
ATCATCGTTGAAAAGAACCAGCGGGTCCCTGCCGACATGATCTTCCTGAGGACATCAGAA
AAAAACGGGTCATGCTTCTTGCGGACGGATCAGCTGGATGGGGAGACGGACTGGAAGCTG
CGGCTTCCCGTGGCCTGCACGCAGAGGCTCCCCACGGCCGCCGACCTTCTTCAGATTCGA
TCGTATGTGTACGCAGAAGAGCCAAATATTGACATTCACAACTTCGTGGGAACTTTTACC
CGAGAAGACAGCGACCCCCCGATCAGCGAGAGCCTGAGCATAGAAACACGCTGTGGGCT
GGCACTGTGGTCGCATCAGGTACTGTTGTGGGTGTTGTTCTTTACACTGGCAGAGAACTC
CGGAGTGTCATGAATACCTCAAATCCCCGAAGTAAGATCGGCCTGTTCGACTTGGAAGTG
AACTGCCTCACCAAGATCCTCTTTGGTGCCCTGGTGGTGGTCTCGCTGGTCATGGTTGCC
CTTCAGCACTTTGCAGGCCGTTGGTACCTGCAGATCATCCGCTTCCTCCTCTTGTTTTCC
AACATCATCCCCATTAGTTTGCGTGTGAACCTGGACATGGGCAAGATCGTGTACAGCTGG
GTGATTCGAAGGGACTCGAAAATCCCCGGGACCGTGGTTCGCTCCAGCACGATTCCTGAG
CAGCTGGGCAGGATTTCGTACTTACTCACAGACAAGACAGGCACTCTTACCCAGAACGAG
ATGATTTTCAAACGGCTCCATCTCGGAACAGTAGCCTACGGCCTCGACTCAATGGACGAA
GTACAAAGCCACATTTTCAGCATTTACACCCAGCAATCCCAGGACCCACCGGCTCAGAAG
GGCCCAACGCTCACCACTAAGGTCCGGCGGACCATGAGCAGCCGCGTGCACGAAGCCGTG
AAGGCCATCGCGCTCTGCCACAACGTGACTCCCGTGTATGAGTCCAACGGTGTGACTGAT
CAGGCTGAGGCCGAGAAGCAGTACGAAGACTCCTGCCGCGTATACCAGGCATCCAGCCCC
GATGAGGTGGCCCTGGTACAGTGGACGGAAAGTGTGGGCTTAACCCTGGTGGGCCGAGAC
CAGTCTTCCATGCAGCTGAGGACCCCTGGCGACCAGATCCTGAACTTCACCATCCTACAG
ATCTTCCCTTTCACCTATGAAAGCAAACGTATGGGCATCATCGTGCGGGATGAATCAACT
GGAGAAATTACGTTTTACATGAAGGGAGCAGATGTGGTCATGGCTGGCATTGTGCAGTAC
AATGACTGGTTGGAGGAAGAGTGTGGCAACATGGCCCGAGAAGGGCTGCGGGTGCTCGTG
GTGGCAAAGAAGTCTCTTGCAGAGGAGCAGTATCAGGACTTTGAAGCCCGCTACGTCCAG
GCCAAGCTGAGTGTGCACGACCGCTCCCTCAAAGTGGCCACGGTGATCGAGAGCCTGGAG
ATGGAGATGGAACTGCTGTGCCTGACGGGCGTGGAGGACCAGCTGCAGGCAGATGTGCGG
CCCACGCTGGAGACCCTGAGGAATGCTGGCATCAAGGTTTGGATGCTGACAGGGGACAAG
CTGGAGACAGCTACGTGCACAGCGAAGAATGCACATCTGGTGACCAGAAACCAAGACATC
CACGTTTTTCGGCTGGTGACCAACCGCGGGGAGGCTCACCTCGAGCTGAACGCCTTCCGC
AGGAAGCATGATTGTGCCCTGGTCATCTCGGGAGACTCCCTGGAGGTTTGCCTCAAGTAC
TATGAGTACGAGTTCATGGAGCTGGCCTGCCAGTGCCCGGCCGTAGTCTGCTGCCGATGT
GCCCCCACCCAGAAGGCCCAGATCGTGCGCCTGCTTCAGGAGCGCACGGGCAAGCTCACC
TGTGCAGTAGGGGACGGAGGCAATGACGTCAGCATGATTCAGGAATCTGACTGCGGCGTG
GGAGTGGAAGGAAAGGAAGGAAAACAGGCTTCGTTGGCTGCAGACTTCTCCATCACTCAA
TTTAAGCATCTTGGCCGGTTGCTTATGGTGCATGGCCGGAACAGCTACAAGCGGTCAGCC
GCCCTCAGCCAGTTCGTGATTCACAGGAGCCTCTGTATCAGCACCATGCAGGCTGTCTTT
TCCTCCGTGTTTTACTTTGCCTCCGTCCCTCTCTATCAAGGATTCCTCATCATTGGGTAC
TCCACAATTTACACCATGTTTCCTGTGTTTTCTCTGGTCCTGGACAAAGATGTCAAATCG
GAAGTTGCCATGCTGTATCCTGAGCTCTACAAGGATCTTCTCAAGGGACGGCCGTTGTCC
TACAAGACATTCTTAATATGGGTTTTGATTAGCATCTATCAAGGGAGCACCATCATGTAC
GGGGCGCTGCTGCTGTTTGAGTCGGAGTTCGTGCACATCGTGGCCATCTCCTTCACCTCG
CTGATCCTCACCGAGCTGCTCATGGTGGCGCTGACCATCCAGACCTGGCACTGGCTCATG
ACAGTGGCGGAGCTGCTCAGCCTGGCCTGCTACATCGCCTCCCTGGTGTTCTTACACGAG
TTCATCGATGTGTACTTCATCGCCACCTTGTCATTCTTGTGGAAAGTCTCCGTCATCACT
CTGGTCAGCTGCCTCCCCCTCTATGTCCTCAAGTACCTGCGAAGACGGTTCTCTCCCCCC
AGCTACTCAAAGCTCACATCA
```

Figure 37

```
   1 GGGAAGCTGT TGCGCACCAC TTAGCTGGGA AGTGCGTTGC TCCCTGTTTC CCAGCCCACC
  61 CGAGATGGCC CCCAAAGTCT CGGATTCCGT GGAACAGCTC CGCGCTGCCG GCAACCAGAA
 121 CTTCCGCAAT GGCCAGTACG GCGAAGCTCG GCGCTGTACG AGCGCGCACT GCGGCTGCTG
 181 CAGGCGCGAG GTAGGAACCC GCCCCACGTT TCCCTCCGGG CCTGCGTCCT CCACCCGCAT
 241 CCCCGCACCG GGCCTCCCGT TGGCCCAGCC TCCCTGGTTT TCCCTTCCCC GCGTCCAGCC
 301 GCCGCACCAG GCCCTCCCAG GGCTTGACCC CGCGATTCTT TCCGTCCCTG GCCGCCTAGC
 361 CGCGGCCCGG TCTACCATCA CCACCCCCCA CCACCCCCAG GCCAGTCGGC TGCGGGCCTT
 421 AAGGGCACGC ATCCGCTGCT TCCACCCGGA AGCTGTTGCG CACTCCTCGG CGGGGAACGG
 481 AGGTGGTCCT TGTTTGCCGG CCTCCCGGGA TGGCCCCCAA ACTCTCAGAC TCTGTGGAAG
 541 AGCTCCGCGC AGCCGGCAAC CAGAGTTTCC GCAACGGACA GTACGCCGAG GCTTCGGCGC
 601 TGTACGAGCG CGCGCTGCGA CTGCTGCAGG CGCGAGGTTC TGCAGACCCC GAAGAAGAAA
 661 GTGTTCTGTA CTCCAACCGT GCAGCGTGCT ACTTGAAGGA TGGGAACTGC ACAGATTGCA
 721 TCAAAGATTG CACTTCCGCG CTGGCCTTGG TTCCCTTCAG CATCAAGCCC TTGCTGCGCA
 781 GAGCATCTGC ATATGAAGCC CTGGAGAAGT ACGCCCTGGC CTACGTTGAC TATAAGACTG
 841 TGCTGCAGAT CGATAACAGT GTGGCATCCG CCCTGGAAGG CATCAACAGA ATAACCAGAG
 901 CTCTCATGGA CTCCCTGGGA CCTGAGTGGC GCCTGAAGCT GCCCCTATC CCTGTGGTGC
 961 CTGTTTCAGC CCAGAAGAGA TGGAATTCCT TGCCTTCAGA TAACCACAAA GAGACAGCTA
1021 AAACCAAATC CAAAGAAGCC ACAGCTACGA AGAGCAGAGT GCCTTCTGCT GGGGATGTGG
1081 AGAGAGCCAA AGCTCTGAAG GAAGAAGGCA ATGACCTTGT AAAGAAGGGC AACCATAAGA
1141 AAGCTATTGA AAGTACAGT GAGAGCCTCT TGTGTAGTAG CCTGGAGTCT GCCACATACA
1201 GCAACAGAGC GCTCTGTCAC CTGGTCCTGA AGCAGTACAA GGAGGCAGTA AAGGACTGCA
1261 CAGAAGCCCT CAAGCTGGAT GGGAAGAATG TAAAGGCGTT TTACAGACGG GCTCAAGCCT
1321 ACAAGGCACT CAAGGACTAT AAGTCAAGCC TTTCGGATAT CAGCAGCCTC CTACAAATTG
1381 AACCCAGGAA TGGCCCTGCA CAGAAGTTAC GGCAGGAAGT TAACCAGAAC ATGAACTAAA
1441 CCGTAGAGGG CAACAGGGAC CCTGAACTTG ACCTTCCCAG AGAAGCCAGG GCCTCCCTTG
1501 CATCTGCCCC AATGCCCAGC ATGCCGCCAA GGGAGTGCAA AATCAACCCC ACTTTGACTC
1561 CTTGGAGAGG TAGCAGCCTT TCACCTGACA CATTTTACTT GTTCAGATTA AGTCCATTAC
1621 AGACAAGCAC AGGACTCTTT TTTTTTTTCT TCTTTTTTTT TTCCAGAAAG GTCCCCACTA
1681 GAGGTTTTTG TTTTGTTTTA TTTTTAATTT AAAAAAGCGT GACGCCAACA GCCCTGGCCT
1741 CATTCGCTTG CTTCTGCCTG GCCCTTGTCA ACACAGTCCT TGGCAACTGT CCCTGACCCA
1801 GATATGCACA GACTGGGTGC CTGTGACTTC CTCTGCCGCC ATAGCTCTGC AGTTCACCTG
1861 AGTGCTGACA GGCTAGAAGT GCTTGCTCGT CCGCAGCCAC AGCGGCCTGT TGAGCTGGTT
1921 CTCCAAGGCT GCCTGCCATC TCCTCGAGGA GACAGCTGCT GTCTGCACCC TGTCCTTGAC
1981 ACAGTGTCCT GTGTTGAGCC CCAGTGCCTT TAGTCCAGGC CCTTTGTGGG AAGGCAGAGC
2041 CTAACCCTTG GAGGCTCTGT GTTGTTGCCT TCTGTCTGAG CTACCTACGA TGTTCAAAGA
2101 GCCCAGATTC CTCCTGCAAT GGGGAGAGAG GCCTCCTTGA GATTAGTGTC CCTCCAGTCT
2161 GAGCAGGAAC TTAACCTTTT CCCCCATAGC AGCAGCCCCT CGGGCTCCTT TGTTTTGTTT
2221 TGTTTTGTTA ATATGTTGGA GTTAATTGAA CTGATTTTAT TGAAGTGTGT GTTGCTGTTG
2281 CATTAAAAGG TTTTCTTCTA TG
```

Figure 38

Click to Display mRNA-Genomic Alignments (spanning 17338 bps)

*Mus musculus* Official Gene Symbol and Name (MGI)
2610100K07Rik: RIKEN cDNA 2610100K07 gene
LocusID: 67145

Overview Submit GeneRIF
Locus Type: gene with protein product, function unknown
Product: RIKEN cDNA 2610100K07

Relationships
Human Homology
Maps:

| | | | | |
|---|---|---|---|---|
| NCBI vs. MGD | 20q12-q13.1 | TOM34 | Mm | Hs |
| UCSC vs. MGD | 20q12-q13.1 | TOM34 | Mm | Hs |
| NCBI vs. MGD | 20q12-q13.1 | TOMM34 | Mm | Hs |

Map Information
Chromosome: 2 mv
Cytogenetic: 2 RefSeq

NCBI Reference Sequences (RefSeq)
Category: PREDICTED
mRNA: NM_025996
Protein: NP_080272 RIKEN cDNA 2610100K07
Domains: TPR Domain    score: 84 mRNA: NM_025996
Protein: NP_080272 RIKEN cDNA 2610100K07
Domains: TPR Domain    score: 84
Tetratricopeptide repeats    score: 88

Figure 39A

| | | | | | | |
|---|---|---|---|---|---|---|
| PUBMED | GENEVIEW | HOMOL | GDB | eI | UCSC | |

*Homo sapiens* Official Gene Symbol and Name (HGNC)

TOMM34: translocase of outer mitochondrial membrane 34

LocusID: 10953

Overview

Proteome Summary: Subunit of the translocase of the outer mitochondrial membrane; component of the mitochondrial protein import complex Locus Type: gene with protein product, function known or inferred Product: translocase of outer mitochondrial membrane 34

Alternate Symbols: TOM34, HTOM34P

Alias: outer mitochondrial membrane translocase (34kD)

Function   Submit GeneRIF   (All Pubs)

GeneRIF: Gene References into Function:

11913975 • Tom34 unlike Tom20 does not interact with the leader sequences of mitochondrial precursor proteins 11913976 • Yeast two-hybrid screening identifies binding partners of human Tom34 that have ATPase activity and form a complex with Tom34 in the cytosol

NCBI Reference Sequences (RefSeq)

Category: PROVISIONAL mRNA: NM_006809

Protein: NP_006800 translocase of outer mitochondrial membrane 34  score: 86

Domains: TPR Domain
Tetratricopeptide repeats score: 87

GenBank Source: BC007423

Category: NCBI Genome Annotation

Genomic Contig: NT_011362    gb sv mv ev mm

Annotated transcripts/proteins for this locus:

Evidence: supported by alignment with both mRNA and ESTs (37)

Model mRNA: XM_029822

Model Protein: XP_029822

Domains: TPR Domain  score: 86
Tetratricopeptide score: 89 repeats

```
MAPKLSDSVE ELRAAGNQSF RNGQYAEASA LYERALRLLQ ARGSADPEEE SVLYSNRAAC
YLKDGNCTDC IKDCTSALAL VPFSIKPLLR RASAYEALEK YALAYVDYKT VLQIDNSVAS
ALEGINRITR ALMDSLGPEW RLKLPPIPVV PVSAQKRWNS LPSDNHKETA KTKSKEATAT
KSRVPSAGDV ERAKALKEEG NDLVKKGNHK KAIEKYSESL LCSSLESATY SNRALCHLVL
KQYKEAVKDC TEALKLDGKN VKAFYRRAQA YKALKDYKSS LSDISSLLQI EPRNGPAQKL
RQEVNQNMN
```

Figure 40

```
MAPKFPDSVEELRAAGNESFRNGQYAEASALYGRALRVLQAQGSSDPEEESVLYSNRAACHLKDGNCRDC
IKDCTSALALVPFSIKPLLRRASAYEALEKYPMAYVDYKTVLQIDDNVTSAVEGINRMTRALMDSLGPEW
RLKLPSIPLVPVSAQKRWNSLPSENHKEMAKSKSKETTATKNRVPSAGDVEKARVLKEEGNELVKKGNHK
KAIEKYSESLLCSNLESATYSNRALCYLVLKQYTEAVKDCTEALKLDGKNVKAFYRRAQAHKALKDYKSS
FADISNLLQIEPRNGPAQKLRQEVKQNLH
```

Figure 41

```
   1 GGCACGAGGC ACCACACGGG GGAGGAAGGA AGGAGCTCCC AACTCGCCGG CCTGGCCACG
  61 GGATGGCCCC CAAATTCCCA GACTCTGTGG AGGAGCTCCG CGCCGCCGGC AATGAGAGTT
 121 TCCGCAACGG CCAGTACGCC GAGGCCTCCG CGCTCTACGG CCGCGCGCTG CGGGTGCTGC
 181 AGGCGCAAGG TTCTTCAGAC CCAGAAGAAG AAAGTGTTCT CTACTCCAAC CGAGCAGCAT
 241 GTCACTTGAA GGATGGAAAC TGCAGAGACT GCATCAAAGA TTGCACTTCA GCACTGGCCT
 301 TGGTTCCCTT CAGCATTAAG CCCCTGCTGC GGCGAGCATC TGCTTATGAG GCTCTGGAGA
 361 AGTACCCTAT GGCCTATGTT GACTATAAGA CTGTGCTGCA GATTGATGAT AATGTGACGT
 421 CAGCCGTAGA AGGCATCAAC AGAATGACCA GAGCTCTCAT GGACTCGCTT GGGCCTGAGT
 481 GGCGCCTGAA GCTGCCCTCA ATCCCCTTGG TGCCTGTTTC AGCTCAGAAG AGGTGGAATT
 541 CCTTGCCTTC GGAGAACCAC AAAGAGATGG CTAAAAGCAA ATCCAAAGAA ACCACAGCTA
 601 CAAAGAACAG AGTGCCTTCT GCTGGGGATG TGGAGAAAGC CAGAGTTCTG AAGGAAGAAG
 661 GCAATGAGCT TGTAAAGAAG GGAAACCATA AGAAAGCTAT TGAGAAGTAC AGTGAAAGCC
 721 TCTTGTGTAG TAACCTGGAA TCTGCCACGT ACAGCAACAG AGCACTCTGC TATTTGGTCC
 781 TGAAGCAGTA CACAGAAGCA GTGAAGGACT GCACAGAAGC CCTCAAGCTG GATGGAAAGA
 841 ACGTGAAGGC ATTCTACAGA CGGGCTCAAG CCCACAAAGC ACTCAAGGAC TATAAATCCA
 901 GCTTTGCAGA CATCAGCAAC CTCCTACAGA TTGAGCCTAG GAATGGTCCT GCACAGAAGT
 961 TGCGGCAGGA AGTGAAGCAG AACCTACACT AAAAACCCAA CAGGGCAACT GGAACCCCTG
1021 CCTGACCTTA CCCAGAGAAG CCATGGGCCA CCTGCTCTGT GCCCGCTCCT GAAACCCAGC
1081 ATGCCCCAAG TGAGCTCTGA AGCCCCCTCC TCAATCCCTT GATGGCCTCC CACCCTGTAA
1141 GAGGCTTTGC TTGTTCAAAT TAAACTCAGT GTAGTCAAAC ACAGACATGG TTGTTGCACC
1201 AGAAAGGTCC CCACTAGAGC TAAGCGTGAA GCTGAAGCTC TGTCCCTATT CCCCAGCCC
1261 AGCTAGCTGA TCACACCAAC AGATCCTCAT CAGCAAAGCA TTTGGCTTTG TCCTGCCCAA
1321 GTGGGCTGCA GACTGAGTGC TGCCCTTGTA GCTTCCCCAG ACCCCAACTC ACTGCAGTTC
1381 ATCTGAACAA CCTGAGCTCC TGGGCCGGGG TGGAAGGAGG GGGATAAACC TAAGGCCCTG
1441 ATCCAAAGCA GCCTGTTGAG CTGGTTCTCC AGGGCTGCAG TCTCTCCAGG TGTACAGCTG
1501 CTGTCCCTGC CCTGTCCTGT CCTTGCACAG TCTCCTATGT CTGAGCCCCA GTGCCTTCTG
1561 TTCGGGCCCT CCTTTGGTGG AAGGCAGAG CCCTGACCCT TGAATGGTTG TCCTTGACTC
1621 TGTGCTGCTG CCTTCTGCAG AGAGGCACCT AAGCTGTTTA AAGAGCCCAG TGATTGTGGC
1681 TGCTCCTCCT AGAGGTGGGA GGGGCAAGA GGCCTCCTTG GTCAGTGTCC ATGCTTTCTG
1741 GGCAGGGACT TGGTTTTTTG TTCCAACAGT GGCCTTCTCC GGGCTTCATA GTTCTTTGTA
1801 ATATGTTGAA GTTAATTTGA ATTGACTGAT TTGTTGAAC TGTGTGTTTA AGCTGTTGCA
1861 TTAAAAAGCT TCTTCTACA TCAATATCTG CTGTGCTTTC ATTTATGCCT TTTCAGCTTT
1921 GCACCTGGAA CTCTGTAGTA ATAATAAAAG TTATTGCTTA TTGGGCATTC AAAAAAAAA
1981 AAAAAAA
```

Figure 42

```
MAPKVSDSVE QLRAAGNQNF RNGQYGEASA LYERALRLLQ ARGSADPEEE SVLYSNRAAC
YLKDGNCTDC IKDCTSALAL VPFSIKPLLR RASAYEALEK YALAYVDYKT VLQIDNSVAS
ALEGINRITR ALMDSLGPEW RLKLPPIPVV PVSAQKRWNS LPSDNHKETA KTKSKEATAT
KSRVPSAGDV ERAKALKEEG NDLVKKGNHK KAIEKYSESL LCSSLESATY SNRALCHLVL
KQYKEAVKDC TEALKLDGKN VKAFYRRAQA YKALKDYKSS LSDISSLLQI EPRNGPAQKL
RQEVNQNMN
```

Figure 43

```
MAPKFPDSVE ELRAAGNESF RNGQYAEASA LYGRALRVLQ AQGSSDPEEE SVLYSNRAAC
HWKNGNCRDC IKDCTSALAL VPFSIKPLLR RASAYEALEK YPMAYVDYKT VLQIDDNVTS
AVEGINRMTR ALMDSLGPEW RLKLPSFPLV PVSAQKRWNF LPSENHKEMA KSKSKETTAT
KNRVPSAGDV EKARVLKEEG NELVKKGNHK KAIEKYSESL LCSNLESATY SNRALCYLVL
KQYTEAVKDC TEALKLDGKN VKAFYRRAQA HKALKDYKSS FADISNLLQI EPRNGPAQKL
RQEVKQNLH
```

Figure 44

```
   1 GACTGGCTGG TGCGGGAAAT ATGCAGGAGA AAAGTCTTTG CATAATGTAG AGCGAGCCGT
  61 GGGGCTCCGG GAGCGGCGCC CCAAGGTCTG GGGCCATGAA CGCGAGCGTG GAAGGAGACA
 121 CCTTTTCTGG ATCGATGCAA ATCCCAGGAG GCACCACGGT CGTGGTGGAG CTGGCACCGG
 181 ACATCCACAT CTGCGGCCTC TGTAAGCAGC ACTTCAGCAA TCTGGATGCC TTTGTGGCCC
 241 ACAAACAGAG CGGCTGCCAG CTGACTACCA CGCCGGTGAC AGCCCCAGC ACGGTCCAGT
 301 TTGTGGCAGA GGAGACAGAG CCTGCCACCC AGACCACCAC AACGACCATC AGTTCAGAGA
 361 CTCAGACTAT CACAGTTTCA GCTCCAGAGT TCGTCTTTGA ACATGGCTAC CAAACTTACC
 421 TGCCCACGGA GAGCACTGAC AACCAGACAG CCACCGTGAT CTCTCTCCCC ACCAAGTCAC
 481 GCACCAAAAA GCCCACAGCA CCCCCTGCTC AGAAGAGACT CGGCTGCTGC TATCCAGGTT
 541 GCCAGTTCAA GACCGCCTAT GGCATGAAGG ACATGGAGCG ACACCTGAAG ATCCACACCG
 601 GTGACAAACC CCACAAGTGT GAGGTGTGCG GGAAGTGCTT CAGCCGGAAG GACAAGCTGA
 661 AGACGCACAT GCGCTGCCAC ACGGGCGTCA AGCCCTACAA GTGCAAGACG TGCGACTACG
 721 CGGCGGCGGA CAGCAGCAGC CTTAACAAGC ACCTGCGCAT CCACTCGGAC GAGCGACCCT
 781 TCAAGTGCCA GATCTGTCCC TACGCCAGCC GCAACTCCAG CCAGCTCACC GTGCACCTGC
 841 GCTCGCACAC GGGGGACGCC CCCTTCCAGT GCTGGCTCTG TAGTGCCAAG TTCAAAATCA
 901 GCTCGGACTT GAAAAGGCAC ATGCGTGTGC ACTCGGGGGA GAAGCCTTTC AAGTGCGAAT
 961 TCTGCAATGT CCGCTGTACC ATGAAGGGGA ACCTCAAATC GCACATCCGC ATCAAGCACA
1021 GTGGGAATAA CTTCAAGTGT CCGCACTGCG ACTTCCTGGG TGACAGCAAA TCCACCCTGC
1081 GGAAGCACAG TCGCCTGCAC CAGTCGGAGC ACCCGGAGAA GTGTCCCGAC TGCAGCTACT
1141 CCTGTTCCAA CAAGGCCGCA CTGCGCGTGC ACGAGCGCAT CCACTGCACC GAGCGCCCGT
1201 TCAAGTGCAG CTACTGCAGC TTCGATACCA AGCAACCCGA CAACCTGAGC AAGCACATGA
1261 AGAAGTTCCA CGCCGACATG CTCAAGAACG AGGCTCCGGA GAAGAAGGAG AGCGGCAGGC
1321 AGAGCAGCCG GCAGGTGGCC AGGCTGGATG CCAAGAAGAC GTTCCACTGC GACATCTGTG
1381 ACGCCTCGTT TATGCGGGAG GACTCGCTCC GCAGCCACAA ACGGCAGCAC AGTGAGTACC
1441 ACAGTAAGAA CTCGGACGTG ACTGTAGTAC AGCTTCACCT TGAACCCAGC AAGCAGCCGC
1501 TGCGCCCCTC ACCGTAGAGC AAATCCAGGT CCCCCTCCAG TCCAGCCAGG TGCCCAGTT
1561 CAGCGAGGGG AGGGTCAAGA TCATCGTGGG GCATTACAGG TGCCTCAGAC GAACCGCCAT
1621 AGTCCAAGCG GCCGCAGCTG CCGTCAACAT TGTGCCCCCC ACCCTGGTAG CCCAGACCCC
1681 AGAGGAGATC CCAGGGAACG GCCGGCTACA GATCCTTCGC CAGGTCAGTC TCATTGCCCC
1741 TCCTCAGTCC TCCGGGTGTC CCGGCGAAGC AGGTGCCCTG AGTCAGCCAA CTGTCCTGCT
1801 GACCACCCAT GATCAGACGG CAGGGGCCGC CCTGCAGCAG GCTCTGATCC CCACCACCCC
1861 GGTTGGGACC CAGGAAGGCA CGGGAAACCA GACATTCATT GCCAGTTCGG CATCGTGCT
1921 CGGACTTGGA AGGCCTTAAG CTCTATTCAG GAGGGAACGA CGGAAGTGAC TGTGGTGAGC
1981 GATGGGGACC AGAGCATCGC AGTGGCCACC ACGGCACCCT CTATCTTCTC TACCCAGCAG
2041 GAACTGCCCA AGCAGACTTA CTCCATCATC CACGGGGCGG CACACCCCGC CCTGCTCTGT
2101 CCCGCCGACT CCATTCCTGA TTAGTCTGGA GGGAGGGGTG ACAGACAAGA CAAACTGCGA
2161 GAGGAGTACT GTGAGAGGCT CCTGGTCCCG CATAAATAAT TGTATTTTAT ACAGTTTATG
2221 TAATTTTTTA ACAGGGTATC AAGCTGAGA CCATTCTCCC TCAAGCTCTT GTTGATTGTG
2281 TCTTAATGGT TACCAAGGCT GATTCCAATG TGGAGTTGGA ATTCACCACA GTAGGACTGA
2341 ATACATTCGT TTGTTTTTCC ATGTTTAGGA TTTAATTTTT TTCAACTGGA ATAAAGGAGT
2401 TTGGGATTTG GGTTAAAAAA
```

Figure 45

```
   1 GAGTCCTCCC CGCCTCGCAG AGTTGGGAGA AGGCAGGGTG GGGGGTGTGG AAAAATAAAA
  61 GGAAAAGTCC TTGCACCATG TAGATCAGCG TCCCCCACTT TGGCATCCCG GCCGGCCGGG
 121 GACCTCCCAG TCTGCGGCCA TGAACGCGAG CAGCGAGGGC GAGAGCTTCG CGGGCTCGGT
 181 GCAAATTCCA GGTGGCACAA CGGTGCTGGT GGAGCTGACT CCCGACATCC ATATCTGCGG
 241 CATCTGCAAG CAGCAGTTTA ACAACCTGGA TGCCTTTGTA GCTCACAAGC AAAGTGGCTG
 301 CCAGCTGACA GGCACATCCG CAGCAGCCCC CAGCACGGTC CAGTTTGTAT CGGAGGAAAC
 361 AGTGCCTGCC ACCCAGACTC AGACCACCAC CAGAACCATC ACCTCGGAGA CCCAGACAAT
 421 CACAGTTTCA GCTCCAGAAT TTGTTTTTGA ACATGGCTAT CAAACTTACC TGCCCACGGA
 481 AAGTAATGAA AACCAGACAG CCACTGTCAT CTCTCTCCCT GCCAAGTCAC GCACCAAAAA
 541 GCCCACAACA CCACCTGCTC AGAAAAGGCT TAACTGTTGC TATCCAGGTT GCCAATTCAA
 601 GACTGCTTAT GGCATGAAGG ACATGGAGCG GCATTTAAAA ATTCACACGG GAGACAAACC
 661 CCATAAGTGT GAAGTCTGTG GCAAGTGCTT TAGCCGGAAA GACAAGCTGA AAACTCACAT
 721 GCGGTGCCAC ACGGGCGTGA AGCCCTACAA GTGTAAGACG TGTGACTACG CCGCTGCCGA
 781 CAGCAGCAGC CTCAACAAGC ACCTGAGGAT CCACTCGGAC GAGCGGCCCT TCAAATGCCA
 841 GATCTGCCCC TACGCCAGCC GCAACTCCAG CCAGCTCACT GTCCACCTGC GATCCCACAC
 901 GGGGGACGCC CCCTTCCAGT GCTGGCTCTG TAGCGCCAAG TTCAAAATCA GCTCGGACTT
 961 GAAAAGGCAC ATGCGGGTGC ACTCGGGGGA GAAGCCTTTC AAGTGCGAGT CTGCAATGT
1021 CCGCTGCACC ATGAAGGGGA ACCTCAAGTC GCACATCCGT ATCAAGCACA GCGGGAATAA
1081 CTTCAAGTGT CCTCATTGCG ACTTCCTGGG TGACAGCAAA GCCACCCTCC GGAAGCACAG
1141 CCGCGTGCAC CAGTCGGAGC ATCCTGAGAA GTGCTCGGAA TGCAGCTACT CCTGCTCCAG
1201 CAAGGCCGCC CTGCGCATCC ACGAGCGTAT CCACTGCACC GACCGCCCTT TCAAGTGCAA
1261 CTACTGCAGC TTCGACACCA AACAGCCCAG CAACCTGAGC AAGCACATGA AGAAGTTCCA
1321 CGGGGACATG GTTAAGACTG AGGCTCTAGA GAGGAAGGAC ACCGGCAGGC AGAGCAGCCG
1381 GCAGGTGGCC AAGCTGGATG CCAAGAAGAG TTTCCACTGC GATATATGCG ATGCCTCCTT
1441 CATGCGGGAG GACTCGCTCC GCAGCCACAA GAGACAGCAC AGTGAGTACA ATGAGAGTAA
1501 GAACTCGGAC GTGACCGTTC TCCAGTTTCA GATCGACCCC AGCAAGCAGC CGCCACGCC
1561 CCTCACTGTG GGACACCTCC AGGTGCCCCT CCAGCCCAGC CAAGTGCCCC AGTTCAGCGA
1621 GGGAAGAGTC AAAATCATCG TTGGGCATCA GGTGCCCCAG GCGAACACCA TCGTCCAGGC
1681 TGCCGCTGCT GCAGTGAACA TCGTCCCGCC TGCCTTGGTG GCCCAGAACC CAGAGGAACT
1741 CCCAGGGAAC AGCCGGCTGC AGATCCTGCG CCAGGTCAGT CTGATCGCCC CCCTCAGTC
1801 CTCGCGGTGT CCGAGCGAGG CGGGCGCAAT GACCCAGCCG GCTGTCCTGC TGACCACCCA
1861 CGAGCAGACG GACGGAGCCA CTCTGCACCA GACTCTCATC CCCACGGCCT CAGGTGGCCC
1921 CCAGGAAGGC TCTGGCAATC AAACTTTCAT TACCAGTTCG GGTATTACTT GCACTGACTT
1981 TGAAGGCCTA AACGCCTTGA TTCAGGAGGG GACAGCAGAA GTGACAGTGG TGAGCGATGG
2041 AGGCCAGAAC ATCGCAGTGG CCACCACAGC GCCACCGGTC TTCTCCTCCT CTTCCCAGCA
2101 AGAACTACCC AAGCAGACCT ACTCCATCAT TCAAGGGGCA GCCCATCCAG CTTTGCTCTG
2161 TCCCGCCGAC TCCATTCCAG ATTAGTGCTT AAAAAACAAA AGGAGTGGGG GAAAGGAATT
2221 GAGAAAAAGA AATCTTAAGT AGAATTCTCT AAAAGGTTTG CTCTTAATGT TTTCTTTGTT
2281 TTGTTTTGTT TTTGAGACGG AGTCTCGCTC TGTTTCCCAG GCTGGAGTGC AGTGGCGCTA
2341 TCTTGGCTCA CTGCAACGTC CGCCTCCAG GTTCAAGCGA TTCTCATGCC TCGGCCCTCC
2401 GAGTAGCTGG GACCACAGGT GTACGACATC ATGACTGGCT AATTTTTGTA TATTTAATAG
2461 AGGCGGGGTT TCATCATGTT GAACTCCTGA CCTCAAGTGA TCTGCCCACC TCAGCCTCCC
2521 AAAGTGCTGG GATTACAGGT GTGAGCCACC ATGCCTGGCC GTGGTTTGCT CTTAATGTTT
2581 TTAAGGATGG TTGTGAATCC CCCTGGCCCC ATAATAAATT GTAATTTTAT ACTGCTTACT
2641 ATAATTTTTT TAACACTGTA ACAACTTTGA GACCACCTCT GAATCGTCGC ATTATAACTG
2701 TTGTAGAATC TTAAATGTTA CCAAGATGAT TCCAATGAGG GGTTGGAATT AAATGCATTA
2761 AGTAGTGAAC TCATGTGTTT GTTTCCAACT TGATTTTCCA ACTCTAATAA AGGTTTCTGT
2821 CCATCTTATT ACATTTGTGT AGTAAATGGT ACTTCCCAGC CTCTCTTTTG CCCCATTCTG
2881 GAATACTCCC CAGAGTTTGG GGGTGTTCAT GTTTTATACA TGTAAGTCTG TTGGCATGAA
2941 GGACCATTTT CTACATAATA TGACATGGAT ACTTGACCCA AAAAAAATGT TTAGTGCTAA
3001 TGAGCAGAAA ATGAATGGTT CCATAATAAA TTGATATCTG ATTAAAAT
```

Figure 46

```
MNASVEGDTF SGSMQIPGGT TVVVELAPDI HICGLCKQHF SNLDAFVAHK QSGCQLTTTP
VTAPSTVQFV AEETEPATQT TTTTISSETQ TITVSAPEFV FEHGYQTYLP TESTDNQTAT
VISLPTKSRT KKPTAPPAQK RLGCCYPGCQ FKTAYGMKDM ERHLKIHTGD KPHKCEVCGK
CFSRKDKLKT HMRCHTGVKP YKCKTCDYAA ADSSSLNKHL RIHSDERPFK CQICPYASRN
SSQLTVHLRS HTGDAPFQCW LCSAKFKISS DLKRHMRVHS GEKPFKCEFC NVRCTMKGNL
KSHIRIKHSG NNFKCPHCDF LGDSKSTLRK HSRLHQSEHP EKCPECSYSC SSKAALRVHE
RIHCTERPFK CSYCSFDTKQ PSNLSKHMKK FHADMLKNEA PEKKESGRQS SRQVARLDAK
KTFHCDICDA SFMREDSLRS HKRQHSEYHS KNSDVTVVQL HLEPSKQPLR PSP
```

Figure 47

```
MNASVEGDTF SGSMQIPGGT TVVVELAPDI HICGLCKQHF SNLDAFVAHK QSGCQLTTTP
VTAPSTVQFV AEETEPATQT TTTTISSETQ TITVSAPEFV FEHGYQTYLP TESTDNQTAT
VISLPTKSRT KKPTAPPAQK RLGCCYPGCQ FKTAYGMKDM ERHLKIHTGD KPHKCEVCGK
CFSRKDKLKT HMRCHTGVKP YKCKTCDYAA ADSSSLNKHL RIHSDERPFK CQICPYASRN
SSQLTVHLRS HTGDAPFQCW LCSAKFKISS DLKRHMRVHS GEKPFKCEFC NVRCTMKGNL
KSHIRIKHSG NNFKCPHCDF LGDSKSTLRK HSRLHQSEHP EKCPECSYSC SSKAALRVHE
RIHCTERPFK CSYCSFDTKQ PSNLSKHMKK FHADMLKNEA PEKKESGRQS SRQVARLDAK
KTFHCDICDA SFMREDSLRS HKRQHSEYHS KNSDVTVVQL HLEPSKQPLR PSP
```

Figure 48

```
MNASVEGDTF SGSMQIPGGT TVLVELAPDI HICGLCKQHF SNLDAFVAHK QSGCQLTTTP
VTAPSTVQFV AEETEPATQT TTTTISSETQ TITVSAPEFV FEHGYQTYLP TESTDNQTAT
VISLPTKSRT KKPTAPPAQK RLGCCYPGCQ FKTAYGMKDM ERHLKIHTGD KPHKCEVCGK
CFSRKDKLKT HMRCHTGVKP YKCKTCDYAA ADSSSLNKHL RIHSDERPFK CQICPYASRN
SSQLTVHLRS HTASVLENDV QKPAGLPAEE SDAQQAPAVT LSLEAKERTA TLGERTFNCR
YPGCHFKTVH GMKDLDRHLR IHTGDKPHKC EFCDKCFSRK DNLTMHMRCH TSVKPHKCHL
CDYAAVDSSS LKKHLRIHSD ERPYKCQLCP YASRNSSQLT VHLRSHTGDT PFQCWLCSAK
FKISSDLKRH MIVHSGEKPF KCEFCDVRCT MKANLKSHIR IKHTFKCLHC AFQGRDRADL
LEHSRLHQAD HPEKCPECSY SCSNPAALRV HSRVHCTDRP FKCDFCSFDT KRPSSLAKHI
DKVHREGAKT ENRAPPGKDG PGESGPHHVP NVSTQRAFGC DKCGASFVRD DSLRCHRKQH
SDWGENKNSN LVTFPSEGIA TGQLGPLVSV GQLESTLEPS HDL
```

Figure 49

```
MNASVEGDTF SGSMQIPGGT TVLVELAPDI HICGLCKQHF SNLDAFVAHK QSGCQLTTTP
VTAPSTVQFV AEETEPATQT TTTTISSETQ TITVSAPEFV FEHGYQTYLP TESTDNQTAT
VISLPTKSRT KKPTAPPAQK RLGCCYPGCQ FKTAYGMKDM ERHLKIHTGD KPHKCEVCGK
CFSRKDKLKT HMRCHTGVKP YKCKTCDYAA ADSSSLNKHL RIHSDERPFK CQICPYASRN
SSQLTVHLRS HTAWRCDCLG STKPWVPSLV TT
```

Figure 50

```
MNASSEGESF AGSVQIPGGT TVLVELTPDI HICGICKQQF NNLDAFVAHK QSGCQLTGTS
AAAPSTVQFV SEETVPATQT QTTTRTITSE TQTITVSAPE FVFEHGYQTY LPTESNENQT
ATVISLPAKS RTKKPTTPPA QKRLNCCYPG CQFKTAYGMK DMERHLKIHT GDKPHKCEVC
GKCFSRKDKL KTHMRCHTGV KPYKCKTCDY AAADSSSLNK HLRIHSDERP FKCQICPYAS
RNSSQLTVHL RSHTGDAPFQ CWLCSAKFKI SSDLKRHMRV HSGEKPFKCE FCNVRCTMKG
NLKSHIRIKH SGNNFKCPHC DFLGDSKATL RKHSRVHQSE HPEKCSECSY SCSSKAALRI
HERIHCTDRP FKCNYCSFDT KQPSNLSKHM KKFHGDMVKT EALERKDTGR QSSRQVAKLD
AKKSFHCDIC DASFMREDSL RSHKRQHSEY NESKNSDVTV LQFQIDPSKQ PATPLTVGHL
QVPLQPSQVP QFSEGRVKII VGHQVPQANT IVQAAAAAVN IVPPALVAQN PEELPGNSRL
QILRQVSLIA PPQSSRCPSE AGAMTQPAVL LTTHEQTDGA TLHQTLIPTA SGGPQEGSGN
QTFITSSGIT CTDFEGLNAL IQEGTAEVTV VSDGGQNIAV ATTAPPVFSS SSQQELPKQT
YSIIQGAAHP ALLCPADSIP D
```

Figure 51

```
MNASSEGESF AGSVQIPGGT TVLVELTPDI HICGICKQQF NNLDAFVAHK QSGCQLTGTS
AAAPSTVQFV SEETVPATQT QTTTRTITSE TQTITGCQFK TAYGMKDMER HLKIHTGDKP
HKCEVCGKCF SRKDKLKTHM RCHTGVKPYK CKTCDYAAAD SSSLNKHLRI HSDERPFKCQ
ICPYASRNSS QLTVHLRSHT GDAPFQCWLC SAKFKISSDL KRHMRVHSGE KPFKCEFCNV
RCTMKGNLKS HIRIKHSGNN FKCPHCDFLG DSKATLRKHS RVHQSEHPEK CSECSYSCSS
KAALRIHERI HCTDRPFKCN YCSFDTKQPS NLSKHMKKFH GDMVKTEALE RKDTGRQSSR
QVAKLDAKKS FHCDICDASF MREDSLRSHK RQHSEYSESK NSDVTVLQFQ IDPSKQPATP
LTVGHLQVPL QPSQVPQFSE GRVKIIVGHQ VPQANTIVQA AAAVNIVPP ALVAQNPEEL
PGNSRLQILR QVSLIAPPQS SRCPSEAGAM TQPAVLLTTH EQTDGATLHQ TLIPTASGGP
QEGSGNQTFI TSSGITCTDF EGLNALIQEG TAEVTVVSDG GQNIAVATTA PPVFSSSSQQ
ELPKQTYSII QGAAHPALLC PADSIPD
```

Figure 52

```
MNASSEGESF AGSVQIPGGT TVLVELTPDI HICGICKQQF NNLDAFVAHK QSGCQLTGTS
AAAPSTVQFV SEETVPATQT QTTTRTITSE TQTITVSAPE FVFEHGYQTY LPTESNENQT
ATVISLPAKS RTKKPTTPPA QKRLNCCYPG CQFKTAYGMK DMERHLKIHT GDKPHKCEVC
GKCFSRKDKL KTHMRCHTGV KPYKCKTCDY AAADSSSLNK HLRIHSDERP FKCQICPYAS
RNSSQLTVHL RSHTGDAPFQ CWLCSAKFKI SSDLKRHMRV HSGEKPFKCE FCNVRCTMKG
NLKSHIRIKH SGNNFKCPHC DFLGDSKATL RKHSRVHQSE HPEKCSECSY SCSSKAALRI
HERIHCTDRP FKCNYCSFDT KQPSNLSKHM KKFHGDMVKT EALERKDTGR QSSRQVAKLD
AKKSFHCDIC DASFMREDSL RSHKRQHSEY SESKNSDVTV LQFQIDPSKQ PATPLTVGHL
QVPLQPSQVP QFSEGRVKII VGHQVPQANT IVQAAAAAVN IVPPALVAQN PEELPGNSRL
QILRQVSLIA PPQSSRCPSE AGAMTQPAVL LTTHEQTDGA TLHQTLIPTA SGGPQEGSGN
QTFITSSGIT CTDFEGLNAL IQEGTAEVTV VSDGGQNIAV ATTAPPVFSS SSQQELPKQT
YSIIQGAAHP ALLCPADSIP D
```

Figure 53

|  | Phenotype 1 | ... | Phenotype M | CC 48-1 | ... | CC 48-Z |
|---|---|---|---|---|---|---|
| Organism 46-1 | Amount 7201-1-1 | ... | Amount 7201-1-M | Level 50-1-1 | ... | Level 50-1-Z |
| Organism 46-2 | Amount 7201-2-1 | ... | Amount 7201-2-M | Level 50-2-1 | ... | Level 50-2-Z |
| ⋮ | ⋮ | ⋮ | ⋮ | ⋮ | ⋮ | ⋮ |
| Organism 46-N | Amount 7201-N-1 | ... | Amount 7201-N-M | Level 50-N-1 | ... | Level 50-N-Z |

FIG. 72

| | |
|---|---|
| Abundance statistic set | ~ 8104-1 |
|   Position 1 | ~ 8404-1-1 |
|     Statistical score | ~ 8406-1-1 |
|   Position 2 | ~ 8404-1-2 |
|     Statistical score | ~ 8406-1-2 |
|   ⋮ | |
|   Position X | ~ 8404-1-X |
|     Statistical score | ~ 8406-1-X |
| ⋮ | |
| Abundance statistic set | ~ 8104-M |
|   Position 1 | ~ 18404-M-1 |
|     Statistical score | ~ 8406-M-1 |
|   Position 2 | ~ 8404-M-2 |
|     Statistical score | ~ 8406-M-2 |
|   ⋮ | |
|   Position X | ~ 8404-M-X |
|     Statistical score | ~ 8406-M-X |
| ⋮ | |

FIG. 84

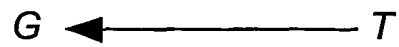
FIG. 85A
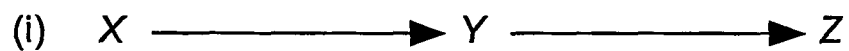
FIG. 85B
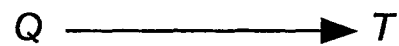
FIG. 85C

FIG. 85D
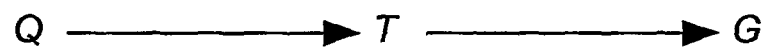
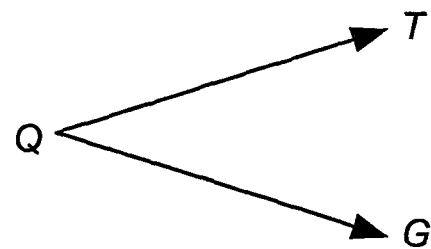
FIG. 85E

```
  1 mdvvdsllvn gsnitppcel glenetlfcl dqprpskewq pavqillysl ifllsvlgnt
 61 lvitvlirnk rmrtvtnifl lslavsdlml clfcmpfnli pnllkdfifg savcktttyf
121 mgtsvsvstf nlvaislery gaickplqsr vwqtkshalk viaatwclsf timtpypiys
181 nlvpftknnn qtanmcrfll pndvmqqswh tflllilfli pgivmmvayg lislelyqgi
241 kfeasqkksa kerkpsttss gkyedsdgcy lqktrpprkl elrqlstgss sranrirsns
301 saanlmakkr virmlivivv lfflcwmpif sanawraydt asaerrlsgt pisfilllsy
361 tsscvnpiiy cfmnkrfrlg fmatfpccpn pgppgargev geeeeggttg aslsrfsysh
421 msasvppq (SEQ ID NO: 30)
```

Fig. 88

55 SNPs identified

CCKAR haplotypes associate with high body fat in females

Percentage body fat (top 15%) females

| P_cor | P-unc | RRisk | PAR | Aff_frq | N_aff | Ctrl_frq | N_ctrl | Info |
|---|---|---|---|---|---|---|---|---|
| 0.002 | 8.42E-07 | 4.0 | 0.163 | 0.11 | 281 | 0.03 | 282 | 0.81 |
| 0.002 | 1.43E-06 | 4.2 | 0.163 | 0.11 | 281 | 0.03 | 279 | 0.75 |

9002

Carrier frequency : 23% obese vs 6% thin and Relative Risk >4

Fig. 90

Controls : Thin females

CCKAR haplotypes associate with thinness in females

Thin (BMI<20) females at ages > 40 yrs

| cor | P-unc | RRisk | PAR | Aff_frq | N_aff | Ctrl_frq | N_ctrl | Info |
|---|---|---|---|---|---|---|---|---|
| 0.02 | 1.61E-05 | 4.4 | 0.119 | 0.08 | 282 | 0.02 | 421 | 0.643 |
| 0.02 | 1.84E-05 | 4.2 | 0.120 | 0.08 | 282 | 0.02 | 421 | 0.647 |

— 9102

Carrier frequency : 17% thin vs 4% obese and Relative Risk >4

Fig. 91

Controls : Obese females

SEQUENCE LISTING

```
<160> NUMBER OF SEQ ID NOS: 30

<210> SEQ ID NO 1
<211> LENGTH: 1583
<212> TYPE: DNA
<213> ORGANISM: Mus musculus

<400> SEQUENCE: 1
gagctattcg gcctctctag gccggcgggt cctccgctcc atggtcctgt ctgtcagcgc      60
tgtgtcagga ggccagtgcc gaggtccggt cgcgctccga cgcttcgacc ctcgagccgg     120
tcgcgggtat cccggcggcc gcgggacgat ggcgtggtgg cactgacagg cgcgggcggc     180
tgccgagccc cgcggccggc atggcgggcc agttccgcag ctacgtgtgg gacccgttgc     240
taatcctgtc gcagatcgta ctcatgcaga ccgtctacta tggctctctg ggcctgtggc     300
tggcgctggt ggacgcgctg gtgcgcaagc ccgtccctgg accagatgtt cgacgcggag     360
atcctgggct tctccacccc tccaggccgg ctctcaatga tgtccttcgt cctcaacgcc     420
ctcacctgtg ccctgggctt gctgtacttc atccggcgag ggaagcagtg cctggatttc     480
actgtcactg tgcatttctt tcacctcctg ggctgctggc tctacagctc ccgtttcccc     540
tcggcgctga cctggtggct ggtccaggct gtgtgcattg cactcatggc cgtcatcggg     600
gagtacctgt gcatgcggac ggagctcaag gagatccccc tcagctcagc ccctaagtcc     660
aatgtctaga gttgggccct ttggacactc tgctggcact tgggcccat caccttgggc     720 tgctcagacc tccagatggg gtctggccca agtctgagca gaaccctgga aatgtgaagt     780
ctgttggtgg agagataatg aggtcccatc ataaaggcag gtagcagcca tgatcacaga     840
tgtaagaatg gcctctgtct gccaaagcct tgatatctgg aggccagtaa gggacctcat     900
ggagggtagt ggcagatttg gaaccatgtc acatgagcca tcatactgtc accagcctgt     960
tattttaaaa agaaaaaaaa aaaatcaagg atatctgatt ggaataaacc actcttctcg    1020
ttgtctgtct tatgcccatg acagccagta cctttgctgt gttgccaaac cacagggatt    1080
ctctgtggag aaatacctga tttctgggtc catagccaca gaaaaagatg taggtacaga    1140
gtgctaggct gctgacagga cgtcgagggg aggaggcatc aagcacaaga aaaatgcatg    1200
gccgtgccgt tagacacaca cacacacttt tgtgtgtgtc caggacccat gactgtctcc    1260
ctccagttcc ctgtatggac tctgccttgc tgttgtcact cagcacagcc agagacagga    1320
cccagagaaa accccagcat ccctcccagc cttcccttca taataaaagc cattgtctgc    1380
tctctggaag tgagcaggca gccagcttct actggaccctc aactgtggca ggagtttctg    1440
```

| | |
|---|---:|
| tttgctgtct tttgagttct gtgatagga gggtgtacta aaggtgctgg aggctcaccc | 1500 |
| tgctaagctt tcttccaagt ggtttcctca ggaagggctg gcagctgtcc ttcctaggta | 1560 |
| cataaataca ctattttcca atc | 1583 |

<210> SEQ ID NO 2
<211> LENGTH: 2677
<212> TYPE: DNA
<213> ORGANISM: Homo sapiens

<400> SEQUENCE: 2

| | |
|---|---:|
| tctaggccgg cagcgcctct cctccatggt cctgtctgtc agcgctgttt tgggagcccg | 60 |
| ccggtgaggc cgggccacgc tcagacactt cgatcgtcga gtctgtcact gggcatggcg | 120 |
| ggtcagttcc gcagctacgt gtgggacccg ctgctgatcc tgtcgcagat cgtcctcatg | 180 |
| cagaccgtgt attacggctc gctgggcctg tggctggcgc tggtggacgg gctagtgcga | 240 |
| cagcccctcg ctggaccaga tgttcgacgc cgagatcctg gcttttccca ccctccagg | 300 |
| ccggctctcc atgatgtcct tcatcctcaa cgccctcacc tgtgccctgg gcttgctgta | 360 |
| cttcatccgg cgaggaaagc agtgtctgga tttcactgtc actgtccatt tctttcacct | 420 |
| cctgggctgc tggttctaca gctcccgttt ccctcggcg ctgacctggt ggctggtcca | 480 |
| agccgtgtgc attgcactca tggctgtcat cggggagtac ctgtgcatgc ggacggagct | 540 |
| caaggagata cccctcaact cagcccctaa atccaatgtc tagaatcagg ccctttggac | 600 |
| atcctgctga cacttgggcc ccttaacacc ttgggctgct cagaccctcc agatgaggtc | 660 |
| cagcccagat ctgagaggaa ccctggaaat gtgaagtctc tgttggtttg ggagagatag | 720 |
| tgagggcctg tcaaagaagg caggtagcag tcagcatgac agctgcaaga atgacctctg | 780 |
| tctgttgaag ccttggtatc tgagaggtca ggaaggggac ctctttgagg gtaataacag | 840 |
| aattggaacc atgccactct tgagccacaa tacctgtcac cagcctgttg ttttaagaga | 900 |
| gaaaaaaaat caaggatatc tgattggagc aaaccacttc tttagtcatc tgtcttaccc | 960 |
| ccctgggaca gctgttacct ttgcagtgtt gccgaatcac agcagttacc tttgcagtgt | 1020 |
| tgccgaatca cagcagttct gttggagaaa cgcttggttt ccggatccag agccacagaa | 1080 |
| agaaatgtag gtgtgaagta ttaggctgct gtcagggaga ggatggcaga tggaggcatc | 1140 |
| aagcacaagg aaaatgcaca acctgtgccc tgttatacac acgttcatgt gcacccaaga | 1200 |
| acctatgact ttcttccagt tccttctacc aggtccccat cctgctgcca gctctcaaca | 1260 |
| tagcaggcca taggacccag agaagaatcc cagcgttgct caaagtctaa ccatcataaa | 1320 |
| gacactgcct gtcttctagg aatgaccagg cacccagctc ccactggact ccaatttttt | 1380 |
| ttcctgccct atttagaatt ctttggcggg aagggtatga tgggttccca gagacaagaa | 1440 |
| gcccaaccct ctggcctggg ctgtgctgat agtgctgagg gagataggaa tttgctgcta | 1500 |
| agattttttct ttggggtgga gttcctctg tgaggggctt gcagctatcc ttcctgtgta | 1560 |
| tacaaataca gtattttcca tggttctgcc tgcacttact ttgtaatgcc acggttgaga | 1620 |
| ttgagagaga tcagcgcagc caggcaaggg aactttaaag aattattagg ccaccttctc | 1680 |
| cctttcctgg accccagagt cattcctcca tttggttaaa atactcagtg cagggaactc | 1740 |
| ttacatcctg tctccttcac ttgcagcgtc ccctgctatg cctcaggtga accacataat | 1800 |
| tcttgggttt ccgttcctac ttgctagtga tttctgaaca tgttcaatgg agcggcacac | 1860 |
| agtctagacc cacttccgca ttgaaacctt cactgttcct ctttggtttc ttcagagctt | 1920 |

```
tcccaagaga gctgtcagtt ttcagctgtc agtaacacaa atgagtttat ggtaacacaa     1980
atgagttttg ctatctctct gagaagctca tctgacctcc tgactctcag ccctacagag     2040
tagggagttg atgctgacag gatgaagatt taggaataaa tatgcctggg aagagactgg     2100
gaaggttcta gggtgaggca cctcagtaac tcatggtacc ttggccaagt tggaaggaag     2160
cagtttgtta atgaggcaca gtaatcctgg ctgcagggtc taggaggtaa gaccagctgg     2220
gatgaccttc cctgggttaa tcaatttccc tctagacaac acaaactgca ggcatgtgac     2280
taactttgaa agaacaccca tcatgtggct gctgtcaccc ttgaccagcc gtggtggtgg     2340
ttactccatc tgtggttgga gcgcctcttt gggattcact tcaaggtctt gtgcctattt     2400
ttctgcatat cttctgtgat gacaaatctc tgtccctga gtgttaattt gattttaga     2460 aatggccaaa agtcacgtga tccaaacttt ttttcagtaa tatggagact gagctgcatg     2520
gtagttgggg atcaaaaata tgtgaccta atgagatttt tatgatttct aaagtaacaa     2580
taaaagcagt ttttagagtt gagttccaga gagggcaggg caatggcagt gacatgtttg     2640
tcattttaat aataaataac atctattgag tgcttaa                              2677

<210> SEQ ID NO 3
<211> LENGTH: 453
<212> TYPE: DNA
<213> ORGANISM: Homo sapiens

<400> SEQUENCE: 3
atggcgggtc agttccgcag ctacgtgtgg gacccgctgc tgatcctgtc gcagatcgtc      60
ctcatgcaga ccgtgtatta cggctcgctg ggcctgtggc tggcgctggt ggacgggcta     120
gtgcgacagc ccctcgctgg accagatgtt cgacgccgag atcctgggct tttccacccc     180
tccaggccgg ctctccatga tgtccttcat cctcaacgcc ctcacctgtg ccctgggctt     240
gctgtacttc atccggcgag gaaagcagtg tctggatttc actgtcactg tccattctt     300 tcacctcctg ggctgctggt tctacagctc ccgtttcccc tcggcgctga cctggtggct     360
ggtccaagcc gtgtgcattg cactcatggc tgtcatcggg gagtacctgt gcatgcggac     420
ggagctcaag gagataccc tcaactcagc ccc                                   453

<210> SEQ ID NO 4
<211> LENGTH: 156
<212> TYPE: PRT
<213> ORGANISM: Mus musculus

<400> SEQUENCE: 4

Met Ala Gly Gln Phe Arg Ser Tyr Val Trp Asp Pro Leu Leu Ile Leu
1               5                   10                  15

Ser Gln Ile Val Leu Met Gln Thr Val Tyr Tyr Gly Ser Leu Gly Leu
            20                  25                  30

Trp Leu Ala Leu Val Asp Ala Leu Val Arg Ser Ser Pro Ser Leu Asp
        35                  40                  45

Gln Met Phe Asp Ala Glu Ile Leu Gly Phe Ser Thr Pro Pro Gly Arg
    50                  55                  60

Leu Ser Met Met Ser Phe Val Leu Asn Ala Leu Thr Cys Ala Leu Gly
65                  70                  75                  80

Leu Leu Tyr Phe Ile Arg Arg Gly Lys Gln Cys Leu Asp Phe Thr Val
                85                  90                  95

Thr Val His Phe Phe His Leu Leu Gly Cys Trp Leu Tyr Ser Ser Arg
            100                 105                 110
```

```
Phe Pro Ser Ala Leu Thr Trp Trp Leu Val Gln Ala Val Cys Ile Ala
            115                 120                 125

Leu Met Ala Val Ile Gly Glu Tyr Leu Cys Met Arg Thr Glu Leu Lys
        130                 135                 140

Glu Ile Pro Leu Ser Ser Ala Pro Lys Ser Asn Val
145                 150                 155

<210> SEQ ID NO 5
<211> LENGTH: 125
<212> TYPE: PRT
<213> ORGANISM: Mus musculus

<400> SEQUENCE: 5

Met Ala Leu Trp Ala Cys Gly Trp Arg Trp Trp Thr Arg Trp Cys Ala
1               5                   10                  15

Gln Pro Val Pro Gly Pro Asp Val Arg Arg Gly Asp Pro Gly Leu Leu
            20                  25                  30

His Pro Ser Arg Pro Ala Leu Asn Asp Val Leu Arg Pro Gln Arg Pro
        35                  40                  45

His Leu Cys Pro Gly Leu Ala Val Leu His Pro Ala Arg Glu Ala Val
    50                  55                  60

Pro Gly Phe His Cys His Cys Ala Phe Leu Ser Pro Gly Leu Leu
65                  70                  75                  80

Ala Leu Gln Leu Pro Phe Pro Leu Gly Ala Asp Leu Val Ala Gly Pro
                85                  90                  95

Gly Cys Val His Cys Thr His Gly Arg His Arg Gly Val Pro Val His
            100                 105                 110

Ala Asp Gly Ala Gln Gly Asp Pro Pro Gln Leu Ser Pro
        115                 120                 125

<210> SEQ ID NO 6
<211> LENGTH: 151
<212> TYPE: PRT
<213> ORGANISM: Mus musculus

<400> SEQUENCE: 6

Met Ala Gly Gln Phe Arg Ser Tyr Val Trp Asp Pro Leu Leu Ile Leu
1               5                   10                  15

Ser Gln Ile Val Leu Met Gln Thr Val Tyr Tyr Gly Ser Leu Gly Leu
            20                  25                  30

Trp Leu Ala Leu Val Asp Ala Leu Val Arg Lys Pro Val Pro Gly Pro
        35                  40                  45

Asp Val Arg Arg Gly Asp Pro Gly Leu Leu His Pro Ser Arg Pro Ala
    50                  55                  60

Leu Asn Asp Val Leu Arg Pro Gln Arg Pro His Leu Cys Pro Gly Leu
65                  70                  75                  80

Ala Val Leu His Pro Ala Arg Glu Ala Val Pro Gly Phe His Cys His
                85                  90                  95

Cys Ala Phe Leu Ser Pro Pro Gly Leu Leu Ala Leu Gln Leu Pro Phe
            100                 105                 110

Pro Leu Gly Ala Asp Leu Val Ala Gly Pro Gly Cys Val His Cys Thr
        115                 120                 125

His Gly Arg His Arg Gly Val Pro Val His Ala Asp Gly Ala Gln Gly
    130                 135                 140

Asp Pro Pro Gln Leu Ser Pro
145                 150
```

<210> SEQ ID NO 7
<211> LENGTH: 156
<212> TYPE: PRT
<213> ORGANISM: Mus musculus

<400> SEQUENCE: 7

Met Ala Gly Gln Phe Arg Ser Tyr Val Trp Asp Pro Leu Leu Ile Leu
1               5                   10                  15

Ser Gln Ile Val Leu Met Gln Thr Val Tyr Tyr Gly Ser Leu Gly Leu
            20                  25                  30

Trp Leu Ala Leu Val Asp Ala Leu Val Arg Ser Ser Pro Ser Leu Asp
        35                  40                  45

Gln Met Phe Asp Ala Glu Ile Leu Gly Phe Ser Thr Pro Pro Gly Arg
    50                  55                  60

Leu Ser Met Met Ser Phe Val Leu Asn Ala Leu Thr Cys Ala Leu Gly
65                  70                  75                  80

Leu Leu Tyr Phe Ile Arg Arg Gly Lys Gln Cys Leu Asp Phe Thr Val
                85                  90                  95

Thr Val His Phe Phe His Leu Leu Gly Cys Trp Leu Tyr Ser Ser Arg
            100                 105                 110

Phe Pro Ser Ala Leu Thr Trp Trp Leu Val Gln Ala Val Cys Ile Ala
        115                 120                 125

Leu Met Ala Val Ile Gly Glu Tyr Leu Cys Met Arg Thr Glu Leu Lys
    130                 135                 140

Glu Val Pro Leu Ser Ser Ala Pro Lys Ser Asn Val
145                 150                 155

<210> SEQ ID NO 8
<211> LENGTH: 151
<212> TYPE: PRT
<213> ORGANISM: Homo sapiens

<400> SEQUENCE: 8

Met Ala Gly Gln Phe Arg Ser Tyr Val Trp Asp Pro Leu Leu Ile Leu
1               5                   10                  15

Ser Gln Ile Val Leu Met Gln Thr Val Tyr Tyr Gly Ser Leu Gly Leu
            20                  25                  30

Trp Leu Ala Leu Val Asp Gly Leu Val Arg Gln Pro Leu Ala Gly Asp
        35                  40                  45

Pro Val Arg Arg Arg Asp Pro Gly Leu Phe His Pro Ser Arg Pro Ala
    50                  55                  60

Leu His Asp Val Leu His Pro Gln Arg Pro His Leu Cys Pro Gly Leu
65                  70                  75                  80

Ala Val Leu His Pro Ala Arg Lys Ala Val Ser Gly Phe His Cys His
                85                  90                  95

Cys Pro Phe Leu Ser Pro Pro Gly Leu Leu Val Leu Gln Leu Pro Phe
            100                 105                 110

Pro Leu Gly Ala Asp Leu Val Ala Gly Pro Ser Arg Val His Cys Thr
        115                 120                 125

His Gly Cys His Arg Gly Val Pro Val His Ala Asp Gly Ala Gln Gly
    130                 135                 140

Asp Thr Pro Gln Leu Ser Pro
145                 150

<210> SEQ ID NO 9
<211> LENGTH: 3685

<212> TYPE: DNA
<213> ORGANISM: Mus musculus
<220> FEATURE:
<221> NAME/KEY: CDS
<222> LOCATION: (52)..(3195)
<220> FEATURE:
<221> NAME/KEY: misc_feature
<222> LOCATION: (3406)..(3406)
<223> OTHER INFORMATION: n is a, c, g, or t

<400> SEQUENCE: 9

```
gcacgagggc gggcgcgcgc gtgggcgcag cgcggagcgg ggcccatggt g cgg ccg      57
                                                         Arg Pro
                                                         1 tgt ccg tcg gtc ggg ccg cgc ggg cgg ctc cgc gcg tgg ccc ggc gct     105
Cys Pro Ser Val Gly Pro Arg Gly Arg Leu Arg Ala Trp Pro Gly Ala
        5                  10                  15 cgc gac ctc gcc cct gcg ctg cgg gcc cgg ccc gcc cgc tgc cgg cgc     153
Arg Asp Leu Ala Pro Ala Leu Arg Ala Arg Pro Ala Arg Cys Arg Arg
 20                  25                  30 ctc ctc ccc ctg ccc cgg ggc ggc gcg gag gcc gcg ggg agc gca ggg     201
Leu Leu Pro Leu Pro Arg Gly Gly Ala Glu Ala Ala Gly Ser Ala Gly
 35                  40                  45                  50 ggc gcg gcg ggc ggc gac atg acg gac agc atc ccg ctg cag ccc gtg     249
Gly Ala Ala Gly Gly Asp Met Thr Asp Ser Ile Pro Leu Gln Pro Val
                 55                  60                  65 cgc cac aag aag cgg gtg gac agt agg ccg cgc gcg ggg tgc tgt gag     297
Arg His Lys Lys Arg Val Asp Ser Arg Pro Arg Ala Gly Cys Cys Glu
             70                  75                  80 tgg ctg aga tgt tgc ggt gga ggg gag ccc agg ccc cgt act gtc tgg     345
Trp Leu Arg Cys Cys Gly Gly Gly Glu Pro Arg Pro Arg Thr Val Trp
         85                  90                  95 ttg gga cac ccc gag aag agg gac cag cgg tac cct cga aat gtc atc     393
Leu Gly His Pro Glu Lys Arg Asp Gln Arg Tyr Pro Arg Asn Val Ile
    100                 105                 110 aac aac cag aag tac aat ttc ttc aca ttt ctt cct ggg gtg ttg ttc     441
Asn Asn Gln Lys Tyr Asn Phe Phe Thr Phe Leu Pro Gly Val Leu Phe
115                 120                 125                 130 agc cag ttc aga tac ttc ttc aac ttc tac ttc ctg ctt ctc gcc tgc     489
Ser Gln Phe Arg Tyr Phe Phe Asn Phe Tyr Phe Leu Leu Leu Ala Cys
                135                 140                 145 tcg cag ttc gtc cca gag atg agg ctt ggc gcc ctg tac acc tac tgg     537
Ser Gln Phe Val Pro Glu Met Arg Leu Gly Ala Leu Tyr Thr Tyr Trp
            150                 155                 160 gtt cct ctg ggc ttc gtg ctg gct gtc acc atc atc cgt gag gca gta     585
Val Pro Leu Gly Phe Val Leu Ala Val Thr Ile Ile Arg Glu Ala Val
        165                 170                 175 gag gag atc cga tgt tat gtg cgt gac aag gag atg aac tcc cag gtc     633
Glu Glu Ile Arg Cys Tyr Val Arg Asp Lys Glu Met Asn Ser Gln Val
    180                 185                 190 tac agc cgg ctc acg tca cga ggg acc gtg aag gtg aag agt tca aac     681
Tyr Ser Arg Leu Thr Ser Arg Gly Thr Val Lys Val Lys Ser Ser Asn
195                 200                 205                 210 atc cag gtg gga gac ctc atc ctt gtg gaa aag aac cag cgg gtc cct     729
Ile Gln Val Gly Asp Leu Ile Leu Val Glu Lys Asn Gln Arg Val Pro
                215                 220                 225 gct gac atg atc ttc ctg agg acg tca gag aaa aac ggc tct tgc ttc     777
Ala Asp Met Ile Phe Leu Arg Thr Ser Glu Lys Asn Gly Ser Cys Phe
            230                 235                 240 ttg cgc acg gat cag ctg gat gga gag aca gac tgg aag ctt cgg ctc     825
Leu Arg Thr Asp Gln Leu Asp Gly Glu Thr Asp Trp Lys Leu Arg Leu
        245                 250                 255
```

-continued

| | |
|---|---|
| ccg gtg gcc tgc aca cag agg ctt ccc acg gct gct gac ctc ctg cag<br>Pro Val Ala Cys Thr Gln Arg Leu Pro Thr Ala Ala Asp Leu Leu Gln<br>260                    265                  270 | 873 |
| att cgg tcc tat gtg tac gct gaa aaa ccc aac atc gac att cac aac<br>Ile Arg Ser Tyr Val Tyr Ala Glu Lys Pro Asn Ile Asp Ile His Asn<br>275                    280                  285                290 | 921 |
| ttc ctg ggg act ttc acc agg gaa aac agt gac cct ccg atc agt gag<br>Phe Leu Gly Thr Phe Thr Arg Glu Asn Ser Asp Pro Pro Ile Ser Glu<br>                  295                  300                305 | 969 |
| agt ctg agc att gag aac acg ctg tgg gcc ggc acc gtc ata gca tca<br>Ser Leu Ser Ile Glu Asn Thr Leu Trp Ala Gly Thr Val Ile Ala Ser<br>310                    315                  320 | 1017 |
| ggc act gtt gta ggc gtt gtt ctc tac act ggc aga aaa ctg cgg agt<br>Gly Thr Val Val Gly Val Val Leu Tyr Thr Gly Arg Lys Leu Arg Ser<br>                  325                  330                335 | 1065 |
| gtc atg aat act tcc gac ccc aga agt aag att ggc ctg ttc gac ctg<br>Val Met Asn Thr Ser Asp Pro Arg Ser Lys Ile Gly Leu Phe Asp Leu<br>340                    345                  350 | 1113 |
| gag gtg aac tgc ctc acc aaa atc ctg ttt ggt gcg ctg gtg gtg gtg<br>Glu Val Asn Cys Leu Thr Lys Ile Leu Phe Gly Ala Leu Val Val Val<br>355                    360                  365                370 | 1161 |
| tcc ctg gtc atg gtg gcc ctg cag cac ttt gcc ggc cgc tgg tac ctg<br>Ser Leu Val Met Val Ala Leu Gln His Phe Ala Gly Arg Trp Tyr Leu<br>                  375                  380                385 | 1209 |
| cag atc atc cgc ttc ctg ctc ctg ttt tcc aac atc att cct atc agc<br>Gln Ile Ile Arg Phe Leu Leu Leu Phe Ser Asn Ile Ile Pro Ile Ser<br>390                    395                  400 | 1257 |
| ttg cgt gtg aac ttg gac atg ggc aag atc gtg tac agc tgg gtg atc<br>Leu Arg Val Asn Leu Asp Met Gly Lys Ile Val Tyr Ser Trp Val Ile<br>                  405                  410                415 | 1305 |
| cgc agg gat tcc aaa atc ccc ggg acc gtg gtt cgt tcc agc aca att<br>Arg Arg Asp Ser Lys Ile Pro Gly Thr Val Val Arg Ser Ser Thr Ile<br>420                    425                  430 | 1353 |
| cct gag cag ctg ggc agg att tcg tac ttg ctc aca gac aag aca gga<br>Pro Glu Gln Leu Gly Arg Ile Ser Tyr Leu Leu Thr Asp Lys Thr Gly<br>435                    440                  445                450 | 1401 |
| acc ctg acc cag aat gag atg gtg ttc aag cgg ctg cac ctg ggt acg<br>Thr Leu Thr Gln Asn Glu Met Val Phe Lys Arg Leu His Leu Gly Thr<br>                  455                  460                465 | 1449 |
| gtg gcc tac ggc ctg gac tcc atg gac gaa gtg cag agt cac atc ttc<br>Val Ala Tyr Gly Leu Asp Ser Met Asp Glu Val Gln Ser His Ile Phe<br>470                    475                  480 | 1497 |
| agc att tac acc cag caa tcc cag gat cca cct gct cag aag ggc ccc<br>Ser Ile Tyr Thr Gln Gln Ser Gln Asp Pro Pro Ala Gln Lys Gly Pro<br>485                    490                  495 | 1545 |
| acg gtc acc acc aag gtc cgg agg acc atg agc agc cgt gtc cac gag<br>Thr Val Thr Thr Lys Val Arg Arg Thr Met Ser Ser Arg Val His Glu<br>500                    505                  510 | 1593 |
| gct gtg aag gcc att gca ctc tgc cac aac gtg aca ccc gtg tac gag<br>Ala Val Lys Ala Ile Ala Leu Cys His Asn Val Thr Pro Val Tyr Glu<br>515                    520                  525                530 | 1641 |
| tcc aat ggt gtg acg gac cag gct gag gct gag aag cag ttt gag gac<br>Ser Asn Gly Val Thr Asp Gln Ala Glu Ala Glu Lys Gln Phe Glu Asp<br>                  535                  540                545 | 1689 |
| tcc tgc cga gtg tac cag gca tcc agc ccg gat gag gtg gct ctg gtc<br>Ser Cys Arg Val Tyr Gln Ala Ser Ser Pro Asp Glu Val Ala Leu Val<br>550                    555                  560 | 1737 |
| cag tgg aca gaa agt gtg gga ctg acg ctg gtg ggt cga gac cag tcc<br>Gln Trp Thr Glu Ser Val Gly Leu Thr Leu Val Gly Arg Asp Gln Ser | 1785 |

```
                   565                 570                 575
tcc atg cag ctg agg acc cct ggt gac cag gtc ctg aat ctc acc atc        1833
Ser Met Gln Leu Arg Thr Pro Gly Asp Gln Val Leu Asn Leu Thr Ile
    580                 585                 590 ctt cag gtc ttc ccg ttc acc tat gag agc aag cgg atg ggc atc atc        1881
Leu Gln Val Phe Pro Phe Thr Tyr Glu Ser Lys Arg Met Gly Ile Ile
595                 600                 605                 610 gtg cgg gat gag tcc acg ggg gaa atc acg ttc tac atg aag gga gca        1929
Val Arg Asp Glu Ser Thr Gly Glu Ile Thr Phe Tyr Met Lys Gly Ala
                615                 620                 625 gac gtc gtc atg gct ggc att gtc cag tac aac gac tgg ctg gag gag        1977
Asp Val Val Met Ala Gly Ile Val Gln Tyr Asn Asp Trp Leu Glu Glu
                    630                 635                 640 gag tgt ggc aac atg gcc cgg gag gga cta cgt gtg ctg gtg gta gcc        2025
Glu Cys Gly Asn Met Ala Arg Glu Gly Leu Arg Val Leu Val Val Ala
                    645                 650                 655 aag aag tcc ctc aca gag gag cag tac caa cac ttt gaa gcc cgc tac        2073
Lys Lys Ser Leu Thr Glu Glu Gln Tyr Gln His Phe Glu Ala Arg Tyr
    660                 665                 670 gtc cag gct aag ctg agt gtc cat gac cgc tcg ctg aag gtg gcc acg        2121
Val Gln Ala Lys Leu Ser Val His Asp Arg Ser Leu Lys Val Ala Thr
675                 680                 685                 690 gtg atc gag agc ttg gag atg gag atg gag ctg ctg tgc ctg act ggt        2169
Val Ile Glu Ser Leu Glu Met Glu Met Glu Leu Leu Cys Leu Thr Gly
                695                 700                 705 gtg gag gac cag ctg cag gca gat gtc agg ccc acg ctg gag acg ctg        2217
Val Glu Asp Gln Leu Gln Ala Asp Val Arg Pro Thr Leu Glu Thr Leu
                    710                 715                 720 cgc aac gct ggc atc aag gtt tgg atg cta aca ggg gac aag ctg gag        2265
Arg Asn Ala Gly Ile Lys Val Trp Met Leu Thr Gly Asp Lys Leu Glu
                    725                 730                 735 aca gcc acg tgc aca gcc aag aac gca cat ctg gtg acc aga aac caa        2313
Thr Ala Thr Cys Thr Ala Lys Asn Ala His Leu Val Thr Arg Asn Gln
    740                 745                 750 gat atc cat gtt ttc cga ctg gtg acc aac cgc ggg gag gcc cac ctg        2361
Asp Ile His Val Phe Arg Leu Val Thr Asn Arg Gly Glu Ala His Leu
755                 760                 765                 770 gag ctg aat gcc ttc cgt agg aag cat gac tgt gcc ctg gtc atc tct        2409
Glu Leu Asn Ala Phe Arg Arg Lys His Asp Cys Ala Leu Val Ile Ser
                775                 780                 785 gga gac tcc ctg gag gtt tgc ctc aaa tac tat gag tac gag ttc atg        2457
Gly Asp Ser Leu Glu Val Cys Leu Lys Tyr Tyr Glu Tyr Glu Phe Met
                    790                 795                 800 gaa ctg gcc tgc cag tgc ccg gct gtg gtg tgc tgc cgc tgt gcc cca        2505
Glu Leu Ala Cys Gln Cys Pro Ala Val Val Cys Cys Arg Cys Ala Pro
                    805                 810                 815 acc cag aag gcc cag att gtt cgg ctg ctc caa gaa cgc acc ggg aaa        2553
Thr Gln Lys Ala Gln Ile Val Arg Leu Leu Gln Glu Arg Thr Gly Lys
    820                 825                 830 ctc acc tgt gca gta tgg gac gga ggc aat gac gtc agc atg atc cag        2601
Leu Thr Cys Ala Val Trp Asp Gly Gly Asn Asp Val Ser Met Ile Gln
835                 840                 845                 850 gaa tcc gac tgc ggc gtg ggc gtg gag ggc aag gaa ggg aag cag gcc        2649
Glu Ser Asp Cys Gly Val Gly Val Glu Gly Lys Glu Gly Lys Gln Ala
                855                 860                 865 tcg ctg gca gcg gac ttc tcc atc acc cag ttc aag cat ctc ggc cgc        2697
Ser Leu Ala Ala Asp Phe Ser Ile Thr Gln Phe Lys His Leu Gly Arg
                    870                 875                 880 ttg ctc atg gtg cac ggt cgg aac agc tac aag cgc tcg gcg gcc ctc        2745
```

| | | | | | | | | | | |
|---|---|---|---|---|---|---|---|---|---|---|
| Leu | Leu | Met | Val | His | Gly | Arg | Asn | Ser | Tyr | Lys | Arg | Ser | Ala | Ala | Leu |
| | | 885 | | | | 890 | | | | 895 | | | | | |

```
agt cag ttt gtg atc cac agg agc ctc tgc atc agc acc atg cag gct    2793
Ser Gln Phe Val Ile His Arg Ser Leu Cys Ile Ser Thr Met Gln Ala
    900                 905                 910 gtc ttc tcg tct gtg ttc tac ttt gca tcc gtt cct ctc tac caa ggc    2841
Val Phe Ser Ser Val Phe Tyr Phe Ala Ser Val Pro Leu Tyr Gln Gly
915                 920                 925                 930 ttc ctg atc att ggg tat tct acc atc tac acg atg ttt ccc gtg ttc    2889
Phe Leu Ile Ile Gly Tyr Ser Thr Ile Tyr Thr Met Phe Pro Val Phe
                935                 940                 945 tcc ctg gtt ttg gac aaa gac gtg aag tcg gaa gtc gcc atg ttg tat    2937
Ser Leu Val Leu Asp Lys Asp Val Lys Ser Glu Val Ala Met Leu Tyr
            950                 955                 960 cct gag ctc tac aag gac ctg ctt aag ggg cgg cca ctg tcc tac aag    2985
Pro Glu Leu Tyr Lys Asp Leu Leu Lys Gly Arg Pro Leu Ser Tyr Lys
        965                 970                 975 acg ttc tta att tgg gtg tta atc agc atc tat caa ggg agc acc atc    3033
Thr Phe Leu Ile Trp Val Leu Ile Ser Ile Tyr Gln Gly Ser Thr Ile
    980                 985                 990 atg tac ggg gcg ctg ctg  ctg ttc gag tcg gag  ttt gta cac atc     3078
Met Tyr Gly Ala Leu Leu  Leu Phe Glu Ser Glu  Phe Val His Ile
995                 1000                1005 gtg  gca atc tcc ttc aca  tcc ctc atc ctc act  gag cta ctg atg    3123
Val  Ala Ile Ser Phe Thr  Ser Leu Ile Leu Thr  Glu Leu Leu Met
1010             1015                 1020 gtg  gcg ctc acc atc cag  acg tgg cac tgg ctc  atg aca gtg gcc    3168
Val  Ala Leu Thr Ile Gln  Thr Trp His Trp Leu  Met Thr Val Ala
1025             1030                 1035 gag  cta ctc agc ctg gcc  tgc tac att gcctccctgg tgttcctcca       3215
Glu  Leu Leu Ser Leu Ala  Cys Tyr Ile
1040             1045
```

| | |
|---|---|
| tgagttcatc gatgtctact tcattgccac cctgtcattc ctctggaagg tgtccgtcat | 3275 |
| caccttggtc agctgtctcc ccctctatgt cctcaagtac ctgcggagac ggttctcccc | 3335 |
| acccagctac tcgaagctca cttcctaagc tgcagggctg cctcgggcag ggcctccggc | 3395 |
| ctccggcgct ntccccagga ggaggtcaag ttccacacgc acgagccgcc tctgctggac | 3455 |
| ggtgcagtca tggctggcac atgaggcttc gctgaggcga cactgggcac ctaatgggga | 3515 |
| tggaacattg gtggaaccgg agggagggac ctgagagctg tacctatcag aaccttgggt | 3575 |
| gctaagctgt gctgaggggg aagacgtggg accggatggc ccgtctgagg tttgtggggt | 3635 |
| cactgtgcaa gcttccctta tggtttgaac ctcttgcctg cagcccgggg | 3685 |

<210> SEQ ID NO 10
<211> LENGTH: 1048
<212> TYPE: PRT
<213> ORGANISM: Mus musculus

<400> SEQUENCE: 10

```
Arg Pro Cys Pro Ser Val Gly Pro Arg Gly Arg Leu Arg Ala Trp Pro
1               5                   10                  15

Gly Ala Arg Asp Leu Ala Pro Ala Leu Arg Ala Arg Pro Ala Arg Cys
            20                  25                  30

Arg Arg Leu Leu Pro Leu Pro Arg Gly Gly Ala Glu Ala Ala Gly Ser
        35                  40                  45

Ala Gly Gly Ala Ala Gly Gly Asp Met Thr Asp Ser Ile Pro Leu Gln
    50                  55                  60
```

```
Pro Val Arg His Lys Lys Arg Val Asp Ser Arg Pro Arg Ala Gly Cys
 65                  70                  75                  80

Cys Glu Trp Leu Arg Cys Cys Gly Gly Gly Glu Pro Arg Pro Arg Thr
                 85                  90                  95

Val Trp Leu Gly His Pro Glu Lys Arg Asp Gln Arg Tyr Pro Arg Asn
            100                 105                 110

Val Ile Asn Asn Gln Lys Tyr Asn Phe Phe Thr Phe Leu Pro Gly Val
        115                 120                 125

Leu Phe Ser Gln Phe Arg Tyr Phe Phe Asn Phe Tyr Phe Leu Leu Leu
    130                 135                 140

Ala Cys Ser Gln Phe Val Pro Glu Met Arg Leu Gly Ala Leu Tyr Thr
145                 150                 155                 160

Tyr Trp Val Pro Leu Gly Phe Val Leu Ala Val Thr Ile Ile Arg Glu
                165                 170                 175

Ala Val Glu Glu Ile Arg Cys Tyr Val Arg Asp Lys Glu Met Asn Ser
            180                 185                 190

Gln Val Tyr Ser Arg Leu Thr Ser Arg Gly Thr Val Lys Val Lys Ser
        195                 200                 205

Ser Asn Ile Gln Val Gly Asp Leu Ile Leu Val Glu Lys Asn Gln Arg
    210                 215                 220

Val Pro Ala Asp Met Ile Phe Leu Arg Thr Ser Glu Lys Asn Gly Ser
225                 230                 235                 240

Cys Phe Leu Arg Thr Asp Gln Leu Asp Gly Glu Thr Asp Trp Lys Leu
                245                 250                 255

Arg Leu Pro Val Ala Cys Thr Gln Arg Leu Pro Thr Ala Ala Asp Leu
            260                 265                 270

Leu Gln Ile Arg Ser Tyr Val Tyr Ala Glu Lys Pro Asn Ile Asp Ile
        275                 280                 285

His Asn Phe Leu Gly Thr Phe Thr Arg Glu Asn Ser Asp Pro Pro Ile
    290                 295                 300

Ser Glu Ser Leu Ser Ile Glu Asn Thr Leu Trp Ala Gly Thr Val Ile
305                 310                 315                 320

Ala Ser Gly Thr Val Gly Val Val Leu Tyr Thr Gly Arg Lys Leu
                325                 330                 335

Arg Ser Val Met Asn Thr Ser Asp Pro Arg Ser Lys Ile Gly Leu Phe
            340                 345                 350

Asp Leu Glu Val Asn Cys Leu Thr Lys Ile Leu Phe Gly Ala Leu Val
        355                 360                 365

Val Val Ser Leu Val Met Val Ala Leu Gln His Phe Ala Gly Arg Trp
    370                 375                 380

Tyr Leu Gln Ile Ile Arg Phe Leu Leu Leu Phe Ser Asn Ile Ile Pro
385                 390                 395                 400

Ile Ser Leu Arg Val Asn Leu Asp Met Gly Lys Ile Val Tyr Ser Trp
                405                 410                 415

Val Ile Arg Arg Asp Ser Lys Ile Pro Gly Thr Val Val Arg Ser Ser
            420                 425                 430

Thr Ile Pro Glu Gln Leu Gly Arg Ile Ser Tyr Leu Leu Thr Asp Lys
        435                 440                 445

Thr Gly Thr Leu Thr Gln Asn Glu Met Val Phe Lys Arg Leu His Leu
    450                 455                 460

Gly Thr Val Ala Tyr Gly Leu Asp Ser Met Asp Glu Val Gln Ser His
465                 470                 475                 480

Ile Phe Ser Ile Tyr Thr Gln Gln Ser Gln Asp Pro Pro Ala Gln Lys
```

-continued

```
                485                 490                 495
Gly Pro Thr Val Thr Lys Val Arg Arg Thr Met Ser Ser Arg Val
                500                 505                 510
His Glu Ala Val Lys Ala Ile Ala Leu Cys His Asn Val Thr Pro Val
                515                 520                 525
Tyr Glu Ser Asn Gly Val Thr Asp Gln Ala Glu Ala Glu Lys Gln Phe
                530                 535                 540
Glu Asp Ser Cys Arg Val Tyr Gln Ala Ser Ser Pro Asp Glu Val Ala
545                 550                 555                 560
Leu Val Gln Trp Thr Glu Ser Val Gly Leu Thr Leu Val Gly Arg Asp
                565                 570                 575
Gln Ser Ser Met Gln Leu Arg Thr Pro Gly Asp Gln Val Leu Asn Leu
                580                 585                 590
Thr Ile Leu Gln Val Phe Pro Phe Thr Tyr Glu Ser Lys Arg Met Gly
                595                 600                 605
Ile Ile Val Arg Asp Glu Ser Thr Gly Glu Ile Thr Phe Tyr Met Lys
                610                 615                 620
Gly Ala Asp Val Val Met Ala Gly Ile Val Gln Tyr Asn Asp Trp Leu
625                 630                 635                 640
Glu Glu Glu Cys Gly Asn Met Ala Arg Glu Gly Leu Arg Val Leu Val
                645                 650                 655
Val Ala Lys Lys Ser Leu Thr Glu Glu Gln Tyr Gln His Phe Glu Ala
                660                 665                 670
Arg Tyr Val Gln Ala Lys Leu Ser Val His Asp Arg Ser Leu Lys Val
                675                 680                 685
Ala Thr Val Ile Glu Ser Leu Glu Met Glu Met Glu Leu Leu Cys Leu
                690                 695                 700
Thr Gly Val Glu Asp Gln Leu Gln Ala Asp Val Arg Pro Thr Leu Glu
705                 710                 715                 720
Thr Leu Arg Asn Ala Gly Ile Lys Val Trp Met Leu Thr Gly Asp Lys
                725                 730                 735
Leu Glu Thr Ala Thr Cys Thr Ala Lys Asn Ala His Leu Val Thr Arg
                740                 745                 750
Asn Gln Asp Ile His Val Phe Arg Leu Val Thr Asn Arg Gly Glu Ala
                755                 760                 765
His Leu Glu Leu Asn Ala Phe Arg Arg Lys His Asp Cys Ala Leu Val
                770                 775                 780
Ile Ser Gly Asp Ser Leu Glu Val Cys Leu Lys Tyr Tyr Glu Tyr Glu
785                 790                 795                 800
Phe Met Glu Leu Ala Cys Gln Cys Pro Ala Val Val Cys Cys Arg Cys
                805                 810                 815
Ala Pro Thr Gln Lys Ala Gln Ile Val Arg Leu Leu Gln Glu Arg Thr
                820                 825                 830
Gly Lys Leu Thr Cys Ala Val Trp Asp Gly Gly Asn Asp Val Ser Met
                835                 840                 845
Ile Gln Glu Ser Asp Cys Gly Val Gly Val Glu Gly Lys Glu Gly Lys
                850                 855                 860
Gln Ala Ser Leu Ala Ala Asp Phe Ser Ile Thr Gln Phe Lys His Leu
865                 870                 875                 880
Gly Arg Leu Leu Met Val His Gly Arg Asn Ser Tyr Lys Arg Ser Ala
                885                 890                 895
Ala Leu Ser Gln Phe Val Ile His Arg Ser Leu Cys Ile Ser Thr Met
                900                 905                 910
```

```
Gln Ala Val Phe Ser Ser Val Phe Tyr Phe Ala Ser Val Pro Leu Tyr
        915                 920                 925

Gln Gly Phe Leu Ile Ile Gly Tyr Ser Thr Ile Tyr Thr Met Phe Pro
    930                 935                 940

Val Phe Ser Leu Val Leu Asp Lys Asp Val Lys Ser Glu Val Ala Met
945                 950                 955                 960

Leu Tyr Pro Glu Leu Tyr Lys Asp Leu Leu Lys Gly Arg Pro Leu Ser
            965                 970                 975

Tyr Lys Thr Phe Leu Ile Trp Val Leu Ile Ser Ile Tyr Gln Gly Ser
        980                 985                 990

Thr Ile Met Tyr Gly Ala Leu Leu  Leu Phe Glu Ser Glu  Phe Val His
        995                 1000                1005

Ile Val  Ala Ile Ser Phe Thr  Ser Leu Ile Leu Thr  Glu Leu Leu
        1010                1015                1020

Met Val  Ala Leu Thr Ile Gln  Thr Trp His Trp Leu  Met Thr Val
        1025                1030                1035

Ala Glu  Leu Leu Ser Leu Ala  Cys Tyr Ile
        1040                1045

<210> SEQ ID NO 11
<211> LENGTH: 1047
<212> TYPE: PRT
<213> ORGANISM: Homo sapiens

<400> SEQUENCE: 11

Met Thr Asp Asn Ile Pro Leu Gln Pro Val Arg Gln Lys Lys Arg Met
1               5                   10                  15

Asp Ser Arg Pro Arg Ala Gly Cys Cys Glu Trp Leu Arg Cys Cys Gly
            20                  25                  30

Gly Gly Glu Ala Arg Pro Arg Thr Val Trp Leu Gly His Pro Glu Lys
        35                  40                  45

Arg Asp Gln Arg Tyr Pro Arg Asn Val Ile Asn Gln Lys Tyr Asn
    50                  55                  60

Phe Phe Thr Phe Leu Pro Gly Val Leu Phe Asn Gln Phe Lys Tyr Phe
65                  70                  75                  80

Phe Asn Leu Tyr Phe Leu Leu Leu Ala Cys Ser Gln Phe Val Pro Glu
                85                  90                  95

Met Arg Leu Gly Ala Leu Tyr Thr Tyr Trp Val Pro Leu Gly Phe Val
            100                 105                 110

Leu Ala Val Thr Val Ile Arg Glu Ala Val Glu Glu Ile Arg Cys Tyr
        115                 120                 125

Val Arg Asp Lys Glu Val Asn Ser Gln Val Tyr Ser Arg Leu Thr Ala
130                 135                 140

Arg Gly Thr Val Lys Val Lys Ser Ser Asn Ile Gln Val Gly Asp Leu
145                 150                 155                 160

Ile Ile Val Glu Lys Asn Gln Arg Val Pro Ala Asp Met Ile Phe Leu
                165                 170                 175

Arg Thr Ser Glu Lys Asn Gly Ser Cys Phe Leu Arg Thr Asp Gln Leu
            180                 185                 190

Asp Gly Glu Thr Asp Trp Lys Leu Arg Leu Pro Val Ala Cys Thr Gln
        195                 200                 205

Arg Leu Pro Thr Ala Ala Asp Leu Leu Gln Ile Arg Ser Tyr Val Tyr
    210                 215                 220

Ala Glu Glu Pro Asn Ile Asp Ile His Asn Phe Val Gly Thr Phe Thr
```

-continued

```
            225                 230                 235                 240
        Arg Glu Asp Ser Asp Pro Ile Ser Glu Ser Leu Ser Ile Glu Asn
                        245                 250                 255
        Thr Leu Trp Ala Gly Thr Val Ala Ser Gly Thr Val Val Gly Val
                    260                 265                 270
        Val Leu Tyr Thr Gly Arg Glu Leu Arg Ser Val Met Asn Thr Ser Asn
                275                 280                 285
        Pro Arg Ser Lys Ile Gly Leu Phe Asp Leu Glu Val Asn Cys Leu Thr
            290                 295                 300
        Lys Ile Leu Phe Gly Ala Leu Val Val Ser Leu Val Met Val Ala
        305                 310                 315                 320
        Leu Gln His Phe Ala Gly Arg Trp Tyr Leu Gln Ile Ile Arg Phe Leu
                        325                 330                 335
        Leu Leu Phe Ser Asn Ile Ile Pro Ile Ser Leu Arg Val Asn Leu Asp
                    340                 345                 350
        Met Gly Lys Ile Val Tyr Ser Trp Val Ile Arg Arg Asp Ser Lys Ile
                355                 360                 365
        Pro Gly Thr Val Val Arg Ser Thr Ile Pro Glu Gln Leu Gly Arg
            370                 375                 380
        Ile Ser Tyr Leu Leu Thr Asp Lys Thr Gly Thr Leu Thr Gln Asn Glu
        385                 390                 395                 400
        Met Ile Phe Lys Arg Leu His Leu Gly Thr Val Ala Tyr Gly Leu Asp
                        405                 410                 415
        Ser Met Asp Glu Val Gln Ser His Ile Phe Ser Ile Tyr Thr Gln Gln
                    420                 425                 430
        Ser Gln Asp Pro Pro Ala Gln Lys Gly Pro Thr Leu Thr Thr Lys Val
                435                 440                 445
        Arg Arg Thr Met Ser Ser Arg Val His Glu Ala Val Lys Ala Ile Ala
            450                 455                 460
        Leu Cys His Asn Val Thr Pro Val Tyr Glu Ser Asn Gly Val Thr Asp
        465                 470                 475                 480
        Gln Ala Glu Ala Glu Lys Gln Tyr Glu Asp Ser Cys Arg Val Tyr Gln
                        485                 490                 495
        Ala Ser Ser Pro Asp Glu Val Ala Leu Val Gln Trp Thr Glu Ser Val
                    500                 505                 510
        Gly Leu Thr Leu Val Gly Arg Asp Gln Ser Ser Met Gln Leu Arg Thr
                515                 520                 525
        Pro Gly Asp Gln Ile Leu Asn Phe Thr Ile Leu Gln Ile Phe Pro Phe
            530                 535                 540
        Thr Tyr Glu Ser Lys Arg Met Gly Ile Ile Val Arg Asp Glu Ser Thr
        545                 550                 555                 560
        Gly Glu Ile Thr Phe Tyr Met Lys Gly Ala Asp Val Val Met Ala Gly
                        565                 570                 575
        Ile Val Gln Tyr Asn Asp Trp Leu Glu Glu Cys Gly Asn Met Ala
                    580                 585                 590
        Arg Glu Gly Leu Arg Val Leu Val Ala Lys Lys Ser Leu Ala Glu
                595                 600                 605
        Glu Gln Tyr Gln Asp Phe Glu Ala Arg Tyr Val Gln Ala Lys Leu Ser
            610                 615                 620
        Val His Asp Arg Ser Leu Lys Val Ala Thr Val Ile Glu Ser Leu Glu
        625                 630                 635                 640
        Met Glu Met Glu Leu Leu Cys Leu Thr Gly Val Glu Asp Gln Leu Gln
                        645                 650                 655
```

```
Ala Asp Val Arg Pro Thr Leu Glu Thr Leu Arg Asn Ala Gly Ile Lys
            660                 665                 670

Val Trp Met Leu Thr Gly Asp Lys Leu Glu Thr Ala Thr Cys Thr Ala
        675                 680                 685

Lys Asn Ala His Leu Val Thr Arg Asn Gln Asp Ile His Val Phe Arg
    690                 695                 700

Leu Val Thr Asn Arg Gly Glu Ala His Leu Glu Leu Asn Ala Phe Arg
705                 710                 715                 720

Arg Lys His Asp Cys Ala Leu Val Ile Ser Gly Asp Ser Leu Glu Val
                725                 730                 735

Cys Leu Lys Tyr Tyr Glu Tyr Glu Phe Met Glu Leu Ala Cys Gln Cys
            740                 745                 750

Pro Ala Val Val Cys Cys Arg Cys Ala Pro Thr Gln Lys Ala Gln Ile
        755                 760                 765

Val Arg Leu Leu Gln Glu Arg Thr Gly Lys Leu Thr Cys Ala Val Gly
    770                 775                 780

Asp Gly Gly Asn Asp Val Ser Met Ile Gln Glu Ser Asp Cys Gly Val
785                 790                 795                 800

Gly Val Glu Gly Lys Glu Gly Lys Gln Ala Ser Leu Ala Ala Asp Phe
                805                 810                 815

Ser Ile Thr Gln Phe Lys His Leu Gly Arg Leu Leu Met Val His Gly
            820                 825                 830

Arg Asn Ser Tyr Lys Arg Ser Ala Ala Leu Ser Gln Phe Val Ile His
        835                 840                 845

Arg Ser Leu Cys Ile Ser Thr Met Gln Ala Val Phe Ser Ser Val Phe
    850                 855                 860

Tyr Phe Ala Ser Val Pro Leu Tyr Gln Gly Phe Leu Ile Ile Gly Tyr
865                 870                 875                 880

Ser Thr Ile Tyr Thr Met Phe Pro Val Phe Ser Leu Val Leu Asp Lys
                885                 890                 895

Asp Val Lys Ser Glu Val Ala Met Leu Tyr Pro Glu Leu Tyr Lys Asp
            900                 905                 910

Leu Leu Lys Gly Arg Pro Leu Ser Tyr Lys Thr Phe Leu Ile Trp Val
        915                 920                 925

Leu Ile Ser Ile Tyr Gln Gly Ser Thr Ile Met Tyr Gly Ala Leu Leu
    930                 935                 940

Leu Phe Glu Ser Glu Phe Val His Ile Val Ala Ile Ser Phe Thr Ser
945                 950                 955                 960

Leu Ile Leu Thr Glu Leu Leu Met Val Ala Leu Thr Ile Gln Thr Trp
                965                 970                 975

His Trp Leu Met Thr Val Ala Glu Leu Leu Ser Leu Ala Cys Tyr Ile
            980                 985                 990

Ala Ser Leu Val Phe Leu His Glu Phe Ile Asp Val Tyr Phe Ile Ala
        995                 1000                1005

Thr Leu Ser Phe Leu Trp Lys Val Ser Val Ile Thr Leu Val Ser
    1010                1015                1020

Cys Leu Pro Leu Tyr Val Leu Lys Tyr Leu Arg Arg Arg Phe Ser
    1025                1030                1035

Pro Pro Ser Tyr Ser Lys Leu Thr Ser
    1040                1045

<210> SEQ ID NO 12
<211> LENGTH: 3141
```

<212> TYPE: DNA
<213> ORGANISM: Homo sapiens

<400> SEQUENCE: 12

```
atgacggaca acatcccgct gcagccggtg cgccagaaga agcggatgga cagcaggccc      60
cgcgccgggt gctgcgagtg gctgagatgc tgcggtggag gggaggccag gccccgcact     120
gtctggctgg ggcaccccga gaagagagac cagaggtatc ctcggaatgt catcaacaat     180
cagaagtaca atttcttcac ctttcttcct ggggtgctgt tcaaccagtt caaatacttt     240
ttcaacctct atttcttact tcttgcctgc tctcagtttg ttcccgaaat gagacttggt     300
gcactctata cctactgggt tccccctggc cttcgtgctgg ccgtcactgt catccgtgag     360
gcggtggagg agatccgatg ctacgtgcgg gacaaggaag tcaactccca ggtctacagc     420
cggctcacag cacgaggcac agtgaaggtg aagagttcta acatccaagt ggagaccttt     480
atcatcgttg aaaagaacca gcgggtccct gccgacatga tcttcctgag gacatcagaa     540
aaaaacgggt catgcttctt gcggacggat cagctggatg gggagacgga ctggaagctg     600
cggcttcccg tggcctgcac gcagaggctc cccacggccg ccgaccttct tcagattcga     660
tcgtatgtgt acgcagaaga gccaaatatt gacattcaca acttcgtggg aactttttacc     720
cgagaagaca gcgaccccce gatcagcgag agcctgagca tagagaacac gctgtgggct     780
ggcactgtgg tcgcatcagg tactgttgtg ggtgttgttc tttacactgg cagagaactc     840
cggagtgtca tgaatacctc aaatccccga agtaagatcg gcctgttcga cttggaagtg     900
aactgcctca ccaagatcct cttttggtgcc ctggtggtgg tctcgctggt catggttgcc     960
cttcagcact ttgcaggccg ttggtacctg cagatcatcc gcttcctcct cttgttttcc    1020
aacatcatcc ccattagttt gcgtgtgaac ctggacatgg gcaagatcgt gtacagctgg    1080
gtgattcgaa gggactcgaa aatccccggg accgtggttc gctccagcac gattcctgag    1140
cagctgggca ggatttcgta cttactcaca gacaagacag gcactcttac ccagaacgag    1200
atgattttca acggctccaa tctcggaaca gtagcctacg gcctcgactc aatggacgaa    1260
gtacaaagcc acatttttcag catttacacc cagcaatccc aggacccacc ggctcagaag    1320
ggcccaacgc tcaccactaa ggtccggcgg accatgagca gccgcgtgca cgaagccgtg    1380
aaggccatcg cgctctgcca caacgtgact cccgtgtatg agtccaacgg tgtgactgat    1440
caggctgagg ccgagaagca gtacgaagac tcctgccgcg tataccaggc atccagcccc    1500
gatgaggtgg ccctggtaca gtggacggaa agtgtgggct taaccctggt gggccgagac    1560
cagtcttcca tgcagctgag gacccctggc gaccagatcc tgaacttcac catcctacag    1620
atcttcccct tcacctatga aagcaaacgt atgggcatca tcgtgcggga tgaatcaact    1680
ggagaaatta cgttttacat gaagggagca gatgtgtca tggctggcat tgtgcagtac    1740
aatgactggt tggaggaaga gtgtggcaac atggcccgag aagggctgcg ggtgctcgtg    1800
gtggcaaaga agtctcttgc agaggagcag tatcaggact tgaagcccg ctacgtccag    1860
gccaagctga gtgtgcacga ccgctccctc aaagtggcca cggtgatcga gagcctggag    1920
atggagatgg aactgctgtg cctgacgggc gtggaggacc agctgcaggc agatgtgcgg    1980
cccacgctgg agaccctgag gaatgctggc atcaaggttt ggatgctgac aggggacaag    2040
ctggagacag ctacgtgcac agcgaagaat gcacatctgg tgaccagaaa ccaagacatc    2100
cacgtttttc ggctggtgac caaccgcggg gaggctcacc tcgagctgaa cgccttccgc    2160
aggaagcatg attgtgccct ggtcatctcg ggagactccc tggaggtttg cctcaagtac    2220
```

```
tatgagtacg agttcatgga gctggcctgc cagtgcccgg ccgtagtctg ctgccgatgt    2280
gcccccaccc agaaggccca gatcgtgcgc ctgcttcagg agcgcacggg caagctcacc    2340
tgtgcagtag gggacggagg caatgacgtc agcatgattc aggaatctga ctgcggcgtg    2400
ggagtggaag gaaaggaagg aaaacaggct tcgttggctg cagacttctc catcactcaa    2460
tttaagcatc ttggccggtt gcttatggtg catggccgga acagctacaa gcggtcagcc    2520
gccctcagcc agttcgtgat tcacaggagc ctctgtatca gcaccatgca ggctgtcttt    2580
tcctccgtgt tttactttgc ctccgtccct ctctatcaag gattcctcat cattgggtac    2640
tccacaattt acaccatgtt tcctgtgttt tctctggtcc tggacaaaga tgtcaaatcg    2700
gaagttgcca tgctgtatcc tgagctctac aaggatcttc tcaagggacg gccgttgtcc    2760
tacaagacat tcttaatatg ggttttgatt agcatctatc aagggagcac catcatgtac    2820
ggggcgctgc tgctgtttga gtcggagttc gtgcacatcg tggccatctc cttcacctcg    2880
ctgatcctca ccgagctgct catggtggcg ctgaccatcc agacctggca ctggctcatg    2940
acagtggcgg agctgctcag cctggcctgc tacatcgcct ccctggtgtt cttacacgag    3000
ttcatcgatg tgtacttcat cgccaccttg tcattcttgt ggaaagtctc cgtcatcact    3060
ctggtcagct gcctccccct ctatgtcctc aagtacctgc gaagacggtt ctctccccccc    3120 agctactcaa agctcacatc a                                              3141
```

<210> SEQ ID NO 13
<211> LENGTH: 2302
<212> TYPE: DNA
<213> ORGANISM: Mus musclus
<220> FEATURE:
<221> NAME/KEY: CDS
<222> LOCATION: (510)..(1439)

<400> SEQUENCE: 13

```
gggaagctgt tgcgcaccac ttagctggga agtgcgttgc tccctgtttc ccagcccacc    60
cgagatggcc cccaaagtct cggattccgt ggaacagctc cgcgctgccg gcaaccagaa   120
cttccgcaat ggccagtacg gcgaagctcg gcgctgtacg agcgcgcact gcggctgctg   180
caggcgcgag gtaggaaccc gccccacgtt tccctccggg cctgcgtcct ccacccgcat   240
ccccgcaccg ggcctcccgt tggcccagcc tccctggttt tcccttcccc gcgtccagcc   300
gccgcaccag gccctcccag ggcttgaccc cgcgattctt tccgtccctg gccgcctagc   360
cgcggcccgg tctaccatca ccacccccca ccacccccag gccagtcggc tgcgggcctt   420
aagggcacgc atccgctgct tccacccgga agctgttgcg cactcctcgg cggggaacgg   480
aggtggtcct tgtttgccgg cctcccggg atg gcc ccc aaa ctc tca gac tct    533
                                 Met Ala Pro Lys Leu Ser Asp Ser
                                  1               5 gtg gaa gag ctc cgc gca gcc ggc aac cag agt ttc cgc aac gga cag   581
Val Glu Glu Leu Arg Ala Ala Gly Asn Gln Ser Phe Arg Asn Gly Gln
 10              15                  20 tac gcc gag gct tcg gcg ctg tac gag cgc gcg ctg cga ctg ctg cag   629
Tyr Ala Glu Ala Ser Ala Leu Tyr Glu Arg Ala Leu Arg Leu Leu Gln
25                  30                  35                  40 gcg cga ggt tct gca gac ccc gaa gaa gaa agt gtt ctg tac tcc aac   677
Ala Arg Gly Ser Ala Asp Pro Glu Glu Glu Ser Val Leu Tyr Ser Asn
                45                  50                  55 cgt gca gcg tgc tac ttg aag gat ggg aac tgc aca gat tgc atc aaa   725
Arg Ala Ala Cys Tyr Leu Lys Asp Gly Asn Cys Thr Asp Cys Ile Lys
            60                  65                  70
```

```
gat tgc act tcc gcg ctg gcc ttg gtt ccc ttc agc atc aag ccc ttg      773
Asp Cys Thr Ser Ala Leu Ala Leu Val Pro Phe Ser Ile Lys Pro Leu
        75                  80                  85 ctg cgc aga gca tct gca tat gaa gcc ctg gag aag tac gcc ctg gcc      821
Leu Arg Arg Ala Ser Ala Tyr Glu Ala Leu Glu Lys Tyr Ala Leu Ala
90                  95                 100 tac gtt gac tat aag act gtg ctg cag atc gat aac agt gtg gca tcc      869
Tyr Val Asp Tyr Lys Thr Val Leu Gln Ile Asp Asn Ser Val Ala Ser
105                 110                 115                 120 gcc ctg gaa ggc atc aac aga ata acc aga gct ctc atg gac tcc ctg      917
Ala Leu Glu Gly Ile Asn Arg Ile Thr Arg Ala Leu Met Asp Ser Leu
                125                 130                 135 gga cct gag tgg cgc ctg aag ctg ccc cct atc cct gtg gtg cct gtt      965
Gly Pro Glu Trp Arg Leu Lys Leu Pro Pro Ile Pro Val Val Pro Val
            140                 145                 150 tca gcc cag aag aga tgg aat tcc ttg cct tca gat aac cac aaa gag     1013
Ser Ala Gln Lys Arg Trp Asn Ser Leu Pro Ser Asp Asn His Lys Glu
                155                 160                 165 aca gct aaa acc aaa tcc aaa gaa gcc aca gct acg aag agc aga gtg     1061
Thr Ala Lys Thr Lys Ser Lys Glu Ala Thr Ala Thr Lys Ser Arg Val
170                 175                 180 cct tct gct ggg gat gtg gag aga gcc aaa gct ctg aag gaa gaa ggc     1109
Pro Ser Ala Gly Asp Val Glu Arg Ala Lys Ala Leu Lys Glu Glu Gly
185                 190                 195                 200 aat gac ctt gta aag aag ggc aac cat aag aaa gct att gag aag tac     1157
Asn Asp Leu Val Lys Lys Gly Asn His Lys Lys Ala Ile Glu Lys Tyr
                205                 210                 215 agt gag agc ctc ttg tgt agt agc ctg gag tct gcc aca tac agc aac     1205
Ser Glu Ser Leu Leu Cys Ser Ser Leu Glu Ser Ala Thr Tyr Ser Asn
                220                 225                 230 aga gcg ctc tgt cac ctg gtc ctg aag cag tac aag gag gca gta aag     1253
Arg Ala Leu Cys His Leu Val Leu Lys Gln Tyr Lys Glu Ala Val Lys
                235                 240                 245 gac tgc aca gaa gcc ctc aag ctg gat ggg aag aat gta aag gcg ttt     1301
Asp Cys Thr Glu Ala Leu Lys Leu Asp Gly Lys Asn Val Lys Ala Phe
250                 255                 260 tac aga cgg gct caa gcc tac aag gca ctc aag gac tat aag tca agc     1349
Tyr Arg Arg Ala Gln Ala Tyr Lys Ala Leu Lys Asp Tyr Lys Ser Ser
265                 270                 275                 280 ctt tcg gat atc agc agc ctc cta caa att gaa ccc agg aat ggc cct     1397
Leu Ser Asp Ile Ser Ser Leu Leu Gln Ile Glu Pro Arg Asn Gly Pro
                285                 290                 295 gca cag aag tta cgg cag gaa gtt aac cag aac atg aac taa             1439
Ala Gln Lys Leu Arg Gln Glu Val Asn Gln Asn Met Asn
                300                 305 accgtagagg gcaacaggga ccctgaactt gaccttccca gagaagccag ggcctcccct   1499
gcatctgccc caatgccccag catgccgcca agggagtgca aaatcaaccc cactttgact   1559
ccttggagag gtagcagcct ttcacctgac acattttact tgttcagatt aagtccatta   1619
cagacaagca caggactctt ttttttttc ttcttttttt tttccagaaa ggtccccact    1679
agaggttttt gttttgtttt attttaatt taaaaaagcg tgacgccaac agccctggcc    1739
tcattcgctt gcttctgcct ggccttgtc aacacagtcc ttggcaactg tccctgaccc    1799
agatatgcac agactgggtg cctgtgactt cctctgccgc catagctctg cagttcacct   1859
gagtgctgac aggctagaag tgcttgctcg tccgcagcca cagcggcctg ttgagctggt   1919
tctccaaggc tgcctgccat ctcctcgagg agacagctgc tgtctgcacc ctgtccttga   1979
cacagtgtcc tgtgttgagc cccagtgcct ttagtccagg ccctttgtgg gaaggcagag   2039
```

```
cctaacccctt ggaggctctg tgttgttgcc ttctgtctga gctacctacg atgttcaaag    2099
agcccagatt cctcctgcaa tggggagaga ggcctccttg agattagtgt ccctccagtc    2159
tgagcaggaa cttaaccttt tcccccatag cagcagcccc tcgggctcct ttgttttgtt    2219
ttgttttgtt aatatgttgg agttaattga actgatttta ttgaagtgtg tgttgctgtt    2279
gcattaaaag gttttcttct atg                                             2302
```

<210> SEQ ID NO 14
<211> LENGTH: 309
<212> TYPE: PRT
<213> ORGANISM: Mus musclus

<400> SEQUENCE: 14

```
Met Ala Pro Lys Leu Ser Asp Ser Val Glu Glu Leu Arg Ala Ala Gly
1               5                   10                  15

Asn Gln Ser Phe Arg Asn Gly Gln Tyr Ala Glu Ala Ser Ala Leu Tyr
            20                  25                  30

Glu Arg Ala Leu Arg Leu Leu Gln Ala Arg Gly Ser Ala Asp Pro Glu
        35                  40                  45

Glu Glu Ser Val Leu Tyr Ser Asn Arg Ala Ala Cys Tyr Leu Lys Asp
    50                  55                  60

Gly Asn Cys Thr Asp Cys Ile Lys Asp Cys Thr Ser Ala Leu Ala Leu
65                  70                  75                  80

Val Pro Phe Ser Ile Lys Pro Leu Leu Arg Arg Ala Ser Ala Tyr Glu
                85                  90                  95

Ala Leu Glu Lys Tyr Ala Leu Ala Tyr Val Asp Tyr Lys Thr Val Leu
            100                 105                 110

Gln Ile Asp Asn Ser Val Ala Ser Ala Leu Glu Gly Ile Asn Arg Ile
        115                 120                 125

Thr Arg Ala Leu Met Asp Ser Leu Gly Pro Glu Trp Arg Leu Lys Leu
    130                 135                 140

Pro Pro Ile Pro Val Val Pro Val Ser Ala Gln Lys Arg Trp Asn Ser
145                 150                 155                 160

Leu Pro Ser Asp Asn His Lys Glu Thr Ala Lys Thr Lys Ser Lys Glu
                165                 170                 175

Ala Thr Ala Thr Lys Ser Arg Val Pro Ser Ala Gly Asp Val Glu Arg
            180                 185                 190

Ala Lys Ala Leu Lys Glu Glu Gly Asn Asp Leu Val Lys Lys Gly Asn
        195                 200                 205

His Lys Lys Ala Ile Glu Lys Tyr Ser Glu Ser Leu Leu Cys Ser Ser
    210                 215                 220

Leu Glu Ser Ala Thr Tyr Ser Asn Arg Ala Leu Cys His Leu Val Leu
225                 230                 235                 240

Lys Gln Tyr Lys Glu Ala Val Lys Asp Cys Thr Glu Ala Leu Lys Leu
                245                 250                 255

Asp Gly Lys Asn Val Lys Ala Phe Tyr Arg Arg Ala Gln Ala Tyr Lys
            260                 265                 270

Ala Leu Lys Asp Tyr Lys Ser Ser Leu Ser Asp Ile Ser Ser Leu Leu
        275                 280                 285

Gln Ile Glu Pro Arg Asn Gly Pro Ala Gln Lys Leu Arg Gln Glu Val
    290                 295                 300

Asn Gln Asn Met Asn
305
```

<210> SEQ ID NO 15
<211> LENGTH: 309
<212> TYPE: PRT
<213> ORGANISM: Homo sapiens

<400> SEQUENCE: 15

Met Ala Pro Lys Phe Pro Asp Ser Val Glu Leu Arg Ala Gly
1               5                   10                  15

Asn Glu Ser Phe Arg Asn Gly Gln Tyr Ala Glu Ala Ser Ala Leu Tyr
                20                  25                  30

Gly Arg Ala Leu Arg Val Leu Gln Ala Gln Gly Ser Ser Asp Pro Glu
            35                  40                  45

Glu Glu Ser Val Leu Tyr Ser Asn Arg Ala Ala Cys His Leu Lys Asp
50                  55                  60

Gly Asn Cys Arg Asp Cys Ile Lys Asp Cys Thr Ser Ala Leu Ala Leu
65                  70                  75                  80

Val Pro Phe Ser Ile Lys Pro Leu Leu Arg Arg Ala Ser Ala Tyr Glu
                85                  90                  95

Ala Leu Glu Lys Tyr Pro Met Ala Tyr Val Asp Tyr Lys Thr Val Leu
            100                 105                 110

Gln Ile Asp Asp Asn Val Thr Ser Ala Val Glu Gly Ile Asn Arg Met
        115                 120                 125

Thr Arg Ala Leu Met Asp Ser Leu Gly Pro Glu Trp Arg Leu Lys Leu
130                 135                 140

Pro Ser Ile Pro Leu Val Pro Val Ser Ala Gln Lys Arg Trp Asn Ser
145                 150                 155                 160

Leu Pro Ser Glu Asn His Lys Glu Met Ala Lys Ser Lys Ser Lys Glu
                165                 170                 175

Thr Thr Ala Thr Lys Asn Arg Val Pro Ser Ala Gly Asp Val Glu Lys
            180                 185                 190

Ala Arg Val Leu Lys Glu Glu Gly Asn Glu Leu Val Lys Lys Gly Asn
        195                 200                 205

His Lys Lys Ala Ile Glu Lys Tyr Ser Glu Ser Leu Leu Cys Ser Asn
210                 215                 220

Leu Glu Ser Ala Thr Tyr Ser Asn Arg Ala Leu Cys Tyr Leu Val Leu
225                 230                 235                 240

Lys Gln Tyr Thr Glu Ala Val Leu Asp Cys Thr Glu Ala Leu Lys Leu
                245                 250                 255

Asp Gly Lys Asn Val Lys Ala Phe Tyr Arg Arg Ala Gln Ala His Lys
            260                 265                 270

Ala Leu Lys Asp Tyr Lys Ser Ser Phe Ala Asp Ile Ser Asn Leu Leu
        275                 280                 285

Gln Ile Glu Pro Arg Asn Gly Pro Ala Gln Lys Leu Arg Gln Glu Val
    290                 295                 300

Lys Gln Asn Leu His
305

<210> SEQ ID NO 16
<211> LENGTH: 1988
<212> TYPE: DNA
<213> ORGANISM: Homo sapiens

<400> SEQUENCE: 16
ggcacgaggc accacacggg ggaggaagga aggagctccc aactcgccgg cctggccacg    60
ggatggcccc caaattccca gactctgtgg aggagctccg cgccgccggc aatgagagtt   120

```
tccgcaacgg ccagtacgcc gaggcctccg cgctctacgg ccgcgcgctg cgggtgctgc    180
aggcgcaagg ttcttcagac ccagaagaag aaagtgttct ctactccaac cgagcagcat    240
gtcacttgaa ggatggaaac tgcagagact gcatcaaaga ttgcacttca gcactggcct    300
tggttccctt cagcattaag cccctgctgc ggcgagcatc tgcttatgag gctctggaga    360
agtaccctat ggcctatgtt gactataaga ctgtgctgca gattgatgat aatgtgacgt    420
cagccgtaga aggcatcaac agaatgacca gagctctcat ggactcgctt gggcctgagt    480
ggcgcctgaa gctgccctca atccccttgg tgcctgtttc agctcagaag ggtggaatt    540 ccttgccttc ggagaaccac aaagagatgg ctaaaagcaa atccaaagaa accacagcta    600
caaagaacag agtgccttct gctggggatg tggagaaagc cagagttctg aaggaagaag    660
gcaatgagct tgtaaagaag ggaaaccata agaaagctat tgagaagtac agtgaaagcc    720
tcttgtgtag taacctggaa tctgccacgt acagcaacag agcactctgc tatttggtcc    780
tgaagcagta cacagaagca gtgaaggact gcacagaagc cctcaagctg atggaaaga    840 acgtgaaggc attctacaga cgggctcaag cccacaaagc actcaaggac tataaatcca    900
gctttgcaga catcagcaac ctcctacaga ttgagcctag gaatggtcct gcacagaagt    960
tgcggcagga agtgaagcag aacctacact aaaaacccaa cagggcaact ggaacccctg   1020
cctgacctta cccagagaag ccatgggcca cctgctctgt gcccgctcct gaaacccagc   1080
atgccccaag tgagctctga agccccctcc tcaatccctt gatggcctcc caccctgtaa   1140
gaggctttgc ttgttcaaat taaactcagt gtagtcaaac acagacatgg ttgttgcacc   1200
agaaaggtcc ccactagagc taagcgtgaa gctgaagctc tgtccctatt cccccagccc   1260
agctagctga tcacaccaac agatcctcat cagcaaagca tttggctttg tcctgcccaa   1320
gtgggctgca gactgagtgc tgcccttgta gcttccccag accccaactc actgcagttc   1380
atctgaacaa cctgagctcc tgggccgggg tggaaggagg gggataaacc taaggccctg   1440
atccaaagca gcctgttgag ctggttctcc agggctgcag tctctccagg tgtacagctg   1500
ctgtccctgc cctgtcctgt ccttgcacag tctcctatgt ctgagcccca gtgccttctg   1560
ttcgggccct cctttggtgg gaaggcagag ccctgaccct tgaatggttg tccttgactc   1620
tgtgctgctg ccttctgcag agaggcacct aagctgttta agagcccagt gattgtggc    1680 tgctcctcct agaggtggga gggggcaaga ggcctccttg gtcagtgtcc atgctttctg   1740
ggcagggact tggttttttg ttccaacagt ggccttctcc gggcttcata gttctttgta   1800
atatgttgaa gttaatttga attgactgat tttgttgaac tgtgtgttta agctgttgca   1860
ttaaaaagct tcttctaca tcaatatctg ctgtgctttc atttatgcct tttcagcttt    1920
gcacctggaa ctctgtagta ataataaaag ttattgctta tgggcattc aaaaaaaaaa    1980 aaaaaaaa                                                            1988
```

<210> SEQ ID NO 17
<211> LENGTH: 309
<212> TYPE: PRT
<213> ORGANISM: Mus musclus

<400> SEQUENCE: 17

Met Ala Pro Lys Val Ser Asp Ser Val Glu Gln Leu Arg Ala Ala Gly
1               5                   10                  15

Asn Gln Asn Phe Arg Asn Gly Gln Tyr Gly Glu Ala Ser Ala Leu Tyr
            20                  25                  30

-continued

```
Glu Arg Ala Leu Arg Leu Leu Gln Ala Arg Gly Ser Ala Asp Pro Glu
                35                  40                  45

Glu Glu Ser Val Leu Tyr Ser Asn Arg Ala Ala Cys Tyr Leu Lys Asp
        50                  55                  60

Gly Asn Cys Thr Asp Cys Ile Lys Asp Cys Thr Ser Ala Leu Ala Leu
65                  70                  75                  80

Val Pro Phe Ser Ile Lys Pro Leu Leu Arg Arg Ala Ser Ala Tyr Glu
                85                  90                  95

Ala Leu Glu Lys Tyr Ala Leu Ala Tyr Val Asp Tyr Lys Thr Val Leu
            100                 105                 110

Gln Ile Asp Asn Ser Val Ala Ser Ala Leu Glu Gly Ile Asn Arg Ile
            115                 120                 125

Thr Arg Ala Leu Met Asp Ser Leu Gly Pro Glu Trp Arg Leu Lys Leu
130                 135                 140

Pro Pro Ile Pro Val Val Pro Val Ser Ala Gln Lys Arg Trp Asn Ser
145                 150                 155                 160

Leu Pro Ser Asp Asn His Lys Glu Thr Ala Lys Thr Lys Ser Lys Glu
                165                 170                 175

Ala Thr Ala Thr Lys Ser Arg Val Pro Ser Ala Gly Asp Val Glu Arg
            180                 185                 190

Ala Lys Ala Leu Lys Glu Glu Gly Asn Asp Leu Val Lys Lys Gly Asn
        195                 200                 205

His Lys Lys Ala Ile Glu Lys Tyr Ser Glu Ser Leu Leu Cys Ser Ser
    210                 215                 220

Leu Glu Ser Ala Thr Tyr Ser Asn Arg Ala Leu Cys His Leu Val Leu
225                 230                 235                 240

Lys Gln Tyr Lys Glu Ala Val Lys Asp Cys Thr Glu Ala Leu Lys Leu
                245                 250                 255

Asp Gly Lys Asn Val Lys Ala Phe Tyr Arg Arg Ala Gln Ala Tyr Lys
            260                 265                 270

Ala Leu Lys Asp Tyr Lys Ser Ser Leu Ser Asp Ile Ser Ser Leu Leu
        275                 280                 285

Gln Ile Glu Pro Arg Asn Gly Pro Ala Gln Lys Leu Arg Gln Glu Val
    290                 295                 300

Asn Gln Asn Met Asn
305

<210> SEQ ID NO 18
<211> LENGTH: 309
<212> TYPE: PRT
<213> ORGANISM: Homo sapiens

<400> SEQUENCE: 18

Met Ala Pro Lys Phe Pro Asp Ser Val Glu Glu Leu Arg Ala Ala Gly
1               5                   10                  15

Asn Glu Ser Phe Arg Asn Gly Gln Tyr Ala Glu Ala Ser Ala Leu Tyr
            20                  25                  30

Gly Arg Ala Leu Arg Val Leu Gln Ala Gln Gly Ser Ser Asp Pro Glu
        35                  40                  45

Glu Glu Ser Val Leu Tyr Ser Asn Arg Ala Ala Cys His Trp Lys Asn
    50                  55                  60

Gly Asn Cys Arg Asp Cys Ile Lys Asp Cys Thr Ser Ala Leu Ala Leu
65                  70                  75                  80

Val Pro Phe Ser Ile Lys Pro Leu Leu Arg Arg Ala Ser Ala Tyr Glu
                85                  90                  95
```

Ala Leu Glu Lys Tyr Pro Met Ala Tyr Val Asp Tyr Lys Thr Val Leu
            100                 105                 110

Gln Ile Asp Asp Asn Val Thr Ser Ala Val Glu Gly Ile Asn Arg Met
        115                 120                 125

Thr Arg Ala Leu Met Asp Ser Leu Gly Pro Glu Trp Arg Leu Lys Leu
    130                 135                 140

Pro Ser Phe Pro Leu Val Pro Val Ser Ala Gln Lys Arg Trp Asn Phe
145                 150                 155                 160

Leu Pro Ser Glu Asn His Lys Glu Met Ala Lys Ser Lys Ser Lys Glu
                165                 170                 175

Thr Thr Ala Thr Lys Asn Arg Val Pro Ser Ala Gly Asp Val Glu Lys
            180                 185                 190

Ala Arg Val Leu Lys Glu Glu Gly Asn Glu Leu Val Lys Lys Gly Asn
        195                 200                 205

His Lys Lys Ala Ile Glu Lys Tyr Ser Glu Ser Leu Leu Cys Ser Asn
    210                 215                 220

Leu Glu Ser Ala Thr Tyr Ser Asn Arg Ala Leu Cys Tyr Leu Val Leu
225                 230                 235                 240

Lys Gln Tyr Thr Glu Ala Val Lys Asp Cys Thr Glu Ala Leu Lys Leu
                245                 250                 255

Asp Gly Lys Asn Val Lys Ala Phe Tyr Arg Arg Ala Gln Ala His Lys
            260                 265                 270

Ala Leu Lys Asp Tyr Lys Ser Ser Phe Ala Asp Ile Ser Asn Leu Leu
        275                 280                 285

Gln Ile Glu Pro Arg Asn Gly Pro Ala Gln Lys Leu Arg Gln Glu Val
    290                 295                 300

Lys Gln Asn Leu His
305

<210> SEQ ID NO 19
<211> LENGTH: 2420
<212> TYPE: DNA
<213> ORGANISM: Homo sapiens

<400> SEQUENCE: 19
gactggctgg tgcgggaaat atgcaggaga aaagtctttg cataatgtag agcgagccgt      60
ggggctccgg gagcggcgcc ccaaggtctg gggccatgaa cgcgagcgtg aaggagaca     120
ccttttctgg atcgatgcaa atcccaggag gcaccacggt cgtggtggag ctggcaccgg    180
acatccacat ctgcggcctc tgtaagcagc acttcagcaa tctggatgcc tttgtggccc    240
acaaacagag cggctgccag ctgactacca cgccggtgac agcccccagc acggtccagt    300
ttgtggcaga ggagacagag cctgccaccc agaccaccac aacgaccatc agttcagaga    360
ctcagactat cacagtttca gctccagagt tcgtctttga acatggctac caaacttacc    420
tgcccacgga gagcactgac aaccagacag ccaccgtgat ctctctcccc accaagtcac    480
gcaccaaaaa gcccacagca cccctgctc agaagagact cggctgctgc tatccaggtt    540
gccagttcaa gaccgcctat ggcatgaagg acatggagcg acacctgaag atccacaccg    600
gtgacaaacc ccacaagtgt gaggtgtgcg ggaagtgctt cagccggaag acaagctga    660
agacgcacat gcgctgccac acgggcgtca agccctacaa gtgcaagacg tgcgactacg    720
cggcggcgga cagcagcagc cttaacaagc acctgcgcat ccactcggac gagcgaccct    780
tcaagtgcca gatctgtccc tacgccagcc gcaactccag ccagctcacc gtgcacctgc    840

```
gctcgcacac ggggggacgcc cccttccagt gctggctctg tagtgccaag ttcaaaatca    900
gctcggactt gaaaaggcac atgcgtgtgc actcggggga gaagcctttc aagtgcgaat    960
tctgcaatgt ccgctgtacc atgaagggga acctcaaatc gcacatccgc atcaagcaca   1020
gtgggaataa cttcaagtgt ccgcactgcg acttcctggg tgacagcaaa tccaccctgc   1080
ggaagcacag tcgcctgcac cagtcggagc acccggagaa gtgtcccgag tgcagctact   1140
cctgttccag caaggccgcg ctgcgcgtgc acgagcgcat ccactgcacc gagcgccgt    1200
tcaagtgcag ctactgcagc ttcgatacca agcaacccag caacctgagc aagcacatga   1260
agaagttcca cgccgacatg ctcaagaacg aggctccgga gaagaaggag agcggcaggc   1320
agagcagccg gcaggtggcc aggctggatg ccaagaagac gttccactgc gacatctgtg   1380
acgcctcgtt tatgcgggag gactcgctcc gcagccacaa cggcagcac agtgagtacc    1440
acagtaagaa ctcggacgtg actgtagtac agcttcacct tgaacccagc aagcagccgc   1500
tgcgcccctc accgtagagc aaatccaggt ccccctccag tccagccagg tgccccagtt   1560
cagcgagggg agggtcaaga tcatcgtggg gcattacagg tgcctcagac gaaccgccat   1620
agtccaagcg gccgcagctg ccgtcaacat tgtgccccc accctggtag cccagacccc    1680
agaggagatc ccagggaacg gccggctaca gatccttcgc caggtcagtc tcattgcccc   1740
tcctcagtcc tccgggtgtc ccggcgaagc aggtgccctg agtcagccaa ctgtcctgct   1800
gaccacccat gatcagacgg caggggccgc cctgcagcag gctctgatcc ccaccaccc    1860
ggttgggacc caggaaggca cgggaaacca gacattcatt gccagttcgg gcatcgtgct   1920
cggacttgga aggccttaag ctctattcag gagggaacga cggaagtgac tgtggtgagc   1980
gatggggacc agagcatcgc agtggccacc acggcaccct ctatcttctc tacccagcag   2040
gaactgccca gcagactta ctccatcatc acggggcgg cacacccgc cctgctctgt      2100
cccgccgact ccattcctga ttagtctgga gggaggggtg acagacaaga caaactgcga   2160
gaggagtact gtgagaggct cctggtcccg cataaataat tgtattttat acagtttatg   2220
taatttttta acagggtatc aagctggaga ccattctccc tcaagctctt gttgattgtg   2280
tcttaatggt taccaaggct gattccaatg tggagttgga attcaccaca gtaggactga   2340
atacattcgt ttgttttttcc atgtttagga tttaatttttt ttcaactgga ataaaggagt   2400
ttgggatttg ggttaaaaaa                                              2420

<210> SEQ ID NO 20
<211> LENGTH: 3048
<212> TYPE: DNA
<213> ORGANISM: Homo sapiens

<400> SEQUENCE: 20
gagtcctccc cgcctcgcag agttggggaga aggcagggtg ggggggtgtgg aaaaataaaa     60
ggaaaagtcc ttgcaccatg tagatcagcg tcccccactt tggcatcccg gccggccggg    120
gacctcccag tctgcggcca tgaacgcgag cagcgagggc gagagcttcg cgggctcggt    180
gcaaattcca ggtggcacaa cggtgctggt ggagctgact cccgacatcc atatctgcgg    240
catctgcaag cagcagttta caacctgga tgcctttgta gctcacaagc aaagtggctg    300
ccagctgaca ggcacatccg cagcagcccc cagcacggtc cagtttgtat cggaggaaac    360
agtgcctgcc acccagactc agaccaccac cagaaccatc acctcggaga cccagacaat    420
cacagtttca gctccagaat ttgttttttga acatggctat caaacttacc tgcccacgga    480
aagtaatgaa aaccagacag ccactgtcat ctctctccct gccaagtcac gcaccaaaaa    540
```

```
gcccacaaca ccacctgctc agaaaaggct taactgttgc tatccaggtt gccaattcaa    600
gactgcttat ggcatgaagg acatggagcg gcatttaaaa attcacacgg gagacaaacc    660
ccataagtgt gaagtctgtg gcaagtgctt tagccggaaa gacaagctga aaactcacat    720
gcggtgccac acgggcgtga agccctacaa gtgtaagacg tgtgactacg ccgctgccga    780
cagcagcagc ctcaacaagc acctgaggat ccactcggac gagcggccct tcaaatgcca    840
gatctgcccc tacgccagcc gcaactccag ccagctcact gtccacctgc gatcccacac    900
gggggacgcc cccttccagt gctggctctg tagcgccaag ttcaaaatca gctcggactt    960
gaaaaggcac atgcgggtgc actcggggga gaagcctttc aagtgcgagt ctgcaatgt    1020
ccgctgcacc atgaagggga acctcaagtc gcacatccgt atcaagcaca gcgggaataa    1080
cttcaagtgt cctcattgcg acttcctggg tgacagcaaa gccaccctcc ggaagcacag    1140
ccgcgtgcac cagtcggagc atcctgagaa gtgctcggaa tgcagctact cctgctccag    1200
caaggccgcc ctgcgcatcc acgagcgtat ccactgcacc gaccgccctt tcaagtgcaa    1260
ctactgcagc ttcgacacca acagcccag caacctgagc aagcacatga gaagttcca    1320
cggggacatg gttaagactg aggctctaga gaggaaggac accggcaggc agagcagccg    1380
gcaggtggcc aagctggatg ccaagaagag tttccactgc gatatatgcg atgcctcctt    1440
catgcgggag gactcgctcc gcagccacaa gagacagcac agtgagtaca atgagagtaa    1500
gaactcggac gtgaccgttc tccagtttca gatcgacccc agcaagcagc ccgccacgcc    1560
cctcactgtg ggacacctcc aggtgcccct ccagcccagc caagtgcccc agttcagcga    1620
gggaagagtc aaaatcatcg ttgggcatca ggtgccccag gcgaacacca tcgtccaggc    1680
tgccgctgct gcagtgaaca tcgtcccgcc tgccttggtg gcccagaacc cagaggaact    1740
cccagggaac agccggctgc agatcctgcg ccaggtcagt ctgatcgccc ccctcagtc    1800
ctcgcggtgt ccgagcgagg cgggcgcaat gacccagccg gctgtcctgc tgaccaccca    1860
cgagcagacg gacggagcca ctctgcacca gactctcatc cccacggcct caggtggccc    1920
ccaggaaggc tctggcaatc aaactttcat taccagttcg ggtattactt gcactgactt    1980
tgaaggccta aacgccttga ttcaggaggg gacagcagaa gtgacagtgg tgagcgatgg    2040
aggccagaac atcgcagtgg ccaccacagc gccaccggtc ttctcctcct cttcccagca    2100
agaactaccc aagcagacct actccatcat tcaaggggca gcccatccag cttttgctctg    2160
tcccgccgac tccattccag attagtgctt aaaaaacaaa aggagtgggg gaaaggaatt    2220
gagaaaaaga aatcttaagt agaattctct aaaaggtttg ctcttaatgt tttctttgtt    2280
ttgttttgtt tttgagacgg agtctcgctc tgtttcccag gctggagtgc agtggcgcta    2340
tcttggctca ctgcaacgtc cgcctccagg gttcaagcga ttctcatgcc tcggccctcc    2400
gagtagctgg gaccacaggt gtacgacatc atgactggct aatttttgta tatttaatag    2460
aggcggggtt tcatcatgtt gaactcctga cctcaagtga tctgcccacc tcagcctccc    2520
aaagtgctgg gattacaggt gtgagccacc atgcctggcc gtggtttgct cttaatgttt    2580
ttaaggatgg ttgtgaatcc ccctggcccc ataataaatt gtaattttat actgcttact    2640
ataatttttt taacactgta acaactttga gaccacctct gaatcgtcgc attataactg    2700
ttgtagaatc ttaaatgtta ccaagatgat tccaatgagg ggttggaatt aaatgcatta    2760
agtagtgaac tcatgtgttt gtttccaact tgattttcca actctaataa aggtttctgt    2820
ccatcttatt acatttgtgt agtaaatggt acttcccagc ctctcttttg ccccattctg    2880
```

```
gaatactccc cagagtttgg gggtgttcat gttttataca tgtaagtctg ttggcatgaa    2940
ggaccatttt ctacataata tgacatggat acttgaccca aaaaaaatgt ttagtgctaa    3000
tgagcagaaa atgaatggtt ccataataaa ttgatatctg attaaaat                 3048
```

<210> SEQ ID NO 21
<211> LENGTH: 473
<212> TYPE: PRT
<213> ORGANISM: Mus musculus

<400> SEQUENCE: 21

```
Met Asn Ala Ser Val Glu Gly Asp Thr Phe Ser Gly Ser Met Gln Ile
1               5                   10                  15

Pro Gly Gly Thr Thr Val Val Val Glu Leu Ala Pro Asp Ile His Ile
            20                  25                  30

Cys Gly Leu Cys Lys Gln His Phe Ser Asn Leu Asp Ala Phe Val Ala
        35                  40                  45

His Lys Gln Ser Gly Cys Gln Leu Thr Thr Thr Pro Val Thr Ala Pro
    50                  55                  60

Ser Thr Val Gln Phe Val Ala Glu Thr Glu Pro Ala Thr Gln Thr
65                  70                  75                  80

Thr Thr Thr Thr Ile Ser Ser Glu Thr Gln Thr Ile Thr Val Ser Ala
                85                  90                  95

Pro Glu Phe Val Phe Glu His Gly Tyr Gln Thr Tyr Leu Pro Thr Glu
            100                 105                 110

Ser Thr Asp Asn Gln Thr Ala Thr Val Ile Ser Leu Pro Thr Lys Ser
        115                 120                 125

Arg Thr Lys Lys Pro Thr Ala Pro Pro Ala Gln Lys Arg Leu Gly Cys
    130                 135                 140

Cys Tyr Pro Gly Cys Gln Phe Lys Thr Ala Tyr Gly Met Lys Asp Met
145                 150                 155                 160

Glu Arg His Leu Lys Ile His Thr Gly Asp Lys Pro His Lys Cys Glu
                165                 170                 175

Val Cys Gly Lys Cys Phe Ser Arg Lys Asp Lys Leu Lys Thr His Met
            180                 185                 190

Arg Cys His Thr Gly Val Lys Pro Tyr Lys Cys Lys Thr Cys Asp Tyr
        195                 200                 205

Ala Ala Ala Asp Ser Ser Ser Leu Asn Lys His Leu Arg Ile His Ser
    210                 215                 220

Asp Glu Arg Pro Phe Lys Cys Gln Ile Cys Pro Tyr Ala Ser Arg Asn
225                 230                 235                 240

Ser Ser Gln Leu Thr Val His Leu Arg Ser His Thr Gly Asp Ala Pro
                245                 250                 255

Phe Gln Cys Trp Leu Cys Ser Ala Lys Phe Lys Ile Ser Ser Asp Leu
            260                 265                 270

Lys Arg His Met Arg Val His Ser Gly Glu Lys Pro Phe Lys Cys Glu
        275                 280                 285

Phe Cys Asn Val Arg Cys Thr Met Lys Gly Asn Leu Lys Ser His Ile
    290                 295                 300

Arg Ile Lys His Ser Gly Asn Asn Phe Lys Cys Pro His Cys Asp Phe
305                 310                 315                 320

Leu Gly Asp Ser Lys Ser Thr Leu Arg Lys His Ser Arg Leu His Gln
                325                 330                 335

Ser Glu His Pro Glu Lys Cys Pro Glu Cys Ser Tyr Ser Cys Ser Ser
            340                 345                 350
```

```
Lys Ala Ala Leu Arg Val His Glu Arg Ile His Cys Thr Glu Arg Pro
            355                 360                 365

Phe Lys Cys Ser Tyr Cys Ser Phe Asp Thr Lys Gln Pro Ser Asn Leu
            370                 375                 380

Ser Lys His Met Lys Lys Phe His Ala Asp Met Leu Lys Asn Glu Ala
385                 390                 395                 400

Pro Glu Lys Lys Glu Ser Gly Arg Gln Ser Arg Gln Val Ala Arg
                405                 410                 415

Leu Asp Ala Lys Lys Thr Phe His Cys Asp Ile Cys Asp Ala Ser Phe
            420                 425                 430

Met Arg Glu Asp Ser Leu Arg Ser His Lys Arg Gln His Ser Glu Tyr
            435                 440                 445

His Ser Lys Asn Ser Asp Val Thr Val Val Gln Leu His Leu Glu Pro
            450                 455                 460

Ser Lys Gln Pro Leu Arg Pro Ser Pro
465                 470

<210> SEQ ID NO 22
<211> LENGTH: 473
<212> TYPE: PRT
<213> ORGANISM: Mus musculus

<400> SEQUENCE: 22

Met Asn Ala Ser Val Glu Gly Asp Thr Phe Ser Gly Ser Met Gln Ile
1               5                   10                  15

Pro Gly Gly Thr Thr Val Val Val Glu Leu Ala Pro Asp Ile His Ile
            20                  25                  30

Cys Gly Leu Cys Lys Gln His Phe Ser Asn Leu Asp Ala Phe Val Ala
            35                  40                  45

His Lys Gln Ser Gly Cys Gln Leu Thr Thr Thr Pro Val Thr Ala Pro
        50                  55                  60

Ser Thr Val Gln Phe Val Ala Glu Glu Thr Glu Pro Ala Thr Gln Thr
65                  70                  75                  80

Thr Thr Thr Thr Ile Ser Ser Glu Thr Gln Thr Ile Thr Val Ser Ala
                85                  90                  95

Pro Glu Phe Val Phe Glu His Gly Tyr Gln Thr Tyr Leu Pro Thr Glu
            100                 105                 110

Ser Thr Asp Asn Gln Thr Ala Thr Val Ile Ser Leu Pro Thr Lys Ser
            115                 120                 125

Arg Thr Lys Lys Pro Thr Ala Pro Pro Ala Gln Lys Arg Leu Gly Cys
130                 135                 140

Cys Tyr Pro Gly Cys Gln Phe Lys Thr Ala Tyr Gly Met Lys Asp Met
145                 150                 155                 160

Glu Arg His Leu Lys Ile His Thr Gly Asp Lys Pro His Lys Cys Glu
            165                 170                 175

Val Cys Gly Lys Cys Phe Ser Arg Lys Asp Lys Leu Lys Thr His Met
            180                 185                 190

Arg Cys His Thr Gly Val Lys Pro Tyr Lys Cys Lys Thr Cys Asp Tyr
            195                 200                 205

Ala Ala Ala Asp Ser Ser Ser Leu Asn Lys His Leu Arg Ile His Ser
        210                 215                 220

Asp Glu Arg Pro Phe Lys Cys Gln Ile Cys Pro Tyr Ala Ser Arg Asn
225                 230                 235                 240

Ser Ser Gln Leu Thr Val His Leu Arg Ser His Thr Gly Asp Ala Pro
```

```
                245                 250                 255
Phe Gln Cys Trp Leu Cys Ser Ala Lys Phe Lys Ile Ser Ser Asp Leu
            260                 265                 270

Lys Arg His Met Arg Val His Ser Gly Glu Lys Pro Phe Lys Cys Glu
        275                 280                 285

Phe Cys Asn Val Arg Cys Thr Met Lys Gly Asn Leu Lys Ser His Ile
    290                 295                 300

Arg Ile Lys His Ser Gly Asn Asn Phe Lys Cys Pro His Cys Asp Phe
305                 310                 315                 320

Leu Gly Asp Ser Lys Ser Thr Leu Arg Lys His Ser Arg Leu His Gln
            325                 330                 335

Ser Glu His Pro Glu Lys Cys Pro Glu Cys Ser Tyr Ser Cys Ser Ser
        340                 345                 350

Lys Ala Ala Leu Arg Val His Glu Arg Ile His Cys Thr Glu Arg Pro
    355                 360                 365

Phe Lys Cys Ser Tyr Cys Ser Phe Asp Thr Lys Gln Pro Ser Asn Leu
370                 375                 380

Ser Lys His Met Lys Lys Phe His Ala Asp Met Leu Lys Asn Glu Ala
385                 390                 395                 400

Pro Glu Lys Lys Glu Ser Gly Arg Gln Ser Arg Gln Val Ala Arg
            405                 410                 415

Leu Asp Ala Lys Lys Thr Phe His Cys Asp Ile Cys Asp Ala Ser Phe
            420                 425                 430

Met Arg Glu Asp Ser Leu Arg Ser His Lys Arg Gln His Ser Glu Tyr
        435                 440                 445

His Ser Lys Asn Ser Asp Val Thr Val Gln Leu His Leu Glu Pro
    450                 455                 460

Ser Lys Gln Pro Leu Arg Pro Ser Pro
465                 470

<210> SEQ ID NO 23
<211> LENGTH: 643
<212> TYPE: PRT
<213> ORGANISM: Mus musculus

<400> SEQUENCE: 23

Met Asn Ala Ser Val Glu Gly Asp Thr Phe Ser Gly Ser Met Gln Ile
1               5                   10                  15

Pro Gly Gly Thr Thr Val Leu Val Glu Leu Ala Pro Asp Ile His Ile
            20                  25                  30

Cys Gly Leu Cys Lys Gln His Phe Ser Asn Leu Asp Ala Phe Val Ala
        35                  40                  45

His Lys Gln Ser Gly Cys Gln Leu Thr Thr Thr Pro Val Thr Ala Pro
    50                  55                  60

Ser Thr Val Gln Phe Val Ala Glu Glu Thr Glu Pro Ala Thr Gln Thr
65                  70                  75                  80

Thr Thr Thr Thr Ile Ser Ser Glu Thr Gln Thr Ile Thr Val Ser Ala
                85                  90                  95

Pro Glu Phe Val Phe Glu His Gly Tyr Gln Thr Tyr Leu Pro Thr Glu
            100                 105                 110

Ser Thr Asp Asn Gln Thr Ala Thr Val Ile Ser Leu Pro Thr Lys Ser
        115                 120                 125

Arg Thr Lys Lys Pro Thr Ala Pro Pro Ala Gln Lys Arg Leu Gly Cys
    130                 135                 140
```

```
Cys Tyr Pro Gly Cys Gln Phe Lys Thr Ala Tyr Gly Met Lys Asp Met
145                 150                 155                 160

Glu Arg His Leu Lys Ile His Thr Gly Asp Lys Pro His Lys Cys Glu
                165                 170                 175

Val Cys Gly Lys Cys Phe Ser Arg Lys Asp Lys Leu Lys Thr His Met
                180                 185                 190

Arg Cys His Thr Gly Val Lys Pro Tyr Lys Cys Lys Thr Cys Asp Tyr
                195                 200                 205

Ala Ala Ala Asp Ser Ser Leu Asn Lys His Leu Arg Ile His Ser
210                 215                 220

Asp Glu Arg Pro Phe Lys Cys Gln Ile Cys Pro Tyr Ala Ser Arg Asn
225                 230                 235                 240

Ser Ser Gln Leu Thr Val His Leu Arg Ser His Thr Ala Ser Val Leu
                245                 250                 255

Glu Asn Asp Val Gln Lys Pro Ala Gly Leu Pro Ala Glu Glu Ser Asp
                260                 265                 270

Ala Gln Gln Ala Pro Ala Val Thr Leu Ser Leu Glu Ala Lys Glu Arg
                275                 280                 285

Thr Ala Thr Leu Gly Glu Arg Thr Phe Asn Cys Arg Tyr Pro Gly Cys
                290                 295                 300

His Phe Lys Thr Val His Gly Met Lys Asp Leu Asp Arg His Leu Arg
305                 310                 315                 320

Ile His Thr Gly Asp Lys Pro His Lys Cys Glu Phe Cys Asp Lys Cys
                325                 330                 335

Phe Ser Arg Lys Asp Asn Leu Thr Met His Met Arg Cys His Thr Ser
                340                 345                 350

Val Lys Pro His Lys Cys His Leu Cys Asp Tyr Ala Ala Val Asp Ser
                355                 360                 365

Ser Ser Leu Lys Lys His Leu Arg Ile His Ser Asp Glu Arg Pro Tyr
                370                 375                 380

Lys Cys Gln Leu Cys Pro Tyr Ala Ser Arg Asn Ser Ser Gln Leu Thr
385                 390                 395                 400

Val His Leu Arg Ser His Thr Gly Asp Thr Pro Phe Gln Cys Trp Leu
                405                 410                 415

Cys Ser Ala Lys Phe Lys Ile Ser Ser Asp Leu Lys Arg His Met Ile
                420                 425                 430

Val His Ser Gly Glu Lys Pro Phe Lys Cys Glu Phe Cys Asp Val Arg
                435                 440                 445

Cys Thr Met Lys Ala Asn Leu Lys Ser His Ile Arg Ile Lys His Thr
450                 455                 460

Phe Lys Cys Leu His Cys Ala Phe Gln Gly Arg Asp Arg Ala Asp Leu
465                 470                 475                 480

Leu Glu His Ser Arg Leu His Gln Ala Asp His Pro Glu Lys Cys Pro
                485                 490                 495

Glu Cys Ser Tyr Ser Cys Ser Asn Pro Ala Ala Leu Arg Val His Ser
                500                 505                 510

Arg Val His Cys Thr Asp Arg Pro Phe Lys Cys Asp Phe Cys Ser Phe
                515                 520                 525

Asp Thr Lys Arg Pro Ser Ser Leu Ala Lys His Ile Asp Lys Val His
                530                 535                 540

Arg Glu Gly Ala Lys Thr Glu Asn Arg Ala Pro Pro Gly Lys Asp Gly
545                 550                 555                 560

Pro Gly Glu Ser Gly Pro His His Val Pro Asn Val Ser Thr Gln Arg
```

```
                        565                 570                 575
Ala Phe Gly Cys Asp Lys Cys Gly Ala Ser Phe Val Arg Asp Asp Ser
                580                 585                 590

Leu Arg Cys His Arg Lys Gln His Ser Asp Trp Gly Glu Asn Lys Asn
                595                 600                 605

Ser Asn Leu Val Thr Phe Pro Ser Glu Gly Ile Ala Thr Gly Gln Leu
            610                 615                 620

Gly Pro Leu Val Ser Val Gly Gln Leu Glu Ser Thr Leu Glu Pro Ser
625                 630                 635                 640

His Asp Leu

<210> SEQ ID NO 24
<211> LENGTH: 272
<212> TYPE: PRT
<213> ORGANISM: Mus musculus

<400> SEQUENCE: 24

Met Asn Ala Ser Val Glu Gly Asp Thr Phe Ser Gly Ser Met Gln Ile
1               5                   10                  15

Pro Gly Gly Thr Thr Val Leu Val Glu Leu Ala Pro Asp Ile His Ile
            20                  25                  30

Cys Gly Leu Cys Lys Gln His Phe Ser Asn Leu Asp Ala Phe Val Ala
        35                  40                  45

His Lys Gln Ser Gly Cys Gln Leu Thr Thr Thr Pro Val Thr Ala Pro
    50                  55                  60

Ser Thr Val Gln Phe Val Ala Glu Glu Thr Glu Pro Ala Thr Gln Thr
65                  70                  75                  80

Thr Thr Thr Thr Ile Ser Ser Glu Thr Gln Thr Ile Thr Val Ser Ala
                85                  90                  95

Pro Glu Phe Val Phe Glu His Gly Tyr Gln Thr Tyr Leu Pro Thr Glu
            100                 105                 110

Ser Thr Asp Asn Gln Thr Ala Thr Val Ile Ser Leu Pro Thr Lys Ser
        115                 120                 125

Arg Thr Lys Lys Pro Thr Ala Pro Pro Ala Gln Lys Arg Leu Gly Cys
    130                 135                 140

Cys Tyr Pro Gly Cys Gln Phe Lys Thr Ala Tyr Gly Met Lys Asp Met
145                 150                 155                 160

Glu Arg His Leu Lys Ile His Thr Gly Asp Lys Pro His Lys Cys Glu
                165                 170                 175

Val Cys Gly Lys Cys Phe Ser Arg Lys Asp Lys Leu Lys Thr His Met
            180                 185                 190

Arg Cys His Thr Gly Val Lys Pro Tyr Lys Cys Lys Thr Cys Asp Tyr
        195                 200                 205

Ala Ala Ala Asp Ser Ser Ser Leu Asn Lys His Leu Arg Ile His Ser
    210                 215                 220

Asp Glu Arg Pro Phe Lys Cys Gln Ile Cys Pro Tyr Ala Ser Arg Asn
225                 230                 235                 240

Ser Ser Gln Leu Thr Val His Leu Arg Ser His Thr Ala Trp Arg Cys
                245                 250                 255

Asp Cys Leu Gly Ser Thr Lys Pro Trp Val Pro Ser Leu Val Thr Thr
            260                 265                 270

<210> SEQ ID NO 25
<211> LENGTH: 681
<212> TYPE: PRT
```

<213> ORGANISM: Homo sapiens

<400> SEQUENCE: 25

```
Met Asn Ala Ser Ser Glu Gly Glu Ser Phe Ala Gly Ser Val Gln Ile
1               5                   10                  15
Pro Gly Gly Thr Thr Val Leu Val Glu Leu Thr Pro Asp Ile His Ile
            20                  25                  30
Cys Gly Ile Cys Lys Gln Gln Phe Asn Asn Leu Asp Ala Phe Val Ala
        35                  40                  45
His Lys Gln Ser Gly Cys Gln Leu Thr Gly Thr Ser Ala Ala Ala Pro
    50                  55                  60
Ser Thr Val Gln Phe Val Ser Glu Glu Thr Val Pro Ala Thr Gln Thr
65                  70                  75                  80
Gln Thr Thr Thr Arg Thr Ile Thr Ser Glu Thr Gln Thr Ile Thr Val
                85                  90                  95
Ser Ala Pro Glu Phe Val Phe Glu His Gly Tyr Gln Thr Tyr Leu Pro
            100                 105                 110
Thr Glu Ser Asn Glu Asn Gln Thr Ala Thr Val Ile Ser Leu Pro Ala
        115                 120                 125
Lys Ser Arg Thr Lys Lys Pro Thr Thr Pro Ala Gln Lys Arg Leu
    130                 135                 140
Asn Cys Cys Tyr Pro Gly Cys Gln Phe Lys Thr Ala Tyr Gly Met Lys
145                 150                 155                 160
Asp Met Glu Arg His Leu Lys Ile His Thr Gly Asp Lys Pro His Lys
                165                 170                 175
Cys Glu Val Cys Gly Lys Cys Phe Ser Arg Lys Asp Lys Leu Lys Thr
            180                 185                 190
His Met Arg Cys His Thr Gly Val Lys Pro Tyr Lys Cys Lys Thr Cys
        195                 200                 205
Asp Tyr Ala Ala Ala Asp Ser Ser Ser Leu Asn Lys His Leu Arg Ile
    210                 215                 220
His Ser Asp Glu Arg Pro Phe Lys Cys Gln Ile Cys Pro Tyr Ala Ser
225                 230                 235                 240
Arg Asn Ser Ser Gln Leu Thr Val His Leu Arg Ser His Thr Gly Asp
                245                 250                 255
Ala Pro Phe Gln Cys Trp Leu Cys Ser Ala Lys Phe Lys Ile Ser Ser
            260                 265                 270
Asp Leu Lys Arg His Met Arg Val His Ser Gly Glu Lys Pro Phe Lys
        275                 280                 285
Cys Glu Phe Cys Asn Val Arg Cys Thr Met Lys Gly Asn Leu Lys Ser
    290                 295                 300
His Ile Arg Ile Lys His Ser Gly Asn Asn Phe Lys Cys Pro His Cys
305                 310                 315                 320
Asp Phe Leu Gly Asp Ser Lys Ala Thr Leu Arg Lys His Ser Arg Val
                325                 330                 335
His Gln Ser Glu His Pro Glu Lys Cys Ser Glu Cys Ser Tyr Ser Cys
            340                 345                 350
Ser Ser Lys Ala Ala Leu Arg Ile His Glu Arg Ile His Cys Thr Asp
        355                 360                 365
Arg Pro Phe Lys Cys Asn Tyr Cys Ser Phe Asp Thr Lys Gln Pro Ser
    370                 375                 380
Asn Leu Ser Lys His Met Lys Lys Phe His Gly Asp Met Val Lys Thr
385                 390                 395                 400
```

Glu Ala Leu Glu Arg Lys Asp Thr Gly Arg Gln Ser Arg Gln Val
                    405                 410                 415

Ala Lys Leu Asp Ala Lys Lys Ser Phe His Cys Asp Ile Cys Asp Ala
            420                 425                 430

Ser Phe Met Arg Glu Asp Ser Leu Arg Ser His Lys Arg Gln His Ser
        435                 440                 445

Glu Tyr Asn Glu Ser Lys Asn Ser Asp Val Thr Val Leu Gln Phe Gln
    450                 455                 460

Ile Asp Pro Ser Lys Gln Pro Ala Thr Pro Leu Thr Val Gly His Leu
465                 470                 475                 480

Gln Val Pro Leu Gln Pro Ser Gln Val Pro Gln Phe Ser Glu Gly Arg
                485                 490                 495

Val Lys Ile Ile Val Gly His Gln Val Pro Gln Ala Asn Thr Ile Val
            500                 505                 510

Gln Ala Ala Ala Ala Val Asn Ile Val Pro Pro Ala Leu Val Ala
        515                 520                 525

Gln Asn Pro Glu Glu Leu Pro Gly Asn Ser Arg Leu Gln Ile Leu Arg
    530                 535                 540

Gln Val Ser Leu Ile Ala Pro Pro Gln Ser Ser Arg Cys Pro Ser Glu
545                 550                 555                 560

Ala Gly Ala Met Thr Gln Pro Ala Val Leu Leu Thr Thr His Glu Gln
                565                 570                 575

Thr Asp Gly Ala Thr Leu His Gln Thr Leu Ile Pro Thr Ala Ser Gly
            580                 585                 590

Gly Pro Gln Glu Gly Ser Gly Asn Gln Thr Phe Ile Thr Ser Ser Gly
        595                 600                 605

Ile Thr Cys Thr Asp Phe Glu Gly Leu Asn Ala Leu Ile Gln Glu Gly
    610                 615                 620

Thr Ala Glu Val Thr Val Val Ser Asp Gly Gly Gln Asn Ile Ala Val
625                 630                 635                 640

Ala Thr Thr Ala Pro Pro Val Phe Ser Ser Ser Gln Gln Glu Leu
                645                 650                 655

Pro Lys Gln Thr Tyr Ser Ile Ile Gln Gly Ala Ala His Pro Ala Leu
            660                 665                 670

Leu Cys Pro Ala Asp Ser Ile Pro Asp
        675                 680

<210> SEQ ID NO 26
<211> LENGTH: 627
<212> TYPE: PRT
<213> ORGANISM: Homo sapiens

<400> SEQUENCE: 26

Met Asn Ala Ser Ser Glu Gly Glu Ser Phe Ala Gly Ser Val Gln Ile
1               5                   10                  15

Pro Gly Gly Thr Thr Val Leu Val Glu Leu Thr Pro Asp Ile His Ile
                20                  25                  30

Cys Gly Ile Cys Lys Gln Gln Phe Asn Asn Leu Asp Ala Phe Val Ala
            35                  40                  45

His Lys Gln Ser Gly Cys Gln Leu Thr Gly Thr Ser Ala Ala Ala Pro
        50                  55                  60

Ser Thr Val Gln Phe Val Ser Glu Glu Thr Val Pro Ala Thr Gln Thr
65                  70                  75                  80

Gln Thr Thr Thr Arg Thr Ile Thr Ser Glu Thr Gln Thr Ile Thr Gly
                85                  90                  95

```
Cys Gln Phe Lys Thr Ala Tyr Gly Met Lys Asp Met Glu Arg His Leu
                100                 105                 110

Lys Ile His Thr Gly Asp Lys Pro His Lys Cys Glu Val Cys Gly Lys
            115                 120                 125

Cys Phe Ser Arg Lys Asp Lys Leu Lys Thr His Met Arg Cys His Thr
        130                 135                 140

Gly Val Lys Pro Tyr Lys Cys Lys Thr Cys Asp Tyr Ala Ala Ala Asp
145                 150                 155                 160

Ser Ser Ser Leu Asn Lys His Leu Arg Ile His Ser Asp Glu Arg Pro
                165                 170                 175

Phe Lys Cys Gln Ile Cys Pro Tyr Ala Ser Arg Asn Ser Ser Gln Leu
            180                 185                 190

Thr Val His Leu Arg Ser His Thr Gly Asp Ala Pro Phe Gln Cys Trp
        195                 200                 205

Leu Cys Ser Ala Lys Phe Lys Ile Ser Ser Asp Leu Lys Arg His Met
210                 215                 220

Arg Val His Ser Gly Glu Lys Pro Phe Lys Cys Glu Phe Cys Asn Val
225                 230                 235                 240

Arg Cys Thr Met Lys Gly Asn Leu Lys Ser His Ile Arg Ile Lys His
                245                 250                 255

Ser Gly Asn Asn Phe Lys Cys Pro His Cys Asp Phe Leu Gly Asp Ser
            260                 265                 270

Lys Ala Thr Leu Arg Lys His Ser Arg Val His Gln Ser Glu His Pro
        275                 280                 285

Glu Lys Cys Ser Glu Cys Ser Tyr Ser Cys Ser Ser Lys Ala Ala Leu
            290                 295                 300

Arg Ile His Glu Arg Ile His Cys Thr Asp Arg Pro Phe Lys Cys Asn
305                 310                 315                 320

Tyr Cys Ser Phe Asp Thr Lys Gln Pro Ser Asn Leu Ser Lys His Met
                325                 330                 335

Lys Lys Phe His Gly Asp Met Val Lys Thr Glu Ala Leu Glu Arg Lys
            340                 345                 350

Asp Thr Gly Arg Gln Ser Ser Arg Gln Val Ala Lys Leu Asp Ala Lys
        355                 360                 365

Lys Ser Phe His Cys Asp Ile Cys Asp Ala Ser Phe Met Arg Glu Asp
370                 375                 380

Ser Leu Arg Ser His Lys Arg Gln His Ser Glu Tyr Ser Glu Ser Lys
385                 390                 395                 400

Asn Ser Asp Val Thr Val Leu Gln Phe Gln Ile Asp Pro Ser Lys Gln
                405                 410                 415

Pro Ala Thr Pro Leu Thr Val Gly His Leu Gln Val Pro Leu Gln Pro
            420                 425                 430

Ser Gln Val Pro Gln Phe Ser Glu Gly Arg Val Lys Ile Ile Val Gly
        435                 440                 445

His Gln Val Pro Gln Ala Asn Thr Ile Val Gln Ala Ala Ala Ala
450                 455                 460

Val Asn Ile Val Pro Pro Ala Leu Val Ala Gln Asn Pro Glu Leu
465                 470                 475                 480

Pro Gly Asn Ser Arg Leu Gln Ile Leu Arg Gln Val Ser Leu Ile Ala
                485                 490                 495

Pro Pro Gln Ser Ser Arg Cys Pro Ser Glu Ala Gly Ala Met Thr Gln
            500                 505                 510
```

```
Pro Ala Val Leu Leu Thr Thr His Glu Gln Thr Asp Gly Ala Thr Leu
            515                 520                 525

His Gln Thr Leu Ile Pro Thr Ala Ser Gly Gly Pro Gln Glu Gly Ser
    530                 535                 540

Gly Asn Gln Thr Phe Ile Thr Ser Ser Gly Ile Thr Cys Thr Asp Phe
545                 550                 555                 560

Glu Gly Leu Asn Ala Leu Ile Gln Gly Thr Ala Glu Val Thr Val
                565                 570                 575

Val Ser Asp Gly Gly Gln Asn Ile Ala Val Ala Thr Thr Ala Pro Pro
            580                 585                 590

Val Phe Ser Ser Ser Gln Gln Glu Leu Pro Lys Gln Thr Tyr Ser
    595                 600                 605

Ile Ile Gln Gly Ala Ala His Pro Ala Leu Leu Cys Pro Ala Asp Ser
    610                 615                 620

Ile Pro Asp
625

<210> SEQ ID NO 27
<211> LENGTH: 681
<212> TYPE: PRT
<213> ORGANISM: Homo sapiens

<400> SEQUENCE: 27

Met Asn Ala Ser Ser Glu Gly Glu Ser Phe Ala Gly Ser Val Gln Ile
1               5                   10                  15

Pro Gly Gly Thr Thr Val Leu Val Glu Leu Thr Pro Asp Ile His Ile
                20                  25                  30

Cys Gly Ile Cys Lys Gln Gln Phe Asn Asn Leu Asp Ala Phe Val Ala
            35                  40                  45

His Lys Gln Ser Gly Cys Gln Leu Thr Gly Thr Ser Ala Ala Ala Pro
        50                  55                  60

Ser Thr Val Gln Phe Val Ser Glu Glu Thr Val Pro Ala Thr Gln Thr
65                  70                  75                  80

Gln Thr Thr Thr Arg Thr Ile Thr Ser Glu Thr Gln Thr Ile Thr Val
                85                  90                  95

Ser Ala Pro Glu Phe Val Phe Glu His Gly Tyr Gln Thr Tyr Leu Pro
                100                 105                 110

Thr Glu Ser Asn Glu Asn Gln Thr Ala Thr Val Ile Ser Leu Pro Ala
            115                 120                 125

Lys Ser Arg Thr Lys Lys Pro Thr Thr Pro Ala Gln Lys Arg Leu
        130                 135                 140

Asn Cys Cys Tyr Pro Gly Cys Gln Phe Lys Thr Ala Tyr Gly Met Lys
145                 150                 155                 160

Asp Met Glu Arg His Leu Lys Ile His Thr Gly Asp Lys Pro His Lys
                165                 170                 175

Cys Glu Val Cys Gly Lys Cys Phe Ser Arg Lys Asp Lys Leu Lys Thr
                180                 185                 190

His Met Arg Cys His Thr Gly Val Lys Pro Tyr Lys Cys Lys Thr Cys
            195                 200                 205

Asp Tyr Ala Ala Ala Asp Ser Ser Ser Leu Asn Lys His Leu Arg Ile
        210                 215                 220

His Ser Asp Glu Arg Pro Phe Lys Cys Gln Ile Cys Pro Tyr Ala Ser
225                 230                 235                 240

Arg Asn Ser Ser Gln Leu Thr Val His Leu Arg Ser His Thr Gly Asp
                245                 250                 255
```

```
Ala Pro Phe Gln Cys Trp Leu Cys Ser Ala Lys Phe Lys Ile Ser Ser
            260                 265                 270

Asp Leu Lys Arg His Met Arg Val His Ser Gly Glu Lys Pro Phe Lys
        275                 280                 285

Cys Glu Phe Cys Asn Val Arg Cys Thr Met Lys Gly Asn Leu Lys Ser
    290                 295                 300

His Ile Arg Ile Lys His Ser Gly Asn Asn Phe Lys Cys Pro His Cys
305                 310                 315                 320

Asp Phe Leu Gly Asp Ser Lys Ala Thr Leu Arg Lys His Ser Arg Val
                325                 330                 335

His Gln Ser Glu His Pro Glu Lys Cys Ser Cys Ser Cys Tyr Ser Cys
            340                 345                 350

Ser Ser Lys Ala Ala Leu Arg Ile His Glu Arg Ile His Cys Thr Asp
        355                 360                 365

Arg Pro Phe Lys Cys Asn Tyr Cys Ser Phe Asp Thr Lys Gln Pro Ser
    370                 375                 380

Asn Leu Ser Lys His Met Lys Lys Phe His Gly Asp Met Val Lys Thr
385                 390                 395                 400

Glu Ala Leu Glu Arg Lys Asp Thr Gly Arg Gln Ser Ser Arg Gln Val
                405                 410                 415

Ala Lys Leu Asp Ala Lys Lys Ser Phe His Cys Asp Ile Cys Asp Ala
            420                 425                 430

Ser Phe Met Arg Glu Asp Ser Leu Arg Ser His Lys Arg Gln His Ser
        435                 440                 445

Glu Tyr Ser Glu Ser Lys Asn Ser Asp Val Thr Val Leu Gln Phe Gln
    450                 455                 460

Ile Asp Pro Ser Lys Gln Pro Ala Thr Pro Leu Thr Val Gly His Leu
465                 470                 475                 480

Gln Val Pro Leu Gln Pro Ser Gln Val Pro Gln Phe Ser Glu Gly Arg
                485                 490                 495

Val Lys Ile Ile Val Gly His Gln Val Pro Gln Ala Asn Thr Ile Val
            500                 505                 510

Gln Ala Ala Ala Ala Val Asn Ile Val Pro Pro Ala Leu Val Ala
        515                 520                 525

Gln Asn Pro Glu Glu Leu Pro Gly Asn Ser Arg Leu Gln Ile Leu Arg
    530                 535                 540

Gln Val Ser Leu Ile Ala Pro Pro Gln Ser Ser Arg Cys Pro Ser Glu
545                 550                 555                 560

Ala Gly Ala Met Thr Gln Pro Ala Val Leu Leu Thr Thr His Glu Gln
                565                 570                 575

Thr Asp Gly Ala Thr Leu His Gly Thr Leu Ile Pro Thr Ala Ser Gly
            580                 585                 590

Gly Pro Gln Glu Gly Ser Gly Asn Gln Thr Phe Ile Thr Ser Ser Gly
        595                 600                 605

Ile Thr Cys Thr Asp Phe Glu Gly Leu Asn Ala Leu Ile Gln Glu Gly
    610                 615                 620

Thr Ala Glu Val Thr Val Val Ser Asp Gly Gly Gln Asn Ile Ala Val
625                 630                 635                 640

Ala Thr Thr Ala Pro Pro Val Phe Ser Ser Ser Gln Gln Glu Leu
                645                 650                 655

Pro Lys Gln Thr Tyr Ser Ile Ile Gln Gly Ala Ala His Pro Ala Leu
            660                 665                 670
```

```
Leu Cys Pro Ala Asp Ser Ile Pro Asp
        675                 680
```

<210> SEQ ID NO 28
<211> LENGTH: 226
<212> TYPE: PRT
<213> ORGANISM: Mus musculus

<400> SEQUENCE: 28

```
Pro Phe Pro Gly Ser Arg Gly Pro Gln Leu Phe Gly Leu Ser Arg Pro
1               5                   10                  15

Ala Gly Pro Pro Leu His Gly Pro Val Cys Gln Arg Cys Val Arg Arg
            20                  25                  30

Pro Val Pro Arg Ser Gly Arg Ala Pro Thr Leu Arg Pro Ser Ser Arg
        35                  40                  45

Ser Arg Val Ser Arg Arg Pro Arg Asp Asp Gly Val Val Ala Leu Thr
    50                  55                  60

Gly Ala Gly Gly Cys Arg Ala Pro Arg Ala Gly Met Ala Gly Gln Phe
65                  70                  75                  80

Arg Ser Tyr Val Trp Asp Pro Leu Leu Ile Leu Ser Gln Ile Val Leu
                85                  90                  95

Met Gln Thr Val Tyr Tyr Gly Ser Leu Gly Leu Trp Trp Arg Trp Trp
            100                 105                 110

Thr Arg Trp Cys Ala Gln Pro Val Pro Gly Pro Asp Val Arg Arg Gly
        115                 120                 125

Asp Pro Gly Leu Leu His Pro Ser Arg Pro Ala Leu Asn Asp Val Leu
    130                 135                 140

Arg Pro Gln Arg Pro His Leu Cys Pro Gly Leu Ala Val Leu His Pro
145                 150                 155                 160

Ala Arg Glu Ala Val Pro Gly Phe His Cys His Cys Ala Phe Leu Ser
                165                 170                 175

Pro Pro Gly Leu Leu Ala Leu Gln Leu Pro Phe Pro Leu Gly Ala Asp
            180                 185                 190

Leu Val Ala Gly Pro Gly Cys Val His Cys Thr His Gly Arg His Arg
        195                 200                 205

Gly Val Pro Val His Ala Asp Gly Ala Gln Gly Asp Pro Pro Gln Leu
    210                 215                 220

Ser Pro
225
```

<210> SEQ ID NO 29
<211> LENGTH: 151
<212> TYPE: PRT
<213> ORGANISM: Mus musculus

<400> SEQUENCE: 29

```
Met Ala Gly Gln Phe Arg Ser Tyr Val Trp Asp Pro Leu Leu Ile Leu
1               5                   10                  15

Ser Gln Ile Val Leu Met Gln Thr Val Tyr Tyr Gly Ser Leu Gly Leu
            20                  25                  30

Trp Leu Ala Leu Val Asp Ala Leu Val Arg Lys Pro Val Pro Gly Pro
        35                  40                  45

Asp Val Arg Arg Gly Asp Pro Gly Leu Leu His Pro Ser Arg Pro Ala
    50                  55                  60

Leu Asn Asp Val Leu Arg Pro Gln Arg Pro His Leu Cys Pro Gly Leu
65                  70                  75                  80
```

```
Ala Val Leu His Pro Ala Arg Glu Ala Val Pro Gly Phe His Cys His
                 85                  90                  95

Cys Ala Phe Leu Ser Pro Pro Gly Leu Leu Ala Leu Gln Leu Pro Phe
            100                 105                 110

Pro Leu Gly Ala Asp Leu Val Ala Gly Pro Gly Cys Val His Cys Thr
        115                 120                 125

His Gly Arg His Arg Gly Val Pro Val His Ala Asp Gly Ala Gln Gly
    130                 135                 140

Asp Pro Pro Gln Leu Ser Pro
145                 150

<210> SEQ ID NO 30
<211> LENGTH: 428
<212> TYPE: PRT
<213> ORGANISM: Homo sapiens

<400> SEQUENCE: 30

Met Asp Val Val Asp Ser Leu Leu Val Asn Gly Ser Asn Ile Thr Pro
1               5                   10                  15

Pro Cys Glu Leu Gly Leu Glu Asn Glu Thr Leu Phe Cys Leu Asp Gln
            20                  25                  30

Pro Arg Pro Ser Lys Glu Trp Gln Pro Ala Val Gln Ile Leu Leu Tyr
        35                  40                  45

Ser Leu Ile Phe Leu Leu Ser Val Leu Gly Asn Thr Leu Val Ile Thr
50                  55                  60

Val Leu Ile Arg Asn Lys Arg Met Arg Thr Val Thr Asn Ile Phe Leu
65                  70                  75                  80

Leu Ser Leu Ala Val Ser Asp Leu Met Leu Cys Leu Phe Cys Met Pro
                85                  90                  95

Phe Asn Leu Ile Pro Asn Leu Leu Lys Asp Phe Ile Phe Gly Ser Ala
            100                 105                 110

Val Cys Lys Thr Thr Thr Tyr Phe Met Gly Thr Ser Val Ser Val Ser
        115                 120                 125

Thr Phe Asn Leu Val Ala Ile Ser Leu Glu Arg Tyr Gly Ala Ile Cys
    130                 135                 140

Lys Pro Leu Gln Ser Arg Val Trp Gln Thr Lys Ser His Ala Leu Lys
145                 150                 155                 160

Val Ile Ala Ala Thr Trp Cys Leu Ser Phe Thr Ile Met Thr Pro Tyr
                165                 170                 175

Pro Ile Tyr Ser Asn Leu Val Pro Phe Thr Lys Asn Asn Asn Gln Thr
            180                 185                 190

Ala Asn Met Cys Arg Phe Leu Leu Pro Asn Asp Val Met Gln Gln Ser
        195                 200                 205

Trp His Thr Phe Leu Leu Leu Ile Leu Phe Leu Ile Pro Gly Ile Val
    210                 215                 220

Met Met Val Ala Tyr Gly Leu Ile Ser Leu Glu Leu Tyr Gln Gly Ile
225                 230                 235                 240

Lys Phe Glu Ala Ser Gln Lys Lys Ser Ala Lys Glu Arg Lys Pro Ser
                245                 250                 255

Thr Thr Ser Ser Gly Lys Tyr Glu Asp Ser Asp Gly Cys Tyr Leu Gln
            260                 265                 270

Lys Thr Arg Pro Pro Arg Lys Leu Glu Leu Arg Gln Leu Ser Thr Gly
        275                 280                 285

Ser Ser Ser Arg Ala Asn Arg Ile Arg Ser Asn Ser Ser Ala Ala Asn
    290                 295                 300
```

-continued

```
Leu Met Ala Lys Lys Arg Val Ile Arg Met Leu Ile Val Ile Val Val
305                 310                 315                 320

Leu Phe Phe Leu Cys Trp Met Pro Ile Phe Ser Ala Asn Ala Trp Arg
                325                 330                 335

Ala Tyr Asp Thr Ala Ser Ala Glu Arg Arg Leu Ser Gly Thr Pro Ile
            340                 345                 350

Ser Phe Ile Leu Leu Leu Ser Tyr Thr Ser Ser Cys Val Asn Pro Ile
        355                 360                 365

Ile Tyr Cys Phe Met Asn Lys Arg Phe Arg Leu Gly Phe Met Ala Thr
    370                 375                 380

Phe Pro Cys Cys Pro Asn Pro Gly Pro Pro Gly Ala Arg Gly Glu Val
385                 390                 395                 400

Gly Glu Glu Glu Glu Gly Gly Thr Thr Gly Ala Ser Leu Ser Arg Phe
                405                 410                 415

Ser Tyr Ser His Met Ser Ala Ser Val Pro Pro Gln
            420                 425
```

COMPUTER SYSTEMS AND METHODS FOR ASSOCIATING GENES WITH TRAITS USING CROSS SPECIES DATA

CROSS-REFERENCE TO RELATED APPLICATIONS

This application claims benefit, under 35 U.S.C. §119(e), of U.S. Provisional Patent Application No. 60/436,684 filed on Dec. 27, 2002 which is incorporated herein, by reference, in its entirety. This application also claims benefit, under 35 U.S.C. §119(e), of U.S. Provisional Patent Application No. 60/460,343 filed Apr. 2, 2003, which is incorporated herein, by reference, in its entirety.

1. FIELD OF THE INVENTION

The field of this invention relates to computer systems and methods for identifying genes and biological pathways associated with traits. In particular, this invention relates to computer systems and methods for using both gene expression data and genetic data to identify gene-gee interactions, gene-phenotype interactions, and biological pathways linked to traits in one species using data from another species.

2. BACKGROUND OF THE INVENTION

A variety of approaches have been taken to identify genes and pathways that are associated with traits, such as human disease. In one approach, attempts have been made to use gene expression data to identify genes and pathways associated with such traits. In another approach, genetic information has been used to attempt to identify genes and pathways associated with traits. For instance, clinical measures of a population may be taken to study a trait such as a disease found in the population. Risk factors for the trait can be established from these clinical measures. Demographic and environmental factors are further used to explain variation with respect to the trait. Further, genetic variations associated with traits, such as disease-related traits, as well as the disease itself are used to identify regions in the genome linked to a disease. For example, genetic variations in a population may be used to determine what percentage of the variation of the trait in the population of interest can be explained by genetic variation of a single nucleotide polymorphism (SNP), haplotype, or short tandem repeat (STR) marker. However, as will be described below, the elucidation of genes involved in biological pathways that influence a trait, such as a disease, using either gene expression or genetic expression approaches, is problematic and generally not successful in many instances.

2.1. Use of Measured Gene Expression Data to Identify Genes and Pathways Associated with Traits Within the past decade, several technologies have made it possible to monitor the expression level of a large number of transcripts at any one time (see, e.g., Schena et al., 1995, Quantitative monitoring of gene expression patterns with a complementary DNA microarray, *Science* 270:467-470; Lockhart et al., 1996, Expression monitoring by hybridization to high-density oligonucleotide arrays, *Nature Biotechnology* 14:1675-1680; Blanchard et al., 1996, Sequence to array. Probing the genome's secrets, *Nature Biotechnology* 14, 1649; U.S. Pat. No. 5,569,588, issued Oct. 29, 1996 to Ashby et al. entitled "Methods for Drug Screening"). In organisms for which the complete genome is known, it is possible to analyze the transcripts of all genes within the cell. With other organisms, such as human, for which there is an increasing knowledge of the genome, it is possible to simultaneously monitor large numbers of the genes within the cell.

Such monitoring technologies have been applied to the identification of genes that are up regulated or down regulated in various diseased or physiological states, the analyses of members of signaling cellular states, and the identification of targets for various drugs. See, e.g., Friend and Hartwell, U.S. Pat. No. 6,165,709; Stoughton, U.S. Pat. No. 6,132,969; Stoughton and Friend, U.S. Pat. No. 5,965,352; Friend and Stoughton, U.S. Pat. No. 6,324,479; and Friend and Stoughton, U.S. Pat. No. 6,218,122, all incorporated herein by reference for all purposes.

Levels of various constituents of a cell are known to change in response to drug treatments and other perturbations of the biological state of a cell. Measurements of a plurality of such "cellular constituents" therefore contain a wealth of information about the effect of perturbations and their effect on the biological state of a cell. Such measurements typically comprise measurements of gene expression levels of the type discussed above, but may also include levels of other cellular components such as, but by no means limited to, levels of protein abundances, protein activity levels, or protein interactions. The collection of such measurements is generally referred to as the "profile" of the cell's biological state. Statistical and bioinformatical analysis of profile data has been used to try to elucidate gene regulation events. Statistical and bioinformatical techniques used in this analysis comprises hierarchical cluster analysis, reference or supervised classification approaches and correlation-based analyses, See, e.g., Tamayo at al., 1999, Interpreting patterns of gene expression with self-organizing maps: methods and application of hematopoietic differentiation, *Proc. Natl. Acad Sci. U.S.A.* 96:2907-2912; Brown et al., 2000, Knowledge-based analysis of microarray gene expression data by using support vector machines, *Proc. Natl. Acad Sci. U.S.A.*: 97, 262-267; Gaasterland and Bekinraov, Making the most of microarray data, *Nat. Genet.*: 24, 204-206, Cohen et al., 2000, A computational analysis of whole-genome expression data reveals chromosomal domains of gene expression, *Nat. Genet.* 24: 5-6, 2000.

The use of gene expression data to identify genes and elucidate pathways associated with traits has typically relied on the clustering of gene expression data over a variety of conditions. See, e.g., Roberts et al., 2000, Signaling and circuitry of multiple MAPK pathways revealed by a matrix of global gene expression profiles; *Science* 287:873; Hughes et al., 2000, Functional Discovery via a Compendium of Expression Profiles, *Cell* 102:109. However, gene expression clustering has a number of drawbacks. First, gene expression clustering has a tendency to produce false positives. Such false positives arise, for example, when two genes coincidentally have correlated expression profiles over a variety of conditions. Second, although gene expression clustering provides information on the interaction between genes, it does not provide information on the topology of biological pathways. For example, clustering of gene expression data over a variety of conditions may be used to determine that genes A and B interact. However, gee expression clustering typically does not provide sufficient information to determine whether gene A is downstream or upstream from gene B in a biological pathway. Third, direct biological experiments are often required to validate the involvement of any gene identified from the clustering of gene expression data in order to increase the confidence that the target is actually valid. For these reasons, the use of gene expression data alone to identify genes involved in traits, such as various complex human diseases, has often proven to be unsatisfactory.

2.2. Use of Genetics Data to Identify Genes and Pathways Associated with Traits Genetics data have been used in the field of trait analysis in order to attempt to identify the genes that affect such traits. A key development in such pursuits has been the development of large collections of molecular/genetic markers, which can be used to construct detailed genetic maps of species, such as humans. These maps are used in Quantitative Trait Locus (QTL) mapping methodologies such as single-marker mapping, interval mapping, composite interval mapping and multiple trait mapping. (For a review, see Doerge, 2002, Mapping and analysis of quantitative trait loci in experimental populations, *Nature Reviews: Genetics* 3:43-62. QTL mapping methodologies provide statistical analysis of the association between phenotypes and genotypes for the purpose of understanding and dissecting the regions of a genome that affect traits.

A quantitative trait locus (QTL) is a region of any genome that is responsible for some percentage of the variation in the quantitative trait of interest. The goal of identifying all such regions that are associated with a specific phenotype is typically difficult to accomplish because of the sheer number of QTL, the possible epistasis or interactions between QTL, as well as many additional sources of variation that can be difficult to model and detect. To address these problems, QTL experiments can be designed with the aim of containing the sources of variation to a limited number in order to improve the chances of dissecting a phenotype. In general, a large sample of individuals has to be collected to represent the total population, to provide an observable number of recombinants and to allow a thorough assessment of the trait under investigation. Using this information, coupled with one of several methodologies to detect or locate QTL, associations between quantitative traits and genetic markers are made as steps toward understanding the genetic basis of trait.

A drawback with QTL approaches is that, even when genomic regions that have statistically significant associations with traits are identified, such regions are usually so large that subsequent experiments, used to identify specific causative genes in these regions, are time consuming and laborious. High density marker maps of the genomic regions are required. Furthermore, physical resequencing of such regions is often required. In fact, because of the size of the genomic regions identified, there is a danger that causative genes within such regions simply will not be identified. In the event of success, and the genomic region containing genes that are responsible for the trait variation are elucidated, the expense and time from the beginning to the end of this process is often too great for identifying genes and pathways associated with traits, such as complex human diseases.

In the case of humans, the use of genetics to identify genes and pathways associated with traits follows a very standard paradigm. First, a genome-wide linkage study is performed using hundreds of genetic markers in family-based data to identify broad regions linked to the trait. The result of this standard sort of linkage analysis is the identification of regions controlling for the trait, thereby restricting attention from the 30,000 plus genes to perhaps as few as 500 to 1000 genes in a particular region of the genome that is linked to the trait. However, the regions identified using linkage analysis are still far too broad to identify candidate genes associated with the trait. Therefore, such linkage studies are typically followed up by fine mapping the regions of linkage using higher density markers in the linkage region, increasing the number of families in the analysis, and identifying alternative populations for study. These efforts further restrict attention to narrower regions of the genome, on the order of 100 genes in a particular region linked to the trait. Even with the more narrowly defined linkage region, the number of genes to validate is still unreasonably large. Therefore, research at this stage focuses on identifying candidate genes based on putative function of known or predicted genes in the region and the potential relevance of that function to the trait. This approach is problematic because it is limited to what is currently known about genes. Often, such knowledge is limited and subject to interpretation. As a result, researchers are often led astray and do not identify the genes affecting the trait.

There are many reasons that standard genetic approaches have not proven very successful in the identification of genes associated with complex traits, such as common human diseases, or the biological pathways associated with such traits. First, common human diseases such as heart disease, obesity, cancer, osteoporosis, schizophrenia, and many others are complex in that they are polygenic. That is, they potentially involve many genes across several different biological pathways and they involve complex gene-environment interactions that obscure the genetic signature. Second, the complexity of the diseases leads to a heterogeneity in the different biological pathways that can give rise to the disease. Thus, in any given heterogeneous population, there may be defects across several different pathways that can give rise to the disease. This reduces the ability to identify the genetic signal for any given pathway. Because many populations involved in genetic studies are heterogeneous with respect to the disease, multiple defects across multiple pathways are operating within the population to give rise to the disease. Third, as outlined above, the genomic regions associated with a linkage to a disease are large and often contain a number of genes and possible variants that are potentially associated with the disease. Fourth, the traits and disease states themselves are often not well defined. Therefore, subphenotypes are often overlooked even though these subphenotypes implicate different sets of biological pathways. This reduces the power of detecting the associations. Fifth, even when genes and trait are highly correlated, the genes may not give the same genetic signature. Sixth, in cases where genes and a trait are moderately correlated, or not correlated at all, the genes may give rise to the same genetic signature.

In addition to the heterogeneity problems discussed above, the identification of genes and biological pathways associated with traits, such as complex human diseases, using genetics data is confounded, when using human subjects, due to the inability to use common genetic techniques and resources in humans. For example, humans cannot be crossed in controlled experiments. Therefore, there is typically very little pedigree data available for humans. Elucidation of genes associated with diseases in humans is also difficult because humans are diploid organisms containing two genomes in each nucleate cell, making it very hard to determine the DNA sequence of the haploid genome. Because of these limitations, genetic approaches to discovering genes and biological pathways associated with human diseases is unsatisfactory.

Companies such as deCode Genetics (Reykjavik, Iceland) study populations that are isolated and so are more homogenous with respect to disease, thereby increasing the power to detect association. The disease variations themselves in such populations are greatly reduced as founder effects for many diseases are evident (i.e., specific forms of diseases in such populations most likely arose from a single or small numbers of founders of the population). Other companies, such as Sequenome (San Diego, Calif.), use twin cohorts to study complex diseases. Identical twins are a powerful tool in establishing the genetic component of a trait. The genetic component of a trait is defined as the degree to which a given trait is under genetic control. Dizygotic twins allow for age, gender and environment matching which helps reduce many of the confounding factors that often reduce the power of genetic studies. In addition, the completion of the human and mouse genomes has made the job of identifying candidate genes in a region of linkage far easier, and it reduces dependency on considering only known genes, since genomic regions can be annotated using ab initio gene prediction software to identify novel candidate genes associated with the disease. Further, the use of demographic, epidemiological and clinical data in more sophisticated models helps explain much of the trait variation in a population. Reducing the overall variation in this way increases the power to detect genetic variation. The identification of millions of SNPs allows finer mapping in any given region of the genome and direct association testing of very large case/control populations, thereby reducing the need to study families and more directly identify the degree to which any genetic variant affects a given population. Finally, our understanding of disease and the need to subphenotype a given disease is now more fully appreciated and aids in reducing the heterogeneity of the disease under study. Technologies such as microarrays have greatly facilitated the ability to subclassify disease subtypes for a given disease. However, all of the methods still fall short when it comes to efficiently identifying genes and pathways associated with diseases.

2.3. Obesity

Obesity represents the most prevalent of body weight disorders, and it is the most important nutritional disorder in the western world, with estimates of its prevalence ranging from 30% to 50% within the middle-aged population. Other body weight disorders, such as anorexia nervosa and bulimia nervosa, which together affect approximately 0.2% of the female population of the western world, also pose serious health threats. Further, such disorders as anorexia and cachexia (wasting) are also prominent features of other diseases such as cancer, cystic fibrosis, and AIDS.

It has been estimated that half of all Americans are overweight. Within the United States about 24% of men and 27% of women are defined as mildly to severely obese. Individuals 20% over ideal weight guidelines are considered obese. Obesity is classified as mild (20-40% overweight), moderate (41-100% overweight), and severe (>100% overweight). Severe obesity is relatively rare, affecting less than 0.5% of all obese individuals and about 0.1% of the total population.

In order to measure obesity, the weight/height ratio may be calculated by obtaining the weight of an individual in kilograms (kg) and dividing this value by the square of the height of the individual in meters. Alternatively, the weight/height ratio of an individual may be obtained by multiplying the weight of the individual in pounds (lbs) by 703 and dividing this value by the square of the height of the individual (in inches (in)). These ratios are typically referred to as BMI. Thus, $BMI=kg/m^2$ or $BMI (lbs.\times 703)/(in)^2$. Where BMI is utilized as a measure of obesity, an individual is considered overweight when BMI values range between 25.0 and 29.9. Obesity is defined as BMI values greater than or equal to 30.0. The World Health Organization assigns BMI values as follows: 25.0-29.9, Grade I obesity (moderately overweight); 30-39.9, Grade II obesity (severely overweight); and 40.0 or greater, Grade III obesity (massive/morbid obesity). Using weight tables, obesity is classified as mild (20-40% overweight), moderate (41-100% overweight), and severe (>100%) overweight. Individuals 20% over ideal weight guidelines are considered obese. Individuals 1-19.9% over ideal weight are classified as overweight.

Obesity also contributes to other diseases. For example, this disorder is responsible for increased incidence of diseases such as coronary artery disease, hypertension, stroke, diabetes, hyperlipidemia, and some cancers (See, e.g., Nishina, P. M. et al., 1994, Metab. 43: 554-558; Grundy, S. M. & Bamrnett, J. P., 1990, Dis. Mon. 36: 641-731). Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity (Friedman, J. M. et al., 1991, Mammalian Gene 1: 130-144).

The epidemiology of obesity strongly shows that the disorder exhibits inherited characteristics (Stunkard, 1990, N. Bug. J. Med. 322: 1438). Moll et al. have reported that, in many populations, obesity seems to be controlled by a few genetic loci (Moll et al., 1991, Am. J. Hum. Gen. 49: 1243). In addition, human twin studies strongly suggest a substantial genetic basis in the control of body weight, with estimates of heritability of 80-90% (Simopoulos, A. P. & Childs, B., eds., 1989, in "Genetic Variation and Nutrition in Obesity", World Review of Nutrition and Diabetes 63, S. Karger, Basel, Switzerland; Borjeson, M., 1976, Acta. Paediatr. Scand. 65: 279-287).

In other studies, non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric intake. In addition, it is a commonplace experience in animal husbandry that different strains of swine, cattle, etc., have different predispositions to obesity. Studies of the genetics of human obesity, and of animal models of obesity demonstrate that obesity results from complex defective regulation of both food intake, food induced energy expenditure, and of the balance between lipid and lean body anabolism.

There are a number of genetic diseases in man and other species that feature obesity among their more prominent symptoms, along with, frequently, dysmorphic features and mental retardation. For example, Prader-Willi syndrome (PWS; reviewed in Knoll, J. H. et al., 1993, Am. J. Med. Genet. 46: 2-6) affects approximately 1 in 20,000 live births, and involves poor neonatal muscle tone, facial and genital deformities, and generally obesity. In addition to PWS, many other pleiotropic syndromes have been characterized that include obesity as a symptom. These syndromes are genetically straightforward, and appear to involve autosomal recessive alleles. Such diseases include, among others, Ahlstroem, Carpenter, Bardet-Biedl, Cohen, and Morgagni-Stewart-Monel Syndromes.

A number of models exists for the study of obesity (see, e.g., Bray, G. A., 1992, Prog. Brain Res. 93: 333-341; and Bray, G. A., 1989, Amer. J. Clin. Nutr. 5: 891-902). For example, animals having mutations that lead to syndromes that include obesity symptoms have also been identified. Attempts have been made to utilize such animals as models for the study of obesity, and the best studied animal models to date for genetic obesity are mice. For reviews, see, e.g., Friedman, J. M. et al, 1991, Mamm. Gen. 1: 130-144; Friedman, J. M. and Liebel, R. L., 1992, Cell 69: 217-220.

Studies utilizing mice have confirmed that obesity is a very complex trait with a high degree of heritability. Mutations at a number of loci have been identified that lead to obese phenotypes. These include the autosomal recessive mutations obese (ob), diabetes (db), fat (fat), and tubby (tub).

Thus, given the above background, what is needed in the art are improved methods for identifying genes and biological pathways that affect complaex traits such as diseases. In particular genes and biological pathways that affect obesity, which poses a major, worldwide health problem, are needed.

Discussion or citation of a reference herein will not be construed as an admission that such reference is prior art to the present invention.

3. SUMMARY OF THE INVENTION

The present invention provides an improvement over the art by uniquely combining gene expression approaches with genetic approaches in order to determine the genes associated with traits, such as complex human diseases. In the computer systems and methods of the present invention, genetic approaches are used to filter out false positive genes from gene expression clusters. Furthermore, the computer systems and methods of the present invention are used to advantageously combine gene expression data with genetics data to elucidate biological pathways associated with traits.

3.1. Associating a Trait with a Gene in a First Species by Using eQTL-cQTL Overlap in a Second Species One aspect of the invention provides a method for associating a gene G in the genome of a first species with a clinical trait T exhibited by the first species and a second species. In the method a gene G' is found in the second species that is an ortholog of the gene G. Further, an expression quantitative trait loci (eQTL) is identified for gene G' using a first quantitative trait loci (QTL) analysis. The first QTL analysis uses a plurality of expression statistics for gene G' as a quantitative trait. Bach expression statistic in the plurality of expression statistics represents an expression value for the gene G' in an organism in a plurality of organisms of the second species. A clinical quantitative trait loci (cQTL) that is linked to the clinical trait T is identified using a second QTL analysis. The second QTL analysis uses a plurality of phenotypic values as a quantitative trait. Bach phenotypic value in the plurality of phenotypic values represents a phenotypic value for the clinical trait T in an organism in the plurality of organisms of the second species. Next, a determination is made as to whether the eQTL and the cQTL colocalize to the same locus in the genome of the second species. When the eQTL and the cQTL colocalize to the same locus, the gene G is associated with the clinical trait T in the first species.

In some embodiments, the above described determining step further comprises determining whether the locus of the eQTL in the genome of the second species corresponds to the physical location of the gene G' in the genome of the second species. When the locus of the eQTL in the genome of the second species corresponds to the physical location of the gene G' in the genome of the second species the gene G is associated with the clinical trait T.

In some embodiments, the eQTL corresponds to the physical location of the gene G' when the eQTL and the gene G' colocalize within about 3 cM or within about 1 cM of each other in the genome of the second species. In some embodiments, the method further comprising testing whether a colocalization of the eQTL and the cQTL is caused by pleiotropy.

In some embodiments, the first QTL analysis and the second QTL analysis each uses a genetic marker map that represents the genome of the second species.

Some embodiments of the present invention include an additional step that is performed prior to the first identifying step. This additional step comprises constructing the genetic marker map from a set of genetic markers associated with a plurality of organisms representing the second species. In some embodiments, the set of genetic markers comprises nucleotide polymorphisms (SNPs), microsatellite markers, restriction fragment length polymorphisms, short tandem repeats, DNA methylation markers, sequence length polymorphisms, random amplified polymorphic DNA, amplified fragment length polymorphisms, or simple sequence repeats. In some embodiments, the genotype data is used in the constructing step and the genotype data comprises knowledge of which alleles, for each marker in the set of genetic markers, are present in each organism in the plurality of organisms representing the second species. In some embodiments, the plurality of organisms representing the second species represents a segregating population and pedigree data is used in the constructing step. Further, this pedigree data shows one or more relationships between organisms in the plurality of organisms representing the second species. In some embodiments, the plurality of organisms representing the second species comprises an F2 population, a $F_t$ population, a $F_{2:3}$ population, or a Design III population and the one or more relationships between organisms in the plurality of organisms representing the second species indicates which organisms in the plurality of organisms representing the second species are members of the F2 population, the $F_t$ population, the $F_{2:3}$ population, or the Design III population.

In some embodiments, each expression value is a normalized expression level measurement for the gene G' in an organism in the plurality of organisms of the second species. In some embodiments, each such expression level measurement is determined by measuring an amount of a cellular constituent encoded by the gene G' in one or more cells from an organism in the plurality of organisms of the second species. In some embodiments, the amount of the cellular constituent comprises a abundance of an RNA present in the one or more calls of the organism. In some embodiments, the abundance of the RNA is measured by a method comprising contacting a gene transcript array with the RNA from the one or more cells of the organism, or with nucleic acid derived from the RNA. In such embodiments, the gene transcript array comprises a positionally addressable surface with attached nucleic acids or nucleic acid mimics. These nucleic acids or nucleic acid mimics are capable of hybridizing with the RNA species, or with nucleic acid derived from the RNA species. The normalized expression level measurement is obtained by a normalization technique such as, for example, Z-score of intensity, median intensity, log median intensity, Z-score standard deviation log of intensity, Z-score mean absolute deviation of log intensity, calibration DNA gene set, user normalization gene set, ratio median intensity correction, or intensity background correction.

In some embodiments, the QTL analysis comprises (i) testing for linkage between (a) the genotype of the plurality of organisms of the second species at a position in the genome of the second species and (b) the plurality of expression statistics for gene G'; (ii) advancing the position in the genome by an amount; and (iii) repeating steps (i) and (ii) until all or a portion of the genome of the second species has been tested. In some embodiments the amount is less than 100 cetiMorgans, less than 10 centiMorgans, less than 5 centiMorgans, or less than 2.5 centiMorgans. In some embodiments, the testing of (i) comprises performing linkage analysis or association analysis. In some embodiments, linkage analysis or association analysis generates a statistical score for the position in the genome of the second species. In some embodiments, testing is linkage analysis and the statistical score is a logarithm of the odds (lod) score. In some embodiments, the eQTL is represented by a lod score that is greater than about 2.0, that is greater than about 3.0, that is greater than about 4.0, or that is greater than about 5.0.

In some embodiments, the second QTL analysis comprises (i) testing for linkage between (a) the genotype of the plurality of organisms of the second species at a position in the genome of the second species and (b) the plurality of phenotypic values; (ii) advancing the position in the genome by an amount; and (iii) repeating steps (i) and (ii) until all or a portion of the genome of the second species has been tested. The amount advanced can be, for example, less than 100 centiMorgans, less than 10 centiMorgans, less than 5 centiMorgans, or less than 2.5 centiMorgans. The testing of (i) in the second QTL analysis may comprise performing linkage analysis or association analysis. This linkage analysis or association analysis generates a statistical score for the position in the genome of the second species. In some embodiments, the testing is linkage analysis and the statistical score is a logarithm of the odds (lod) score. In some embodiments, the cQTL is represented by a lod score that is greater than about 2.0, by a lod score that is greater than about 3.0, by a lod score that is greater than about 4.0, or by a lod score that is greater than about 5.0.

In some embodiments, the first species is human. In some embodiments, the second species is a plant or an animal. In some embodiments, the second species is corn, beans, rice, tobacco, potatoes, tomatoes, cucumbers, apple trees, orange trees, cabbage, lettuce, or wheat. In some embodiments, the second species is a mammal, a primate, mice, rats, dogs, cats, chickens, horses, cows, pigs, or monkeys. In still other embodiments, the second species is *Drosophila*, yeast, a virus, or *Caenorhabditis elegans*.

In some embodiments, the clinical trait T is a complex trait. In some embodiments, the complex trait T is characterized by an allele that exhibits incomplete penetrance in the second species. In some embodiments, the complex trait is a disease that is contracted by an organism in the plurality of organisms of the second species. Further, the organism inherits no predisposing allele to the disease. In some embodiments, the complex trait arises when any of a plurality of different genes in the genome of the second species is somatically mutated. In some embodiments, the complex trait requires the simultaneous presence of mutations in a plurality of genes in the genome of the second species. In still other embodiments, the complex trait is associated with a high frequency of disease-causing alleles in the second species. In yet other embodiments, the complex trait is a phenotype that does not exhibit Mendelian recessive or dominant inheritance attributable to a gene locus. In some embodiments the complex trait is susceptibility to heart disease, hypertension, diabetes, cancer, infection, polycystic kidney disease, early-onset Alzheimer's disease, maturity-onset diabetes of the young, hereditary nonpolyposis colon cancer, ataxia telangiectasia, obesity, nonalcoholic steatohepatitis (NASH), nonalcoholic fatty liver (NAFL), or xeroderma pigmentosum.

In some embodiments, the eQTL and the cQTL colocalize to the same locus in the genome of the second species when the physical location of the eQTL in the genome is within about 40 cM of the physical location of the cQTL in the genome, within about 20 cM of the physical location of the cQTL in the genome, within about 10 cM of the physical location of the cQTL in the genome, or within about 6 cM of the physical location of the cQTL in the genome.

Another aspect of the present invention provides a computer program product for use in conjunction with a computer system. The computer program product comprises a computer readable storage medium and a computer program mechanism embedded therein. The computer program mechanism associates a gene G in the genome of a first species with a clinical trait T exhibited by the first species and a second species. The computer program mechanism comprises an ortholog identification module for finding a gene G' in the second species that is an ortholog of the gene G. The computer program mechanism further comprises an expression quantitative trait loci (eQTL) identification module for identifying an expression quantitative trait loci (eQTL) for the gene G' using a first quantitative trait loci (QTL) analysis. The first QTL analysis uses a plurality of expression statistics for the gene G' as a quantitative trait and each expression statistic in the plurality of expression statistics represents an expression value for the gene G' in an organism in the plurality of organisms of the second species. The computer program mechanism further comprises a clinical quantitative trait loci (cQTL) identification module for identifying a clinical quantitative trait loci (cQTL) that is linked to the clinical trait T using a second QTL analysis. The second QTL analysis uses a plurality of phenotypic values as a quantitative trait. Each phenotypic value in the plurality of phenotypic values represents a phenotypic value for the clinical trait T in an organism in the plurality of organisms of the second species. The computer program mechanism also comprises a determination module for determining whether the eQTL and the cQTL colocalize to the same locus in the genome of the second species, wherein, when the eQTL and the cQTL colocalize to the same locus, the gene G is associated with the clinical trait T in the first species.

Another aspect of the present invention provides a computer system for associating a gene G in the genome of a first species with a clinical trait T exhibited by the first species and a second species. The computer system comprises a central processing unit and a memory coupled to the central processing unit. The memory stores an ortholog identification module, an expression quantitative trait loci (eQTL) identification module, a clinical quantitative trait loci (cQTL) identification module, and a determination module. The ortholog identification module comprises instructions for finding a gene G' in the second species that is an ortholog of the gene G. The expression quantitative trait loci (eQTL) identification module comprises instructions for identifying an expression quantitative trait loci (eQTL) for the gene G' using a first quantitative trait loci (QTL) analysis. The first QTL analysis uses a plurality of expression statistics for gene G' as a quantitative trait. Each expression statistic in the plurality of expression statistics represents an expression value for the gene G' in an organism in a plurality of organisms of the second species. The clinical quantitative trait loci (cQTL) identification module comprises instructions for identifying a clinical quantitative trait loci (cQTL) that is linked to the clinical trait T using a second QTL analysis. The second QTL analysis uses a plurality of phenotypic values as a quantitative trait. Each phenotypic value in the plurality of phenotypic values represents a phenotypic value for the clinical trait T in an organism in the plurality of organisms of the second species. The determination module comprises instructions for determining whether the eQTL and the cQTL colocalize to the same locus in the genome of the second species. When the cQTL and the cQTL colocalize to the same locus, the gene G is associated with the clinical trait T.

3.2. Associating a QTL with a Complex Trait in a First Species by Clustering QTL Data from a Second Species Another aspect of the present invention provides a method for associating a gene G in the genome of a first species with a clinical trait T exhibited by the first species and a second species. In the method, quantitative trait locus data from a plurality of quantitative trait locus analyses is clustered to form a quantitative trait locus interaction map. Each quantitative trait locus analysis in the plurality of quantitative trait locus analyses is performed for a gene in a plurality of genes in the genome of the second species using a genetic marker map and a quantitative trait in order to produce the quantitative trait locus data. For each quantitative trait locus analysis, the quantitative trait comprises an expression statistic for the gene for which the quantitative trait locus analysis is performed. The genetic marker map is constructed from a set of genetic markers associated with the plurality of organisms of the second species. The quantitative trait locus interaction map is analyzed to identify a gene G' associated with a trait. Then, the gene G in the first species that is the ortholog of the gene G' of the second species is identified, thereby associating a gene G in the genome of the first species with a clinical trait T exhibited by the first species. In some embodiments, the method further comprises an additional step that is performed prior to the clustering step. This additional step comprises performing each of the quantitative trait locus analyses in the plurality of quantitative trait locus analyses.

In some embodiments, the expression statistic for gene G' is computed by a method comprising transforming an expression level measurement of gene G' from each organism in the plurality of organisms of the second species. In some embodiments, each quantitative trait locus analysis comprises: (i) testing for linkage between a position in a chromosome, in the genome of the second species, and the quantitative trait used in the quantitative trait locus analysis; (ii) advancing the position in the chromosome by an amount; and (iii) repeating steps (i) and (ii) until all or a portion of the genome has been tested. In some embodiments, the quantitative trait locus data produced from each respective quantitative trait locus analysis comprises a logarithmic of the odds score computed at each position tested. In some embodiments, the testing comprises performing linkage analysis or association analysis.

In some embodiments, the clustering of the quantitative trait locus data from each quantitative trait locus analysis comprises applying a hierarchical clustering technique, applying a k-means technique, applying a fuzzy k-means technique, applying a Jarvis-Patrick clustering, applying a self-organizing map technique, or applying a neural network technique.

Some embodiments of the method include an additional step in which a gene expression cluster map is constructed from each expression statistic created by the transforming step. In some embodiments, construction of the gene expression cluster map comprises creating a plurality of gene expression vectors, each gene expression vector in the plurality of gene expression vectors representing an expression level measurement of a gene, in the plurality of genes in the genome of the second species, in each of the plurality of organisms of the second species. Then, a plurality of correlation coefficients are computed. Each correlation coefficient in the plurality of correlation coefficients is computed between a gene expression vector pair in the plurality of gene expression vectors. The plurality of gene expression vectors are clustered based on the plurality of correlation coefficients in order to form the gene expression cluster map. In some embodiments, the step of analyzing the quantitative trait locus interaction map comprises filtering the quantitative trait locus interaction map in order to obtain a candidate pathway group. The filtering comprises identifying a quantitative trait locus in the candidate pathway group in the gene expression cluster map. In some embodiments, construction of the gene expression cluster map comprises (i) creating a plurality of gone expression vectors, each gene expression vector in the plurality of gene expression vectors representing a gene in the plurality of genes, (ii) computing a plurality of metrics, wherein each metric in the plurality of metrics is computed between a gene expression vector pair in the plurality of gene expression vectors; and (iii) clustering the plurality of gene expression vectors based on the plurality of metrics in order to form the gene expression cluster map. In some embodiments, the plurality of genes comprises at least five genes.

Another embodiment of the present invention provides a computer program product for use in conjunction with a computer system. The computer program product comprises a computer readable storage medium and a computer program mechanism embedded therein. The computer program mechanism comprises a clustering module, an analysis module, and an ortholog identification module. The clustering module is used for clustering quantitative trait locus data from a plurality of quantitative trait locus analyses to form a quantitative trait locus interaction map. Each quantitative trait locus analysis in the plurality of quantitative trait locus analyses is performed for a gene in a plurality of genes in the genome of a second species using a genetic marker map and a quantitative trait in order to produce the quantitative trait locus data. For each quantitative trait locus analysis, the quantitative trait comprises an expression statistic for the gene for which the quantitative trait locus analysis is performed, for each organism in a plurality of organisms of the second species. Further, the genetic marker map is constructed from a set of genetic markers associated with the plurality of organisms of the second species. The analysis module is for analyzing the quantitative trait locus interaction map to identify a gene G' associated with a trait exhibited by a first species and the second species. The ortholog identification module is for finding a gene G in the first species that is an ortholog of the gene G' in the second species.

Some embodiments of the present invention provide a computer system for associating a gene G in the genome of a first species with a clinical trait T exhibited by the first species and a second species. The computer system comprises a central processing unit and a memory coupled to the central processing unit. The memory stores a clustering module, an analysis module and an ortholog identification module. The clustering module is for clustering quantitative trait locus data from a plurality of quantitative trait locus analyses to form a quantitative trait locus interaction map. Each quantitative trait locus analysis in the plurality of quantitative trait locus analyses is performed for a gene in a plurality of genes in the genome of the second species using a genetic marker map and a quantitative trait in order to produce the quantitative trait locus data. For each quantitative trait locus analysis, the quantitative trait comprises an expression statistic for the gene for which the quantitative trait locus analysis is performed, for each organism in a plurality of organisms of the second species. The genetic marker map is constructed from a set of genetic markers associated with the plurality of organisms of the second species. The analysis module is for analyzing the quantitative trait locus interaction map to identify a gene G' associated with a trait exhibited by the first species and the second species. The ortholog identification module is for finding a gene G in the first species that is an ortholog of the gene G' of the second species.

3.3. Associating a Complex Trait with a Gene in a First Species by Subdividing a Second Species Population Another aspect of the present invention provides a method for identifying a quantitative trait locus for a complex trait in a first species. The complex trait is exhibited by the first species and a second species. In the method, a plurality of organisms of the second species are divided into a plurality of subpopulations using a classification scheme that classifies each organism in the plurality of organisms of the second species into at least one of the subpopulations. The classification scheme uses a plurality of cellular constituent measurements from each organism of the second species. Further, for at least one subpopulation in the plurality of subpopulations, the method provides the step of performing quantitative genetic analysis on the subpopulation in order to identify a quantitative trait locus for the complex trait in the second species. The method further provides the step of finding the quantitative trait loci in the first species that is the ortholog of the quantitative trait locus of the second species, thereby identifying the quantitative trait locus for the complex trait in the first species.

In some embodiments, the complex trait is a disease that is contracted by an organism in the first species or the second species where the organism inherits no predisposing allele to the disease. In some embodiments, the complex trait arises when any of a plurality of different genes in the genome of the first species or the second species is mutated. In some embodiments, the complex trait is associated with a high frequency of disease-casing alleles in first species or the second species.

In some embodiments, the complex trait is a phenotype that does not exhibit Mendelian recessive or dominant inheritance attributable to a gene locus. In some embodiments, the complex trait is susceptibility to heart disease, hypertension, diabetes, cancer, infection, polycystic kidney disease, early-onset Alzheimer's disease, maturity-onset diabetes of the young, hereditary nonpolyposis colon cancer, ataxia telangiectasia, obesity, or xeroderma pigmentosum.

In some embodiments, the plurality of cellular constituent measurements from each organism of the second species comprises the measurement of the cellular constituent levels often or more cellular constituents in each organism. In some embodiments, the dividing step comprises determining whether a class predictor is available, and when a class predictor is available, using a supervised classification scheme to classify each organism in the plurality of organisms of the second species into a subpopulation in the plurality of subpopulations. When a class predictor is not available, an unsupervised classification scheme is used to classify each organism in the plurality of organisms of the second species into a subpopulation in the plurality of subpopulations.

In some embodiments, the classification scheme is a supervised classification scheme. In some embodiments, the classification scheme is an unsupervised classification scheme. In some embodiments, the unsupervised classification scheme is a hierarchical cluster analysis that uses a nearest-neighbor algorithm, a farthest-neighbor algorithm, an average linkage algorithm, a centroid algorithm, or a sum-of-squares algorithm to determine the similarity between (i) the plurality of cellular constituent measurements from one organism in the plurality of organisms of the second species and (ii) the plurality of cellular constituent measurements from another organism in the plurality of organisms of the second species.

Another aspect of the present invention provides a computer program product for use in conjunction with a computer system. The computer program product comprises a computer readable storage medium and a computer program mechanism embedded therein. The computer program mechanism comprises a classification module, a genetic analysis module, and an ortholog identification module. The classification module is for dividing a plurality of organisms of a second species into a plurality of subpopulations using a classification scheme that classifies each organism in the plurality of organisms of the second species into at least one of the subpopulations. The classification scheme uses a plurality of cellular constituent measurements from each organism in the second species. The genetic analysis module is used, for at least one subpopulation in the plurality of subpopulations, to perform quantitative genetic analysis on the subpopulation in order to identify a quantitative trait locus for a complex trait that is exhibited by the second species and a first species. The ortholog identification module is used for finding the quantitative trait locus in the first species that is the ortholog of the quantitative trait locus of the second species.

Another aspect of the present invention provides a computer system for identifying a quantitative trait locus for a complex trait in a first species. The complex trait is exhibited by the first species and a second species. The computer system comprises a central processing unit and a memory coupled to the central processing unit. The memory is used for storing a classification module, a genetic analysis module, and an ortholog identification module. The classification module includes instructions for dividing a plurality of organisms of a second species into a plurality of subpopulations using a classification scheme that classifies each organism in the plurality of organisms of the second species into at least one of the subpopulations. The classification scheme uses a plurality of cellular constituent measurements from each organism in the second species. The genetic analysis module includes instructions that, for at least one subpopulation in the plurality of subpopulations, performs quantitative genetic analysis on the subpopulation in order to identify the quantitative trait locus for the complex trait. The ortholog identification module comprises instructions for finding the quantitative trait locus in the first species that is the ortholog of the quantitative trait locus in the second species.

3.4. Obesity Related Genes and Obesity Related Gene Products

Another aspect of the present invention provides a method for determining whether a candidate molecule affects a body weight disorder associated with an organism. The method comprises the step of (a) contacting a cell from the organism with, or recombinantly expressing within the cell from the organism, the candidate molecule. The method further comprises the step of (b) determining whether the RNA expression or protein expression in the cell of at least one open reading frame is changed in step (a) relative to the expression of the open reading frame in the absence the candidate molecule. Each open reading frame is regulated by a promoter native to a nucleic acid sequence selected from the group consisting of SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20, and homologs of each of the foregoing. The method further comprises the step of (c) determining that the candidate molecule affects a body weight disorder associated with the organism when the RNA expression or protein expression of the at least one open reading frame is changed, or determining that the candidate molecule does not affect a body weight disorder associated with the organism when the RNA expression or protein expression of the at least one open reading frame is unchanged. In some embodiments, the body weight disorder is obesity, anorexia nervosa, bulimia nervosa or cachexia.

In some embodiments, the cell from the organism that is contacted with the candidate molecule exhibits a lower expression level of a protein sequence selected from the group consisting of SEQ ID NO: 4, SEQ ID NO: 5, SEQ ID NO: 6, SEQ ID NO: 7, SEQ ID NO: 8, SEQ ID NO: 10, SEQ ID NO: 11, SEQ ID NO: 14, SEQ ID NO: 15, SEQ ID NO: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29 relative to a cell from the organism that is not contacted with the candidate molecule. In some embodiments, step (b) comprises determining whether RNA expression is changed. In some embodiments, step (b) comprises determining whether protein expression is changed. In some embodiments, step (b) comprises determining whether RNA or protein expression of at least two of the open reading frames is changed. In some embodiments, step (a) comprises contacting the cell with the candidate molecule and step (a) is carried out in a liquid high throughput-like assay.

In some embodiments, the cell comprises a promoter region of at least one gene selected from the group consisting of SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20, and homologs of each of the foregoing, each promoter region being operably linked to a marker gene. Further, step (b) comprises determining whether the RNA expression or protein expression of the marker gene(s) is changed in step (a) relative to the expression of the marker gene in the absence of the candidate molecule. Illustrative marker genes include, but are not limited to, green fluorescent protein, red fluorescent protein, blue fluorescent protein, luciferase, LEU2, LYS2, ADE2, TRP1, CAN1, CYH2, GUS, CUP1 and chloramphenicol acetyl transferase.

Another aspect of the invention provides a method of identifying a molecule that specifically binds to a ligand selected from the group consisting of (i) a protein encoded by a gene selected from the group consisting of SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20, and homologs of each of the foregoing, and (ii) a biologically active fragment of SEQ ID NO: 4, SEQ ID NO: 5, SEQ ID NO: 6, SEQ ID NO: 7, SEQ ID NO: 8, SEQ ID NO: 10, SEQ ID NO: 11, SEQ ID NO: 14, SEQ ID NO: 15, SEQ ID NO: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29. The method comprises the step of (a) contacting the ligand with one or more candidate molecules under conditions conducive to binding between the ligand and the candidate molecules. The method further comprises the step of (b) identifying a molecule within the one or more candidate molecules that binds to the ligand.

Another aspect of the invention provides a purified protein comprising the amino acid sequence of SEQ ID NO: 8. Still another aspect of the invention provides a purified protein encoded by a nucleic acid hybridizable to a DNA having a sequence consisting of the coding region of SEQ ID NO: 2. Yet another aspect of the invention provides a purified protein comprising an amino acid sequence that has at least 90% identity to the amino acid sequence set forth in SEQ ID NO: 8, in which percentage identity is determined over an amino acid sequence of identical size as SEQ ID NO: 8. Still another aspect of the invention provides a purified protein comprising an amino acid sequence that has at least 95% identity to the amino acid sequence set forth in SEQ ID NO: 8, in which percentage identity is determined over an amino acid sequence of identical size as SEQ ID NO: 8.

Another embodiment of the present invention provides an isolated nucleic acid comprising the nucleotide sequence of SEQ ID NO: 2, a coding region of SEQ ID NO: 2, SEQ ID NO: 3, a coding region of SEQ ID NO: 3, or the complement of any of the foregoing. In some embodiments, this nucleic acid is DNA. Another embodiment of the present invention provides an antibody that binds to a protein consisting of the amino acid sequence of SEQ ID NO: 8. This antibody may be monoclonal. Another embodiment of the present invention provides a molecule comprising a fragment of the antibody, which fragment binds a protein consisting of the amino acid sequence of SEQ ID NO: 8.

Another embodiment of the present invention provides a method of treating or preventing a body weight disorder. The method comprises administering to a subject in which treatment is desired a therapeutically effective amount of a molecule that inhibits a function of one or more of the group consisting of SEQ ID NO: 8, SEQ ID NO: 11, SEQ ID NO: 15, SEQ ID NO: 18, SEQ ID NO: 25, SEQ ID NO: 26, and SEQ ID NO: 27. In some embodiments, the subject is human. In some embodiments, the molecule that inhibits a function of one or more of the group consisting of SEQ ID NO: 8, SEQ ID NO: 11, SEQ ID NO: 15, SEQ ID NO: 18, SEQ ID NO: 25, SEQ ID NO: 26, and SEQ ID NO: 27 is selected from the group consisting of an antibody that binds to one of SEQ ID NO: 8, SEQ ID NO: 11, SEQ ID NO: 15, SEQ ID NO: 18, SEQ ID NO: 25, SEQ ID NO: 26, and SEQ ID NO: 27 or a fragment or derivative therefore containing the binding region thereof a nucleic acid complementary to the RNA produced by transcription of a gene encoding one of SEQ ID NO: 8, SEQ ID NO: 11, SEQ ID NO: 15, SEQ ID NO: 18, SEQ ID NO: 25, SEQ ID NO: 26, and SEQ ID NO: 27. In some embodiments, the molecule that inhibits a function of one or more of the group consisting of SEQ ID NO: 8, SEQ ID NO: 11, SEQ ID NO: 15, SEQ ID NO: 18, SEQ ID NO: 25, SEQ ID NO: 26, and SEQ ID NO: 27 is an oligonucleotide that (a) consists of at least six nucleotides; (b) comprises a sequence complementary to at least a portion of an RNA transcript of a gene encoding one of SEQ ID NO: 8, SEQ ID NO: 11, SEQ ID NO: 15, SEQ ID NO: 18, SEQ ID NO: 25, SEQ ID NO: 26 or SEQ ID NO: 27; and (c) is hybridizable to the RNA transcript under moderately stringent conditions.

Yet another aspect of the present invention provides a method of treating or preventing a body weight disorder. The method comprises administering to a subject in which treatment is desired a therapeutically effective amount of a molecule that enhances a function of one or more of the group consisting of SEQ ID NO: 8, SEQ ID NO: 11, SEQ ID NO: 15, SEQ ID NO: 18, SEQ ID NO: 25, SEQ ID NO: 26, and SEQ ID NO: 27. In some embodiments the subject is human.

Still another aspect of the present invention provides a method of diagnosing a disease or disorder or the predisposition to the disease or disorder. The disease or disorder is characterized by an aberrant level of one of SEQ ID NO: 1 through SEQ ID NO: 29 in a subject. The method comprising measuring the level of any one of SEQ ID NO: 1 through SEQ ID NO: 29 in a sample derived from the subject, in which an increase or decrease in the level of one of SEQ ID NO: 1 through SEQ ID NO: 29 in the sample, relative to the level of one of the SEQ ID NO: 1 through SEQ ID NO: 29 found in an analogous sample not having the disease or disorder, indicates the present of the disease or disorder in the subject. In some embodiments the disease or disorder is a body weight disorder. In some embodiments, the body weight disorder is obesity, anorexia nervosa, bulimia nervosa, or cachexia.

Another aspect of the present invention provides a method of diagnosing or screening for the presence of or predisposition for developing a disease or disorder involving a body weight disorder in a subject. The method comprises detecting one or more mutations in at least one of SEQ ID NO: 1 through SEQ ID NO: 29 in a sample derived from the subject, in which the presence of the one or more mutations indicates the presence of the disease or disorder or a predisposition for developing the disease or disorder.

Still another aspect of the present invention provides a recombinant non-human animal that is the product of a process comprising introducing a nucleic acid encoding at least a domain of one of SEQ ID NO: 8, SEQ ID NO: 15, SEQ ID NO: 18, SEQ ID NO: 25, SEQ ID NO: 26, and SEQ ID NO: 27 into the recombinant non-human animal.

3.5. Using Cross Species Data to Associate Genes with Traits of Interest

One embodiment of the present invention provides a method for confirming the association of a query QTL or a query gene in the genome of a second species with a clinical trait T exhibited by the second species. The method comprises (a) finding a first QTL or a first gene in a first species that is linked to a trait T', wherein trait T' is indicative of trait T; (b) mapping a region of the genome of the first species that comprises the first QTL or the first gene to a region of the genome of the second species; and (c) finding a query QTL or a query gene in the second species that is potentially associated with the trait T, wherein the potential association of the query QTL or the query gene with the clinical trait T is confirmed when the query QTL or the query gene is in the region of the genome of the second species.

In some embodiments, the finding step (a) comprises (i) crossing a first strain and a second strain of the first species in order to obtain a segregating population; (ii) stratifying the segregating population into a plurality of subpopulations, wherein a subpopulation in the plurality of subpopulations represents a phenotypic extreme of the trait T'; (iii) using cellular constituent measurements from organisms in the plurality of subpopulations to identify a cellular constituent set that exhibits a cellular constituent measurement pattern associated with the phenotypic extreme; (iv) clustering the segregating population based on measurements of the cellular constituent set in organisms in the segregating population to obtain a plurality of population clusters; and (v) for at least one population cluster in the plurality of population clusters, performing quantitative genetic analysis on the population cluster in order to find the first QTL or the first gene in the first species that is linked to the trait T'.

3.6. Using Causality in a First Species to Associate Genes or Loci with Traits of Interest in a Second Species One aspect of the present invention provides a method of identifying a molecular target for a second trait in a second species. In the method a first gene in a segregating population that is causal for a first trait exhibited by all or a portion of the segregating population is identified. Each member of the segregating population is a member of a first species and the second trait in the second species corresponds to the first trait in the first species. The first gene in the first species is mapped to a corresponding locus in the genome of the second species. Next, a determination is made as to whether a marker or a haplotype in the corresponding locus in the genome of the second species associates with the second trait. Then the marker or the haplotype associates with the second trait in the second species, the locus is identified as the molecular target.

In some embodiments, the marker or the haplotype is in a second gene in the corresponding locus and the second gene is identified as the molecular target. In some embodiments, the first gene and the second gene are orthologous. In some embodiment the first gene in the segregating population that is causal for the first trait exhibited by all or a portion of the segregating population is identified by a method that comprises: (a) identifying a test gene in the first species that has at least one abundance quantitative trait locus (eQTL) coincident with a respective clinical quantitative trait loom (cQTL) for the first trait; and (b) testing, for one or more respective cQTL in the at least one eQTL, whether (i) the genetic variation of the eQTL across the segregating population and (ii) the variation of the first trait across the segregating population are correlated conditional on an abundance pattern of the test gene across the segregating population. When the genetic variation of (1) one or more respective eQTL tested in step (b) and (2) the variation of the first trait across the segregating population are correlated conditional on an abundance pattern of the test gene across the segregating population, the test gene is identified as the first gene. In some embodiments, the second species is mammalian. In particular, in some embodiments, the second species is human. In some embodiments, the second trait is asthma, ataxia telangiectasia, bipolar disorder, cancer, common late-onset Alzheimer's disease, diabetes, heart disease, hereditary early-onset Alzheimer's disease, hereditary nonpolyposis colon cancer, hypertension, infection, maturity-onset diabetes of the young, mellitus, migraine, nonalcoholic fatty liver, nonalcoholic steatohepatitis, non-insulin-dependent diabetes mellitus, obesity, polycystic kidney disease, psoriases, schizophrenia, or xeroderma pigmentosum. In some embodiments, the molecular target is a gene, an exon, an intron, or a regulatory element of a gene. In some embodiments the marker is a single nucleotide polymorphism, a microsatellite marker, a restriction fragment length polymorphism, a short tandem repeat, a DNA methylation marker, a sequence length polymorphism, a random amplified polymorphic DNA, an amplified fragment length polymorphisms, or a simple sequence repeat.

Another aspect of the present invention provides a method of identifying a molecular target for a second trait in a second species. In the method, a first gene in a segregating population that is causal for a first trait exhibited by all or a portion of the segregating population is identified. Here, each member of the segregating population is a member of a first species and the second trait in the second species corresponds to the first trait in the first species. A locus in the genome of the second species that is (1) linked to the second trait and (2) maps to the position in the genome of the first species where the first gene resides is identified. Finally, a determination is made as to whether a marker or a haplotype in the corresponding locus in the genome of the second species associates with the second trait. When the marker or the haplotype associates with the second trait in the second species, the locus is identified as the molecular target. In some embodiments, the marker or the haplotype is in a second gene in the corresponding locus and the second gene is identified as the molecular target. In some embodiments, the first gene and the second gene are orthologous. In some embodiments, the method of identifying the first gene in the segregating population that is causal for the first trait exhibited by all or a portion of the segregating population comprises: (a) identifying a test gene in the first species that has at least one abundance quantitative trait locus (eQTL) coincident with a respective clinical quantitative trait locus (cQTL) for the first trait; and (b) testing, for one or more respective eQTL in the at least one eQTL, whether (i) the genetic variation of the eQTL across the segregating population and (ii) the variation of the first trait across the segregating population are correlated conditional on an abundance pattern of the test gene across the segregating population. When the genetic variation of (1) the one or more respective eQTL tested in step (a) and (2) the variation of the first trait across the segregating population are correlated conditional on an abundance pattern of the test gene across the segregating population, the test gene is identified as the first gene.

Another aspect of the invention provides a method of identifying a molecular target for a second trait in a second species. In the methods, a first gene in a segregating population that is causal for a first trait exhibited by all or a portion of the segregating population is identified. Here, each member of the segregating population is a member of a first species and the second trait in the second species corresponds to the first trait in the first species. A second gene in the genome of the second species that is orthologous to the first gene is identified such that the variation of the abundance of the second gene across biological samples taken from a plurality of members of the second species and (ii) the variation of the second trait across the plurality of members of the second species are associated. This second gene is the sought after molecular target. In some embodiments, the method further comprises validating the second gene by determining whether a marker or a haplotype in the second gene associates with the second trait. When the marker or the haplotype associates with the second trait in the second species, the second gene is validated. In some instances, the first gene in a segregating population that is causal for a first trait exhibited by all or a portion of the segregating population is identified by (a) finding a test gene in the first species that has at least one abundance quantitative trait locus (eQTL) coincident with a respective clinical quantitative trait locus (cQTL) for the first trait; and (b) testing, for one or more respective eQTL in the at leat one eQTL, whether (i) the genetic variation of the eQTL across the segregating population and (ii) the variation of the first trait across the segregating population are correlated conditional on an abundance pattern of the test gene across the segregating population. When the genetic variation of (1) the one or more respective eQTL tested in step (b) and (2) the variation of the first trait across the segregating population are correlated conditional on an abundance pattern of the test gene across the segregating population, the test gene is identified as the first gene.

Still another aspect of the present invention provides a computer system for identifying a molecular target for a second trait in a second species. The computer system comprises a central processing unit and a memory coupled to the central processing unit. The memory stores instructions for identifying a first gene in a segregating population that is causal for a first trait exhibited by all or a portion of the segregating population. Bach member of the segregating population is a member of a first species and the second trait in the second species corresponds to the first trait in the first species. The memory further includes instructions for mapping the first gene in the first species to a corresponding locus in the genome of the second species. The memory further includes instructions for determining whether a marker or a haplotype in the corresponding locus the genome of the second species associates with the second trait.

Yet another aspect of the present invention provides a computer program product for use in conjunction with a computer system, the computer program product comprising a computer readable storage medium and a computer program mechanism embedded therein. The computer program mechanism comprises instructions for identifying a first gene in a segregating population that is causal for a first trait exhibited by all or a portion of the segregating population. Each member of the segregating population is a member of a first species and the second trait in the second species corresponds to the first trait in the first species. The computer program mechanism further includes instructions for mapping the first gene in the first species to a corresponding locus in the genome of the second species. The computer program mechanism also includes instructions or determining whether a marker or a haplotype in the corresponding locus in the genome of the second species associates with the second trait.

Still another embodiment of the present invention provides a computer program product for use in conjunction with a computer system, the computer program product comprising a computer readable storage medium and a computer program mechanism embedded therein. The computer program mechanism comprises instructions for identifying a first gene in a segregating population that is causal for a first trait exhibited by all or a portion of the segregating population. Each member of the segregating population is a member of a first species and the second trait in the second species corresponds to the first trait in the first species. The computer program mechanism further includes instructions for identifying a locus in the genome of the second species that is (1) linked to the second trait and (2) maps to the position in the genome of the first species where the first gene resides. The computer program mechanism further comprises instructions for determining whether a marker or a haplotype in the corresponding locus in the genome of the second species associates with the second trait. Yet another embodiment of the invention provides a computer system for identifying a molecular target for a second trait in a second species. The computer system comprises a central processing unit and a memory, coupled to the central processing unit. The memory stores instructions for identifying a first gene in a segregating population that is causal for a first trait exhibited by all or a portion of the segregating population. Each member of the segregating population is a member of a first species. Further, the second trait in the second species corresponds to the first trait in the first species. The memory further stores instructions for identifying a second gene in the genome of the second species that is orthologous to the first gene such that (i) the variation of the abundance of the second gene across biological samples taken from a plurality of members of the second species and (ii) the variation of the second trait across the plurality of members of the second species are associated.

Still another aspect of the invention provides a compute program product for use in conjunction with a computer system. The computer program product comprises a computer readable storage medium and a computer program mechanism embedded therein. The computer program mechanism comprises instructions for identifying a first gene in a segregating population that is causal for a first trait exhibited by all or a portion of the segregating population. Each member of the segregating population is a member of a first species. The second trait in the second species corresponds to the first trait in the first species. The computer program mechanism further includes instructions for identifying a second gene in the genome of the second species that is orthologous to the first gene such that (i) the variation of the abundance of the second gene across biological samples taken from a plurality of members of the second species and (ii) the variation of the second trait across the plurality of members of the second species are associated.

4. BRIEF DESCRIPTION OF THE DRAWINGS

Figure 6:
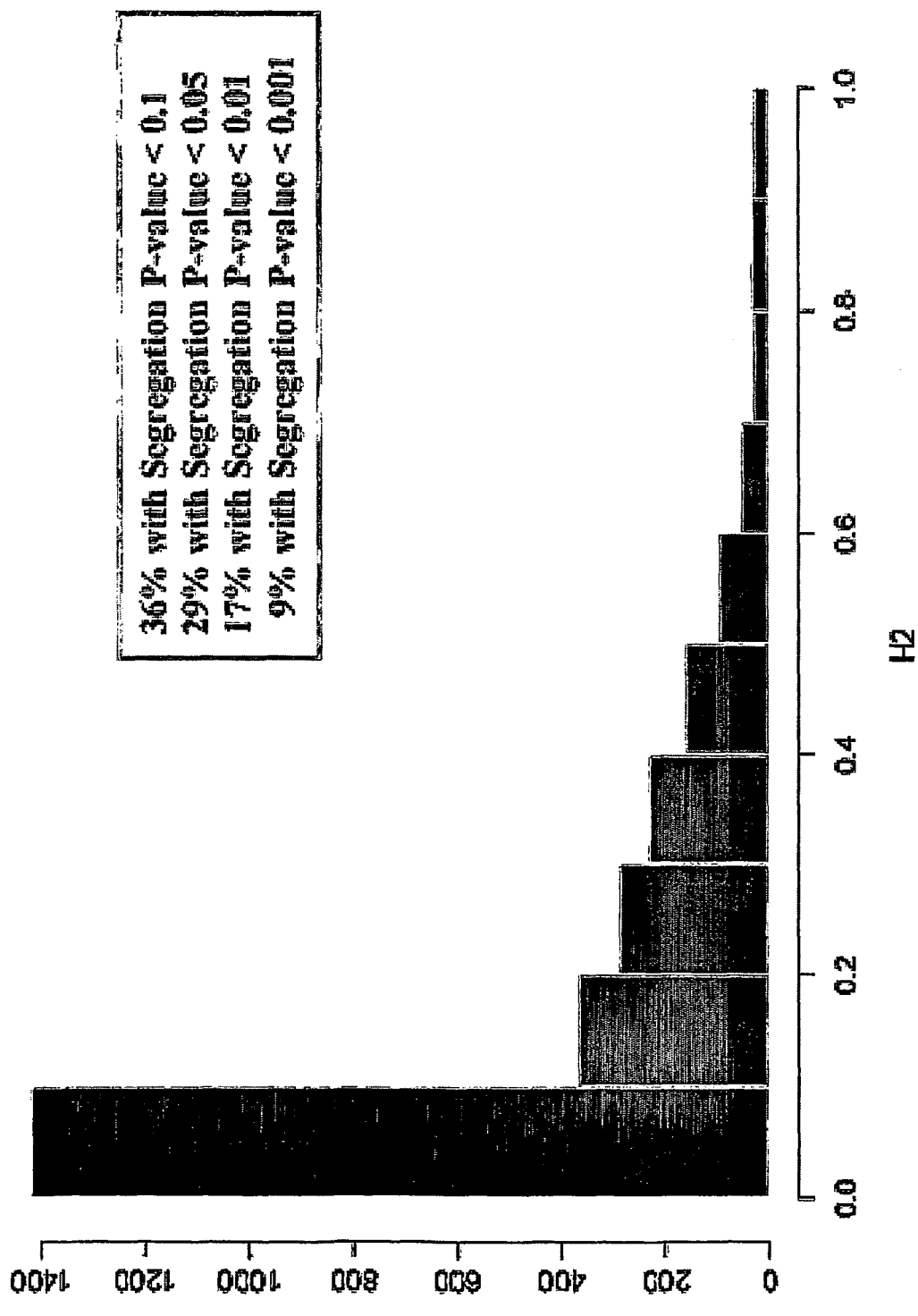

FIG. 6 provides a histogram for p-values of segregation analyses performed on 2,726 genes across four CEPH families in accordance with one embodiment of the present invention.

FIG. 7 illustrates expression quantitative trait loci ("eQTL") identified for a diversity of transcript abundance polymorphisms in accordance with one embodiment of the present invention.

Figure 8:
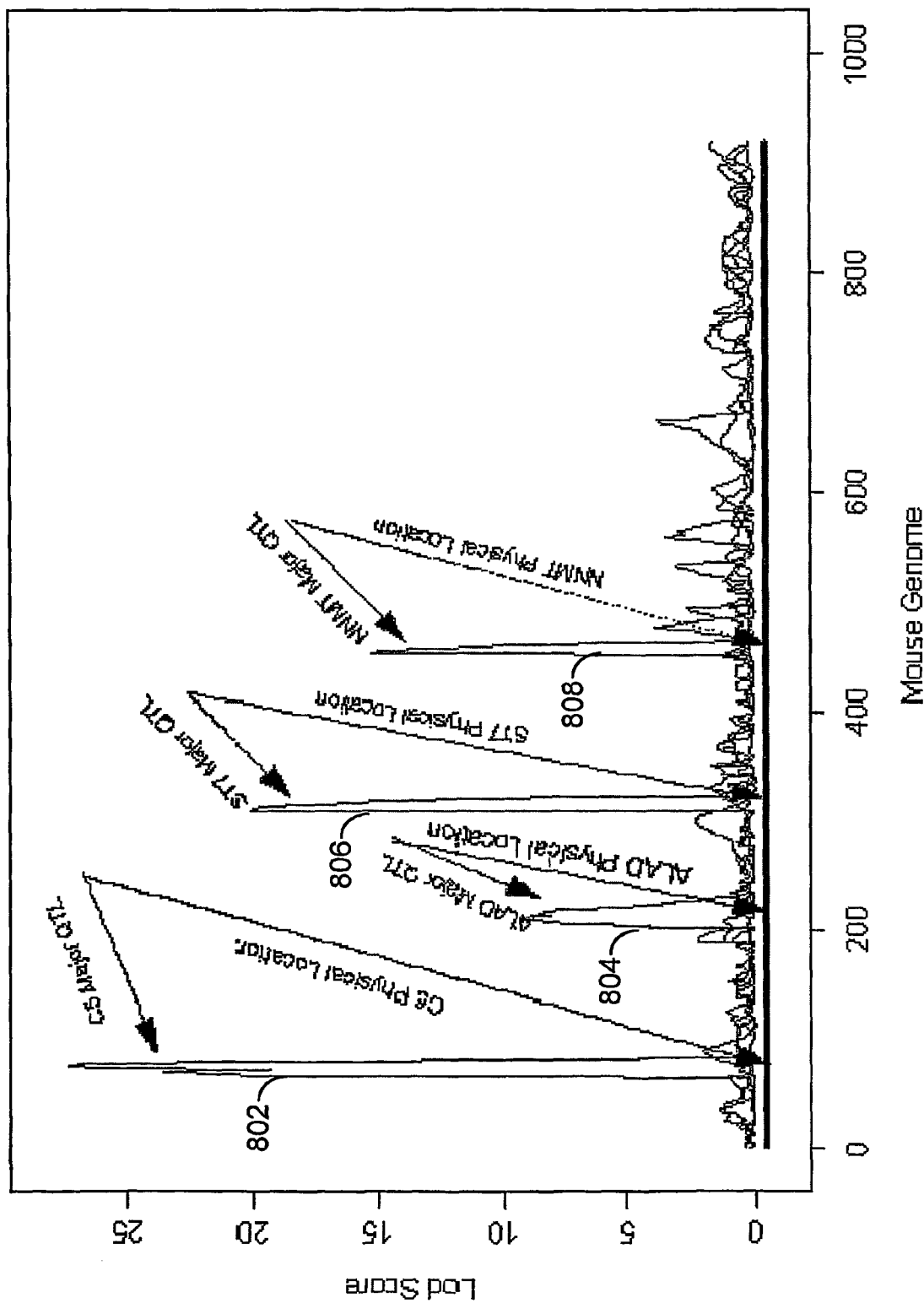

FIG. 8 highlights a range of gene-centered polymorphisms known to exist between DBA and B6 mouse strains, in accordance with one embodiment of the present invention.

Figure 9:
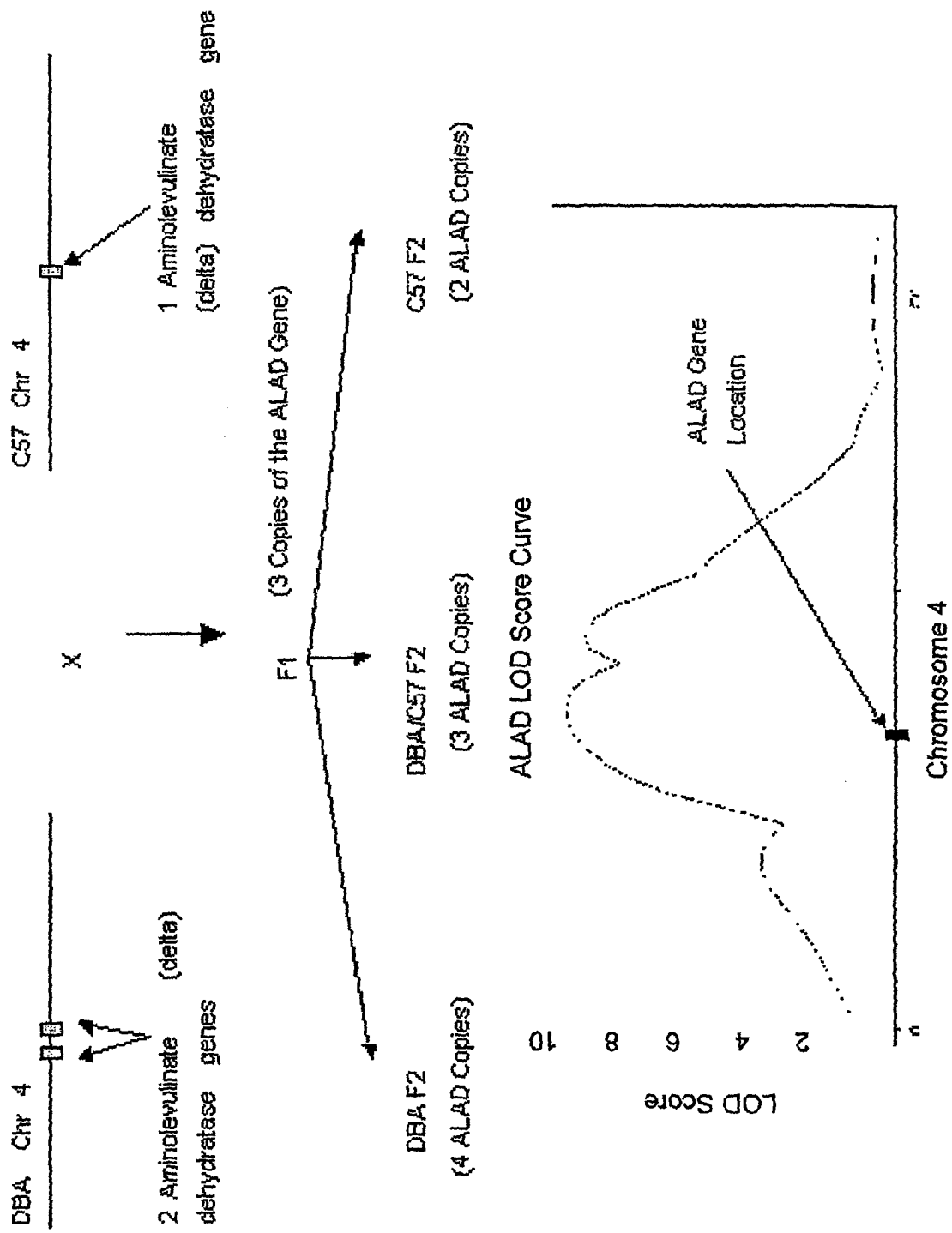

FIG. 9 illustrates how quantitative trait loci analysis using gene expression as a quantitative trait can detect a quantitative trait loci for a gene that has a higher copy number in one parent than the other, in accordance with one embodiment of the present invention.

Figure 10:
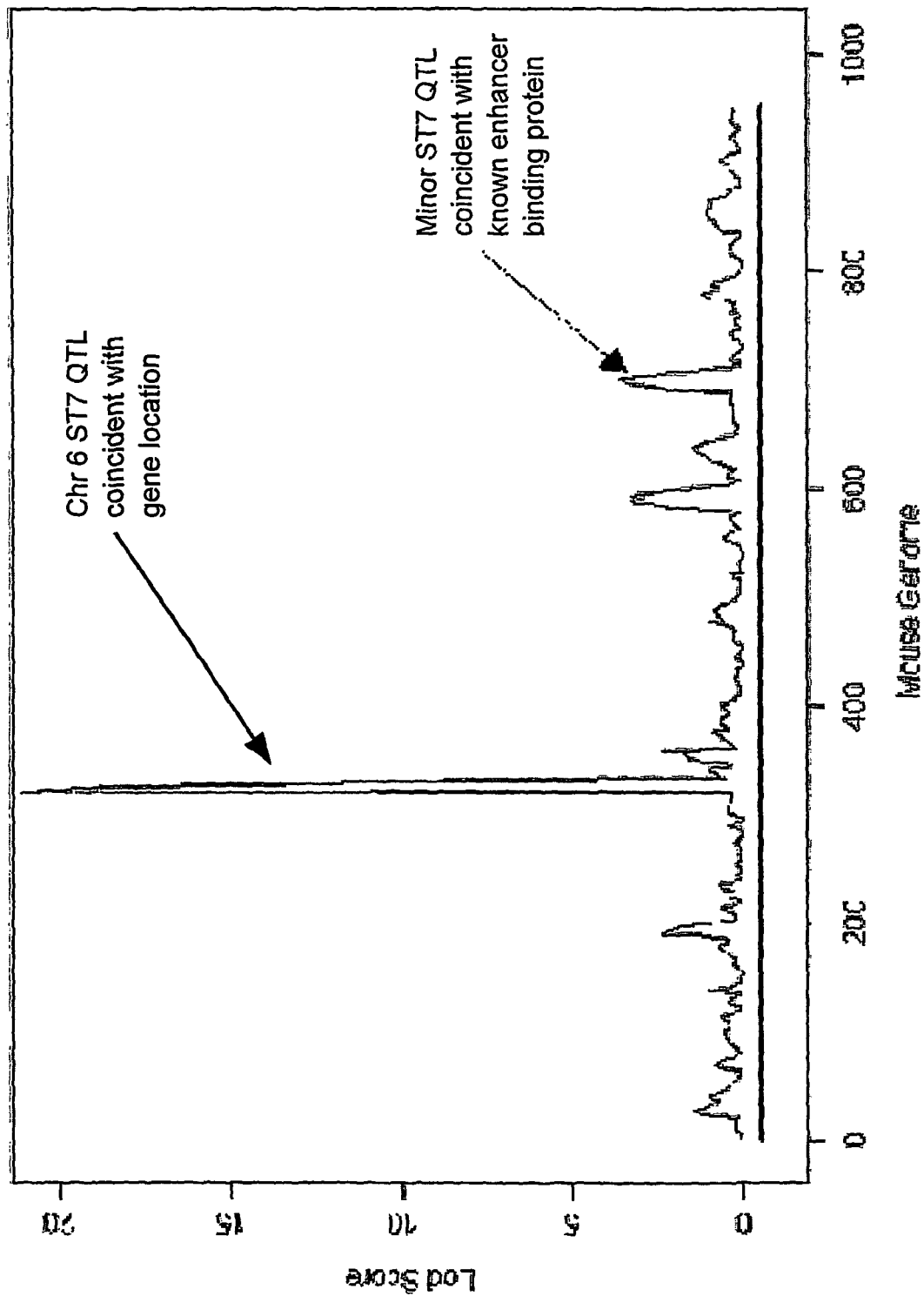

FIG. 10 illustrates how the use of expression data as a quantitative trait can detect differential splicing, in accordance with one embodiment of the present invention.

Figure 11:
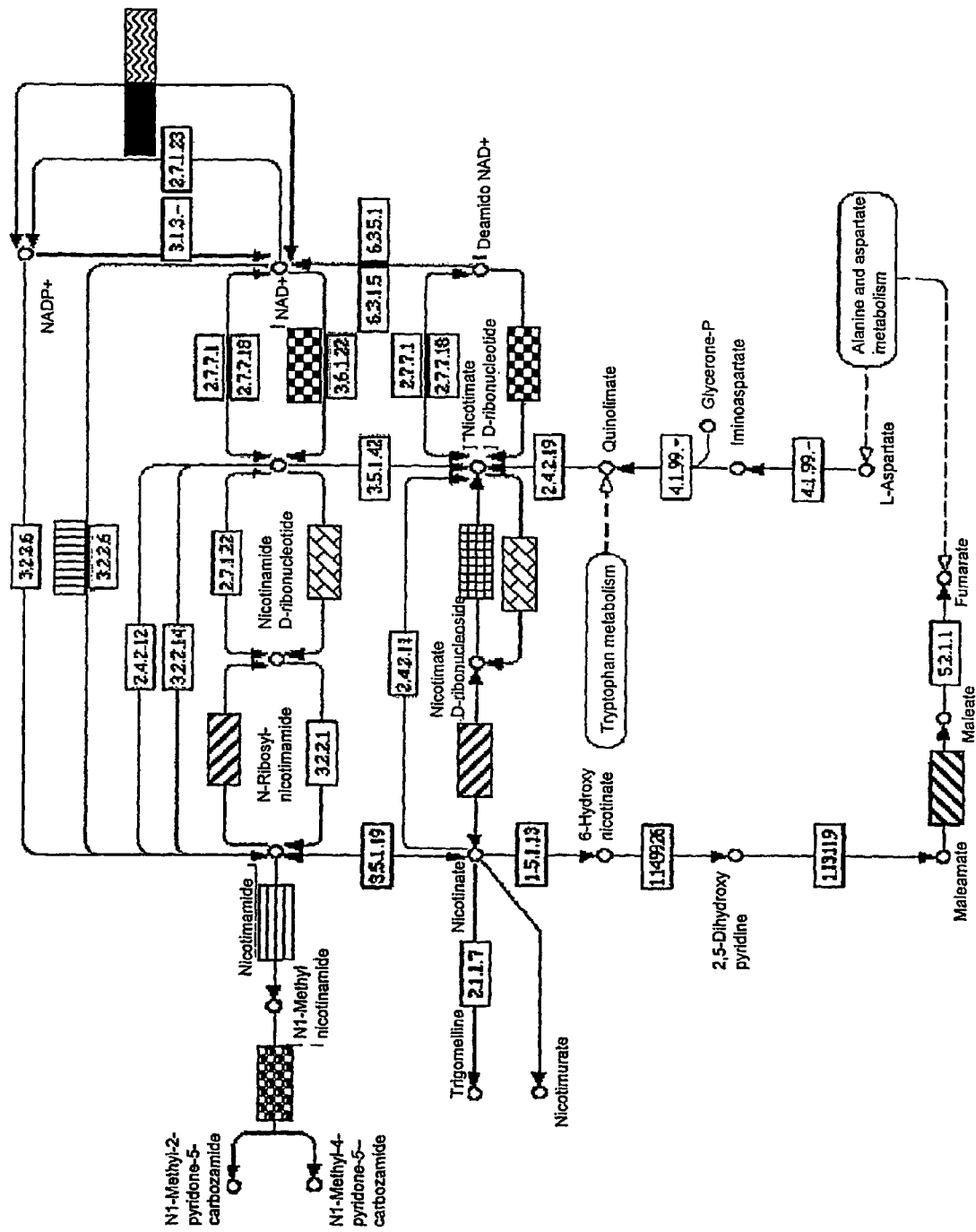

FIG. 11 illustrates the pathways associated with nicotinate and nicotinamide metabolism in accordance with the prior art.

FIG. 12 provides a key for important enzymes in the pathways associated with nicotinate and nicotinamide metabolism that are illustrated in FIG. 11.

Figure 13:
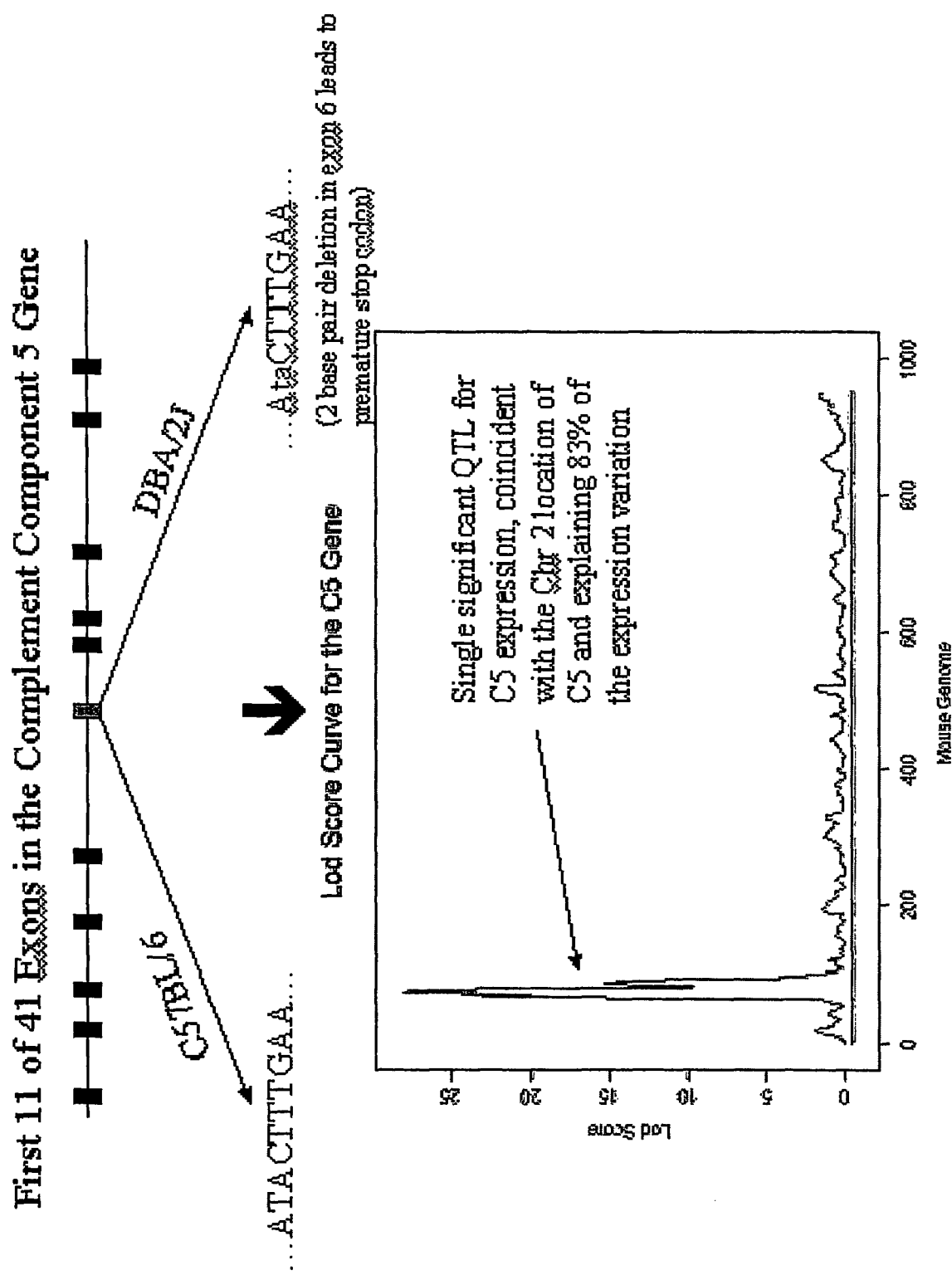

FIG. 13 illustrates how the use of expression data as a quantitative trait can detect nonsense mutations, in accordance with one embodiment of the present invention.

Figure 14:
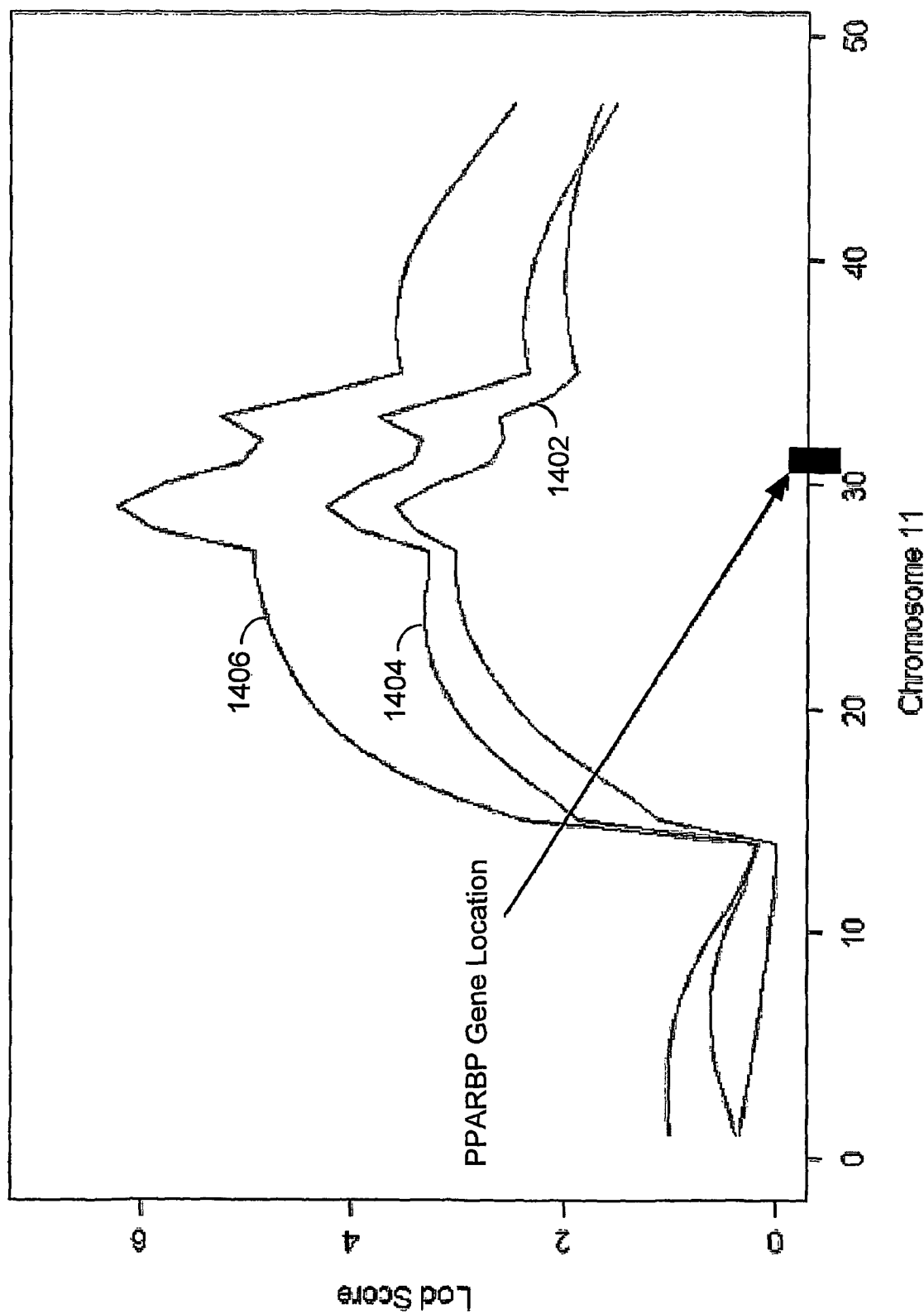

FIG. 14 illustrates the results of a QTL analysis in a region of mouse chromosome 11 for the phenotypic traits "free fatty acid" (curve 1402) and "triglyceride level" (curve 1404), in accordance with one embodiment of the present invention.

Figure 15:
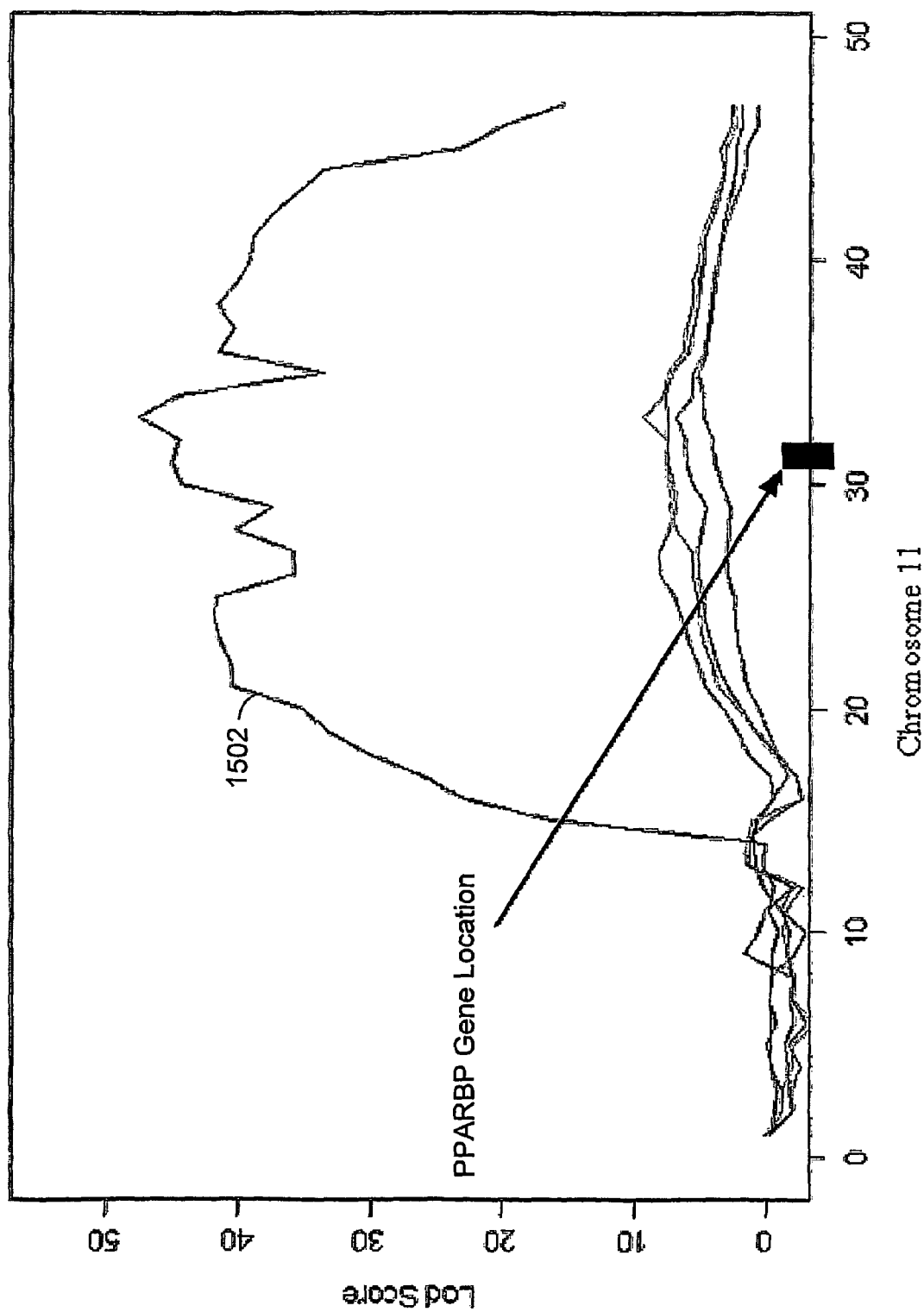

FIG. 15 illustrates expression QTL ("eQTL") from several genes that are known to be involved with glucose and lipid metabolism which overlap with the "free fatty acid" and "triglyceride lever" clinical trait QTL ("cQTL") on chromosome 11, in accordance with one embodiment of the present invention.

Figure 16:
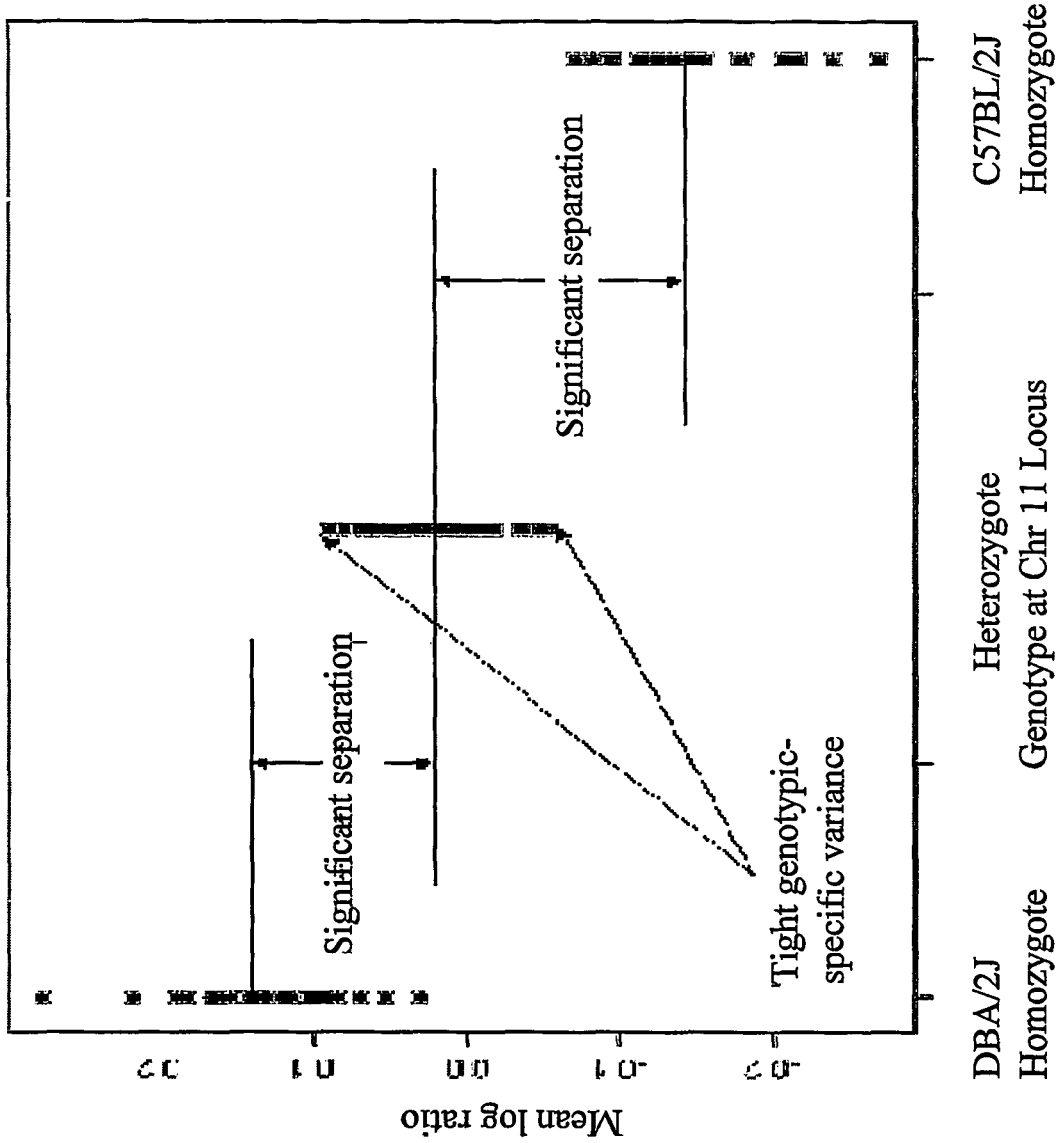

FIG. 16 shows a scatter plot that breaks down the mean log ratios for the mouse peroxisome proliferator activated receptor (PPAR) binding protein by mouse genotype at the chromosome 11 location across the F2 mouse population (120 F2 mouse livers) that was profiled in accordance with one embodiment of the present invention.

Figure 17:
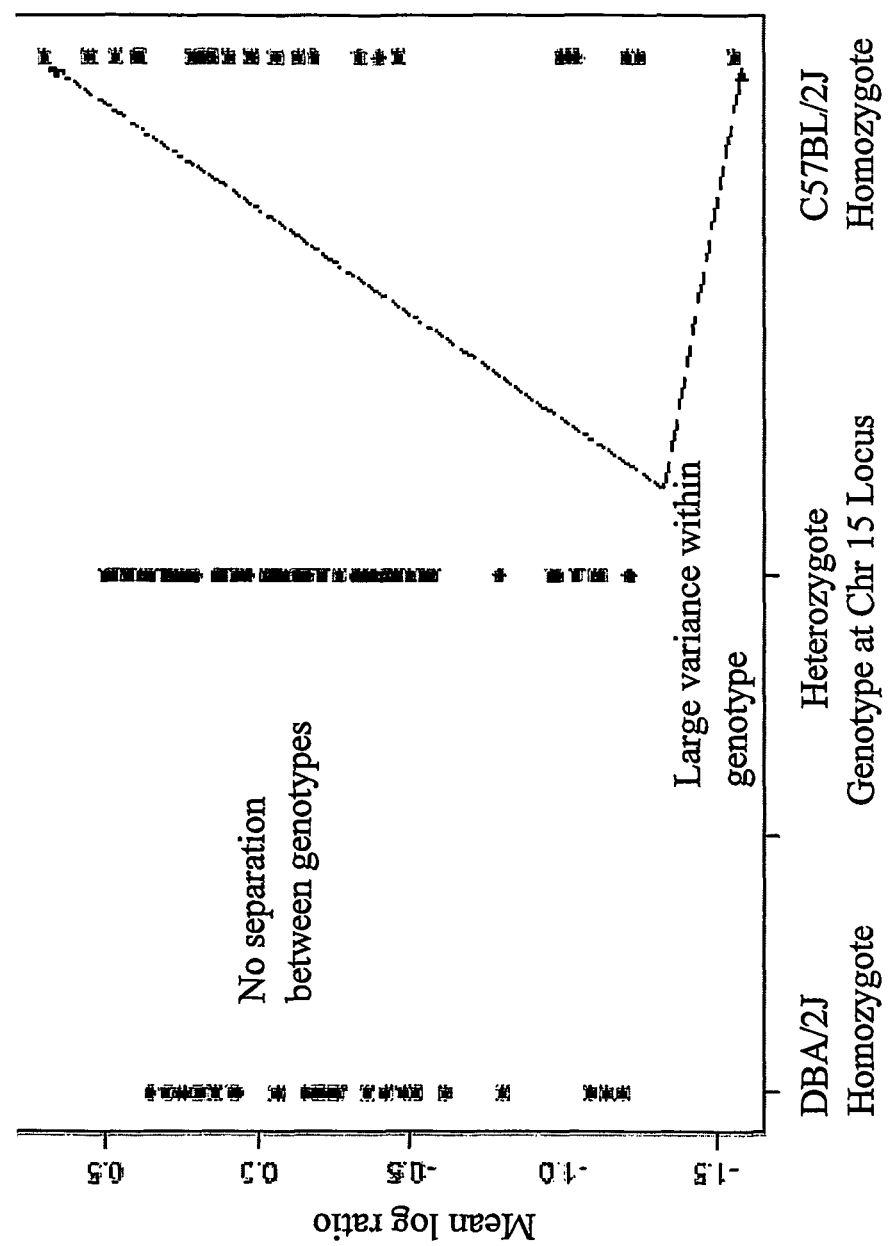

FIG. 17 shows a scatter plot that breaks down the mean log ratios for the mouse PPAR binding protein by mouse genotype at the chromosome 15 location across the F2 mouse population (120 F2 mouse livers) that was profiled in accordance with one embodiment of the present invention.

Figure 18:
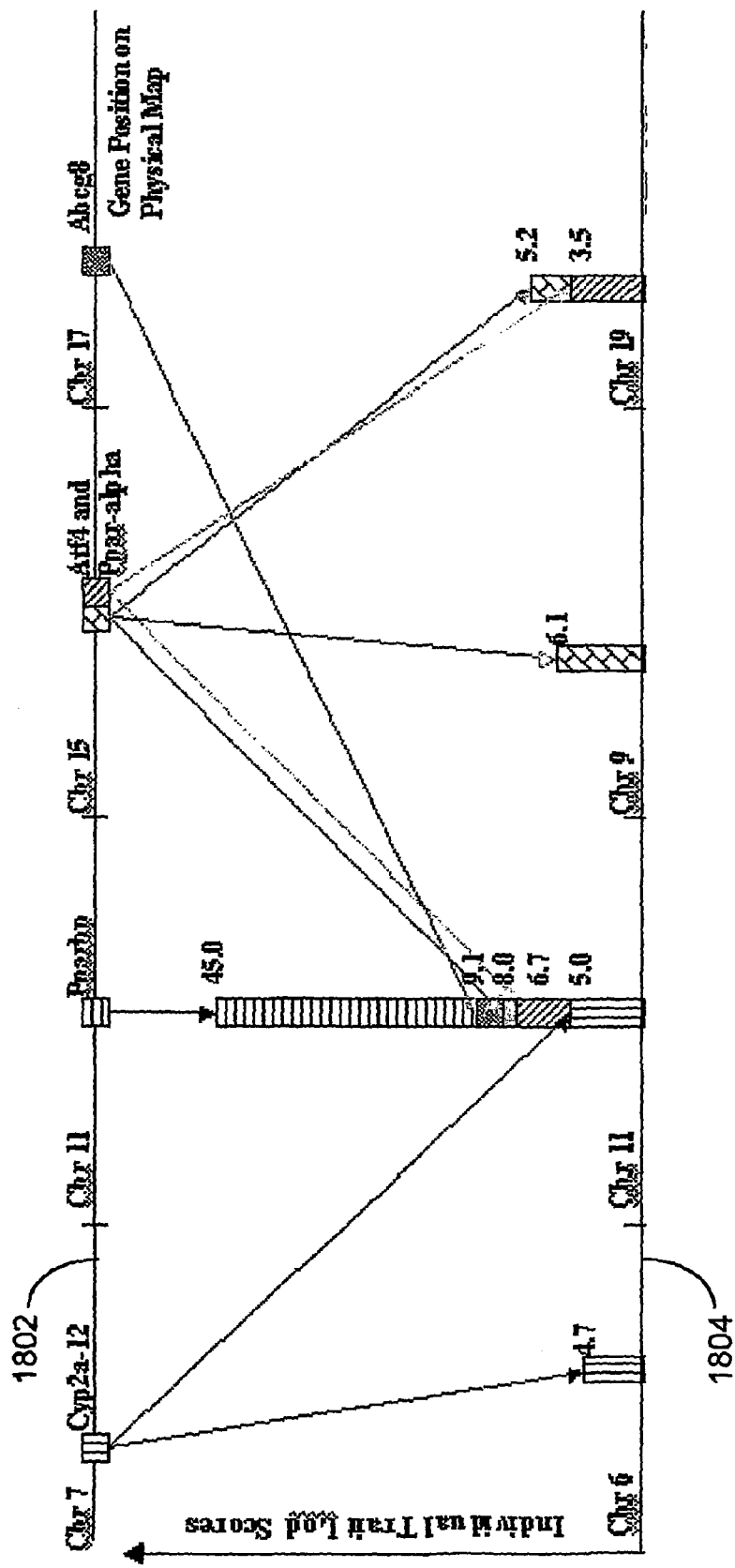

FIG. 18 is a plot that illustrates how genes known to be involved in lipid metabolism are linked by eQTL analysis to the same genetic locus, even though they physically reside at different unlinked locations.

Figure 19:
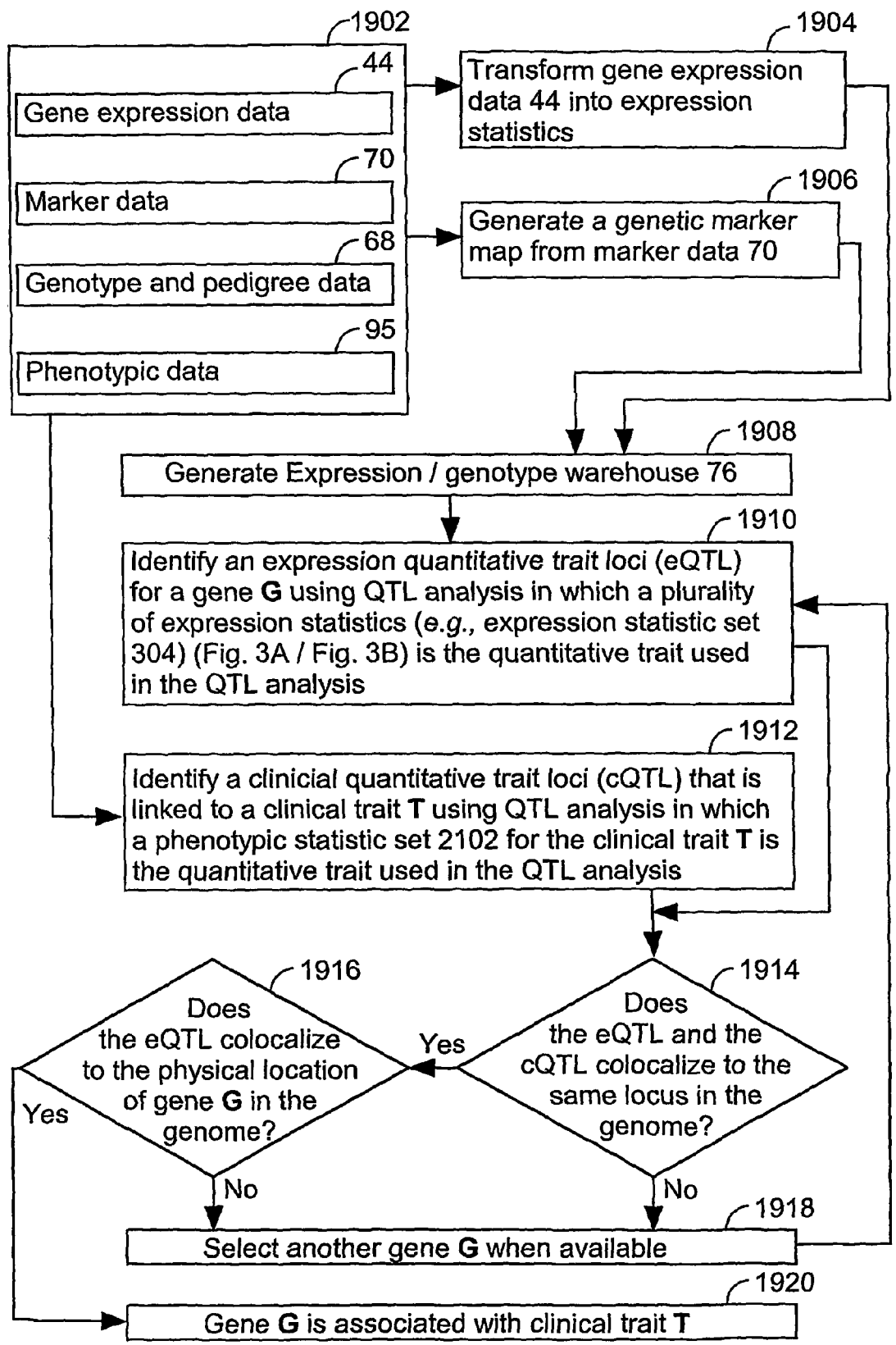

FIG. 19 illustrates processing steps for associating a gene G in the genome of a single species with a clinical trait T that is exhibited by one or more organisms in a plurality of organisms of the single species, in accordance with an embodiment of the present invention.

Figure 20:
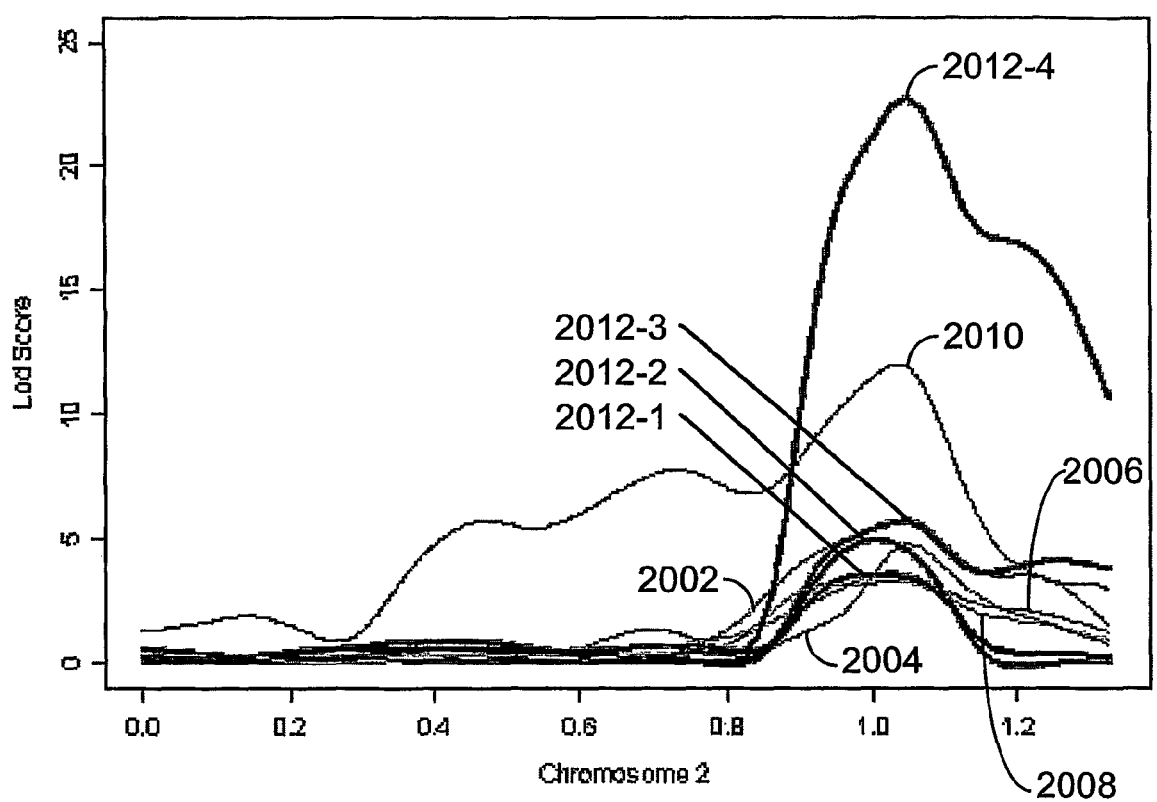

FIG. 20 illustrates clinical quantitative trait loci (cQTL) for four mouse obesity-related traits that co-localize with the expression QTL (eQTL) for four genes at a QTL hot spot on mouse chromosome 2, in accordance with an embodiment of the present invention.

Figure 21:
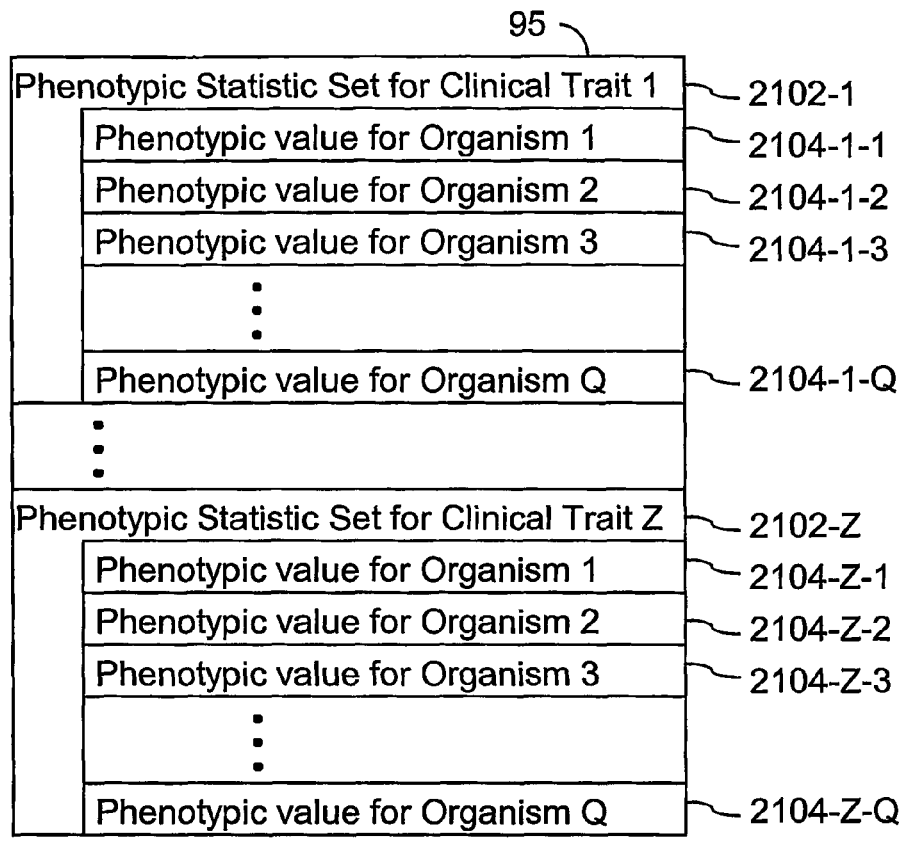

FIG. 21 illustrates a plurality of phenotypic statistics sets, in accordance with an embodiment of the present invention.

Figure 22:
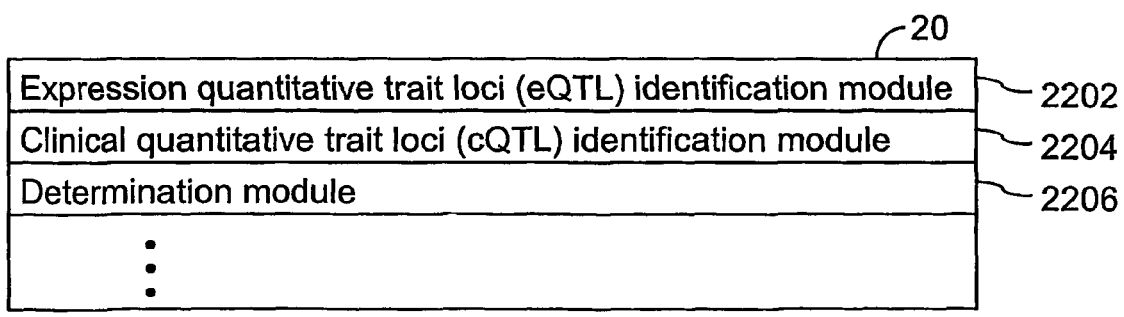

FIG. 22 illustrates computing modules in accordance with an embodiment of the present invention.

Figure 23:
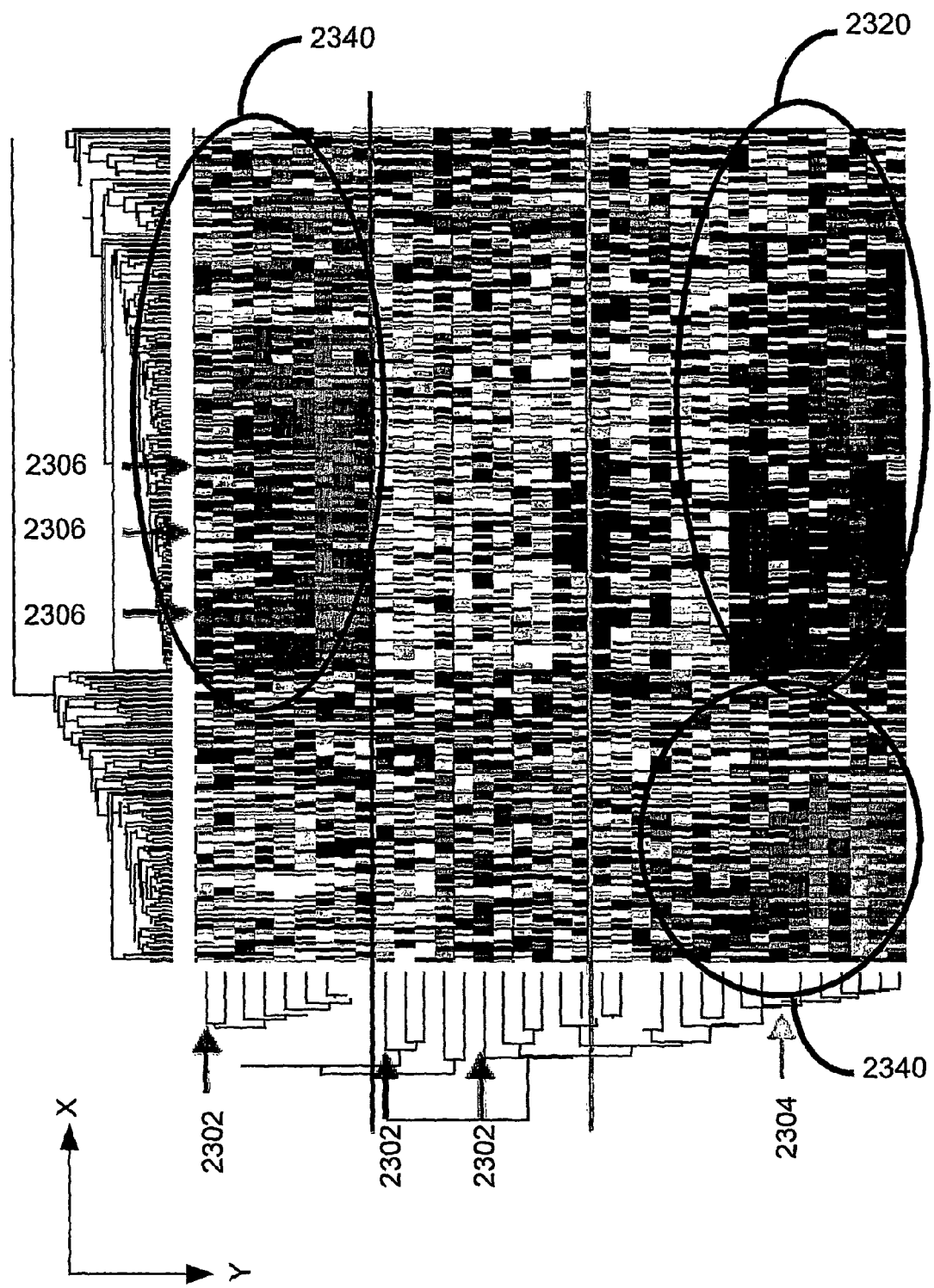

FIG. 23 illustrates the hierarchical clustering of 123 genes that are linked to a particular chromosome 2 locus or are highly correlated with genes that are linked to this locus (x-axis) against the hierarchical clustering of F2 mice in the highest and lowest quartile for the phenotype "subcutaneous fat pad mass" (y-axis), in accordance with one embodiment of the present invention.

Figure 24:
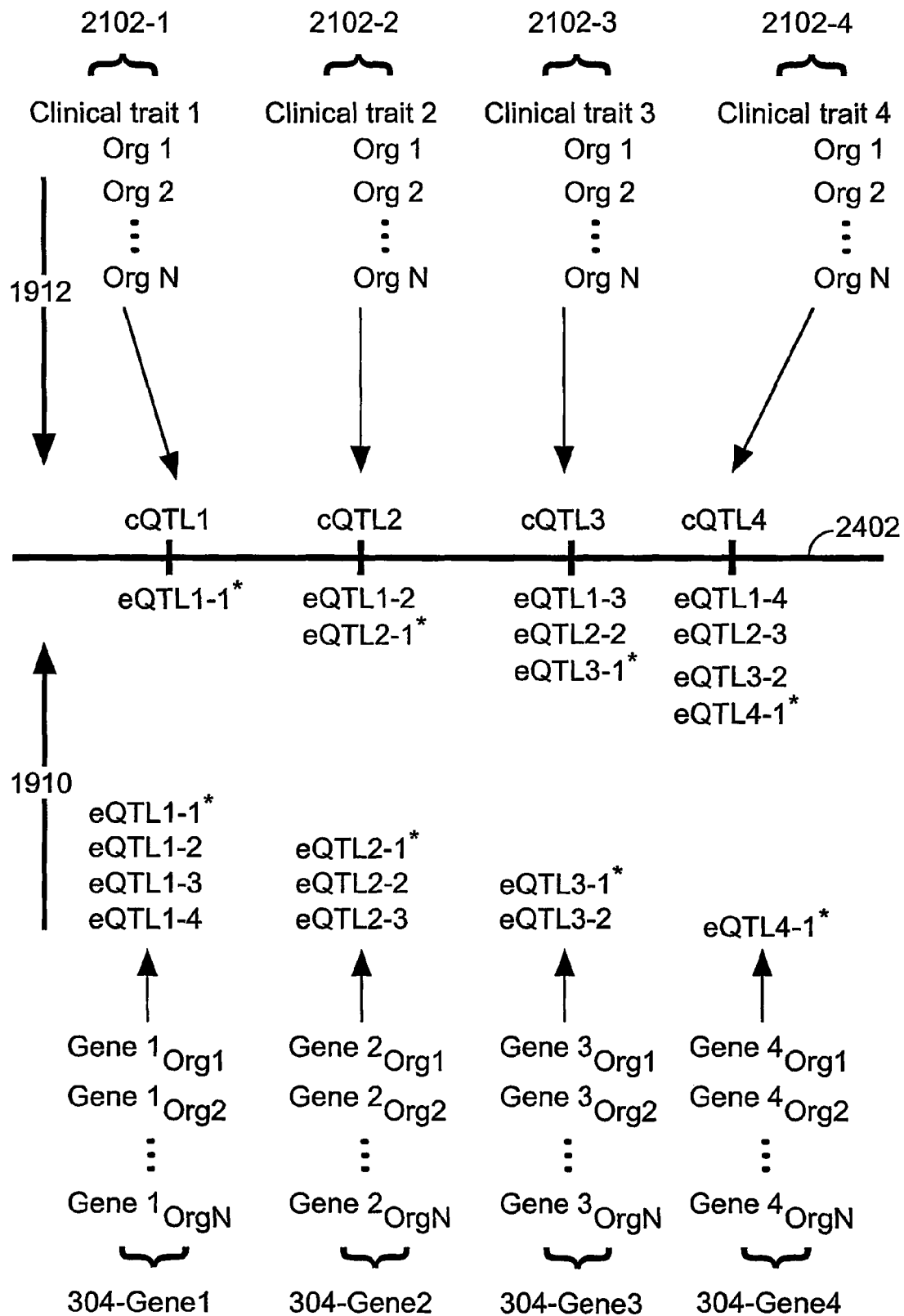

FIG. 24 illustrates a hypothetical example in which a biological pathway that affects the complex trait obesity is deduced, in accordance with one embodiment of the present invention.

Figure 25:
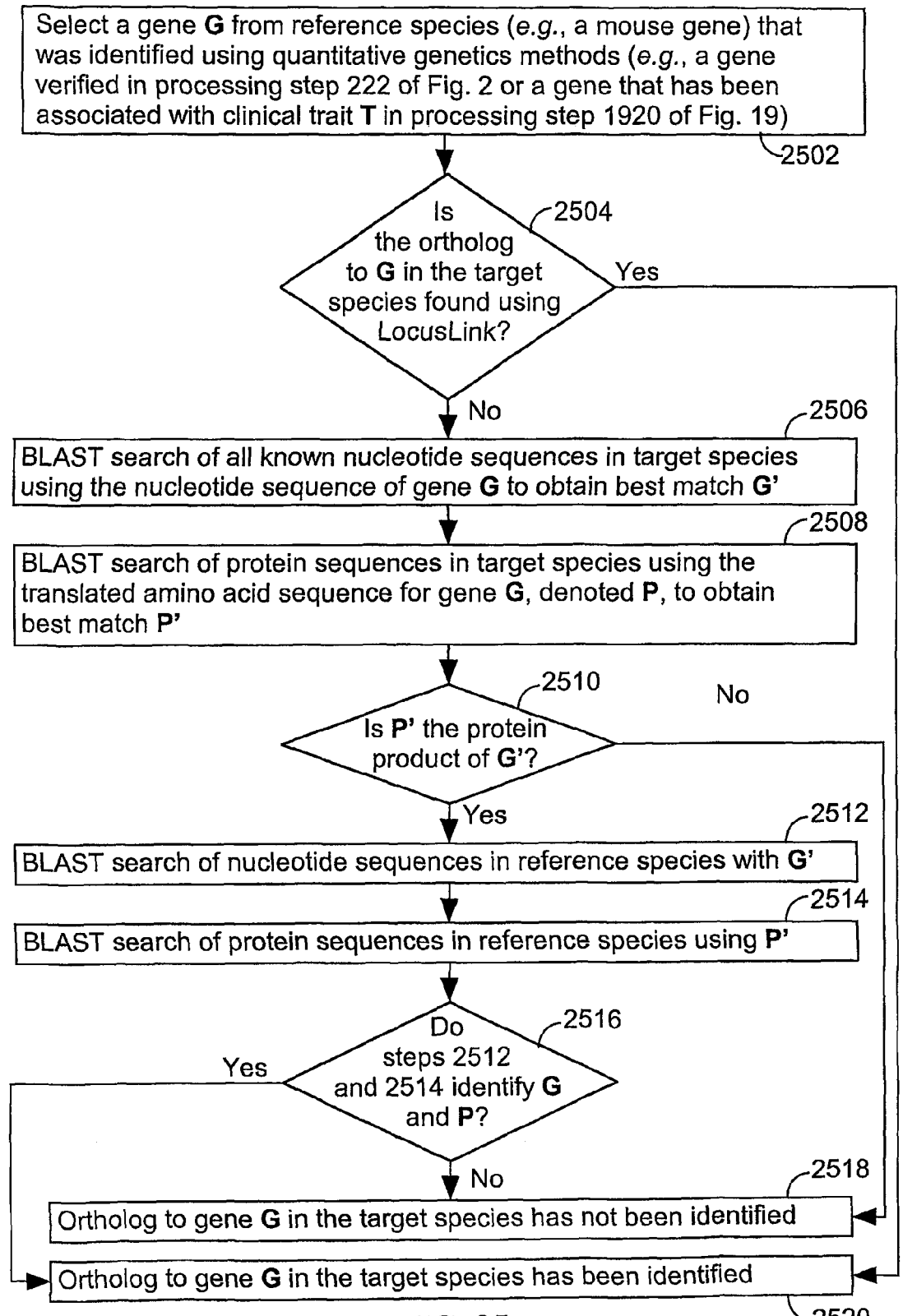

FIG. 25 illustrates sequence-based processing steps for identifying an ortholog in a reference species to a gene associated with a complex trait in a target species in accordance with one embodiment of the present invention.

Figure 26:
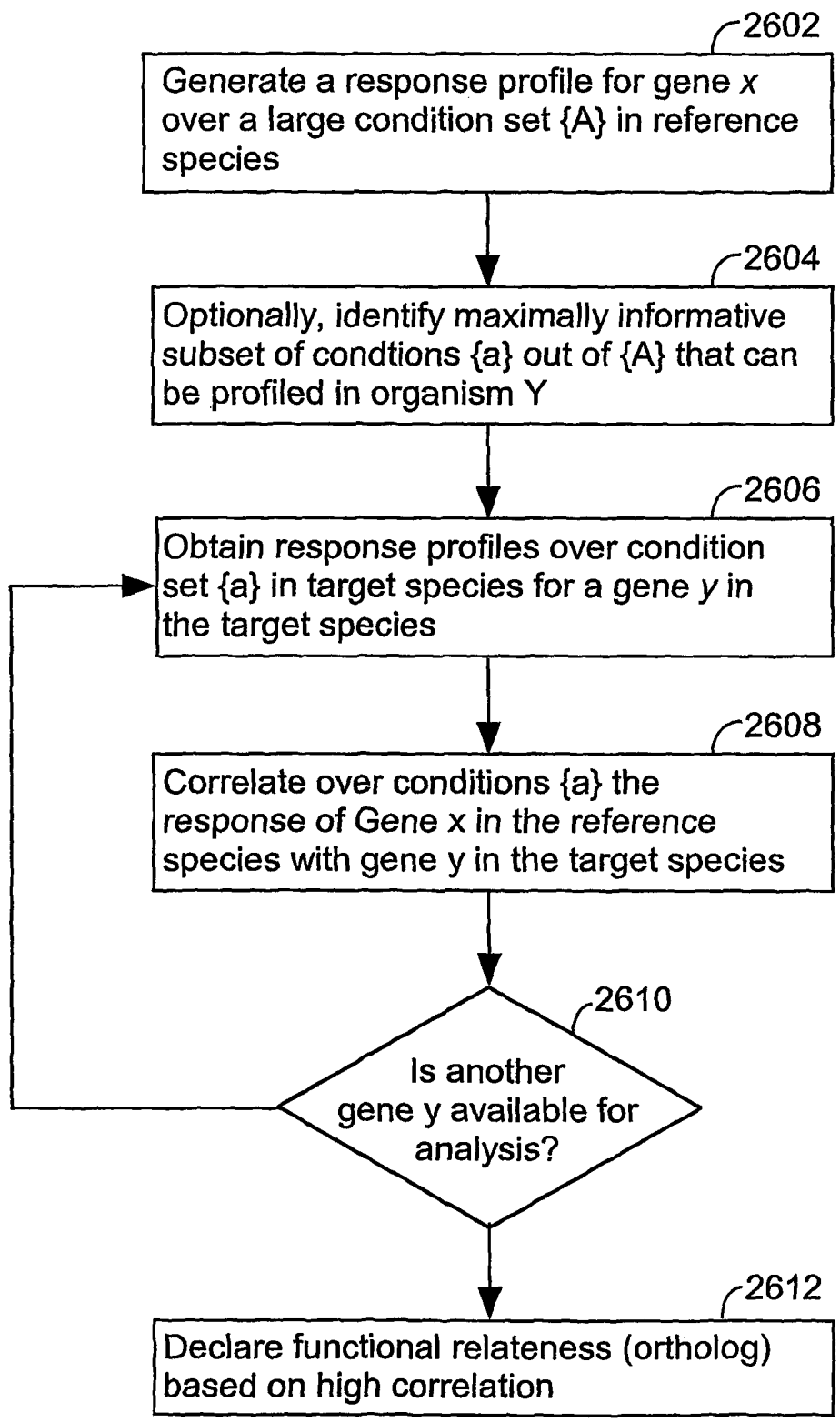

FIG. 26 illustrates nonsequence-based processing steps for identifying an ortholog in a reference species to a gene associated with a complex trait in a target species in accordance with one embodiment of the present invention.

FIG. 27 illustrates the nucleotide sequence of the *Mus musculus* gene NM_025575 (SEQ ID NO: 1), also known as the 2610042O14Rik gene.

FIG. 28 illustrates the human mRNA that corresponds to the *Mus musculus* gene NM_025575, a corrected form of AL591714.1 (SEQ ID NO: 2).

FIG. 29 illustrates the portion of SEQ ID NO: 2 that codes for the human protein that corresponds to *Mus musculus* NP_079851 (SEQ ID NO: 3).

FIGS. 30A through 30D illustrate four *Mus musculus* amino acid sequences that correspond to the 2610042O14Rik gene, namely Q9CQK0 (SEQ ID NO: 4), Q9CYM5 (SEQ ID NO: 5), Q9CYX5 (SEQ ID NO: 6), and Q9DAU8 (SEQ ID NO: 7).

FIG. 31 illustrates the human amino acid sequence that corresponds to the corrected form of accession number AL491714 (FIG. 28) (SEQ ID NO: 8).

FIG. 32 illustrates the nucleotide sequence for the *Mus musculus* gene NM_015731 (SEQ ID NO: 9), which is also known as ATP9A.

FIG. 33 illustrates the human relationships field of a LocusLink query of ATP9A, indicating a human chromosomal location of 20q13.11-13.2

FIG. 34 illustrates the nucleotide and protein sequence associated with human chromosome position 20q13:11-13.2

FIG. 35 illustrates the amino acid sequence of the *Mus musculus* protein NM__015731 (SEQ ID NO: 10) that corresponds to the *Mus musculus* gene NM__015731.

FIG. 36 illustrates the human ortholog to the *Mus musculus* protein NM__015731, namely O75110 (SEQ ID NO: 11).

FIG. 37 illustrates the inferred mRNA sequence for O75110 (SEQ ID NO: 12).

FIG. 38 illustrates the *Mus musculus* gene NM__025996 (SEQ ID NO: 13).

FIGS. 39A and 39B illustrate the LocusLink record for the *Mus musculus* gene NM__025996 (SEQ ID NO: 13).

FIG. 40 illustrates the mouse protein that corresponds to the *Mus musculus* gene NM__025996 (SEQ ID NO: 13), which is NP__080272 (SEQ ID NO: 14).

FIG. 41 illustrates the human protein NP__006800 (SEQ ID NO: 15) which corresponds to the mouse protein NP__080272 (SEQ ID NO: 14).

FIG. 42 illustrates the human nucleotide sequence NM__0068092 (SEQ ID NO: 16), which corresponds to the human protein NP__006800 (SEQ ID NO: 15).

FIG. 43 illustrates the *Mus musculus* protein sequence TR_Q9CYG7 (SEQ ID NO: 17) which is a TrEMBL database entry which is nearly identical to the *Mus musculus* protein NP__080272 (SEQ ID NO: 14).

FIG. 44 illustrates the human protein TR_Q15785 (SEQ ID NO: 18) which corresponds to the human nucleotide sequence NM__006809 (SEQ ID NO: 16).

FIG. 45 illustrates the nucleotide sequence for the *Mus musculus* gene NM__009564 (SEQ ID NO: 19).

FIG. 46 illustrates the human nucleotide sequence NM__018197.1 (SEQ ID NO: 20), which corresponds to the *Mus musculus* gene NM__009564 (SEQ ID NO: 19).

FIG. 47 illustrates the *Mus musculus* amino acid sequence NP__033590 (SEQ ID NO: 21), which corresponds to the *Mus musculus* gene NM__009564 (SEQ ID NO: 19).

FIG. 48 illustrates the *Mus musculus* TrBMBL database entry TRP97365 (SEQ ID NO: 22), which corresponds to the *Mus musculus* gene NM__009564 (SEQ ID NO: 19).

FIG. 49 illustrates the *Mus musculus* TrEMBL database entry TR_Q99KE8 (SEQ ID NO: 23), which corresponds to the *Mus musculus* gene NM__009564 (SEQ ID NO: 19).

FIG. 50 illustrates the *Mus musculus* TrBMBL database entry TR_Q9CWR3 (SEQ ID NO: 24), which corresponds to the *Mus musculus* gene NM__009564 (SEQ ID NO: 19).

FIG. 51 illustrates the human amino acid sequence NP__060667 (SEQ ID NO: 25) that corresponds to the human nucleotide sequence NM__018197 (SEQ ID NO: 20).

FIG. 52 illustrates the TrEMBL database entry TR_Q9NPA5 (SEQ ID NO: 26) that also corresponds to the *Mus musculus* gene NM__009564 (SEQ ID NO: 19).

FIG. 53 illustrates the TrEMBL database entry TR_Q9NTS7 (SEQ ID NO: 27) that also corresponds to the *Mus musculus* gene NM__009564 (SEQ ID NO: 19).

Figure 54:
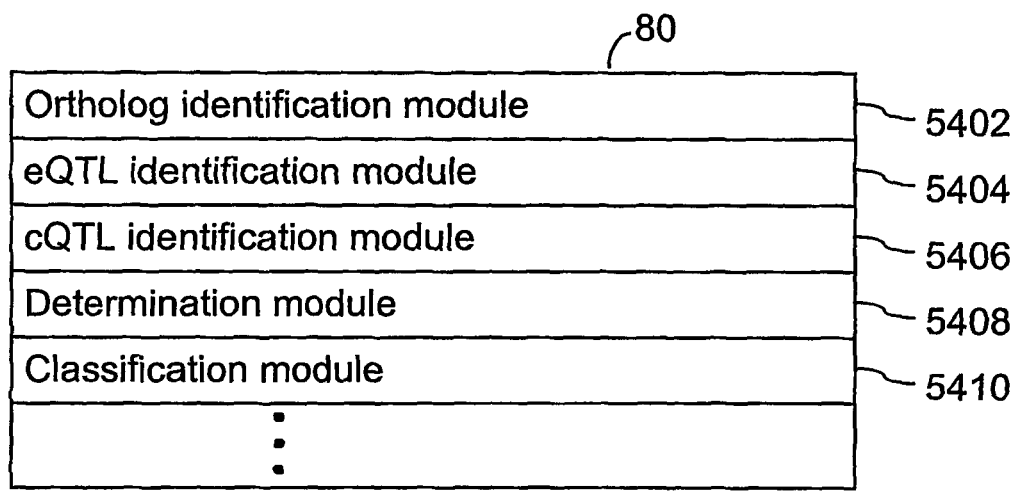

FIG. 54 illustrates an embodiment of a QTL analysis module in accordance with the present invention.

Figure 55:
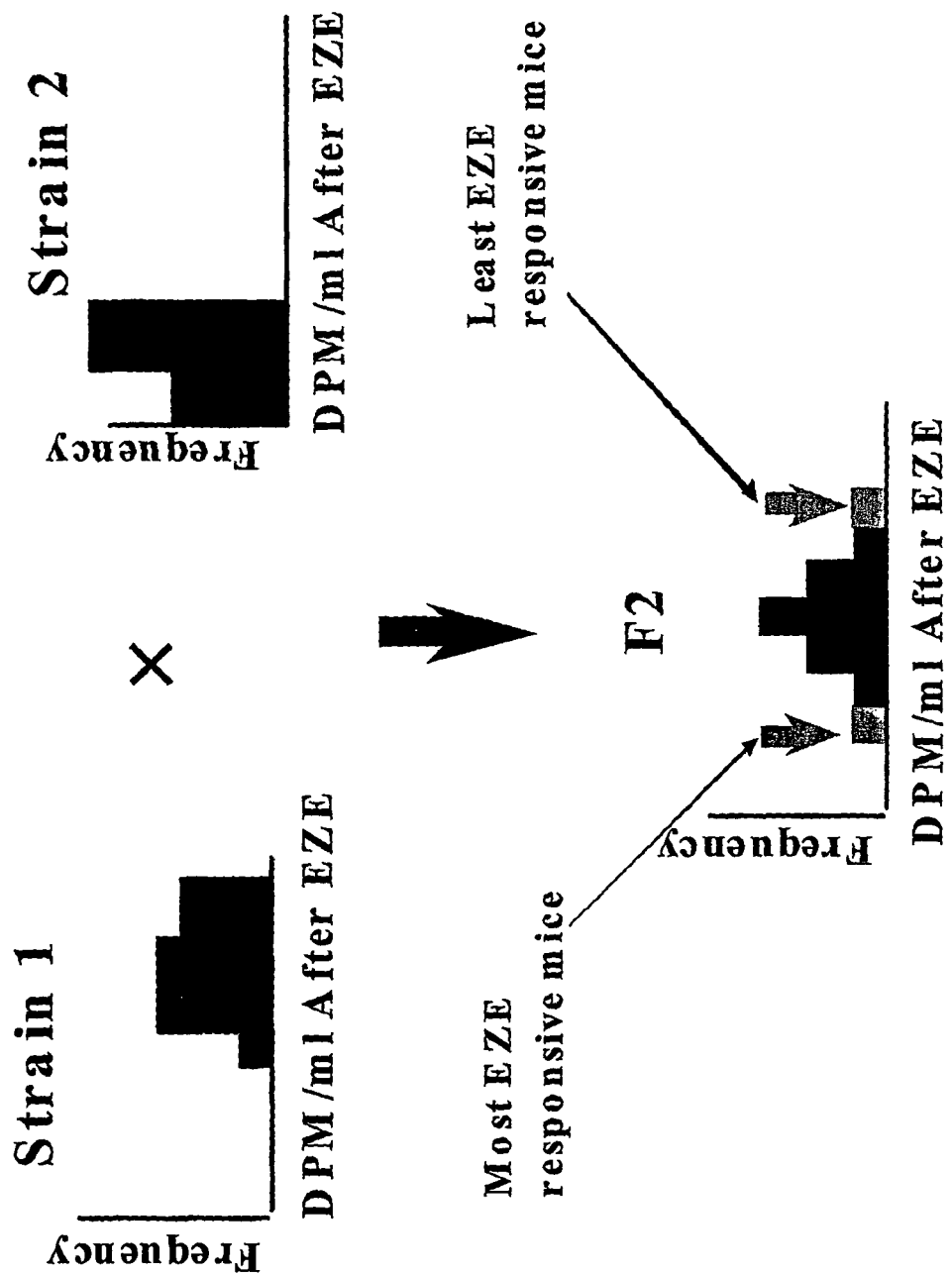

FIG. 55 illustrates an experimental protocol in which two inbred strains that exhibit polymorphic behavior with respect to a trait of interest are crossed to obtain an F2, back-cross or other such segregating population in order to generate a population where the trait of interest is segregating, in accordance with one embodiment of the present invention.

Figure 56:
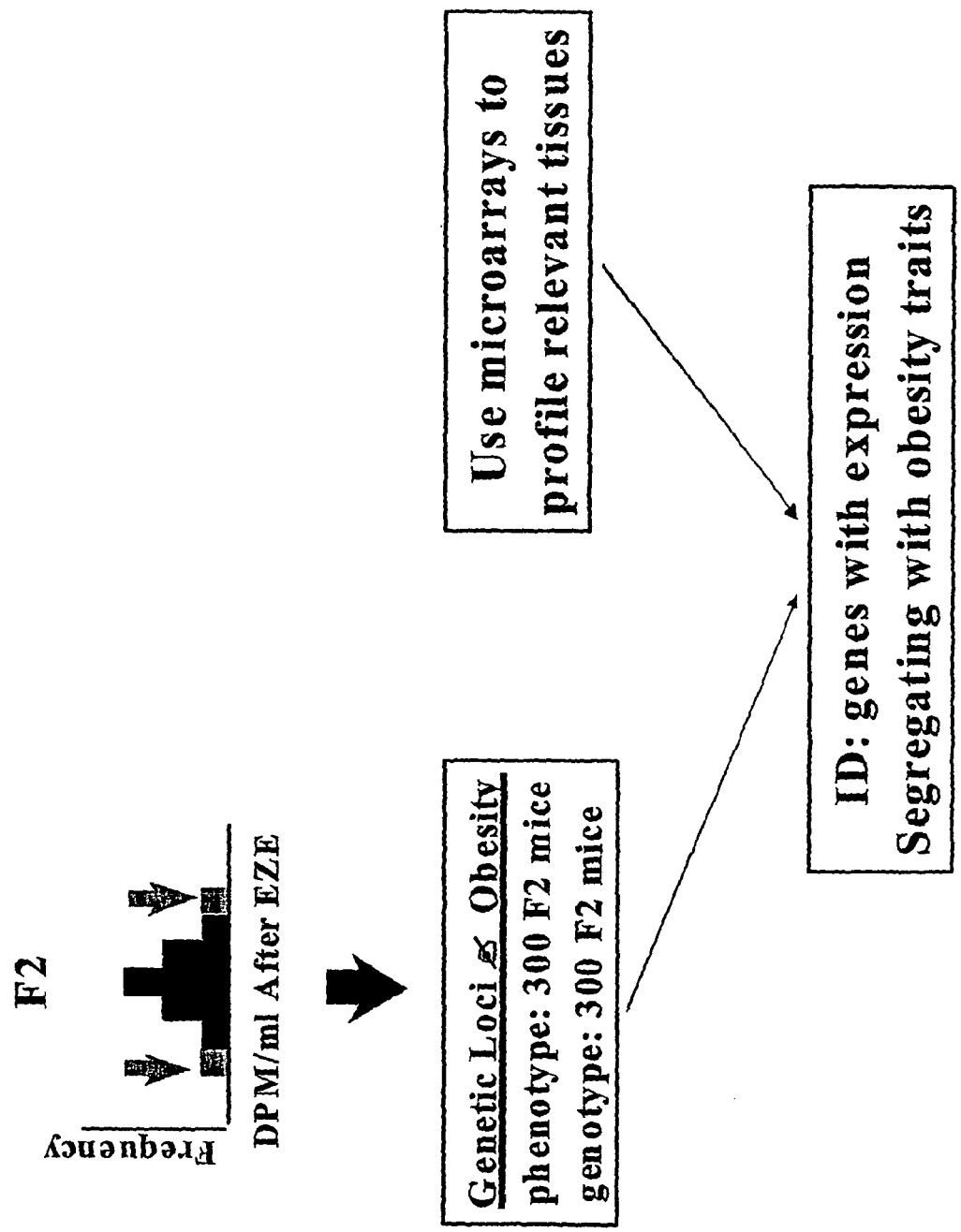

FIG. 56 illustrates an experimental protocol in which a segregating population is genotyped based upon a marker map, scored with respect to phenotypes associated with the trait of interest, and tissues relevant to the trait under study are isolated from samples of the segregating population for expression profiling, in accordance with some embodiments of the present invention.

Figure 57:
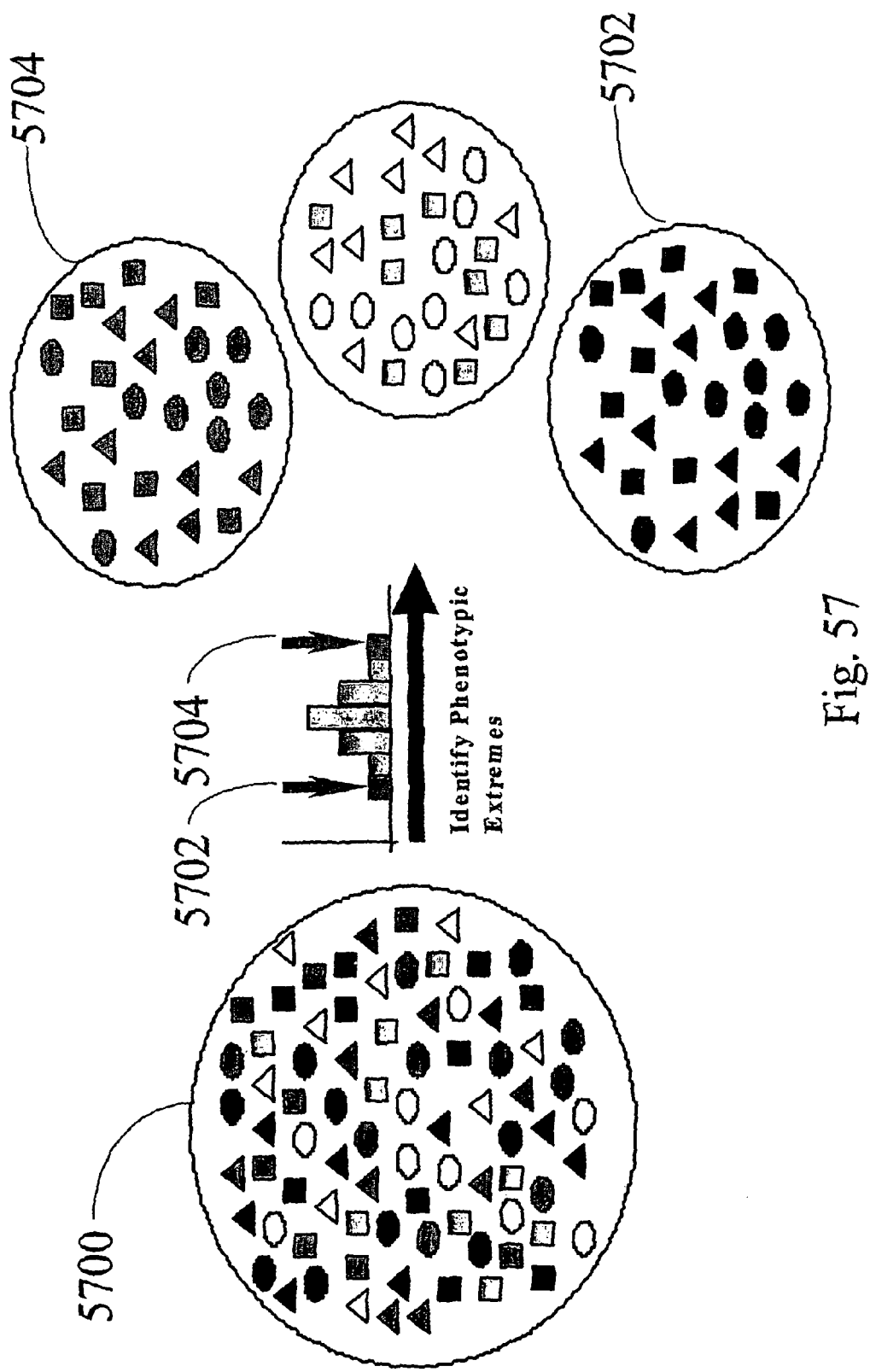

FIG. 57 illustrates the identification of those subgroups within a whole population that exhibit different trait subtypes, in accordance with one embodiment of the present invention.

Figure 58:
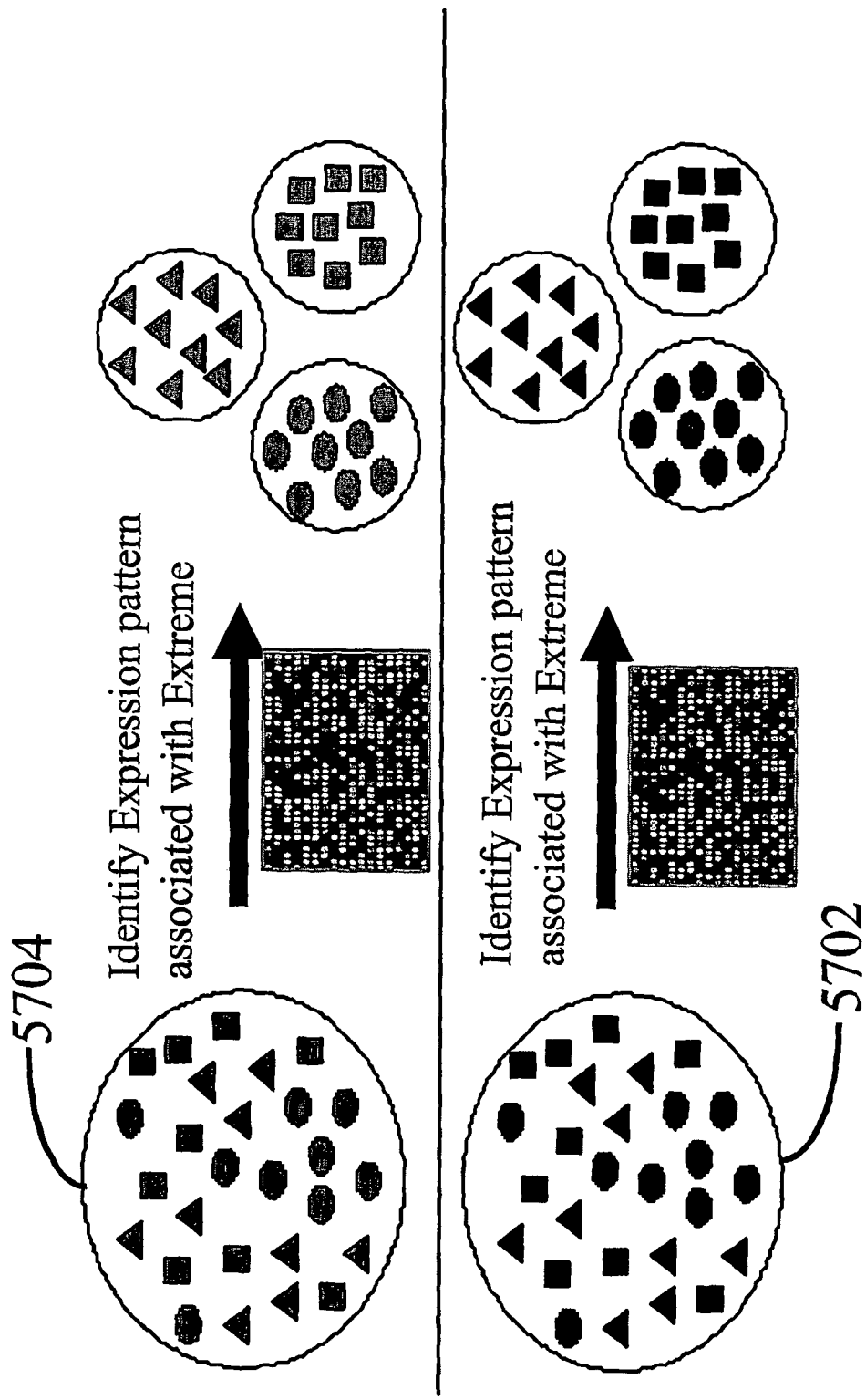

FIG. 58 illustrates the identification of subtypes within a population that are most extreme with respect to the trait under study using microarray expression data in accordance with one embodiment of the present invention.

Figure 59:
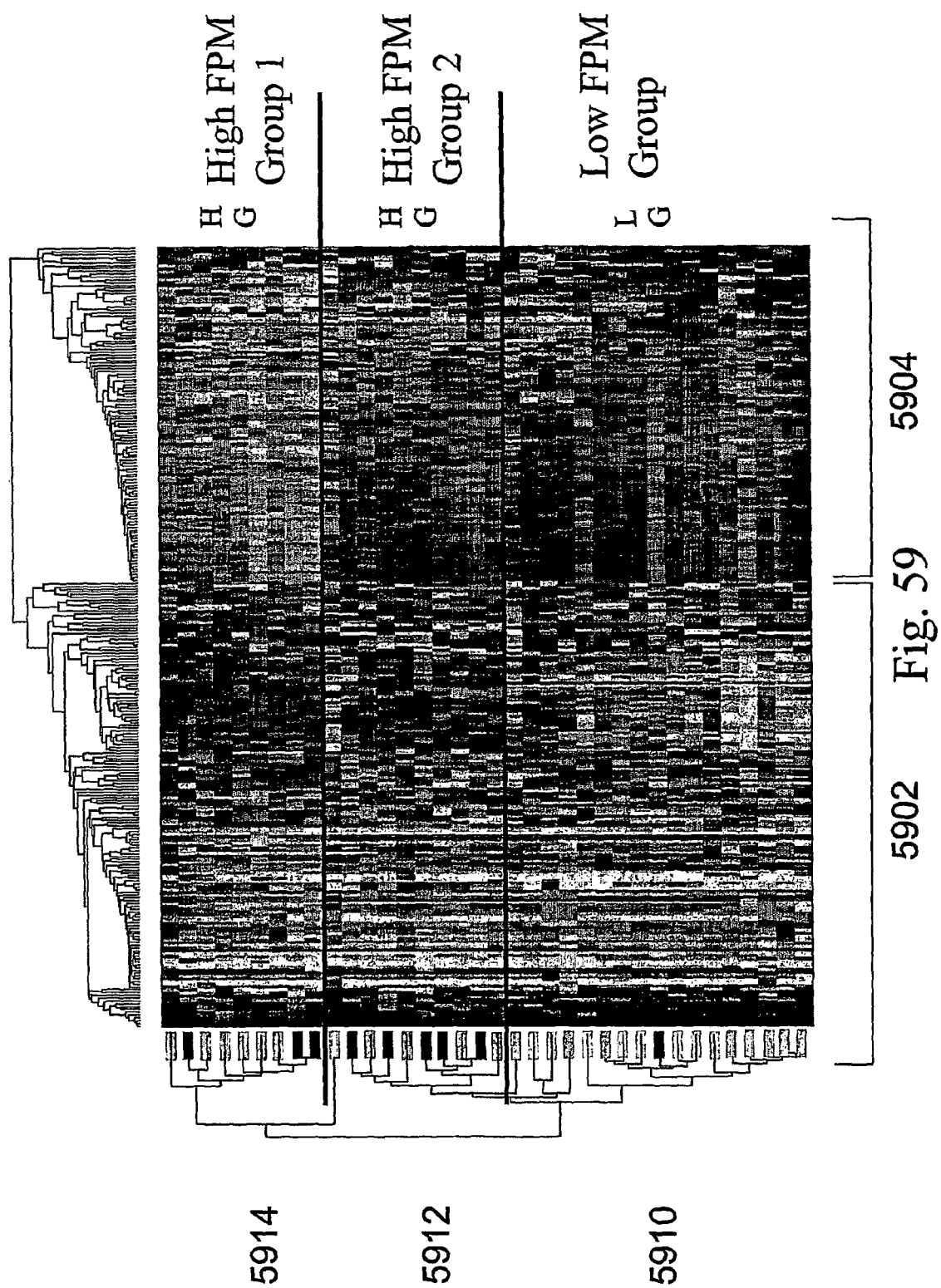

FIG. 59 is a depiction of a two-dimensional cluster of the most differentially expressed set of genes in mice comprising the upper and lower $25^{th}$ percentiles of the subcutaneous fat pad mass (FPM) trait in a segregating population, in accordance with one embodiment of the present invention.

Figure 60:
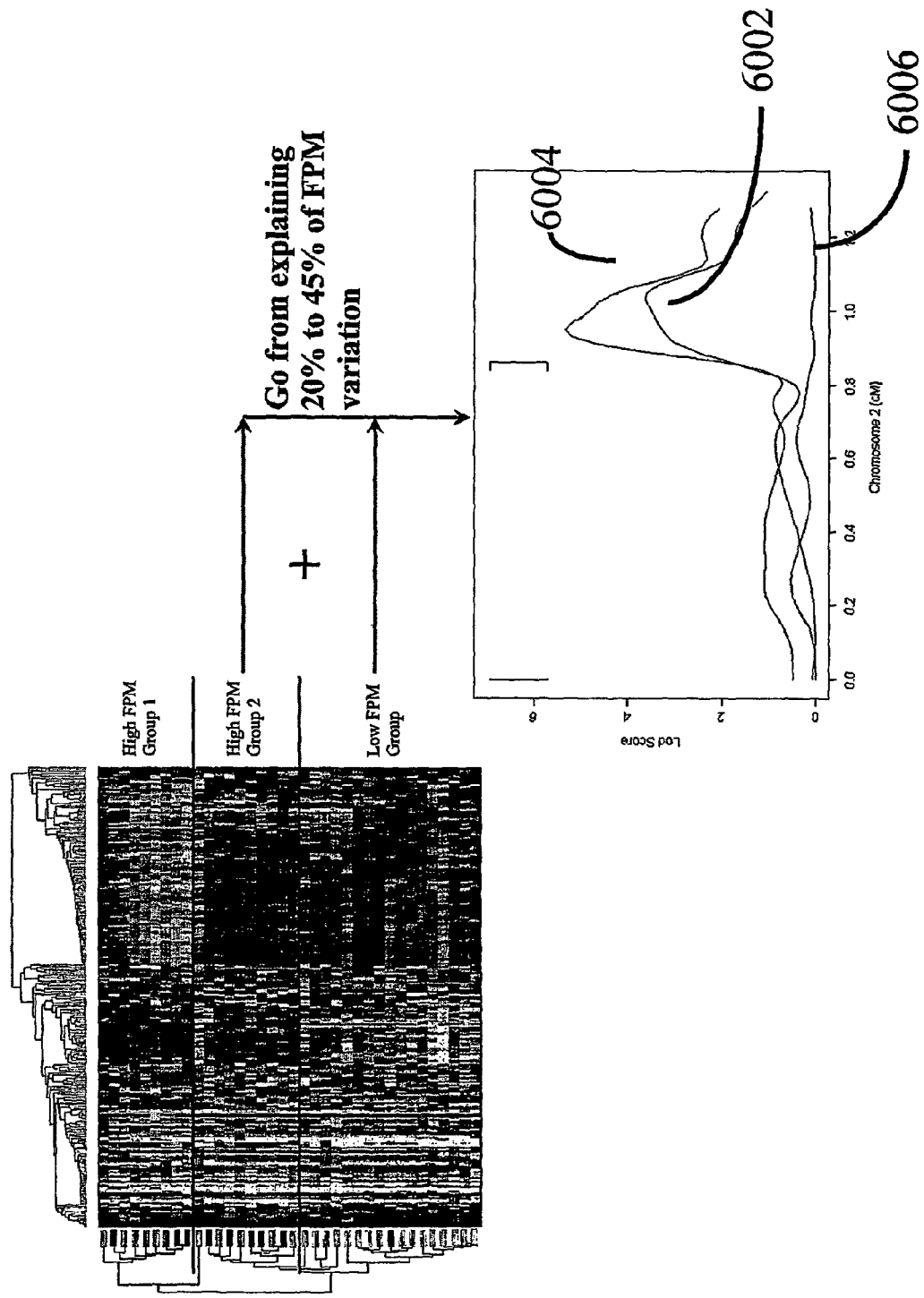
Figure 61:
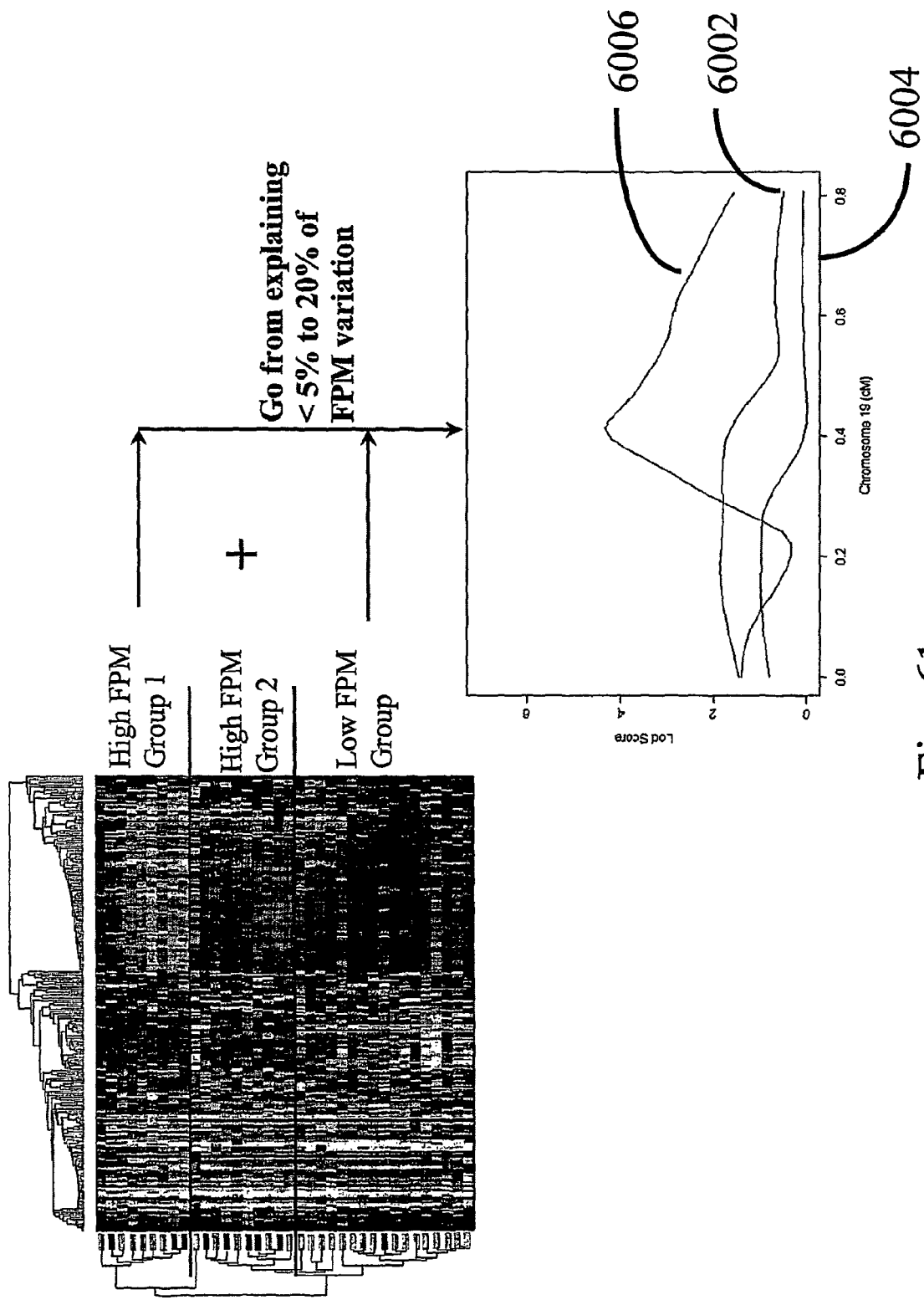

FIGS. 60 and 61 illustrates that one subgroup of mice is not under the control of a particular QTL, but that another subgroup of mice is under the control of the QTL in a given segregating population.

Figure 62:
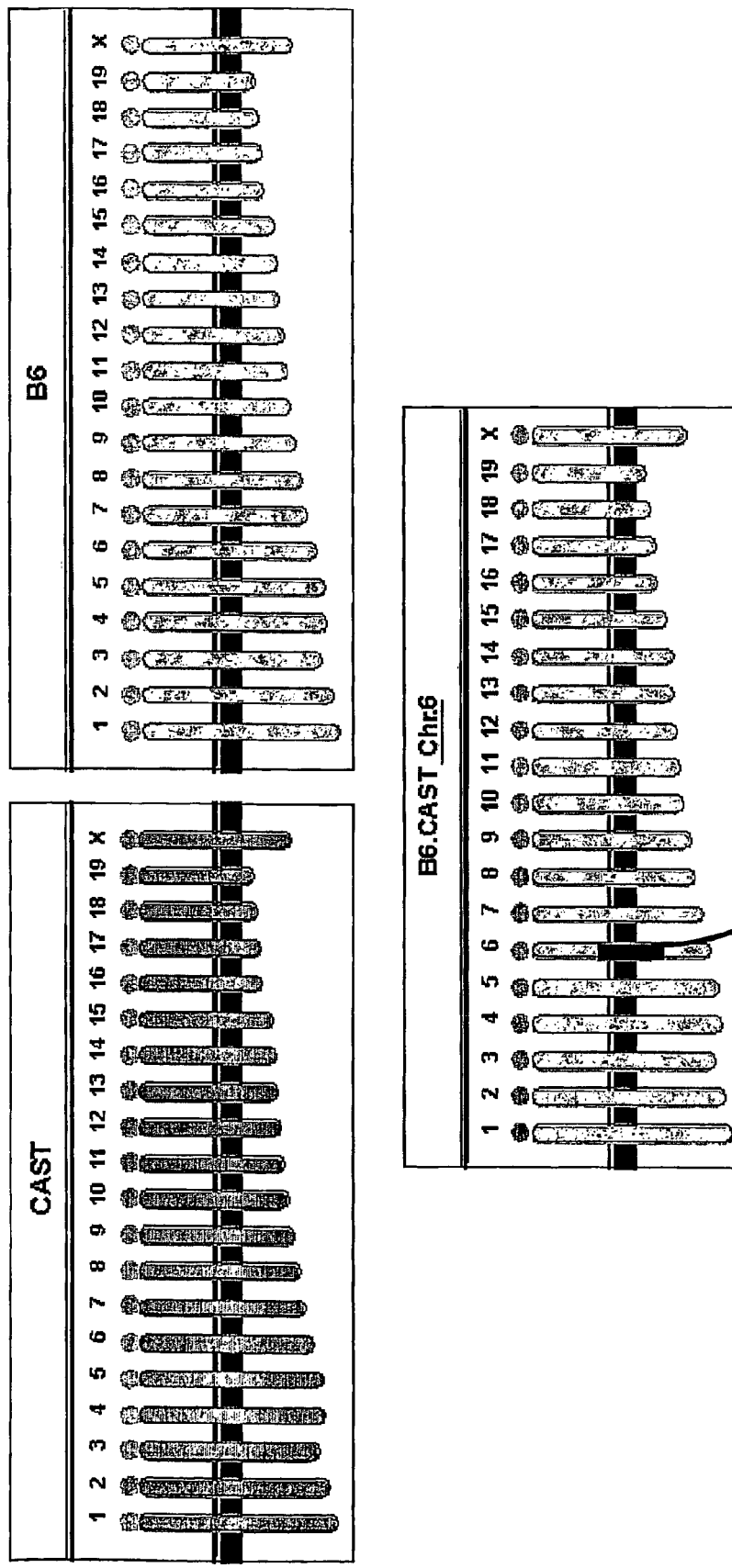

FIG. 62 illustrates a congenic strain that is constructed from two inbred strains, B6 and CAST, where B6 serves as the background strain and CAST serves as the donor strain.

Figure 63:
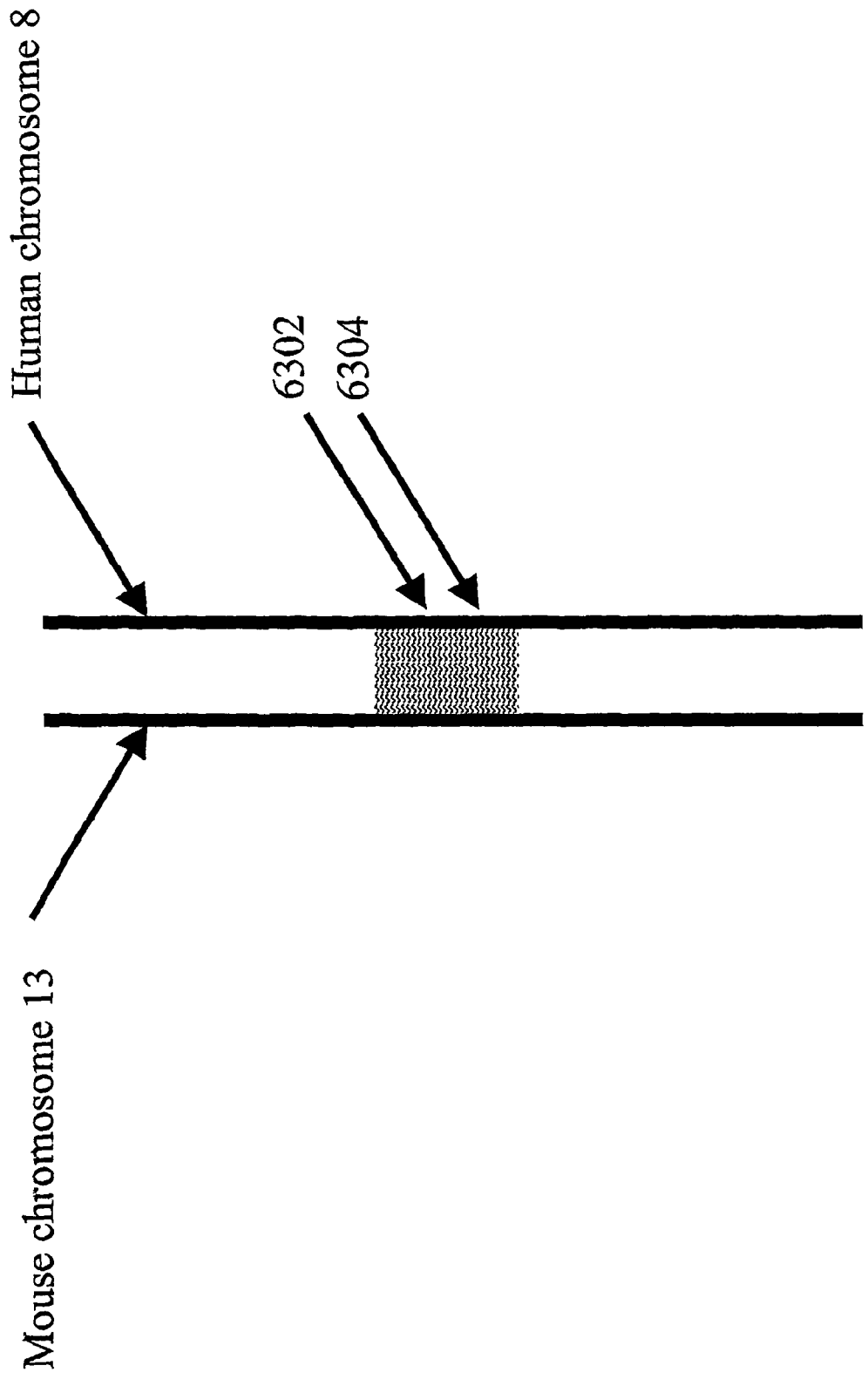

FIG. 63 illustrates two hypothetical QTL that are linked to a human obesity-related risk trait. The hypothetical QTL are an human chromosome 8 and are mapped to a portion of mouse chromosome 13 using a syntenic map between human and mouse in accordance with one embodiment of the present invention.

Figure 64:
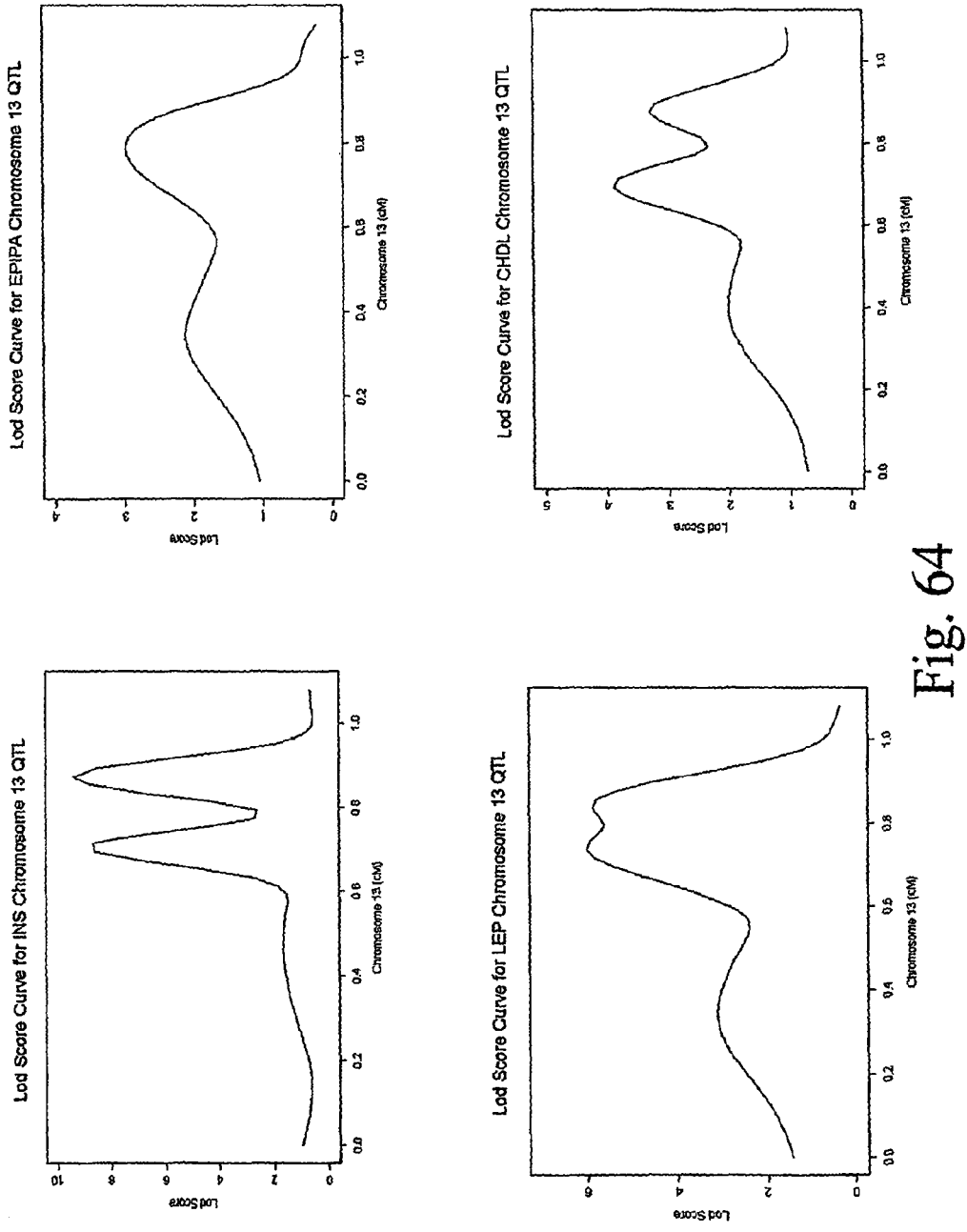

FIG. 64 lists four lod score curves for obesity-related traits in mouse.

Figure 65:
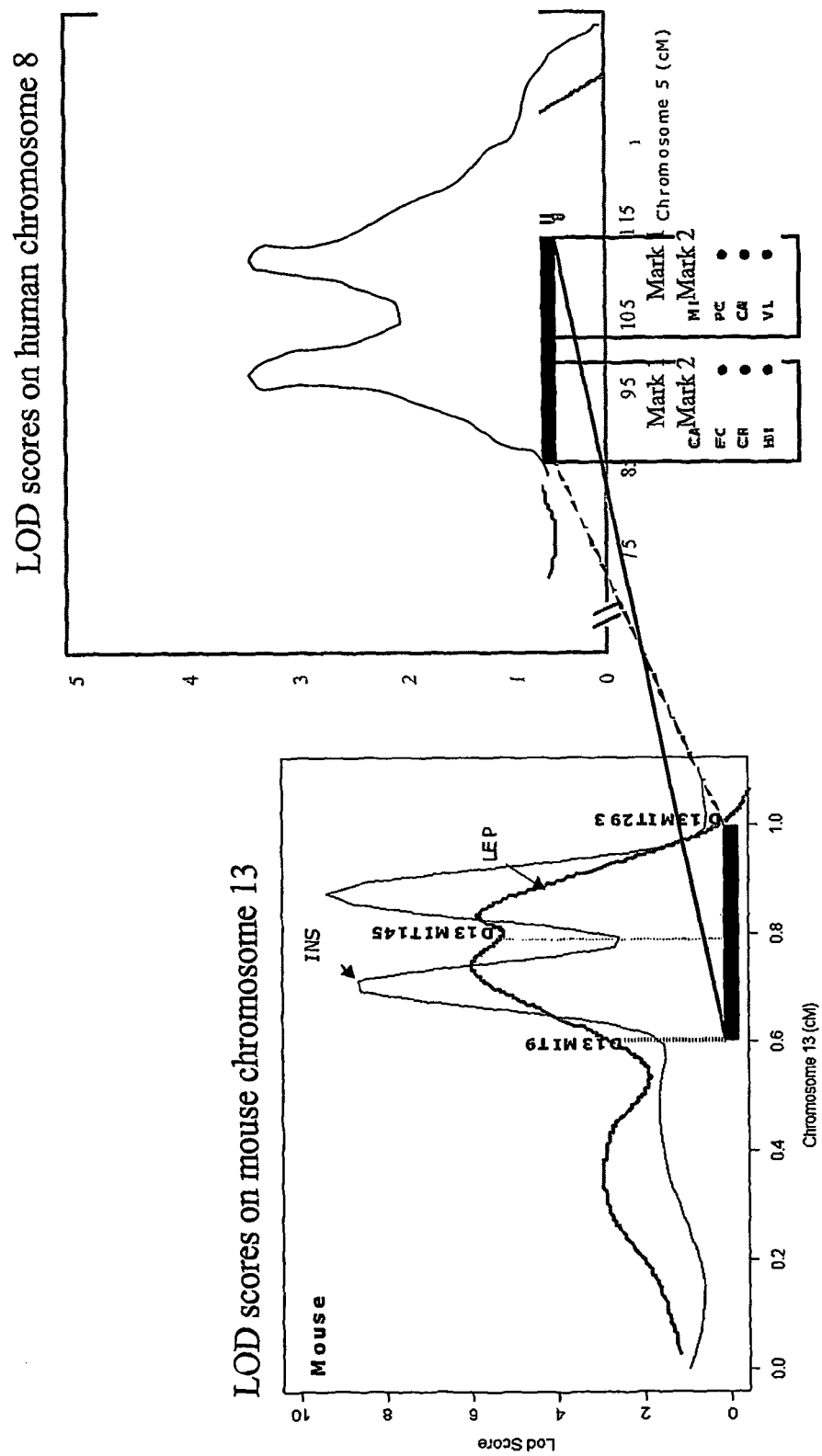

FIG. 65 is an overlay of two hypothetical human QTL and two mouse QTL that shows that the peaks of the two hypothetical human QTL are aligned with the peaks of the two mouse QTL.

Figure 66:
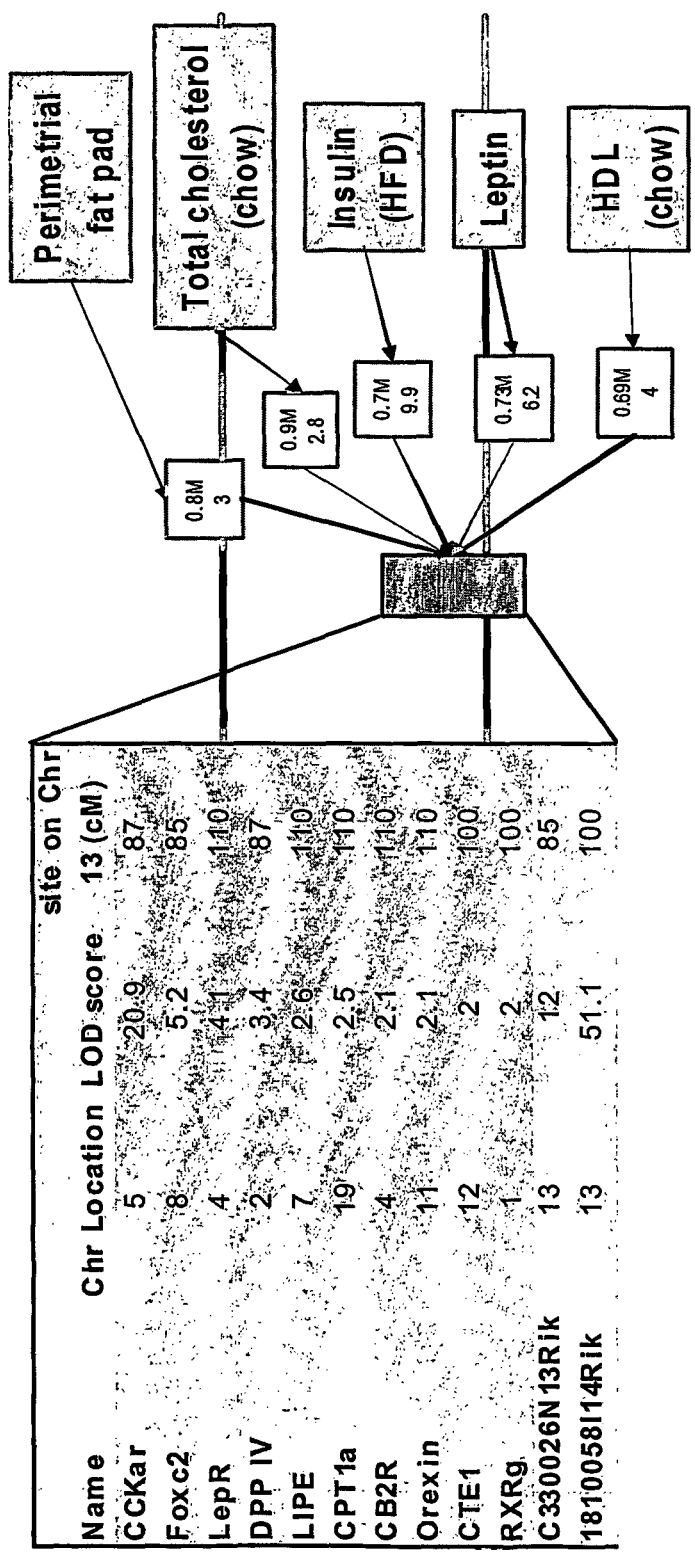

FIG. 66 is an illustration showing that the chromosome 13 region in mouse is a hotpot activity for eQTL linkage with hundreds of eQTL linking to one of two BMI QTL peaks.

Figure 67:
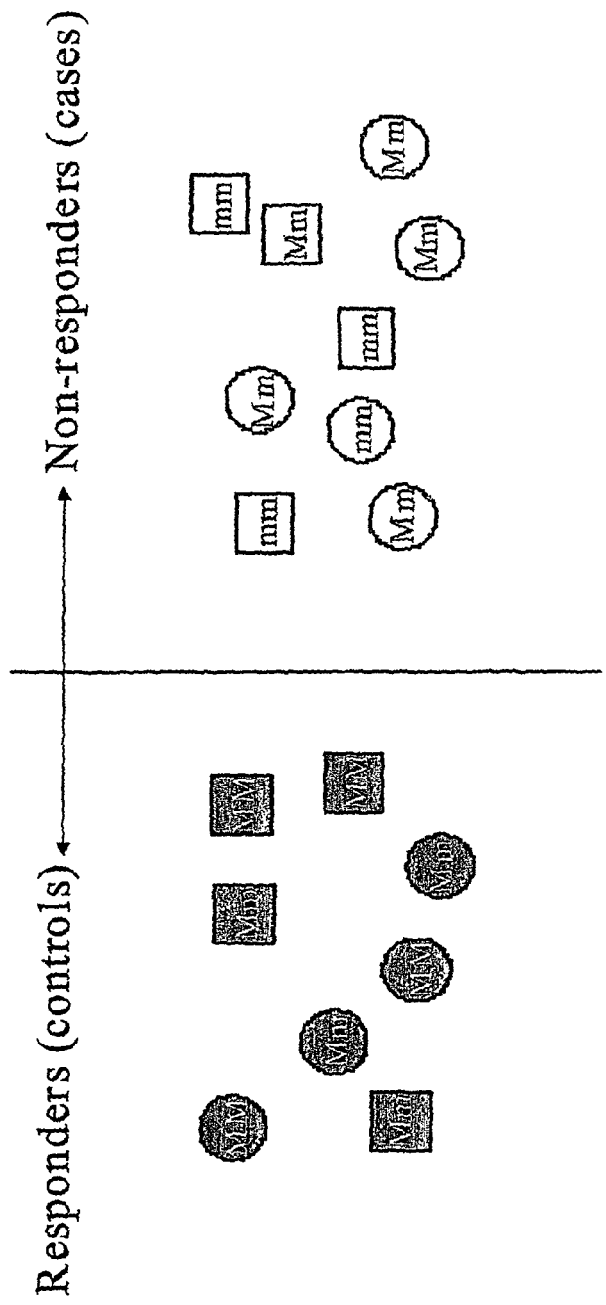

FIG. 67 illustrates a method for directly validating genes identified in mice using association methods in human populations in accordance with one embodiment of the present invention.

Figure 68:
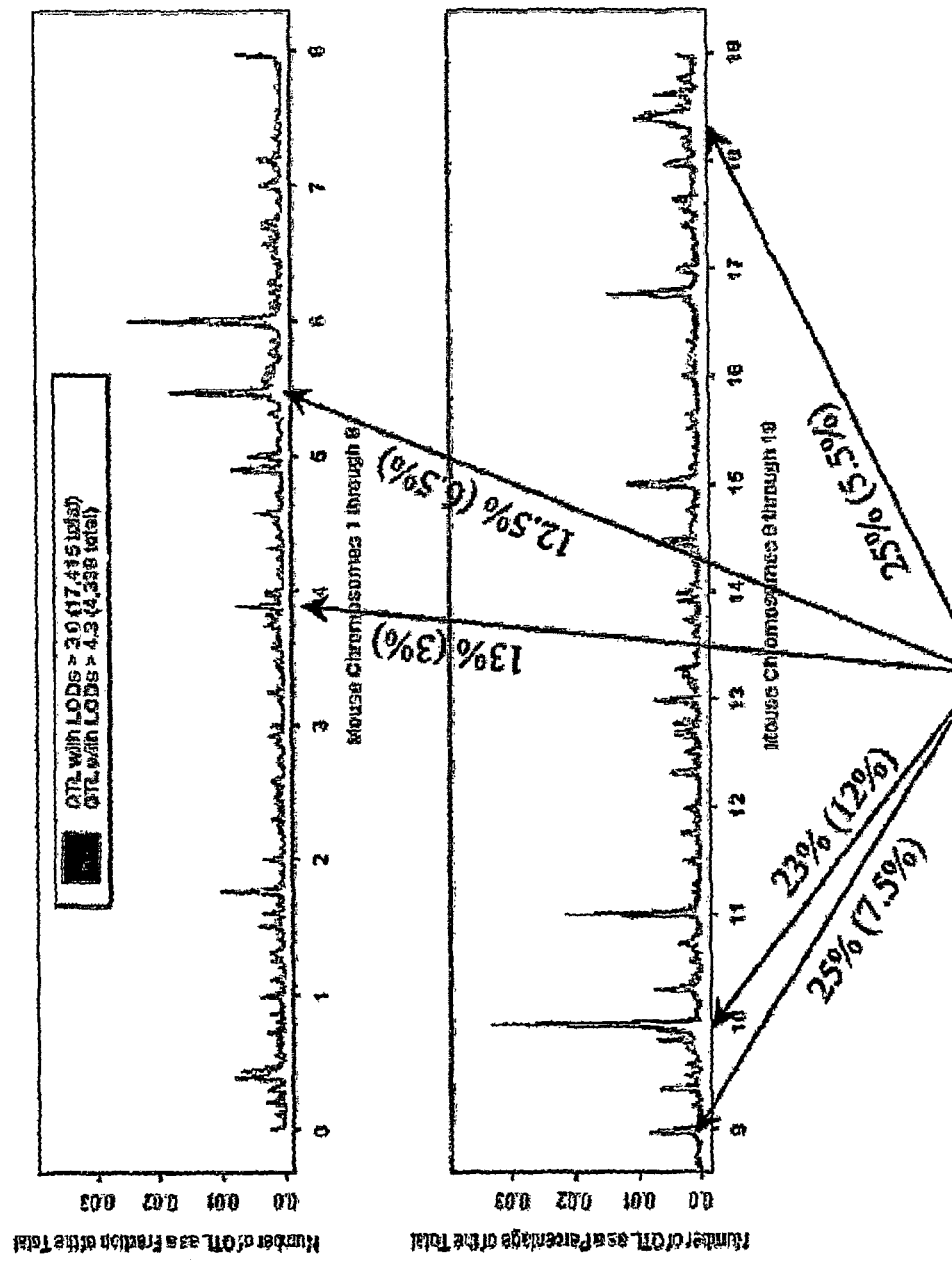

FIG. 68 plots the percentage of eQTL at different lod score thresholds across 920 evenly-spaced bins, each 2 cM wide, covering the mouse genome in a quantitative genetic analysis performed in accordance with one embodiment of the present invention.

Figure 69:
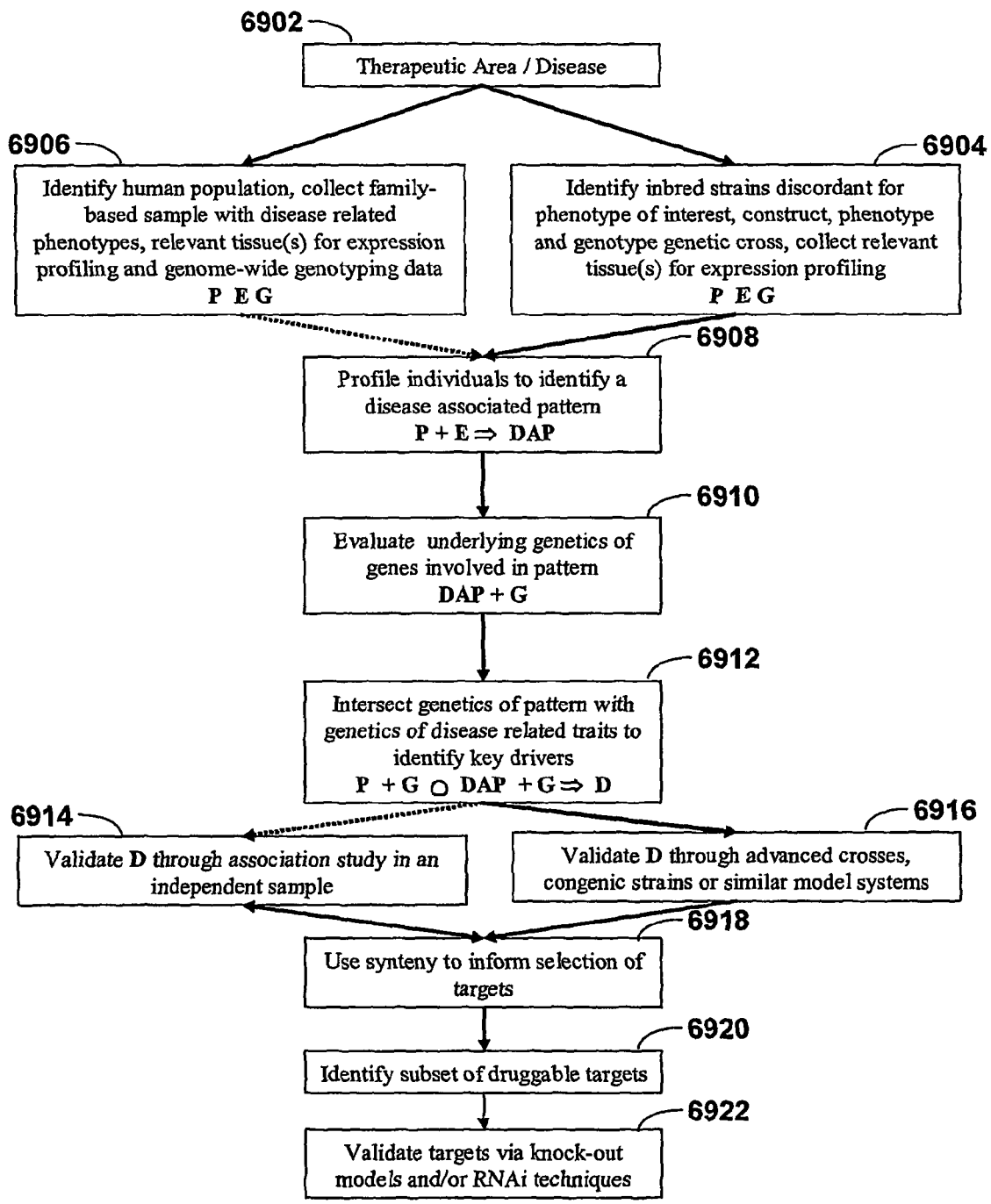

FIG. 69 illustrates a drug discovery paradigm in accordance with one embodiment of the present invention.

Figure 70:
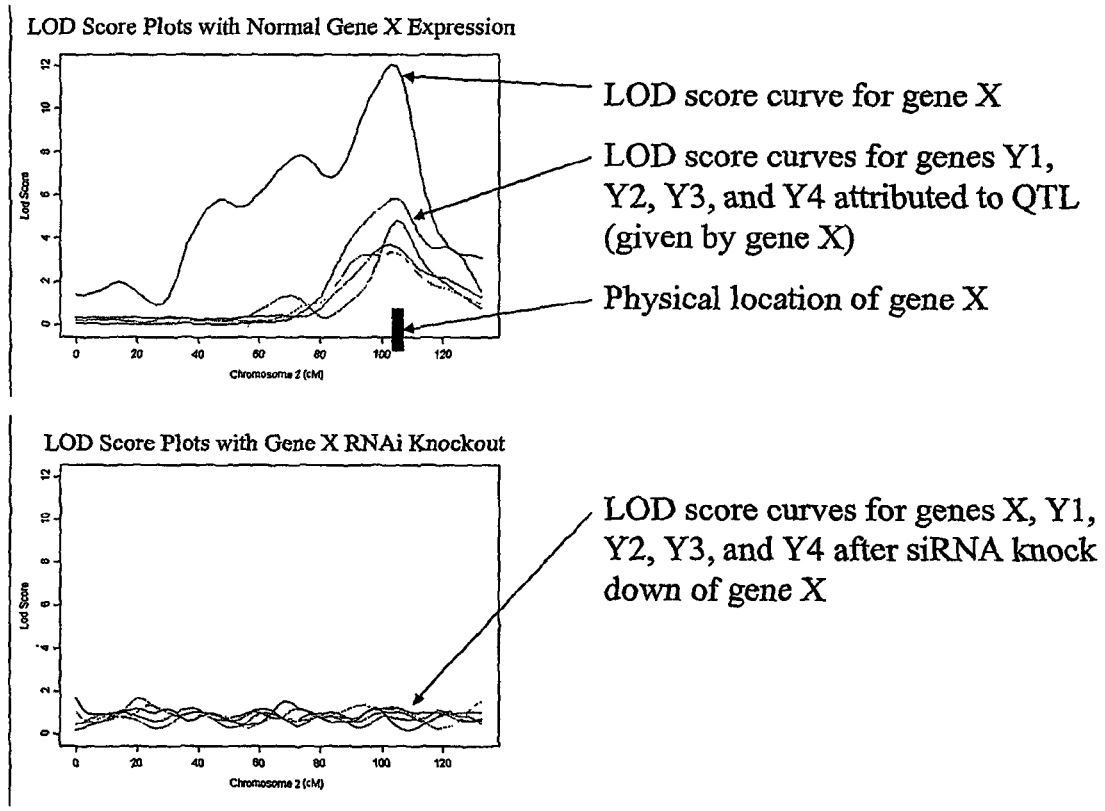

FIG. 70 illustrates an in vivo RNAi strategy in accordance with one embodiment of the present invention.

Figure 71A:
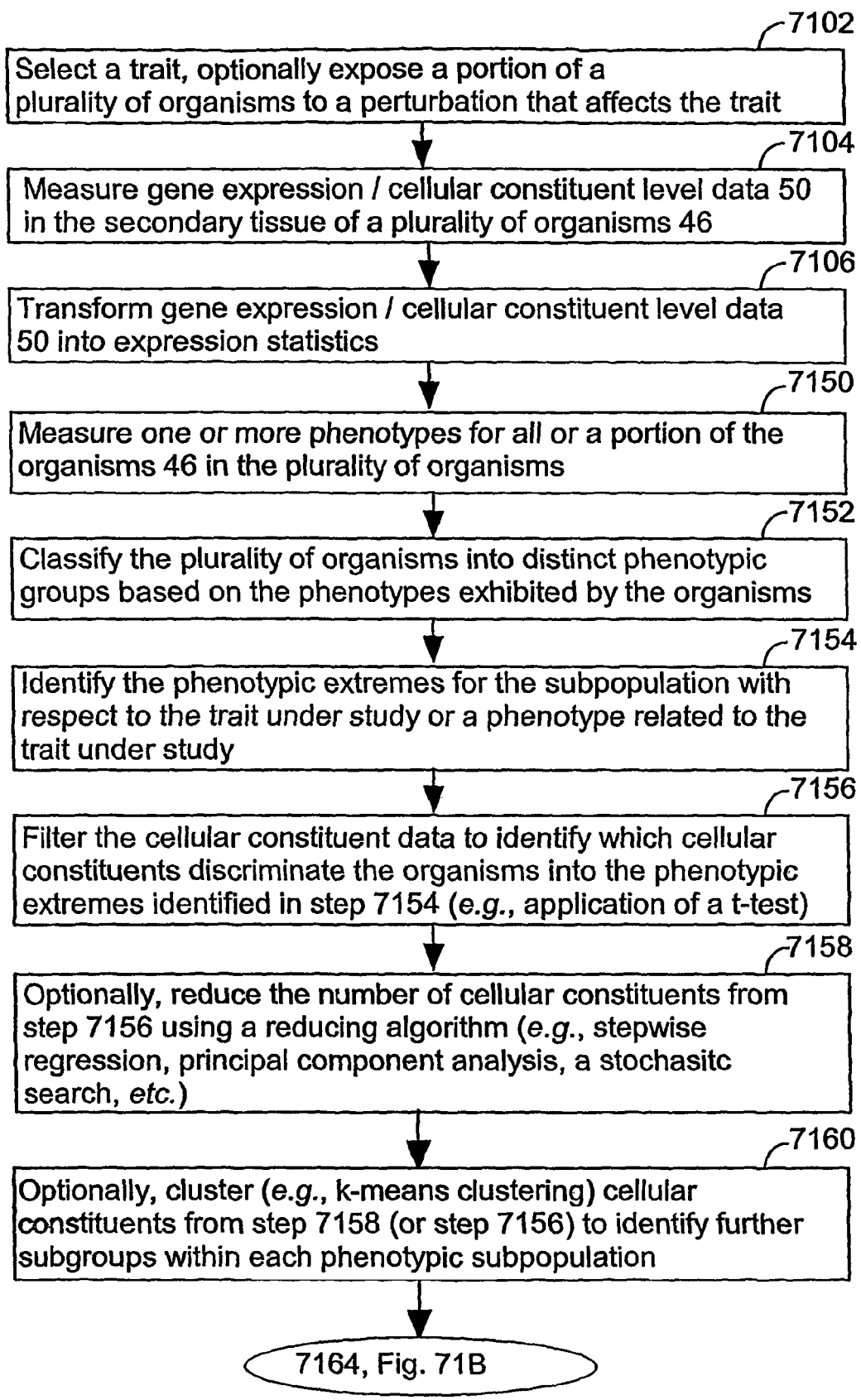
Figure 71B:
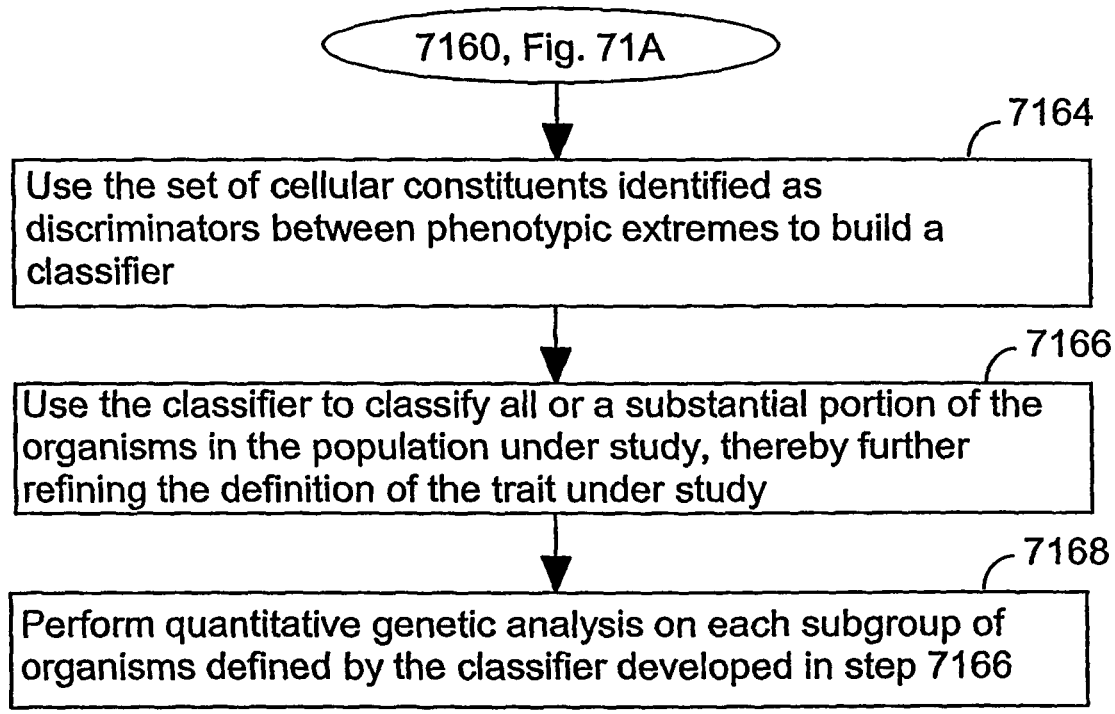

FIG. 71 illustrates processing steps for subdividing a disease population P into a subgroups in accordance with a preferred embodiment of the present invention.

FIG. 72 illustrates a data structure that comprises that data used to identify cellular constituents that discriminate a trait under study.

Figure 73:
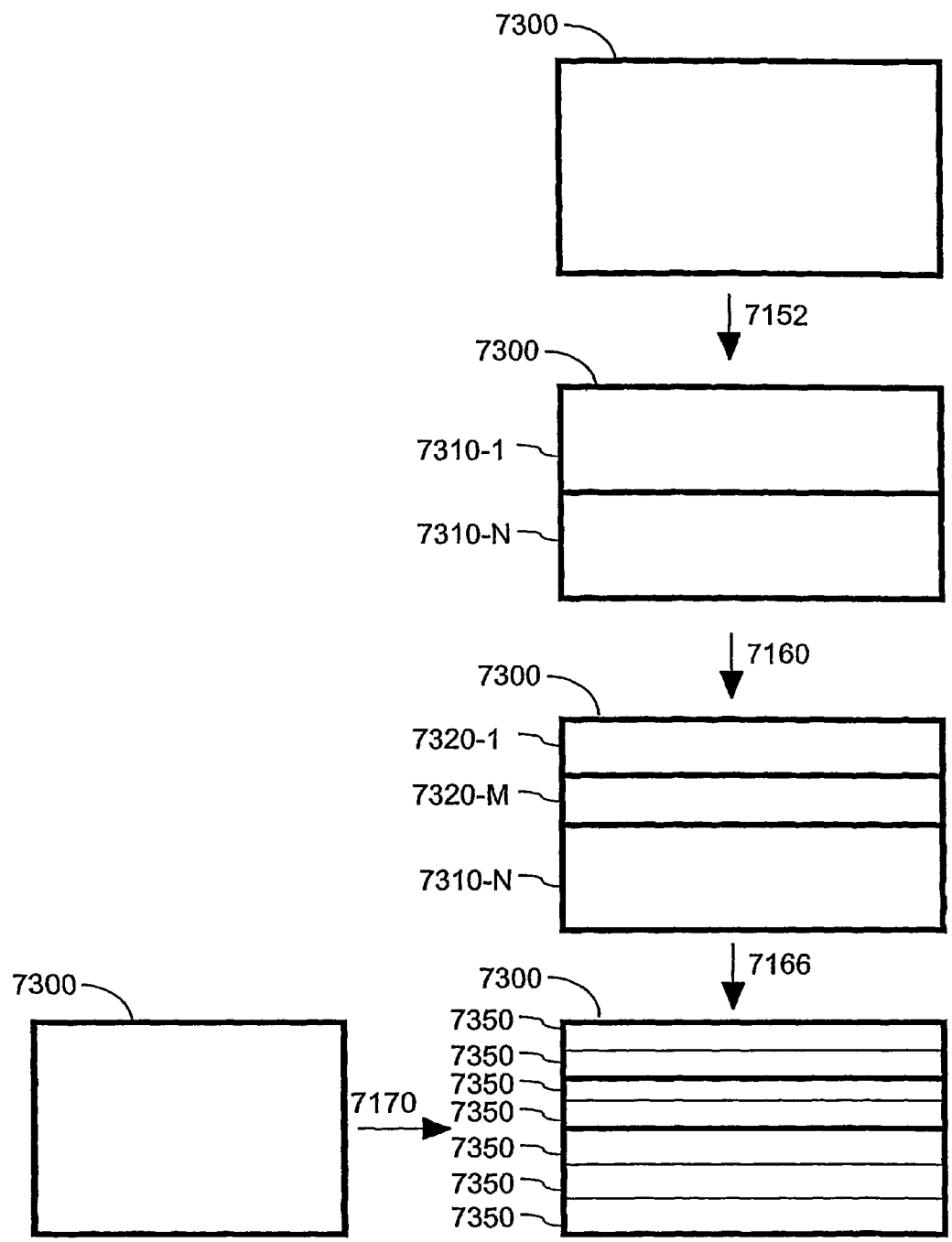

FIG. 73 illustrates the classification of a trait of interests into subtraits in accordance with one embodiment of the present invention.

Figure 74:
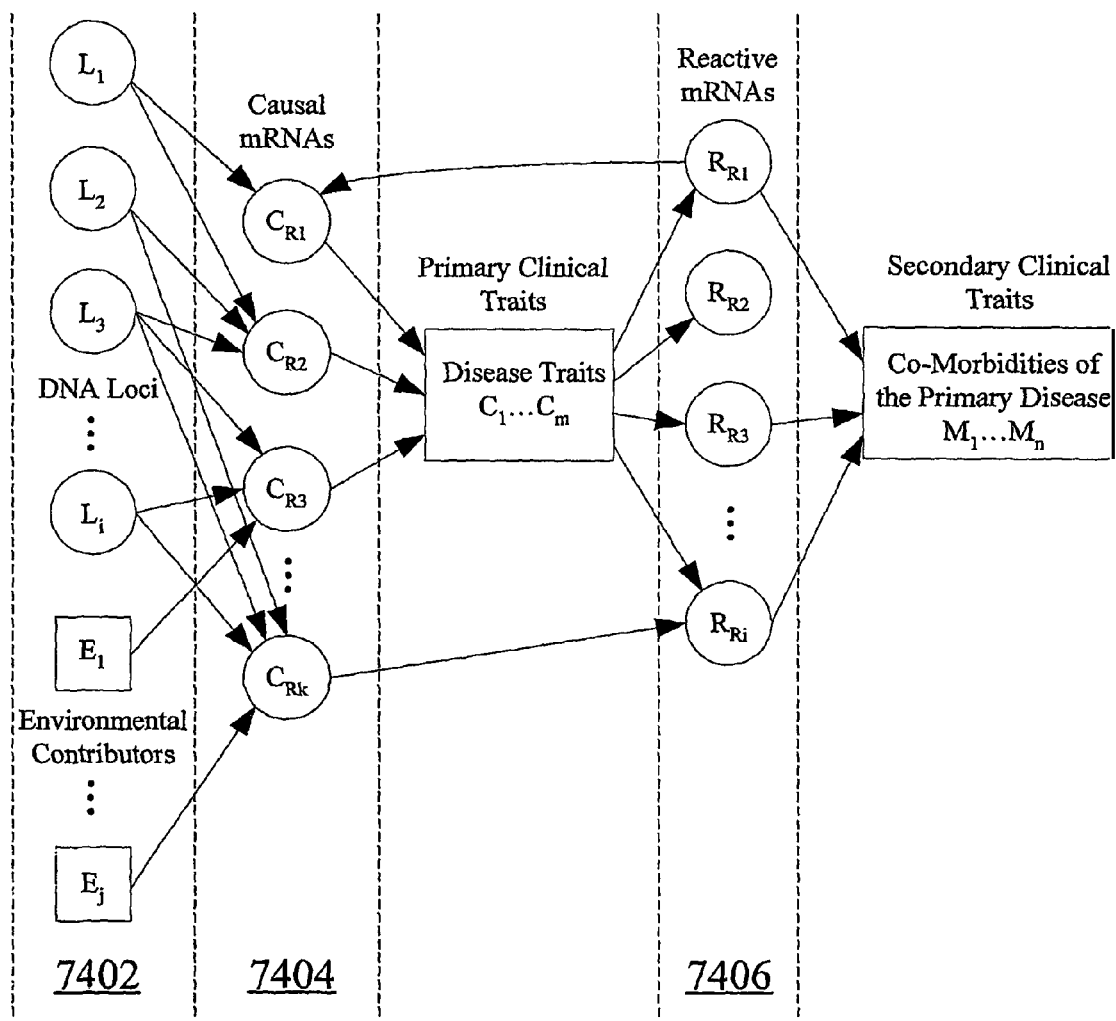

FIG. 74 illustrates a topology for how causal genes affect pathways that affect a primary disease which, in turn, affects reactive genes.

Figure 75A:
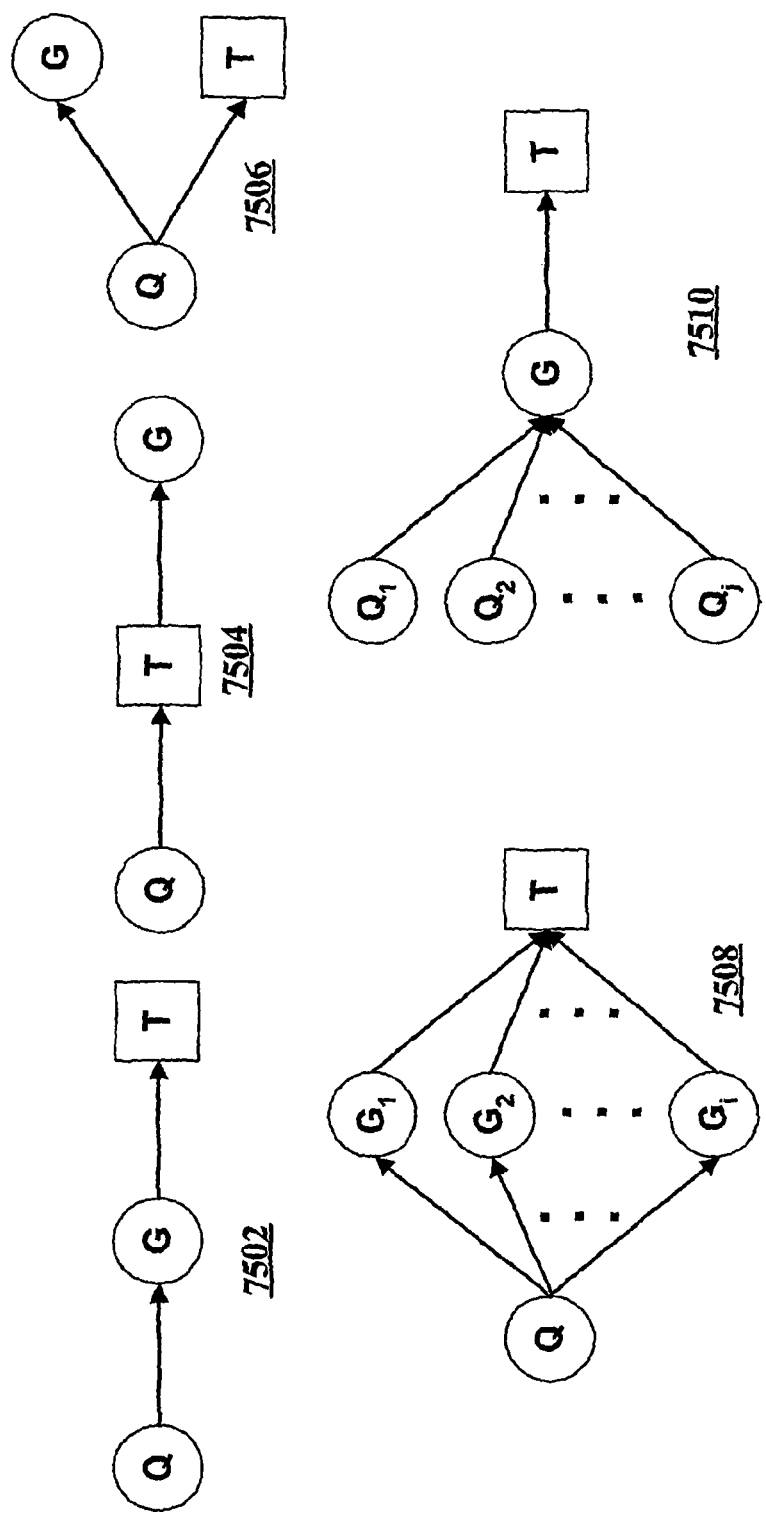

FIG. 75A illustrates possible relationships between quantitative trait loci (QTL), genes and disease traits once the expression of the gene (G) and the disease trait (I) have been shown to be under the control of a common QTL (Q).

Figure 75B:
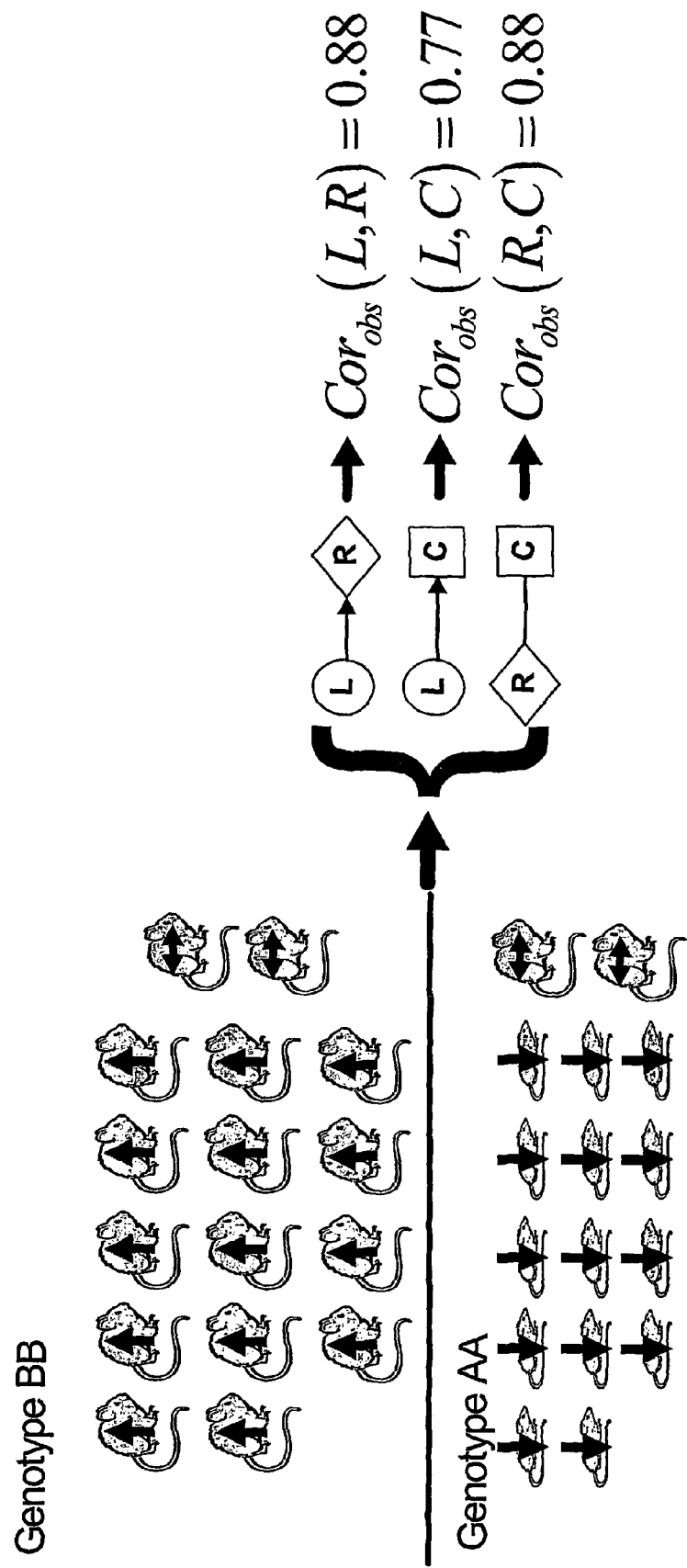

FIG. 75B illustrates obese and lean animals segregating with the genotypes given at the locus, with up arrows indicating up regulation of the gene, horizontal arrows indicating no differential regulation, and down arrows indicating down regulation.

Figure 3A:
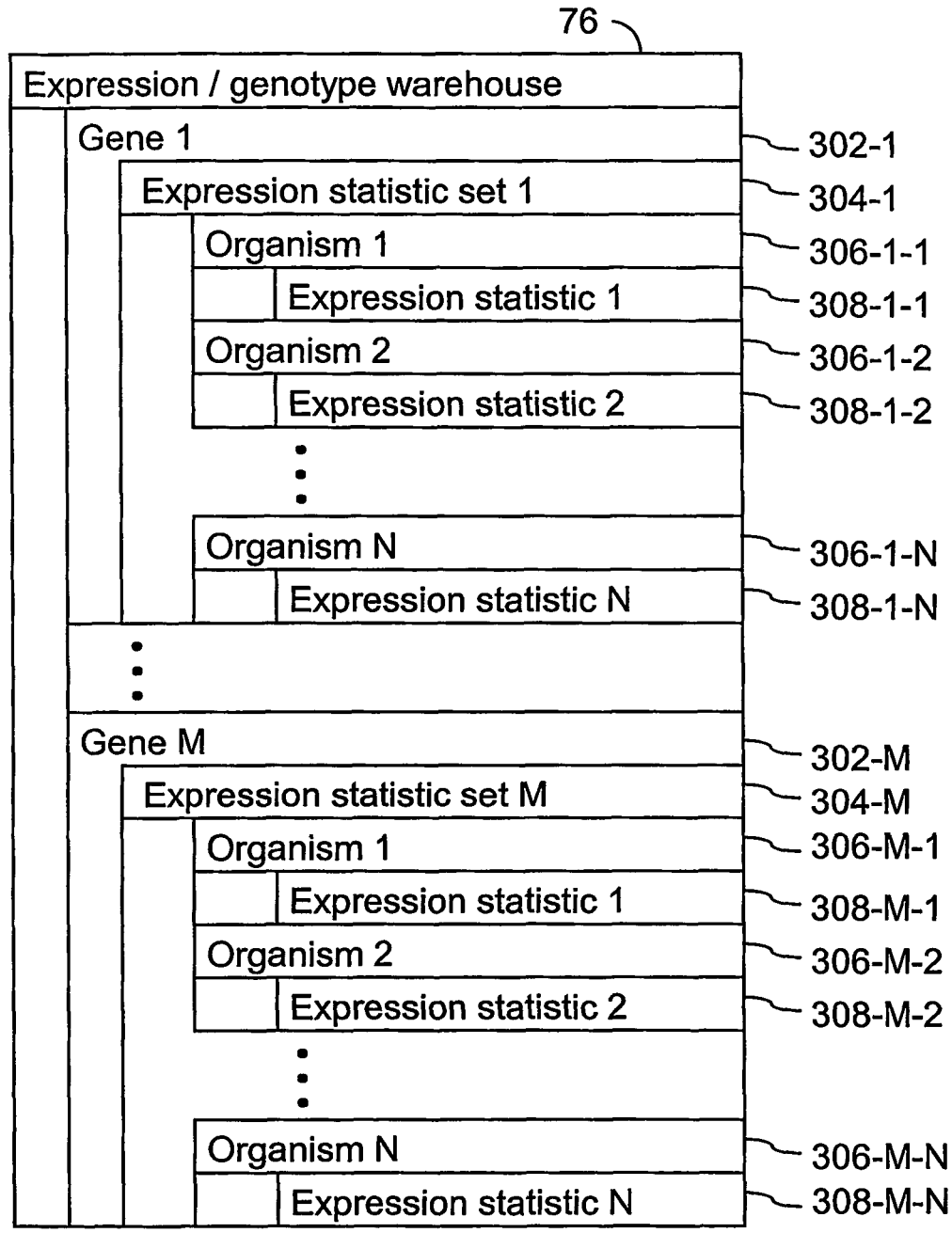
FIG. 3A illustrates an expression/genotype warehouse in accordance with one embodiment of the present invention.
Figure 3B:
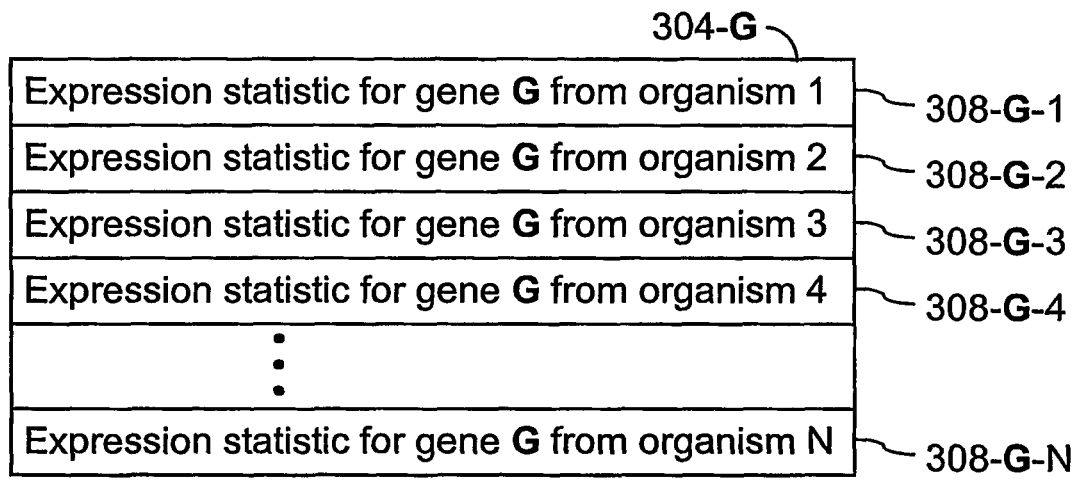
FIG. 3B illustrates a gene expression statistic found in an expression/genotype warehouse in accordance with one embodiment of the present invention.
Figure 75C:
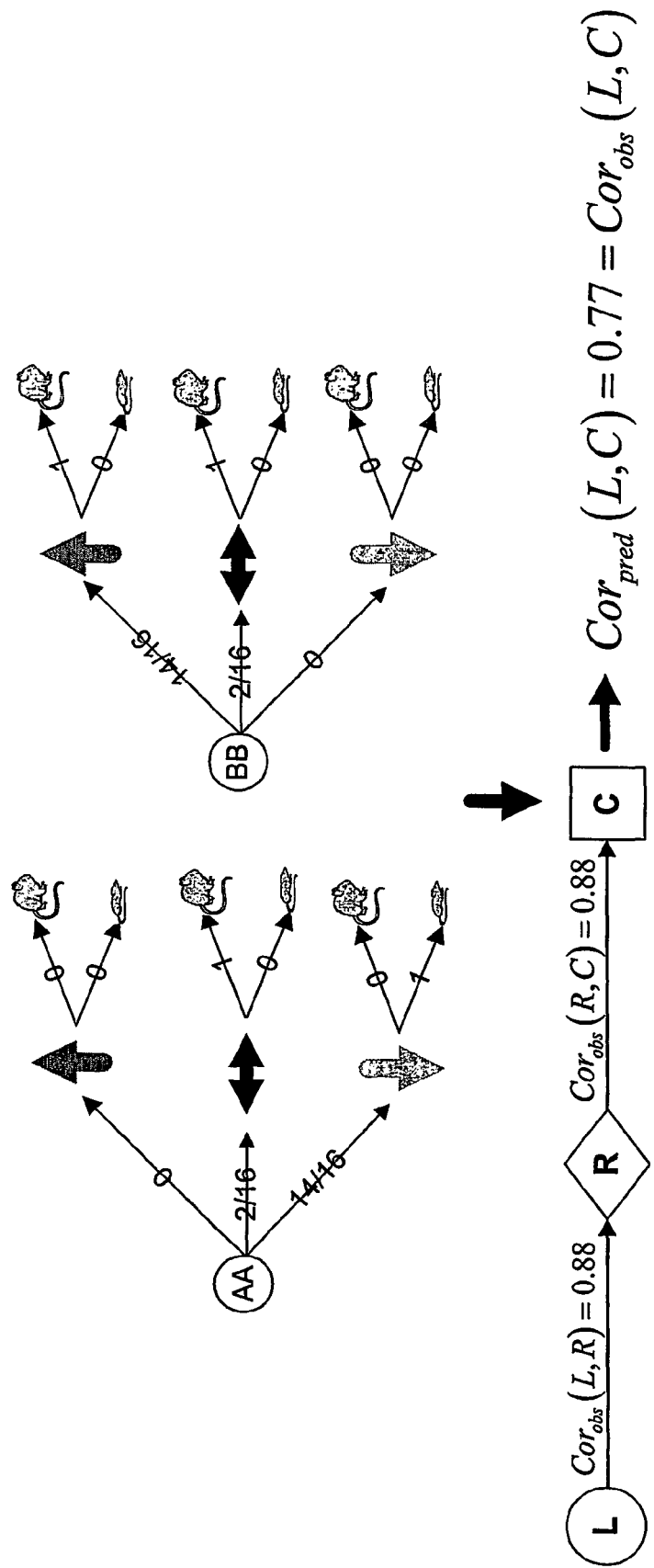

FIG. 75C illustrates an analysis of the observed correlation structure between the locus, gene expression trait, and obesity trait of FIG. 3B under a causal model.

Figure 75D:
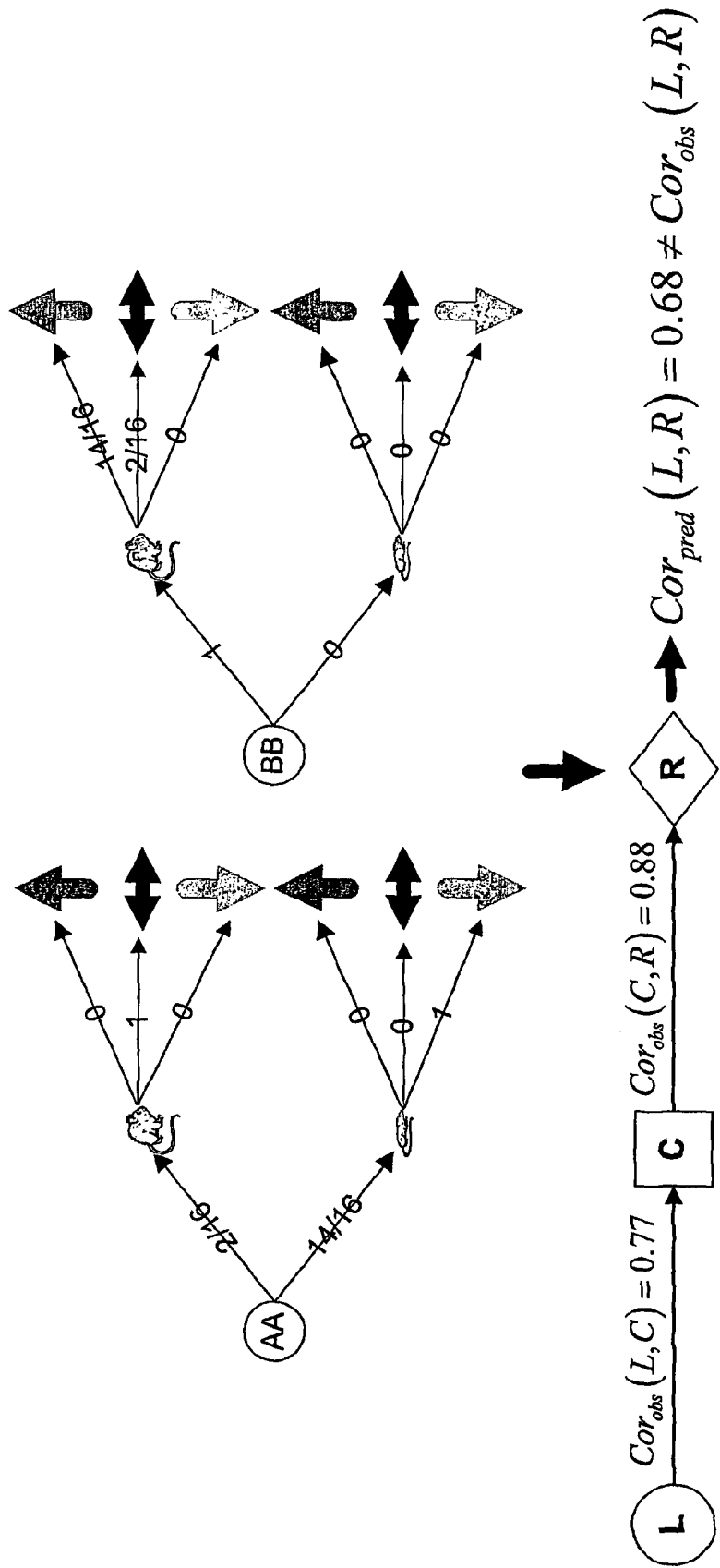

FIG. 75D illustrates an analysis of the observed correlation structure between the locus, gene expression trait, and obesity trait of FIG. 3B under a reactive model.

Figure 75E:
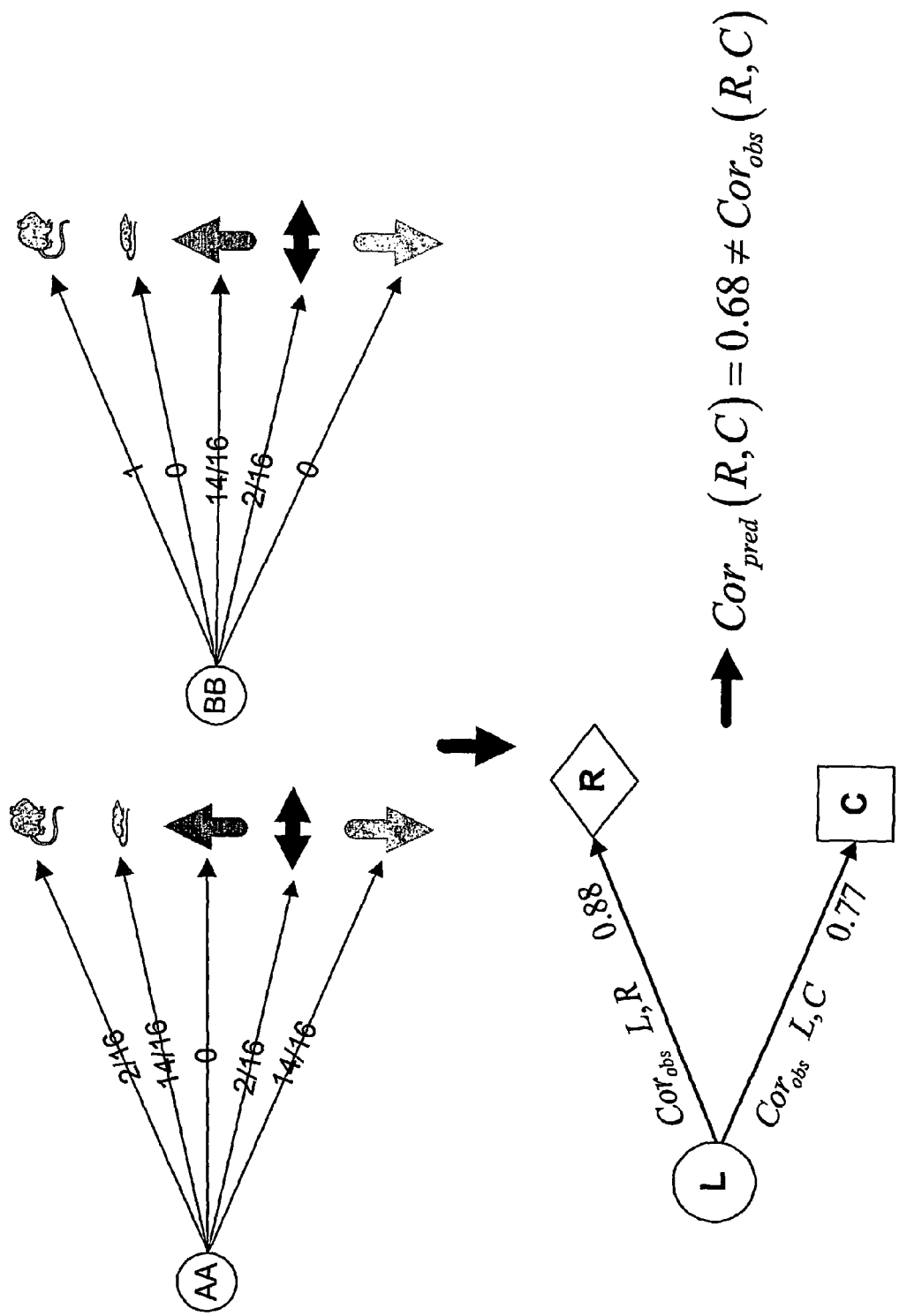

FIG. 75E illustrates an analysis of the observed correlation structure between the locus, gene expression trait, and obesity trait of FIG. 3B under an independent model.

Figure 76:
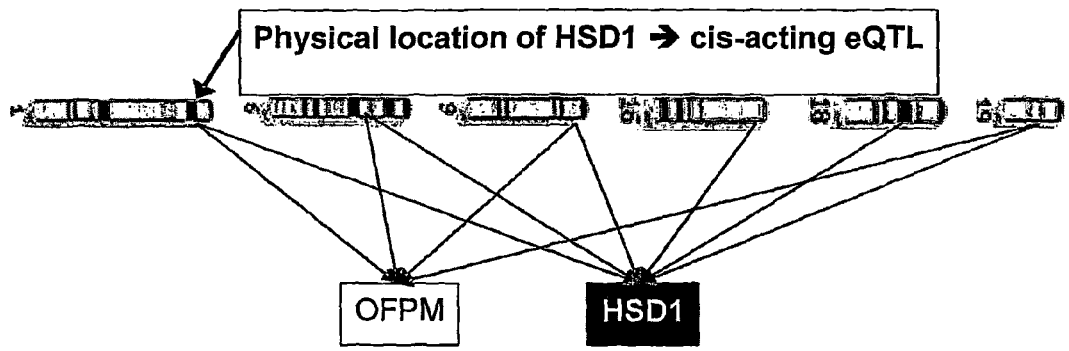

FIG. 76 illustrates the genomic positions of the cQTL that are linked to the trait omental fat pad masses (OFPM) as well as the eQTL that are linked to expression of the gene HSD1 in a segregating mouse population.

Figure 77:
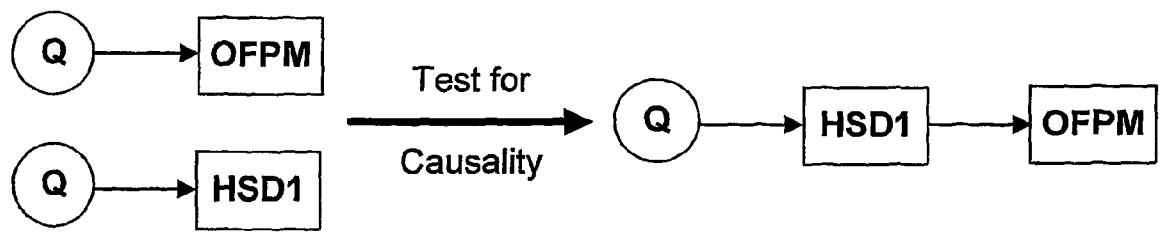

FIG. 77 illustrates a potential relationship between a specific QTL (which controls for both the trait OFPM and HSD1 expression), HSD1, and OFPM.

Figure 78:
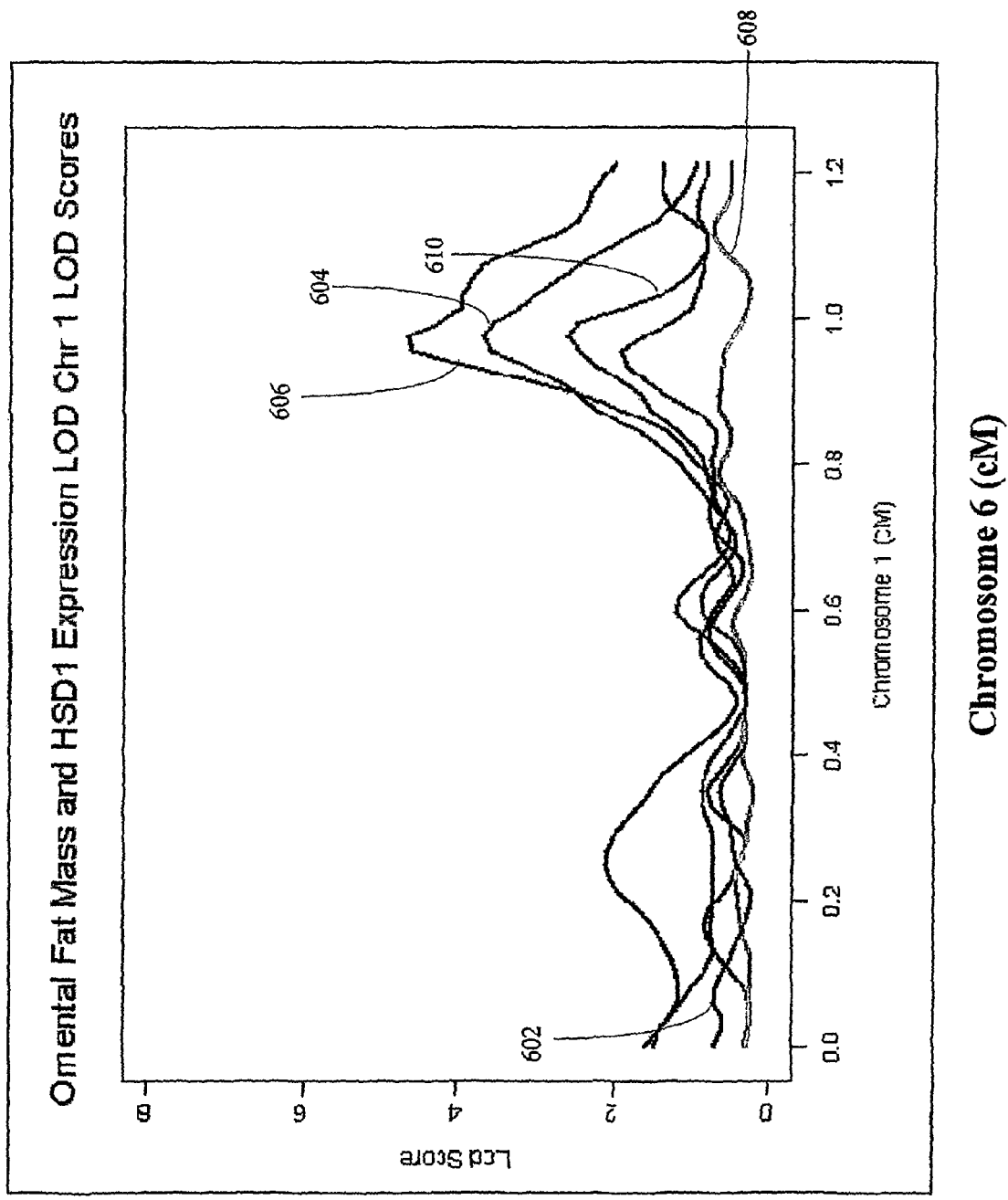

FIG. 78 illustrates LOD score curves for HSD1 expression, the trait OFPM, the simultaneous consideration of HSD1 expression and the trait OFPM, as well as OFPM after conditioning on HSD1 expression.

FIG. 79 illustrates processing steps for identifying a gene that affects a trait in accordance with one embodiment of the present invention.

Figure 80:
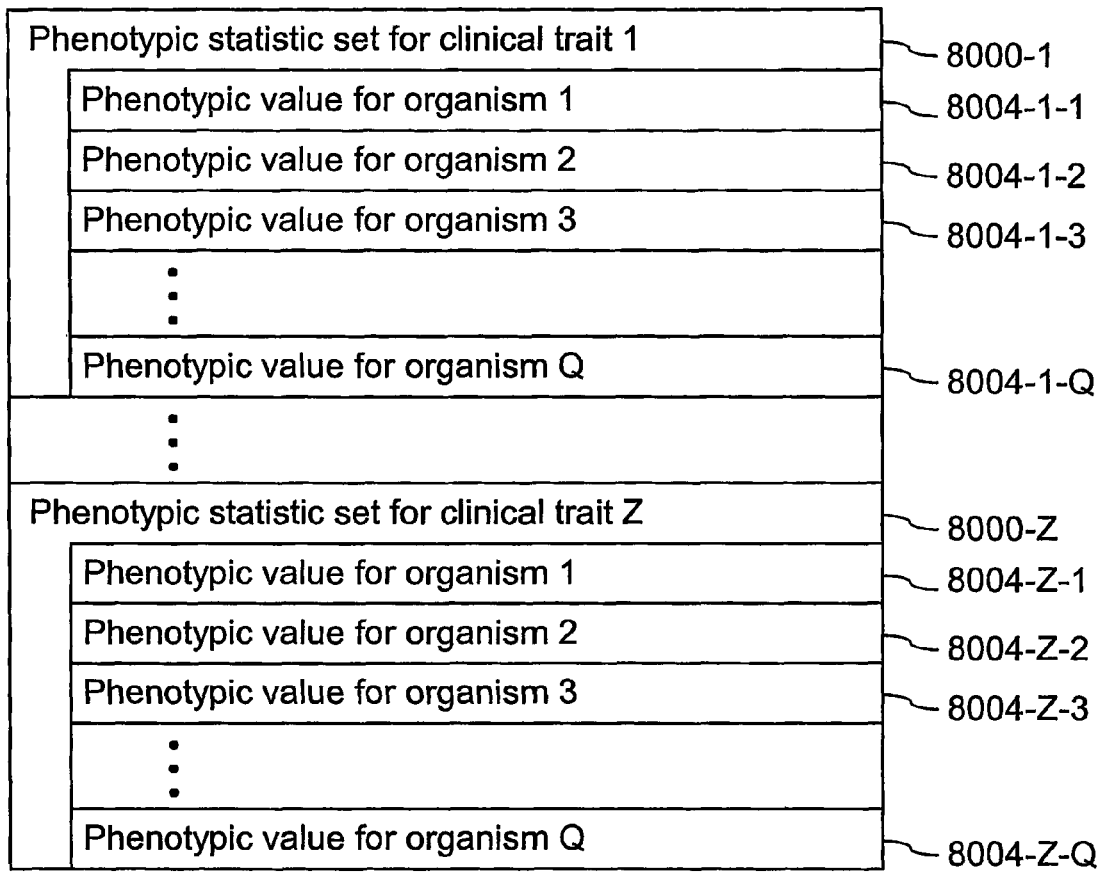

FIG. 80 illustrates the data structure for phenotypic statistic sets in accordance with one embodiment of the present invention.

Figure 81:
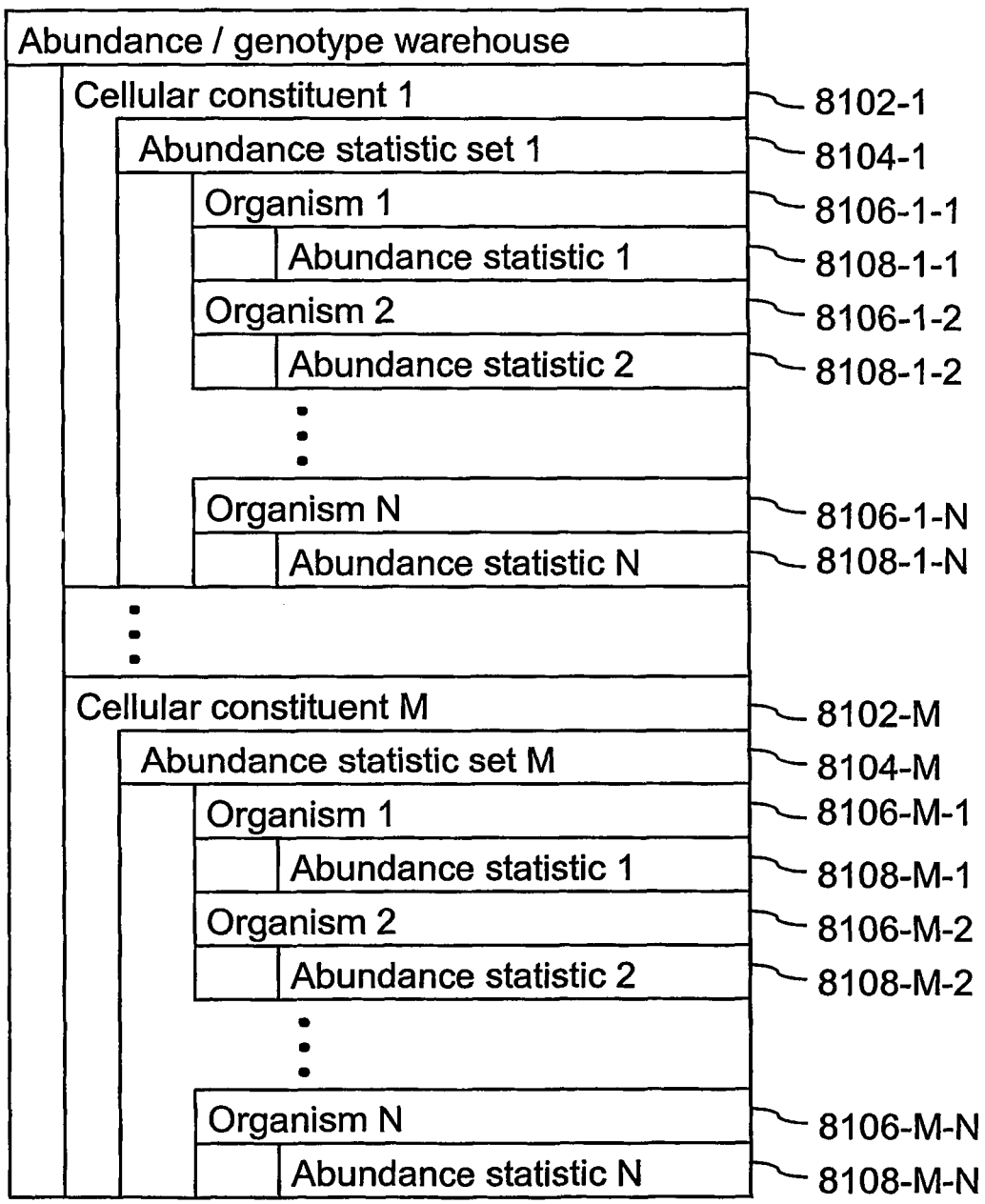

FIG. 81 illustrates a data structure for storing cellular constituent abundance data in accordance with one embodiment of the present invention.

Figure 82:
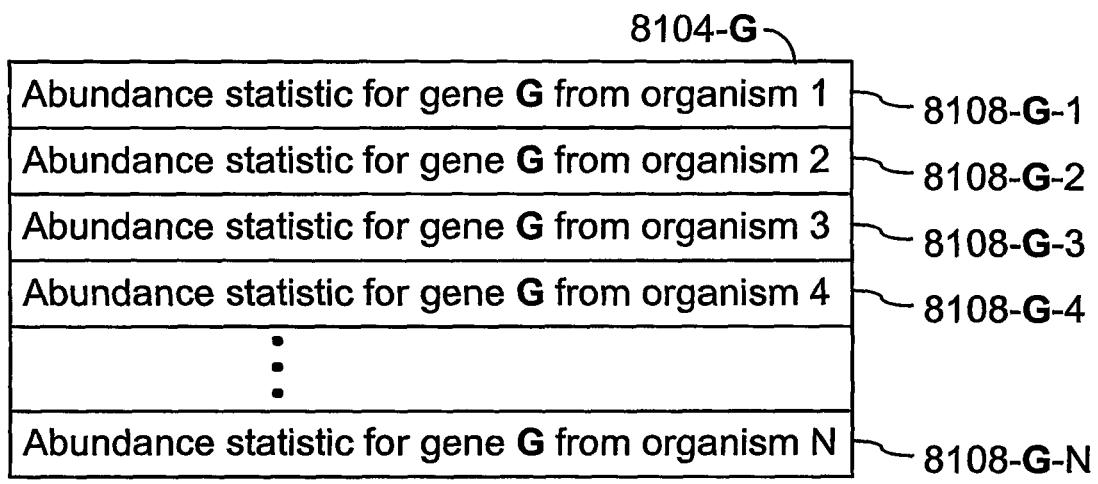

FIG. 82 illustrates the data structure for a cellular constituent expression statistic in accordance with one embodiment of the present invention.

Figure 83:
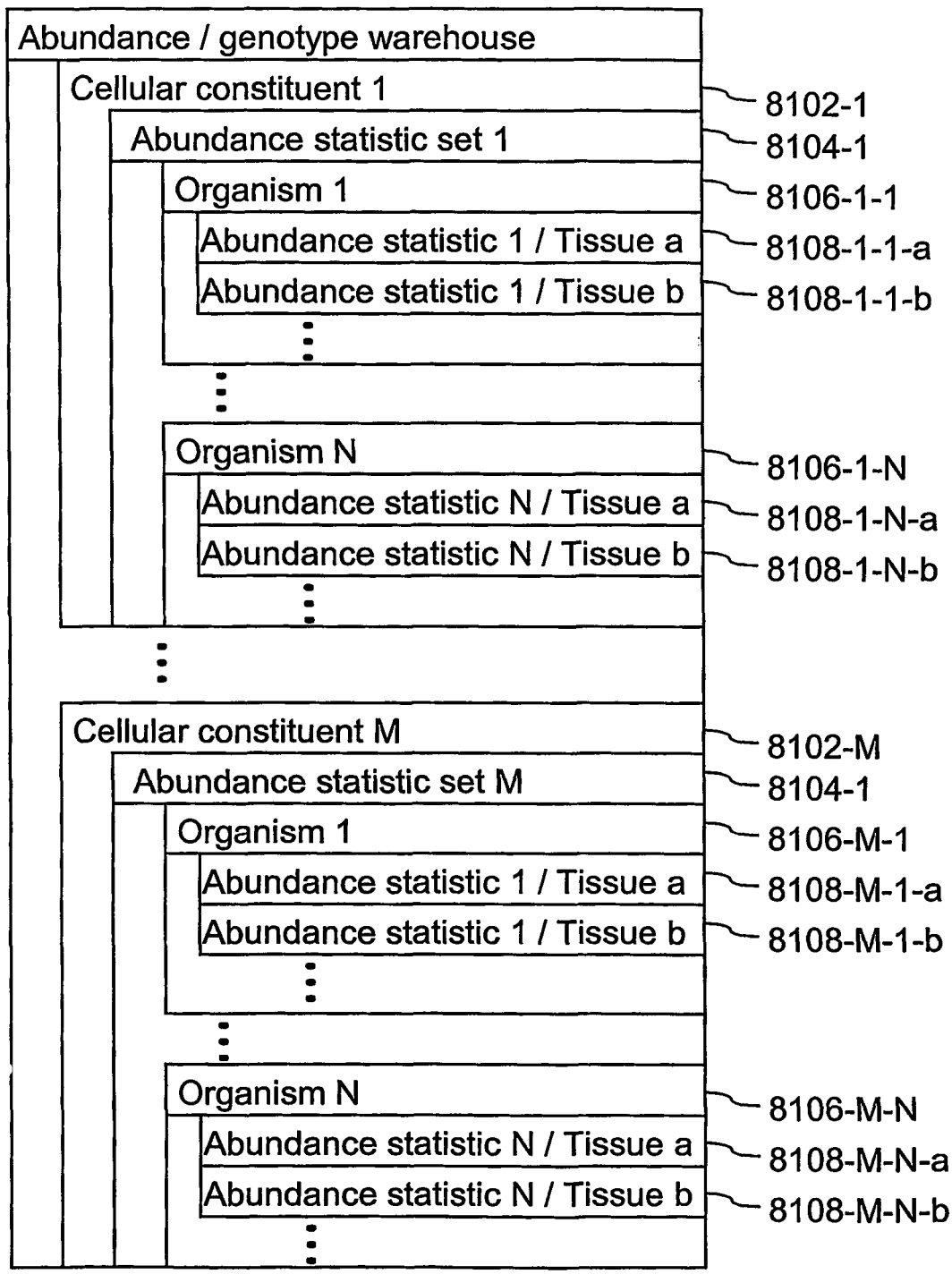

FIG. 83 illustrates a data structure for storing cellular constituent abundance data from a plurality of different tissue types in accordance with one embodiment of the present invention.

FIG. 84 illustrates a QTL results database in accordance with the present invention FIGS. 85A-85E illustrates several possible genetic relationships.

FIGS. 86A-86D depict cQTL for several clinical traits in the BXD cross (HDL, plasma insulin levels, plasma leptin levels, and epididymal fat mass) located on murine chromosome 13.

Figure 86A:
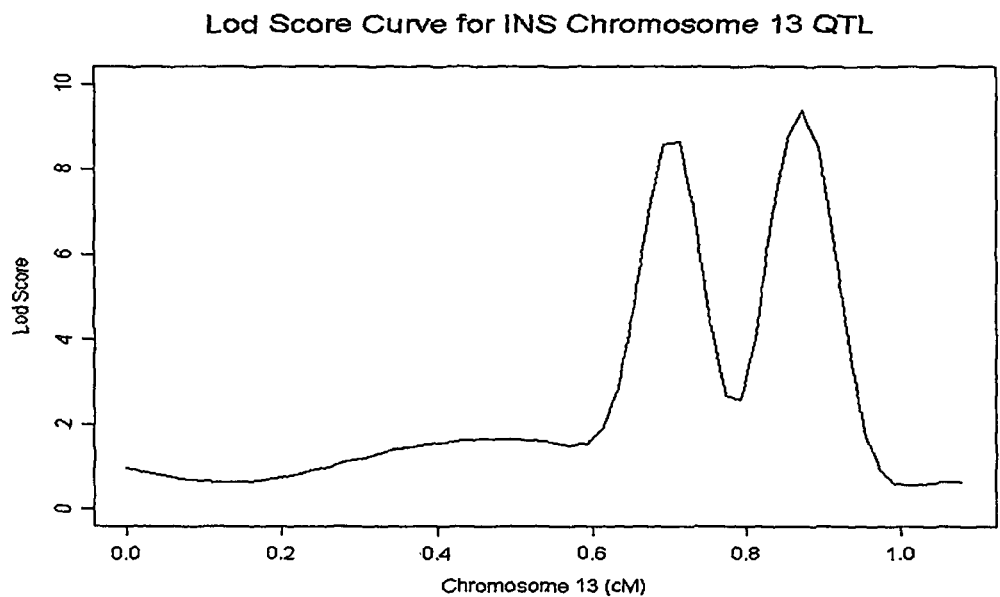
Figure 86B:
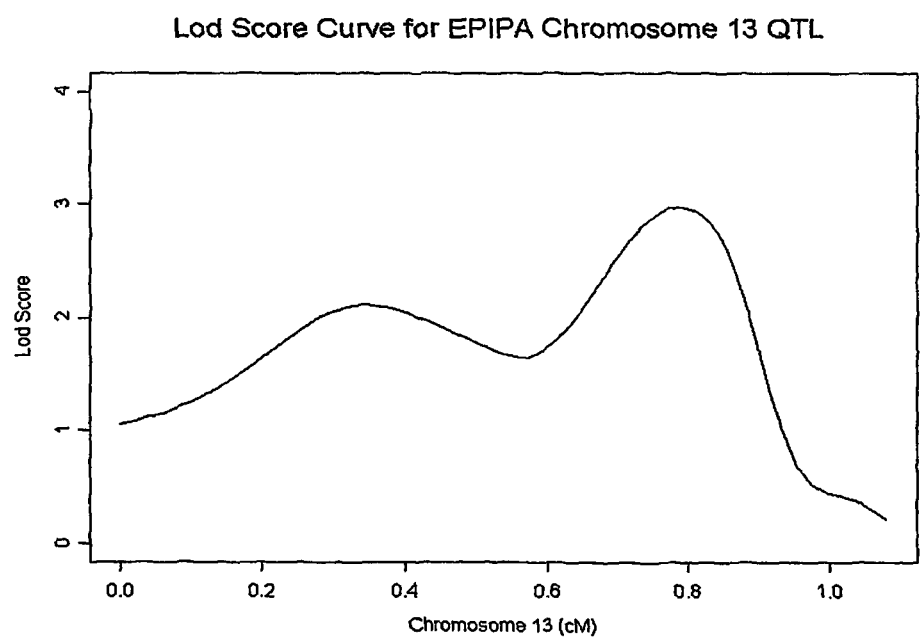
Figure 86C:
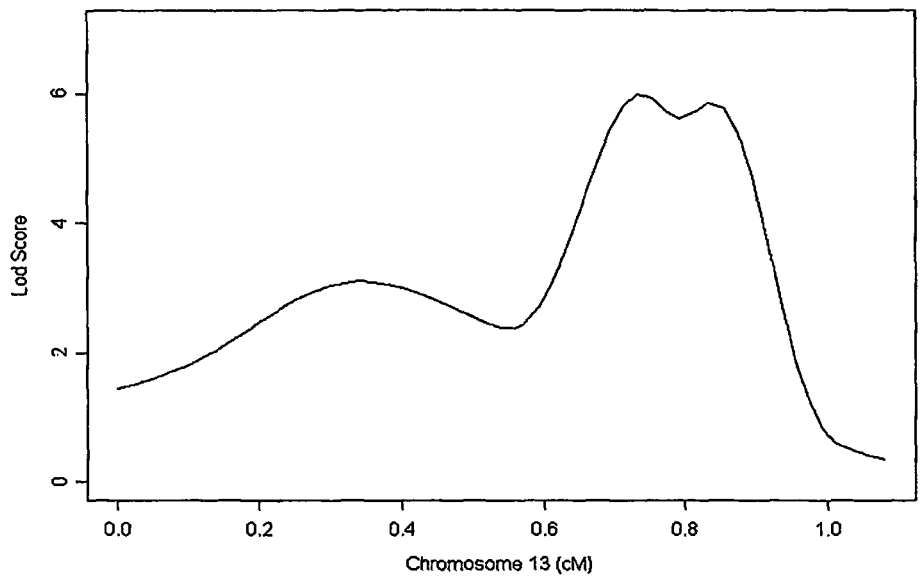
Figure 86D:
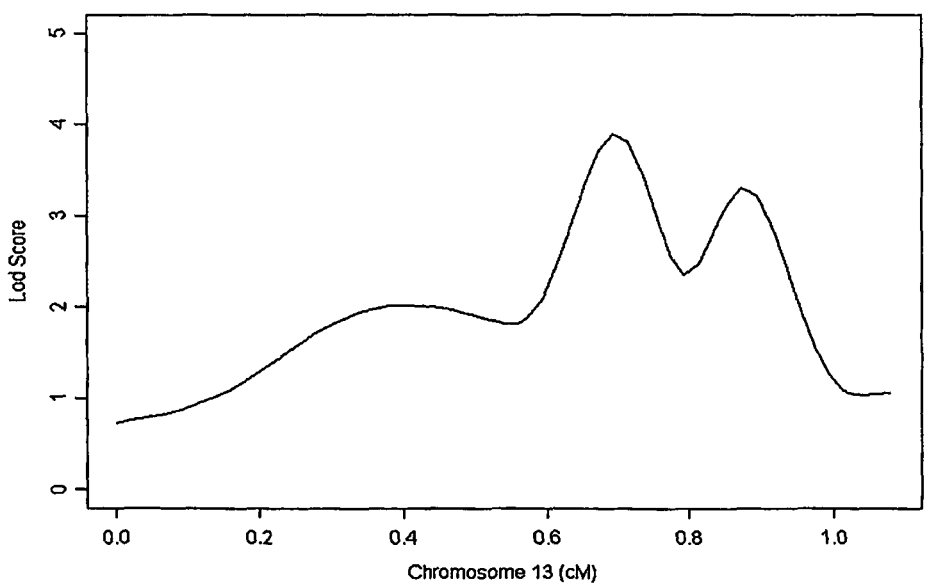
Figure 87:
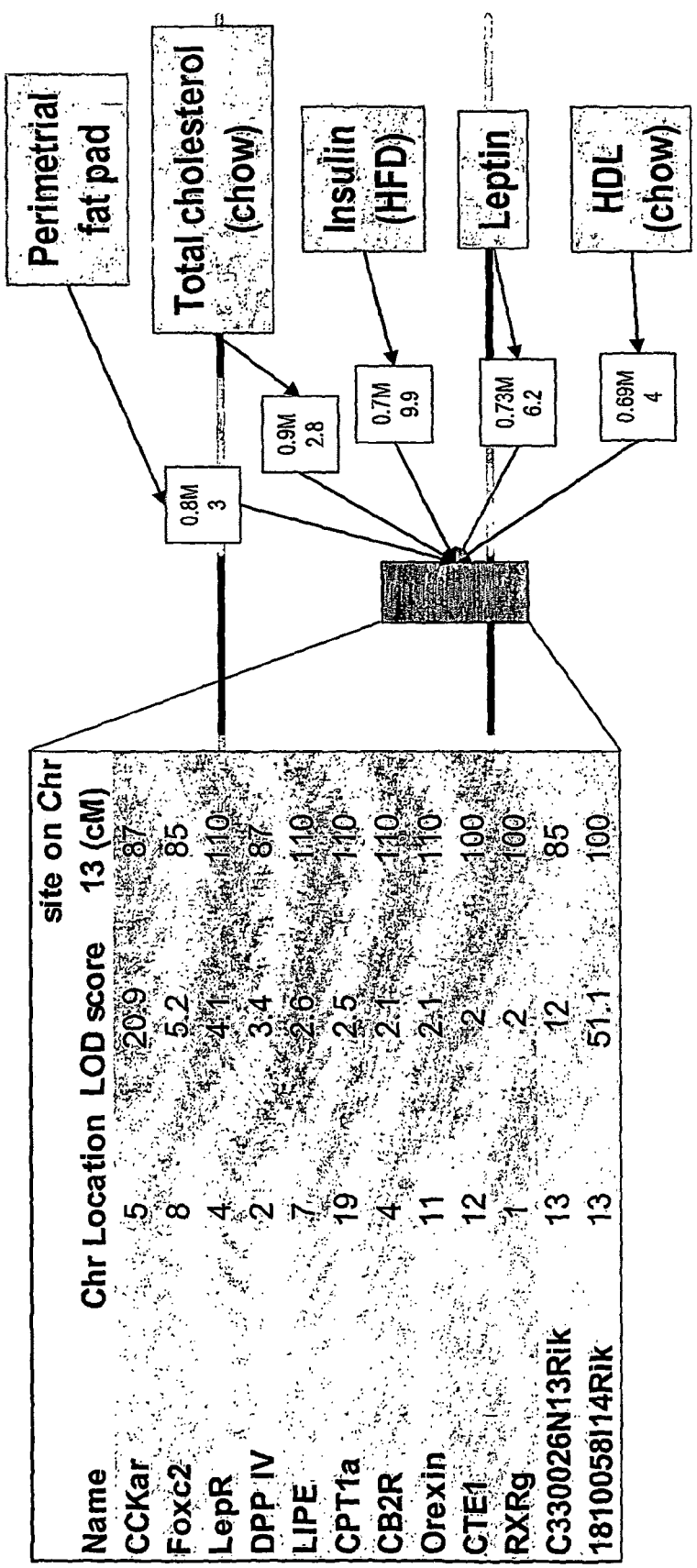

FIG. 87 highlights a subset of the genes whose expression in the liver of F2 animals derived from a cross of C57BL/6J of DBA/2J mice are controlled by the chromosome 13 cQTL given in FIG. 86.

FIG. 88 is the human amino acid sequence of the cholecystokinin type A receptor (CCKAR) SEQ ID NO: 30.

Figure 89:
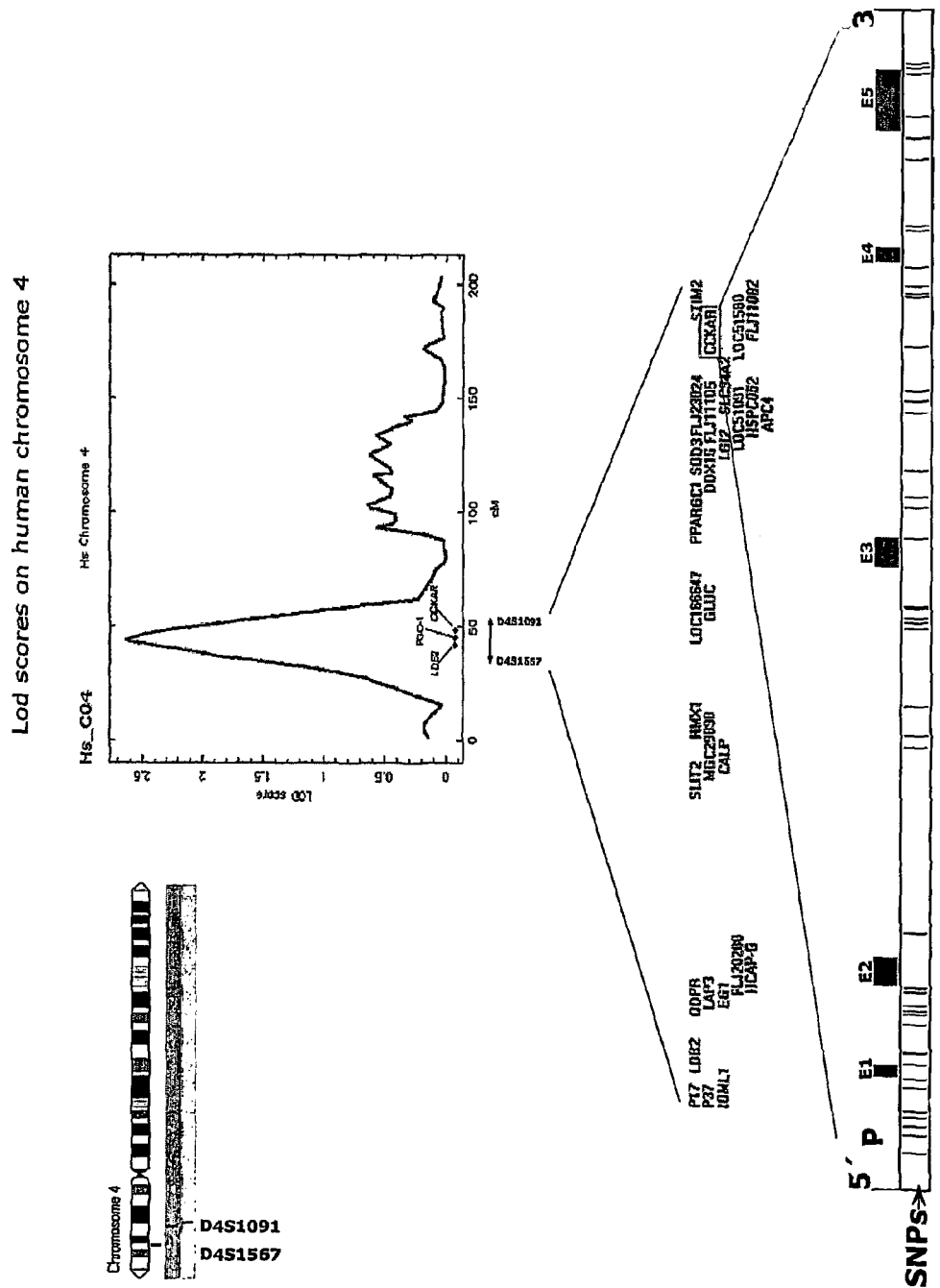

FIG. 89 highlights a lod score curve on human chromosome 4 for percent body fat in females in an Icelandic population.

FIG. 90 highlights two related human haplotypes that are strongly associated with percent body fat in females of an Icelandic population.

FIG. 91 illustrates a set of haplotypes identified in the CCKAR gene that are significantly associated with thinness in an Icelandic population.

Like reference numerals refer to corresponding parts throughout the several views of the drawings.

5. DETAILED DESCRIPTION

The present invention provides an apparatus and method for associating a gene with a trait exhibited by one or more organisms in a plurality of organisms of a single first species. In some embodiments, experimental data is used from a single second species. Exemplary single first species and single second species include, but are not limited to, plants and animals. In typical embodiments, the single first species and the single second species are different species. In specific embodiments, the exemplary single first species and the single second species are each drawn from a list of species that includes, but is not limited to plants such as corn, beans, rice, tobacco, potatoes, tomatoes, cucumbers, apple trees, orange trees, cabbage, lettuce, and wheat. In specific embodiments, exemplary organisms include, but are not limited to animals such as mammals, primates, humans, mice, rats, dogs, cats, chickens, horses, cows, pigs, and monkeys. In yet other specific embodiments, the single first species and/or the single second species are each selected from the group consisting of *Drosophila*, yeast, viruses, and *Caenorhabditis elegans* (*C. elegans*).

In some instances, the gene is associated with the trait by identifying a biological pathway in which the gene product participates. In some embodiments of the present invention, the trait of interest is a complex trait such as a human disease. Exemplary human diseases include, but are not limited to, diabetes, obesity, cancer, asthma, schizophrenia, arthritis, multiple sclerosis, and rheumatosis. In some embodiments, the trait of interest is a preclinical indicator of disease, such as, but not limited to, high blood pressure, abnormal triglyceride levels, abnormal cholesterol levels, or abnormal high-density lipoprotein/low-density lipoprotein levels. In a specific embodiment of the present invention, the trait is low resistance to an infection by a particular insect or pathogen. Additional exemplary diseases are found in Section 5.12, infra. In the invention, the expression level measurement of each gene in each of a plurality of organisms is transformed into a corresponding expression statistic. An "expression level measurement" of a gene can be, for example, a measurement of the level of its encoded RNA (or cDNA) or proteins or activity levels of encoded proteins. In some embodiments, this transformation is a normalization routine in which raw gene expression data is normalized to yield a mean log ratio, a log intensity, and a background-corrected intensity. Further, a genetic marker map 78 (FIG. 1) is constructed from a set of genetic markers associated with the plurality of organisms. Then, for each gene G in a plurality of genes expressed by an organism in the population, a quantitative trait locus (QTL) analysis is performed using the genetic marker map in order to produce QTL data. A set of expression statistics represents the quantitative trait used in each QTL analysis. QTL analyses are explained in greater detail, infra, in conjunction with FIG. 2, element 210. This set of expression statistics, for any given gene G, comprises an expression statistic for gene G, for each organism in the plurality of organisms. Next, the QTL data obtained from each QTL analysis is clustered to form a QTL interaction map. Identification of tightly clustered QTLs in the QTL interaction map helps to identify genes that are genetically interacting. This information, in turn, helps to elucidate biological pathways that are affected by complex traits, such as human disease. In some embodiments of the present invention, tightly clustered QTLs in the QTL interaction map are considered candidate pathway groups. These candidate pathway groups are subjected to multivariate analysis in order to verify whether the genes in the candidate pathway group affect a particular complex trait.

One embodiment of the present invention provides a method for associating a gene with a trait exhibited by one or more organisms in a plurality of organisms of a single species. In the method, quantitative trait locus data from a plurality of quantitative trait locus analyses are clustered to form a quantitative trait locus interaction map. Each quantitative trait locus analysis in the plurality of quantitative trait locus analyses are performed for a gene G in a plurality of genes in the genome of the plurality of organisms using a genetic marker map and a quantitative trait in order to produce the quantitative trait locus data. For each quantitative trait locus analysis, the quantitative trait comprises an expression statistic for the gene G for which the quantitative trait locus analysis has been performed, for each organism in the plurality of organisms. The genetic marker map is constructed from a set of genetic markers associated with the plurality of organisms. Further, in the method, the quantitative trait locus interaction map is analyzed to identify a gene associated with a trait, thereby associating the gene with the trait exhibited by one or more organisms in the plurality of organisms.

5.1. Overview of the Invention

Figure 1:
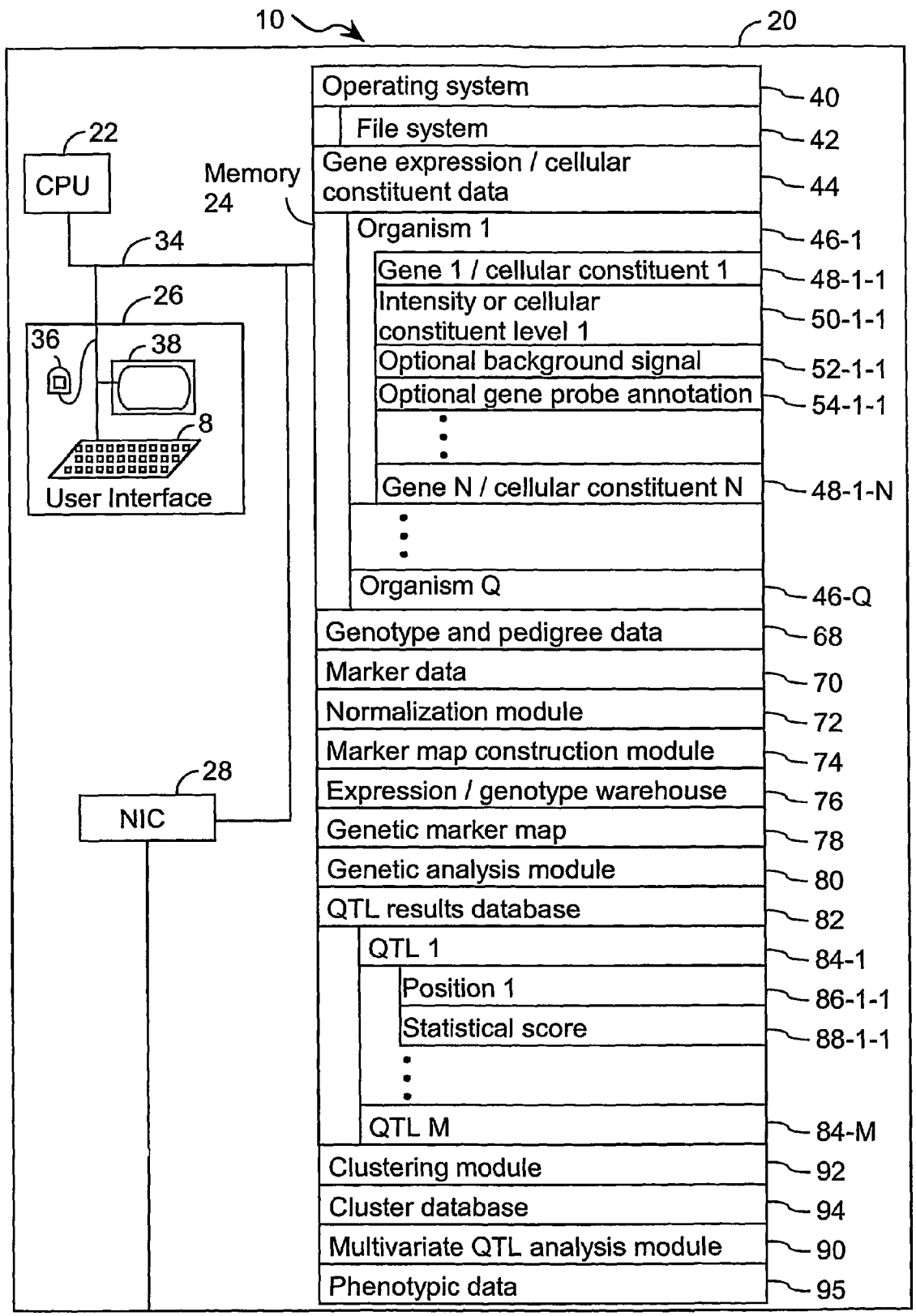
FIG. 1 illustrates a computer system for associating a gene with a trait exhibited by one or more organisms in a plurality of organisms in accordance with one embodiment of the present invention.
Figure 2:
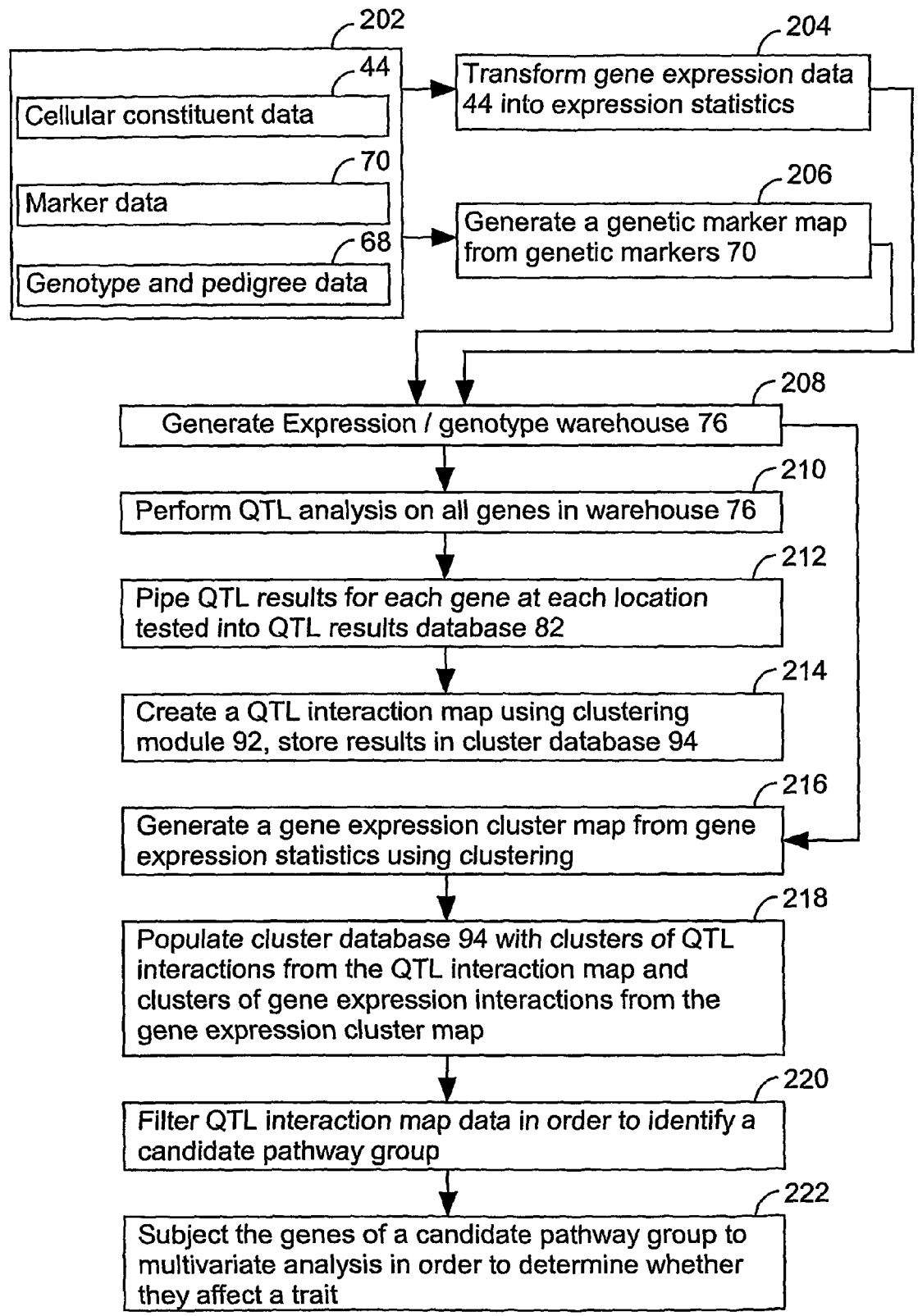
FIG. 2 illustrates processing steps for associating a gene with a trait exhibited by one or more organisms in a plurality of organisms of a single species using a clustering approach, in accordance with an embodiment of the present invention.

FIG. 1 illustrates a system 10 that is operated in accordance with one embodiment of the present invention. In addition, FIG. 2 illustrates the processing steps that are performed in accordance with one embodiment of the present invention. These figures will be referenced in this section in order to disclose the advantages and features of the present invention. System 10 comprises at least one computer 20 (FIG. 1). Computer 20 comprises standard components including a central processing unit 22, memory 24 (including high speed random access memory as well as non-volatile storage, such as disk storage) for storing program modules and data structures, user input/output device 26, a network interface 28 for coupling server 20 to other computers via a communication network (not shown), and one or more busses 34 that interconnect these components. User input/output device 26 comprises one or more user input/output components such as a mouse 36, display 38, and keyboard 8.

Memory 24 comprises a number of modules and data structures that are used in accordance with the present invention. It will be appreciated that, at any one time during operation of the system, a portion of the modules and/or data structures stored in memory 24 is stored in random access memory while another portion of the modules and/or data structures is stored in non-volatile storage. In a typical embodiment, memory 24 comprises an operating system 40. Operating system 40 comprises procedures for handling various basic system services and for performing hardware dependent tasks. Memory 24 further comprises a file system 42 for file management. In some embodiments, file system 42 is a component of operating system 40.

The present invention begins with gene expression data 44 (e.g., from a gene expression study or a proteomics study) and a genotype and/or pedigree data 68 from an experimental cross or human cohort under study (FIG. 1; FIG. 2, step 202). In one embodiment, gene expression data 44 consists of the processed microarray images for each individual (organism) 46 in a population under study. In some embodiments, such data comprises, for each individual 46, intensity information 50 for each gene 48 represented on the array, background signal information 52, and associated annotation information 54 describing the gene probe (FIG. 1). In some embodiments, gene expression data is, in fact, protein levels for various proteins in the organisms 46 under study. In one aspect of the present invention, the expression level of a gene in an organism in the population of interest is determined by measuring an amount of at least one cellular constituent that corresponds to the gene in one or more cells of the organism. As used herein, the term "cellular constituent" comprises individual genes, proteins, mRNA expressing a gene, and/or any other variable cellular component or protein activity, degree of protein modification (e.g., phosphorylation), for example, that is typically measured in a biological experiment by those skilled in the art. Although for simplicity the disclosure often makes reference to single cells, it will be understood by those of skill in the art that more often any particular step of the invention will be carried out using a plurality of genetically similar cells, g., f from a cultured cell line. Such similar cells are referred to herein as a "cell type." In one embodiment, the amount of the at least one cellular constituent that is measured comprises abundances of at least one RNA species present in one or more cells. Such abundances may be measured by a method comprising contacting a gene transcript array with RNA from one or more cells of the organism, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species. In some embodiments, gene expression data 44 is taken from tissues that have been associated with the complex trait under study. For example, in one nonlimiting embodiment where the complex trait under study is human obesity, gene expression data is taken from the liver, brain, or adipose tissues.

In some embodiments of the present invention, gene expression/cellular constituent data 44 is measured from multiple tissues of each organism 46 (FIG. 1) under study. For example, in some embodiments, gene expression/cellular constituent data 44 is collected from one or more tissues selected from the group of liver, brain, heart, skeletal muscle, white adipose from one or more locations, and blood. In such embodiments, the data is stored in an exemplary data structure such as that disclosed in FIG. 3C. This data structure is described in more detail below.

Genotype and/or pedigree data 68 (FIG. 1) comprise the actual alleles for each genetic marker typed in each individual under study, in addition to the relationships between these individuals. The extent of the relationships between the individuals under study may be as simple as an F2 population or as complicated as extended human family pedigrees. Exemplary sources of genotype and pedigree data are described in Section 6.1, infra. In some embodiments of the present invention, pedigree data is optional.

Marker data 70 at regular intervals across the genome under study or in gene regions of interest is used to monitor segregation or detect associations in a population of interest. Marker data 70 comprises those markers that will be used in the population under study to assess genotypes. In one embodiment, marker data 70 comprises the names of the markers, the type of markers the physical and genetic location of the markers in the genomic sequence. Exemplary types of markers include, but are not limited to, restriction fragment length polymorphisms "RFLPs", random amplified polymorphic DNA "RAPDs", amplified fragment length polymorphisms "AFLPs", simple sequence repeats "SSRs", single nucleotide polymorphisms "SNPs", microsatellites, etc.). Further, in some embodiments, marker data 70 comprises the different alleles associated with each marker. For example, a particular microsatellite marker consisting of 'CA' repeats may have represented ten different alleles in the population under study, with each of the ten different alleles in turn consisting of some number of repeats. Representative marker data 70 in accordance with one embodiment of the present invention is found in Section 5.2, infra. In one embodiment of the present invention, the genetic markers used comprise single nucleotide polymorphisms (SNPs), microsatellite markers, restriction fragment length polymorphisms, short tandem repeats, DNA methylation markers, and/or sequence length polymorphisms.

Once starting data are assembled, the first step (FIG. 2, step 204) is to transform gene expression data 44 into expression statistics that are used to treat each cellular constituent abundance in gene expression data 44 as a quantitative trait. In some embodiments, gene expression data 44 (FIG. 1) comprises gene expression data for a plurality of genes or cellular constituents that correspond to the plurality of genes. In one embodiment, the plurality of genes comprises at least five genes. In another embodiment, the plurality of genes comprises at least one hundred genes, at least one thousand genes, at least twenty thousand genes, or more than thirty thousand genes. The expression statistics commonly used as quantitative traits in the analyses in one embodiment of the present invention include, but are not limited to the mean log ratio, log intensity, and background-corrected intensity. In other embodiments, other types of expression statistics are used as quantitative traits. In one embodiment, this transformation (FIG. 2, step 204) is performed using normalization module 72 (FIG. 1). In such embodiments, the expression level of a plurality of genes in each organism under study are normalized. Any normalization routine may be used by normalization module 72. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines may be run. Exemplary normalization routines in accordance with the present invention are disclosed in more detail in Section 5.3, infra. The expression statistics formed from the transformation are then stored in Expression/genotype warehouse 76, where they are ultimately matched with the corresponding genotype information.

In addition to the generation of expression statistics from gene expression data 44, a genetic marker map 78 is generated from genetic markers 70 (FIG. 1; FIG. 2, step 206). In one embodiment of the present invention, a genetic marker map is created using marker map construction module 74 (FIG. 1). Further, in one embodiment, genotype probability distributions for the individuals under study are computed. Genotype probability distributions take into account information such as marker information of parents, known genetic distances between markers, and estimated genetic distances between the markers. Computation of genotype probability distributions generally requires pedigree data. In some embodiments of the present invention, pedigree data is not provided and genotype probability distributions are not computed.

Once the expression data has been transformed into corresponding expression statistics and genetic marker map 78 has been constructed, the data is transformed into a structure that associates all marker, genotype and expression data for input into QTL analysis software. This structure is stored in expression/genotype warehouse 76 (FIG. 1; FIG. 2, step 208).

A quantitative trait locus (QTL) analysis is performed using data corresponding to each gene in a plurality of genes as a quantitative trait (FIG. 2, step 210). For 20,000 genes, this results in 20,000 separate QTL analyses. For embodiments in which multiple tissues samples are collected for each organism, this results in even more separate QTL analysis. For example, in embodiments in which samples are collected from two different tissues, an analysis of 20,000 genes requires 40,000 separate QTL analyses. In one embodiment, each QTL analysis is performed by genetic analysis module 80 (FIG. 1). In one example, each QTL analysis steps through each chromosome in the genome of the organism of interest. Linkages to the gene under consideration are tested at each step or location along the length of the chromosome. In such embodiments, each step or location along the length of the chromosome is at regularly defined intervals. In some embodiments, these regularly defined intervals are defined in Morgans or, more typically, centiMorgans (cM). A Morgan is a unit that expresses the genetic distance between markers on a chromosome. A Morgan is defined as the distance on a chromosome in which one recombinational event is expected to occur per gamete per generation. In some embodiments, each regularly defined interval is less than 100 cM. In other embodiments, each regularly defined interval is less than 10 cM, less than 5 cM, or less than 2.5 cM.

In each QTL analysis, data corresponding to a gene selected from a plurality of genes under study is used as a quantitative trait. More specifically, for any given gene, the quantitative trait used in the QTL analysis is an expression statistic sat such as set 304 (FIG. 3A). Expression statistic set 304 comprises the corresponding expression statistic 308 for the gene 302 from each organism 306 in the population under study. FIG. 3B illustrates an exemplary expression statistic set 304 in accordance with one embodiment of the present invention. Exemplary expression statistic set 304 includes the expression level 308 of a gene G (or cellular constituent that corresponds to gene G) from each organism in a plurality of organisms. For example, consider the case where the are ten organisms in the plurality of organisms, and each of the ten organisms expresses gene G. In this case, expression statistic set 304 includes ten entries, each entry corresponding to a different one of the ten organisms in the plurality of organisms. Further, each entry represents the expression level of gene G in the organism represented by the entry. So, entry "1" (308-G-1) corresponds to the expression level of gene G in organism 1, entry "2" (308-G-2) corresponds to the expression level of gene G in organism 2, and so forth.

Figure 3C:
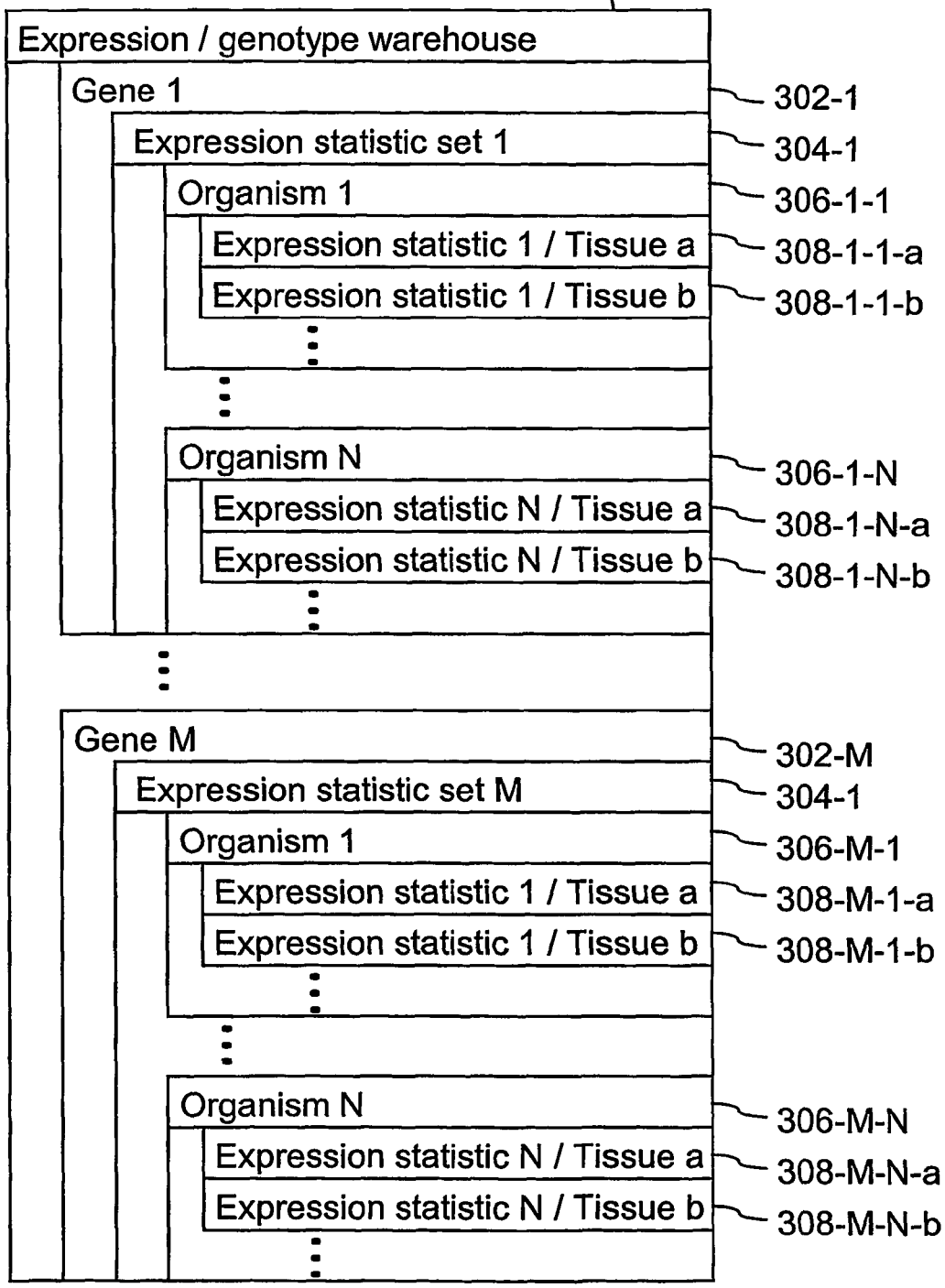
FIG. 3C illustrates an expression/genotype warehouse in accordance with another embodiment of the present invention.

Referring to FIG. 3C, in some embodiments of the present invention, expression data from multiple tissue samples of each organism 306 (FIG. 1, 46) under study are collected. When this is the case, the data can be stored in the exemplary data structure illustrated in FIG. 3C. In FIG. 3C, a plurality of genes 302 are represented. Further, there is an expression statistic set 304 for each gene 302. Each expression statistic set 304 represents the expression level (308) of the gene or an abundance of a cellular constituent (308) that corresponds to the gene in each of a plurality of organisms 306 (FIG. 1, 46). In one example, a cellular constituent is a particular protein and the cellular constituent corresponds to a gene when the gene codes for the cellular constituent.

In one embodiment of the present invention, each QTL analysis (FIG. 2, step 210) comprises: (i) testing for linkage between a position in a chromosome and the quantitative trait used in the quantitative trait locus (QTL) analysis, (i) advancing the position in the chromosome by an amount, and (iii)

repeating steps (i) and (ii) until all or a portion of the genome has been tested. In typical embodiments, the quantitative trait is the expression statistic set 304, such as the set illustrated in FIG. 3B. In some embodiments, testing for linkage between a given position in the chromosome and the expression statistic set 304 comprises correlating differences in the expression levels found in the expression level statistic with differences in the genotype at the given position using single marker tests (for example using t-tests, analysis of variance, or simple linear regression statistics). See, e.g., *Statistical Methods*, Snedecor and Cochran, 1985, Iowa State University Press, Ames, Iowa. However, there are many other methods for testing for linkage between expression statistic set 304 and a given position in the chromosome. In particular, if expression statistic set 304 is treated as the phenotype (in this case, a quantitative phenotype), than methods such as those disclosed in Doerge, 2002, Mapping and analysis of quantitative trait loci in experimental populations, *Nature Reviews: Genetics* 3:43-62, may be used. Concerning steps (i) through (iii) above, if the genetic length of a given chromosome is N cM and 1 cM steps are used, then N different tests for linkage are performed on the given chromosome. For organisms having multiple chromosomes, this process is repeated for each chromosome in the genome.

In some embodiments, the QTL data produced from each respective QTL analysis comprises a logarithm of the odds score (lod) computed at each position tested in the genome under study. A lod score is a statistical estimate of whether two loci are likely to lie near each other on a chromosome and are therefore likely to be genetically linked. In the present case, a lod score is a statistical estimate of whether a given position in the genome under study is linked to the quantitative trait corresponding to a given gene. lod scores are further defined in Section 5.4, infra. Generally, a lod score of three or more suggests that two loci are genetically linked, a lod score of 4 or more is strong evidence that two loci are genetically linked, and a lod score of 5 or more is very strong evidence that two loci are genetically linked. However, the significance of any given lod score actually varies from species to species depending on the model used. The generation of lod scores requires pedigree data. Accordingly, in embodiments in which a lod score is generated, processing step 210 is essentially a linkage analysis, as described in Section 5.13, with the exception that the quantitative trait under study is derived from data, such as cellular constituent expression statistics, rather than classical phenotypes such as eye color.

In situations where pedigree data is not available, genotype data from each of the organisms 46 (FIG. 1) for each marker in genetic marker map 78 may be compared to each quantitative trait (expression statistic set 304) using allelic association analysis, as described in Section 5.14, infra, in order to identify QTL that are linked to each expression statistic set 304. In one form of association analysis, an affected population is compared to a control population. In particular, haplotype or allelic frequencies in the affected population are compared to haplotype or allelic frequencies in a control population in order to determine whether particular haplotypes or alleles occur at significantly higher frequency amongst affected compared with control samples. Statistical tests such as a chi-square test are used to determine whether there are differences in allele or genotype distributions.

Regardless of whether linkage analysis or association analysis is used in step 210, the results of each QTL analysis am stored in QTL results database 82 (FIG. 1; FIG. 2, step 212). For each quantitative trait 84 (expression statistic set 304), QTL results database 82 comprises all positions 86 in the genome of the organism that were tested for linkage to the quantitative trait 84. Positions 86 are obtained from genetic marker map 70. Further, for each position 86, genotype data 68 provides the genotype at position 86, for each organism in the plurality of organisms under study. For each such position 86 analyzed by QTL analysis, a statistical measure (e.g., statistical score 88), such as the maximum lod score between the position and the quantitative trait 84, is listed. There is a lod score for the entire population tested as well as individual lod scores for each of the individuals under study. Thus, data structure 82 comprises all the positions in the genome of the organism of interest that are genetically linked to each quantitative trait 84 tested.

Figure 4:
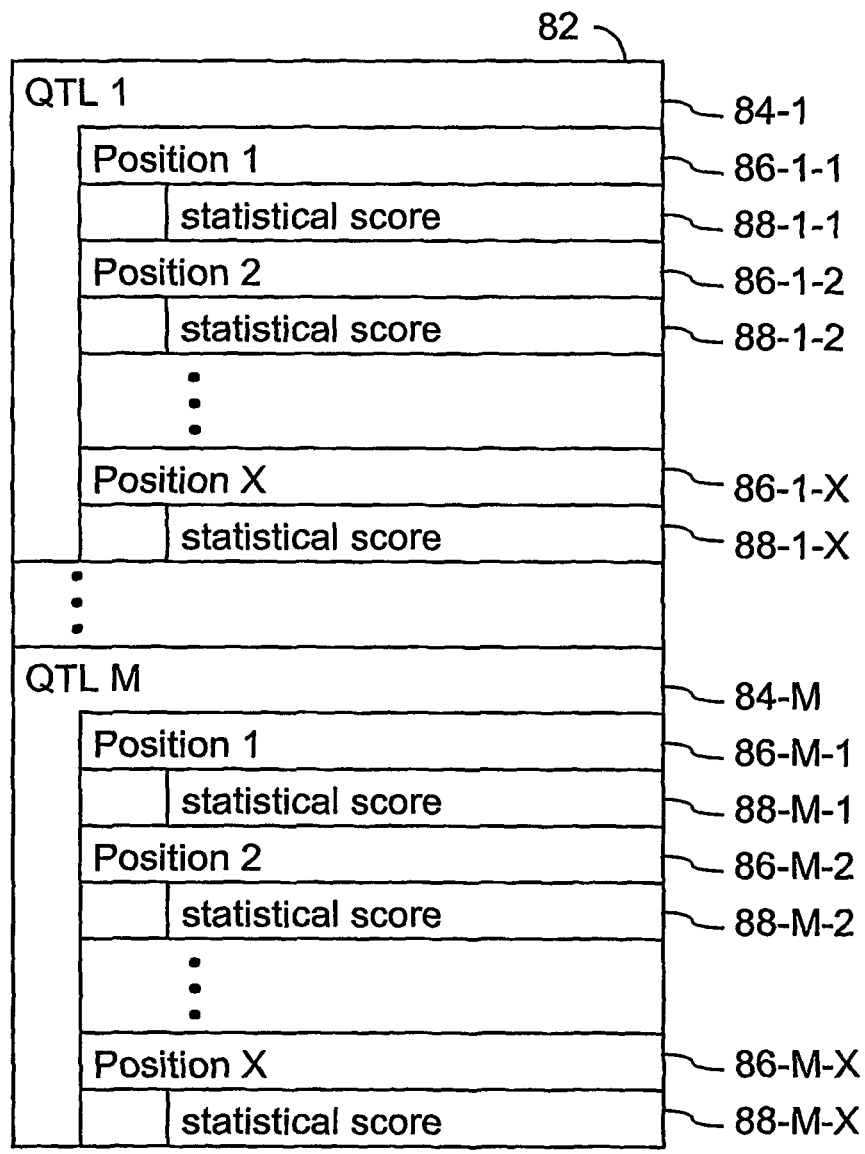
FIG. 4 illustrates quantitative trait locus results database in accordance with one embodiment of the present invention.

FIG. 4 provides a more detailed illustration of QTL results database 82. Each statistical score 88 (e.g. lod score) measures the degree to which a given position 86 is linked to the corresponding quantitative trait 84 (e.g., expression statistic set 304). The set of statistical scores 88 for any given quantitative trait 84 may be considered (may be viewed as) a QTL vector. Thus, in some embodiments of the present invention, a QTL vector is created for each gene tested in the chromosome of the organism studied. Each element of the QTL vector is a statistical score (e.g., lod score) at a different position in the genome of the species under study. In some embodiments in which gene expression/cellular constituent data 44 is collected from multiple tissue samples in each organism under study, a separate QTL vector is created for each tissue type from which data 44 was collected. For example, consider the case in which data 44 (FIG. 1) is collected from two different tissues types from each organism 46 under study. In such embodiments, two QTL vectors are created for each cellular constituent (e.g., gene, protein) 48 tested. The first QTL vector for a given gene cellular constituent 48 corresponds to one tissue type sample and the second QTL vector for the given gene/cellular constituent 48 corresponds to the second tissue type sampled. Thus, in effect, in some embodiments in which data from multiple tissues is collected, the data from each tissue type is treated for purposes of processing steps 202 through 220 as if the data were collected from independent organism. However, in step 222, the data from multiple tissues types is optionally compared in order to determine the affect that tissue type has on the linkage analysis. Methods that incorporated data from multiple tissues types are described in more detail in conjunction with step 222 below as well as Section 5.6, below.

In same embodiments, a QTL vector is created for each gene tested in the entire genome of the organism studied. The QTL vector comprises the statistical score at each position tested by the quantitative trait locus (QTL) analysis corresponding to the gene. In addition to QTL vectors, gene expression vectors may be constructed from transformed gene expression data 44. Each gene expression vector represents the transfoned expression level of the gene from each organism in the population of interest. Thus, any given gene expression vector comprises the transformed expression level of the gene from a plurality of different organisms in the population of interest.

With the QTL vectors generated, the next step of the present invention involves the generation of QTL interaction maps from the QTL vectors (FIG. 2, step 214). To generate QTL interaction maps, the QTL vectors are clustered into groups of QTLs based on the strength of interaction between the QTL vectors. In some embodiments of the present invention, QTL interaction maps are generated by clustering module 92. In embodiments in which QTL vectors generated from several different tissue types, the QTL vectors from the various tissue types are clustered since gene expression in one tissue may drive expression in another tissue. In some requirements, QTL representing diverse tissues types are clustered. In one embodiment of the present invention, agglomerative hierarchical clustering is applied to the QTL vectors. In this clustering, similarity is determined using Pearson correlation coefficients between the QTL vectors pairs. In other embodiments, the clustering of the QTL data from each QTL analysis comprises application of a hierarchical clustering technique application of a k-means technique, application of a fuzzy k-means technique, application of Jarvis-Patrick clustering technique, application of a self-organizing map or application of a neural network. In some embodiments, the hierarchical clustering technique is an agglomerative clustering procedure. In other embodiments, the agglomerative clustering procedure is a nearest-neighbor algorithm, a farthest-neighbor algorithm, an average linkage algorithm, a centroid algorithm, or a sum-of-squares algorithm. In still other embodiments, the hierarchical clustering technique is a divisive clustering procedure. Illustrative clustering techniques that may be used to cluster QTL vectors are described in Section 5.5, infra.

Since each QTL corresponds to a given gene in a plurality of genes in the population of interest, QTL interaction maps provide information on which QTLs are linked. Such information may be combined with gene expression data to help elucidate biological pathways that affect complex traits. In one embodiment of the present invention, a gene expression cluster map is constructed from gene expression statistics (FIG. 2, step 216). A plurality of gene expression vectors are created. Bach gene expression vector in the plurality of gene expression vectors represents the expression level, activity, or degree of modification of a particular cellular constituent, such as a gene or gene product, in a plurality of cellular constituents in the population of interest. Then, a plurality of correlation coefficients is computed. Bach correlation coefficient in the plurality of correlation coefficients is computed between a gene expression vector pair in the plurality of gene expression vectors. Then, the plurality of gene expression vectors are clustered based on the plurality of correlation coefficients in order to form the gene expression cluster map. In one embodiment of the present invention, each correlation coefficient in the plurality of correlation coefficients is a Pearson correlation coefficient. In another embodiment of the present invention, clustering of the plurality of gene expression vectors comprises application of a hierarchical clustering technique, application of a k-means technique, application of a fuzzy k-means technique, application of a self-organizing map or application of a neural network. In one embodiment of the present invention, the hierarchical clustering technique is an agglomerative clustering procedure such as a nearest-neighbor algorithm, a farthest-neighbor algorithm, an average linkage algorithm, a centroid algorithm, or a sum of squares algorithm. In another embodiment of the invention, the hierarchical clustering technique is a divisive clustering procedure. Illustrative clustering techniques that may be used to cluster the gene expression vectors are described in Section 5.5, infra.

At this stage, the QTL interaction map provides information on individual genes in gene expression clusters found in gene expression cluster maps. Gene expression clusters found in gene expression cluster maps may be considered to be in the same candidate pathway group. QTL interactions can be used to identify those genes that are "closer" together in a candidate pathway group than other genes. Furthermore, genes in gene expression clusters found in a gene expression map that are not at all genetically interacting may be downweighted with respect to those genes that are genetically interacting. In this way, QTL interaction maps help to refine candidate pathway groups that are identified in gene expression cluster maps. However, the QTL interaction map does not provide the actual topology of the pathway. An illustrative topology of a biological pathway may be, for example, that gene A is upstream of gene B. Another drawback of the QTL interaction map is that the map may include false positives. For example, a cluster within the QTL interaction map may include genes that do not interact genetically. To shed light on the topology of biological pathways associated with complex diseases, as well as to eliminate false positive genes, processing steps 216 through 222 are performed, as described in detail below.

In one embodiment of the present invention, the next step involves mapping all probes used to generate gene expression data 44 (FIG. 1) to their respective genomic and genetic coordinates. This information aids in establishing the potential for a given gene to correspond directly to a particular QTL (Le., that a gene actually was the QTL).

In one embodiment of the present invention, clusters of QTL interactions from the QTL interaction maps and clusters of gene expression interactions from the gene expression cluster maps are represented in cluster database 94 (FIG. 1; FIG. 2, step 218). Cluster database 94 is used to identify the patterns that feed a multivariate QTL analyses. In addition to the QTL and gene expression cluster information, the physical locations of the QTLs and genes are represented in cluster database 94.

In some embodiments of the present invention, a gene is identified in the QTL interaction map by filtering the QTL interaction map in order to obtain a candidate pathway group. In one embodiment, this filtering comprises selecting those QTL for the candidate pathway group that interact most strongly with another QTL in the QTL interaction map. In some embodiments, the QTL that interact most strongly with another QTL in the QTL interaction map are all QTL, represented in the QTL interaction map, that share a correlation coefficient with another QTL in the QTL interaction map that is higher than 75%, 85%, or 95% of all correlation coefficients computed between QTLs in the QTL interaction map.

In one embodiment of the present invention, cluster database 94 is used to associate a gene with a trait. Typically, the trait of interest is a complex trait. Representative traits include, but are not limited to, disease status, tumor stage, triglyceride levels, blood pressure, and/or diagnostic test results. In this embodiment, the QTL interaction map and/or data stored in cluster database 94 is filtered in order to obtain a candidate pathway group (FIG. 2, step 220). This filtering comprises identifying a QTL in the candidate pathway group in the gene expression cluster map. In one example in accordance with this embodiment of the present invention, the QTL interaction map is filtered by identifying groups of QTL within the QTL interaction map that interact closely with one another. The genes associated with each QTL in the groups of QTL that interact closely with one another in a QTL interaction map are considered candidate pathway groups. In some embodiments, the filtering further comprises looking up the genes in each of the candidate pathway groups in the gene expression interaction map. Of interest is whether the genes in the candidate pathway groups identified in the QTL interaction map interact closely with each other in the gene expression interaction map. In some embodiments, the topology of pathway groups (e.g., biological pathways) can be determined by identifying genes that colocalize with one of their QTL, as described in Section 6.7.1, infra.

In general, patterns of interest may be identified by querying cluster database 94. Such groups may be identified by filtering on strength of QTL-QTL interactions, which identifies those genes that are most strongly genetically interacting, and then combining this information with genes that are the most tightly clustered within these groups. The size of these groups is easily adjusted by scaling the threshold parameters used to identify QTL and/or genes that are interacting. Such groups could themselves be considered putative pathway groups. However, another approach is to fit the groups to genetic models in order to test whether the genes are actually part of the same pathway.

In one embodiment in accordance with the present invention, the degree to which each QTL making up a candidate pathway group belongs with other QTLs within the candidate pathway group is tested by fitting a multivariate statistical model to the candidate pathway group (FIG. 2; step 222). Multivariate statistical models have the capability of simultaneously considering multiple quantitative traits, modeling epistatic interactions between the QTL and testing other interesting variations that test whether genes in a candidate pathway group belong to the same or related biological pathway. Specific tests can be done to determine if the traits under consideration are actually controlled by the same QTL (pleiotropic effects) or if they are independent.

Importantly, multivariate statistical analysis can be used to simultaneously consider multiple traits at the same time. This is of use to determine whether the traits are genetically linked to each other. Accordingly, in such embodiments, a cluster of QTL found in the QTL interaction map produced in step 214 and verified using the gene expression cluster map produced in step 216 can be subjected to multivariate statistical analysis in order to determine whether the QTL are all genetically linked. Such an analysis may determine that some of the QTL in the cluster found in the QTL interaction map are, in fact, linked whereas other QTL in the cluster a not linked.

Multivariate statistical analysis can also be used to study the same trait from multiple tissues. Multivariate statistical analysis of the same trait from multiple tissues can be used to determine whether genetic linkage varies on a tissue specific basis. Such techniques are of use, for example, in instances where a complex disease has a tissue specific etiology. In some instance, multivariate analysis can be used to simultaneously consider multiple traits from multiple tissues. Exemplary multivariate statistical models that may be used in accordance with the present invention are found in Section 5.6, infra.

The results of the multivariate QTL analysis are used to "validate" the candidate pathway groups. These validated groups are then represented in a database and made available for the final stage of analysis, which involves reconstructing the pathway. At this stage the database comprises genes that are under some kind of common genetic control, interact to some degree at the expression level, and that have been shown to be strongly enough interacting at these different levels to perhaps belong to the same or related pathways. Thus, in some instance, the association of a gene with a trait exhibited by one or more organisms in a population of interest results in the placement of the gene in a pathway group that comprises genes that are part of the same or related pathway.

The final step involves an attempt to partially reconstruct the pathways within a given pathway group. For each candidate pathway group, the interactions between the representative QTL vectors and gene expression vectors can be examined. Furthermore, QTL and probe location information can be used to begin to piece together causal pathways. In addition, graphical models can be fit to the data using the interaction strengths, QTL overlap and physical location information accumulated from the previous steps to weight and direct the edges that link genes in a candidate pathway group. Application of such graphical models is used to determine which genes are more closely linked in a candidate pathway group and therefore suggests models for constraining the topology of the pathway. Thus, such models test whether it is more likely that the candidate pathway proceeds in a particular direction, given the evidence provided by the interactions, QTL overlaps, and physical QTL/probe location. The end result of this process, after starting with expression data, genotype data, marker data, and clinical trait data, is a set of pathway groups consisting of genes that are supported as being part of the same or related pathway, and causal information that indicates the exact relationship of genes in the pathway (or of a partial set of genes in the pathway).

5.2. Sources of Marker Data

Several forms of genetic markers that are used to construct marker map 78 are known in the art. A common genetic marker is single nucleotide polymorphisms (SNPs). SNPs occur approximately once every 600 base pairs in the genome. See, for example, Kruglyak and Nickerson, 2001, Nature Genetics 27, 235. The present invention contemplates the use of genotypic databases such as SNP databases as a source of genetic markers. Alleles making up blocks of such SNPs in close physical proximity are often correlated, resulting in reduced genetic variability and defining a limited number of "SNP haplotypes" each of which reflects descent from a single ancient ancestral chromosome. See Fullerton et at., 2000, Am. J. Hum. Genet. 67, 881. Such haplotype structure is useful in selecting appropriate genetic variants for analysis. Patil et al. found that a very dense set of SNPs is required to capture all the common haplotype information. Once common haplotype information is available, it can be used to identify much smaller subsets of SNPs useful for comprehensive whole-genome studies. See Patil et al., 2001, Science 294, 1719-1723.

Other suitable sources of genetic markers include databases that have various types of gene expression data from platform types such as spotted microarray (microarray), high-density oligonucleotide array (HDA), hybridization filter (filter) and serial analysis of gene expression (SAGE) data. Another example of a genetic database that can be used is a DNA methylation database. For details on a representative DNA methylation database, see Granau et al., in press, MethDB- a public database for DNA methylation data, *Nucleic Acids Research*; or the URL http://genome.imb-jena.de/public.html.

In one embodiment of the present invention, a set of genetic markers is derived from any type of genetic database that tracks variations in the genome of an organism of interest Information that is typically represented in such databases is a collection of locus within the genome of the organism of interest. For each locus, strains for which genetic variation information is available are represented. For each represented strain, variation information is provided. Variation information is any type of genetic variation information. Representative genetic variation information includes, but is not limited to, single nucleotide polymorphisms, restriction fragment length polymorphisms, microsatellite markers, restriction fragment length polymorphisms, and short tandem repeats. Therefore, suitable genotypic databases include, but are not limited to:

| Genetic variation type | Uniform resource location |
|---|---|
| SNP | http://bioinfo.pal.roche.com/usuka_bioinformatics/cgi-bin/msnp/msnp.pl |
| SNP | http://snp.cshl.org/ |
| SNP | http://www.ibc.wustl.edu/SNP/ |
| SNP | http://www-genome.wi.mit.edu/SNP/mouse/ |
| SNP | http://www.ncbi.nlm.nih.gov/SNP/ |
| Microsatellite markers | http://www.informatics.jax.org/searches/polymorphism_form.shtml |
| Restriction fragment length polymorphisms | http://www.informatics.jax.org/searches/polymorphism_form.shtml |
| Short tandem repeats | http://www.cidr.jhmi.edu/mouse/mmset.html |
| Sequence length polymorphisms | http://mcbio.med.buffalo.edu/mit.html |
| DNA methylation database | http://genome.imb-jena.de/public.html |
| Short tandem-repeat polymorphisms | Broman et al., 1998, Comprehensive human genetic maps: Individual and sex-specific variation in recombination, American Journal of Human Genetics 63, 861-869 |
| Microsatellite markers | Kong et al., 2002, A high-resolution recombination map of the human genome, Nat Genet 31, 241-247 |

In addition, the genetic variations used by the methods of the present invention may involve differences in the expression levels of genes rather than actual identified variations in the composition of the genome of the organism of interest. Therefore, genotypic databases within the scope of the present invention include a wide array of expression profile databases such as the one found at the URL: http://www.ncbi.nlm.nih.gov/geo/.

Another form of genetic marker that may be used to construct marker map 78 is restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction endonuclease. Generally, the resulting fragments are separated according to size and hybridized with a probe; single copy probes are preferred. As a result, restriction fragments from homologous chromosomes are revealed. Differences in fragment size among alleles represent an RFLP (see, for example, Helentjeris et al., 1985, Plant Mol. Bio. 5:109-118, and U.S. Pat. No. 5,324,631). Another form of genetic marker that may be used to construct marker map 78 is random amplified polymorphic DNA (RAPD). The phrase "random amplified polymorphic DNA" or "RAPD" refers to the amplification product of the distance between DNA sequences homologous to a single oligonucleotide primer appearing on different sites on opposite strands of DNA. Mutations or rearrangements at or between binding sites will result in polymorphisms as detected by the presence or absence of amplification product (see, for example, Welsh and McClelland, 1990, Nucleic Acids Res. 18:7213-7218; Hu and Quiros, 1991, Plant Cell Rep. 10:505-511). Yet another form of genetic marker map that may be used to construct marker map 78 is amplified fragment length polymorphism (AFLP). AFLP technology refers to a process that is designed to generate large numbers of randomly distributed molecular markers (see, for example, European Patent Application No. 0534858 A1). Still another form of genetic marker map that may be used to construct marker map 78 is "simple sequence repeats" or "SSRs". SSRs are di-, tri- or tetra-nucleotide tandem repeats within a genome. The repeat region may vary in length between genotypes while the DNA flanking the repeat is conserved such that the same primers will work in a plurality of genotypes. A polymorphism between two genotypes represents repeats of different lengths between the two flanking conserved DNA sequences (see, for example, Akagi et al., 1996, Theor. Appl. Genet. 93, 1071-1077; Bligh et al., 1995, Euphytica 86:83-85; Struss et al., 1998, Theor. Appl. Genet. 97, 308-315; Wu et al., 1993, Mol. Gen. Genet. 241, 225-235; and U.S. Pat. No. 5,075,217). SSR are also known as satellites or microsatellites.

As described above, many genetic markers suitable for use with the present invention are publicly available. Those skilled in the art can also readily prepare suitable markers. For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., 7-21.

5.3. Exemplary Normalization Routines

A number of different normalization protocols may be used by normalization module 72 to normalize gene expression data 44. Some such normalization protocols are described in this section. Typically, the normalization comprises normalizing the expression level measurement of each gene in a plurality of genes that is expressed by an organism in a population of interest. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score)

for intensity IV for probe i (hybridization probe, protein, or other binding entity) and spot j is computed as:

$$Z\text{-score}^{ij} = (I_{ij} - mnI_i)/sdI_i,$$

and $$Z\text{diff}_j(x,y) = Z\text{-score}_{xj} - Z\text{-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (medianI$_i$) for all of the spots in that sample. Thus, upon normalization by the median intensity normalization method, the raw intensity I$_{ij}$ for probe i and spot j, has the value Im$_{ij}$ where $$Im_{ij} = (I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (medianI$_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity I$_{ij}$ for probe i and spot j, has the value Im$_{ij}$ where, $$Im_{ij} = \log(1.0 + (I_{ij}/\text{median}I_i)).$$

Yet another normalization protocol is the Z-score standard deviation log of intensity protocol. In this protocol, raw expression intensities are normalized by the mean log intensity (mnLI$_i$) and standard deviation log intensity (sdLI$_i$). For microarray data, the mean log intensity and the standard deviation log intensity is computed for the log of raw intensity of control genes. Then, the Z-score intensity ZlogS$_{ij}$ for probe i and spot j is:

$$Z \log S_{ij} = (\log(I_{ij}) - mnLI_i)/sdLI_i.$$

Still another normalization protocol is the Z-score mean absolute deviation of log intensity protocol. In this protocol, raw expression intensities are normalized by the Z-score of the log intensity using the equation (log(intensity)-mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity mnLI$_i$ and the mean absolute deviation log intensity madLI$_j$ are computed for the log of raw intensity of control genes. Then, the Z-score intensity ZlogA$_{ij}$ for probe i and spot j is:

$$Z \log A_{ij} = (\log(I_{ij}) - mnLI_i)/madLI_i.$$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. (see Section 5.8.1.5.). In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5-medianBkgdCy5)/(medianCy3-medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

5.4. Logarithm of the Odds Scores

Denoting the joint probability of inheriting all genotypes P(g), and the joint probability of all observed data x (trait and marker species) conditional on genotypes P(x|g), the likelihood L for a set of data is $$L = \Sigma P(g) P(x|g)$$

where the summation is over all the possible joint genotypes g (trait and marker) for all pedigree members. What is unknown in this likelihood is the recombination fraction θ, on which P(g) depends.

The recombination fraction θ is the probability that two loci will recombine during meioses. The recombination fraction θ is correlated with the distance between two loci. By definition, the genetic distance is defined to be infinity between the loci on different chromosomes (nonsyntenic loci), and for such unlinked loci, θ=0.5. For linked loci on the same chromosome (syntenic loci), θ<0.5, and the genetic distance is a monotonic function of θ. See, e.g., Ott, 1985, *Analysis of Human Genetic Linkage*, first edition, Baltimore, Md., John Hopkins University Press. The essence of linkage analysis described in Section 5.13, is to estimate the recombination fraction θ and to test whether θ=0.5. When the position of one locus in the genome is known, genetic linkage can be exploited to obtain an estimate of the chromosomal position of a second locus relative to the first locus. In linkage analysis described in Section 5.2, linkage analysis is used to map the unknown location of genes predisposing to various quantitative phenotypes relative to a large number of marker loci in a genetic map. In the ideal situation, where recombinant and nonrecombinant meioses can be counted unambiguously, θ is estimated by the frequency of recombinant meioses in a large sample of meioses. If two loci are linked, then the number of nonrecombinant meioses N is expected to be larger than the number of recombinant meioses R. The recombination fraction between the new locus and each marker can be estimated as:

$$\hat{\theta} = \frac{R}{N+R}$$

The likelihood of interest is:

$$L = \Sigma P(g|\theta) P(x|g)$$

and inferences are based about a test recombination fraction θ an the likelihood ratio Λ=L(θ)/L(½) or, equivalently, its logarithm.

Thus, in a typical clinical genetics study, the likelihood of the trait and a single marker is computed over one or more relevant pedigrees. This likelihood function L(θ) is a function of the recombination fraction θ between the trait (e.g., classical trait or quantitative trait) and the marker locus. The standardized loglikelihood $Z(\theta)\text{-}\log_{10}[(L(\theta)/L(\frac{1}{2})]$ is referred to as a lod score. Here, "lod" is an abbreviation for "logarithm of the odds." A lod score permits visualization of linkage evidence. As a rule of thumb, in human studies, geneticists provisionally accept linkage if $$Z(\hat{\theta}) \geq 3$$

at its maximum θ on the interval [0,½], where $\hat{\theta}$ represents the maximum θ on the interval. Further, linkage is provisionally rejected at a particular θ if $$Z(\hat{\theta}) \leq -2.$$

However, for complex traits, other rules have been suggested. See, for example, Lander and Kruglyak, 1995, Nature Genetics 11, p. 241.

Acceptance and rejection are treated asymmetrically because, with 22 pairs of human autosomes, it is unlikely that a random marker even falls on the same chromosome as a trait locus. See Lange, 1997, *Mathematical and Statistical Methods for Genetic Analysis*, Springer-Verlag. New York; Olson, 1999, Tutorial in Biostatistics: Genetic Mapping of Complex Traits, *Statistics in Medicine* 18, 2961-2981.

When the value of L is large, the null hypothesis of no linkage, L(½), to a marker locus of known location can be rejected, and the relative location of the locus corresponding to the quantitative trait can be estimated by $\hat{\theta}$. Therefore, lod scores provide a method to calculate linkage distances as well as to estimate the probability that two genes (and/or QTLs) are linked.

Those of skill in the art will appreciate that lod score computation is species dependent. For example, methods for computing the lod score in mouse different from that described in this section. However, methods for computing lod scores are known in the art and the method described in this section is only by way of illustration and not by limitation.

5.5. Clustering Techniques

The subsections below describe exemplary methods for clustering. Such techniques can be used to cluster QTL vectors in order to form QTL interaction maps. The same techniques can be applied to gene expression vectors in order to form gene expression cluster maps. Further, these techniques can be used to perform unsupervised or supervised classification in accordance with processing step 106 and/or step 108 (FIG. 2). In these techniques, QTL vectors, gene expression vectors, or sets of cellular constituent measurements from different organisms in a population are clustered based on the strength of interaction between the data (e.g. QTL vectors, gene expression vectors, or sets of cellular constituents). More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; Backer, 1995, *Computer-Assisted Reasoning in Cluster Analysis*, Prentice Hall, Upper Saddle River, N.J.; and Duda et al., 2001, *Pattern Classification*, John Wiley & Sons, New York, N.Y.

5.5.1. Hierarchical Clustering Techniques

Hierarchical cluster analysis is a statistical method for finding relatively homogenous clusters of elements based on measured characteristics. Consider a sequence of partitions of n samples into c clusters. The first of these is a partition into n clusters, each cluster containing exactly one sample. The next is a partition into n−1 clusters, the next is a partition into n−2, and so an until the $n^{th}$, in which all the samples form one cluster. Level k in the sequence of partitions occurs when c=n−k+1. Thus, level one corresponds to n clusters and level n corresponds to one cluster. Given any two samples x and x*, at some level they will be grouped together in the same cluster. If the sequence has the property that whenever two samples are in the same cluster at level k they remain together at all higher levels, than the sequence is said to be a hierarchical clustering. Duda et al., 2001, *Pattern Classification*, John Wiley & Sons, New York, 2001: 551.

5.5.1.1. Agglomerative Clustering

In some embodiments, the hierarchical clustering technique used to cluster gene analysis vectors is an agglomerative clustering procedure. Agglomerative (bottom-up clustering) procedures start with n singleton clusters and form a sequence of partitions by successively merging clusters. The major steps in agglomerative clustering are contained in the following procedure, where c is the desired number of final clusters, $D_i$ and $D_j$ are clusters, $x_i$ is a gene analysis vector, and there are n such vectors:

```
1  begin initialize c, ĉ ← n, D_i ← {x_i}, i = 1, ..., n
2     do ĉ ← ĉ − 1
3        find nearest clusters, say, D_i and D_j
4        merge D_i and D_j
5     until c = ĉ
6     return c clusters
7  end
```

In this algorithm, the terminology a←b assigns to variable a the new value b. As described, the procedure terminates when the specified number of clusters has been obtained and returns the clusters as a set of points. A key point in this algorithm is how to measure the distance between two clusters $D_i$ and $D_j$. The method used to define the distance between clusters $D_i$ and $D_j$ defines the type of agglomerative clustering technique used. Representative techniques include the nearest-neighbor algorithm, farthest-neighbor algorithm, the average linkage algorithm, the centroid algorithm, and the sum-of-squares algorithm.

Nearest-Neighbor Algorithm.

The nearest-neighbor algorithm uses the following equation to measure the distances between clusters:

$$d\min(Di, Dj) = \min_{\substack{x \in Di \\ x' \in Dj}} \|x - x'\|.$$

This algorithm is also known as the minimum algorithm. Furthermore, if the algorithm is terminated when the distance between nearest clusters exceeds an arbitrary threshold, it is called the single-linkage algorithm. Consider the case in which the data points are nodes of a graph, with edges forming a path between the nodes in the same subset $D_i$. When dmin( ) is used to measure the distance between subsets, the nearest neighbor nodes determine the nearest edges. The merging of $D_i$ and $D_j$ corresponds to adding an edge between the nearest pair of nodes in $D_i$ and $D_j$. Because edges linking clusters always go between distinct clusters, the resulting graph never has any closed loops or circuits; in the terminology of graph theory, this procedure generates a tree. If it is allowed to continue until all of the subsets are linked, the result is a spanning tree. A spanning tree is a tree with a path from any node to any other node. Moreover, it can be shown that the sum of the edge lengths of the resulting tree will not exceed the sum of the edge lengths for any other spanning tree for that set of samples. Thus, with the use of dmin( ) as the distance measure, the agglomerative clustering procedure becomes an algorithm for generating a minimal spanning tree. See Duda et al., id, pp. 553-554.

Farthest-Neighbor Algorithm.

The farthest-neighbor algorithm uses the following equation to measure the distances between clusters:

$$d\max(Di, Dj) = \max_{\substack{x \in Di \\ x' \in Dj}} \|x - x'\|.$$

This algorithm is also known as the maximum algorithm. If the clustering is terminated when the distance between the nearest clusters exceeds an arbitrary threshold, it is called the complete-linkage algorithm. The farthest-neighbor algorithm discourages the growth of elongated clusters. Application of this procedure can be thought of as producing a graph in which the edges connect all of the nodes in a cluster. In the terminology of graph theory, every cluster contains a complete subgraph. The distance between two clusters is terminated by the most distant nodes in the two clusters. When the nearest clusters are merged, the graph is changed by adding edges between every pair of nodes in the two clusters.

Average Linkage Algorithm.

Another agglomerative clustering technique is the average linkage algorithm. The average linkage algorithm uses the following equation to measure the distances between clusters:

$$d_{avg}(Di, Dj) = \frac{1}{n_i n_j} \sum_{x \in Di} \sum_{x' \in Dj} \|x - x'\|.$$

Hierarchical cluster analysis begins by making a pair-wise comparison of all gene analysis vectors in a set of such vectors. After evaluating similarities from all pairs of element in the set, a distance matrix is constructed. In the distance matrix, a pair of vectors with the shortest distance (i.e. most similar values) is selected. Then, when the average linkage algorithm is used, a "node" ("cluster") is constructed by averaging the two vectors. The similarity matrix is updated with the new "node" ("cluster") replacing the two joined elements, and the process is repeated n−1 times until only a single element remains. Consider six elements, A-F having the values:

A{49}, B{8.2}, C{3.0}, D{5.2}, E{8.3}, F{2.3}.

In the first partition, using the average linkage algorithm, one matrix (sol. 1) that could be computed is:

(sol. 1) A {4.9}, B-E{8.25}, C{3.0}, D{5.2}, F{2.3}.

Alternatively, the first partition using the average linkage algorithm could yield the matrix:

(sol 2) A {4.9}, C{3.0}, D{5.2}, E-B{8.25}, F{2.3}.

Assuming that solution 1 was identified in the first partition, the second partition using the average linkage algorithm will yield:

(sol 1-1) A-D{5.05}, B-E{8.25}, C{3.0}, F{2.3} or (sol. 1-2) B-E{8.25}, C{3.0}, D-A{5.05}, F{2.3}.

Assuming that solution 2 was identified in the first partition, the second partition of the average linkage algorithm will yield:

(sol 2-1) A-D{5.05}, C{3.0}, E-B{8.25}, F{2.3} or (sol. 2-2) C{3.0}, D-A{5.05}, E-B{8.25}, F{23}.

Thus, after just two partitions in the average linkage algorithm, there are already four matrices. See Duda et al., Pattern Classification, John Wiley & Sons, New York, 2001, p. 551.

5.5.1.2. Clustering with Pearson Correlation Coefficients

In one embodiment of the present invention, QTL vectors and/or gene expression vectors are clustered using agglomerative hierarchical clustering with Pearson correlation coefficients. In this form of clustering, similarity is determined using Pearson correlation coefficients between the QTL vectors pairs, gene expression pairs, or sets of cellular constituent measurements. Other metrics that can be used, in addition to the Pearson correlation coefficient, include but are not limited to, a Euclidean distance, a squared Euclidean distance, a Euclidean sum of squares, a Manhattan metric, and a squared Pearson correlation coefficient. Such metrics may be computed using SAS (Statistics Analysis Systems Institute, Cary, N.C.) or S-Plus (Statistical Sciences, Inc., Seattle, Wash.).

5.5.1.3. Divisive Clustering

In some embodiments, the hierarchical clustering technique used to cluster QTL vectors and/or gene expression vectors is a divisive clustering procedure. Divisive (top-down clustering) procedures start with all of the samples in one cluster and form the sequence by successfully splitting clusters. Divisive clustering techniques are classified as either a polythetic or a monthetic method. A polythetic approach divides clusters into arbitrary subsets.

5.5.2. K-Means Clustering

In k-means clustering sets of QTL vectors, gee expression vectors, or sets of cellular constituent measurements are randomly assigned to K user specified clusters. The centroid of each cluster is computed by averaging the value of the vectors in each cluster. Then, for each i=1, . . . , N, the distance between vector $x_i$ and each of the cluster centroids is computed. Each vector $x_i$ is then reassigned to the cluster with the closest centroid. Next, the centroid of each affected cluster is recalculated. The process iterates until no more reassignments are made. See Duda et al., 2001, *Pattern Classification*, John Wiley & Sons, New York, N.Y., pp. 526-528. A related approach is the fuzzy k-means clustering algorithm, which is also known as the fuzzy c-means algorithm. In the fuzzy k-means clustering algorithm, the assumption that every QTL vector, gene expression vector, or set of cellular constituent measurements is in exactly one cluster at any given time is relaxed so that every vector (or set) has same graded or "fuzzy" membership in a cluster. See Duda et al., 2001, *Pattern Classification*, John Wiley & Sons, New York, N.Y., pp. 528-530.

5.5.3. Jarvis-Patrick Clustering

Jarvis-Patrick clustering is a nearest-neighbor non-hierarchical clustering method in which a set of objects is partitioned into clusters on the basis of the number of shared nearest-neighbors. In the standard implementation advocated by Jarvis and Patrick, 1973, *IEEE Trans. Comput.*, C-22: 1025-1034, a preprocessing stage identifies the K nearest-neighbors of each object in the dataset. In the subsequent clustering stage, two objects i and j join the same cluster if (i) i is one of the K nearest-neighbors of j, (ii) j is one of the K nearest-neighbors of i, and (iii) i and j have at least $k_{min}$ of their K nearest-neighbors in common, where K and $k_{min}$ are user-defined parameters. The method has been widely applied to clustering chemical structures on the basis of fragment descriptors and has the advantage of being much less computationally demanding than hierarchical methods, and thus more suitable for large databases. Jarvis-Patrick clustering may be performed using the Jarvis-Patrick Clustering Package 3.0 (Barnard Chemical Information, Ltd., Sheffield, United Kingdom).

5.5.4. Neural Networks

A neural network has a layered structure that includes a layer of input units (and the bias) connected by a layer of weights to a layer of output units. In multilayer neural networks, there are input units, hidden units, and output units. In fact, any function from input to output can be implemented as a three-layer network. In such networks, the weights are set based an training patterns and the desired output. One method for supervised training of multilayer neural networks is back-propagation. Back-propagation allows for the calculation of an effective error for each hidden unit, and thus derivation of a learning rule for the input-to-hidden weights of the neural network.

The basic approach to the use of neural networks is to start with an untrained network, present a training pattern to the input layer, and pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood . . . estimation of the weight values in the model defined by the network topology. In batch training, all patterns are presented to the network before learning takes place. Typically, in batch training, several passes are made through the training data. In online training, each pattern is presented once and only once to the net.

5.5.5. Self-Organizing Maps

A self-organizing map is a neural-network that is based on a divisive clustering approach. The aim is to assign genes to a series of partitions on the basis of the similarity of their expression vectors to reference vectors that are defined for each partition. Consider the case in which there are two microarrays from two different experiments. It is possible to build up a two-dimensional construct where every spot corresponds to the expression levels of any given gene in the two experiments. A two-dimensional grid is built, resulting in several partitions of the two-dimensional construct. Next, a gene is randomly picked and the identify of the reference vector (node) closest to the gene picked is determined based on a distance matrix. The reference vector is then adjusted so that it is more similar to the vector of the assigned gene. That means the reference vector is moved one distance unit on the x axis and y-axis and becomes closer to the assigned gene. The other nodes are all adjusted to the assigned gene, but only are moved one half or one-fourth distance unit. This cycle is repeated hundreds of thousands times to converge the reference vector to fixed value and where the grid is stable. At that time, every reference vector is the center of a group of genes. Finally, the genes are mapped to the relevant partitions depending on the reference vector to which they are most similar.

5.6. Multivariate Statistical Models

Using the methods of the present invention, candidate pathway groups are identified from the analysis of QTL interaction map data and gene expression cluster maps. Each candidate pathway group includes a number of genes. The methods of the present invention are advantageous because they filter the potentially thousands of genes in the genome of the population of interest into a few candidate pathway groups using clustering techniques. In a typical case, a candidate pathway group represents a group of genes that tightly cluster in a gene expression cluster map. The genes in a candidate pathway group may also cluster tightly in a QTL interaction map. The QTL interaction map serves as a complementary approach to defining the genes in a candidate pathway group. For example, consider the case in which genes A, B, and C cluster tightly in a gone expression cluster map. Furthermore, genes A, B, C and D cluster tightly in the corresponding QTL interaction map. In this example, analysis of the gene expression cluster map alone suggest that genes A, B, and C form a candidate pathway group. However, analysis of both the QTL interaction map and the gene expression cluster map suggest that the candidate pathway group comprises genes A, B, C, and D.

Once candidate pathway groups have been identified, multivariate statistical techniques can be used to determine whether each of the genes in the candidate pathway group affect a particular trait, such as a complex disease trait. The form of multivariate statistical analysis used in some embodiments of the present invention is dependent upon on the type of genotype and/or pedigree data that is available.

Typically, more pedigree data is available in cases where the population to be studied is plants or animals. In such instances, the multivariate statistical models such as those of Jiang and Zeng 1995, *Nature Genetic* 140, pp. 1111-1127, as well as the techniques implemented in QTL Cartographer (Basten and Zeng, 1994, Zmap-a QTL cartographer, *Proceeding of the 5th World Congress on Genetics Applied to Livestock Production: Computing Strategies and Software* 22, Smith et al. eds., pp. 65-66, The Organizing Committee, 5th World Congress on Genetics Applied to Livestock Production, Guelph, Ontario, Canada; Basten et al., 2001, *QTL Cartographer, Version* 1.15, Department of Statistics, North Carolina State University, Raleigh, N.C. In addition, marker regression (joint mapping, marker-difference regression, MDR), interval mapping with marked cofactors, and composite interval mapping can be used. See, for example, Lynch & Walsh, 1998, *Genetic and Analysis of Quantitative Traits*, Sinsuer Associates, Inc., Sunderland, Mass.

Jiang and Zeng have developed a multiple-trait extension to composite interval mapping (CIM). See, for example, Jiang and Zang, 1995, Genetics 140, p. 1111. CIM refers to the general approach of adding marker cofactors to an otherwise standard interval analysis (e.g., QTL detection using linear models or via maximum likelihood). CIM handles multiple QTLs by incorporating mutlilocus marker information from organisms by modifying standard interval mapping to include additional markers as cofactors for analysis. See, for example, Jansen, 1993, Genetics 135, p. 205; Zeng, 1994, Genetics 136, p. 1457. The multiple-trait extension to CIM developed by Jiang and Zeng provides a framework for testing the candidate pathway groups that are constructed using the methods of the present invention in cases where the genes in these candidate pathway groups link to the same genetic region. The methods of Jiang and Zeng allow for the determination as to whether expression values (for the genes in the candidate pathway group) linking to the same region are controlled by a single gene pleiotropy) or by two closely linked genes. If the methods of Jiang and Zeng suggest that multiple genes are actually controlled by closely linked loci (closely linked genes), then there is not support that the genes linking to the same region are in the same pathway. Moreover, the components (hierarchy) of a pathway can be deduced by testing subsets of the pathway group to see which genes have an underlying pleiotropic relationship with respect to other genes. Further, the definition of the candidate pathway group can be refined by eliminating specific genes in the candidate pathway group that do not have a pleiotropic relationship with other genes in the candidate pathway group. The idea is to determine which of the genes linking to given region, have other genes linking to their physical location, indicating the order for hierarchy and control.

Presently, the practical limits are that no more than ten genes can be handled at once using multivariate methods such as the Jiang and Zeng methods. Theoretically, the number of genes is limited by the amount of data available to fit the model, but the particular limitation is that the optimization techniques are not effective for greater than 10 dimensions. However, in some embodiments, more than 10 genes can be handled at once by implementing dimensionality reductions techniques (like principal components).

For human genotype and pedigree data, methods described in Allison, 1998, Multiple Phenotype Modeling in Gene-Mapping Studies of Quantitative Traits: Power Advantages, *Am J. Hum. Genetics* 63, pp. 1190-1201, are used, including, but not limited to, those of Amos et al., 1990, *Am J. Hum. Genetics* 47, pp. 247-254.

In some embodiments, gene expression data 44 is collected for multiple tissue types. In such instances, multivariate analysis can be used to determine the true nature of a complex disease. Multivariate techniques used in this embodiment of the invention are described, in part, in Williams et al., 1999, *Am J Hum Genet* 65(4): 1134-47; Amos et al., 1990, *Am J Hum Genet* 47(2): 247-54, and Jiang and Zeng, 1995, *Nature Genetics* 140:1111-1127.

Asthma provides one example of a complex disease that can be studied using expression data from multiple tissue types. Asthma is expected to, in part, be influenced by immune system response not only in lungs but also in blood. By measuring expression of genes in the lung and in blood, the following model could be used to dissect the shared genetic effect in a model system, e.g. an F2 mouse cross:

$$y_{j1} = \alpha_1 + b_1 x_j + d_1 z_j + e_{j1}$$
$$y_{j2} = \alpha_2 + b_2 x_j + d_2 z_j + e_{j2}$$
$$\vdots$$
$$y_{jm} = \alpha_m + b_m x_j + d_m z_j + e_{jm}$$

where, for individual j and a putative QTL:

$y_{j1}, \ldots, y_{jm}$ consists of asthma relevant phenotypes, expression data for gene expression in the lung and expression data for gene expression in blood;

$x_j$ is the number of QTL alleles from a specific parental line;

$z_j$ is 1 if the individual is heterozygous for the QTL and 0 otherwise;

$\alpha_i$ represents the mean for phenotype i;

$b_i$ and $d_i$ represent the additive and dominance effects of the QTL on phenotype i; and $e_{ij}$ is the residual error for individual j and phenotype i.

It is typically assumed that the residuals are uncorrelated between individuals, and the correlation between residuals within an individual are modeled as $\text{Cov}(e_{jk}, e_{jl}) = \rho_{kl} \sigma_k \sigma_l$. Assuming a multivariate normal distribution for the residuals, likelihood analysis can be used to test for joint linkage of a QTL to the trait vector and to test for pleiotropic effects versus close linkage. With such information, it would be possible to detect a QTL that influences susceptibility to asthma through causing changes in gene expression for a set of genes expressed in blood and for a set of potentially overlapping, genes expressed in lung. Such multivariate analyses in accordance with the present invention, combined with high quality phenotypic data that includes expression data across multiple tissues, allows for improved detection of those genes truly influencing susceptibility to complex diseases.

5.7. Analytic Kit Implementation

In a preferred embodiment, the methods of this invention can be implemented by use of kits for determining the responses or state of a biological sample. Such kits contain microarrays, such as those described in Subsections below. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In a particular embodiment, the probes contained in the kits of this invention are nucleic acids capable of hybridizing specifically to nucleic acid sequences derived from RNA species in cells collected from an organism of interest.

In a preferred embodiment, a kit of the invention also contains one or more databases described above and in FIG.

1, encoded on computer readable medium, and/or an access authorization to use the databases described above from a remote networked computer.

In another preferred embodiment, a kit of the invention further contains software capable of being loaded into the memory of a computer system such as the one described supra, and illustrated in FIG. 1. The software contained in the kit of this invention, is essentially identical to the software described above in conjunction with FIG. 1. Alternative kits for implementing the analytic methods of this invention will be apparent to one of skill in the art and are intended to be comprehended within the accompanying claims.

5.8. Transcriptional State Measurements

This section provides some exemplary methods for measuring the expression level of genes, which are one type of cellular constituent. One of skill in the art will appreciate that this invention is not limited to the following specific methods for measuring the expression level of genes in each organism in a plurality of organisms.

5.8.1. Transcript Assay Using Microarrays

The techniques described in this section are particularly useful for the determination of the expression state or the transcriptional state of a cell or cell type or any other cell sample by monitoring expression profiles. These techniques include the provision of polynucleotide probe arrays that may be used to provide simultaneous determination of the expression levels of a plurality of genes. These technique farther provide methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundances or abundance rations. Preferably, measurement of the expression profile is made by hybridization to transcript arrays, which are described in this subsection. In one embodiment, "transcript arrays" or "profiling arrays" are used. Transcript arrays can be employed for analyzing the expression profile in a cell sample and especially for measuring the expression profile of a cell sample of a particular tissue type or developmental state or exposed to a drug of interest.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. Microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number or very small number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used can include one or more test probes, each of which has a polynucleotide sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (i.e., the sequence) of each probe can be determined from its position on the array (i.e., on the support or surface). In some embodiments, the arrays are ordered arrays.

Preferably, the density of probes on a microarray or a set of microarrays is about 100 different (i.e., non-identical) probes per 1 cm$^2$ or higher. More preferably, a microarray used in the methods of the invention will have at least 550 probes per 1 cm$^2$, at least 1,000 probes per 1 cm$^2$, at least 1,500 probes per 1 cm$^2$ or at least 2,000 probes per 1 cm$^2$. In a particularly preferred embodiment, the microarray is a high density array, preferably having a density of at least about 2,500 different probes per 1 cm$^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (e.g., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sit s for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different sequence segments of the gene or the exon. Such polynucleotides are preferably of the length of 15 to 200 bases, more preferably of the length of 20 to 100 bases, most preferably 40-60 bases. Each probe sequence may also comprise linker sequences in addition to the sequence that is complementary to its target sequence. As used herein, a linker sequence is a sequence between the sequence that is complementary to its target sequence and the surface of support. For example, in preferred embodiments, the profiling arrays of the invention comprise one probe specific to each target gene or exon. However, if desired, the profiling arrays may contain at least 2, 5, 10, 100, or 1000 or more probes specific to some target genes or exons. For example, the array may contain probes tiled across the sequence of the longest mRNA isoform of a gene at single base stops.

In specific embodiments of the invention, when an exon has alternative spliced variants, a set of polynucleotide probes of successive overlapping sequences, i.e., tiled sequences, across the genomic region containing the longest variant of an exon can be included in the axon profiling arrays. The set of polynucleotide probes can comprise successive overlapping sequences at steps of a predetermined base intervals, e.g. at steps of 1, 5, or 10 base intervals, apan, or are tiled across, the mRNA containing the longest variant. Such sets of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In some cases, the probe set contains variant junction probes specifically hybridizable to each of all different splice junction sequences of the axon. In other cases, the probe set contains exon specific probes specifically hybridizable to the common sequences in all different variants of the exon, and/or variant junction probes specifically hybridizable to the different splice junction sequences of the exon.

In some cases, an exon is represented in the exon profiling arrays by a probe comprising a polynucleotide that is complementary to the full length exon. In such instances, an exon is represented by a single binding site on the profiling arrays. In some preferred cases, an axon is represented by one or more binding sites on the profiling arrays, each of the binding sites comprising a probe with a polynucleotide sequence that is complementary to an RNA fragment that is a substantial portion of the target axon. The lengths of such probes are normally between about 15-600 bases, preferably between about 20-200 bases, more preferably between about 30-100 bases, and most preferably between about 40-80 bases. The average length of an exon is about 200 bases (see, e.g., Lewin, Genes V, Oxford University Press, Oxford, 1994). A probe of length of about 40-80 allows more specific binding of the axon than a probe of shorter length, thereby increasing the specificity of the probe to the target exon. For certain genes, one or more targeted exons may have sequence lengths less than about 40-80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced axon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target axon that is shorter than the desired probe length is involved in alternative splicing, probes comprising flanking sequences in different alternatively spliced mRNA as are designed so that expression level of the exon expressed in different alternatively spliced mRNAs can be measured.

In some instances, when alternative splicing pathways and/or axon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same act of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes at also encompassed.

Preferably, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau at a, 1996, *Science* 274: 546-567). In contrast, the human genome is estimated to contain approximately 30,000 to 130,000 genes (see Crollius et al., 2000, *Nature Genetics* 25:235-238; Ewing et al., 2000, *Nature Genetics* 25:232-234). Genome sequences for other organisms, including but not limited to *Drosophila, C. elegans*, plants, e.g., rice and *Arabidopsis*, and mammas, e.g., mouse and human, are also completed or nearly completed. Thus, in preferred embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In one embodiment, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drag-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA Microarray, *Science* 270:467-470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual,* 2nd ed., Vol. 1-3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level s measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve.

In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at about 2, 4, 6, 10, 12, 16, 18, 48 or 72 times as long as the first hybridization time.

5.8.1.1. Preparing Probes for Microarrays

As noted above, the "probe" to which a particular polynucleotide molecule, such as an exon, specifically hybridizes according to the invention is a complementary polynucleotide sequence. Preferably one or more probes are selected for each target exon. For example, when a minimum number of probes are to be used for the detection of an axon, the probes normally comprise nucleotide sequences greater than about 40 bases in length. Alternatively, when a large set of redundant probes is to be used for an exon, the probes normally comprise nucleotide sequences of about 40-60 bases. The probes can also comprise sequences complementary to full length exons. The lengths of exons can range from less than 50 bases to more than 200 bases. Therefore, when a probe length longer than axon is to be used, it is preferable to augment the exon sequence with adjacent constitutively spliced exon sequences such that the probe sequence is complementary to the continuous mRNA fragment that contains the target axon. This will allow comparable hybridization stringency among the probes of an axon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each axon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymeras chain reaction (PCR) amplification of axon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Method and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-209).

5.8.1.2. Attaching Nucleic Acids to the Solid Surface

Performed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al., 1995, *Science* 270:467-470. This method is especially useful for preparing microarrays of cDNA (See also, DeRisi et al., 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). Wham these methods are used, oligonucleotides (e.g., 60-mars) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small array will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111-123).

5.8.1.3. Target Polynucleotide Molecules

Target polynucleotides which may be analyzed by the methods and compositions of the invention include RNA molecules such as, but by no means limited to, messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, et. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian calls, the target polynucleotides may correspond to particular fragments of a gene transcript. For example, the target polynucleotides may correspond to different aeons of the same gene, e.g., so that different splice variants of that gene may be detected and/or analyzed.

In preferred embodiments, the target polynucleotide to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-seine RNA. Anti-sense RNAs or cRNAs are then transcribed from the second strand of the double-stranded cDNAs using an RNA polymerase (see, e.g., U.S. Pat. Nos. 5,891,636, 5,716,785; 5,545,522 and 6,132,997; see also, U.S. Pat. No. 6,271,002, and U.S. Provisional Patent Application Ser. No. 60/253,641, filed on Nov. 28, 2000, by Ziman et al.) Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, inmminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOB"), N,N,N',N'-tetramethyl-6-carboxy-rhodamine ("TAMRA"), 6'carboxy-X-rhodamine ("ROX"), HBX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.8.1.4. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena at al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B.V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.8.1.5. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an axon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no affect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

When fluorescently labeled probes are used, the fluorescence missions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an axon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of differences of an order of about 1.5 fold to about 3-fold.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.8.2. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primer (see e.g., European Patent O 534858 A1, filed Sep. 24, 1992, by Zabeau et al.), or methods selecting restriction fragments with sites closest to a defined mRNA and (sea e.g., Prashar et al., 1996, *Proc. Natl. Acad. Sci. USA* 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA and (se, e.g., Velculescu, 1995, *Science* 270:484-487).

5.9. Measurement of Other Aspects of the Biological State

In various embodiments of the present invention, aspects of the biological state other than the transcriptional state, such as the translational state, the activity state, or mixed aspects can be measured. Thus, in such embodiments, gene expression data 44 (FIG. 1) may include translational state measurements or even protein expression measurements. In fact, in some embodiments, rather than using gene expression interaction maps based on gene expression, protein expression interaction maps based on protein expression maps are used. Details of embodiments in which aspects of the biological state other than the transcriptional state are described in this section.

5.10. Translational State Measurements

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Nat. Acad. Sci. USA* 93:1440-1445; Sagliocco et al., 1996, *Yeast* 12:1519-1533; Lander, 1996, *Science* 274:536-539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

5.11. Measuring Other Aspects of the Biological State

Even though methods of this invention are illustrated by embodiments involving gene expression or translation, the methods of the invention are applicable to any cellular constituent that can be monitored. For example, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are derived from cellular phenotypic techniques. One such cellular phenotypic technique uses cell respiration as a universal reporter. In one embodiment, 96-well microtiter plate, in which each well contains its own unique chemistry is provided. Each unique chemistry is designed to test a particular phenotype. Cells from the organism of interest are pipetted into each well. If the cells exhibits the appropriate phenotype, they will respire and actively reduce a tetrazolium dye, forming a strong purple color. A weak phenotype results in a lighter color. No color means that the cells don't have the specific phenotype. Color changes can be recorded as often as several times each hour. During one incubation, more than 5,000 phenotypes can be tested. See, for example, Bochner et al., 2001, Genome Research 11, p. 1246.

In some embodiments of the present invention, cellular constituent measurements are derived from cellular phenotypic techniques. One such cellular phenotypic technique uses cell respiration as a universal reporter. In one embodiment, 96-well microtiter plates, in which each well contains its own unique chemistry is provided. Bach unique chemistry is designed to test a particular phenotype. Cells from the organism 46 (FIG. 1) of interest are pipetted into each well. If the calls exhibit the appropriate phenotype, they will respire and actively reduce a tetrazolium dye, forming a strong purple color. A week phenotype results in a lighter color. No color means that the cells don't have the specific phenotype. Color changes may be recorded as often as several times each hour. During one incubation, more than 5,000 phenotypes can be tested. See, for example, Bochner et al., 2001, Genome Research 11, 1246-55.

In some embodiments of the present invention, the cellular constituents that are measured (gene expression data 44) are metabolites. Metabolites include, but are not limited to, amino acids, metals, soluble sugars, sugar phosphates, and complex carbohydrates. Such metabolites may be measured, for example, at the whole-cell level using methods such as pyrolysis mass spectrometry (Irwin, 1982, *Analytical Pyrolysis: A Comprehensive Guide*, Marcel Dekker, New York; Meuzelaar et al., 1982, *Pyrolysis Mass Spectrometry of Recent and Fossil Biomaterials*, Elsevier, Amsterdam), fourier-transform infrared spectrometry (Griffiths and de Haseth, 1986, *Fourier transform infrared spectrometry*, John Wiley, New York; Helm et al., 1991, J. Gen. Microbiol. 137, 69-79; Naumann et al., 1991, Nature 351, 81-82; Naumann et al., 1991, In. *Modern techniques for rapid microbiological analysis*, 43-96, Nelson, W. H., ad, VCH Publishers, New York), Raman spectrometry, gas chromatography-mass spectroscopy (GC-MS) (Fiehn et al., 2000, Nature Biotechnology 18, 1157-1161, capillary electrophoresis (CE)/MS, high pressure liquid chromatography I mass spectroscopy (HPLC/MS), as well as liquid chromatography (LC)-Electrospray and cap-LC-tandem-electrospray mass spectrometries. Such methods can be combined with established chemometric methods that make use of artificial neural networks and genetic programming in order to discriminate between closely related samples.

5.12. Exemplary Diseases

As discussed supra, the present invention provides an apparatus and method for associating a gene with a trait exhibited by one or more organisms in a plurality of organisms of a single species. In some instances, the gene is associated with the trait by identifying a biological pathway in which the gene product participates. In some embodiments of the present invention, the trait of interest is a complex trait, such as a disease, e.g., a human disease. Exemplary diseases include asthma, ataxia telangiectasia (Jaspers and Bootsma, 1982, *Proc. Natl. Acad. Sci. U.S.A.* 79: 2641), bipolar disorder, common cancers, common late-onset Alzheimer's disease, diabetes, heart disease, hereditary early-onset Alzheimer's disease (George-Hyslop et al., 1990, *Nature* 347: 194), hereditary nonpolyposis colon cancer, hypertension, infection, maturity-onset diabetes of the young (Barbosa et al., 1976, *Diabete Metab.* 2: 160), mellitus, migraine, nonalcoholic fatty liver (NAFL) (Younossi, et al., 2002, Hepatology 35, 746-752), nonalcoholic steatohepatitis (NASH) (James & Day, 1998, *J. Hepatol.* 29: 495-501), non-insulin-dependent diabetes mellitus, obesity, polycystic kidney disease (Reeders et al., 1987, *Human Genetics* 76: 348), psoriases, schizophrenia, steatohepatitis and xeroderma pigmentosum (De Weerd-Kastelein, *Nat. New Biol.* 238: 80). Genetic heterogeneity hampers genetic mapping, because a chromosomal region may cosegregate with a disease in some families but not in others.

5.13. Linkage Analysis

This section describes a number of standard quantitative trait locus (QTL) linkage analysis algorithms that can be used in various embodiments of processing step 210 (FIG. 2) and/or processing step 1910 (FIG. 19). Such linkage analysis is also sometimes referred to as QTL analysis. See, for example, Lynch and Walsch, 1998, *Genetics and Analysis of Quantitative Traits*, Sinauer Associates, Sunderland, Mass. The primary aim of linkage analysis is to determine whether there exist pieces of the genome that are passed down through each of several families with multiple afflicted organisms in a pattern that is consistent with a particular inheritance model and that is unlikely to occur by chance alone. In other words, the purpose of these algorithms is to identify a loci (e.g., a QTL) for a phenotypic trait exhibited by one or more organisms 46. A QTL is a region of a genome of a species that is responsible for a percentage of variation in a phenotypic trait in the species under study.

The recombination fraction can be denoted by $\theta$ and is bounded between 0 and 0.5. If $\theta=0.5$ for two loci, then alleles at the two loci are transmitted independently with half of the gametes being recombinant, for the two loci, and half parental. In this case, the loci are unlinked. If $\theta<0.5$, then alleles are not transmitted independently, and the two loci are linked. The extreme scenario is when $\theta=0$, so that the two loci are completely linked, and there will be no recombination between the two loci during meiosis, i.e. all gametes are parental. Linkage analysis tests whether a marker locus, of known location, is linked to a locus of unknown location, that influences the phenotype under study. In other words, a QTL is identified by comparing genotypes of organisms in a group to a phenotype exhibited by the group using pedigree data. The genotype of each organism at each marker in a plurality of markers in a genetic map produced by marker genotypic data is compared to a given phenotype of each organism. The genetic map is created by placing genetic markers in genetic (linear) map order so that the positional relationships between markers are understood. The information gained from knowing the relationships between markers that is provided by a marker map provides the setting for addressing the relationship between QTL effect and QTL location.

In some embodiments of the present invention, linkage analysis is based on any of the QTL detection methods disclosed or referenced in Lynch and Walsch, 1998, *Genetics and Analysis of Quantitative Traits*, Sinauer Associates, Inc., Sunderland, Mass.

5.13.1. Phenotypic Data Used

It will be appreciated that the present invention provides no limitation on the type of phenotypic data that can be used to perform QTL analysis. The phenotypic data can, for example, represent a series of measurements for a quantifiable phenotypic trait in a collection of organisms. Such quantifiable phenotypic traits can include, for example, tail length, life span, eye color, size and weight. Alternatively, the phenotypic data can be in a binary form that tracks the absence or presence of some phenotypic trait. As an example, a "1" can indicate that a particular species of the organism of interest possesses a given phenotypic trait and a "0" can indicate that a particular species of the organism of interest lacks the phenotypic trait. The phenotypic trait can be any form of biological data that is representative of the phenotype of each organism in the population under study. In some embodiments, the phenotypic traits are quantified and are often referred to as quantitative phenotypes.

5.13.2. Genotypic Data Used

In order to provide the necessary genotypic data for linkage analysis, the genotype of each marker in the genetic marker map is determined for each organism in a population under study. In essence, the genotypic information comprises information about polymorphism at each marker location in the genome of the population under study. Representative forms of polymorphisms used to construct genotypic information include, but are not limited to, single nucleotide polymorphisms, microsatellite markers, restriction fragment length polymorphisms, short tandem repeats, sequence length polymorphisms, aid DNA methylation patterns.

Linkage analyses use the genetic map derived from marker genotypic data as the framework for location of QTL for any given quantitative trait. In some embodiments, the intervals that are defined by ordered pairs of markers are searched in increments (for example, 2 cM), and statistical methods are used to test whether a QTL is likely to be present at the location within the interval. In one embodiment, linkage analysis statistically tests for a single QTL at each increment across the ordered markers in a genetic map. The results of the tests are expressed as lod scores, which compares the evaluation of the likelihood function under a null hypothesis (no QTL) with the alternative hypothesis (QTL at the testing position) for the purpose of locating probable QTL. More details on lod scores are found in Section 5.4, as well as in Lander and Schork, 1994, Science 265, p. 2037-2048. Interval mapping searches through the ordered genetic markers in a systematic, linear (one-dimensional) fashion, testing the same null hypothesis and using the same form of likelihood at each increment.

5.13.3. Pedigree Data Used

Linkage analysis requires pedigree data for organisms in the population under study in order to statistically model the segregation of markers. The various forms of linkage analysis can be categorized by the type of population used to generate the pedigree data (inbred versus outbred).

Some forms of linkage analysis use pedigree data for populations that originate from inbred parental lines. The resulting $F_1$ lines will tend to be heterozygous at all markers and QTL. From the $F_1$ population, crosses are made. Exemplary crosses include backcrosses, $F_2$ intercrosses, $F_t$ populations (formed by randomly mating $F_1$s for t−1 generations), $F_{2:3}$ design ($F_2$ individuals are genotyped and then selfed), Design III ($F_2$ from two inbred lines are backcrossed to both parental lines). Thus, in some embodiments of the present invention, organisms represent a population, such as an $F_2$ population, and pedigree data for the $F_2$ population is known. This pedigree data is used to compute logarithm of the odds (lod) scores, as discussed in further detail below.

For many organisms, including humans, manipulatable inbred lines are not available and outbred populations must be used to perform linkage analysis. Linkage analysis using outbred populations detect QTL responsible for within-population variation whereas linkage analysis using inbred populations detect QTLs responsible for fixed differences between lines, or even different species. Using within-population variation (outbred population), as opposed to fixed differences between populations (inbred population) results in decreased power in QTL detection. With inbred lines, all $F_1$ parents have identical genotypes (including the same linkage phase), so all individuals are informative, and linkage disequilibrium is maximized. As with inbred lines, a variety of designs have been proposed for obtaining samples with linkage disequilibrium required for linkage analysis. Typically, collections of relatives are relied upon.

The major difference between QTL analysis using inbred-line crosses versus outbred populations is that while the parents in the former are genetically uniform, parents in the latter are genetically variable. This distinction has several consequences. First, only a fraction of the parents from an outbred population are informative. For a parent to provide linkage information, it must be heterozygous at both a marker and a linked QTL, as only in this situation can a marker-trait association be generated in the progeny. Only a fraction of random parents from an outbred population are such double heterozygotes. With inbred lines, $F_1$'s are heterozygous at all loci that differ between the crossed lines, so that all parents are folly informative. Second, there are only two alleles segregating at any locus in an inbred-line cross design, while outbred populations can be segregating any number of alleles. Finally, in an outbred population, individuals can differ in marker-QTL linkage phase, so that an M-bearing gamete might by associated with QTL allele Q in one parent, and with q in another. Thus, with outbred populations, marker-trait associations might be examined separately for each parent. With inbred-line crosses, all $F_1$ parents have identical genotypes (including linkage phase), so one can average marker-trait associations over all off-spring, regardless of their parents. See Lynch and Walsh, *Genetics and Analysis of Quantitative Traits*, Sinauer Associates, Sunderland, Mass.

5.13.4. Model Free Versus Model Based Linkage Analysis

Linkage analyses can generally be divided into two classes: model-based linkage analysis and model-free linkage analysis. Model-based linkage analysis assumes a model for the mode of inheritance whereas model-free linkage analysis does not assume a mode of inheritance. Model-free linkage analyses are also known as allele-sharing methods and non-parametric linkage methods. Model-based linkage analyses are also known as "maximum likelihood" and "lod score" methods. Either form of linkage analysis can be used in the present invention.

Model-based linkage analysis is most often used for dichotomous traits and requires assumptions for the trait model. These assumptions include the disease allele frequency and penetrance function. For a disease trait, particularly those of interest to public health, the true underlying model is complex and unknown, so that these procedures are not applicable. The other form of linkage analysis (model-free linkage analysis) makes use of allele-sharing. Allele-sharing methods rely on the idea that relatives with similar phenotypes should have similar genotypes at a marker locus if and only if the marker is linked to the locus of interest. Linkage analyses are able to localize the locus of interest to a specific region of a chromosome, but the scope of resolution is typically limited to no less than 5 cM or roughly 5000 kb. For more information on model-based and model-free linkage analysis, see Olson et al., 1999, Statistics in Medicine 18, p. 2961-2981; Lander and Schork 1994, Science 265, p. 2037; and Elston, 1998, Genetic Epidemiology 15, p. 565, as well as the sections below.

5.13.5. Known Programs for Performing Linkage Analysis

Many known programs can be used to perform linkage analysis in accordance with this aspect of the invention. One such program is MapMaker/QTL, which is the companion program to MapMaker and is the original QTL mapping software. MapMaker/QTL analyzes $F_2$ or backcross data using standard interval mapping. Another such program is QTL Cartographer, which performs single-marker regression, interval mapping (Lander and Botstein, Id.), multiple interval mapping and composite interval mapping (Zeng, 1993, PNAS 90: 10972-10976; and Zeng, 1994, Genetics 136: 1457-1468). QTL Cartographer permits analysis from $F_2$ or backcross population. QTL Cartographer is available from http://statgen.ncsu.edu/qtlcart/cartographer.html (North Carolina State University). Another program that can be used by processing step 114 is Qgene, which performs QTL mapping by either single-marker regression or interval regression (Martinez and Curnow 1994 Heredity 73:198-206). Using Qgene, eleven different population types (all derived from inbreeding) can be analyzed. Qgene is available from http://www.qgene.org/. Yet another program is MapQTL, which conducts standard interval mapping (Lander and Botstein, Id.), multiple QTL mapping (MQM) (Jansen, 1993, Genetics 135: 205-211; Jansen, 1994, Genetics 138: 871-881), and nonparametric mapping (Kruskal-Wallis rank sum test). MapQTL can analyze a variety of pedigree types including outbred pedigrees (cross pollinators). MapQTL is available from Plant Research International, Plant Research International, P.O. Box 16, 6700 AA Wageningen, The Netherlands; http://www.plant.wageningen-ur.nl/default.asp?sction=products). Yet another program that may be used in some embodiments of processing step 210 is Map Manager QT, which is a QTL mapping program (Manly and Olson, 1999, Mamm Genome 10: 327-334). Map Manager QT conducts single-marker regression analysis, regression-based simple interval mapping (Haley and Knott, 1992, Heredity 69, 315-324), composite interval mapping (Zeng 1993, PNAS 90: 10972-10976), and permutation tests. A description of Map Manager QT is provided by the reference Manly and Olson, 1999, Overview of QTL mapping software and introduction to Map Manager QT, Mammalian Genome 10: 327-334.

Yet another program that may be used to perform linkage analysis is MultiCross QTL, which maps QTL from crosses originating from inbred lines. MultiCross QTL uses a linear regression-model approach and handles different methods such as interval mapping, all-marker mapping, and multiple QTL mapping with cofactors. The program can handle a wide variety of simple mapping populations for inbred and outbred species. MultiCross QTL is available from Unité de Biométrie et Intelligence Artificelle, INRA, 31326 Castanet Tolosan, France.

Still another program that can be used to perform linkage analysis is QTL Café. The program can analyze most populations derived from pure line crosses such as $F_2$ crosses, backcrosses, recombinant inbred lines, and doubled haploid lines. QTL Café incorporates a Java implementation of Haley & Knotts' flanking marker regression as well as Marker regression, and can handle multiple QTLs. The program allows three types of QTL analysis single marker ANOVA, marker regression (Kearsey and Hyne, 1994, Theor. Appl. Genet., 89: 698-702), and interval mapping by regression, (Haley and Knott, 1992, Heredity 69: 315-324). QTL Café is available from http://web.bham.ac.uk/g.g.seaton/.

Yet another program that can be used to perform linkage analysis is MAPL, which performs QTL analysis by either interval mapping (Hayashi and Ukai, 1994, Theor. Appl. Gent. 87:1021-1027) or analysis of variance. Different population types including $F_2$, back-cross, recombinant inbreds derived from $F_2$ or back-cross after a given generations of selfing can be analyzed. Automatic grouping and ordering of numerous markers by metric multidimensional scaling is possible. MAPL is available from the Institute of Statistical Genetics on Internet (ISGI), Yasuo, UKAI, http://web-.bham.ac.uk/g.g.seaton/.

Another program that can be used for linkage analysis is R/qtl. This program provides an interactive environment for mapping QTL in experimental crosses. R/qtl makes uses of the hidden Markov model (HMM) technology for dealing with missing genotype data. R/qtl has implemented many HMM algorithms, with allowance for the presence of genotyping errors, for backcrosses, intercrosses, and phase-known four-way crosses. R/qtl includes facilities for estimating genetic maps, identifying genotyping errors, and performing single-QTL genome scans and two-QTL two-dimensional genome scans, by interval mapping with Haley-Knott regression, and multiple imputation. R/qtl is available from Karl W. Broman, Johns Hopkins University, http://biosun01.biostat.jhsaph.edu/~kbroman/qtl/.

Those of skill in the art will appreciate that there are several other programs and algorithms that can be used in the steps of the methods of the present invention where quantitative genetic analysis is needed, and all such programs and algorithms are within the scope of the present invention.

5.13.6. Model-Based Parametric Linkage Analysis

In model-based linkage analysis, (also termed "LOD score" methods or parametric methods), the details of a traits mode of inheritance is being modeled. Typically, particular values of the allele frequencies and the penetrance function are specified.

5.13.6.1. Interval Mapping Via Maximum Likelihood/Inbred Population

In one embodiment of the present invention, linkage analysis comprises QTL interval mapping in accordance with algorithms derived from those first proposed by Lander and Botstein, 1989, "Mapping Mendelian factors underlying quantitative traits using RFLP linkage maps," Genetics 121: 185-199. The principle behind interval mapping is to test a model for th presence of a QTL at many positions between two mapped marker loci. The model is fit, and its goodness is tested using a technique such as the maximum likelihood method. Maximum likelihood theory assumes that when a QTL is located between two biallelic markers, the genotypes (i.e. AABB, AAbb, aaBB, aabb for doubled haploid progeny) each contain mixtures of quantitative trait locus (QTL) genotypes. Maximum likelihood involves searching for QTL parameters that give the best approximation for quantitative trait distributions that are observed for each marker class. Models are evaluated by computing the likelihood of the observed distributions with and without fitting a QTL effect.

In some embodiments of the present invention, linkage analysis is performed using the algorithm of Lander, as implemented in program such as GeneHunter. See, for example, Kruglyak et al., 1996, Parametric and Nonparametric Linkage Analysis: A Unified Multipoint Approach, American Journal of Human Genetics 58:1347-1363, Kruglyak and Lander, 1998, Journal of Computational Biology 5:1-7; Kruglyak, 1996, American Journal of Human Genetics 58, 1347-1363. In such embodiments, unlimited markers may be used but pedigree size is constrained due to computational limitations. In other embodiments, the MENDEL software package is used. (See http://bimas.dcrt.nih.gov/linkage/ltools.html). In such embodiments, the size of the pedigree can be unlimited but the number of markers that can be used in constrained due to computational limitations. The techniques described in this Section typically require an inbred population.

5.13.6.2. Interval Mapping Using Linear Regression/Inbred Population

In some embodiments of the present invention, interval mapping is based on regression methodology and gives estimates of QTL position and effect that are similar to those given by the maximum likelihood method. Since the QTL genotypes are unknown in mapping based on regression methodology, genotypes are replaced by probabilities estimated using genotypes at the nearest flanking markers or all linked markers. See, e.g., Haley and Knott, 1992, Heredity 69, 315-324; and Jiang and Zeng, 1997, Genetica 101:47-58. The techniques described in this Section typically require an inbred population.

5.13.7. Model-Free Nonparametric Linkage Analysis

Model-based linkage analysis (classical linkage analysis) calculates a lod score that represents the chance that a given loci in the genome is genetically linked to a trait, assuming a specific mode of inheritance for the trait Namely the allele frequencies and penetrance values are included as parameters and are subsequently estimated. In the case of complex diseases, it is often difficult to model with any certainty all the causes of familial aggregation. In other words, when the trait exhibits non-mendelian segregation it can be difficult to obtain reliable estimates of penetrance values, including phenocopy risks, and the allele frequency of the disease mutation. Indeed it can be the case that different mutations at different loci have different kinds of effect on susceptibility, some major and some minor, some dominant and some recessive. If different modes of transmission are operative in different families, or if different loci interact in the same family, then no one transmission model may be appropriate. It is conceivable that if the transmission model for a linkage analysis is specified incorrectly the results produced from it will not be valid nor interpretable.

As a result of the difficulties described above, a variety of methods have been developed to test for linkage without the need to specify values for the parameters defining the transmission model, and these methods are termed model-free linkage analyses (meaning that they can be applied without regard to the true transmission model). Such methods are based on the premise that relatives who are similar with respect to the phenotype of interest will be similar at a marker locus, sharing identical marker alleles, only if a locus underlying the phenotype is linked to the marker.

Model-free linkage analyses (allele-sharing methods) are not based on constructing a model, but rather on rejecting a model. Specifically, one tries to prove that the inheritance pattern of a chromosomal region is not consistent with random Mendelian segregation by showing that affected relatives inherit identical copies of the region more often then expected by chance. Affected relatives should show excess allele sharing in regions linked to the QTL even in the presence of incomplete penetrance, phenocopy, genetic heterogeneity, and high-frequency disease alleles.

5.13.7.1. Identical by Descent-Affected Pedigree Member (IBD-APM) Analysis/Outbred Population In one embodiment, nonparametric linkage analysis involves studying affected relatives 46 (FIG. 1) in a pedigree 310 to see how often a particular copy of a chromosomal region is shared identical-by descent (IBD), that is, is inherited from a common ancestor within the pedigree. The frequency of IBD sharing at a locus can then be compared with random expectation. An identity-by-descent affected-pedigree-member (IBD-APM) statistic can be defined as:

$$T(s) = \sum_{i,j} x_{ij}(s).$$

where $x_{ij}(s)$ is the number of copies shared IBD at position s along a chromosome, and where the sum is taken over all distinct pairs (i,j) of affected relatives 46 in a pedigree 310. The results from multiple families can be combined in a weighted sum T(s). Assuming random segregation, T(s) tends to a normal distribution with a mean $\mu$ and a variance a that can be calculated on the basis of the kinship coefficients of the relatives compared. See, for example, Blackwelder and Elston, 1985, Genet. Epidemiol. 2, p. 85; Whittemore and Halpern, 1994, Biometrics 50, p. 118; Weeks and Lange, 1988, Am. J. Hum. Genet. 42, p. 315; and Elston, 1998, Genetic Epidemiology 15, p. 565. Deviation from random segregation is detected when the statistic $(T-\mu)/\sigma$ exceeds a critical threshold. The techniques in this section typically use an outbred population.

5.13.7.2. Affected SIB Pair Analysis/Outbred Population

Affected sib pair analysis is one form of IBD-APM analysis (Section 5.13.7.1). For example, two sibs can show IBD sharing for zero, one, or two copies of any locus (with a 25%-50%-25% distribution expected under random segregation). If both parents are available, the data can be partitioned into separate IBD sharing for the maternal and paternal chromosome (zero or one copy, with a 50%-50% distribution expected under random segregation). In either case, excess allele sharing can be measured with a $\chi^2$ test. In the ASP approach, a large number of small pedigrees (affected siblings and their parents) are used. DNA samples we collected from each organism and genotyped using a large collection of markers (e.g., microsatellites, SNPs). Then a check for functional polymorphism is performed. See, for example, Suarez et al., 1978, Ann. Hum. Gent. 42, p. 87; Weitkamp, 1981, N. Engl. J. Med. 305, p. 1301; Knapp et al., 1994, Hum. Hered. 44, p. 37; Holmans, 1993, Am. J. Hum. Genet. 52, p. 362; Rich et at, 1991, Diabetologica 34, p. 350; Owerbach and Gabbay, 1994, Am. J. Hum. Genet. 54, p. 909; and Berrettini et al., Proc. Natl. Acid. Sci. USA 91, p. 5918. For more information on Sib pair analysis, see Hamer et al., 1993, Science 261, p. 321.

In some embodiments, ASP statistics that test whether affected siblings pairs have a mean proportion of marker genes identical-by-descent that is >0.50 were computed. See, for example, Blackwelder and Elston, 1985, Genet. Epidemiol. 2, p. 85. In some embodiments, such statistics are computed using the SIBPAL program of the SAGE package. See, for example, Tran et al. 1991, (SIB-PAL) *Sib-pair linkage program* (Elston, New Orleans), Version 2.5. These statistics are computed on all possible affected pairs. In some embodiments the number of degrees of freedom of the t test is set at the number of independent affected pairs (defined per sibship as the number of affected individuals minus 1) in the sample instead of the number of all possible pairs. See, for example, Suarez and Eerdewegh, 1984, Am. J. Med. Genet. 18, p. 135. The techniques in this section typically use an outbred population.

5.13.7.3. Identical by State-Affected Pedigree Member (IBS-APM) Analysis/Outbred Population In some instances, it is not possible to tell whether two relatives inherited a chromosomal region IBD, but only whether they have the same alleles at genetic markers in the region, that is, are identical by state (IBS). IBD can be inferred from IBS when a dense collection of highly polymorphic markers has been examined, but the early stages of genetic analysis can involve sparser maps with less informative markers so that IBD status can not be determined exactly. Various methods are available to handle situations in which IBD cannot be inferred from IBS. One method infers IBD sharing on the basis of the marker data (expected identity by descent affected-pedigree-member; IBD-APM). See, for example, Suarez et al., 1978, Ann. Hum. Genet. 42, p. 87; and Amos et al., 1990, Am J. Hum. Genet. 47, p. 842. Another method uses a statistic that is based explicitly on IBS sharing (an IBS-APM method). See, for example, Weeks and Lange, 1988, Am J. Hum. Genet. 42, p. 315; Lange, 1986, Am. J. Hum. Genet. 39, p. 148; Jeunemaitre et al., 1992, Cell 71, p. 169; and Pericak-Vance et al., 1991, Am. J. Hum. Genet. 48, p. 1034.

In one embodiment the IBS-APM techniques of Weeks and Lange, 1988, Am J. Hum. Genet. 42, p. 315; and Weeks and Lange, 1992, Am. J. Hum. Genet. 50, p. 859 are used. Such techniques use marker information of affected individuals to test whether the affected persons within a pedigree are more similar to each other at the marker locus than would be expected by chance. In some embodiments, the marker similarity is measured in terms of identity by state. In some embodiments, the APM method uses a marker allele frequency weighting function, $f(p)$, where p is the allele frequency, and the APM test statistics are presented separately for each of three different weighting functions, $f(p)=1$, $f(p)=1/\sqrt{p}$, and $f(p)=1/p$. Whereas the second and third functions render the sharing of a rare allele among affected persons a more significant event, the first weighting function uses the allele frequencies only in calculation of the expected degree of marker allele sharing. The third function, $f(p)=1/p$, can lead (more frequently than the first two) to a non-normal distribution of the test statistic. The second function is a reasonable compromise for generating a normal distribution of the test statistic while incorporating an allele frequency function. In some instances, the APM test statistics are sensitive to marker locus and allele frequency mispecification. See, for example, Babron, t al, 1993, Genet. Epidemiol. 10, p. 389. In some embodiments, allele frequencies are estimated from the pedigree data using the method of Boehnke, 1991, Am J. Hum. Genet. 48, p. 22, or by studying alleles. See, also, for example, Berrettini et al., 1994, Proc. Natl. Acad. Sci. USA 91, p. 5918.

In some embodiments, the significance of the APM test statistics is calculated from the theoretical (normal) distribution of the statistic. In addition, numerous replicates (e.g., 10,000) of these data, assuming independent inheritance of marker alleles and disease (i.e., no linkage), are simulated to assess the probability of observing the actual results (or a more extreme statistic) by chance. This probability is the empirical P value. Each replicate is generated by simulating an unlinked marker segregating through the actual pedigrees. An APM statistic is generated by analyzing the simulated data set exactly as the actual data at is analyzed. The rank of the observed statistic in the distribution of the simulated statistics determines the empirical P value. The techniques in this section typically use an outbred population.

5.13.7.4. Quantitative Traits

Model-free linkage analysis can also be applied to quantitative traits. An approach proposed by Haseman and Elston, 1972, Behav. Genet. 2, p. 3, is based on the notion that the phenotypic similarity between two relatives should be correlated with the number of alleles shared at a trait-causing locus. Formally, one performs regression analysis of the squared difference $\Delta^2$ in a trait between two relatives and the number x of alleles shared IBD at a locus. The approach can be suitably generalized to other relatives (Blackwelder and Elston, 1982, Commun. Stat. Theor. Methods 11, p. 449) and multivariate phenotypes (Amos et al., 1986, Genet. Epidemiol. 3, p. 255). See also, Marsh et al., 1994, Science 264, p. 1152, and Morrison et al., 1994, Nature 367, p. 284; Amos, 1994, Am. J. Hum Genet. 54, p. 535; and Elston, Am J. Hum. Genet. 63, p. 931.

5.14. Association Analysis

This section describes a number of association tests that can be used in the present invention. Association studies can be done with samples of pedigrees or samples of unrelated individuals. Further, association studies can be done for a dichotomous trait (e.g., disease) or a quantitative trait. See, for example, Nepom and Ehrlich, 1991, Annu. Rev. Immunol. 9, p. 493; Strittmatter and Roses, 1996, Annu. Rev. Neurosci. 19, p. 53; Vooberg et al., 1994, Lancet 343, p. 1535; Zoller et al., Lancet 343, p. 1536; Bennett et al., 1995, Nature Genet. 9, p. 284; Grant et al., 1996, Nature Genet. 14, p. 205; and Smith et al., 1997, Science 277, p. 959. As such, association studies test whether a disease and an allele show correlated occurrence across the population, whereas linkage studies determine whether there is correlated transmission within pedigrees.

Whereas linkage analysis involves the pattern of transmission of gametes from one generation to the next, association is a property of the population of gametes. Association exists between alleles at two loci if the frequency, with which they occur within the same gamete, is different from the product of the allele frequencies. If this association occurs between two linked loci, then utilizing the association will allow for fine localization, since the strength of association is in large part due to historical recombinations rather than recombination within a few generations of a family. In the simplest scenario, association arises when a mutation, which causes disease, occurs at a locus at some time, $t_0$. At that time, the disease mutation occurs on a specific genetic background composed of the alleles at all other loci; thus, the disease mutation is completely associated with the alleles of this background. As time progresses, recombination occurs between the disease locus and all other loci causing the association to diminish. Loci that are closer to the disease locus will generally have higher levels of association, with association rapidly dropping off for markers further away. The reliance of association on evolutionary history can provide localization to a region as small as 50-75 kb. Association is also called linkage disequilibrium. Association (linkage disequilibrium) can exist between alleles at two loci without the loci being linked.

Two forms of association analysis are discussed in the sections below, population based association analysis and family based association analysis. More generally, those of skill in the art with appreciate that there are several different forms of association analysis, and all such forms of association analysis can be used in steps of the present invention that require the use of quantitative genetic analysis.

In some embodiments, whole genome association studies are performed in accordance with the present invention. Two methods can be used to perform whole-genome association studies, the "direct-study" approach and the "indirect-study" approach. In the direct-study approach, all common functional variants of a given gene are catalogued and tested directly to determine whether there is an increased prevalence (association) of a particular functional variant in affected individuals within the coding region of the given gene. The "indirect-study" approach uses a very dense marker map that is arrayed across both coding and noncoding regions. A dense panel of polymorphisms (e.g., SNPs) from such a map can be tested in controls to identify associations that narrowly locate the neighborhood of a susceptibility or resistance gene. This strategy is based on the hypothesis that each sequence variant that causes disease must have arisen in a particular individual at some time in the past, so the specific alleles for polymorphisms (haplotype) in the neighborhood of the altered gene in that individual can be inherited in all of his or her descendants. The presence of a recognizable ancestral haplotype therefore becomes an indicator of the disease-associated polymorphism. In actuality, some of the alleles will be in association while others will not due to recombination occurring between the mutation and other polymorphisms.

5.14.1. Population-Based (Model-Free) Association Analysis

In population-based (model-free) association studies, allele frequencies in afflicted organisms are contrasted with allele frequencies in control organisms in order to determine if there is an association between a particular allele and a complex trait. Population-based association studies for dichotomous traits are also referred to as case-control studies. A case-control study is based on the comparison of unrelated affected and unaffected individuals from a population. An allele A at a gene of interest is said to be associated with the phenotype if it occurs at significantly higher frequency among affected compared with control individuals. Statistical significance can be tested by a number a methods, including, but not limited to, logistic regression. Association studies are discussed in Lander, 1996, Science 274, 536; Lander and Schork, 1994, Science 265, 2037; Rich and Merikangas, 1996, Science 273, 1516; and Collins et al., 1997, Science 278, 1533.

As is true for case-control studies generally, confounding is a problem for inferring a causal relationship between a disease and a measured risk factor using population-based association analysis. One approach to deal with confounding is the matched case-control design, where individual controls are matched to cases on potential confounding factors (for example, age and sex) and the matched pairs are then examined individually for the risk factor to see if it occurs more frequently in the case than in its matched control. In some embodiments, cases and controls are ethnically comparable. In other words, homogeneous and randomly mating populations are used in the association analysis. In some embodiments, the family-based association studies described below are used to minimize the effects of confounding due to genetically heterogeneous populations. See, for example, Risch, 2000, Nature 405, p. 847.

5.14.2. Family-Based Association Analysis

Family-based association analysis is used in some embodiments of the invention. In some embodiments, each affected organism is matched with one or more unaffected siblings (see, for example, Curtis, 1997, Ann. Hum. Genet. 61, p. 319) or cousins (see, for example, Witte, et al., 1999, Am J. Epidemiol. 149, p. 693) and analytical techniques for matched case-control studies is used to estimate effects and to test a hypotheses. See, for example, Breslow and Day, 1989, Statistical methods in cancer research I, The analysis of case-control studies 32, Lyon: IARC Scientific Publications. The following subsections describe some forms of family-based association studies. Those of skill in the art will recognize that there are numerous forms of family-based association studies and all such methodologies can be used in the present invention.

5.14.2.1. Haplotype Relative Risk Test

In some embodiments, the haplotype relative risk test is used. In the haplotype relative risk method, all marker alleles compared arise from the same person. The marker alleles that parents transmit to an affected offspring (case alleles) are compared with those that they do not transmit to such an offspring (control alleles). One can also compare transmitted and nontransmitted genotypes. Consider the 2n parents of n affected persons. This population can be classified into a fourfold table according to whether the transmitted allele is a marker allele (M) or some other allele $\overline{M}$ and according to whether the nontransmitted allele is similarly M or $\overline{M}$:

| Transmitted allele | Nontransmitted allele | | |
|---|---|---|---|
| | M | $\overline{M}$ | Total |
| M | a | b | a + b |
| $\overline{M}$ | c | d | c + d |
| | a + c | b + d | 2n = a + b + c + d |

To test for association, a determination is made as to whether the proportion of M alleles that are transmitted, a/(a+b), differs significantly from the proportion of M alleles that are nontransmitted, a/(a+c). One appropriate statistical test for this determination is comparison of $(b-c)^2/(b+c)$ to a chi-square distribution with one degree of freedom when the sample is large.

The row totals for the table above are the numbers of transmitted alleles that are M and $\overline{M}$, while the column totals are the numbers of nontransmitted alleles that are M and $\overline{M}$. These four totals can be put into a fourfold table that classifies the 4n parental alleles, rather than the 2n parents:

| Marker allele | Transmitted | Non-transmitted | Total |
|---|---|---|---|
| M | a + b | a + c | 2a + b + c |
| $\overline{M}$ | c + d | b + d | b + c + 2d |
| Total | 2n | 2n | 4n |

The haplotype relative risk ratio is defined as (a+b)(c+d)(a+c)(c+d). A chi-square distribution using one degree of freedom can be used to determine whether the haplotype relative risk ratio differs significantly from one. See, for example, Rudorfer, et al., 1984, Br. J. Clin. Pharmacol. 17, 433; Mueller and Young, 1997, *Emery's Elements of Medical Genetics*, Kalow ed., p. 169-175, Churchill Livingstone, Edinburgh; and Roses, 2000, Nature 405, p. 857, Bison, 1998, Genetic Epidemilogy, 15, p. 565.

5.14.2.2. Transmission Equilibrium Test

In some embodiments, the transmission equilibrium test (TDT) is used. TDT considers parents who are heterozygous for an allele and evaluates the frequency with which that allele is transmitted to affected offspring. By restriction to heterozygous parents, the TDT differs from other model-free tests for association between specific alleles of a polymorphic marker and a disease locus. The parameters of that locus, genotypes of sampled individuals, linkage phase, and recombination frequency are not specified. Nevertheless, by considering only heterozygous parents, the TDT is specific for association between linked loci.

TDT is a test of linkage and association that is valid in heterogeneous populations. It was originally proposed for data consisting of families ascertained due to the presence of a diseased child. The genetic data consists of the marker genotypes for the parents and child. The TDT is based on transmissions, to the diseased child, from heterozygous parents, or parents whose genotypes consist of different alleles. In particular, consider a biallelic marker with alleles $M_1$ and $M_2$. The TDT counts the number of times, $n_{12}$, that $M_1 M_2$ parents transmit marker allele $M_1$ to the diseased child and the number of times, $n_{21}$, that $M_2$ is transmitted. If the marker is not linked to the disease locus, i.e. $\theta = 0.5$, or if there is no association between $M_1$ and the disease mutation, then conditional on the number of heterozygous parents, and in the absence of segregation distortion, $n_{12}$ is distributed binomially: $B(n_{12}+n_{21}, 0.5)$. The null hypothesis of no linkage or no association can be tested with the statistic $$T_{TDT} = \frac{(n_{12} - n_{21})^2}{n_{12} + n_{21}}$$

with statistical significance level approximated using the $\chi 2$ distribution with one df or computed exactly with the binomial distribution. When transmissions from more than one diseased child per family are included in the TDT statistic, the test is valid only as a test of linkage.

Several extensions of the TDT test have been proposed and all such extensions are within the scope of the present invention. See, for example, Mortin and Collins, 1998, Proc. Natl. Acad. Sci. USA 95, p. 11389; Terwilliger, 1995, Am J Hum Genet 56, p. 777. See also, for example, Mueller and Young, 1997, *Emery's Elements of Medical Genetics*, Kalow ed., p. 169-175, Churchill Livingstone, Edinburgh; Zhao et al., 1998, Am. J. Hum. Genet. 63, p. 225; Roses, 2000, Nature 405, p. 857; Spielman et al., 1993, Am J. Hum. Genet. 52, p. 506; and Ewens and Spielman; Am. H. Hum. Genet. 57, p. 455.

5.14.2.3. SIBSHIP-Based Test

In some embodiments, the sibship-based test is used. See, for example, Wiley, 1998, Cur. Pharmaceut. Des. 4, p. 417; Blackstock and Weir, 1999, Trends Biotechnol. 17, p. 121; Kozian and Kirschbaum, 1999, Trends Biotechnol. 17, p. 73; Rockett et al., Xenobiotica 29, p. 655; Roses, 1994, J. Neuropathol. Exp. Neurol 53, p. 429; and Roses, 2000, Nature 405, p. 857.

5.15. Complex Traits

In some embodiments of the present invention, the term "complex trait" refers to any clinical trait T that does not exhibit classic Mendelian inheritance. In some embodiments, the term "complex trait" refers to a trait that is affected by two or more gene loci. In some embodiments, the term "complex trait" refers to a trait that is affected by two or more gene loci in addition to one or more factors including, but not limited to, age, sex, habits, and environment. See, for example, Lander and Schork, 1994, *Science* 265: 2037. Such "complex" traits include, but are not limited to, susceptibilities to heart disease, hypertension, diabetes, obesity, cancer, and infection. Complex traits arise when the simple correspondence between genotype and phenotype breaks down, either because the same genotype can result in different phenotypes (due to the effect of chance, environment, or interaction with other genes) or different genotypes can result in the same phenotype.

In some embodiments, a complex trait is one in which there exists no genetic marker that shows perfect cosegregation with the trait due to incomplete penetrance, phenocopy, and/or nongenetic factors (e.g., age, sex, environment, and affect or other genes). Incomplete penetrance means that some individuals who inherit a predisposing allele may not manifest the disease. Phenocopy means that some individuals who inherit no predisposing allele may nonetheless get the disease as a result of environmental or random causes. Thus, the genotype at a given locus may affect the probability of disease, but not fully determine the outcome. The penetrance function $f(G)$, specifying the probability of disease for each genotype G, may also depend on nongenetic factors such as age, sex, environment, and other genes. For example, the risk of breast cancer by ages 40, 55, and 80 is 37%, 66%, and 85% in a woman carrying a mutation at the BCRA1 locus as compared with 0.4%, 3%, and 8% in a noncarrier (Easton et al., 1993, *Cancer Surv.* 18: 1995; Ford et al., 1994, *Lancet* 343: 692). In such cases, genetic mapping is hampered by the fact that a predisposing allele may be present in some unaffected individuals or absent in some affected individuals.

In some embodiments a complex trait arises because any one of several genes may result in identical phenotypes (genetic heterogeneity). In cases where there is genetic heterogeneity, it may be difficult to determine whether two patients suffer from the same disease for different genetic reasons until the genes are mapped. Examples of complex diseases that arise due to genetic heterogeneity in humans include polycystic kidney disease (Reeders et al., 1987, *Human Genetics* 76: 348), early-onset Alzheimer's disease (George-Hyslop et al., 1990, *Nature* 347: 194), maturity-onset diabetes of the young (Barbosa et al., 1976, *Diabete Metab.* 2: 160), hereditary nonpolyposis colon cancer (Fishel et al., 1993, *Cell* 75: 1027) ataxia telangiectasia (Jaspers and Bootsma, 1982, *Proc Natl. Acad. Sci. U.S.A.* 79: 2641), obesity, nonalcoholic steatohepatitis (NASH) (James & Day, 1998, *J. Hepatol.* 29: 495-501), nonalcoholic fatty liver (NAFL) (Younossi, et al., 2002, Hepatology 35, 746-752), and xeroderma pigmentosum (De Weerd-Kastelein, *Nat. New Biol.* 238: 80). Genetic heterogeneity hampers genetic mapping, because a chromosomal region may cosegregate with a disease in some families but not in others.

In still other embodiments, a complex trait arises due to the phenomenon of polygenic inheritance. Polygenic inheritance arises when a trait requires the simultaneous presence of mutations in multiple genes. An example of polygenic inheritance in humans is one form of retinitis pigmentosa, which requires the presence of heterozygous mutations at the perpherin/RDS and ROM1 genes (Kajiwara et al., 1994, *Science* 264: 1604). It is believed that the proteins coded by RDS and ROM1 are thought to interact in the photoreceptor outer pigment disc membranes. Polygenic inheritance complicates genetic mapping, because no single locus is strictly required to produce a discrete trait or a high value of a quantitative trait.

In yet other embodiments, a complex trait arises due to a high frequency of disease-casing allele "D". A high frequency of disease-causing allele will cause difficulties in mapping even a simple trait if the disease-causing allele occurs at high frequency in the population. That is because the expected Mendelian inheritance pattern of disease will be confounded by the problem that multiple independent copies of D may be segregating in the pedigree and that some individuals may be homozygous for D, in which case one will not observe linkage between D and a specific allele at a nearby genetic marker, because either of the two homologous chromosomes could be passed to an affected offspring. Late-onset Alzheimer's disease provides one example of the problems raised by high frequency disease-causing alleles. Initial linkage studies found weak evidence of linkage to chromosome 19q, but they were dismissed by many observers because the lod score (logarithm of the likelihood ratio for linkage) remained relatively low, and it was difficult to pinpoint the linkage with any precision (Pericak-Vance et al., 1991, *Am J. Hum. Genet.* 48: 1034). The confusion was finally resolved with the discovery that the apolipoprotein E type 4 allele appears to be the major causative factor on chromosome 19. The high frequency of the allele (about 16% in most populations) had interfered with the traditional linkage analysis (Corder et al., 1993, *Science* 261: 921). High frequency of disease-causing alleles becomes an even greater problem if genetic heterogeneity is present.

5.16. Algorithms for Elucidating Genes that Affect a Complex Trait Using eQT-cQTL Overlap The present invention provides additional methods for associating a gene with a complex trait. FIG. 19, discloses one such method. Referring to FIG. 19, the first step is to assemble starting data (step 1902). The starting data includes the gene expression data 44, marker data 70, and genotype and pedigree data 68 as described in Section 5.1 in conjunction with FIG. 1. Marker data 70-includes genome annotation information (e.g., where a gene is located within the genome). In some embodiments, rather than using gene expression data 44, data such as protein expression levels in a plurality of organism under study is used. In some embodiments, gene expression data 44 is collected from multiple different tissue types. In addition, in some embodiments, phenotypic data is gathered in step 1902. The phenotypic data 95 differs from gene expression data 44 in the sense that phenotypic data 95 includes quantitative measurements of traits other than cellular constituent quantities (e.g., classical phenotypes). Thus in mice, for example, phenotypic data 95 includes data for clinical traits such as subcutaneous fat pad mass, perimetrial fat pad mass, omental fat pad mass, and adopisity. In plants, for example, phenotypic data 95 includes data for clinical traits such as barren plants, brittle stalks, yield, disease resistance, drydown, early growth, growing degree units (GDU), GDU to physical maturity, GDU to shed, GDU to silk, harvest moisture, plant height, protein rating, root lodging, seedling vigor, grain composition amino acids, and grain composition carbohydrates. These clinical traits are defined in U.S. Pat. No. 6,368,806 to Openshaw et al. Those of skill in the art will appreciate that there are a large number of other possible clinical traits and all such traits are within the scope of the present invention. Such clinical traits may include, but are not limited to, measurements such as life span, presence or absence of a particular disease (e.g. a disease associated with a complex trait), bone density, cholesterol level, obesity, blood sugar level, eye color, blood type, coordination.

Once starting data are assembled, gene expression data 44 is transformed into a plurality of expression statistics (e.g., expression statistic set 304, FIGS. 3A, 3B) for gene G. Exemplary expression statistics include, but are not limited to, the mean log ratio, log intensity, or background-corrected intensity for gene G. Bach expression statistic (e.g. expression statistic 308, FIG. 3A) represents an expression value for a gene G. In one embodiment, each expression value is a normalized expression level measurement for gene G in an organism in a plurality of organisms under study. In one embodiment, normalization module 72 (FIG. 1) is used to normalize the expression level measurement for gene G. In some embodiments, each expression level measurement is determined by measuring an amount of a cellular constituent encoded by the gene G in one or more cells from an organism in the plurality of organisms. In one embodiment, the amount of the cellular constituent comprises an abundance of an RNA present in one or more cells of the organism. In one embodiment, the abundance of RNA is measured by a method comprising contacting a gene transcript array with the RNA from one or more cells of the organism, or with a nucleic acid derived from the RNA. The gene transcript array comprises a positionally addressable surface with attached nucleic acids or nucleic acid mimics. The nucleic acid mimics are capable of hybridizing with the RNA species or with nucleic acid derived from the RNA species.

In embodiments where the expression level measurement is normalized, any normalization routine may be used. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines may be run. Exemplary normalization routines in accordance with the present invention are disclosed in more detail in Section 5.3, infra.

In addition to the generation of expression statistics from gene expression data 44, a genetic marker map 78 is generated from genetic markers 70 (FIG. 1; FIG. 19, step 1906). In one embodiment of the present invention, a genetic marker map is created using marker map construction module 74 (FIG. 1). Further, in one embodiment, genotype probability distributions for the organisms under study are computed. Genotype probability distributions take into account information such as marker information of parents, known genetic distances between markers, and estimated genetic distances between the markers. Computation of genotype probability distributions generally requires pedigree data. In some embodiments of the present invention, pedigree data is not provided and genotype probability distributions are not computed.

Generally, a genetic marker map is constructed from a set of genetic markers 78 associated with a plurality of organisms 78 of the single species under study. The set of genetic markers can comprise single nucleotide polymorphisms (SNPs), microsatellite markers, restriction fragment length polymorphisms, short tandem repeats, DNA methylation markers, sequence length polymorphisms, random amplified polymorphic DNA, amplified fragment length polymorphisms, simple sequence repeats, or any combination thereof. In some embodiments, genotype data is used to construct the genetic marker map. Such genotype data comprises knowledge of which alleles, for each marker in the set of genetic markers used to construct the map, are present in each organism in the plurality of organisms under study. In some embodiments, the plurality of organisms under study represents a segregating population and pedigree data is also used to construct the marker map. Such pedigree data shows one or more relationships between organisms in the plurality of organisms. In some embodiments, the plurality of organisms under study comprises an F2 population and the one or more relationships between organisms in the plurality of organisms indicates which organisms in the plurality of organisms are members of the F2 population.

Once the expression data has been transformed into corresponding expression statistics and genetic marker map 78 has been constructed, the data is transformed into a structure that associates all marker, genotype and expression data for input into QTL analysis software. This structure is stored in expression/genotype warehouse 76 (FIG. 1; FIG. 19, step 1908). FIG. 3C illustrates an expression/genotype warehouse 76 that is used in some embodiments where gene expression/cellular constituent data 44 was measured from multiple tissue types.

A quantitative trait locus (QTL) analysis is performed using data corresponding to a gene G as a quantitative trait (FIG. 19, step 1910). In some embodiments of the present invention, step 1910 is performed by an embodiment of expression quantitative trait loci (eQTL) identification module 2202 (FIG. 22), which is resident in memory 24 of computer 20 in system 10 (FIG. 1). In one embodiment, this QTL analysis is performed by genetic analysis module 80 (FIG. 1).

In one example, the QTL analysis steps through a genetic marker map 78 that represents the genome of the single species. Linkages to gene G are tested at each step or location along marker map. In such embodiments, each step or location along the length of the marker map is at regularly defined intervals. In some embodiments, these regularly defined intervals are defined in Morgans or, more typically, catiMorgans (cM). In some embodiments, each regularly defined interval is less than 100 cM. In other embodiments, each regularly defined interval is less than 10 cM, less than 5 cM, or less than 2.5 cM.

In the QTL analysis of step 1910, data corresponding to gene G is used as a quantitative trait. More specifically, the quantitative trait used in the QTL analysis is an expression statistic set, such a set 304 (FIG. 3A), that corresponds to gene G. That is, the expression statistic set 304 comprises the expression statistic 308 for gene G from each organism 306 in the population under study. FIG. 3B illustrates an exemplary expression statistic set 304 in accordance with one embodiment of the present invention. Exemplary expression statistic set 304 includes the expression level 308 of gene G from each organism in a plurality of organisms. For example, consider the case where there are ten organisms in the plurality of organisms, and each of the ten organisms expresses gene G. In this case, expression statistic set 304 includes ten entries, each entry corresponding to a different one of the ten organisms in the plurality of organisms. Further, each entry represents the expression level of gene G in the organism represented by the entry. So, entry "1" (308-G-1) corresponds to the expression level of gene G in organism 1, entry "2" (308-G-2) corresponds to the expression level of gene G in organism 2, and so forth. Expression statistic set 304 comprises a plurality of expression statistics 308 for gene G.

In one embodiment of the present invention, the QTL analysis (FIG. 19, step 1910) comprises: (i) testing for linkage between (a) the genotype of the plurality of organisms at a position in the genome of the single species and (b) the plurality of expression statistics for gene G (e.g., expression statistic set 304), (ii) advancing the position in the genome by an amount, and (iii) repeating steps (i) and (ii) until the genome has been tested. In some embodiments, the amount advanced in each instance of (ii) is less than about 100 centiMorgans, less than about 10 centiMorgans, loss than about 5 centiMorgans, or less than about 2.5 centiMorgans. In some embodiments, the testing comprises performing linkage analysis (Section 5.13) or association analysis (Section 5.14) that generates a statistical score for the position in the genome of the single species. As detailed below, in some embodiments, the testing is linkage analysis and the statistical score is a logarithm of the odds (lod) score. Thus, in some embodiments, a eQTL identified in processing step 1910 is represented by a lod score that is greater than about 2.0, greater than about 3.0, greater than about 4.0, or greater than about 5.0.

In situations where pedigree data is not available, genotype data from each of the organisms 46 (FIG. 1) for each marker in genetic marker map 78 may be compared to each quantitative trait (expression statistic set 304) using allelic association analysis, as described in Section 5.14, supra, in order to identify QTL that are linked to each expression statistic set 304. In one form of association analysis, an affected population is compared to a control population. In particular, haplotype or allelic frequencies in the affected population are compared to haplotype or allelic frequencies in a control population in order to determine whether particular haplotypes or alleles occur at significantly higher frequency amongst affected compared with control samples. Statistical tests such as a chi-square test can be used to determine whether there are differences in allele or genotype distributions.

In some embodiments, testing for linkage between a given position in the chromosome and the expression statistic set 304 comprises correlating differences in the expression levels found in the expression level statistic with differences in the genotype at the given position using single marker tests (for example using t-tests, analysis of variance, or simple linear regression statistics). See, e.g., *Statistical Methods*, Snedecor and Cochran, Iowa State University Press, Ames, Iowa (1985). However, there are many other methods for testing for linkage between expression statistic set 304 and a given position in the chromosome. In particular, if expression statistic set 304 is treated as the phenotype (in this case, a quantitative phenotype), then methods such a those disclosed in Doerge, 2002, Mapping and analysis of quantitative trait loci in experimental populations, *Nature Review: Genetics* 3:43-62, may be used. Concerning steps (i) through (iii) above, if the genetic length of the genome is N cM and 1 cM steps are used, then N different tests for linkage are performed on the given chromosome.

In some embodiments, the QTL data produced from QTL analysis 1910 comprises a logarithm of the odds score (lod) computed at each position tested in the genome under study. A lod score is a statistical estimate of whether two loci are likely to lie near each other on a chromosome and are therefore likely to be genetically linked. In the present case, a lod score is a statistical estimate of whether a given position in the genome under study is linked to the quantitative trait corresponding to a given gene. Lod acres are further described in Section 5.4, supra. A lod score of three or more is generally taken to indicate that two loci are genetically linked. The generation of lod scores requires pedigree data. Accordingly, in embodiments in which a lod score is generated, processing step 1910 is essentially a linkage analysis, as described in Section 5.13, with the exception that the quantitative trait under study is derived from data, such as cellular constituent expression statistics, rather than classical phenotypes such as eye color. In situations where pedigree data is not available, genotype data from each of the organisms 46 (FIG. 1) for each marker in genetic marker map 78 may be compared to each quantitative trait (e.g., expression statistic set 304) using association analysis, as described in Section 5.14, supra, in order to identify QTL that are linked to the quantitative trait.

In some embodiments, processing step 1910 yields a data structure that includes all positions 86 (FIG. 1) in the genome of the organisms 46 that were tested for linkage to the expression statistic set 304 (quantitative trait 84) in step 1910. In one embodiment, this data structure is an entry in data structure 82 (FIG. 1). Positions 86 are obtained from genetic marker map 78. For each position 86, genotype data 68 provides the genotype at position 86 for each organism in the plurality of organisms under study. For each such position 86 analyzed by QTL analysis 1910, a statistical measure (e.g., statistical score 88), such as the maximum lad score between the position and the expression statistic at, is provided by processing step 1910. Thus, processing step 1910 yields all the positions in the genome of the organism of interest that are linked to the expression statistic set 304 tested in step 1910. Such positions are referred to as the eQTL for the linked gene G tested in step 1910.

In processing step 1912, a clinical quantitative trait loci (cQTL) that is linked to a clinical trait T is identified using QTL analysis. In some embodiments of the present invention, step 1912 is performed by an embodiment of clinical quantitative trait loci (cQTL) identification module 2204 (FIG. 22).

In some embodiments, a phenotypic statistic set 2102 for the clinical trait T serves as the clinical trait used in the QTL analysis. FIG. 21 illustrates exemplary phenotypic statistic sets 2102 that are a stored as phenotypic data 95 in memory 24 within system 10 (FIG. 1). In FIG. 21, each phenotypic statistic set 2102 includes the phenotypic value for a different organism in a plurality of organisms under study. As used herein, a phenotypic value is any form of measurement of a phenotypic trait. For example, if the phenotypic trait is cholesterol level in the organism, the phenotypic value may be milligrams of cholesterol per liter of blood.

In one embodiment, processing step 1912 comprises a classical form of QTL analysis in which a phenotypic trait is quantified. In some embodiments, processing step 1912 employs a whole genome search of genetic markers using marker map 78. For each such position 86 in the genome that is analyzed by QTL analysis 1912, processing step 1912 provides a statistical measure (e.g., statistical score 88), such as the maximum lod score between the position and the phenotypic statistic set 2102. Thus, processing step 1912 yields all the positions in the genome of the organism of interest that are linked to the expression statistic set 304 tested in step 1912. Such embodiments of processing step were first described by Lander and Botstein in Genetics 121, 174-179 (1989). They are also described in International Application WO 90/04651, International Application WO 99/13107, Lander and Schork, Science 265, 2037-2048 (1994), and Doerge, Nature Reviews Genetics 3, 43-62, (2002). In other embodiments of processing step 1912, association analysis, as described in Section 5.14 is used rather than linkage analysis. Association analysis does not require pedigree data.

In one embodiment of the present invention, the QTL analysis (FIG. 19, step 1912) comprises: (i) testing for linkage between (a) the genotype of a plurality of organisms at a position in the genome of a single species and (b) the phenotypic statistic set 2102 (e.g., plurality of phenotypic values), (ii) advancing the position in the genome by an amount, and (iii) repeating steps (i) and (ii) until the genome has been tested. In some embodiments, the amount advanced in each instance of (ii) is less than about 100 centiMorgans, less than about 10 centiMorgans, less than about 5 centiMorgans, or less than about 2.5 centiMorgans. In some embodiments, the testing comprises performing linkage analysis (Section 5.13) or association analysis (Section 5.14) that generates a statistical score for the position in the genome of the single species. In some embodiments, the testing is linkage analysis and the statistical score is a logarithm of the odds (lod) score (Section 5.4). Thus, in some embodiments, an eQTL identified in processing step 1912 is represented by a lod score that is greater than about 2.0, greater than about 3.0, greater than about 4.0, or greater than about 5.0.

Processing step 1910 identifies any number of expression quantitative trait loci (eQTL) for a gene G whereas processing step 1912 identifies any number of clinical quantitative trait loci (cQTL) for a clinical trait T. In processing step 1914, the question is asked whether an eQTL from processing step 1910 colocalizes with a cQTL from processing step 1912 at the same point in the genome. In some embodiments of the present invention, processing step 1910 is performed by an embodiments of determination module 2206 (FIG. 22). In some embodiments, an eQTL and a cQTL are considered colocalized if they fall within about 50 centiMorgans (cM) of each other within the genome of the species under study. In some embodiments, an eQTL and cQTL are considered colocalized if they fall within about 40 cM, about 30 cM, about 20 cM, about 15 cM or about 10cM of each other within the genome of the species under study. In some embodiments, an eQTL and cQTL are considered colocalized if they fall within about 8 cM, about 6 cM, about 4 cM, or about 2 cM of each other within the genome of the species under study.

In some embodiments of the present invention, when an eQTL for gene G colocalizes with a cQTL for a clinical trait T (1914—Yes), gene G is associated with the clinical trait T (step 1920). If this condition is not satisfied (1914—No), then another gene G in the genome of the species under study is selected and process control returns to step 1910 (FIG. 19). In other embodiments, the condition is imposed that the eQTL for gene G colocalizes to the physical location of gene G in the genome (1916—Yes) before gene G is associated with the clinical trait T (step 1920). In other words, the eQTL must correspond to the physical location of gene G in the genome of the single species in order for the gene to be linked to a clinical trait T. In some embodiments, an eQTL corresponds to the physical location of gene G if the eQTL and G colocalize within about 5 cM, 4cM, 3cM, 2cM, 1cM, or less in the genome of the single species. In embodiments where condition 1916 is imposed, when the condition is not satisfied (1916—No), another gene G in the genome of the species under study is selected and process control returns to step 1910.

5.17. Algorithms for Finding an Ortholog in a First Species to a Gene that Affects a Complex Trait in a Second Species The methods of the present invention are used to identify gene-gene interactions, gene-phenotype interactions, and biological pathways linked to complex traits in one species (target species, first species) using data from another species (reference species, second species). For example, in one embodiment of the present invention, genes identified using the processing steps described in Section 5.1, above, and illustrated in FIG. 2, are used to identify genes associated with a complex trait in a reference species. Then, the genes that are orthologs of the genes identified in the reference species are identified in the target species. In another example, genes identified using the processing steps described in Section 5.16, above, and illustrated in FIG. 19, are used to identify genes associated with a complex trait in the reference species. Then, the genes that are the orthologs of the genes identified in the reference species are identified in a target species. Orthologs represent the same protein from different species. That is, an ortholog is a gene that is equivalent in two different species by sharing the same common ancestor. Stated differently, an ortholog is a functional counterpart of a gene in another genome that has arisen from speciation. See, for example, Fitch, 1970, Systematic Zoology 19:99-113.

5.17.1. Finding Orthologs Using Sequence-Based Methods

In one embodiment of the present invention, genes in a target species that are homologous to genes in a reference species are identified using the steps outlined in FIG. 25. In step 2502, a gene G from a reference species that was identified using a quantitative genetics method is selected. Typical reference species include, but are not limited to, mouse, monkey, and dog. Typical target species, include, but are not limited to, humans. Once a gene G from the reference species has been selected, the remaining processing steps in FIG. 25 are used to identify the gene in the target species that is the ortholog to the gene G. In processing step 2504, a determination is made as to whether the ortholog to gene G can simply be found in curated sequence databases through a search tool such as LocusLink. See, for example, Pruitt and Maglott, 2001, Nucleic Acids Res 29, 137-140 and Pruitt at, 2000, Trends Genet. 16, 44-47. If so (2504—Yes) the process comes to an end with the ortholog to gene G in the target species identified (2520).

If an automated search of curated databases fails (2504—No), then a manual process is used to identify the ortholog of gene G in the target species (processing steps 2506 through 2516). In this process, a search tool such as Basic Local Alignment Search Tool (BLAST) is used. Alternatively a program such as PSI-BLAST, PHI-BLAST, WU-BLAST-2, MBGABLAST, BlastN, and BlastP can be used. See Altschul et al., 1990, J. Mol. Biol. 215, 403-410; Altschul et al., 1996, Methods in Enzymology 266, 460-480; and Karlin et al., 1993, PNAS USA 90, 5873-5787.

In processing step 2506, BLAST (or an alternative program) is used to search known nucleotide sequences in the target species using the nucleotide sequence of gene G. The highest scoring gene sequence in the target species is denoted G'. Next, BLAST (or an alternative program) is used to search protein sequences in the target species using the amino acid translation of G (step 2508). The highest scoring sequence from the search in 2508 is designated P'. If P' is not the protein product of G' (2510—No), it is likely that the ortholog to gene G in the target species has not been identified by processing steps 2506 and 2508. That is, the ortholog could be an unidentified gene corresponding to P' or alternatively, gene G'. Further still, the ortholog in the target species could remain completely unidentified. In some embodiments of the present invention, condition 2510 is satisfied if the protein product P' is in the top tier of the search results in 2508. For example, in some embodiments, condition 2510 is satisfied when the protein product P' appears anywhere in the top 10 search results in step 2508. In other embodiments, condition 2510 is satisfied when the expectation value for the protein product P' in the search of step 2508 is $1e^{-5}$ or less, $1e^{-10}$ or less, $1e^{-12}$ or less, or $1e^{-15}$ or less.

When the condition 2510—No arises, steps 2506 and 2508 may be repeated using a subset of gene G. Alternatively, steps 2506 and 2508 may be repeated using different search settings, as disclosed in Altschul et al., 1990, J. Mol. Biol. 215, 403-410; Altschul et al., 1996, Methods in Enzymology 266, 460-480; and Karlin et al., 1993, PNAS USA 90, 5873-5787. Further still, other methods for identifying orthologs may be used as disclosed in Section 5.17.2, below.

If P' is the protein product of G' (2510—Yes), it is likely that the ortholog to gene G in the target species has been identified by processing steps 2506 and 2608. However, as confirmation, additional processing steps (2512 and 2514) may be performed. Steps 2512 and 2514 perform reverse searches in which P' and G' are used to respectively find P and G in databases corresponding to the reference species. Thus, for example, in processing step 2512, the nucleotide sequence G' is used to identify the sequence G in a database of reference species gene sequences. It is expected that this search (e.g., a BLAST search or some equivalent to a BLAST search) will identify G in the database of reference species sequences with the highest score. Next, in processing step 2514, the protein sequence P' is used to identify the protein P in a database of reference species protein sequences. It is expected that this search (e.g., a BLAST search or some equivalent to a BLAST search) will identify P in the database of reference species sequences with the highest score. In processing step 2516, a determination is made as to whether steps 2512 and 2514 identified P and G. If so (2616—Yes), the ortholog to gene G in the target species has been identified as G' (2520). In some embodiments of the present invention, P and G are considered identified when they appear in the top tier of the respective search results of steps 2512 and 2514. For example, in some embodiments, condition 2516 is satisfied (2516—Yes) when the protein product P appears anywhere in the top 10 search results in step 2514. In other embodiments, condition 2516 is satisfied when the expectation value for the protein product P or the gene G has an expectation value of $1e^{-5}$ or less, $1e^{-10}$ or less, $1e^{-12}$ or less, or $1e^{-15}$ or less in the respective search results of steps 2512 and 2514. When condition 2516 is not satisfied (2516—No), it is possible that the ortholog to gene G has not been identified and other methods for identifying orthologs need to be used to identify the ortholog.

5.17.2. Finding Orthologs Using Nonsequence-Based Methods

Another approach for finding orthologs is disclosed in FIG. 26. The approach illustrated in FIG. 26 is disclosed in greater detail in U.S. patent application Ser. No. 09/779,004 entitled "Functioning Genomes with Cross-Species Coregulation" filed Feb. 7, 2001, which is hereby incorporated by reference in its entirety. The approach involves analysis of biological responses (e.g., response profiles) that are obtained or provided from measurements of one or more aspects of the biological state of a reference cell or organism in response to a set of perturbations. The perturbations may include, for example, drug exposure, targeted mutations or targeted changes in levels of protein activity or expression. Other exemplary conditions or perturbations include changes in environmental conditions such as exposure to different conditions of temperature, radiation, sunlight, oxygen or aeration to name a few, as well as different nutritional conditions such as growth or incubation of the reference cell or organism in the presence or absence of particular nutrients (e.g., one or more particular amino acids and/or sugars). Still further, exemplary perturbations also include exposure of the reference cell or organism to one or more toxins including, but not limited to, exposure to pesticides (including, e.g., fungicides or insecticides) or herbicides.

Particular aspects of the biological state of a cell, such as the transcriptional state, the translational state or the activity state are obtained or measured in response to the plurality of perturbations. Preferably, the measurements are differential measurements of the change in genes identified in response, e.g., to a drug at certain concentrations and times of treatment. The collection of these measurements, which are optionally graphically represented, are called herein the "pertubation response" or "drug response" or, alternatively, the "response profile." In preferred embodiments of the invention, a plurality of different response profiles are obtained or provided for a plurality of different perturbations or for a plurality of cellular constituents.

In more detail, a first response profile is first obtained or provided (FIG. 26, step 2602) for a particular cellular constituent from a reference species under some particular set of perturbations. Typically, this cellular constituent studied in step 2602 is a cellular constituent corresponding to a gene G from a reference species that was identified using quantitative genetics methods (e.g., a gene verified in processing step 222 of FIG. 2 or a gene that has been associated with clinical trait T in processing step 1920 of FIG. 19). In some embodiments, a cellular constituent is a gene, a gene product of the gene (e.g., a protein). Thus, a cellular constituent may be, for example, the mRNA or cDNA that corresponds to a particular gene. The set of perturbations for which a response profile is obtained is referred to herein as the "condition set" and is denoted {A}.

In some embodiments, the number of different conditions or perturbations contained in the condition set {A} is very large. In some embodiments, {A} includes at least 10 different conditions or perturbations, in other embodiments, {A} includes at least 50 different conditions or perturbations, in still other embodiments, {A} includes at least 100 different conditions or perturbations, in yet other embodiments, {A} includes at least 500 different conditions or perturbations, and in still other embodiments, {A} includes at least 1000 different conditions or perturbations. However, in order to practice the methods of the invention most efficiently, the response profiles obtained for condition set {A} are optionally evaluated (step 2604, FIG. 26) and a "perturbation subset," denoted herein as {a}, is selected. Perturbation subset {a} consists of those perturbations or conditions in the condition set (perturbation sot) {A} for which the profiles of gene x, or in more preferred embodiments of a plurality of genes, in reference species are maximally informative (e.g., strongest and, preferably, most diverse).

For example, if several of the profiles obtained for the reference species are closely correlated with each other, then typically only one of the conditions or perturbations from this group is selected for further analysis according to the methods of the present invention. Many techniques of analysis are known in the art that can be used to assess the similarity and/or correlation between two or more different profiles. Such techniques are disclosed in copending application Ser. No. 09/779,004 entitled "Functioning genomes with cross-species coregulation" which is hereby incorporated by reference.

In step 2606 (FIG. 26), a response profile is also obtained or provided for a particular cellular constituent (e.g., a particular gene or gene product) in a sample of the target species (e.g. a cell culture from the target species) under a particular set of perturbations. The set of perturbations for which responses are obtained or provided for cellular constituents y of the target species preferably consist of the same perturbations for which responses are obtained or provided for cellular constituents of the first cell or organism representing the reference species. That is, the set of perturbations for which responses are obtained or provided for cellular constituents of the target call or species are preferably members of the perturbation set {A}. More preferably, the set of perturbations for which responses are obtained or provided for cellular constituents y of the target species are preferably members of the perturbation subset {a}. In fact, most preferably, the set of perturbations for which a response profile is obtained or provided for cellular constituents y of the target cell or species include all of the perturbations that are members of the optional perturbation subset {a}.

In step 2608, the response profiles obtained for a cellular constituent x in the reference species and the cellular constituent y in the target species are used to evaluate the coregulation of x and y across a common set of conditions or perturbations, most preferably across the perturbation subset {a}. For example, the similarity (e.g., correlation) of the response profile of the genes or gene products x and y can be evaluated by means of the equation:

$$\rho_{xy} = \frac{\sum_i x_i \sum_i y_i}{\left(\sum_i x_i^2 \sum_i y_i^2\right)^{1/2}}$$

in which $x_i$ and $Y_i$ denote respective changes in expression, abundance, activity levels or amount of modification of the cellular constituents corresponding to genes x and y, respectively, under the condition or perturbation i. If $\rho_{xy}$ is particularly high then, x and y are identified as functionally related and are thus determined to be candidate orthologs (candidate functional orthologs). Preferably, the candidate ortholog identified according to the methods of the invention have a correlation p, that is at least 0.5 (i.e. at least 50%). More preferably, the candidate functional orthologs identified according to the methods of the invention have a correlation that is at least 0.75 (i.e., at least 75%), 0.8 (i.e., at least 80%) or at least 0.85 (i.e., at least 85%). In fact, the candidate functional orthologs identified according to the methods of the invention most preferably have a correlation that is at least 0.9 (i.e., at least 90%).

Other forms of determining correlation between two datasets, besides the correlation coefficient above are well known in the art. Indeed, any statistical method for determining the probability that two datasets are related may be used in accordance with the methods of the present invention in order to identify orthologs. Correlation based on ranks is also possible, where $x_i$ and $y_i$ are the ranks of the measurement in ascending or descending numerical order. See e.g., Conover, *Practical Nonparametric Statistics*, $2^{nd}$ ed., Wiley, (1971). Shannon mutual information also can be used as a measure of similarity. See e.g., Pierce, *An Introduction To Information Theory: Symbols, Signals, and Noise*, Dover, (1980).

In processing step 2612, a determination is made as to whether there is any additional cellular constituents y in the target species available for analysis. In some embodiments of the present invention, it is desirable to analyze as many cellular constituents y as possible in order to maximize the chances of finding the ortholog of cellular constituent x. When an additional cellular constituent y is available (2610—Yes), process control returns to step 2606 and 2608 where the additional cellular constituent y is evaluated. When no further cellular constituent y is available for analysis is available (2610—No), process control passes to step 2612 where the cellular constituent y that had the highest similarity to cellular constituent x in an instance of step 2608 is defined as the ortholog to cellular constituent x.

5.17.3. Exemplary Applications

One aspect of the invention provides a method for associating a gene G in the genome of a single first species with a clinical trait T exhibited by the single first species and a single second species. In the method, a gene G' is found in the single second species that is an ortholog of the gene G. In some embodiments, this is accomplished using the techniques disclosed in Section 5.17.1 and/or Section 5.17.2. Further, an expression quantitative trait loci (eQTL) is identified for gene G' using a first quantitative trait loci (QTL) analysis. This aspect of the present invention uses techniques disclosed in U.S. Patent Application Ser. No. 60/400,522, entitled "Computer systems and methods that use clinical and expression quantitative trait loci to associate genes with traits," filed Aug. 2, 2002, which is hereby incorporated by reference. The first QTL analysis uses a plurality of expression statistics for gee G' as a quantitative trait. Each expression statistic in the plurality of expression statistics represents an expression value for the gene G' in an organism in a plurality of organisms of the single second species. A clinical quantitative trait loci (cQTL) that is linked to the clinical trait T is identified using a second QTL analysis. The second QTL analysis uses a plurality of phenotypic values as a quantitative trait. Bach phenotypic value in the plurality of phenotypic values represents a phenotypic value for the clinical trait T in an organism in the plurality of organisms of the single second species. Next, a determination is made as to whether the eQTL and the cQTL colocalize to the same locus in the genome of the single second species. For more disclosure on these techniques see, for example, Section 5.16. When the eQTL and the cQTL colocalize to the same locus, the gene G is associated with the clinical trait T in the single first species.

Another aspect of the present invention provides a computer program product for use in conjunction with a computer system. The computer program product comprises a computer readable storage medium and a computer program mechanism embedded therein. The computer program mechanism associates a gene G in the genome of a single first species with a clinical trait T exhibited by the single first species sad a single second species. The computer program mechanism comprises a specialized form of genetic analysis module 80 (FIG. 1) which is illustrated in FIG. 54. The genetic analysis module 80 in accordance with this aspect of the invention includes an ortholog identification module 5401 for finding a gene G' in the single second species that is an ortholog of gene G. In some embodiments, this is accomplished using the techniques disclosed in Section 5.17.1 and/or Section 5.17.2. The genetic analysis module 80 in accordance with this aspect of the invention further comprises an expression quantitative trait loci (eQTL) identification module 5404 for identifying an expression quantitative trait loci (eQTL) for the gene G' using a first quantitative trait loci (QTL) analysis. This aspect of the present invention uses techniques disclosed in U.S. Patent Application Ser. No. 60/400,522, entitled "Computer systems and methods that use clinical and expression quantitative trait loci to associate genes with traits," filed Aug. 2, 2002. The first QTL analysis uses a plurality of expression statistics for the gene G' as a quantitative trait and each expression statistic in the plurality of expression statistics represents an expression value for the gene G' in an organism in the plurality of organisms of the single second species. The QTL analysis module in accordance with this aspect of the invention further comprises a clinical quantitative trait loci (cQTL) identification module 5406 for identifying a clinical quantitative trait loci (cQTL) that is linked to the clinical trait T using a second QTL analysis. The second QTL analysis uses a plurality of phenotypic values as a quantitative trait. Each phenotypic value in the plurality of phenotypic values represents a phenotypic value for the clinical trait T in an organism in the plurality of organisms of the single second species. The QTL analysis module in accordance with this aspect of the invention further comprises a determination module 5408 for determining whether the eQTL and the cQTL colocalize to the same locus in the genome of the single second species. For more disclosure on these techniques see, for example, Section 5.16. When the eQTL and the cQTL colocalize to the same locus, the gene G is associated with the clinical trait T in the single first species.

Another aspect of the present invention provides a computer system for associating a gene G in the genome of a single first species with a clinical trait T exhibited by the single first species and a single second species. The computer system comprises a central processing unit and a memory coupled to the central processing unit. The memory stores an ortholog identification module 5402 (FIG. 54), an expression quantitative trait loci (eQTL) identification module 5404 (FIG. 54), a clinical quantitative trait loci (cQTL) identification module 5406 (FIG. 54), and a determination module 5408 (FIG. 54). Ortholog identification module 5402 comprises instructions for finding a gene G' in the single second species that is an ortholog of the gene G. Expression quantitative trait loci (eQTL) identification module 5404 comprises instructions for identifying an expression quantitative trait loci (eQTL) for the gene G' using a first quantitative trait loci (QTL) analysis. The first QTL analysis uses a plurality of expression statistics for gene G' as a quantitative trait. This aspect of the present invention uses techniques disclosed in U.S. Patent Application Ser. No. 60/400,522, entitled "Computer systems and methods that use clinical and expression quantitative trait loci to associate genes with traits," filed Aug. 2, 2002. Each expression statistic in the plurality of expression statistics represents an expression value for the gene G' in an organism in a plurality of organisms of the single second species. Clinical quantitative trait loci (cQTL) identification module 5406 comprises instructions for identifying a clinical quantitative trait loci (cQTL) that is linked to the clinical trait T using a second QTL analysis. The second QTL analysis uses a plurality of phenotypic values as a quantitative trait. Each phenotypic value in the plurality of phenotypic values represents aphenotypic value for the clinical trait T in an organism in the plurality of organisms of the single second species. Determination module 5408 comprises instructions for determining whether the eQTL and the cQTL colocalize to the same locus in the genome of the single second species. When the eQTL and the cQTL colocalize to the same locus, the gene G is associated with the clinical trait T.

Another aspect of the present invention provides a method for associating a gene G in the genome of a single first species with a clinical trait T exhibited by the single first species and a single second species. In the method, quantitative trait locus data from a plurality of quantitative trait locus analyses is clustered to form a quantitative trait locus interaction map. This aspect of the present invention uses techniques disclosed in U.S. Patent Application Ser. No. 60/381,437, entitled "Computer system and method for identifying genes and determining pathways associated with traits," filed May 16, 2002, which is hereby incorporated by reference. Each quantitative trait locus analysis in the plurality of quantitative trait locus analyses is performed for a gene in a plurality of genes in the genome of the single second species using a genetic marker map and a quantitative trait in order to produce the quantitative trait locus data. For each quantitative trait locus analysis, the quantitative trait comprises an expression statistic for the gene for which the quantitative trait locus analysis is performed. For each organism in a plurality of organisms of the single second species, the genetic marker map is constructed from a set of genetic markers associated with the plurality of organisms of the second species. The quantitative trait locus interaction map is analyzed to identify a gene G' associated with a trait. See, for example, Section 5.1. Then, the gene G in the single first species that is the ortholog of the gene G' of the single second species is identified, thereby associating a gene G in the genome of the single first species with a clinical trait T exhibited by the single first species. See for, example, Sections 5.17.1 and 5.172. In some embodiments, the method further comprises an additional step that is performed prior to the clustering step. This additional step comprises performing each of the quantitative trait locus analyses in the plurality of quantitative trait locus analyses.

Another aspect of the present invention provides a computer program product for use in conjunction with a computer system. The computer program product comprises a computer readable storage medium and a computer program mechanism embedded therein. The computer program mechanism comprises a clustering module 92 (FIG. 1), an analysis module (QTL analysis module) 80 FIG. 1, and an ortholog identification module 5402 (FIG. 54). Clustering module 92 is used for clustering quantitative trait locus data from a plurality of quantitative trait locus analyses to form a quantitative trait locus interaction map. This aspect of the present invention uses techniques disclosed in U.S. Patent Application Ser. No. 60/381,437, entitled "Computer system and method for identifying genes and determining pathways associated with traits," filed May 16, 2002. See also, for example, Section 5.1. Each quantitative trait locus analysis in the plurality of quantitative trait locus analyses is performed for a gene in a plurality of genes in the genome of a single second species using a genetic marker map and a quantitative trait in order to produce the quantitative trait locus data. For each quantitative trait locus analysis, the quantitative trait comprises an expression statistic for the gene for which the quantitative trait locus analysis is performed, for each organism in a plurality of organisms of the single second species. Further, the genetic marker map is constructed from a set of genetic markers associated with the plurality of organisms of the single second species. The analysis module is for analyzing the quantitative trait locus interaction map to identify a gene G' associated with a trait exhibited by a single first species and the single second species. Ortholog identification module 5402 is for finding a gene G in the single first species that is an ortholog of the gene G' in the single second species. See for, example, Sections 5.17.1 and 5.17.2.

Some embodiments of the present invention provide a computer system for associating a gene G in the genome of a single first species with a clinical trait T exhibited by the single first species and a single second species. The computer system comprises a central processing unit and a memory coupled to the central processing unit. The memory stores a clustering module 90 (FIG. 1), an analysis module (QTL analysis module) 80 and an ortholog identification module 5402 (FIG. 54). Clustering module 92 is for clustering quantitative trait locus data from a plurality of quantitative trait locus analyses to form a quantitative trait locus interaction map. This aspect of the present invention uses techniques disclosed in U.S. Patent Application Ser. No. 60/381,437, entitled "Computer system and method for identifying genes and determining pathways associated with traits," filed May 16, 2002. Each quantitative trait locus analysis in the plurality of quantitative trait locus analyses is performed for a gene in a plurality of genes in the genome of the single second species using a genetic marker map and a quantitative trait in order to produce the quantitative trait locus data. For each quantitative trait locus analysis, the quantitative trait comprises an expression statistic for the gene for which the quantitative trait locus analysis is performed, for each organism in a plurality of organisms of the single second species. The genetic marker map is constructed from a set of genetic markers associated with the plurality of organisms of the single second species. Genetic analysis module 80 is for analyzing the quantitative trait locus interaction map to identify a gene G' associated with a trait exhibited by the single first species and the single second species. Ortholog identification module 5402 (FIG. 54) is for finding a gene G in the single first species that is an ortholog of the gene G' of the single second species.

Another aspect of the present invention provides a method for identifying a quantitative trait locus for a complex trait in a single first species. Some embodiments in accordance with this aspect of the present invention use techniques disclosed in U.S. Patent Application Ser. No. 60/382,036, entitled "Computer systems and methods for subdividing a complex disease into component diseases," filed May 20, 2002, which is hereby incorporated by reference.

The complex trait is exhibited by the single first species and a single second species. In the method, a plurality of organisms of the single second species are divided into a plurality of subpopulations using a classification scheme that classifies each organism in the plurality of organisms of the single second species into at least one of the subpopulations. One way this can be accomplished is described in Section 15.17.4, below. The classification scheme uses a plurality of cellular constituent measurements from each organism of the single second species. Further, for at least one subpopulation in the plurality of subpopulations, the method provides the step of performing quantitative genetic analysis on the subpopulation in order to identify a quantitative trait locus for the complex trait in the single second species. The method farther provides the step of finding the quantitative trait loci in the single first species that is the ortholog of the quantitative trait locus of the single second species, thereby identifying the quantitative trait locus for the complex trait in the single first species. See for example, Sections 5.17.1 and 5.17.2.

Still another aspect of the present invention provides a computer program product for use in conjunction with a computer system. The computer program product comprises a computer readable storage medium and a computer program mechanism embedded therein. The computer program mechanism comprises a classification module 5410 (FIG. 54), a genetic analysis module (QTL analysis module) 80 (FIG. 1), and an ortholog identification module 5402 (FIG. 54). Classification module 5410 is for dividing a plurality of organisms of a single second species into a plurality of subpopulations using a classification scheme that classifies each organism in the plurality of organisms of the single second species into at least one of the subpopulations. This aspect of the present invention uses techniques disclosed in U.S. Patent Application Ser. No. 60/382,036, entitled "Computer systems and methods for subdividing a complex disease into component diseases," filed May 20, 2002. The classification scheme uses a plurality of cellular constituent measurements from each organism in the single second species. The genetic analysis module is used, for at least one subpopulation in the plurality of subpopulations, to perform quantitative genetic analysis on the subpopulation in order to identify a quantitative trait locus for a complex trait that is exhibited by the single second species and a single first species. Ortholog identification module 5402 is used for finding the quantitative trait locus in the single first species that is the ortholog of the quantitative trait locus of the single second species. See, for example, Sections 5.17.1 and 5.172.

Another aspect of the present invention provides a computer system for identifying a quantitative trait locus for a complex trait in a single first species. The complex trait is exhibited by the single first species and a single second species. The computer system comprises a central processing unit and a memory coupled to the central processing unit. The memory is used for storing a classification module 5410 (FIG. 54), a genetic analysis module 80 (FIG. 1); and an ortholog identification module 5402 (FIG. 54). Classification module 5410 includes instructions for dividing a plurality of organisms of a single second species into a plurality of subpopulations using a classification scheme that classifies each organism in the plurality of organisms of the single second specis into at least one of the subpopulations. This aspect of the present invention uses techniques disclosed in U.S. Patent Application Ser. No. 60/382,036, entitled "Computer systems and methods for subdividing a complex disease into component diseases," filed May 20, 2002. The classification scheme uses a plurality of cellular constituent measurements from each organism in the single second species. Genetic analysis module 80 includes instructions that, for at least one subpopulation in the plurality of subpopulations, performs quantitative genetic analysis on the subpopulation in order to identify the quantitative trait locus for the complex trait. Ortholog identification module 5402 comprises instructions for finding the quantitative trait locus in the single first species that is the ortholog of the quantitative trait locus in the single second species. See, for example, Sections 5.17.1 and 1.17.2.

5.17.4. Subdividing Schemes

This section describes an approach to subdividing a population into subpopulations.

Step 7102. In step 7102 (FIG. 71A), a trait is selected for study in a species. In some embodiments, the trait is a complex trait. The species can be a plant, animal, human, or bacterial. In some embodiments, the species is human, cat, dog, mouse, rat, monkey, pigs, *Drosophila*, or corn. In some embodiments, a plurality of organisms representing the species are studied. The number of organism in the species can be any number. In some embodiments, the plurality of organisms studied is between 5 and 100, between 50 and 200, between 100 and 500, or more than 500.

In some embodiments, a portion of the organisms under study are subjected to a perturbation that affects the trait. The perturbation can be environmental or genetic. Examples of environmental perturbations include, but are not limited to, exposure of an organism to a test compound, an allergen, pain, hot or cold temperatures. Additional examples of environmental perturbations include diet (e.g. a high fat diet or low fat diet), sleep deprivation, isolation, and quantifying a natural environmental influences (e.g., smoking, diet, exercise). Examples of genetic perturbations include, but are not limited to, the use of gene knockouts, introduction of an inhibitor of a predetermined gene or gene product, N-Ethyl-N-nitrosourea (ENU) mutagenesis, siRNA knockdown of a gene, or quantifying a trait exhibited by a plurality of organisms of a species.

The perturbation optionally used in step 7102 is selected because of some relationship between the perturbation and the trait. For example, the perturbation could be the siRNA knockdown of a gene that is thought to influence the trait under study. Examples of traits that can be studied in the systems and methods of the present invention are disclosed in Section 5.15.

Step 7104. In step 7104 (FIG. 71A), the levels of cellular constituents are measured from the plurality of organisms 46 in order to derive gene expression/cellular constituent data 44. The identity of the tissue from which such measurements are made will depend on what is known about the trait under study. In some embodiments, cellular constituent measurements are made from several different tissues.

Generally, the plurality of organisms 46 exhibit a genetic variance with respect to the trait. In some embodiments, the trait is quantifiable. For example, in instances where the trait is a disease, the trait can be quantified in a binary form (e.g., "1" if the organism has contracted the disease and "0" if the organism has not contracted the disease). In some embodiments, the trait can be quantified as a spectrum of values and the plurality of organisms 46 will represent several different values in such a spectrum. In some embodiments, the plurality of organisms 46 comprise an untreated (e.g., unexposed, wild type, etc.) population and a treated population (e.g., exposed, genetically altered, etc.). In some embodiments, for example, the untreated population is not subjected to a perturbation whereas the treated population is subjected to a perturbation. In some embodiments, the secondary tissue that is measured in step 7104 is blood, white adipose tissue, or some other tissue that is easily obtained from organisms 46.

In varying embodiments, the levels of between 5 cellular constituents and 100 cellular constituents, between 50 cellular constituents and 100 cellular constituents, between 300 and 1000 cellular constituents, between 800 and 5000 cellular constituents, between 4000 and 15,000 cellular constituents, between 10,000 and 40,000 cellular constituents, or more than 40,000 cellular constituents are measured.

In one embodiment, gene expression/cellular constituent data 44 comprises the processed microarray images for each individual (organism) 46 in a population under study. In some embodiments, such data comprises, for each individual 46, intensity information 50 for each gene/cellular constituent 48 represented on the microarray. In some embodiment, cellular constituent data 44 is, in fact, protein expression levels for various proteins in a particular tissue in organisms 46 under study.

In one aspect of the present invention, cellular constituent levels are determined in step 7104 by measuring an amount of the cellular constituent in a predetermined tissue of the organism. As used herein, the term "cellular constituent" comprises individual genes, proteins, mRNA expressing genes, metabolites and/or any other cellular components that can affect the trait under study. The level of a cellular constituent can be measured in a wide variety of methods. Cellular constituent levels, for example, can be amounts or concentrations in the secondary tissue, their activities, their states of modification (e.g., phosphorylation), or other measurements relevant to the trait under study.

In one embodiment, step 7104 comprises measuring the transcriptional state of cellular constituents 48 in tissues of organisms 46. The transcriptional state includes the identities and abundances of the constituent RNA species, especially mRNAs, in the tissue. In this case, the cellular constituents are RNA, cRNA, cDNA, or the like. The transcriptional state of the cellular constituents can be measured by techniques of hybridization to arrays of nucleic acid or nucleic acid mimic probes, or by other gene expression technologies. Transcript arrays are discussed in Section 5.8.

In another embodiment, step 7104 comprises measuring the translational state of cellular constituents 48. In this case, the cellular constituents are proteins. The translational state includes the identities and abundances of the proteins in the organisms 46. In one embodiment, whole genome monitoring of protein (i.e., the "proteome," Goffeau et al., 1996, Science 274, p. 546) can be carried out by constructing a microarray in which binding sites comprise immobilized, preferably monoclonal, antibodies specific to a plurality of protein species encoded by the secondary tissue. Preferably, antibodies are present for a substantial fraction of the encoded proteins. Methods for making monoclonal antibodies are well known. See, for example, Harlow and Lane, 1998, *Antibodies: A Laboratory Manual*, Cold Spring Harbor, N.Y. In one embodiment, monoclonal antibodies are raised against synthetic peptide fragments designed based on genomic sequences. With such an antibody array, proteins from the organism are contacted with the array and their binding is assayed with assays known in the art. In some embodiments, antibody arrays for high-throughput screening of antibody-antigen interactions are used. See, for example, Wildt et al., Nature Biotechnology 18, p. 989.

Alternatively, large scale quantitative protein expression analysis can be performed using radioactive (e.g., Gygi et al., 1999, Mol. Cell. Biol 19, p. 1720) and/or stable iostope ($^{15}N$) metabolic labeling (e.g., Oda et al. Proc. Natl. Acad. Sci. USA 96, p. 6591) followed by two-dimensional (2D) gel separation and quantitative analysis of separated proteins by scintillation counting or mass spectrometry. Two-dimensional gal electrophoresis is well-known in the art and typically involves focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, Proc Nat'l Acad. Sci. USA 93, p. 1440; Sagliocco at al., 1996, Yeast 12, p. 1519; Lander 1996, Science 274, p. 536; and Naaby-Haansen at al., 2001, TRENDS in Pharmacological Science 22, p. 376. Electropherograms can be analyzed by numerous techniques, including mass spectrometric techniques, western blotting and immunoblot analysis using polyclonal and monoclonal antibodies, and internal and N-terminal microsequencing. See, for example, Gygi, et al., 1999, Nature Biotechnology 17, p. 994. In some embodiments, fluorescence two-dimensional difference gel electrophoresis (DIGE) is used. See, for example, Beaumont et al., Life Science News 7, 2001. In some embodiments, quantities of proteins in the secondary tissue of organisms 46 are determined using isotope-coded affinity tags (ICATs) followed by tandem mass spectrometry. See, for example, Gygi et al., 1999, Nature Biotech 17, p. 994. Using such techniques, it is possible to identify a substantial fraction of the proteins expressed in a predetermined secondary tissue in organisms 46.

In other embodiments, step 7104 comprises measuring the activity or post-translational modifications of the cellular constituents in the plurality of organisms 46. See for example, Zhu and Snyder, Curr. Opin. Chem. Biol 5, p. 40; Martzen et al., 1999, Science 286, p. 1153; Zhu et al., 2000, Nature Genet. 26, p. 283; and Caveman, 2000, J. Cell. Sci. 113, p. 3543. In some embodiments, measurement of the activity of the cellular constituents is facilitated using techniques such a protein microarrays. See, for example, MacBeath and Schreiber, 2000, Science 289, p. 1760; and Zhu et al., 2001, Science 293, p. 2101. In some embodiments, post-translation modifications or other aspects of the state of cellular constituents are analyzed using mass spectrometry. See, for example, Aebersold and Goodlett, 2001, Chem Rev 101, p. 269; Petricoin III, 2002, The Lancet 359, p. 572.

In some embodiments, the proteome of organisms 46 under study is analyzed in step 7104. The analysis of the proteome (e.g., the quantification of all proteins and the determination of their post-translational modifications) typically involves the use of high-throughput protein analysis methods such as microarray technology. See, for example, Templin et al., 2002, TRENDS in Biotechnology 20, p. 160; Albala and Humphrey-Smith; 1999, Curr. Opin. Mol. Ther. 1, p. 680; Cahill, 2000, *Proteomics: A Trends Guide*, p. 47-51; Emili and Cagney, 2000, Nit. Biotechnol., 18, p. 393; and Mitchell, Nature Biotechnology 20, p. 225.

In still other embodiments, "mixed" aspects of the amounts cellular constituents are measured in step 7104. In one example, the amounts or concentrations of one set of cellular constituents in the organisms 46 under study are combined with measurements of the activities of certain other cellular constituents in such organisms.

In some embodiments, different allelic forms of a cellular constituent in a given organism are detected and measured in step 7104. For example, in a diploid organism, there are two copies of any given gene, one descending from the "father" and the other from the "mother." In some instances, it is possible that each copy of the given gene is expressed at different levels. This is of significant interest since this type of allelic differential expression could associate with the trait under study, particularly in instances where the trait under study is complex.

Step 7106. Once gene expression/cellular constituent data 44 has been obtained, the data is transformed (FIG. 71A, step 7106) into expression statistics. In some embodiments, cellular constituent data 44 (FIG. 1) comprises transcriptional data, translational data, activity data, and/or metabolite abundances for a plurality of cellular constituents. In one embodiment, the plurality of cellular constituents comprises at least five cellular constituents. In another embodiment, the plurality of cellular constituents comprises at least one hundred cellular constituents, at least one thousand cellular constituents, at least twenty thousand cellular constituents, or more than thirty thousand cellular constituents.

The expression statistics commonly used as quantitative traits in the analyses in one embodiment of the present invention include, but are not limited to, the mean log ratio, log intensity, and background-corrected intensity derived from transcriptional data. In other embodiments, other types of expression statistics are used as quantitative traits.

In one embodiment, this transformation (FIG. 71A, step 7106) is performed using normalization module (not shown). In such embodiments, the expression level of each of a plurality of genes in each organism under study is normalized. Any normalization routine can be used by the normalization module. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines can be run. Exemplary normalization routines in accordance with the present invention are disclosed in more detail in Section 5.3.

Step 7150. In the preceding steps, a trait is identified, cellular constituent level data is measured, and the cellular constituent data is transformed into expression statistics. In step 7150 (FIG. 71A), one or more phenotypes are measured for each organism 46 in the population under study. FIG. 72 summarizes the data that is measured as a result of steps 7102-7106 and 7150. For each organism 46 in the population under study there are at least two classes of data collected. The first class of data collected is phenotypic information 7201. Phenotypic information 7201 can be anything related to the trait under study. For example, phenotypic information 7201 can be a binary event, such as whether or not a particular organism exhibits the phenotype (+/−). The phenotypic information can be some quantity, such as the results of an obesity measurement for the respective organism 246. As illustrated in FIG. 72, there can be more than one phenotypic measurement made per organism 46.

The second class of data collected for each organism 46 in the population under study is cellular constituent levels 50 (e.g., amounts, abundances) for a plurality of cellular constituents (steps 1204-1206, FIG. 71A). Although not illustrated in FIG. 71, there can be several sets of cellular constituent measurements for each organism. Each of these sets could represent cellular constituent measurements measured in the respective organism 46 after the organism has been subjected to a perturbation that affects the trait under study. Representative perturbations include, but are not limited to, exposing the organism 46 to an amount of a compound. Further, each set of cellular constituents for a respective organism 46 could represent measurements taken from a different tissue in the organisms. For example, one set of cellular constituent measurements could be from a blood sample taken from the respective organism while another set of cellular constituent measurements could be from fat tissue from the respective organism.

Step 7152. In step 7152 (FIG. 71A), the phenotypic data 7201 (FIG. 72) collected in step 7150 is used to divide the population into phenotypic groups 7310 (FIG. 73). The method by which step 7152 is accomplished is dependent upon the type of phenotypic data measured in step 7150. For example, in the case where the only phenotypic data is whether or not the organism 46 exhibits a particular trait, step 7152 is straightforward. Those organisms 46 that exhibit the trait are placed in a first group and those organisms 46 that do not exhibit the trait are placed in a second group. A slightly more complex example is where amounts 7201 represent gradations of a quantified trait exhibited by each organism 46. For example, in the case where the trait is obesity, each amount 7201 can correspond to an obesity index (e.g., body mass index, etc.) for the respective organism 46. In this second example, organisms 46 can be binned into phenotypic groups 7310 as a function of the obesity index.

In yet another example in accordance with the invention, several phenotypic measurements can be collected for a given organism 46. In such embodiments, each phenotypic measurement 7201 for a respective organism 46 can be treated as elements of a phenotypic vector corresponding to the respective organism 46. These phenotypic vectors can then be clustered using, for example, any of the clustering techniques disclosed in Section 5.5 in order to derive phenotypic groups 7310. To illustrate, in one example, the organisms 46 are human and measurements 7201 are derived from a standard 12-lead electrocardiogram graph (ECG). The standard 12-lead ECG is a representation of the heart's electrical activity recorded from electrodes on the body surface. The ECG provides a wealth of phenotypic data including, but not limited to, heart rate, heart rhythm, conduction, wave form description, and ECG interpretation (typically a binary event, e.g., normal, abnormal). Each of these different phenotypes (heart rate, heart rhythm) can be quantified as elements in a phenotypic vector. Further, some elements of the phenotypic vector (e.g., ECG interpretation) can be given more weight during clustering. For instance, the ECG measurements can be augmented by additional phenotypes such as blood cholesterol level, blood triglyceride level, sex, or age in order to derive a phenotypic vector for each respective organism 46. Once suitable phenotypic vectors are constructed, they can be clustered using any of the clustering algorithms in Section 5.5 in order to identify phenotypic groups 7310.

In some embodiments, step 7152 is an iterative process in which various phenotypic vectors are constructed and clustered until a form of phenotypic vector that produces clear, distinct groups is identified. Of particular interest are those phenotypic vectors that are capable of producing phenotypic groups 7310 that are uniquely characterized by certain phenotypes (e.g., an abnormal ECG/high cholesterol subgroup, a normal ECG/low cholesterol subgroup).

Using the example presented above, phenotypic vectors that can be iteratively tested include a vector that has ECG data only, one that has blood measurements only, one that is a combination of the ECO data and blood measurements, one that has only select ECG data, one that has weighted ECG data, and so forth. Furthermore, optimal phenotypic vectors can be identified using search techniques such as stochastic search techniques (e.g., simulated annealing, genetic algorithm). See, for example, Duda et al., 2001, *Pattern Recognition*, second edition, John Wiley & Sons, New York.

Step 7154. In step 7154, the phenotypic extremes within the population are identified. For example, in one case, the trait of interest is obesity. In step 7154, very obese and very skinny organisms 46 can be selected as the phenotypic extremes. In one embodiment of the present invention, a phenotypic extreme is defined as the top or lowest $40^{th}$, $30^{th}$, $20^{th}$, or $10^{th}$ percentile of the population with respect to a given phenotype exhibited by the population.

Step 7156. In step 7156, a plurality of cellular constituents (levels 50, FIG. 72) for the species represented by organisms 46 are filtered. Only levels 50 measured for phenotypically extreme organisms 46 selected in step 7154 are used in this filtering. To illustrate using FIG. 73, consider the case in which organism 46-1 and organism 46-N represent phenotypic extremes with respect to some phenotype whereas organism 46-2 does not. Then, in this instance, levels 50 measured for organism 46-6 and 46-N will be considered in the filtering whereas levels 50 measured for organism 46-2 will not be considered in the filtering.

In some embodiments, cellular constituent levels 50 (measured in phenotypically extreme organisms) for a given cellular constituent 48 are subjected to a t-test (or a multivariate test) to determine whether the given cellular constituent 48 can discriminate between the phenotypic groups 7310 (FIG. 73) that were identified in step 7152, above. A cellular constituent 48 will discriminate between phenotypic groups when the cellular constituent is found at characteristically different levels in each of the phenotypic groups 7310. For example, in the case where there are two phenotypic groups 7310, a cellular constituent will discriminate between the two groups 7310 when levels 50 of the cellular constituent (measured in phenotypically extreme organisms) are found at a first level in the first phenotypic group and are found at a second level in the second phenotypic group, where the first and second level are distinctly different.

In preferred embodiments, each cellular constituent is subjected to a t-test without consideration of the other cellular constituents in the organism. However, in other embodiments, groups of cellular constituents are compared in a multivariate analysis in step 7156 in order to identify those cellular constituents that discriminate between phenotypic groups 7310.

Step 7158. Typically, there will be a large number of cellular constituents expressed in phenotypically extreme organisms that appear to differentiate between the phenotypic groups identified in step 7152. In some instances, this number of cellular constituents 48 can exceed the number of organisms 46 available for study. For instance, in some embodiments, 25,000 genes or more are considered in previous steps. Thus, there may be hundreds if not thousands of genes that discriminate. In some instances, these discriminating cellular constituents are analyzed in subsequent steps with statistical models that involve many statistical parameters that increase with the number of predictors. In such instances, it is desirable to reduce the number of cellular constituents using a reducing algorithm. However, in other instances, other forms of statistical analysis are used that do not require reduction in the number of cellular constituents under consideration.

The reducing algorithms that are optionally used in step 7158 use the p-value or other form of metric computed for each cellular constituent in step 7156 as a basis for reducing the dimensionality of the cellular constituent set identified in step 7156. A few exemplary reducing algorithms will be discussed. However, those of skill in the art will appreciate that many reducing algorithms are known in the art and all such algorithms can be used in step 7158.

One reducing algorithm is stepwise regression. The basic procedure in stepwise regression involves (1) identifying an initial model (e.g., an initial set of cellular constituents), (2) iteratively "stepping," that is, repeatedly altering the model at the previous step by adding or removing a predictor variable (cellular constituent) in accordance with the "stepping criteria," and (3) terminating the search when stepping is no longer possible given the stepping criteria, or when a specified maximum number of steps has been reached. Forward stepwise regression starts with no model terms (i.e., no cellular constituents). At each step the regression adds the most statistically significant term until there are none left. Backward stepwise regression starts with all the terms in the model and removes the least significant cellular constituents until all the remaining cellular constituents are statistically significant. It is also possible to start with a subset of all the cellular constituents and then add significant cellular constituents or remove insignificant cellular constituents until a desired dimensionality reduction is achieved.

Another reducing algorithm that can be used in step 7158 is all-possible-subset regression. In fact, all-possible-subset regression can be used in conjunction with stepwise regression. The stepwise regression search approach presumes there is a single "best" subset of cellular constituents and seeks to identify it. In the all-possible-subset regression approach, the range of subset sizes that could be considered to be useful is made. Only the "best" of all possible subsets within this range of subset sizes are then considered. Several different criteria can be used for ordering subsets in terms of "goodness", such as multiple R-square, adjusted R-square, and Mallow's Cp statistics. When all-possible-subset regression is used in conjunction with stepwise methods, the subset multiple R-square statistic allows direct comparisons of the "best" subsets identified using each approach.

Another approach to reducing higher dimensional space into lower dimensional space in accordance with step 7158 (FIG. 71A) of the present invention is the use of linear combinations of cellular constituents. In effect, linear methods project high-dimensional data onto a lower dimensional space. Two approaches for accomplishing this projection include Principal Component Analysis (PCA) and Multiple-Discriminant Analysis (MDA). PCA seeks a projection that best represents the data in a least-squares sense whereas MDA seeks a projection that bests separates the data in a least-squares sense. See, for example, Duda et al., 2001, *Pattern Classification*, Chapters 3 and 10.

The ultimate goal of step 7158 is to identify a classifier derived from the set of cellular constituents identified in step 7156 or a subset of the cellular constituents identified in step 7156 that satisfactorily classifies organisms 46 into the phenotypic groups 7310 identified in step 7152. In some embodiments of the present invention, stochastic search methods such as simulated annealing can be used to identify such a classifier or subset. In the simulated annealing approach, for example, each cellular constituent under consideration can be assigned a weight in a function that assesses the aggregate ability of the set of cellular constituents identified in step 7156 to discriminate the organisms 46 into the phenotypic classes identified in step 7152. During the simulated annealing algorithm these weights can be adjusted. In fact, some cellular constituents can be assigned a zero weight and, therefore, be effectively eliminated during the anneal thereby effectively reducing the number of cellular constituents used in subsequent steps. Other stochastic methods that can be used in step 7158 include, but are not limited to, genetic algorithms. See, for example, the stochastic methods in Chapter 7 of Duda et al., 2001, *Pattern Classification*, second edition, John Wiley & Sons, New York.

Step 7160. In some embodiments, the cellular constituents identified in steps 7156 and/or 7158 are clustered in order to further identify subgroups within each phenotypic subpopulation. To perform such clustering, an expression vector is created for each cellular constituent under consideration. To create an expression vector for a respective cellular constituent, the levels 7201 measured for the respective cellular constituent in each of the phenotypically extreme organisms is used as an element in the vector. For example, consider the case in which an expression vector for cellular constituent 48-1 is to be constructed from organisms 46-1, 46-2, and 46-3. Levels 50-1-1, 50-2-1, and 50-3-1 would serve as the three elements of the expression vector that represents cellular constituent 48-1. Each of the expression vectors are then clustered using for example, any of the clustering techniques described in Section 5.5. In one embodiment, k-means clustering (Section 5.5.2) is used.

An advantage of step 7160 is that subpopulations 7320 (FIG. 73) that cannot be differentiated based upon phenotype can be identified. Such subgroups 7320 can be used to refine a classifier that classifies organisms into classes, as detailed in the following steps.

Step 7164. In step 7164, the set of cellular constituents identified as discriminators between phenotypic extremes that were identified in previous steps (or principal components derived from such cellular constituents) are used to build a classifier. This set of cellular constituents actually refines the definition of the cinical phenotype under study.

A number of pattern classification techniques can be used to accomplish this task, including, but not limited to, Bayesian decision theory, maximum-likelihood estimation, linear discriminant functions, multilayer neural networks, and supervised as well as unsupervised learning.

In one embodiment in accordance with step 7164, the set of cellular constituents that discriminate the phenotypically extreme organisms into phenotypic groups is used to train a neural network using, for example, a back-propagation algorithm. In this embodiment, the neural network serves as a classifier. First, the neural network is trained with the set of cellular constituents that discriminate the phenotypically extreme organisms into phenotypic groups. In more detail, the cellular constituent values (e.g., measured levels 50 of cellular constituents 48 selected in previous steps) from all the organisms 46 in the phenotypically extreme groups are used to train the neural network. Then, the trained neural network is used to classify the general population into phenotypic groups. In some embodiments the neural network that is trained is a multilayer neural network. In other embodiments, a projection pursuit regression, a generalized additive model, or a multivariate adaptive regression spline is used. See for, example, any of the techniques disclosed in Chapter 6 of Duda et al., 2001, *Pattern Classification*, second edition, John Wiley & Sons, Inc., New York.

In another embodiment in accordance with step 7164, Bayesian decision theory can be used to build a classifier using the selected cellular constituent data. Bayesian decision theory plays a role when there is some a priori information about the things to be classified. Here, the set of cellular constituents that discriminate the phenotypically extreme organisms into phenotypic groups serves as the a priori information. More specifically, the intensity or cellular constituent levels 50 for the cellular constituents 48 selected in steps 7156-7160 from each of the phenotypically extreme organisms 46 serve as the a priori information. For more information on Bayesian decision theory, see for, example, any of the techniques disclosed in Chapters 2 and 3 of Duda et al., 2001, *Pattern Classification*, second edition, John Wiley & Sons, Inc., New York.

In still another embodiment in accordance with step 7164, linear discriminate analysis (functions), linear programming algorithms, or support vector machines are used to create a classifier that is capable of classifying the general population of organisms 46 into phenotypic groups 7310. This classification is based on the cellular constituent data 50 for the cellular constituents 248 that refined the definition of the clinical phenotype (i.e. the cellular constituents selected in steps 7156, 7158, and/or 7160. For more information on this class of pattern classification functions, see for, example, any of the techniques disclosed in Chapter 5 of Duda et al., 2001, *Pattern Classification*, second edition, John Wiley & Sons, Inc., New York.

Step 7166. In step 7166, the classifier derived in step 7164 is used to classify all or a substantial portion (&g., more than 30%, more than 50%, more than 75%) of the population under study. Essentially, the classifier bins the remaining population (the portions of the population that do not include the phenotypic extremes) without taking their phenotypic (e.g., phenotype amounts 7201, FIG. 72) into consideration. The process of using the classifier to classify the general population produces phenotypic subgroups 7350 (FIG. 73). Phenotypic subgroups 7350 are, in fact, a refinement of the trait under study.

Step 7168. The steps leading to and including step 7160 serve to identify cellular constituents that are capable of classifying organisms into phenotypic groups. In step 7164, this set of cellular constituents is used to construct a classifier that is capable of classifying the general population under study into phenotypic groups 7310. In many pattern classification techniques, such as a back-propagation algorithm that uses a multilayer network, the classifier constructed in step 7164 will no longer be the simple subset of cellular constituents identified in steps 7156 through 7160. Rather, the form of the classifier will depend on the type of pattern recognition technique used to develop the classifier. In some embodiments, however, the classifier derived in step 7164 can be a set of cellular constituents in the case where the classification scheme is a simple decision tree (e.g., if level for constituent 5 is greater than 50 than place in phenotypic class B).

Regardless of its form, the classifier formed in step 7164 serves to further refine the phenotypic groups 7310 defined in step 7152 or the subgroups 7320 defined in step 7160. As such, the methods disclosed in this section can be used to refine a trait under study. This refinement is illustrated in FIG. 73. At the outset, the trait under study is exhibited by some population 7300 of organisms 46. In step 7152 of the method, observation of gross (visible, measurable) phenotypes (other than cellular constituent levels) related to the trait are used to divide the general population 7300 into two or more phenotypic groups 7310 (FIG. 73). In step 7160 of the method, optional clustering of select cellular constituents serves to refine a phenotypic group into subphenotypic groups 7320 (FIG. 73).

A benefit of step 7160 is that the clustering in step 7160 refines the trait under study into groups 7320 (FIG. 73) that are not distinguishable using gross observable phenotypic data (other than cellular constituent levels) such as amounts 7201 (FIG. 72). As such, optional step 7160 provides a powerful way to refine the definition of the clinical trait under study by focusing on those cellular constituents that actually give rise to the clinical trait or well reflects the varied biochemical response to that trait. However, the refinement provided in step 7160 is incomplete because it is based on only a select portion of the general population under study, those organisms that represent phenotypic extremes. Accordingly, in step 7164, a more robust classifier is built using the initial set of cellular constituents selected based upon phenotypic extremes organisms 46 as a starting point. As illustrated in FIG. 73, in step 7166, the classifier derived in step 7164 classifies the trait under study into highly refined subgroups 7350. Thus, although only gross categories such as groups 7310 or 7320 were used to develop the classifier, the classifier will split the population into clusters that can fall within groups 7310 and/or 1120. These clusters are denoted as subgroups 7350 in FIG. 73. Each of these subgroups 7350 serves to refine the trait under study. In other words, each of the subgroups 7350 is a more homogenous form of the overall trait under study. The classifier classifies the general population without considering phenotypic data (e.g., levels 7201, FIG. 72). Therefore, it is possible that the groups 7350 will not fall neatly within groups 7320 and/or 7310.

The classifier developed using the methods described in this section serves to refine the definition of a trait of interest. Thus, each group 7350 in FIG. 73 identified using the classifier represents a more homogenous population with respect to the trait of interest. Cellular constituent measurements from organisms in respective groups 7350 can be used as quantitative traits in quantitative genetic studies such as linkage analysis (Section 5.13) or association analysis (5.14). It is expected that linkage analysis and/or association analysis using data from individual groups 7350 rather than the general population will provide improved results, particularly in situations where the trait under study is complex and/or is driven by many different genes. In such instances, the individual groups 7350 could represent a more homogenous population or state. Consequently the genes that drive or link to the QTL (or loci) patterns in such populations 7350 could be easier to identify than in the case where cellular constituent data form the entire population is used as quantitative traits in such studies. An example where quantitative genetic analysis on subgroups rather than the general population was used to identify genes associated with a trait of interest is provided in Schadt et al., 2003, Nature 422, p. 297.

5.18. Obesity Related Genes and Obesity Related Gene Products

In Section 6.7.1, four genes were discovered on mouse chromosome number 2 by co-localizing cQTL for the mouse obesity related traits (1) subcutaneous fat pad mass (FIG. 20, curve 2002), (2) perimetrial fat pad mass (FIG. 20, curve 2004), (3) omental fat pad mass (FIG. 20, curve 2006), and (4) adiposity (FIG. 20, curve 2008) with four cQTL with lod scores greater than 3.0 that correspond to genes whose physical locations are within the vicinity (e.g., 2 cM) of the four cQTL.

Using the methods of the present invention as described, for example, in Section 5.17 above, the human orthologs to these four mouse genes were determined. The four mouse genes, their gene products, and their human orthologs are summarized in Tables 3 and 4 in Section 6.7.5 below (SEQ ID NO: 1 through SEQ ID NO: 29). Together, these genes and proteins are referred to as "obesity related genes" and "obesity related gene products" of the present invention.

The term "obesity related genes" includes cDNAs or other nucleic acids that encode any one of SEQ ID NO: 4, SEQ ID NO: 5, SEQ ID NO: 6, SEQ ID NO: 7, SEQ ID NO: 8, SEQ ID NO: 10, SEQ ID NO: 11, SEQ ID NO: 14, SEQ ID NO: 15, SEQ ID NO: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29 in whole or in part. As such, the term "obesity related genes" includes the nucleic acid sequence set forth in SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20. The "obesity related genes" of the invention include human and mouse genes as well as related genes (homologs or orthologs) in other species.

The term "obesity related gene products" includes amino acid macromolecules that includes a sequence as substantially set forth in any one of SEQ ID NO: 4, SEQ ID NO: 5, SEQ ID NO: 6, SEQ ID NO: 7, SEQ ID NO: 8, SEQ ID NO: 10, SEQ ID NO: 11, SEQ ID NO: 14, SEQ ID NO: 15, SEQ ID NO: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29 as described in Section 6.7.5.

In specific embodiment, the "obesity related genes" and "obesity related gene products" are from vertebrates, or more particularly, mammals. Production of the foregoing proteins and derivatives, e.g., by recombinant methods, is provided.

The invention also relates to obesity related gene products that are functionally active, i.e., they are capable of displaying one or more known functional activities associated with a full-length (wild-type) obesity related gene product.

The invention further relates to fragments, and derivatives thereof; of obesity related gene products that comprise one or more domains of an obesity related gene product. Antibodies to obesity related gene products and derivatives of such antibodies (e.g., the binding domain of such antibodies) are further provided by the present invention.

The present invention further relates to therapeutic and diagnostic methods and compositions based on obesity related genes and/or obesity related gene products as well as antibodies that bind to the obesity related gene products.

Animal models, diagnostic methods and screening methods for predisposition to disorders are also provided by the invention.

The invention further provides methods of treatment of obesity and obesity related diseases such as anorexia nervosa, bulimia nervosa, and cachexia using modulators of the obesity related genes and obesity related gene products described in Section 6.7.5. Modulator, e.g., inhibitors and agonists, of the obesity related genes and obesity related gene products described in Section 6.7.5. can be identified by any method known in the art. In particular, molecules can be assayed for their ability to promote or inhibit (modulate) the expression of the obesity related genes described in Section 6.7.5. Once modulators are identified, they can be assayed for therapeutic efficacy using any assay available in the art for obesity.

Modulators may be identified by screening for molecules that bind to the obesity related gene products described in Section 6.7.5. Molecules that bind such gene products may be identified in many ways that are well known and routine in the art. For example, but not by way of limitation, by overexpressing such a gene product (e.g., SEQ ID NO: 8, SEQ ID NO: 11, SEQ ID NO: 15, SEQ ID NO: 18, SEQ ID NO: 25, SEQ ID NO: 26, or SEQ ID NO: 27) in a cell line that endogenously expresses little or none of the gene product and assaying for molecules that bind to the cells overexpressing the gene product and that do not bind to the cells not overexpressing the gene product; or by conjugating the gene product to a solid support (e.g., a chromatography resin) contacting the conjugated gene product to a solid support with a molecule of interest, isolating the solid support and determining whether the molecule of interest bound to the gene product. Other methods include, screening phage display libraries, combinatorial chemical libraries and the like for binding to one or more of the gene products described in Section 6.7.5.

5.18.1. Screening for Obesity Related Gene Agonists and Antagonists

The amino acid and nucleotide sequences for the obesity related genes and obesity related gene products of the present invention are illustrated in FIGS. 27-32, 34-38, and 40-53. Thus, these nucleotide and amino acid sequences can be used to prepare protein for screening by methods that are routine and well known in the art (see, e.g., Sambrook et al., 2001, Molecular Cloning, A Laboratory Manual, Third Edition, Cold Spring Harbor Laboratory Press, N.Y.; and Ausubel et al., 1989, Current Protocols in Molecular Biology, Green Publishing Associates and Wiley Interscience, N.Y., both of which are hereby incorporated by reference in their entireties). For example, using any of the gene sequences disclosed in Section 6.7.5, oligonucleotide primers for PCR amplification can be designed. PCR amplification is then used to amplify specifically the obesity related protein coding sequence, which can be cloned into an appropriate expression vector using routine techniques. That vector may then be introduced into bacterial or cultured eukaryotic cells (e.g., cultured mammalian cells, insect cells, etc) such that the obesity related gene product is expressed in the bacterial or cultured call. The obesity related gene product may then be isolated from the bacterial or eukaryotic cell culture.

By way of example, diversity libraries, such a random or combinatorial peptide or nonpeptide libraries can be screened for molecules that specifically bind to and/or modulate the function of the obesity related gene product. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767-773; Houghton et al., 1991, Nature 354:84-86; Lam et al., 1991, Nature 354:82-84; Medynski, 1994, BioTechnology 12:709-710; Gallop et al., 1994, J. Medicinal Chemistry 37(9):1233-1251; Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayaw-ickreme et al., 1994, Proc. Natl. Acad. Sci. USA 91:1614-1618; Salmon at a., 1993, Proc. Natl. Acad. Sci. USA 90:11708-11712; PCT Publication No. WO 93/20242; and Brenner and Lerner, 1992, Proc. Natl. Acad. Sci. USA 89:5381-5383.

Examples of phage display libraries are described in Scott and Smith, 1990, Science 249:386-390; Devlin et al., 1990, Science, 249:404-406; Christian, R. B., et al., 1992, J. Mol. Biol. 227:711-718; Lenstra, 1992, J. Immunol. Meth. 152: 149-157; Kay a al., 1993, Gene 128:59-65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022-9026.

By way of examples of nonpeptide libraries, a benzodiazepine library (see e.g., Bunin et al., 1994, Proc. Natl. Acad. Sci. USA 91:4708-4712) can be adapted for use. Peptoid libraries (Simon et al., 1992, Proc. Natl. Acad. Sci. USA 89:9367-9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138-11142).

Screening the libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg at al., 1992, Proc. Natl. Acad. Sci. USA 89:5393-5397; Yu et al., 1994, Cell 76:933-945; Standt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. No. 5,096,815, U.S. Pat. No. 5,223,409, and U.S. Pat. No. 5,198,346, all to Ladner et al.; Rebar and Pabo, 1993, Science 263:671-673; and PCT Publication No. WO 94/18318.

In a specific embodiment, screening can be carried out by contacting the library members with an obesity related gene product disclosed in Section 6.7.5 (or nucleic acid or derivative) immobilized on a solid phase and harvesting those library members that bind to the protein (or nucleic acid or derivative). Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited hereinabove.

In another embodiment, the two-hybrid system for selecting interacting proteins in yeast (Fields and Song, 1989, Nature 340.245-246; Chien et al., 1991, Proc. Natl. Acad. Sci. USA 88:9578-9582) can be used to identify molecules that specifically bind to an obesity related gene product disclosed in Section 6.7.5 or derivative.

5.18.2. Isolation of Obesity Related Genes

The invention relates to the nucleotide sequences of nucleic acids. In a specific embodiment, the invention relates to nucleic acids that encode an amino acid sequence substantially as set forth in SEQ ID NO: 8 (FIG. 31), such as, for example, SEQ ID NO: 2 and SEQ ID NO: 3 (FIG. 28, 29). In further specific embodiments, nucleic acids of the present invention comprise the cDNA sequences of SEQ ID NO: 2 or SEQ ID NO: 3, the coding regions thereof or the complements thereto.

The invention provides purified nucleic acids consisting of at least 10 nucleotides (i.e., a hybridizable portion) of a nucleotide sequence encoding a SEQ ID NO: 2 or SEQ ID NO:3; in other embodiments, the nucleic acids consist of at least 10, 20, 50, 100, 150, or 200 contiguous nucleotides of a nucleotide sequence encoding SEQ ID NO: 2 or SEQ ID NO: 3, or a full-length coding sequence. In another embodiment, the nucleic acids are smaller than 35, 200 or 500 nucleotides in length. Nucleic acids can be single or double stranded. In another embodiment, the nucleic acids comprise a sequence of at least 10 nucleotides that encode a fragment of SEQ ID NO: 8, wherein the fragment of the SEQ ID NO: 8 displays one or more functional activities of SEQ ID NO: 8.

5.18.2.1. Low Stringency Conditions

The invention also relates to nucleic acids hybridizable to or complementary to the foregoing sequences. In specific aspects, nucleic acids are provided that comprise a sequence complementary to at least 10, 25, 50, 100, or 200 nucleotides or the entire coding region of a gene encoding SEQ ID NO: 8. The invention further relates to nucleic acid sequences that bind under conditions of low stringency to a nucleic acid that encodes SEQ ID NO: 8.

By way of example and not limitation, procedures using such conditions of low stringency are as follows (see also Shilo and Weinberg, 1981, Proc. Natl. Acad. Sci. U.S.A. 78:6789-6792): Filters containing DNA are pretreated for 6 h at 40° C. in a solution containing 35% formamide, 5×SSC, 50 mM Tris-HC (pH 7.5), 5 mM EDTA, 0.1% PVP, 0.1% Ficoll, 1% BSA, and 500 mg/ml denatured salmon sperm DNA. Hybridizations are carried out in the same solution with the following modifications: 0.02% PVP, 0.02% Ficoll, 0.2% BSA, 100 mg g/ml salmon sperm DNA, 10% (wt/vol) dextran sulfate, and 5–20×10$^6$ cpm 32P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and reexposed to film. Other conditions of low stringency that may be used are well known in the art (e.g., as employed for cross-species hybridizations).

5.18.2.2. High Stringency Conditions

In another specific embodiment, a nucleic acid hybridizable to a nucleic acid encoding SEQ ID NO: 8 under conditions of high stringency is provided. By way of example and not limitation, procedures using such conditions of high stringency are as follows. Prehybridization of filters containing DNA is carried out for 8 hours to overnight at 65° C. in buffer composed of 6×SSC, 50 mM Tris-HC (pH 7.5), 1 mM EDTA, 0.02% PVP, 0.02% Ficoll, 0.02% BSA, and 500 mg/ml denatured salmon sperm DNA. Filters are hybridized for 48 hours at 65° C. in prehybridization mixture containing 100 mg/ml denatured salmon sperm DNA and 5–20×10$^6$ cpm of 32P-labeled probe. Washing of filters is done at 37° C. for one hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency that may be used are well known in the art.

5.18.2.3. Moderate Stringency Conditions

In another specific embodiment, a nucleic acid that is hybridizable to a nucleic acid encoding SEQ ID NO: 8 under conditions of moderate stringency is provided. As used herein, conditions of moderate stringency, as known to those having ordinary skill in the art, and as defined by Sambrook et al., *Molecular Cloning: A Laboratory Manual*, 2 Ed. Vol. 1, pp. 1.101-104, Cold Spring Harbor Laboratory Press, 1989, include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, or Stark's solution, in 50% formamide at 42° C.), and washing conditions of about 60° C., 0.5×SSC, 0.1% SDS. See also, Ausubel et al., eds., in the *Current Protocols in Molecular Biology series of laboratory technique manuals*, © 1987-1997, Current Protocols, © 1994-1997, John Wiley and Sons, Inc.). The skilled artisan will recognize that the temperature, salt concentration, and chaotrope composition of hybridization and wash solutions may be adjusted as necessary according to factors such as the length and nucleotide base composition of the probe.

5.18.2.4. Derivatives and Antisense Nucleic Acids

Nucleic acids encoding derivatives of SEQ ID NO: 8 and antisense nucleic acids to genes encoding SEQ ID NO: 8 are additionally provided. As is readily apparent, as used herein, a nucleic acid encoding a fragment or portion of SEQ ID NO: 8 shall be construed as referring to a nucleic acid encoding only the recited fragment or portion of the specific SEQ ID NO: 8 and not the other contiguous portions of SEQ ID NO: 8a a continuous sequence.

5.18.2.5. Molecular Biology

For expression cloning (a technique commonly known in the art), an expression library is constructed by methods known in the at. For example, mRNA (e.g., human) is isolated, cDNA is made and ligated into an expression vector (e.g., a bacteriophage derivative) such that it is capable of being expressed by the host cell into which it is then introduced. Various screening assays can than be used to select for the expressed protein product. In one embodiment, anti-SEQ ID NO: 8 antibodies can be used for selection.

In another embodiment of the invention, polymerase chain reaction (PCR) is used to amplify the desired sequence in a genomic or cDNA library, prior to selection. Oligonucleotide primers representing known SEQ ID NO: 8-encoding sequences can be used as primers in PCR. In a preferred aspect, the oligonucleotide primers represent at least part of the conserved segments of strong homology between SEQ ID NO: 8-encoding genes of different species. The synthetic oligonucleotides may be utilized as primers to amplify by PCR sequences from RNA or DNA, preferably a cDNA library, of potential interest. Alternatively, one can synthesize degenerate primers for use in the PCR reactions.

In PCR according to the invention, the nucleic acid being amplified can include RNA or DNA, for example, mRNA, cDNA or genomic DNA from any eukaryotic species. PCR can be carried out, e.g., by use of a Perkin-Elmer Cetus thermal cycler and Taq polymerase. It is also possible to vary the stringency of hybridization conditions used in priming the PCR reactions, to allow for greater or lesser degrees of nucleotide sequence similarity between a known TCAP nucleotide sequence and a nucleic acid homolog being isolated. For cross-species hybridization, low stringency conditions are preferred. For same-species hybridization, moderately stringent conditions are preferred. After successful amplification of a segment of a SEQ ID NO: 8 gene homolog, that segment may be cloned, sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding SEQ ID NO: 8 may be identified.

The above recited methods are not meant to limit the following general description of methods by which clones of genes encoding SEQ ID NO: 8 may be obtained.

Any eukaryotic cell potentially can serve as the nucleic acid source for the molecular cloning of a SEQ ID NO: 8-encoding gene. The nucleic acid sequences encoding a SEQ ID NO: 8 homolog or ortholog can be isolated from vertebrate, mammalian, human, porcine, bovine, feline, avian, equine, canine, as well as additional primate sources. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989 *Molecular Coning, A Laboratory Manual*, 2$^{nd}$ ed., Cold Spring Harbor Laboratory Press, Cold Spring Harbor, N.Y.; Glover, D. M. (ed.), 1985, *DNA Cloning: A Practical Approach*, MRL Press, Ltd., Oxford, U.K. Vol. I, II). Clones derived from genomic DNA may contain regulatory and intron DNA regions in addition to coding regions; clones derived from. cDNA will contain only axon sequences. Whatever the source, the gene should be cloned into a suitable vector for propagation of the gene.

In the cloning of the gene from genomic DNA, DNA fragments are generated, some of which will encode the desired gene. The DNA may be cleaved at specific sites using various restriction enzymes. Alternatively, one may use DNASE in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if a gene encoding SEQ ID NO: 8 (of any species) or its specific RNA, or a fragment thereof is available and can be purified and labeled, the generated DNA fragments may be screened by nucleic acid hybridization to the labeled probe (Benton and Davis, 1977, Science 196:180; Grunstein & Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the gene may be detected by assays based on the physical, chemical, or immunological properties of its expressed product. For example, cDNA clones, or DNA clones that hybrid-select the proper mRNAs, can be selected that produce a protein having e.g., similar or identical electrophoretic migration, isoelectric focusing behavior, proteolytic digestion maps, kinase activity, inhibition of cell proliferation activity, substrate binding activity, or antigenic properties as known for SEQ ID NO: 8. If an antibody to SEQ ID NO: 8 is available, SEQ ID NO: 8 may be identified by binding of labeled antibody to the clone(s) putatively producing SEQ ID NO: 8 in an ELISA (enzyme-linked immunosorbent assay)-type procedure.

Alternatives to isolating the genomic DNA encoding SEQ ID NO: 8 include, but are not limited to, chemically synthesizing the gene sequence itself from a known sequence or making cDNA to the mRNA which encodes SEQ ID NO: 8. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Strataegne). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and SEQ ID NO: 8-encoding gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a Ashotgun approach. Enrichment for the desired gene, for example, by size fractionization, can be done before insertion into the cloning vector.

In specific embodiments, transformation of host cells with recombinant DNA molecules that incorporate the isolated SEQ ID NO: 8-encoding gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The nucleotide sequences encoding SEQ ID NO: 8 that are provided by the instant invention include those nucleotide sequences encoding substantially the same amino acid sequences as found in native SEQ ID NO: 8 proteins, and those encoded amino acid sequences with functionally equivalent amino acids. Sequences suitable for hybridization to SEQ ID NO: 12, SEQ ID NO: 16, and SEQ ID NO: 20 may be obtained in a similar fashion.

5.18.3. Placement of Obesity Related Genes in Expression Vectors

The nucleotide sequence coding for SEQ ID NO: 8 or a functionally active fragment or other derivative thereof can be inserted into an appropriate expression vector, i.e., a vector that contains the necessary elements for the transcription and translation of the inserted protein-coding sequence. The necessary transcriptional and translational signals can also be supplied by the native SEQ ID NO: 8 gene and/or its flanking regions. A variety of host-vector systems may be utilized to express the protein-coding sequence. These include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA.

The expression elements of vectors vary in their strengths and specificities. Depending on the host-vector system utilized, any one of a number of suitable transcription and translation elements may be used. In specific embodiments, the gene encoded by SEQ ID NO: 2 and SEQ ID NO: 3 is expressed, or a sequence encoding a functionally active portion of human SEQ ID NO: 8 encoded by one of these genes is expressed. In yet another embodiment, a fragment of SEQ ID NO: 8 comprising a domain of the particular protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding SEQ ID NO: 8 or peptide fragment thereof may be regulated by a second nucleic acid sequence so that the SEQ ID NO: 8 or peptide fragment thereof is expressed in a host transformed with the recombinant DNA molecule. For example, expression of SEQ ID NO: 8 may be controlled by any promoter/enhancer element known in the art. In a specific embodiment, the promoter is not a native promoter of the specific SEQ ID NO: 8-encoding gene. Promoters that may be used to control expression of SEQ ID NO: 8-encoding genes include, but are not limited to, the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78: 1441-1445), the regulatory sequences of the metallothionein gene (Brinster et al., 1982, Nature 296:39-42); prokaryotic expression vectors such as the b-lactamase promoter (Villa-Kamaroffer al., 1978, Proc. Natl. Acad. Sci. U.S.A. 75: 3727-3731), or the tat promoter (DeBoer et al., 1983, Proc. Natl. Acad. Sci. U.S.A. 80: 21-25); see also "Useful proteins from recombinant bacteria", Scientific American, 242: 74-94 (1980); or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region active in pancreatic acinar cells (Swift et al., 1984, Cell 38: 639-646; Ornitz et al., 1986, Cold Spring Harbor Symp. Quant. Biol. 50: 399-409; MacDonald, 1987, Hepatology 7:425-515); insulin gene control region active in pancreatic beta cells (Hanahan, 1985, Nature 315:115-122), immunoglobulin gene control region active in lymphoid cells (Grosschedl et al., 1984, Cell 38: 647-658); Adames et al., 1985, Nature 318:533-538); Alexander et al., 1987, Mol. Cell. Biol. 7:1436-1444), mouse mammary tumor virus control region active in testicular, breast, lymphoid and mast cells (Leder et al., 1986, Cell 45:485-495), albumin gene control region active in liver (Pinkert et al., 1987, Genes and Devel. 1: 268-276), alpha-fetoprotein gene control region active in liver (Krumlauf et al., 1985, Mol. Cell. Biol. 5: 1639-1648); Hammer et al., 1987, Science 235:53-58); alpha 1-antitrypsin gene control region active in the liver (Kelsey et al., 1987, Genes and Devel. 1:161-171), beta-globin gene control region active in myeloid cells (Mogram et al., 1985, Nature 315:338-340; Kollias et al., 1986, Cell 46:89-94; myelin basic protein gene control region active in oligodendrocyte cells in the brain (Readhead et al., 1987, Cell 48: 703-712); myosin light chain-2 gene control region active in skeletal muscle (Sani, 1985, Nature 314:283-286), and gonadotropic releasing hormone gene control region active in the hypothalamus (Masan et al., 1986, Science 234: 1372-1378).

In a specific embodiment, a vector is used that comprises a promoter operably linked to a SEQ ID NO: 8-encoding nucleic acid, one or more origins of replication, and, optionally, one or more selectable markers (e.g., an antibiotic resistance gene). In a specific embodiment, an expression construct is made by subcloning the coding sequence from a SEQ ID NO: 8 encoding gene into the EcoRI restriction site of each of the three pGEX vectors (Glutathione S-Transferase expression vectors; Smith and Johnson, 1988, Gene 7: 31-40). This allows for the expression of the SEQ ID NO: 8 product from the subclone in the correct reading frame.

Expression vectors containing SEQ ID NO: 8-encoding gene inserts can be identified by three general approaches: (a) nucleic acid hybridization, (b) presence or absence of marker gene functions, and (c) expression of inserted sequences. In the first approach, the presence of a SEQ ID NO: 8-encoding gene inserted in an expression vector can be detected by nucleic acid hybridization using probes comprising sequences that are homologous to an inserted SEQ ID NO: 8-encoding gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a SEQ ID NO: 8 encoding gene in the vector. For example, if the SEQ ID NO: 8-encoding gene is inserted within the marker gene sequence of the vector, recombinants containing the insert can be identified by the absence of the marker gene function. In the third approach, recombinant expression vectors can be identified by assaying the specific SEQ ID NO: 8 product expressed by the recombinant. Such assays can be based, for example, on the physical or functional properties of SEQ ID NO: 8 in in vitro assay systems, e.g., kinase activity, binding with antibodies directed to SEQ ID NO: 8, or inhibition of cell function(s) performed, facilitated or affected by SEQ ID NO: 8.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors that can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors.

In addition, a host cell strain may be chosen that modulates the expression of the inserted sequences, or modifies and processes the gene product in the specific fashion desired. Expression from certain promoters can be elevated in the presence of certain inducers; thus, expression of the genetically engineered SEQ ID NO: 8 may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. Far example, expression in a bacterial system can be used to produce an unglycosylated core protein product. Expression in yeast will produce a glycosylated product. Expression in mammalian cells can be used to ensure native glycosylation of a heterologous protein. Furthermore, different vector/host expression systems may affect processing reactions to different degrees.

In other specific embodiments, the SEQ ID NO: 8, or fragment or derivative thereof may be expressed as a fusion, or chimeric protein product, comprising the protein, fragment or derivative joined via a peptide bond to a protein sequence derived from a different protein. Such a chimeric product can be made by ligating the appropriate nucleic acid sequences encoding the desired amino acid sequences to each other by methods known in the art, in the proper coding frame, and expressing the chimeric product by methods commonly known in the art. In one embodiment, therefore, the invention includes an isolated nucleic acid comprising a sequence of at least 10 nucleotides encoding a chimeric SEQ ID NO: 8, wherein the chimeric SEQ ID NO: 8 displays at least one of the functional activities of the wild-type SEQ ID NO: 8, and at least one non-SEQ ID NO: 8 functional activity. Alternatively, such a chimeric product may be made by protein synthetic techniques, e.g., by use of a peptide synthesizer.

A person of skill in the art will appreciate that cDNA, genomic, and synthesized sequences can be cloned and expressed. One way to accomplish such expression is by transferring a SEQ ID NO: 8 encoding gene or fragment thereof, to cells in tissue culture. The expression of the transferred gene may be controlled by its native promoter, or can be controlled by a non-native promoter. In addition to transferring a nucleic acid comprising a nucleic acid sequence encoding an entire SEQ ID NO: 8 (i.e., equivalent to the wild type), the transferred nucleic acids can encode a functional portion of SEQ ID NO: 8, or a protein having at least 60% sequence identity to SEQ ID NO: 8 disclosed herein, as compared over the length SEQ ID NO: 8, or a polypeptide having at least 60% sequence similarity to a SEQ ID NO: 8 fragment, as compared over the length of the SEQ ID NO: 8 fragment. Introduction of the nucleic acid into the cell is accomplished by such methods as electroporation, lipofection, calcium phosphate mediated transfection, or viral infection. Usually, the method of transfer includes the transfer of a selectable marker to. the cells. The cells are then placed under selection to isolate those cells that have taken. up and are expressing the transferred gene. The expressed SEQ ID NO: 8 or fragments thereof are isolated and purified as described below, SEQ ID NO: 12, SEQ ID NO: 16, and SEQ ID NO: 20 may be manipulated in a similar fashion.

5.18.4. Purification of Obesity Related Gene Products

In particular aspects, the invention provides amino acid sequences of SEQ ID NO: 8, and fragments and derivatives thereof that comprise an antigenic determinant (i.e., can be recognized by an antibody) or which are otherwise functionally active, as well as nucleic acid sequences encoding the foregoing. A functionally active SEQ ID NO: 8 material as used herein refers to that material displaying one or more known functional activities associated with a full-length (wild-type) SEQ ID NO: 8.

In specific embodiments, the invention provides fragments of SEQ ID NO: 8 consisting of at least 6 amino acids, at least 10 amino acids, or at least 50 amino acids. In other embodiments, the proteins comprise or consist essentially of a functional domain of SEQ ID NO: 8. Nucleic acids encoding the foregoing are also provided.

Once a recombinant that expresses the SEQ ID NO: 8-encoding gene sequence, or part thereof is identified, the resulting product can be analyzed. This analysis is achieved by assays based on the physical or functional properties of the product, including radioactive labeling of the product followed by analysis by gel electrophoresis, immunoassay, etc. Once SEQ ID NO: 8, or a fragment thereof, is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay.

Alternatively, once SEQ ID NO: 8 produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller et al., 1984, Nature 310:105-111).

In another alternate embodiment, native SEQ ID NO: 8 protein is purified from natural sources, by standard methods such as those described above (e.g., immunoaffinity purification).

In a specific embodiment of the present invention, SEQ ID NO: 8, whether produced by recombinant DNA techniques or by chemical synthetic methods or by purification of native proteins, include but are not limited to those containing, as a primary amino acid sequence, all or part of the amino acid sequence substantially as depicted in FIG. 31 as well as fragments and other derivatives thereof including proteins homologous thereto. SEQ ID NO: 12, SEQ ID NO: 16, and SEQ ID NO: 20 may be purified in a similar fashion.

One embodiment of the present invention provides a purified protein comprising the amino acid sequence of SEQ ID NO: 8. Another embodiment of the present invention provides a purified protein encoded by a nucleic acid hybridizable under conditions of low stringency (see Section 5.18.2.1), high stringency (see Section 5.18.2.2), or moderate stringency (see Section 5.18.2.3) to a DNA having a sequence consisting of the coding region of SEQ ID NO: 2. Still another embodiment of the present invention provides a purified protein comprising an amino acid sequence that has at least 60% identity to the amino acid sequence set forth in SEQ ID NO: 8, in which percentage identity is determined over an amino acid sequence of identical size as SEQ ID NO: 8. Yet another embodiment of the present invention provides a purified protein comprising an amino acid sequence that has at least 90% identity to the amino acid sequence act forth in SEQ ID NO: 8, in which percentage identity is determined over an amino acid sequence of identical size as SEQ ID NO: 8. Some embodiments of the present invention provide an isolated nucleic acid comprising the nucleotide sequence of SEQ ID NO: 2, a coding region of SEQ ID NO: 2, SEQ ID NO: 3, a coding region of SEQ ID NO: 3, or the complement of any of the foregoing. In some embodiments, the isolated nucleic acid is a DNA. Some embodiments of the present invention provides an isolated nucleic acid comprising a nucleotide sequence encoding the protein of any protein described in this section, or the complement thereof.

5.18.5. Structure of Obesity Related Genes and Encoded Proteins

The structure of the obesity related genes of the present invention and the obesity related protein products of the present invention can be analyzed by various methods known in the art, as described in this section.

5.18.5.1. Genetic Analysis

The cloned DNA or cDNA corresponding to an obesity related gene can be analyzed by methods including, but not limited to, Southern hybridization (Southern, 1975, J. Mol. Biol. 98: 503-517), Northern hybridization (see e.g., Freeman et al., 1983, Proc. Natl. Acad. Sci. U.S.A. 80: 4094-4098), restriction endonuclease mapping (Maniatis, 1982, *Molecular Cloning*, A Laboratory, Cold Spring Harbor, N.Y.), and DNA sequence analysis. Polymerase chain reaction (PCR; U.S. Pat. Nos. 4,683,202, 4,683,195 and 4,889,818; Gyllenstein et al., 1988, Proc. Natl. Acad. Sci. U.S.A. 85: 7652-7656; Ochman et al., 1988 Genetics 120:621-623; Loh et al., 1989, Science 243: 217-220) followed by Southern hybridization with a probe specific to one of the obesity related genes can allow the detection of that particular obesity related gene in DNA from various cell types from various vertebrate sources. Methods of amplification other than PCR are commonly known and can also be employed. In one embodiment, Southern hybridization can be used to determine the genetic linkage of a particular obesity related gene. Northern hybridization analysis can be used to determine the expression of a particular obesity related gene. Various cell types, at various states of development or activity can be tested for expression of a particular obesity related gene. In one preferred embodiment, screening arrays comprising probes homologous to the exons of particular obesity related genes are used to determine the state of expression of these genes, or specific exons of these genes, in various cell types, under particular environmental or perturbance conditions, or in various vertebrates. The stringency of the hybridization conditions for both Southern and Northern hybridization can be manipulated to ensure detection of nucleic acids with the desired degree of relatedness to the specific probe used. Modifications of these methods and other methods commonly known in the art can be used.

Restriction endonuclease mapping can be used to roughly determine the genetic structure of an obesity related gene. Restriction maps derived by restriction endonuclease cleavage can be confirmed by DNA sequence analysis. The genetic structure of an obesity related gene can also be determined using scanning oligonucleotide arrays, wherein the expression of one exon is Correlated with the expression of a plurality of neighboring exons, such that the correlation indicates the correlated exons are contained within the same gene. The structure so determined can be confirmed by PCR.

DNA sequence analysis can be performed by any techniques known in the art, including but not limited to the method of Maxam and Gilbert, 1980, Meth. Buzymol. 65: 499-5601, the Sanger dideoxy method (Sanger et al., 1977, Proc. Natl. Acad. Sci. U.S.A. 74: 5463), the use of T7 DNA polymerase (Tabor & Richardson, U.S. Pat. No. 4,795,699), or use of an automated DNA Sequenator (e.g., Applied Biosystems, Foster City, Calif.). The sequencing method may use radioactive or fluorescant labels.

5.18.5.2. Protein Analysis

The amino acid sequence of a particular obesity related gene product can be derived by deduction from the DNA sequence, or alternatively, by direct sequencing of the protein, e.g., with an automated amino acid sequencer. The protein sequence of an obesity related gene product can be characterized by a hydrophilicity analysis (Hopp and Woods, 1981, Proc. Natl. Acad. Sci. U.S.A. 78: 3824). A hydrophilicity profile is used to identify the hydrophobic and hydrophilic regions of an obesity related gene product and the corresponding regions of the gene sequence that encode such regions.

Secondary structural analysis (Chou and Fasman, 1974, Biochemistry 13: 222) can also be done, to identify regions of particular obesity related gene products that assume specific secondary structures, such as α-helices and β-pleated sheets. Manipulation, translation, secondary structure prediction, open reading frame prediction and plotting, as well as determination of sequence homologies, can also be accomplished using computer software programs and nucleotide and protein sequence databases available in the art. Protein and/or nucleotide sequence homologies to known proteins or DNA sequences can be used to deduce the likely function of a particular TCAP, or domains thereof.

Other methods of structural analysis can also be employed. These include but are not limited to X-ray crystallography (Engstrom, 1974, Biochem. Exp. Biol. 11: 7-13) and computer modeling (Fletterick, and Zoller, (ads.), Computer Graphics and Molecular Modeling, in *Current Communications in Molecular Biology*, Cold Spring Harbor Laboratory, Cold Spring Harbor, N.Y. (1986)).

In addition to determinations of obesity related gene product protein structure, the invention provides methods of identifying a molecule that specifically binds to a ligand selected from the group consisting of an obesity related gene product, an obesity related gene product fragment, a domain of an obesity related protein, and a nucleic acid encoding the obesity related protein or fragment thereof comprising (a) contacting the ligand with a plurality of test molecules under conditions conducive to binding between the ligand and the molecules; and (b) identifying a molecule within the plurality that specifically binds to the ligand.

5.18.6. Obesity Related Gene Product Antibodies

In a specific embodiment, the modulator of an obesity related gene disclosed in Section 6.7.5 is an antibody that specifically binds (I.e., is not competed off of the obesity related gene product by a non-specific protein such as bovine serum albumin) the obesity related gene product or an active fragment or analog thereof and inhibits the function of the obesity related gene product.

Antibodies of the invention include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g.; anti-Id antibodies to antibodies of the invention), and epitope-binding fragments of any of the above. In particular, antibodies of the present invention include immunoglobulin molecules and immunologically active portions of immunoglobulin molecules, i.e., molecules that contain an antigen binding site that immunospecifically binds to osteopontin. The immunoglobulin molecules of the invention can be of any type (e.g., Igg, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule.

The antibodies of the invention may be from any animal origin including birds and mammals (e.g., human, murine, donkey, sheep, rabbit, goat, guinea pig, camel, home, or chicken). Preferably, the antibodies of the invention are human or humanized monoclonal antibodies. As used herein, "human" antibodies include antibodies having the amino acid sequence of a human immunoglobulin and include antibodies isolated from human immuoglobulin libraries The antibodies of the present invention may be monospecific, bispecific, trispecific or of greater multispecificity. Multispecific antibodies may be specific for different epitopes of an osteopontin polypeptide or may be specific for both an osteopontin polypeptide as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147: 60-69 (1991); U.S. Pat. Nos. 4,474,893; 4,714,681; 4,925, 648; 5,573,920; 5,601,819; Kostelny et al., J. Immunol. 148: 1547-1553 (1992).

The antibodies of the invention include derivatives that are modified, e.g., by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The present invention encompasses antibodies or fragments thereof recombinantly fused or chemically conjugated (including both covalently and non-covalently conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies may be used to target heterologous polypeptides to particular cell types either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., Harbor et al., supra, and PCT publication WO 93/21232; BP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising heterologous polypeptides fused or conjugated to antibody fragments. For example, the heterologous polypeptides may be fused or conjugated to a Fab fragment, Fd fragment Fv fragment, F(ab)$_2$ fragment, or portion thereof. Methods for fusing or conjugating polypeptides to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88: 10535-10539 (1991); Zheng et al., J. Immumol. 154: 5590-5600 (1995); and Vil et al., Proc. Natl. Acad. Sci. USA 89:11337-11341 (1992), which are hereby incorporated by reference in their entireties.

Additional fusion proteins of the invention may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,637,458, and Patten at al., 1997, Curr. Opinion Biotechnol. 8:724-33; Harayama, 1998, Trends Biotechnol. 16(2):76-82; Hanson et al., 1999, J. Mol. Biol. 287:265-76; and Lorenzo and 1998, Blasco, Biotechniques 24(2):308-13, which are hereby incorporated by reference in their entireties.

In one embodiment, antibodies or fragments thereof, or the encoded antibodies or fragments thereof, are altered by subjecting them to random mutagenesis by error-prone PCR, random nucleotide insertion or other methods, prior to recombination. In another embodiment, one or more portions of a polynucleotide encoding an antibody or antibody fragment, which portions immunospecifically bind to an osteopontin antigen may be recombined with one or more components, motifs, sections, parts, domains, fragments, etc. of one or more heterologous molecules.

Moreover, the antibodies of the present invention or fragments thereof can be fused to marker sequences such as a peptide, to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824 for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., meclorethamine, thioepa chlorambucil, melphalan, carmustine (BSNU) and lomustine (CCNU), cyclothosphamide, busulfan, dibronomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, an antibody or fragment thereof may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (se, International Publication No. WO 97/33899), AIM II (see, International Publication No. WO 97/34911), Fas Ligand (Takahashi et al., 1994, J. Iminunol, 6:1567-1574), and VEGI (see, International Publication No. WO. 991231051a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF" and granulocyte colony stimulating factor ("G-CSF"), or a growth factor (e.g., growth hormone ("GH")).

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (ads.), pp. 243-56 (Alan R Liss, Inc. 1985); Hellstrom et al., "Antibodies For Drug Delivery", in *Controlled Drug Delivery* (2$^{nd}$ Ed.), Robinson et al. (eds., pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (ads.), pp. 475-506 (1985); "Analysis, Results, And Future Prospective Of The Therapeutic Use Of Radiolabeled Antibody In Cancer Therapy", in *Monoclonal*

*Antibodies For Cancer Detection And Therapy*, Baldwin et al. (eds.), pp. 303-16 (Academic Press 1985), and Thorpe et al., 1982, Immunol. Rev. 62:119-58.

An antibody or fragment thereof with or without a therapeutic moiety conjugated to it, administered alone or in combination with cytotoxic factor(s) and/or cytokine(s) can be used as a therapeutic.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Antibodies of the present invention or fragments thereof may be characterized in a variety of ways. In particular, antibodies of the invention or fragments thereof may be assayed for the ability to immunospecifically bind to obesity related gene products of the present invention. Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310) (each of these references is incorporated herein in its entirety by reference). Antibodies or fragments thereof that have been identified to immunospecifically bind to the obesity related gene products of the present invention or a fragment thereof can then be assayed for their specificity and affinity for the obesity related gene products of the present invention.

The antibodies of the invention or fragments thereof may be assayed for immunospecific binding to the obesity related gene products of the present invention and cross-reactivity with other antigens by any method known in the art. Immunoassays that can be used to analyze immunospecific binding and cross-reactivity include, but are not limited to, competitive and non-competitive assay systems using techniques such as western blots, radioimmunoassay, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the at (see, e.g., Ausubel et al, eds, 1994, *Current Protocols in Molecular Biology*, Vol. 1, John Wiley & Sons, Inc., New York, which is incorporated by reference herein in its. entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the call lysate, incubating for a period of time (e.g., one to four hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, *Current Protocols in Molecular Biology*, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Asubel et al., ads, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, *Current Protocol in Molecular Biology*, Vol 1, John Wiley & Sons, Inc., New York at 112.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3H$ or $^{125}I$) with the antibody of interest in the presence of increasing amounts of unlabeled antigen, and the detection of the antibody bound to the labeled antigen. The affinity of an antibody of the present invention or a fragment thereof for the obesity related gene products of the present invention and the binding off-rates can be determined from the data by scatchard plot analysis. Competition with a second antibody can also be determined using radioimmunoassays. In this case, osteopontin is incubated with an antibody of the present invention or a fragment thereof conjugated to a labeled compound (e.g., $^3$H or $^{125}$I) in the presence of increasing amounts of an unlabeled second antibody.

BIAcore kinetic analysis may also be used to determine the binding on and off rates of antibodies or fragments thereof to the obesity related gene products of the present invention. BIAcore kinetic analysis comprises analyzing the binding and dissociation of osteopontin from chips with immobilized antibodies or fragments thereof on their surface.

One aspect of the invention provides an antibody that binds to a protein consisting of the amino acid sequence of SEQ ID NO: 8. In some embodiments, the antibody is monoclonal. Another aspect of the invention provides a molecule comprising a fragment of an antibody that binds to a protein consisting of the amino acid sequence of SEQ ID NO: 8, which fragment binds a protein consisting of the amino acid sequence of SEQ ID NO: 8.

5.18.7. Obesity Related Gene Product Antibody Production

The antibodies of the invention or fragments thereof can be produced by any method known in the art for the synthesis of antibodies, in particular, by chemical synthesis or preferably, by recombinant expression techniques.

Polyclonal antibodies can be produced by various procedures well known in the art. For example, an obesity related gene product of the present invention, as disclosed in Section 6.7.5, or an immunogenic or antigenic fragment thereof can be administered to various host animals including, but not limited to, rabbits, mice, rats, etc. to induce the production of sera containing polyclonal antibodies specific for the obesity related gene product. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, $2^{nd}$ ed. 1988); Hammerling, et al., in: *Monoclonal Antibodies and T-Cell Hybridoma* 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with osteopontin or an immunogenic or antigenic fragment thereof and once an immune response is detected, e.g., antibodies specific for osteopontin are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding the obesity related gene products of the present invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an obesity related gene product of the present invention or an immunogenic or antigenic fragment thereof with myeloma cells and then screening the hybridomas resulting from the fusion for hybridoma clones that secrete an antibody able to bind osteopontin. The hybridomas may be further screened for secretion of antibodies that inhibit osteopontin function.

Antibody fragments which recognize specific osteopontin epitopes may be generated by any technique known to those of skill in the rt. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles that carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in *E. coli* and the B. col is infected with helper phage. Phage used in these methods are typically filmentous phage including fd and M13 and the VH and VL domains are usually recombinantly fused to either the phage gene I or gene VIII. Phage expressing an antigen binding domain that binds to an antigen of interest can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames ea al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 37:191-280; PCT application No. PCT/GB91/O1 134; PCT publications WO 90/02809; WO 91/10737; WO 92/01047; WO 92/18619; WO 93/1 1236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired bost, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication WO 92/22324; Mullinax t al, 1992, BioTechniques 12(6): 864-869; and Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clone. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express fell-length antibodies, e.g., IgG, using techniques known to those of skill in the art.

For some uses, including in who use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice that are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immuoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunmol.* 13:65-93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661, 016; 5,545,806; 5,814,318; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules such as antibodies having a variable region derived from a human antibody and a non-human immunoglobulin constant region. Methods for producing chimeric antibodies are known in the at. See e.g., Morrison, 1985, Science 229:1202; Oi et al., 1986, BioTechniques 4:214; Gillies et al., 1989, J. Immunol. Methods 125:191-202; U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule can be produced using a variety of techniques known in the art including, for example, CDR-grafting (EP 239,400; PCT publication WO 91/09967; U.S. Pat. Nos. 5,225,539; 5,530,101; and 5,585,089), veneering or resurfacing (BP 592,106; EP 519,596; Padlan, 1991, Molecular Immunology 28(4/5):489-498; Studnicka et al., 1994, Protein Engineering 7(6):805-814; Roguska t at., 1994, PNAS 91:969-973), and chain shuffling (U.S. Pat. No. 5,565,332).

Further, the antibodies of the invention can, in turn, be utilized to generate anti-idiotype antibodies that "mimic" one or more of the obesity related gene products of the present invention using techniques well known to those skilled in the art (See, e.g., Greenapan & Bona, 1989, FASEB J. 7(5):437-444; and Nissinoff 1991, J. Immunol. 147(8):2429-2438).

5.18.8. Polynucleotides Encoding an Obesity Related Gene Product Antibody

The invention provides polynucleotides comprising a nucleotide sequence encoding an antibody of the invention or a fragment thereof. The invention also encompasses polynucleotides that hybridize under high stringency, intermediate or lower stringency hybridization conditions, e.g., as defined supra, to polynucleotides that encode an antibody of the invention.

The polynucleotides may be obtained, and the nucleotide sequence of the polynucleotides determined, by any method known in the art. Nucleotide sequences encoding these antibodies can be determined using any nucleic acid sequencing method known in the art. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Coning, A Laboratory Manual*, $2^{nd}$ Ed., Cold Spring Harbor Laboratory, Cold Spring Harbor, N.Y. and Ausubel et al., eds., 1998, *Current Protocols in Molecular Biology*, John Wiley & Sons, NY, which are both incorporated by reference herein in their entireties), to generate antibodies having a different amino acid sequence, for example to create amino acid substitutions, deletions, and/or insertions.

5.18.9. Recombinant Expression of an Antibody to an Obesity Related Gene Product Recombinant expression of an antibody of the invention, derivative or analog thereof (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof or a heavy or light chain CDR, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof; or a heavy or light chain thereof or portion thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter, the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7O3O and HsS78Bst.

For long-term, high-yield production of recombinant proteins, stable expression is preferred. For example, cell lines that stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalaski, 1992, Proc. Natl. Acad. Sci. USA 48.202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoahev, 1993, Ann. Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-215); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), *Current Protocols in Human Genetics*, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase. See, for example, Crouse et al., 1983, Mol. Cell. Biol. 3:257.

The host cell may be co-transfected with two expression vectors of the invention, the first vector encoding a heavy chain derived polypeptide and the second vector encoding a light chain derived polypeptide. The two vectors may contain identical selectable markers that enable equal expression of heavy and light chain polypeptides. Alternatively, a single vector may be used that encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Nat. Acad. Sci. USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.18.10. Obesity Related Gene Anti-Sense Nucleic Acids

The function of the obesity related genes disclosed in Section 6.7.5 may be inhibited by use of antisense nucleic acids.

The present invention provides the therapeutic or prophylactic use of nucleic acids of at least six nucleotides that are antisense to a gene or cDNA encoding an obesity related gene product disclosed in Section 6.7.5, or portions thereof. An "antisense" nucleic acid as used herein refers to a nucleic acid capable of hybridizing to a portion of a nucleic acid disclosed in Section 6.7.5 (preferably mRNA, e.g., the sequence of SEQ ID NO: 2, SEQ ID NO: 3, SEQ ID NO: 12, SEQ ID NO: 16 and/or SEQ ID NO: 20) by virtue of some sequence complementarity. The antisense nucleic acid may be complementary to a coding and/or noncoding region of an obesity related mRNA.

The antisense nucleic acids can be oligonucleotides that are double-stranded or single-stranded RNA or DNA or a modification or derivative thereof, which can be directly administered to a cell, or which can be produced intracellularly by transcription of exogenous, introduced sequences.

The antisense nucleic acids are of at least six nucleotides and are preferably oligonucleotides (ranging from 6 to about 200 oligonucleotides). In specific aspects, the olignucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The olignucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553-6556; Lemaitre et al., 1987, Proc. Natl. Acad. Sci. 84: 648-652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6: 958-976) or intercalating agents (see, e.g., Zon, 1988, Pharm. Res. 5: 539-549).

In a preferred aspect of the invention, the antisense oligonucleotide is provided, preferably as single-stranded DNA. The oligonucleotide may be modified at any position on its structure with constituents generally known in the art.

The antisense oligonucleotides may comprise at least one modified base moiety that is selected from the group including, but not limited to, 5-fluoroaracil, 5-bromouracil, 5-chlororuracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, a formacetal, or analogs thereof.

In yet another embodiment, the oligonucleotide is α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625-6641).

The oligonucleotide may be conjugated to another molecule, e.g., a peptide, hybridization triggered cross-linking agent, transport agent, hybridization-triggered cleavage agent, etc.

Oligonucleotides may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stain et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448-7451), etc.

In a specific embodiment, the antisense oligonucleotides comprise catalytic RNAs, or ribozymes (see, e.g., PCT International Publication WO 90/11364, published Oct. 4, 1990; Sarver et al., 1990, Science 247: 1222-1225). In another embodiment, the oligonucleotide is a 2'-0-methylribonucleotide (Inoue et al., 1987, Nucl. Acids Res. 15: 6131-6148), or a chimeric RNA-DNA analog (Inoue et al., 1987, FEBS Lett. 215: 327-330).

In an alternative embodiment, antisense nucleic acids are produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding an antisense nucleic acid. Such a vector can remain episomal or became chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in mammalian, preferably human, cells. Such promoters can be inducible or constitutive. Such promoters include, but are not limited to, the SV40 early promote region (Bernoist and Chambon, 1981, Nature 290: 304-310), the promoter contained in the 3' long terminal repeat of Rous sarcoma virus (Yamamoto et al., 1980, Cell 22: 787-797), the herpes thymidine kinase promoter (Wagner et al., 1981, Proc. Natl. Acad. Sci. U.S.A. 78: 1441-1445), the regulatory sequences of the metallothionein gene (Brinster et al., 1982, Nature 296: 39-42), etc.

The antisense nucleic acids of the invention comprise a sequence complementary to at least a portion of an RNA transcript of a gene disclosed in Section 6.7.5. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid.

Generally, the longer the hybridizing nucleic acid, the more base mismatches with an obesity related RNA (target RNA) it may contain and still form a stable duplex (or triplex, as the case may be). One skilled in the art can ascertain a tolerable degree of mismatch by use of standard procedures to determine the melting point of the hybridized complex.

Pharmaceutical compositions of the invention, comprising an effective amount of an antisense nucleic acid in a pharmaceutically acceptable carrier can be administered in therapeutic methods of the invention.

The amount of antisense nucleic acid that will be effective in the treatment of a particular disorder or condition will depend on the nature of the disorder or condition, and can be determined by standard clinical techniques. Where possible, it is desirable to determine the antisense cytotoxicity in vitro, and then in useful animal model systems prior to testing and use in humans.

In a specific embodiment, pharmaceutical compositions comprising antisense nucleic acids are administered via liposomes, microparticles, or microcapsules. In various embodiments of the invention it may be useful to use such compositions to achieve sustained release of antisense nucleic acids. In a specific embodiment, it may be desirable to utilize liposomes targeted via antibodies to specific identifiable central nervous system cell types (Leonetti et al., 1990, Proc. Natl. Acad. Sci. U.S.A. 87: 2448-2451; Renneisen et al., 1990, J. Biol. Chem. 265: 16337-16342).

5.18.11. Obesity Related Gene Product Analogs, Derivatives and Fragments

The invention further provides methods of modulating the obesity related genes disclosed in Section 6.7.5 using agonists and promoters of such genes. Agonists include, but are not limited to, active fragments thereof (wherein a fragment is at least 10, 15, 20, 30, 50, 75, 100, or 150 amino acid portion of an obesity related gene product disclosed in Section 6.7.5) and analogs and derivatives thereof, and nucleic acids encoding any of the foregoing.

For recombinant expression of obesity related gene products, and fragments, derivatives and analogs thereof, the nucleic acid containing all or a portion of the nucleotide sequence encoding the protein can be inserted into an appropriate expression vector, e.g., a vector that contains the necessary elements for the transcription and translation of the inserted protein coding sequence. In a preferred embodiment, the regulatory elements (e.g., promoter) are heterologous (i.e., not the native gene promoter). Promoters which may be used include but are not limited to the SV40 early promoter (Bernoist and Chambon, 1981, Nature 290: 304-310), the promoter contained in the 3' long terminal repeat of Rous sarcoma virus (Yamamoto et al., 1980, Cell 22: 787-797), the herpes thymidine kinase promoter (Wagner et al., 1981, Proc. Natl. Acad. Sci. USA 78: 1441-1445), the regulatory sequences of the metallothionein gene (Brinster et al., 1982, Nature 296: 39-42); prokaryotic expression vectors such as the f-lactamase promoter (Villa-Kamaroff et al., 1978, Proc. Natl. Acad. Sci. USA 75: 3727-3731) or the tac promoter (DeBoer et al., 1983, Proc. Natl. Acad. Sci. USA 80: 21-25; see also "Useful Proteins from Recombinant Bacteria": in Scientific American 1980, 242:79-94); plant expression vectors comprising the nopaline synthetase promoter (Herrar-Estrella et al., 1984, Nature 303: 209-213) or the cauliflower mosaic virus 355 RNA promoter (Garder et al., 1981, Nucleic Acids Res. 9:2871), and the promoter of the photosynthetic enzyme ribulose bisphosphate carboxylase (Herra-Estrella et al., 1984, Nature 310: 115-120); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been utilized in transgenic animals: elastase I gene control region which is active in pancreatic acinar cells (Swift et al., 1984, Cell 38: 639-646; Ornitz et al., 1986, Cold Spring Harbor Symp. Quant. Biol 50: 399-409; MacDonald 1987, Hepatology 7: 425-515); insulin gene control region which is active in pancreatic beta cells (Hanahan et al., 1985, Nature 315: 115-122), immunoglobulin gene control region which is active in lymphoid cells (Grosschedl et al., 1984, Cell 38: 647-658; Adams et al., 1985, Nature 318: 533-538; Alexander et al., 1987, Mol. Cell Biol. 7: 1436-1444), mouse mammary tumor virus control region which is active in testicular, breast, lymphoid and mast cells (Leder et al., 1986, Cell 45: 485-495), albumin gene control region which is active in liver (Pinckert et al., 1987, Genes and Devel. 1: 268-276), alpha-fetoprotein gene control region which is active in liver (Krumlauf et al., 1985, Mol. Cell. Biol. 5: 1639-1648; Hammer et al., 1987, Science 235: 53-58), alpha-I antitrypsin gene control region which is active in liver (Kelsey et al., 1987, Genes and Devel. 1: 161-171), beta globin gene control region which is active in myeloid cells (Mogram et al., 1985, Nature 315: 338-340; Kollias et al., 1986, Cell 46: 89-94), myelin basic protein gene control region which is active in oligodendrocyte cells of the brain (Readhead et al., 1987, Cell 48: 703-712), myosin light chain-2 gene control region which is active in skeletal muscle (Sani 1985, Nature 314: 283-286), and gonandotrophic releasing hormone gene control region which is active in gonadotrophs of the hypothalamus (Mason as al., 1986, Science 234: 1372-1378).

A variety of host-vector systems may be utilized to express the protein coding sequence. These include, but are not limited to, mammalian cell systems infected with virus (e.g., vaccinia virus, adenovirus, etc.); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Once an obesity related gene product disclosed in Section 6.7.5, or fragment, derivative or analog thereof has been recombinantly expressed, it may be isolated and purified by standard methods including chromatography (e.g., ion exchange, affinity, and sizing column chromatography), centrifugation, differential solubility, or by any other standard technique for the purification of proteins. An obesity related gene product may also be purified by any standard purification method from natural sources.

Alternatively, an obesity related gene product, analog or derivative thereof of the present invention can be synthesized by standard chemical methods known in the art (e.g., see Hunkapiller et al., 1984, Nature 310:105-111).

Standard techniques known to those of skill in the art can be used to introduce mutations in the nucleotide sequence encoding a molecule of the invention, including, for example, site-directed mutagenesis and PCR-mediated mutagenesis that results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonin tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In a specific embodiment, the obesity related gene analog, derivative or fragment thereof is encoded by a nucleotide sequence that hybridizes to the nucleotide sequence of SEQ ID NO:2, SEQ ID NO: 3, SEQ ID NO: 12, SEQ ID NO: 16, or SEQ ID NO: 20 under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions that are known to those of skill in the art (see, for example, Ausubel, F. M. at al, ads., 1989, *Current Protocols in Molecular Biology*, Vol. I, Green Publishing Associates, Inc. and John Wiley & Sons, Inc., New York at pages 6.3.1-6.3.6 and 2.10.3).

In another embodiment, the analog, derivative or fragment comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of SEQ ID NO: 8, SEQ ID NO: 11, SEQ ID NO: 15, SEQ ID NO: 18, SEQ ID NO: 25, SEQ ID NO: 26, or SEQ ID NO: 27.

Additionally, the nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including, but not limited to, chemical mutagenesis, in vitro site-directed mutagenesis (Hutchinson, C., et al., 1978, J. Biol. Chem 253:6551), use of TAB linkers (Pharmacia), etc.

Manipulations of the sequence may also be made at the protein level. Included within the scope of the invention are protein fragments or other derivatives or analogs that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques including, but not limited to, specific chemical cleavage by cyanogen bromide, trypsin, chymotrypsin, papain, V8 protease, $NaBH_4$, acetylation, formylation, oxidation, reduction; metabolic synthesis in the presence of tunicamycin, etc.

In addition, analogs and derivatives of can be chemically synthesized. Furthermore, if desired, nonclassical amino acids or chemical amino acid analogs can be introduced as a substitution or addition into the sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acids used to make the analogs and derivatives can be D (dextrorotary), L (levorotary), or some combination of D and L.

In a specific embodiment, the derivative is a chimeric, or fusion, protein comprising an obesity related gene product disclosed in Section 6.7.5 or fragment thereof (preferably consisting of at least one protein domain or protein structural motif, or at least 15, preferably 20, amino acids of the obesity related protein) joined at its amino- or carboxy-terminus via a peptide bond to an amino acid sequence of a different protein. In one embodiment, such a chimeric protein is produced by recombinant expression of a nucleic acid encoding the protein (comprising an obesity related protein-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of obesity related gene product (e.g. SEQ ID NO: 8, SEQ ID NO: 11, SEQ ID NO: 15, SEQ ID NO: 18, SEQ ID NO: 25, SEQ ID NO: 26, or SEQ ID NO: 27) fused to any heterologous protein-encoding sequences may be constructed.

5.18.12. Pharmaceutical Compositions and Methods of Administration

The invention provides methods of treatment, prophylaxis, and amelioration of one or more symptoms associated with obesity by administrating to a subject of an effective amount of an obesity related gene (e.g. SEQ ID NO: 2, SEQ ID NO: 3, SEQ ID NO: 12, SEQ ID NO. 16, SEQ ID NO: 20) modulator, or pharmaceutical composition comprising an obesity related gene modulator. In a preferred aspect, the obesity related gene modulator is substantially purified (e.g., substantially free from substances that limit its effect or produce undesired side-effects). The subject is preferably a mammal such as non-primate (e.g., cows, pigs, horses, cats, dogs, rats etc.) and a primate (e.g., monkeys or humans). In a preferred embodiment, the subject is a human.

5.18.12.1. Delivery Systems

Various delivery systems are known and can be used to administer modulators of the invention or fragment thereof, e.g., encapsulation in liposomes, microparticles, microcapsules, recombinant cells capable of expressing a protein or antibody modulator, receptor-mediated endocytosis (see, e.g., Wu and Wu, 1987, J. Biol. Chem. 262:4429-4432), construction of a nucleic acid as part of a retroviral or other vector, etc. Methods of administering a modulator, or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, modulators of the present invention or fragments thereof or pharmaceutical compositions are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,309, 5,934,272, 5,874,064, 5,290,540, and 4,880,078, and PCT Publication No. WO 92/19244. In a preferred embodiment, the pharmaceutical composition is delivered locally to the site of neural tissue damage, e.g., using osmotic or other types of pumps.

5.18.12.2. Pharmaceutical Compositions

The invention also provides that the pharmaceutical composition is packaged in a hermetically sealed container such as an ampule or sachette indicating the quantity of modulator. In one embodiment, the modulator is supplied as a dry sterilized lyophilized powder or water free concentrate in a hermetically sealed container and can be reconstituted, e.g., with water or saline to the appropriate concentration for administration to a subject. Preferably, the modulator is supplied as a dry sterile lyophilized powder in a hermetically sealed container at a unit dosage of at least 5 mg, more preferably at least 10 mg at least 15 mg, at least 25 m, at least 35 mg, at least 45 mg, at least 50 mg, or at least 75 mg. Preferably, the liquid form is supplied in a hermetically sealed container at least 1 mg/ml, more preferably at least 2.5 mg/ml, at least 5 mg/ml, at least 8 mg/ml, at least 10 mg/ml, or at least 25 mg/ml.

In a specific embodiment, it may be desirable to administer the pharmaceutical compositions of the invention locally to the area in need of treatment; this may be achieved by, for example, and not by why of limitation, local infusion, by injection, or by means of an implant, said implant being of a porous, non-porous, or gelatinous material, including membranes, such as sialastic membranes, or fibers. A particularly useful application involves coating, imbedding or derivatizing fibers, such as collagen fibers, protein polymers, etc. with a modulator of the invention. Other useful approaches are described in Otto et al., 1989, J Neuroscience Research 22, 83-91 and Otto and Unsicker, 1990, J Neuroscience 10, 1912-1921, both of which are incorporated herein in their entireties. Preferably, when administering the modulator, care must be taken to use materials to which the modulator does not absorb.

In another embodiment, the composition can be delivered in a vesicle, in particular a liposome (see Langer, 1990, Science 249:1527-1533 1990); Treat et al., 1989, in Liposomes in the Therapy of Infectious Disease and Cancer, Lopez-Berestein and Fidler (eds.), Lisa, New York, pp. 353-365; and Lopez-Berestein, ibid., pp. 3 17-327; see generally ibid.).

In yet another embodiment, the composition can be delivered in a controlled release system. In one embodiment, a pump may be used (see Langer, supra; Sefton, 1987, CRC Crit. Ref. Biomed. Bng. 14:20; Buchwald et al., 1980, Surgery 88:507; Saudek et al., 1989, N. Engl. J. Med. 321:574). In another embodiment, polymeric materials can be used (see e.g., *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. In yet another embodiment, a controlled release system can be placed in proximity of the therapeutic target, i.e., nervous tissue (see, e.g., Goodson, 1984, in *Medical Applications of Controlled Release*, supra, vol. 2, pp. 115-138). Other controlled release systems are discussed in the review by Langer, 1990, Science 249:1527-1533.

In a specific embodiment, where the composition of the invention is a nucleic acid encoding modulator, the nucleic acid can be administered in vivo to promote expression of its encoded modulator by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Aced. Sci. USA 88:1864-1868), etc. Alternatively, a nucleic acid can be introduced intracellularly and incorporated within host cell DNA for expression by homologous recombination.

The pharmaceutical compositions of the invention comprise a prophylactically or therapeutically effective amount of an obesity related gene modulator, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gal, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition delivered is that amount that will be effective in the methods of treatment of the invention.

Some embodiments of the present invention provide a pharmaceutical composition comprising a therapeutically effective amount of SEQ ID NO: 8, and a pharmaceutically acceptable carrier. Some embodiments of the present invention provide a pharmaceutical composition comprising a therapeutically effective amount of an antibody that binds to SEQ ID NO: 8; and a pharmaceutically acceptable carrier. Some embodiments of the present invention provide a pharmaceutical composition comprising a therapeutically effective amount of a fragment or derivative of an antibody that binds to SEQ ID NO: 8, wherein the fragment or derivative contains the binding domain of the antibody, and a pharmaceutically acceptable carrier.

Some embodiments of the present invention provide a pharmaceutical composition comprising a therapeutically effective amount of any one of the following proteins, and a pharmaceutically acceptable carrier:

a) a purified protein comprising the amino acid sequence of SEQ ID NO: 8;

b) purified protein encoded by a nucleic acid hybridizable to a DNA having a sequence consisting of the coding region of SEQ ID NO: 2;

c) a purified protein comprising an amino acid sequence that has at least 60% identity to the amino acid sequence set forth in SEQ ID NO: 8, in which percentage identity is determined over an amino acid sequence of identical size as SEQ ID NO: 8; or d) a purified protein comprising an amino acid sequence that has at least 90% identity to the amino acid sequence set forth in SEQ ID NO: 8, in which percentage identity is determined over an amino acid sequence of identical size as SEQ ID NO: 8.

Some embodiments of the present invention provide a pharmaceutical composition comprising a therapeutically effective amount of one of the following nucleic acids and a pharmaceutically acceptable carrier:

a) an isolated nucleic acid comprising the nucleotide sequence of SEQ ID NO: 2, a coding region of SEQ ID NO: 2, SEQ ID NO: 3, a coding region of SEQ ID NO: 3, or the complement of any of the foregoing;

b) an isolated nucleic acid of selected from (a) that is a DNA; or an isolated nucleic acid comprising a nucleotide sequence encoding any one of the following proteins or the complement thereof i) a purified protein comprising the amino acid sequence of SEQ ID NO: 8;

ii) purified protein encoded by a nucleic acid hybridizable to a DNA having a sequence consisting of the coding region of SEQ ID NO: 2;

iii) a purified protein comprising an amino acid sequence that has at least 60% identity to the amino acid sequence set forth in SEQ ID NO: 8, in which percentage identity is determined over an amino acid sequence of identical size as SEQ ID NO: 8; or iv) a purified protein comprising an amino acid sequence that has at least 90% identity to the amino acid sequence set forth in SEQ ID NO: 8, in which percentage identity is determined over an amino acid sequence of identical size as SEQ ID NO: 8.

Some embodiments of the present invention provide a pharmaceutical composition comprising a therapeutically effective amount of any one of the following recombinant cells and a pharmaceutically acceptable carrier a) a recombinant cell containing an isolated nucleic acid comprising the nucleotide sequence of SEQ ID NO: 2, a coding region of SEQ ID NO: 2, SEQ ID NO: 3, a coding region of SEQ ID NO: 3, or the complement of any of the foregoing, in which the nucleotide sequence is under the control of a promoter heterologous to the nucleotide sequence; or b) a recombinant cell containing a nucleic acid vector that comprises the nucleotide sequence of SEQ ID NO: 2, a coding region of SEQ ID NO: 2, SEQ ID NO: 3, a coding region of SEQ ID NO: 3, or the complement of any of the foregoing.

Some embodiments of the present invention provide a pharmaceutical composition comprising a therapeutically effective amount of an antibody that binds to a protein comprising the amino acid sequence of any one of the following, and a pharmaceutically acceptable carrier:

i) a purified protein comprising the amino acid sequence of SEQ ID NO: 8;

ii) a purified protein encoded by a nucleic acid hybridizable to a DNA having a sequence consisting of the coding region of SEQ ID NO: 2;

iii) a purified protein comprising an amino acid sequence that has at least 60% identity to the amino acid sequence set forth in SEQ ID NO: 8, in which percentage identity is determined over an amino acid sequence of identical size as SEQ ID NO: 8; and iv) a purified protein comprising an amino acid sequence that has at least 90% identity to the amino acid sequence set forth in SEQ ID NO: 8, in which percentage identity is determined over an amino acid sequence of identical size a SEQ ID NO: 8.

5.18.12.3. Gene Therapy

In some embodiments, the compositions are delivered by gene therapy. Gene therapy refers to therapy performed by the administration to a subject of an expressed or expressible nucleic acid. In this embodiment of the invention, the nucleic acids produce their encoded modulator that mediates a therapeutic effect. Any of the methods for gene therapy available in the art can be used according to the present invention. Exemplary methods are described below.

For general reviews of the methods of gene therapy, see Goldspiel or al., 1993, Clinical Pharmacy 12:488-505; Wu and Wu, 1991, Biotherapy 3:87-95; Tolstoehev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215. Methods commonly known in the art of recombinant DNA technology which can be used are described in Ansubel et al. (eds.), *Current Protocols in Molecular Biology*, John Wiley & Sons, NY (1993); and Kriegler, *Gene Transfer and Expression*, A Laboratory Manual, Stockton Press, NY (1990).

In a preferred aspect, a composition of the invention comprises nucleic acids encoding a modulator. These nucleic acids are part of an expression vector that expresses the modulator in a suitable host. In particular, such nucleic acids have promoters, preferably heterologous promoters, operably linked to the antibody coding region, the promoter being inducible or constitutive, and, optionally, tissue-specific. In another particular embodiment, nucleic acid molecules are used in which the modulator coding sequences and any other desired sequences are flanked by regions that promote homologous recombination at a desired site in the genome, thus providing for intrachromosomal expression of the modulator encoding nucleic acids (Koller and Smithies, 1989, Proc. Natl. Acad. Sci. USA 86:8932-8935; Zijlstra et al., 1989, Nature 342:435-438). In specific embodiments, where the modulator is an antibody, the expressed antibody molecule is a single chain antibody. Alternatively, the nucleic acid sequences include sequences encoding both the heavy and light chains, or fragments thereof, of the antibody.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/203 16; WO93/14188, WO 93/20221). Alternatively, the nucleic acid can be introduced intracellularly and incorporated within host cell DNA for expression, by homologous recombination (Koller and Smithies, 1989, Proc. Natl. Acad. Sci. USA 86:8932-8935; and Zijlstra et al., 1989, Nature 342:435-438).

In a specific embodiment, viral vectors that contains nucleic acid sequences encoding an antibody of the invention or fragments thereof are used. For example, a retroviral vector can be used (see Miller et al., 1993, Meth. Enzymol. 217:581-599). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a subject. More detail about retroviral vectors can be found in Boesen et al., 1994, Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy are Clowes et al., 1994, J. Clin. Invest. 93:644-651; Klein et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy and can be targeted to the central nervous system. Adenoviruses have the advantage of being capable of infecting non-dividing cells. Kozarsky and Wilson, 1993, *Current Opinion in Genetics and Development* 3:499-503 present a review of adenovirus-based gene therapy. Other instances of the use of adenoviruses in gene therapy can be found in Rosenfeld et al., 1991, Science 252:431-434; Rosenfeld at a., 1992, Cell 68:143-155; Mastrangeli et al., 1993, J. Clin. Invest. 91:225-234; PCT Publication WO94/12649; and Wang et al., 1995, Gene Therapy 2:775-783. Adeno-associated virus (AAV) has also been proposed for use in gene therapy (Walsh et al., 1993, Proc. Soc. Exp. Biol. Med. 204: 289-300; and U.S. Pat. No. 5,436,146).

Another approach to gene therapy involves transferring a gene to cells in tissue culture by such methods as electroporation, lipofetion, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell mediated gene transfer, spheroplast fusion, etc. Numerous techniques are known in the art for the introduction of foreign genes into cells (see, e.g., Loeffler and Behr, 1993, Meth. Enzymol. 217:599-618; and Cohen et al., 1993, Meth. Enzymol. 217:618-644) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include bat are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. In a preferred embodiment, the cell is a neural cell. In a preferred embodiment, the cell used for gene therapy is autologous to the subject.

Some embodiments of the present invention provide a recombinant cell containing an isolated nucleic acid comprising SEQ ID NO: 2, SEQ ID NO: 3, or the complement thereto. These recombinant cells may be used for gene therapy or other purposes. Some embodiments of the present invention provide a recombinant cell that contains SEQ ID NO: 2, SEQ ID NO: 3, or the complement thereto, in which the nucleotide sequence encoding SEQ ID NO: 2, SEQ ID NO: 3, or the complement thereto, is not native to the cell. Some embodiments of the present invention provide a recombinant cell containing an isolated nucleic acid comprising SEQ ID NO: 2, a coding region of SEQ ID NO: 2, SEQ ID NO: 3, a coding region of SEQ ID NO: 3, or the complement of any of the foregoing, in which the nucleotide sequence is under the control of a promoter heterologous to the nucleotide sequence. Some embodiments of the present invention provide a recombinant cell containing a nucleic acid vector that comprises a nucleic acid comprising SEQ ID NO: 2, a coding region of SEQ ID NO: 2, SEQ ID NO: 3, a coding region of SEQ ID NO: 3, or the complement of any of the foregoing.

One aspect of the present invention provides a method of producing protein. In the method, a recombinant cell containing any one of the following nucleic acids:

(i) an isolated nucleic acid comprising the nucleotide sequence of SEQ ID NO: 2, a coding region of SEQ ID NO: 2, SEQ ID NO: 3, a coding region of SEQ ID NO: 3, or the complement of any of the foregoing;

(ii) the isolated nucleic acid of claim (i) that is a DNA;

(iii) an isolated nucleic acid comprising a nucleotide sequence, or the complement thereof encoding any of the following proteins:

a) a purified protein comprising the amino acid sequence of SEQ ID NO: 8;

b) a purified protein encoded by a nucleic acid hybridizable to a DNA having a sequence consisting of the coding region of SEQ ID NO: 2;

c) a purified protein comprising an amino acid sequence that has at least 60% identity to the amino acid sequence set forth in SEQ ID NO: 8, in which percentage identity is determined over an amino acid sequence of identical size as SEQ ID NO: 8;

d) a purified protein comprising an amino acid sequence that has at least 90% identity to the amino acid sequence set forth in SEQ ID NO: 8, in which percentage identity is determined over an amino acid sequence of identical size as SEQ ID NO: 8.

In this aspect of the present invention, the nucleic acid sequence is under the control of a promoter heterologous to the nucleotide sequence. The cell is grown such that the protein encoded by the nucleic acid is expressed by the cell. Then the expressed protein is recovered. One embodiment of the present invention provides an isolated protein that is the product of this process.

One aspect of the present invention provide a method of producing SEQ ID NO: 8. The method comprises (i) growing a recombinant cell containing a SEQ ID NO: 2, SEQ ID NO: 3, or the complement thereto, in which the nucleic acid sequence encoding SEQ ID NO: 2, SEQ ID NO: 3, or the complement thereto is under a promoter that is not native to SEQ ID NO: 2, SEQ ID NO: 3, such that encoded SEQ ID NO: 8 is expressed in the cell; and (ii) recovering the expressed SEQ ID NO: 8. Some embodiments of the present invention provide the product of a process in accordance with this aspect of the invention.

In an embodiment in which recombinant cells are used in gene therapy, nucleic acid sequences encoding a modulator are introduced into the cells such that they are expressible by the cells or their progeny, and the recombinant cells are then administered in vivo for therapeutic effect. In a specific embodiment, stem or progenitor cells are used. Any stem and/or progenitor cells that can be isolated and maintained in vitro can potentially be used in accordance with this embodiment of the present invention (see e.g., PCT Publication WO 94/08598; Stemple and Anderson, 1992, Cell 7 1:973-985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gme therapy comprises an inducible promoter operably linked to the coding region, such that expression of the nucleic acid is controllable by controlling the presence or absence of the appropriate inducer of transcription

5.18.13. Demonstration of Therapeutic Utility

The modulators of the invention can be assayed by any method well known in the art. The modulators of the invention or fragments thereof are preferably tested in vitro, and then in vivo for the desired therapeutic or prophylactic activity, prior to use in humans. For example, in vitro assays that can be used to determine whether administration of a specific composition of the present invention is indicated, include in vitro cell culture assays in which a subject tissue sample is grown in culture, and exposed to or otherwise administered a composition of the present invention, and the effect of such a composition of the present invention upon the tissue sample is observed. The following subsections describe various assays that can be used to determine the efficacy of the modulators of the invention.

5.18.13.1. Single Dose Effects on Food and Water Intake and Body Weight Gain in Fasted Rats Subjects.

Male Sprague-Dawley rats (Sasco, St. Louis, Mo.) weighing 210-300 g at the beginning of the experiment are used. Animals are triple-housed in stainless steel hanging cages in a temperature (22° C.) and humidity (40-70% RH) controlled animal facility with a 12:12 hour light-dark cycle. Food (Standard Rat Chow, PMI Feeds Inc., #5012) and water are available ad libitum.

Apparatus.

Consumption data is collected while the animals are housed in Nalgene Metabolic cages (Model #650-0100). Each cage comprises subassemblies made of clear polymethylpentene (PMP), polycarbonate (PC), or stainless steel (SS). The entire cylinder-shaped plastic and SS cage rests on a SS stand and houses one animal. The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment.

The second assembly includes a water bottle support, a PC water bottle (100 ml capacity) and a graduated water spillage collection tube. The water bottle support funnels any spilled water into the water spillage collection tube. The lower chamber consists of a PMP separating tone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube.

Food consumption, water consumption, and body weight are measured with an Ohaus Portable Advanced scale (±0.1 gram accuracy).

Procedure.

Prior to the day of testing, animals are habituated to the testing apparatus by placing each animal in a Metabolic cage for one hour. On the day of the experiment, animals that are food deprived the previous night are weighed and assigned to treatment groups. Assignments are made using a quasi-random method utilizing the body weights to assure that the treatment groups have similar average body weight. Animals are then administered either vehicle (generally 0.5% methyl cellulose, MC) or test compound. At that time, the feeding drawer is filled with pulverized chow, and the filled water bottle, the empty urine and feces collection tubes are weighed. Two hours after test compound treatment, each animal is weighed and placed in a Metabolic Cage. Following a one hour test session, animals are removed and body weight obtained. The food and water containers are then weighed and the data recorded.

Test Compound.

Test Compound is administered orally (0.1-50 mg/kg for oral (PO) dosing) using a gavage tube connected to a 3 or 5 ml syringe at a volume of 10 ml/kg. In some instances test compound is administered by a systemic route (e.g. by intravenous injection 0.1-20 mg/kg for i.v. dosing). Test compound for oral dosing is made into a homogenous suspension by stirring and ultrasonicating for at least one hour prior to dosing.

Statistical Analyses.

The means and standard errors of the mean (SBM) for food consumption, water consumption, and body weight change are calculated. One-way analysis of variance using Sytat (5.2.1) is used to test for group differences. A significant effect is defined as having a p value of <0.05.

The following parameters are defined: Body weight change is the difference between the body weight of the animal immediately prior to placement in the metabolic cage and its body weight at the end of the one hour test session. Food consumption is the difference in the weight of the food drawer prior to testing and the weight following the one hour test session. Water consumption is the difference in the weight of the water bottle prior to testing and the weight following the one hour test session.

5.18.13.2. Overnight Food Intake

Subjects.

Male Sprague-Dawley rats (Sasco, St. Louis, Mo.) weighing 210-300 g at the beginning of the experiment are used. Animals are pair or triple-housed in stainless steel hanging cages in a temperature (22° C.) and humidity (40-70% RH) controlled animal facility with a 12:12 hour light-dark cycle. Food (Standard Rat Chow, PMI Feeds Inc., #5012) and water are available ad libitum.

Apparatus.

Consumption and elimination data are obtained while the animals are housed in Nalgene Metabolic cages (Model #650-0100). Each cage is comprised of subassemblies made of clear polymethlypentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 grams of pulverized rat chow, and a food spillage compartment. The animal is allowed access to the pulverized chow by an opening in the SS floor of the feeding chamber. The floor of the feeding chamber does not allow access to the food dropped into the spillage compartment. The second assembly includes a water bottle support, a PC water bottle (100 ml capacity) and a graduated water spillage collection tube. The water bottle support funnels any spilled water into the water spillage collection tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube.

Food consumption, water consumption, urine excretion, feces excretion, and body weight are measured with an Ohaus Portable Advanced scale (±0.1 gram accuracy).

Procedure.

On the day of the experiment, animals are weighed and assigned to treatment groups. Assignments are made using a quasi-random method utilizing the body weights to assure that the treatment groups have similar average body weight. Two hours prior to lights off (1830 hours), animals are administered either vehicle (0.5% methyl cellulose, MC) or test compound. At that time, the feeding drawer filled with pulverized chow, the filled water bottle, and the empty urine and feces collection tubes are weighed. Following dosing, each animal is weighed and placed in the Metabolic Cage. Animals are removed from the Metabolic Chamber the following morning (0800 hours) and body weight obtained. The food and water containers, and the feces and urine collection tubes, are weighed and the data recorded.

Test Compound.

Test compound is administered orally (PO) using a gavage tube connected to a 3 or 5 ml syringe at a volume of 10 mVkg. Test compound is made into a homogenous suspension by stirring and ultrasonicating for at least one hour prior to dosing. In some experiments, animals are tested for more than one night. In these studies, animals are administered, on subsequent nights, the same treatment (test compound or 0.5% MC) they had received the first night.

Statistical Analyses.

The means and standard errors of the man (SEM) for food consumption, water consumption, urine excretion, feces excretion, and body weight change are calculated. One-way analysis of variance using Sytat (5.2.1) is used to test for group differences. A significant effect is defined as having a p value of <0.05.

The following parameters are defined: Body weight change is the difference between the body weight of the animal immediately prior to placement in the metabolic cage (1630 hours) and its body weight the following morning (0800 hours). Food. consumption is the difference in the weight of the food drawer at 1630 and the weight at 0800. Water consumption is the difference in the weight of the water bottle at 1630 and the weight at 0800. Fecal excretion is the difference in the weight of the empty focal collection tube at 1630 and the weight at 0800. Urinary excretion is the difference in the weight of the empty urine collection tube at 1630 and the weight at 0800.

5.18.14. Methods for Detecting Changes in Gene Expression or Protein Expression This invention provides several methods for detecting changes in gene expression or protein expression, including but not limited to the expression of SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20, homologs of each of the foregoing, and marker genes operably linked to each of the forgoing. SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20 are described in Section 6.7.5, below. Assays for changes in gene expression are well known in the art (se, e.g., PCT Publication No. WO 96/34099, published Oct. 31, 1996, which is incorporated by reference herein in its entirety). Such assays may be performed in vitro using transformed cell lines, immortalized cell lines, or recombinant cell lines.

The RNA expression or protein expression of an open reading frame (which may be of a marker gene or may be of a gene described in Section 6.7.5), regulated by a promoter native to the gene described in Section 6.7.5 may be measured by measuring the amount or abundance of the RNA (as RNA or cDNA) or protein. In particular, the assays may detect the presence of increased or decreased expression of a gene described in Section 6.7.5 (e.g., SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20) on the basis of increased or decreased mRNA expression (using, e.g., nucleic acid probes), increased or decreased levels of protein products (using, e.g., antibodies thereto), or increased or decreased levels of expression of a marker gene (e.g., green fluorescent protein "GFP") operably linked to a the 5' promoter region in a recombinant construct The present invention envisions monitoring changes in gene expression (e.g., a gene disclosed in Section 6.7.5, below) or marker gene expression by any expression analysis technique known to one of skill in the art, including but not limited to, differential display, serial analysis of gene expression (SAGE), nucleic acid may technology, oligonucleotide array technology, GeneChip expression analysis, dot blot hybridization, northern blot hybridization, subtractive hybridization, protein chip arrays, Western blot, immunopre- cipitation followed by SDS PAGE, immunocytochemistry, proteome analysis and mass-spectrometry of two-dimensional protein gels.

Methods of gene expression profiling to measure changes in gene expression are well-known in the art, as exemplified by the following references describing subtractive hybridization (Wang and Brown, 1991, *Proc. Natl. Acad. Sci. U.S.A.* 88:11505-11509), differential display (Liang and Pardee, 1992, *Science* 257:967-971), SAGE (Velculescu et al., 1995, *Science* 270:484-487), proteome analysis (Humphery-Smith et al., 1997, *Electrophoresis* 18:1217-1242; Dainese et al., 1997, *Electrophoresis* 18:432-442), and hybridization-based methods employing nucleic acid arrays (Heller et al., 1997, *Proc. Natl. Acad. Sci. U.S.A.* 94:2150-2155; Lashkari et al., 1997, *Proc. Natl. Acad. Sci. U.S.A.* 94:13057-13062; Wodicka et al., 1997, *Nature Biotechnol.* 15:1259-1267). Microarray technology is described in more detail below.

In one series of embodiments, various expression analysis techniques may be used to identify molecules that affect expression of a gene disclosed in Section 6.7.5 or marker gene expression, by comparing a cell line expressing a gene disclosed in Section 6.7.5 (e.g., SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20) or a marker gene under the control of a gene promoter sequence in the absence of a test molecule to a cell line expressing the same gene or marker gene under the control of the same promoter sequence in the presence of the test molecule. In a preferred embodiment, expression analysis techniques are used to identify a molecule that upregulates a gene disclosed in Section 6.7.5 or upregulates marker gene expression upon treatment of a cell with the molecule.

5.18.15. Methods for Monitoring Reporter Gene Expression of a Gene of the Present Invention

5.18.15.1. Heterologous Reporter Gene Construct

In a preferred embodiment, the cell being assayed for reporter gee expression contains a fusion construct of at least one transcriptional promoter region for a gene disclosed in Section 6.7.5 (e.g., SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20) (also referred to herein as the test gene) or homologs of the foregoing, each operably linked to a marker gene expressing a detectable and/or selectable product. Increased expression of a marker gene operably linked to a gene promoter indicates increased expression of the test gene.

The marker gene is a sequence encoding a detectable or selectable marker, the expression of which is regulated by at least one gene promoter region in the heterologous construct used in the present invention. Preferably, the assay is carried out in the absence of background levels of marker gene expression (e.g., in a cell that is mutant or otherwise lacking in the marker gene). If not already lacking in endogenous marker gene activity, cells mutant in the marker gene may be selected by known methods, or the cells can be made mutant in the marker gene by known gene-disruption methods prior to introducing the marker gene (Rothstein, 1983, *Meth. Enzymol.* 101:202-211).

A marker gene of the invention may be any gene that encodes a detectable and/or selectable product. The detectable marker can be any molecule that can give rise to a detectable signal, e.g., a fluorescent protein or a protein that can be readily visualized or that is recognizable by a specific antibody or that gives rise enzymatically to a signal. The selectable marker can be any molecule that can be selected for its expression, e.g., which gives cells a selective advantage over cells not having the selectable marker under appropriate (selective) conditions. In preferred aspects, the selectable marker is an essential nutrient in which the cell in which the interaction assay occurs is mutant or otherwise lacks or is deficient, and the selection medium lacks such nutrient. In one embodiment, one type of marker gene is used to detect gene expression. In another embodiment, more than one type of marker gene is used to detect gene expression.

Preferred marker genes include but are not limited to, green fluorescent protein (GFP) (Cubitt et al., 1995, Trends Biochem. Sci. 20:448-455), red fluorescent protein, blue fluorescent protein, luciferase, LEU2, LYS2, ADB2, TRP1, CAN1, CYH2, GUS, CUP1 or chloramphenicol acetyl transferase (CAT). Other marker genes include, but are not limited to, URA3, HIS3 and/or the lacZ genes (see e.g., Rose and Botstein, 1983, *Meth. Enzymol.* 101:167-180) operably linked to GAL4 DNA-binding domain recognition elements. Alam and Cook disclose non-limiting examples of detectable marker genes that can be operably linked to a glucan synthase pathway reporter gene promoter region (Alam and Cook, 1990, *Anal Biochem.* 188:245-254).

In a preferred embodiment, more than one different marker gene is used to detect transcriptional activation, e.g., one encoding a detectable marker, and one or more encoding one or more different selectable marker(s), or e.g., different detectable markers. Expression of the marker genes can be detected and/or selected for by techniques known in the art (see e.g. U.S. Pat. Nos. 6,057,101 and 6,083,693).

Methods to construct a suitable reporter construct are disclosed herein by way of illustration and not limitation and any other methods known in th art may also be used. In a preferred embodiment, the reporter gene construct is a chimeric reporter construct comprising a marker gene that is transcribed under the control of a gene promoter sequence comprising all or a portion of a promoter region of SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20. If not already a part of the DNA sequence, the translation initiation codon, ATG, is provided in the correct reading frame upstream of the DNA sequence.

Vectors comprising all or portions of the gene sequences of SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20 useful in the construction of recombinant reporter gene constructs and cells are provided. The vectors of this invention also include those vectors comprising DNA sequences that hybridize under stringent conditions to SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20 gene sequences, and conservatively modified variations thereof.

The vectors of this invention may be present in transformed or transfected cells, cell lysates, or in partially purified or substantially pure forms. DNA vectors may contain a means for amplifying the copy number of the gene of interest, stabilizing sequences, or alternatively may be designed to favor directed or non-directed integration into the host cell genome.

Given the strategies described herein, one of skill in the art can construct a variety of vectors and nucleic acid molecules comprising functionally equivalent nucleic acids. DNA cloning and sequencing methods are well known to those of skill in the art and are described in an assortment of laboratory manuals, including Sambrook et al., 1989, supra; and Ausubel et al., 2002 Supplement.

Transformation and other methods of introducing nucleic acids into a host cell (e.g., transfection, electroporation, liposome delivery, membrane fusion techniques, high velocity DNA-coated pellets, viral infection and protoplast fusion) can be accomplished by a variety of methods that are well known in the art (see, for instance, Ausubel, supra, and Sambrook, supra). *S. cerevisiae* cells of the invention can be transformed or transfected with an expression vector, such as a plasmid, a cosmid, or the like, wherein the expression vector comprises the DNA of interest. Alternatively, the cells may be infected by a viral expression vector comprising the DNA or RNA of interest.

Particular details of the transfection and expression of nucleic acid sequences are well documented and are understood by those of skill in the art. Further details on the various technical aspects of each of the steps used in recombinant production of foreign genes in expression systems can be found in a number of texts and laboratory manuals in the art (see, e.g., Ausubel et al., 2002, herein incorporated by reference).

5.18.15.2. Other Methods for Monitoring Reporter Gene Expression

In accordance with the present invention, reporter gene expression can be monitored at the RNA or the protein level. In a specific embodiment, molecules that affect reporter gene expression may be identified by detecting differences in the level of marker protein expressed by cells contacted with a test molecule versus the level of marker protein expressed by cells in the absence of the test molecule.

Protein expression can be monitored using a variety of methods that are well known to those of skill in the art. For example, protein chips or protein microarrays (e.g., ProteinChip™, Ciphergen Biosystem) and two-dimensional electrophoresis (see e.g., U.S. Pat. No. 6,064,754 which is incorporated herein by reference in its entirety) can be utilized to monitor protein expression levels. As used herein "two-dimensional electrophoresis") (2D-electrophoresis) means a technique comprising isoelectric focusing, followed by denaturing electrophoresis, generating a two-dimensional gel (2D-gel) containing a plurality of proteins. Any protocol for 2D-electrophoresis known to one of ordinary skill in the art can be used to analyze protein expression by the reporter genes of the invention. For example, 2D electrophoresis can be performed according to the methods described in O'Farrell, 1975, J. Biol. Chem. 250: 4007-4021.

Liquid High Throughput-Like Assay.

In a preferred embodiment, a liquid high throughput-like assay is used to determine the protein expression level of a reporter gene. The following exemplary, but not limiting, assay may be used:

A reporter construct is transformed into a cell strain. Cultures from solid media plate are used to innoculate liquid cultures in Casamino Acids media or an equivalent media. This liquid culture is grown and then diluted in Casamino Acids media or an equivalent media.

A test molecule is selected for the assay, preferably but not necessarily along with a negative control molecule. The test molecule and negative control molecule are separately added to an assay plate containing multiple wells and serially diluted (e.g., 1 to 2) into Casamino Acids media plus DMSO in sequential columns, so that each plate contains a range of concentrations of each drug. If a negative control is being used, one column of each plate may be used as a "no drug" control, containing only Casamino Acids media plus DMSO.

The skilled artisan will note that different assay plates may be used, such as those with 96, 384 or 1536 well format.

An aliquot of liquid reporter strain is added to each well of the serial dilution plates from above and mixed. The assay plates are then incubated. After incubation the assay plates are analyzed for detectable marker gene product. In a preferred embodiment, the assay plates are imaged in a Molecular Dynamics Fluorimager SI to measure the fluorescence from the GFP reporters.

The results are than analyzed, as described above. If the drug is an inhibitor of the gene product (e.g., an inhibitor of SEQ ID NO: 4, SEQ ID NO: 5, SEQ ID NO: 6, SEQ ID NO: 7, SEQ ID NO: 8, SEQ ID NO: 10, SEQ ID NO: 11, SEQ ID NO: 14, SEQ ID NO: 15, SEQ ID NO: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO, 28, and SEQ ID NO: 29, the reporter will show increases in fluorescence for the higher drug concentrations versus the lower drug concentrations and/or the no drug controls.

5.18.15.3. Specific Embodiments

One embodiment of the present invention provides a method for determining whether a candidate molecule affects a body weight disorder associated with an organism. In step (a) of the method, a cell from the organism is contacted with the candidate molecule. Alternatively, the candidate molecule is recombinantly expressed within the call. In step (b) of the method, a determination is made as to whether the RNA expression or protein expression in the call of at least one open reading frame is changed in stop (a) relative to the expression of the open reading frame in the absence of the candidate molecule, where each open reading frame is regulated by a promoter native to a nucleic acid sequence selected from the group consisting of SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20, and homologs of each of the foregoing. The candidate molecule affects a body weight disorder associated with the organism when the RNA expression or protein expression of the at least one open reading frame is changed. The candidate molecule does not affect a body weight disorder associated with the organism when the RNA expression or protein expression of the at least one open reading frame is unchanged. In some embodiments, the body weight disorder is obesity, anorexia nervosa, bulimia nervosa or cachexia.

In some embodiments, the candidate molecule affects a body weight disorder associated with the organism when a call from the organism that is contacted with the candidate molecule exhibits a lower expression level of a protein sequence in the group consisting of SEQ ID NO: 4, SEQ ID NO: 5, SEQ ID NO: 6, SEQ ID NO: 7, SEQ ID NO: 8, SEQ ID NO: 10, SEQ ID NO: 11, SEQ ID NO: 14, SEQ ID NO: 15, SEQ ID NO: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29, relative to a cell from the organism that is not contacted with the candidate molecule.

In some embodiments step (b) comprises determining whether RNA expression is changed. In some embodiments step (b) comprises determining whether protein expression is changed. In some embodiments, step (b) comprises determining whether RNA or protein expression of at least two of the open reading frames is changed. In some embodiments, step (a) comprises contacting the cell with the candidate molecule and step (a) is carried out in a liquid high throughput-like assay.

In some embodiments, the cell comprises a promoter region of at least one gene selected from the group consisting of SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20, and homologs of each of the foregoing, each promoter region being operably linked to a marker gene. Further, in such embodiments, step (b) comprises determining whether the RNA expression or protein expression of the marker gene(s) is changed in step (a) relative to the expression of the marker gene in the absence of the candidate molecule. In some embodiments, the marker gene is selected from the group consisting of green fluorescent protein, red fluorescent protein, blue fluorescent protein, luciferase, LEU2, LYS2, ADB2, TRP1, CAN1, CYH2, GUS, CUP1 and chloramphenicol acetyl transferase.

Another aspect of the invention provides a method of identifying a molecule that specifically binds to a ligand selected from the group consisting of (i) a protein encoded by a gene selected from the group consisting of SEQ ID NO: 1, SEQ ID NO: 2, SEQ ID NO: 3, SEQ ID NO: 9, SEQ ID NO: 12, SEQ ID NO: 13, SEQ ID NO: 16, SEQ ID NO: 19, SEQ ID NO: 20, and homologs of each of the foregoing, and (ii) a biologically active fragment of SEQ ID NO: 4, SEQ ID NO. 5, SEQ ID NO: 6, SEQ ID NO: 7, SEQ ID NO: 8, SEQ ID NO: 10, SEQ ID NO: 11, SEQ ID NO: 14, SEQ ID NO: 15, SEQ ID NO: 17, SEQ ID NO: 18, SEQ ID NO: 21, SEQ ID NO: 22, SEQ ID NO: 23, SEQ ID NO: 24, SEQ ID NO: 25, SEQ ID NO: 26, SEQ ID NO.: 27, SEQ ID NO: 28, and SEQ ID NO: 29. The method comprises (a) contacting the ligand with one or more candidate molecules under conditions conducive to binding between the ligand and the candidate molecules; and (b) identifying a molecule within the one or more candidate molecules that binds to the ligand.

5.18.16. Method of Treating or Preventing Body Weight Disorders

One aspect of the invention provides a method of treating or preventing a body weight disorder. The method comprises administering to a subject in which treatment is desired a therapeutically effective amount of a molecule that inhibits a function of one or more of the group consisting of SEQ ID NO: 8, SEQ ID NO: 11, SEQ ID NO: 15, SEQ ID NO: 18, SEQ ID NO: 25, SEQ ID NO: 26, and SEQ ID NO: 27. In some embodiments, the subject is human. In some embodiments, the molecule that inhibits a function of one or more of the group consisting of SEQ ID NO: 8, SEQ ID NO: 11, SEQ ID NO: 15, SEQ ID NO: 18, SEQ ID NO: 25, SEQ ID NO: 26, and SEQ ID NO: 27 is selected from the group consisting of an antibody that binds to one of SEQ ID NO: 8, SEQ ID NO: 11, SEQ ID NO: 15, SEQ ID NO: 18, SEQ ID NO: 25, SEQ ID NO: 26, and SEQ ID NO: 27 or a fragment or derivative therefore containing the binding region thereof, a nucleic acid complementary to the RNA produced by transcription of a gene encoding one of SEQ ID NO: 8, SEQ ID NO: 11, SEQ ID NO: 15, SEQ ID NO: 18, SEQ ID NO: 25, SEQ ID NO: 26, and SEQ ID NO: 27. In some embodiments, the molecule that inhibits a function of one or more of the group consisting of SEQ ID NO: 8, SEQ ID NO: 11, SEQ ID NO: 15, SEQ ID NO: 18, SEQ ID NO: 25, SEQ ID NO: 26, and SEQ ID NO: 27 is an oligonucleotide that (a) consists of at least six nucleotides; (b) comprises a sequence complementary to at least a portion of an RNA transcript of a gene encoding one of SEQ ID NO: 8, SEQ ID NO: 11, SEQ ID NO: 15, SEQ ID NO: 18, SEQ ID NO: 25, SEQ ID NO: 26 or SEQ ID NO: 27; and (c) is hybridizable to said RNA transcript under moderately stringent conditions.

Another aspect of the invention provides a method of treating or preventing a body weight disorder. The method comprises administering to a subject in which treatment is desired a therapeutically effective amount of a molecule that enhances a function of one or more of the group consisting of SEQ ID NO: 8, SEQ ID NO: 11, SEQ ID NO: 15, SEQ ID NO: 18, SEQ ID NO: 25, SEQ ID NO: 26, and SEQ ID NO: 27. In some embodiments, the subject is human.

Yet another aspect of the invention provides a method of diagnosing a disease or disorder or the predisposition to said disease or disorder, wherein the disease or disorder is characterized by an aberrant level of one of SEQ ID NO: 1 through SEQ ID NO: 29 in a subject. The method comprises measuring the level of any one of SEQ ID NO: 1 through SEQ ID NO: 29 in a sample derived from the subject, in which an increase or decrease in the level of one of SEQ ID NO: 1 through SEQ ID NO: 29 in the sample, relative to the level of one of said SEQ ID NO: 1 through SEQ ID NO: 29 found in an analogous sample not having the disease or disorder, indicates the present of the disease or disorder in the subject. In some embodiments, the disease or disorder is a body weight disorder, such as obesity, anorexia nervosa, bulimia nervosa, or cachexia.

Still another aspect of the invention provides a method of diagnosing or screening for the presence of or predisposition for developing a disease or disorder involving a body weight disorder in a subject comprising detecting one or more mutations in at least one of SEQ ID NO: 1 through SEQ ID NO: 29 in a sample derived from the subject, in which the presence of the one or more mutations indicates the presence of the disease or disorder or a predisposition for developing the disease or disorder.

5.18.17. Transgenic Animals

The invention also provides animal models. Transgenic animals that have incorporated and express a constitutively-functional obesity related gene have use as animal models of diseases and disorders involving in T-cell overactivation or over-proliferation, or in which cell proliferation is desired. Such animals can be used to screen for or test molecules for the ability to suppress activation and/or proliferation of T-cells and thus treat or prevent such diseases and disorders. In one embodiment, animal models for diseases and disorders involving obesity related disorders am provided. Such animals can be initially produced by promoting homologous recombination between an obesity related gene in its chromosome and an exogenous obesity related gene that has been rendered biologically inactive. Preferably the sequence inserted is a heterologous sequence, e.g., an antibiotic resistance gene. In a preferred aspect, this homologous recombinalion is carried out by transforming embryo-derived stem (ES) cells with a vector containing an insertionally inactivated gene, wherein the active gene encodes a particular obesity related gene, such that homologous recombination occurs; the ES cells are then injected into a blastocyst, and the blastocyst is implanted into a foster mother, followed by the birth of the chimeric animal, also called a "knockout animal," in which an obesity related gene has been inactivated (see Capecchi, 1989, Science 244: 1288-1292). The chimeric animal can be bred to produce additional knockout animals. Chimeric animals can be and are preferably non-human mammals such as mice, hamsters, sheep, pigs, cattle, etc. In a specific embodiment, a knockout mouse is produced.

Such knockout animals are expected to develop or be predisposed to developing diseases or disorders involving obesity and thus can have use as animal models of such diseases and disorders, e.g., to screen for or test molecules for the ability to promote activation or proliferation and thus treat or prevent such diseases or disorders.

In a different embodiment of the invention, transgenic animals that have incorporated and express a constitutively-functional obesity related gene have use as animal models of diseases and disorders involving in T-cell overactivation, or in which T cell activation is desired.

In particular, each transgenic line expressing a particular key gene under the control of the regulatory sequences of a characterizing gene is created by the introduction, for example by pronuclear injection, of a vector containing the transgene into a founder animal, such that the transgene is transmitted to offspring in the line. The transgene preferably randomly integrates into the genome of the founder but in specific embodiments may be introduced by directed homologous recombination. In a preferred embodiment, the transgene is present at a location on the chromosome other than the site of the endogenous characterizing gene. In a preferred embodiment, homologous recombination in bacteria is used for target-directed insertion of the key gene sequence into the genomic DNA for all or a portion of the characterizing gene, including sufficient characterizing gene regulatory sequences to promote expression of the characterizing gene in its endogenous expression pattern. In a preferred embodiment, the characterizing gene sequences are on a bacterial artificial chromosome (BAC). In specific embodiments, the key gene coding sequences are inserted as a 5' fusion with the characterizing gene coding sequence such that the key gene coding sequences are inserted in frame and directly 3' from the initiation codon for the characterizing gene coding sequences. In another embodiment, the key gene coding sequences are inserted into the 3' untranslated region (UTR) of the characterizing gene and, preferably, have their own internal ribosome entry sequence (IRE).

The vector (preferably a BAC) comprising the key gene coding sequences and characterizing gene sequences is then introduced into the genome of a potential founder animal to generate a line of transgenic animals. Potential founder animals can be screened for the selective expression of the key gene sequence in the population of cells characterized by expression of the endogenous characterizing gene. Transgenic animals that exhibit appropriate expression (e.g., detectable expression of the key gene product having the same expression pattern within the animal as the endogenous characterizing gene) are selected as founders for a line of transgenic animals.

One aspect of the invention provides a recombinant non-human animal that is the product of a process comprising introducing a nucleic acid encoding at least a domain of one of SEQ ID NO: 8, SEQ ID NO: 15, SEQ ID NO: 18, SEQ ID NO: 25, SEQ ID NO: 26, and SEQ ID NO: 27 into the non-human animal.

5.19. Using Cross Species Data to Associate Genes with Traits of Interest

Another aspect of the invention provides processes by which cross-species data (e.g., mouse and human data) are used to associate genes with a trait of interest (e.g., obesity). In this aspect of the invention, QTL and genes of interest are identified in a first species using techniques such as those described in Sections 5.19.1 and 5.19.3, below. Then, the QTL and genes identified in the first species are used to identify regions of the genome of a second species, or specific genes in the second species, that contribute, cause, or are otherwise associated with a trait of interest using the techniques described in Section 5.19.2, below.

One aspect of the present invention provides ways to identify genes associated with a trait using data from multiple species. In this aspect of the invention, causal genes are identified in a first species using the techniques disclosed in Section 5.19.1, Section 5.19.3, U.S. Patent Application Ser. No. 60/492,682, filed Aug. 5, 2003 entitled "Computer systems and methods for inferring causality from cellular constituent abundance data", U.S. Patent Application Ser. No. 60/497, 480, filed Aug. 21, 2003, entitled "Computer systems and methods for inferring causality from cellular constituent abundance data", U.S. Patent Application Ser. No. 60/400, 522 filed Aug. 2, 2002 entitled "Computer systems and methods that use clinical and expression quantitative trait loci to associate genes with traits", and U.S. Patent Application Ser. No. 60/460,303 filed Apr. 2, 2003, entitled "Computer systems and methods that use clinical and expression quantitative trait loci to associate genes with traits." Typically, this first species is a segregating population such as a mouse cross. The second species is typically humans or some other outbred population in which controlled crosses are either impossible to arrange or are prohibitively expensive. The identity of the causal genes, or the key drivers, for traits related to a disease under study in the first population can be used to identity candidate genes causal for a related disease under study in a second species in any one of at least three different approaches.

In a first approach, the causal genes from the first species are directly mapped to the corresponding genes (orthologous gem) in the second species using standard comparative genomics procedures. Such genes can be validated using association-based testing in a case/control population in the second species. For example, consider the case in which 30 genes have been identified as causal in a controlled cross of a first species using the techniques disclosed in Section 5.19.3. The identity of these 30 genes is used to find the orthologous genes in the second species. Alternatively or additionally, the identity of the 30 genes is used to find corresponding loci in the second species using a syntenic map between the two species. Next, each locus or gene identified in the second species is validated using marker-based association studies in appropriately selected case/control populations.

For example, consider a candidate gene in the second species orthologous to a gene in the first species that has been identified as causal for a trait under study using the techniques of Section 5.19.3. To validate the gene in the second species, a cohort of the second species is assembled. One portion of the cohort will comprise the cases related to the trait under study (e.g., those individuals in some population identified as obese) and the second portion of the cohort population will comprise the controls (e.g., a random sampling of individuals from the population). Each member of the cohort is genotyped with respect to markers in the gene. Such genotyping can involve ascertainment of the allele of known markers in the gene or a separate discovery component for and ascertainment of new markers in the gene. In one approach, the sequence of the gene from each member of the cohort population is obtained and used to identify single nucleotide polymorphisms (SNPs) within the gene. Such SNPs typically have a major allele and a minor allele. Those SNPs with a minor allele frequency present in at least two percent (or some other minimum threshold number) of the cohort are used as markers. Each marker is then tested to see if the marker associates with the trait under study in the cohort population.

In addition, haplotypes can be reconstructed from the collection of SNP data collected in the cohort under study using standard techniques, and association testing can then be carried out directly using the haplotypes. Further, the haplotypes can be used to reduce the number of SNPs that need to be genotyped in extended cohorts or other studies that involve association testing between SNPs in the gene region and the disease trait of interest.

For instance, a marker will associate with a trait under study when the frequency of one of the alleles for the marker differs significantly between the cases and controls. A marker will not associate with a trait under study when there is no frequency difference for any given allele for the marker between the cases and controls. In preferred embodiments, the genotyped markers are haplotyped using conventional haplotype techniques known by those of skill in the art and each such haplotype or representative SNPs comprising each haplotype are used in an association study to see if the haplotype or representative SNPs associate with the trait under study.

To summarize genetic techniques that rely on pedigree information and that are described in Sections 5.19.1 and/or 5.193 are used to identify potentially causal genes in a segregating population (first species) such as that of a mouse cross. Genes orthologous to these genes are identified in another species (second species) such as humans. Alternatively, loci that syntenically map to such causal genes are identified. The genes or loci in the second species are genotyped, haplotypes are constructed and/or individual markers are used in association studies based upon a cohort assembled with respect to the trait of interest. Those genes or loci that have one or more makers and or haplotypes that associate with the disease are considered validated as causal for the trait under study and are subjected to further analysis.

In a second approach, quantitative or qualitative genetic studies are used to identify cQTL or loci for traits in the second species. To be effective, the trait analyzed in the second species has some nexus with the corresponding trait in the first species. For example, the trait in the first species could be omental fat pad mass whereas the trait in the second species could be obesity or visceral fat mass. In this second approach, a gene in the second species is identified as a causal candidate when both of the following conditions hold true: (i) the gene is within a one lod score drop of a cQTL or other form of loci in the second species and (ii) the corresponding gene in the first species is identified as causal using the techniques disclosed in Section 19.3. In such cases, genes so identified can be validated using the type of association-based method described in the first approach above.

In a third approach, an expression-based association analysis is performed with the second species. Genes that (i) have expression patterns that associate with a disease or trait under study in the first species and are orthologous to genes in a segregating population of a first species that are causal for a related disease or trait in the first species are selected for further analysis. To perform the association analysis, a cohort of the second species is assembled as described above for the first approach. Once a cohort has been assembled, a biopsy is taken from each member of the cohort for a particular tissue of interest (e.g., adipose tissue). These biopsies are used to obtain cellular constituent abundance data for each member of the cohort. For example, in the case of obesity, the biopsy taken from each subject could be subcutaneous fat tissue and the cellular constituent abundance data could be the expression levels of genes expressed in the subcutaneous fat tissue. Next, an association analysis is run on all or a portion of the cellular constituents for which cellular constituent abundance data is available. The goal of such a study is to identify which of the cellular constituents associate with the trait under study.

For example, a cellular constituent will associate with the trait if the abundance level of the cellular constituent is consistently high in the portion of the cohort population that exhibits the disease and is consistently low in the portion of the cohort that is randomly selected from the population. Reciprocally, a cellular constituent will associate with the trait if the abundance level of the cellular constitutent is consistently low in the portion of the cohort that exhibits the disease and is consistently high in the portion of the cohort randomly selected from the population. A cellular constituent will not associate with a trait when the abundance level of the cellular constituent has no defined pattern with respect to the cohort. In other words, a cellular constituent will not associate with a trait if the cellular constituent does not have a pattern of high (or low) abundance in the portion of the cohort that has the trait or the portion of the cohort representing a random sampling from the population. Association analyses are further discussed in Section 5.15.1.

Thus, in the third approach, genes in the outbred second species (e.g. humans) that are associated with a complex trait are identified. Those genes that (i) have expression patterns that associate with a disease or trait under study in the second species and (ii) are orthologs of genes that are identified as causal for a related disease or trait in the first inbred species (e.g., a mouse population) using the techniques discussed, for example, in Section 5.19.3 are selected as candidates for further validation. Such validation can include association-based testing in a case/control cohort population using the association techniques described in the first approach.

One embodiment in accordance with this aspect of the invention provides a method for confirming the association of a query QTL or a query gene in the genome of a second species with a clinical trait T exhibited by the second species. In the method, a first QTL or a first gene in a first species that is linked to a trait T' is found. Here, trait T' (exhibited by the first species) is indicative of trait T (exhibited by the second species). See Section 5.19.1, below. A region of the genome of the first species that comprises the first QTL or the first gene is mapped to a region of the genome of the second species. A query QTL or a query gene in the second species that is potentially associated with the trait T is found. The potential association of the query QTL or the query gene with the clinical trait T is confirmed when the query QTL or the query gene is in the region of the genome of the second species. See Section 5.19.2, below.

Sections 5.19.1 and 5.19.2 provide an example in which trait T is obesity and trait T' is indicative of obesity (trait T). However, the present invention is not limited to the obesity trait. Many other traits T can be studied using the techniques disclosed in this section. Such traits T include, but are not limited to asthma; ataxia telangiectasia, bipolar disorder, cancer, common late-onset Alzheimer's disease, diabetes, heart disease, hereditary early-onset Alzheimer's disease, hereditary nonpolyposis colon cancer, hypertension, infection, maturity-onset diabetes of the young, mellitus, migraine, nonalcoholic fatty liver, nonalcoholic steatohepatitis, non-insulin-dependant diabetes mellitus, obesity, polycystic kidney disease, psoriases, schizophrenia, or xeroderma pigmentosum. Those of skill in the art will recognize the traits T' that are indicative of such traits T.

5.19.1. Identifying QTL and Genes in a First Species that are Linked to a Trait of Interest In one embodiment in accordance with this aspect of the invention, a first QTL or a first gene in a first species is found by identifying two inbred strains of the first species that exhibit polymorphic behavior with respect to a trait T'. In one example, the trait T is obesity in the second species (human) and trait T' is percent body fat in inbred strains of mice (first species). In the example, inbred strains of mice that vary significantly with respect to trait T' are crossed to obtain an F2, back-cross or other such segregating population. Other types of inbred populations are possible, including, but not limited to, backcrosses, $F_2$ intercrosses, $F_t$ populations (formed by randomly mating $F_1$s for t−1 generations), $F_{2:3}$ design ($F_2$ individuals are genotyped ad then selfed), Design III ($F_2$ from two inbred lines are backcrossed to both parental lines). The goal at this stage is to generate a population where trait T' (percent body fat) is segregating. This process is depicted graphically in FIG. 55 for EZE responsiveness. More than one trait T' can be studied at the same time. In one example, trait T is obesity in human and the traits T' are high density lipoprotein (HDL) level, low density lipoprotein level LDL and very low density lipoprotein (VLDL) level, free fatty acid level, fat pad masses at several depots, and BMI in mice. BMI is defined in Section 2.3, above. In such cases, traits T' in mice (HDL level, etc.) are indicative of the trait T in human (obesity). Those of skill in the art will appreciate that there are a large number of cases where traits T' in one species are indicative of a trait T in another species, and all such cases are within the scope of the present invention.

Once a segregating population of the first species has been obtained, it is genotyped based upon, for example, a marker map 78 (FIG. 1). For details on marker maps 78 see Section 5.2, above. In addition, the segregating population may be scored with respect to phenotypes associated with the trait of interest. Further, tissues relevant to the trait T are isolated for expression profiling. The trait data 70, expression data 44 and genotype data 68 (FIG. 2) are then analyzed using methods such as those described in Section 5.1 and depicted in FIG. 2 in order to identify genes and patterns of expression associated with the traits of interest. This process is depicted in FIG. 56.

One use of expression data 44 is to refine the definition of the trait T' (e.g., to refine the definition of percent body fat in mice). In essence, this refinement of the trait T' equates to identifying those subgroups within the whole population that are homogenous with respect to trait T'. FIG. 57 depicts the general case where the population under study is homogenous with respect to T'. Circle 5700 comprises different shapes to represent different trait subtypes represented in the population. The different subtypes may be phenotypically similar (e.g., all obese), but they can be stratified based on differences in the underlying mechanisms that lead to the phenotype of interest (T').

There are many different ways to identify subtypes within a population using expression data 44. In other words, there are many different ways to stratify a population into different subpopulations in order to refine the definition of trait T'. Bach subpopulation has a more refined definition of trait T'. To illustrate, consider the case in which a population exhibits trait T'. In this illustration, cellular constituent expression data for each organism in the population is used as a discriminator to break the population down into two or more subpopulations. The first subpopulation exhibits trait $T_1$, the second subpopulation exhibits trait $T_2$, and so forth. All the subpopulations exhibit trait T', but now the trait has been refined into trait $T_1$, $T_2$, etc. based on the expression data.

One way to stratify a population in order to better characterize (or subcharacterize) trait T' is depicted in FIGS. 57 and 58. First, those individuals in the subpopulation that are most extreme with respect to trait T' (subpopulations 5702 and 5704) are identified. For example, when trait T' is fat pad mass, the mice with highest fat pad mass and lowest fat pad mass in the population are selected as depicted in FIG. 57. The idea here is to enrich for patterns associated with the different subtypes of trait T' by focusing on the phenotypic extremes of trait T'. In one embodiment of the present invention, a phenotypic extreme is defined as the top or lowest $40^{th}$, $30^{th}$, $20^{th}$, or $10^{th}$ percentile of the population with respect to a given trait T' exhibited by the population. Once the phenotypic extremes have been identified, clustering approaches and pattern recognition techniques described in Section 5.1 and FIG. 2 can be used to identify patterns of expression that appear to define different subgroups ($T_{1'}$, $T_{2'}$, etc.) within the extreme that, when considered together, appear to discriminate between the extreme phenotypes.

In one example, the upper and lower $25^{th}$ percentiles of a segregating F2 population of mice with respect to fat pad mass were examined. The F2 intercross was constructed from C57BL/6J and DBA/2J strains of mice. Mice were on a rodent chow diet up to 12 months of age, and then switched to a atherogenic high-fat, high-cholesterol diet for another four months. Parental and F2 mice were sacrificed at 16 months of age. At death the livers were immediately removed, flash-frozen in liquid nitrogen and stored at –80 C. Total cellular RNA was purified from 25 mg portions using an Rneasy Mini kit according to the manufacturer's instructions (Qiagen, Valencia, Calif.). Further details on this cross are found in Section 6.4, below.

FIG. 59 depicts a two-dimensional cluster of the most differentially expressed set of genes in mice comprising the upper and lower $25^{th}$ percentiles of the subcutaneous fat pad mass (FPM) trait in the segregating F2 population. In FIG. 59, the y-axis represents the 280 genes in mice that are most differentially expressed in extreme subpopulations of the mouse population and the x-axis represents the mouse population itself. This set of genes (the FPM set) can be considered as the most transcriptionally active set of genes for mice falling the in tails of the FPM trait (T) distribution. The selection of this gene set for clustering was not biased by selecting genes based on eQTL linkage information, their ability to discriminate between the FPM trait extremes, nor on their correlation to genes identified by eQTL and/or trait-discrimination properties. Despite this, when clustering on this set of genes over the F2 population, the mice cluster almost perfectly into high FPM and low FMP groups as shown in FIG. 59. In addition, there appear to be two distinct expression patterns for mice in the high FPM group (high PPM group 1; high FPM group 2), indicating some degree of heterogeneity in the high PPM mice. This example shows how a gene set can be used to cluster a population exhibiting a trait T' into subpopulations, where each subpopulation exhibits a different trait $T_{1'}$ that is defined by a characteristic expression pattern of the gene set.

The patterns realized in FIG. 59 serve to define subcategories of the obesity trait, FPM. In fact, these patterns refine the definition of FPM into subcategories ($T_{1'}$, $T_{2'}$, etc.) for the trait in a way that would not be possible without the expression data. There are clearly two distinct expression patterns associated with high FPM mice depicted in FIG. 59 over the gene set. This heterogeneity of expression patterns associated with the clinical trait T' almost certainly points to heterogeneity in the complex disease itself.

For the FPM trait, a genome-wide scan revealed 4 cQTL with lod scores greater than 2.0. Taken together, these cQTL explained slightly less than 50% of the variation in the PPM trait values. To further elucidate this clinical trait T', the 111 F2 animals for which clinical and gene expression data existed were classified into one of the three groups depicted in FIG. 59 (i.e., high PPM Group 1, high FPM group 2, low PPM group).

Subsequently, separate genetic analysis were performed. FIGS. 60 and 61 respectively depict these analysis for chromosome 2 and chromosome 19 of the mouse genome. Experimental details for this QTL analysis are provided in Section 6.4, below. For each chromosome (2 and 19) three separate analyses were run. The first analysis used the entire set of 111 F2 animals (curve 6002). The second set used the set of F2 animals that comprise the high FPM group 1 and low FPM animals (curve 6006). The third analysis used the set of F2 animals that comprise the high FPM group 2 and low PPM animals (curve 6004). FIG. 60 shows that high FPM group 1 is not under the control of the chromosome 2 QTL, but that high FPM group 2 is under the control of the chromosome 2 QTL. FIG. 61 shows that the high fat animal group is not under the control of the chromosome 2 locus (high FPM group 1), is under the control of a chromosome 19 locus, while high FPM group 2 is not. These results indicate that chromosome 2 and 19 QTL each significantly affect only a subset of the F2 population, a form of heterogeneity that speaks directly to the complexity underlying traits such as obesity. The chromosome 19 QTL explains 19% of the variation in the PPM trait for the high FPM group 1/low FPM subset, but would have been completely missed if the expression data had not been used to define subphenotypes.

The significance of the QTL with the highest lod scores depicted in FIGS. 60 and 61 were assessed by repeatedly sampling (10,000 times) from the full set of F2 animals so that groups equal in size to the high FPM group 1/low PPM and high FPM group 2/low FPM groups were obtained for each iteration. None of the 10,000 samplings achieved QTL matching the significances of those given in FIGS. 60 and 61.

To summarize, one embodiment in accordance with the present invention identifies a first QTL or a first gene in a first species that is linked to a trait T' by crossing a first strain and a second strain of the first species in order to obtain a segregating population. Next, the population is stratified into a plurality of subpopulations. At least one subpopulation in the plurality of subpopulations represents a phenotypic extreme of trait T'.

Cellular constituent measurements from organisms in the plurality of subpopulations is used to identify a cellular constituent set that exhibits a cellular constituent measurement pattern associated with the phenotypic extreme. Then the segregating population is clustered based on measurements of the cellular constituent set in organisms in the segregating population to obtain a plurality of population clusters (e.g., the high PPM group 1, high FPM group 2, and low PPM group of FIG. 59). Quantitative genetic analysis is performed on these population clusters in order to find a first QTL or a first gene that is linked to trait T'. In some embodiments, the quantitative genetic analysis is performed using a method that uses one or more techniques selected from the group consisting of linkage analysis (Section 5.13), quantitative genetic analysis that uses a plurality of cellular constituent measurements as a phenotypic trait (Section 5.1), and association analysis (Section 5.14). In some embodiments, this linkage arises when the first QTL has a lod score greater than 2.0, 2.5, 3.0, 3.5, 4.0, 4.5, 5.0, or 8.0. In some embodiments, the cellular constituent measurements are transcriptional state measurements or translational state measurements. In some embodiments, the cellular constituent measurements are translational state measurements that are performed using an antibody array or two-dimensional gel electrophoresis. In some embodiments, the cellular constituent set comprises a plurality of metabolites and the plurality of cellular constituent measurements are derived by it cellular phenotypic technique (e.g., a metabolomic technique in which a plurality of levels of metabolites in one or more organisms in the segregating population is measured). In some embodiments, the metabolites comprise an amino acid, a metal, a soluble sugar, or a complex carbohydrate. In some embodiment, the cellular constituent measurements comprise gene expression levels, abundance of mRNA, protein expression levels, or metabolite levels.

In another embodiment in accordance with the present invention a first QTL or a first gene in a first species that is linked to a trait T' is found by crossing a first strain and a second strain of the first species in order to obtain a segregating population. Next, the segregating population is divided into a plurality of subpopulations using a classification scheme that classifies each organism in the segregating population into at least one of the subpopulations. The subpopulations may or may not represent phenotypic extremes. The classification scheme uses cellular constituent measurements of a plurality of cellular constituents from each organism in the segregating population. Various classification schemes that may be used to perform this step are found in copending U.S. Patent Application No. 60/382,036 filed May 20, 2002 entitled "Computer systems and methods for subdividing a complex disease into component diseases" which is hereby incorporated by reference in its entirety. For at least one subpopulation in the plurality of subpopulations, quantitative genetic analysis on the subpopulation is performed in order to find the first QTL or the first gene. In some embodiments, the cellular constituent measurements are transcriptional state measurements or translational state measurements. In some embodiments, the cellular constituent measurements are translational state measurements that are performed using an antibody array or two-dimensional gel electrophoresis. In some embodiments, the plurality of cellular constituent measurements comprise a plurality of metabolites and the plurality of cellular constituent measurements are derived by a cellular phenotypic technique such as a metabolomic technique in which a plurality of levels of metabolites in each of the organisms is measured. Representative metabolites comprise amino acids, metals, soluble sugars, and complex carbohydrates. In some embodiments, the cellular constituent comprises gene expression levels, abundance of mRNA, protein expression levels, or metabolite levels. In some embodiments, the quantitative genetic analysis is performed using a method that uses one or more techniques selected from the group consisting of linkage analysis (Section 5.13), quantitative genetic analysis that uses a plurality of cellular constituent measurements as a phenotypic trait (Section 5.1), and association analysis (Section 5.14).

The experiments summarized by FIGS. 59 through 61 focus on the use of mouse crosses to elucidate complex traits. However, the present invention provides alternative methods for elucidating complex traits. For instance, instead of scoring phenotypes and expression profiling F2 animals, a set of congenic mice that span the entire genome could be profiled. FIG. 62 gives an example of a congenic strain. The congenic strain is constructed from two inbred strains, B6 and CAST, where B6 serves as the background strain and CAST serves as the donor strain. The construction of the congenics results in a segment of one chromosome from the donor strain (CAST in FIG. 62) becoming intergrossed onto the genome of the background strain (B6 in FIG. 62). For example, in FIG. 62, region 6202 of chromosome 6 from CAST becomes intergrossed with chromosome 6 of B6, yielding congenic strain B6.CAST Chr.6. Whole sets of such congenics can be constructed such that each strain in the set covers a part of some chromosome, with the set taken as a whole covering the entire genome of the donor strain.

The advantage of the congenic sets is that they can be used to screen all mice making up the set for the trait of interest and to identify those strains that exhibit the trait of interest, compared to the background strain. For instance, in studying obesity, the congenic sets can be used to identify those congenic strains that are significantly heavier than the background strain. Once such strains are identified, a large amount of work identifying the genes underlying the trait of interest has already been accomplished because the causal gene will reside in the congenic region.

Congenics are also useful once QTL have been identified in an F2 population constructed from the same inbred strains making up the congenic set. For instance, once a QTL is identified for the trait of interest, the strain whose congenic region covers the QTL region can be identified and studied with respect to the same phenotype. Further, more complicated genetic models can be constructed using the congenics, based on QTL results from, for example, an F2 cross. For example, suppose from the F2 cross, two QTL that were strongly interacting are identified. The congenic strains covering the two QTL regions could be identified and bred to construct a new congenic strain that had two congenic regions, each covering one of the QTL of interest. These mice could than be studied with respect to the phenotype of interest. The advantage to this sort of construction is that the congenic strains are stable and can be constantly bred to generate progeny that are genetically identical (unlike the F2 populations, where there is no hope of recovering the same genetic background).

Congenics are useful in studying traits first studied in an F2 population. The trait itself may vary considerably over the F2 population, but once QTL are identified in the F2 that lead to a particular trait value (e.g., low fat), the congenic corresponding to the QTL can be identified and scored for the same trait. In many cases, the congenic will exhibit the same trait values as those F2 mice under the control of the associated QTL.

Various techniques have been disclosed for identifying QTL and/or genes in a first species that are linked to one or more traits T'. Additional techniques for identifying such QTL and/or genes are found in copending U.S. Patent Applications 60/382,036, filed May 20, 2002, entitled "Computer systems and methods for subdividing a complex disease into component diseases", 60/381,437, filed May 16, 2002, entitled "Computer system and method for identifying genes and determining pathways associated with traits"; and 60/400,522, filed Aug. 2, 2002, entitled "Computer systems and methods that use clinical and expression quantitative trait loci to associate genes with traits" which are hereby incorporated by reference in their entireties.

5.19.2. Identifying Regions of the Genome of a Second Species that are Linked to a Trait of Interest In the present invention, once the genes and/or QTL in a first species that are linked to trait T' (e.g., the mouse models described in Section 5.19.1) have been identified, those QTL and genes of interest are mapped to the genome of a second species (e.g., humans). In one embodiment, this mapping happens through the construction of syntenic maps between the first species and the second species (e.g., between mouse and human). The syntenic map is constructed by mapping conserved regions between the two species such as EST, mRNA, conserved STS markers, conserved regulatory regions, etc.

Traits T in populations of the second species that are similar to traits T' studied in the first species are identified. Further, regions in the genome of the second species that are associated with the identified traits T are determined. FIG. 63 shows an example in which the first species is human and the second species is mouse. In FIG. 63, two hypothetical QTL (6302 and 6304) that are linked to a human obesity-related risk trait are on a portion of human chromosome 8. The human genome region that includes hypothetical QTL 6302 and 6304 is mapped to the mouse genome using a syntenic map between mouse and human. It will be appreciated that genes are not mapped at this point. Rather, whole regions are mapped. In some embodiments, the region that is mapped is a portion of a chromosome, a region that is less than 100 centiMorgans, less than 10 centiMorgans, or less than 5 centiMorgans. Using syntenic mapping, it is determined that hypothetical QTL 6302 and 6304 map to a portion of mouse chromosome 13.

Next, the QTL data from the first species is combined with that from the second species. For example, FIG. 64 lists four lod score curves for obesity-related traits in mouse (HDL levels, leptin levels, insulin levels and fat pad masses). The QTL for all of these mouse traits are overlapping. However, in FIG. 65 in which hypothetical human QTL 6302 and 6304 (FIG. 63) and the mouse QTL given in FIG. 64 are overlayed, the peaks of human hypothetical QTL (6302 and 6304) are aligned with the peaks of two of the mouse QTL depicted in FIG. 63. Thus FIG. 65 describes a relationship in which two fairly closely linked QTL in humans for an obesity related trait overlap with two closely linked QTL in mice for obesity-related phenotypes. Further, as depicted in FIG. 66, this chromosome 13 region in mouse is a hotspot activity for eQTL linkage as well, with hundreds of eQTL linking to one of the two peaks, but usually not both. This data supports the notion that there are actually two genes here underlying the mouse and human QTL.

In some embodiments, traits T are identified in the second species using any of the techniques described in Section 5.19.1, above or in copending U.S. Patent Applications 60/382,036, filed May 20, 2002, entitled "Computer systems and methods for subdividing a complex disease into component diseases", 60/381,437, filed May 16, 2002, entitled "Computer system and method for identifying genes and determining pathways associated with traits"; and 60/400,522, filed Aug. 2, 2002, entitled "Computer systems and methods that use clinical and expression quantitative trait loci to associate genes with traits" which are hereby incorporated by reference in their entireties. However, in a typical embodiment, the second species is human. As such, QTL or gene identification techniques that make use of congenic strains or planned crosses cannot be used. Therefore, in some embodiments, association analysis techniques such as those described in Section 5.14, above, are used.

The information revealed using the techniques described in this section is extremely valuable in deciding what regions to pursue in the second species (e.g., humans). The overlaps can be used to refine the interval that will be fine-mapped in humans to identify the underlying gene. This results in narrowing the region that must be pursued, thereby decreasing the amount of time needed to map an interval. Further, methods described in this application can be used to directly identify genes in mice in QTL intervals of interest, and directly validate those using association methods in human populations (FIG. 67). This is a process that can short-circuit the fine mapping approach and accelerate the process of identifying genes for complex human diseases.

5.19.3. Identifying QTL and Genes in a First Species Using Causality

The starting point for the traditional forward genetics approach to dissecting complex traits, including common human diseases, is identification of QTL controlling for a disease trait of interest. For more information on complex traits, see Section 5.15. Genome-wide scans are performed to identify markers spaced along the length of the genome that are correlated with the disease trait under study. The end result of such a screen is a number of cQTL identified for the disease trait. This is graphically depicted in FIG. 74. In particular, FIG. 74 illustrates a hypothetical disease-specific genetic network for disease traits and related co-morbidities. The quantitative trait loci ($L_n$) and environmental effects ($E_n$) (panel 7402) represent the most upstream drivers of the disease traits in a given population. In other words, a quantitative disease trait in a segregating population can be described as being made up of genetic and environmental components, with or without interactions among the genetic components and/or between the genetic and environmental components. As depicted in FIG. 74, the QTL and environmental effects (7402) influence other "causative" mRNAs ($C_{Rk}$) (panel 204) singly or in pathways that can interact in complicated ways (most generally, as a genetic network), but that ultimately lead to the disease state (primary clinical traits). A genetic network can be represented as an acyclic directed graph having nodes and edges, where the nodes represent genes and each respective edge represents confidence that the two nodes, connected by the respective edge, are related as determined by an analysis of genotypic and gene expression data using the methods of the present invention. Variations in the causal mRNAs or in the primary clinical traits can in turn affect reactive mRNAs ($R_{Ni}$) (panel 7406) in other pathways that in turn lead to co-morbidities of the disease trait, or they can provide positive/negative feedback control to the causal pathways. Instead of restricting the search for disease-causing genes to the QTL regions associated with the complex trait, the classic approach in mouse and human genetics, the present invention broadens the search to any of the cellular constituents that operate in the causal portion of the genetic network associated with the disease trait (circles 7404). Identifying cellular constituents in pathways that are under the control of the same QTL that are controlling for the disease trait, where the cellular constituents can be shown to act as transmitters of information from these multiple QTL to the disease trait itself (as opposed to acting as responders to the disease trait), potentially represent key intervention points that can be targeted to modulate the disease trait.

In the absence of cellular constituent abundance data or other molecular phenotyping data on the population under study, the biological/biochemical processes that take place that ultimately lead to the disease state, starting from the most upstream genetic components of the disease detected as QTL, are completely hidden from view. Therefore, as depicted in FIG. 74, those pathways (cellular constituents 7404) that are impacted by the DNA variations underlying the QTL and that ultimately lead to the disease state (causal), in addition to those pathways that are impacted as a result of the system being in the disease state (reactive cellular constituents 7406), are not available for study.

The generation of large-scale gene expression data on the relevant populations can significantly expose the many pathways and complicated interactions among cellular constituents associated with disease, as detailed by Schadt et al., 2003, Nature 422, 297. The complex networks of interactions that are causal for the disease (7404), as well as those that are reactive to it (7406), make up the patterns of expression that are associated with a disease trait Several examples of this have been provided in the recent literature. See, for example, Schadt et al., 2003, Nature 422, 297, van de Vijver et al., 2002, N. Engl. J. Med 347; van't Veer et al., 2002, Nature 415, 530.

Gene expression traits and disease traits can be modulated by the same QTL. Therefore, performing genome-wide scans to map eQTL for the gene expression traits allows one to assess the amount of correlation between the gene expression and disease traits that is due to common genetic effects. The QTL provide. anchors in the complex network of interactions that lead to disease, and it is this causal information that provides for the opportunity to identify cellular constituents 7404 that transmit "information" from single or multiple disease QTL, to the disease trait itself. Because the QTL can modulate the disease trait through intermediates, identifying the intermediates using the combination of genetics and gene expression data (or other cellular constituent abundance data) has the potential to elucidate key control points in the complex network associated with the disease.

Since one of the primary aims of the target discovery process is to identify targets for therapeutic intervention in complex human diseases, it is advantageous to partition cellular constituents (e.g., genes) making up the patterns of expression associated with the disease trait and that are modulated by QTL overlapping the disease trait QTL, into two groups: 1) cellular constituents under the control of the disease QTL that fall between the causal and reactive boundaries depicted in FIG. 74 (cellular constituents 7404), and 2) cellular constituents that appear to be reactive to the disease state (cellular constituents 7406). Once cellular constituents have been partitioned into causal set 7404 and reactive set 7406, attention can shift to those cellular constituents in causative set 7404 to identify key targets for the disease.

Approaching the dissection of complicated genetic networks associated with disease from this partitioning standpoint greatly simplifies the more general problem of reconstructing whole genetic networks. The reconstruction of genetic networks has been vigorously pursued in many settings and has met with some success in microbial organisms. See, for example, Marcotte, 1999, Science 285, 751; and Lee et al., 2002, Science 298, p. 799. The genetic network reconstruction problem is not yet tractable for mammalian systems, mainly due to the complexity and extent of data that would be required to undertake such a reconstruction. See, for example, van Someren et al., 2002, Pharmacogenomics 3, 507. Reducing the genetic network problem to one of partitioning sets of cellular constituents should make the problem tractable and directly relevant to the identification of targets for complex human diseases.

The partitioning approach requires that a basic set of causal scenarios be tested to determine whether a cellular constituent under the control of disease QTL is causal for the disease or reactive to it. For each cellular constituent under consideration, first a determination is made as to whether changes in the abundance (e.g., expression) of the cellular constituent are associated with QTL that explain variations in the disease trait. Then a determination is made as to whether the QTL act on the disease trait through the gene.

FIG. 75A presents the possible relationships between QTL, cellular constituents and disease traits once the abundance of a cellular constituent (e.g., gene G) and the disease trait (T) have been shown to be under control of a common QTL (Q). Pathway 7502 represents the simplest causal relationship of a single QTL, Q, for the quantitative trait T, where Q acts on T through cellular constituent G. Pathway 7504 represents the simplest reactive diagram for a single QTL, Q, for the quantitative trait T, where in this case the abundance of cellular constituent G is responding to T. In pathway 306, the QTL, Q, is causative for the trait T and the abundance of cellular constituent G, but acts on these traits independently. Pathway 7508 represents a more complicated causal diagram where QTL Q affects the abundance of cellular constituents and these cellular constituents, in turn, act on the trait T. Pathway 7510 represents the ideal causal diagram for target identification, where a number of QTL explain a significant amount of the variation in the trait T, but all of these QTL act on T through a single cellular constituent G.

To illustrate how partitioning genes into causal and reactive classes can be accomplished given gene expression data from a segregating population, consider a hypothetical mouse population in which half of the mice have the AA genotype and the other half have the BB genotype at a given locus. As depicted in FIG. 75B, all mice with the BB genotype are obese, while 87.5% of the mice with the AA genotype are lean and the other 12.5% are obese. Further, 87.5% of the BB mice have higher transcript levels of a specific gene, while the other 12.5% have unchanged levels, and similarly, 87.5% of the AA mice have lower transcript levels of the same gene, while the other 12.5% have unchanged levels. If the clinical and expression trait were uncorrelated with the genotype at locus L (e.g., not significantly linked to this locus), it is expected that an equal percentage for each of the expression/clinical trait combinations for each genotype at locus L. Since this is clearly not true in FIG. 75B, the expression and clinical traits we significantly linked to locus L.

To determine in this case if the mRNA is a cause or consequence of the clinical state, the data are fit to the three competing models. FIG. 75C highlights the Causative model, where the correlation between genotype and clinical trait predicted from the model is seen to be consistent with the observed correlation. In one embodiment described below, this scenario will translate into a situation where the correlation between the clinical trait and genotype, given the gene expression state, is seen to be 0. Because the clinical trait and genotype are uncorrelated once we condition on transcript abundances, we can tentatively conclude the mRNA is causal for the clinical trait. FIG. 75D highlights the Reactive model, where the observed correlation between the gene expression trait and genotype is 0.88, but now the correlation between the gene expression trait and genotype given any of the clinical trait values is not equal to 0, e.g., the correlation between the expression trait and genotype predicted from the model does not equal the observed correlation. Because the expression trait and genotypes are still significantly correlated after conditioning on the clinical trait values, it is possible to confirm that the mRNA levels are not responding to the clinical trait. Finally, FIG. 75B highlights the Independent model, where again the correlation between the gene expression and clinical traits predicted from the model is not consistent with the observed correlation. Therefore, given the results of the fits to these three models, the data for this hypothetical example indicate that the Causative model is the most parsimonious and thus is the best explanation of the underlying biology. It is concluded that the AA/BB locus controls variation in the mRNA levels and that this mRNA, in turn, controls variation in the clinical trait, rather than the mRNA levels changing as a consequence of the obesity. By applying a statistically rigorous version of this causality testing to the whole genome (described below), the genes controlling variation in mRNA levels that in turn control clinical traits can be identified. In another embodiment likelihoods are created for each of the possible models (independent, causative, and reactive) based on relationships depicted in each model and then maximized with respect to model parameters. In this other embodiment, the causative model gives rise to the largest likelihood.

The models in FIG. 75A are the ideal, simplest cases. In reality there will usually be a number of loci and mRNAs that cause disease, related by a complex network of interactions, as depicted in FIG. 74. In the approach detailed below, this complexity in a segregating population can be harnessed to identify specific genes that transmit information from the disease trait QTL to the clinical disease trait itself. Specially, a disease trait QTL will modulate the disease trait through intermediates. Identifying the intermediates using the combination of genetics and gene expression data has the potential to elucidate key control points in the complex network associated with the disease.

Figure 79A:
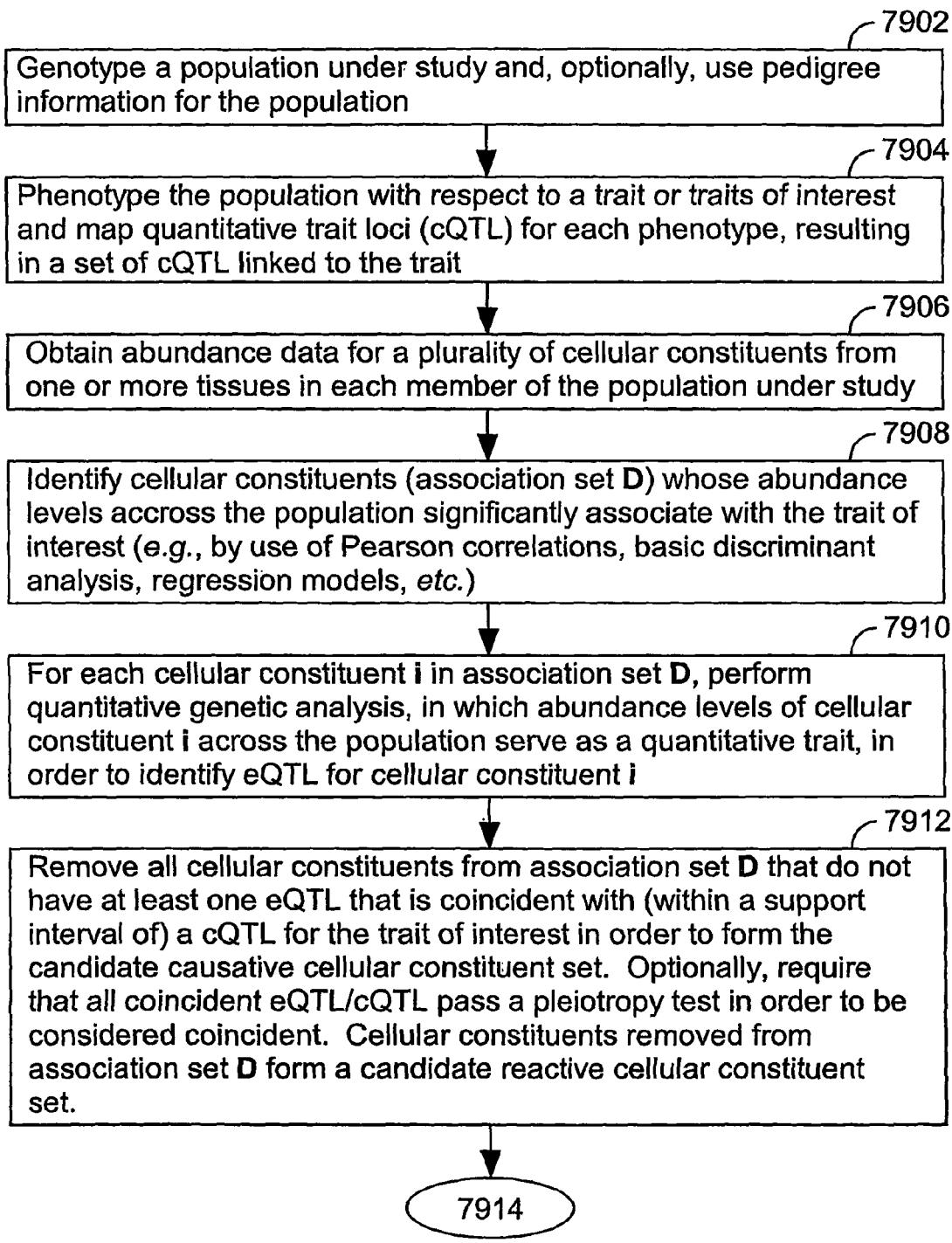
Figure 79B:
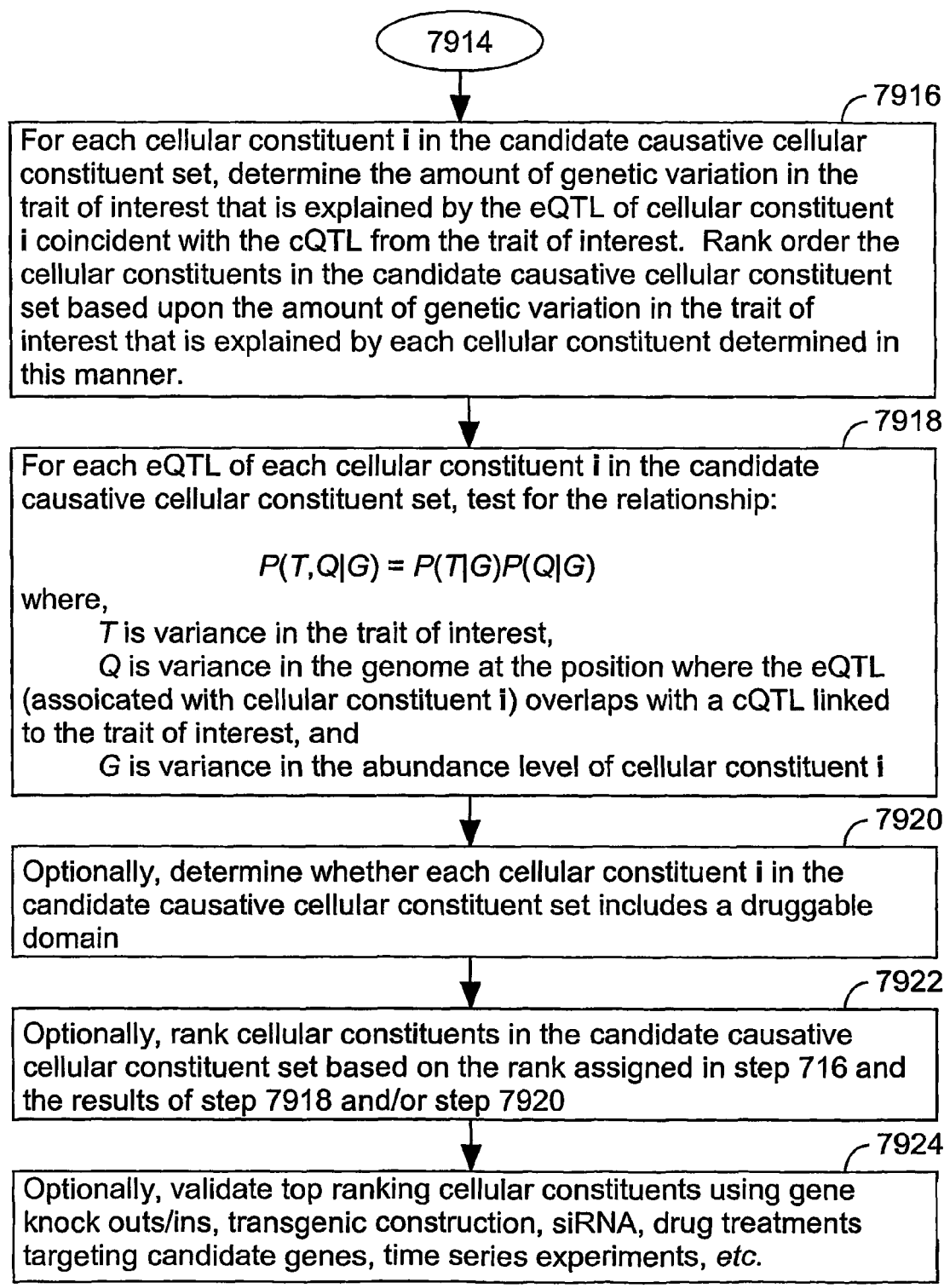

FIGS. 79A and 79B illustrate the processing steps that are performed in accordance with one embodiment of the present invention. Those figures will be referenced in this section in order to disclose the advantages and features of the present invention.

Step 7902. The present invention begins with the step of obtaining genotype data 68. Genotype data 68 comprises the actual alleles for each genetic marker typed in each individual in a plurality of individuals under study. In some embodiments, the plurality of individuals under study is human. Genotype data 68 includes marker data at intervals across the genome under study or in gene regions of interest. In some embodiments, such data is used to monitor segregation or detect associations in a population of interest. Marker data comprises those markers that will be used in the population under study to assess genotypes. In one embodiment, marker data comprises the names of the markers, the type of markers, and the physical and genetic location of the markers in the genomic sequence. Exemplary types of markers include, but are not limited to, restriction fragment length polymorphisms "RFLPs", random amplified polymorphic DNA "RAPDs", amplified fragment length polymorphisms "AFLPs", simple sequence repeats "SSRs", single nucleotide polymorphisms "SNPs", microsatellites, etc.). Further, in some embodiments, marker data comprises the different alleles associated with each marker. For example, a particular microsatellite marker consisting of 'CA' repeats can represent ten different alleles in the population under study, with each of the ten different alleles, in turn, consisting of some number of repeats. Representative marker data in accordance with one embodiment of the present invention is found in Section 5.2. In one embodiment of the present invention, the genetic markers used comprise single nucleotide polymorphisms (SNPs), microsatellite markers, restriction fragment length polymorphisms, short tandem repeats, DNA methylation marker sequence length polymorphisms, random amplified polymorphic DNA, amplified fragment length polymorphisms, or simple sequence repeats.

In some embodiments, step 7902 uses pedigree data. Pedigree data comprises the relationships between individuals in the population under study. The extent of the relationships between the individuals under study can be as simple as an inbred $F_2$ population, an $F_1$ population, an $F_{2:3}$ population, a Design$_{III}$ population, or as complicated as extended human family pedigrees. Exemplary sources of genotype and pedigree data are described in Section 5.2.

In some embodiments, a genetic map is generated from genotype data and pedigree data. Such a genetic map includes the genetic distance between each of the markers present in the genotype data. These genetic distances are computed using pedigree data. In some embodiments, the plurality of organisms under study represents a segregating population and pedigree data is used to construct the marker map. As such, in one embodiment of the present invention, genotype probability distributions for the individuals under study are computed. Genotype probability distributions take into account information such as marker information of parents, known genetic distances between markers, and estimated genetic distances between the markers. Computation of genotype probability distributions generally require pedigree data. In some embodiments of the present invention, pedigree data is not provided and genotype probability distributions are not computed. In some embodiments, a genetic map is not computed.

Using Populations Derived from Multiple Founders

In some embodiments the population that is used for the methods illustrated in FIG. 79 is a population that is derived from a select set of strains (e.g., a small, but diverse number of founding mice) or individuals (e.g., the Icelandic population, which was founded by a small number of individuals). In some embodiments, between 2 and 100, between 5 and 500, more than five, or less than 1000 strains of a species diverse with respect to complex phenotypes associated with common human disease are chosen. In some embodiments, the species is mice. In some embodiments, between 2 and 10 (e.g., 6) strains of mice that are diverse with respect to complex phenotypes associated with common human disease are selected. Representative common human diseases include, but are not limited to, obesity, diabetes, atherosclerosis and associated morbidities, metabolic syndrome, depression/anxiety, osteoporosis, bone development, asthma, and chronic obstructive pulmonary disease. The actual number of founding strains is not as important a factor as ensuring that these "founders" are diverse so as to introduce extensive heterogeneity into the population. In one representative embodiment, the species under study is mice and all or a portion of the following strains are used: B6_DBA GTMs (Jake Lusis, University of California, Los Angeles), B6_CAST GTMs (Jake Lusis, University of California, Los Angeles), B6_DBA Consomics (Joe Nadaeu, Case Western Reserve University), AXB recombinant inbred (RI) lines (JAX, Bar Harbor Me.), BXA RI lines (JAX), LXS RI lines (Rob Williams, University of Tennessee), AKXD RI lines (JAX), 8-way cross mice (Rob Hitzmann, Oregon Health and Science University), D129S1/SvImJ (JAX), A/J (JAX), C57BL/6J (JAX), BALB/cJ (JAX), C3H/HeJ (JAX), CAST/Ei (JAX), DBA/2J (JAX), NOD/LtJ (JAX), NZB/B1NJ (JAX), SJL/J (JAX), AKR/J (JAX), CBA/J (JAX), FVB/NJ (JAX), and SWR/J (JAX).

In preferred embodiments, the species that is selected for study using the methods illustrated in FIG. 79 can be crossed. In such preferred embodiments, crosses (e.g. $F_2$ intercross) between all pairs of the founding strains are performed. For example, in one embodiment, six founding strains are used so a total of 15 crosses are performed. In some embodiments, rather that performing an $F_2$ intercross, other cross designs are used. For example, in some embodiments, a backcross or $F_2$ random mating scheme is employed. In preferred embodiments each of the crosses (for example the 15 crosses using the 6 founder strains) is treated as a single large pedigree. In some embodiments, the final population size that is studied has a size of more than 1,000 organisms, between 100 and 100,000 organisms, less than 500,000 organisms, or, more preferably, between 5,000 and 25,000 organisms. This population is treated as a single large pedigree and genotype information is collected from this population using a standard set of, for example, more than 500 markers.

The advantage of the different crosses and large numbers is that it introduces a significant amount of trait heterogeneity into the population, which allows for more connections between more pathways relating directly to the diseases of interest, and with such large numbers, it will be possible to detect first and second order interactions. Further, with such large numbers of organisms 46 (FIG. 1) over different strains, there will be enough recombination to solve problems regarding describing genetic correlation (genetic correlation is a function of linkage disequilibrium and pleiotropy, and in single small crosses, these components are confounded). Further, as illustrated below, detection of epistatic interactions and minimization of the effects of linkage disequilibrium on genetic correlation would allow for the reconstruction of pathways more reliably.

Step 7904. In step 7904, the population under study is phenotyped with respect to a trait or traits of interest using quantitative trait loci (QTL) analysis in which a phenotypic statistic set, representing the trait of interest, is used as the quantitative trait in the QTL analysis thereby identifying one or more clinical quantitative trait locus (cQTL) that link to the trait. In processing step 7904, a cQTL that is linked to a trait of interest is identified using QTL analysis.

In some embodiments, a phenotypic statistic set (plurality of phenotypic values) for the trait of interest serves as the clinical trait used in the QTL analysis. FIG. 80 illustrates exemplary phenotypic statistic sets. In FIG. 80, each phenotypic statistic set 8000 includes a phenotypic value 8004 for a given phenotype for a each organism in a plurality of organisms under study. As used herein, a phenotypic value is any form of measurement of a phenotypic trait associated with the trait of interest (e.g., complex disease). For example, if the trait of interest is obesity, a suitable phenotypic trait could include cholesterol level in the blood of the organism. In such an example, the phenotypic value can be milligrams of cholesterol per liter of blood.

In one embodiment, processing step 7904 comprises a classical form of QTL analysis in which a phenotypic trait is quantified to form a phenotypic statistic set. In some embodiments, processing step 7904 employs a whole genome search of genetic markers using the genotypic data from step 7902. For each genotypic position in the genome of the population that is analyzed, processing step 7904 provides a statistical measure (e.g., statistical score), such as the maximum lod score between the genomic position and the phenotypic statistic set. Thus, processing step 7904 yields all the positions in the genome of the organism of interest that are linked to the expression statistic set tested. Such embodiments of processing step were described by Lander and Botstein in Genetics 121, 174-179 (1989). They are also described in International Application WO 90/04651, International Application WO 99/13107, Lander and Schork, Science 265, 2037-2048 (1994), and Doerge, Nature Reviews Genetics 3, 43-62, (2002). In other embodiments of processing step 7904, association analysis, a described, for example, in Section 5.14 is used rather than linkage analysis.

In one embodiment of the present invention, the QTL analysis (FIG. 79A, step 7904) comprises: (i) testing for linkage between (a) the genotype of a plurality of organisms at a position in the genome of a single species and (b) the phenotypic statistic set (e.g., plurality of phenotypic values), (ii) advancing the position in the genome by an amount, and (iii) repeating steps (i) and (ii) until all or a portion of the genome has been tested. In some embodiments, the amount advanced in each instance of (ii) is less than 100 centiMorgans, less than 10 centiMorgans, less than 5 centiMorgans, or less than 2.5 centiMorgans, or between 2.5 centiMorgans and 500 centiMorgans. A Morgan is a unit that expresses the genetic distance between markers on a chromosome. A Morgan is defined as the distance on a chromosome in which one recombinational event is expected to occur per gamete per generation. In some embodiments, the testing comprises performing linkage analysis (Section 5.13) or association analysis (Section 5.14) that generates a statistical score for the position in the genome of the single species. In some embodiments, the testing is linkage analysis and the statistical score is a logarithm of the odds (lod) score (Section 5.4). Thus, in some embodiments, a cQTL identified in processing step 7904 is represented by a lod score that is greater than 2.0, greater than 3.0, greater than 4.0, or greater than 5.0.

In embodiments where more than one cross is considered in step 7902, a separate phenotypic statistic set is created for the progeny of each cross. For example, consider the case where the phenotypic value under consideration is blood cholesterol level. Further, in this example, there are six founder strains and a total of fifteen crosses. In this example, fifteen phenotypic statistic sets are constructed for blood cholesterol level, one for the progeny of each of the fifteen strains. Then, a separate QTL analysis is performed with the progeny of each of the fifteen crosses. For each of these crosses, the phenotypic statistic set associated with the cross is used as the quantitative trait in the QTL analysis. It will be appreciated that a large number of clinical traits can be considered. For each such clinical trait, measurements of the organisms 46 are made. Then, phenotypic statistic sets are created for each clinical trait considered. Further, as described above, in the case where there are multiple crosses, the phenotypic measurements from the progeny of each cross are used to form respective phenotypic statistic set that is associated with the cross.

In some embodiments, the progeny of each cross are subjected to a perturbation prior to phenotyping. In some embodiment, this perturbation is a drug treatment, variable diet and/or fasting/refeeding. Then, a phenotypic statistic set is created from the progeny of the crosses prior to quantitative trait loci (QTL) analysis.

In the case where multiple QTL analyses are performed with the same trait, each such analysis corresponding to the progeny of a different cross in a plurality of crosses, there remains the task of combining the results of each such QTL analysis. For example, in the case where the phenotype is blood cholesterol level and there are fifteen crosses in the population, fifteen QTL analyses are performed using blood cholesterol as the quantitative trait, resulting in fifteen lod score curves across the genome of the species under consideration. In some embodiments the lod score curves for the QTL overlapping in each of the crosses are combined in an additive fashion to assess the overall significance of the QTL over the different crosses. However, this type of method ignores the relationship between the crosses that exists if they share a common parent. For example, if you have two crosses constructed from three inbred lines of mice (so they share a common parent), then the progeny of each cross will share a larger percentage of alleles over the entire genome than would be expected by chance. By taking this relationship into account over the multiple crosses that are present in some embodiments of the present invention, a significant increase in the power to detect QTL, detect interactions between QTL, and detect interactions between QTL and environmental conditions is achieved.

In one embodiment of the present invention, multiple lod score curves, where each curve represents a QTL analysis of the progeny of a different cross using a given quantitative trait, are simultaneously considered. However, rather than simply combining the lod score curves in an additive fashion, "identical by descent" (IBD) matrices are calculated. Such matrices assess the probability that any two animals from the different crosses have inherited a common allele at any given position in the genome. These IBD matrices are then used to appropriately weight the different distributions in the phenotype of interest that can arise when the phenotype is linked to a particular region in the genome. For example, regions that are likely to have inherited a common allele are downweighted relative to regions that are likely to have inherited from different alleles.

The embodiments that follow in this paragraph apply to instances where the species under study are mice. Based on this disclosure, those of skill in the art will realize corresponding phenotypes that can be measured in other species and all such phenotypes are within the scope of the present invention. In some embodiments, the disease of interest is diabetes and/or insulin resistance and the phenotypes that are measured in step 7904 include plasma glucose, plasma insulin, insulin glucose, and a glucose tolerance test (GTT). In some embodiments, the disease of interest is atherosclerosis, and the phenotypes that are measured in step 7904 include aortic lesion and fatty streak (i. levels, ii. parafilm 5 μm section immunohistochemistry for several markers such as FLAP, 5LO, dendritic cells, T cells, CD11b mono infiltration, Brdu proliferation, apoptosis, iii. endothelial cells and macrophage function), brain lesion, vascular calcification, paraoxonase, osteopontin, and PAI-1. In some embodiments, the disease of interest is obesity, and the phenotypes that are measured in step 704 include body weight, anal-nasal length, fat pad weights (e.g., perimetrial fat pad mass, mesenteric omental fat pad mass, subcutaneous fat pad mass, and retroperitoneal fat pad mass), NMR fat mass, NMR muscle mass, leptin levels, food intake, liver weight, glucagon, adiponectin, and IGF-1. In some embodiments, the disease of interest is hypertension, and the phenotypes that are measured in step 7904 include blood pressure, and response to angiotensin II. In some embodiments, the disease of interest is asthma and chronic obstructive pulmonary disease (COPD) and the phenotypes that are measured in step 704 include airway hyper-responsiveness with and without antigen challenge and airway hyper-responsiveness in mice exposed to smoke for a significant length of time. In some embodiments, the trait of interest is plasma lipase activity and the phenotypes that are measured in step 7904 include lipoprotein lipase (LPL), hepatic lipase (HL), and endothelial lipase activity. In some embodiments, the trait of interest is plasma lipids and the phenotypes that are measured in step 7904 include total cholesterol (TC), high-density lipoprotein cholesterol (HDL), very low density lipid lipoprotein/low density lipoprotein (VLDL/LDL), triglycerides, fatty acids, ketone bodies, lactate, LDL oxidation, and HDL protection. In some embodiments, the trait of interest is plasma cytokines and the phenotypes that are measured in step 7904 include interleukin 6 levels, interleukin1-beta levels, tumor necrosis factor alpha/gamma (TNF-alpha/gamma), and interleukin 4 levels. In some embodiments, the phenotypes that are measured include monocyte isolation from plasma and ELISA or LC-MS for leukotrienes. In some embodiments, the disease under study is inflammation and the phenotypes that are measured in step 7904 include EO6/MDA oxLDL ELISA, lipoprotein properties, macrophage/T cell interactions, and INF-gamma levels. In some embodiments, cardial related traits are of interest and the phenotypes that are measured in step 7904 include heart/brain weight ratio, heart rate/femur length, cardiac fibrosis, and myocardial calcification. In some embodiments, bone traits are of interest and the phenotypes that are measured in step 7904 include bone density (scans), femur CT BMD, total femur x-ray BMD, total femur x-ray BMC, femur CT-determined BMC, femur diaphyseal BMC, femur diaphyseal BMD, intertrochanteric BMC, intertrochanteric BMD, femur volume by CT, femur x-ray area, femur diaphyseal cortical thickness, femur width at the diaphysis, right and left femur length, right and left tibia length, right and left length of forepaw $1^{st}$, $2^{nd}$, $3^{rd}$, $4^{th}$, and $5^{th}$ digits, right and left humerus length, right and left radius length, right and left ulna length, femur width at the intertrochanteric region, femur fracture energy, stiffness of femur, and strength of femur.

Step 7906. In step 7906 cellular constituent abundance data 44 (e.g., from a gene expression study or a proteomics study) is obtained for a plurality of cellular constituents from one or more tissues in each member of the population under study. In some embodiments, cellular constituent abundance data 44 comprises the processed microarray images for each individual (organism) 46 in a population under study. For example, in one such embodiment, this data comprises, for each individual 46, cellular constituent abundance information 50 for each cellular constituent 48 represented on the array, optional background signal information 52, and optional associated annotation information 54 describing the probe used for the respective cellular constituent 48 (FIG. 1). See, for example, Section 5.8, below.

In various embodiments of the present invention, aspects of the biological state other than the transcriptional state, such as the translational state, the activity state, or mixed aspects can be measured and used as cellular constituent abundance data. See, for example, Section 5.9, below. For instance, in some embodiment, cellular constituent abundance data 44 is, in fact, protein levels for various proteins in the organisms 46 under study. Thus, in some embodiments, cellular constituent abundance data comprises amounts or concentrations of the cellular constituent in tissues of the organisms under study, cellular constituent activity levels in one or more tissues of the organism under study, the state of cellular constituent modification (e.g., phosphorylation), or other measurements relevant to the trait under study.

In one aspect of the present invention, the expression level of a gene in an organism in the population of interest is determined by measuring an amount of at least one cellular constituent that corresponds to the gene in one or more cells of the organism. In one embodiment, the amount of the at least one cellular constituent that is measured comprises abundances of at least one RNA species present in one or more cells. Such abundances can be measured by a method comprising contacting a gene transcript may with RNA from one or more cells of the organism, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species. In one particular embodiment, the abundance of the RNA is measured by contacting a gene transcript array with the RNA from one or more cells of an organism in the plurality of organisms under study, or with nucleic acid derived from the RNA, such that the gene transcript array comprises a positionally addressable surface with attached nucleic acids or nucleic acid mimics, where the nucleic acids or nucleic acid mimics are capable of hybridizing with the RNA species, or with nucleic acid derived from the RNA species.

In some embodiments, cellular constituent abundance data 44 is taken from tissues that have been associated with a trait under study. For example, in one nonlimiting embodiment where the complex trait under study is human obesity, cellular constituent abundance data 44 is taken from the liver, brain, or adipose tissues. More generally, in some embodiments of the present invention, cellular constituent abundance data 44 is measured from multiple tissues of each organism 46 (FIG. 1) under study. For example, in some embodiments, cellular constituent abundance data 44 is collected from one or more tissues selected from the group of liver, brain, heart, skeletal muscle, white adipose from one or more locations, and blood. In such embodiments, the data is stored in a data structure such as data structure of FIG. 83. This data structure is described in more detail below.

In some embodiments, particularly in embodiments where multiple crosses are simultaneously considered, each progeny mouse (and a number of parental and F1 mice) are extensively phenotyped by collecting multiple tissues from each such mouse for expression profiling. For example, tissue samples that can be collected for profiling include, but are not limited to, brain (possibly different brain parts), liver, white adipose tissue, skeletal muscle, heart, blood, kidney, lung, intestine, and stomach. In some embodiments, expression profiles for at least three of these tissues across some number of animals is performed. This rich set of clinical/biochemical phenotypes and gene expression traits over many tissues across multiple crosses allows for reconstruction of pathways involved in any of the clinical traits represented.

In some embodiments, once cellular constituent abundance data has been assembled, the data is transformed into abundance statistics that are used to treat each cellular constituent abundance in cellular constituent abundance data 44 as a quantitative trait. In some embodiments, cellular constituent abundance data 44 (FIG. 1) comprises gene expression data for a plurality of genes (or cellular constituents that correspond to the plurality of genes). In one embodiment, the plurality of genes comprises at least five genes. In another embodiment, the plurality of genes comprises at least one hundred genes, at least one thousand genes, at least twenty thousand genes, or more than thirty thousand genes. The expression statistics commonly used as quantitative traits in the analyses in one embodiment of the present invention include, but are not limited to the mean log ratio, log intensity, and background-corrected intensity. In other embodiment other types of expression statistics are used as quantitative traits. In such embodiments, the expression levels of a plurality of genes in each organism under study are normalized. Any normalization routine can be used. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines can be used. Exemplary normalization routines in accordance with the present invention are disclosed in more detail in Section 5.3, below. The expression statistics formed from the transformation are then stored in abundance/genotype warehouse 76, where they are ultimately matched with the corresponding genotype information.

Once cellular constituent abundance data has been transformed into corresponding expression statistics and a genetic marker map has been constructed, the data is transformed into a structure that associates all marker, genotype and expression data for input into QTL analysis software. This structure is stored in abundance/genotype warehouse 76.

Step 7908. Given gene expression data for a specific tissue of interest in a population that has been genotyped and phenotyped with respect to a disease trait of interest, the next step is to identify all cellular constituents that are significantly associated with the disease trait. A variety of methods can be used to establish associations between cellular constituent abundance and clinical traits, including simple Pearson correlations, basic discriminant analysis, t-tests, and ANOVA, in order to identify those cellular constituent abundance values that discriminate the extremes of the clinical trait, as well as more advanced regression models that specifically assess relationships between cellular constituent abundance values and clinical traits. In some embodiments, only the cellular constituents that are differentially expressed in at least ten percent, at least twenty percent, or at least thirty percent of the organisms profiled are considered. Then, of these differentially expressed cellular constituents, only those cellular constituents whose abundance values across the population has a Pearson correlation coefficient (p-value) that is less than 0.00001, 0.0001, 0.001 or 0.01 with the trait of interest T, as exhibited by organisms profiled, are considered. The product of step 708 is a set of cellular constituents (association set D) whose abundance levels across the population under study significantly associate with the trait of interest.

To illustrate, consider the hypothetical cellular constituent A in a population of 100 organisms. If just one tissue is considered in this population, then there will be 100 abundance values for cellular constituent A, one from each of the 100 organisms. Likewise, there will be 100 measurements of the trait of interest (e.g., tail length), one for each of the 100 organisms. In step 708, then, the question is asked whether the 100 cellular constituent abundance values significantly correlate with the 100 trait measurement values. As indicated above, a statistical measure, such as the Pearson correlation coefficient between the abundance value and the Trait measurements, can be used. If a certain threshold correlation value or other metric is achieved, the cellular constituent is considered significantly associated with the trait.

In some embodiments, multiple crosses are considered simultaneously. For the purposes of step 7908, the progeny of the multiple crosses can be treated as a single large population. So that, for example, if there are fifty organisms from a first cross and fifty organisms from a second cross, the combined total of 100 organisms is treated as a single population. Alternatively, the progeny of each cross can be considered independently. Thus, in the example where there are two crosses, each with fifty progeny, an independent determination can be made of the cellular constituents whose abundance levels significantly associate with the trait of interest. Then the test sets of cellular constituents that associate with the trait in the respective crosses can be combined. For instance, consider the case where cellular constituents A and B significantly associate with the trait in the progeny of a first cross and cellular constituents B and C significantly associate with the trait in the progeny of the second cross. In this instance, the sets can be combined such that step 7908 realizes an association set D comprising cellular constituents A, B, and C. There are any number of rules that can be devised to combine the results when crosses are considered separately in step 7908. The case of single addition (e.g., A, B, and C) has been presented above. Alternatively, only those cellular constituents that are significantly associated with the trait in all the crosses (or a majority of the crosses or some other percentage of the crosses) are placed in association set D.

Step 7910. In step 7910, a quantitative trait locus (QTL) analysis is performed using data corresponding to each cellular constituent i in association set D. For 1,000 cellular constituents, this results in 1,000 separate QTL analyses. For embodiments in which multiple tissue samples are collected for each organism, this results in even more separate QTL analyses. For example, in embodiments in which samples are collected from two different tissues, an analysis of 1,000 cellular constituents can require 2,000 separate QTL analyses. In embodiments where multiple crosses are considered, the crosses are preferably considered in the QTL analysis as a single population. In one example, each QTL analysis steps through the genome of the organism of interest. Linkages to the gene under consideration are tested at each step or location along the length of the genome. In such embodiments, each step or location along the length of the chromosome is at regularly defined intervals. In some embodiments, these regularly defined intervals are defined in Morgans or, more typically, centiMorgans (cM). In other embodiments, each regularly defined interval is less than 10 cM, less than 5 cM, or less than 2.5 cM.

In each QTL analysis, data, corresponding to a cellular constituent selected from discriminating set D, is used as a quantitative trait. More specifically, for any given cellular constituent i, the quantitative trait used in the QTL analysis is an abundance statistic at such as set 8104 (FIG. 81). Abundance statistic set 8104 comprises the corresponding abundance statistic 8108 for the corresponding cellular constituent 8102 from each organism 8106 in the population under study. FIG. 82 illustrates an exemplary abundance statistic set 8104 in accordance with one embodiment of the present invention for the case in which abundance data from only one tissue type is considered and cellular constituent abundance is gene expression. The exemplary abundance statistic set 8104 of FIG. 82 includes the abundance level 8108 of a gene G (or cellular constituent that corresponds to gene G) from each organism in a plurality of organisms. For example, consider the case where there are ten organisms in the plurality of organisms, and each of the ten organisms expresses gene G. In this case, abundance statistic set 8104 includes ten entries, each entry corresponding to a different one of the ten organisms in the plurality of organisms. Further, each entry represents the abundance level (e.g., expression level) of gene G in the organism represented by the entry. So, entry "1" (8108-G-1) (FIG. 82) corresponds to the abundance level of gene G in organism 1, entry "2" (8108-G-2) (FIG. 82) corresponds to the abundance level of gene G in organism 2, and so forth.

Referring to FIG. 83, in some embodiments of the present invention, abundance data from multiple tissue samples of each organism 8106 under study are collected. When this is the case, the data can be stored in the exemplary data structure illustrated in FIG. 83. In FIG. 83, a plurality of cellular constituents 8102 are represented. Further, there is an abundance statistic set 8104 for each cellular constituent 8102. Each abundance statistic set 8104 represents an abundance of the corresponding cellular constituent in each of a plurality of organisms.

In one embodiment of the present invention, each QTL analysis (FIG. 79A, step 7910) comprises: (i) testing for linkage between a position in a genome and an abundance statistic set 7904, (ii) advancing the position in the genome by an amount (e.g., less than 100 cM, less than 5 cM), and (iii) repeating steps (i) and (ii) until the entire genome is tested. In some embodiments, testing for linkage between a given position in the genome and the abundance statistic set comprises correlating differences in the abundance found in the abundance level statistic with differences in the genotype at the given position using single marker tests (for example using t-tests, analysis of variance, or simple linear regression statistics). See, e.g., *Statistical Methods*, Snedecor and Cochran, 1985, Iowa State University Press, Ames, Iowa. However, there are many other methods for testing for linkage between abundance statistic set and a given position in the chromosome. In particular, if abundance statistic sat is treated as the phenotype (in this case, a quantitative phenotype), then methods such as those disclosed in Doerge, 2002, Mapping and analysis of quantitative trait loci in experimental populations, *Nature Reviews: Genetics* 3:43-62, may be used. Concerning steps (i) through (iii) above, if the genetic length of a given genome is N cM and 1 cM steps are used, then N different tests for linkage are performed.

In some embodiments, the QTL data produced from each respective QTL analysis comprises a logarithm of the odds score (lod) computed at each position tested in the genome under study. A lod score is a statistical estimate of whether two loci are likely to lie near each other on a chromosome and are therefore likely to be genetically linked. In the present case, a lod score is a statistical estimate of whether a given position in the genome under study is linked to the quantitative trait corresponding to a given gene. Lod cores are further defined in Section 5.4, below. In some embodiments, a lod score of 2.0 or more is generally taken to indicate that two loci are genetically linked. In some embodiments, a lod score of 3.0 or more is generally taken to indicate that two loci are genetically linked. In some embodiments, a lod score of 4.0 or more is generally taken to indicate that two loci are genetically linked. The generation of lod scores requires pedigree data. Accordingly, in embodiments in which a lod sore is generated, processing step 7910 is essentially a linkage analysis, as described in Section 5.13, with the exception that the quantitative trait under study is derived from data, such as cellular constituent expression statistics, rather than classical phenotypes such as eye color.

In situations where pedigree data is not available, genotype data from each of the organisms 46 (FIG. 1) can be compared to each abundance statistic set using allelic association analysis, as described in Section 5.14, in order to identify QTL that are linked to each expression statistic set. In one form of association analysis, an affected population is compared to a control population. In particular, haplotype or allelic frequencies in the affected population are compared to haplotype or allelic frequencies in a control population in order to determine whether particular haplotypes or alleles occur at significantly higher frequency amongst affected compared with control samples. Statistical tests such as a chi-square test are used to determine whether there are differences in allele or genotype distributions.

Regardless of whether linkage analysis or association analysis is used in step 7910, the results of each QTL analysis can be stored in a QTL results database (FIG. 84). For each abundance statistic set (FIG. 81), QTL results database comprises all tested positions in the genome of the organism that were tested for linkage to the quantitative trait. For each position 8104, genotype data 68 provides the genotype at position 8404 for each organism in the plurality of organisms under study. For each such position 8404 analyzed by quantitative genetic analysis in step 7910, a statistical measure (e.g., statistical score 8406), such as the maximum lod score between the position and the abundance statistic, is listed. Thus, data structure comprises all the positions in the genome of the organism of interest that are genetically linked to each abundance statistic tested.

Step 7912. In step 7912, those cellular constituents in association set D that do not have at least one eQTL coincident with at least one cQTL from step 7904 form a candidate reactive cellular constituent set (FIG. 74, 7906). All cellular constituents in association set D that have at least one eQTL coincident with at least one cQTL from step 7904 form a candidate causal cellular constituent set (FIG. 74, 7904). In some embodiments, an eQTL is coincident with a cQTL when the eQTL and the cQTL colocalize within 40 cM of each other, within 30 cM of each other, within 20 cM of each other, within 10 cM of each other, within 3 cM of each other, or within 1 cM of each other in the genome of the species under consideration.

As an example of step 7912, consider the case in which the phenotypic statistic et is omental fat pad mass in a mouse population and that a QTL analysis in accordance with step 7904 yields 5 cQTL with LOD scores over 2.0 located on chromosomes 1 at 111 cM, 5 at 90 cM, 6 at 43 cM, 9 at 8 cM, and 19 at 28 cM. All cellular constituents in association set D that form eQTL at any of these chromosomal locations will be placed in the causal candidate cellular constituent set (FIG. 74, 7904). All cellular constituents in association set D that do not form eQTL at any of these chromosomal location will be placed in the reactive candidate cellular constituent set (FIG. 74, 7906).

Each cellular constituent in the candidate causal cellular constituent set gives rise to at least one eQTL that overlaps with at least one cQTL from step 7904 (an eQTL/cQTL overlap). There are generally two reasons that two or more traits (here an eQTL and a cQTL) can be genetically correlated: 1) gametic phase disequilibrium (also known as linkage disequilibrium) and 2) a single gene affecting multiple traits (pleiotropy). In some embodiments of the present invention, in order for an eQTL and a cQTL to be coincident, the QTL associated with the position of the eQTL and cQTL must truly be common to the clinical and expression trait (due to a pleiotropic effect of a common QTL) rather than simply represent two closely linked QTL (due to linkage disequilibrium between two distinct QTL). In such embodiments, a test is implemented to test the positions between the eQTL and the cQTL to determine whether the positions are statistically indistinguishable.

In considering a test for pleiotropy in accordance with the present invention, let $Y_1$ and $Y_2$ represent quantitative trait random variables, with QTL $Q_1$ and $Q_2$ at positions p and $p_2$, respectively. It is of interest to determine whether $p_1=p_2$, indicating a pleiotropic effect at the QTL for traits $Y_1$ and $Y_2$. Jiang and Zeng, 1995, Genetics 140, 1111, devised statistical tests to assess whether the positions are equal. A generalization of this test is implemented in some embodiments of step 7912. Since the positions under consideration usually will be relatively close together on a given chromosome (e.g., within 20 cM), it is expected that $Y_1$ and $Y_2$ will be correlated, and so the most basic model for these traits under the control of single, common QTL is formed as:

$$\begin{pmatrix} y_1 \\ y_2 \end{pmatrix} = \begin{pmatrix} \mu_1 \\ \mu_2 \end{pmatrix} + \begin{pmatrix} \beta_1 \\ \beta_2 \end{pmatrix} Q + \begin{pmatrix} \varepsilon_1 \\ \varepsilon_2 \end{pmatrix},$$

where Q is an categorical random variable indicating the genotypes at the position of interest, and $$\begin{pmatrix} \varepsilon_1 \\ \varepsilon_2 \end{pmatrix}$$

is distributed as a bivariate normal random variable with mean $$\begin{pmatrix} 0 \\ 0 \end{pmatrix}$$

and covariance matrix $$\begin{pmatrix} \sigma_1^2 & \sigma_1\sigma_2 \\ \sigma_2\sigma_1 & \sigma_2^2 \end{pmatrix}.$$

The case where $p_1=p_2$ represents the null hypothesis of pleiotropy. The aim is to test this null hypothesis against a more general alternative hypothesis that indicates $p_1 \neq p_2$. The alternative hypotheses of interest can be captured by the following model:

$$\begin{pmatrix} y_1 \\ y_2 \end{pmatrix} = \begin{pmatrix} \mu_1 \\ \mu_2 \end{pmatrix} + \begin{pmatrix} \beta_1 & \beta_2 \\ \beta_3 & \beta_4 \end{pmatrix} \begin{pmatrix} Q_1 \\ Q_2 \end{pmatrix} + \begin{pmatrix} \varepsilon_1 \\ \varepsilon_2 \end{pmatrix},$$

where the $\epsilon_1$ are distributed as for the pleiotropy model. The null hypothesis can be compared against any of a series of alternative hypotheses. The likelihoods for the two competing models (null hypothesis and alternative hypothesis) are easily formed, and maximum likelihood methods are then employed to estimate the model parameters ($\mu_i$, $\beta_j$, and $\sigma_k$). With the maximum likelihood estimates in hand, the likelihood ratio test statistic can be formed to directly test the null hypothesis against the alternative.

There are several alternative hypotheses that can be tested in this setting including:

$H_A: \beta_1 \neq 0, \beta_4 \neq 0, \beta_2 \neq 0, \beta_3 \neq 0$,
indicating closely linked QTL with no pleiotropic affects, $H_A: \beta_1 \neq 0, \beta_4 \neq 0, \beta_2 \neq 0, \beta_3 \neq 0$,
indicating closely linked QTL with pleiotropic effects at the first position, $H_A: \beta_1 \neq 0, \beta_4 \neq 0, \beta_2 \neq 0, \beta_2 \neq 0$,
indicating closely linked QTL with pleiotropic effects at the second position, and $H_A: \beta_1 \neq 0, \beta_4 \neq 0, \beta_2 \neq 0, \beta_2 \neq 0$,
indicating closely linked QTL with pleiotropic effects at both positions. Other null hypotheses and corresponding alternative hypotheses naturally follow from the general models presented here.

Thus, in embodiments where a pleiotropy test is applied, each cellular constituent in the candidate cellular constituent has at least one eQTL that is coincident with a respective cQTL for the trait of interest, where the at least one eQTL passes a test for pleiotropy with the respective cQTL.

Step 7916. In step 7916, the cellular constituents in the candidate causative cellular constituent set are ranked ordered based upon the amount of genetic variation in the trait of interest that is explained by the eQTL of the cellular constituent that are coincident with cQTL from the trait of interest. More specifically, for each cellular constituent i in the candidate causative cellular constituent set, a determination is made as to the amount of genetic variation in the trait of interest that is explained by the eQTL of the respective cellular constituent i coincident with the cQTL from the trait of interest. Then, the cellular constituents in the candidate causative cellular constituent set are rank ordered based upon the amount of genetic variation in the trait of interest that is explained by each cellular constituent determined in this manner.

To illustrate, consider the case in which the trait of interest produces five cQTL. Further, a cellular constituent i in the candidate causative cellular constituent set has five eQTL. Four of the eQTL overlap with four of the cQTL for the trait of interest. However, only three of the eQTL pass the test for pleiotropy. In this example, only the three eQTL that are coincident with respective cQTL for the trait of interest and that pass the test for pleiotropy described in step 7912, above, are used to determine how well they explain the genetic variation in the trait of interest. Thus, in the example, if the first of the three qualifying eQTL explains ten percent of the genetic variation in the trait of interest, the second of the three qualifying eQTL explains twenty percent of such genetic variation, and the third eQTL explains thirty percent of such genetic variation, the three eQTL, together, explain sixty percent of the genetic variation in the trait of interest In some embodiments, the determination as to how much the qualifying eQTL of a given cellular constituent explain the genetic variation in the trait of interest is performed using a joint analysis of the trait of interest at each of the qualifying coincident eQTL. This joint analysis leads to a lod score as described by Jiang and Zeng, 1995, Genetics 140, p. 1111 and applied by Schadt et al., 2003, Nature 422, p. 297, to gene expression traits. Then, cellular constituent can be rank ordered based on their lod score.

Step 7918. Step 7918 tests the cellular constituents in the candidate causative cellular constituent set in a manner that is independent of the pleiotropy test of step 7916. Step 7918 applies a causality test that, in one embodiment, serves to determine whether the genetic variation in each eQTL of a given cellular constituent that is coincident with a cQTL of a trait of interest is correlated with the variation in the trait of interest conditional on an abundance pattern of the cellular constituent I in the plurality of organisms.

Specific tests can be developed to identify the true relationship between QTL (Q), cellular constituent abundance (G) and disease trait (T) from the set of possible relationships depicted in FIG. 75A. However, to maximize the information that can be derived from the genetics and expression data, the causality test used in step 7918 is best considered in the context of scenario 7910 of FIG. 79A. Scenario 7910 represents an optimal situation where a cellular constituent (e.g., gene) is under the control of multiple disease QTL and still causative for the disease, thereby providing maximal causal information relating to the disease under study.

The aim of the causality test is to distinguish between the relationships that indicate a cellular constituent is causal for the clinical trait (scenarios 7902, 7908, and 7910 of FIG. 79A) from those that are reactive to, or independent of the disease trait (scenarios 7904 and 7906, respectively, of FIG. 79A). The test for causality involving QTL, cellular constituent abundance (e.g., gene expression) and disease trait data is based on the same conditional probabilities that underlie mutual information measures that form the basis of the more general Bayesian network reconstruction problems. See, for example, Pearl, 1983, *Probabilistic Reasoning in Intelligent Systems: Networks of Plausible Inference*, Morgan Kaufman Publishers, Inc., San Francisco. The causality test assesses whether the QTL (Q) and the disease trait (T) are correlated conditional on the cellular constituent abundance trait (G).

Genetic linkages for disease and cellular constituent abundance traits give rise to information on causality, thereby restricting the number of relationships to consider since they establish sub-relationships with absolute certainty (e.g., it is known that Q causes variations in G and T). This restriction allows for a robust, statistical test to determine whether scenarios 7902 and 7910 of FIG. 79A hold over the relationships given by scenarios 7904 and 7906. Since the test begins with data that indicate G and T are partially under the control of a common QTL Q, the problem is significantly simplified over that of the classic network reconstruction problem, where positioning G with respect to T would require additional traits related to G and T. If one started with no a priori information on causality between the traits, the exact relationship could not be unambiguously identified without additional experimentation. See, for example, Pearl, 1983, *Probabilistic Reasoning in Intelligent Systems: Networks of Plausible Inference*, Morgan Kaufman Publishers, Inc., San Francisco.

If it is assumed that traits T and G are jointly distributed as a bivariate normal random variable with a common QTL between them, then a determination can be made as to whether the following relationship holds:

$P(T,Q|G)=P(T|G)P(Q|G)$, where the P's represent probability density functions and, by definition, $$P(T, Q \mid G) = \frac{P(T, Q, G)}{P(G)}$$

$$P(T \mid G) = \frac{P(T, G)}{P(G)} = \frac{P(G \mid Q)P(Q)}{P(G)}$$

and $$P(Q \mid G) = \frac{P(Q, G)}{P(G)}.$$

Here, P(T, Q|G) is read, "the probability of T and Q given G". This relationship P(T,Q|G)=P(T|G)P(Q|G) indicates that even though T and Q can be significantly correlated (this holds by definition for a QTL), conditioning on relative abundances G leads to functional independence between Q and T, as was noted in the example for FIG. 79C. If this relationship holds, then it can be concluded that the information passed from Q to disease trait T is via G, which supports G a being causal for T. See, for example, Pearl, 1983, *Probabilistic Reasoning in Intelligent Systems: Network of Plausible*, Inference Morgan Kaufman Publishers, Inc., San Francisco, Section 3.1.2. If conditional on G, Q and T are not independent (e.g., P(T,Q|G)≠P(T|G)P(Q|G)), then one of the relationships given in scenarios 7904 and 7906 more likely holds (the relationships in these Figures can be tested in a like manner). Conditional independence is tested by first forming the likelihood functions based on the conditional probabilities discussed above, for the two competing hypotheses: 1) the null hypothesis that T and Q are independent given G (G is causal for T), and 2) the alternative hypothesis that T and Q are dependent given G (G is not causal for T). The likelihood functions can then be maximized with respect to the parameters of the underlying genetic model, and the likelihood ratio test statistic farmed, which in the present case, under the null hypothesis, would be chi-square distributed with two degrees of freedom. For more information on the likelihood functions and likelihood ratio statistics used, see Section 5.19.4, below.

In one embodiment, the correlation between T and Q is considered in terms of a LOD score. Significant correlation between T and Q is consistent with a significant LOD score for T at position Q. After conditioning on the gene expression trait G, the causality test determines whether there is still a significant LOD score for T at Q. If the LOD score for the QTL drops to zero after conditioning on G, this indicates G effectively blocks transmission of the information from the QTL to the trait, indicating that scenario 7902 (FIG. 79A) is the more likely explanation of the relationship between T and G (or one of the variants given in scenarios 7908 or 7910 of FIG. 79A). While this form of the null hypothesis given above has interesting statistical issues to consider, given causality is assumed under the null hypothesis, it is consistent with the traditional null hypothesis of linkage analysis that a given trait is not linked to a particular locus under consideration.

Those cellular constituents in the candidate causative cellular constituent set in which the null hypothesis of causality is accepted for all of their associated eQTL overlapping with (coincident with) cQTL represent the strongest set of causal candidates for the trait of interest.

In another embodiment, models 7902 (causative), 7904 (reactive), and 7906 (independent) of FIG. 79A are compared directly using a maximum likelihood approach.

In this approach, for each model (independent, causative and reactive), the following likelihoods are formed based on the relationships depicted in the model:

model 7902 (causative) $P(Q,G,T)=P(G|Q)P(T|G)$
model 7904 (reactive) $P(Q,G,T)=P(T|Q)P(G|T)$
model 7906 (independent) $P(Q,G,T)=P(T|Q)P(G|Q)$ where, as in FIG. 79A, Q is the DNA locus controlling cellular constituent levels and/or clinical traits, G is cellular constituent level, and T is clinical trait. The likelihoods are then maximized with respect to the model parameters, given the genotypic data, cellular constituent abundance data 44, and phenotype data 72 (FIG. 1) for the trait (or traits) of interest. These maximum likelihood values are then compared using standard techniques, where the model giving rise to the largest likelihood is declared the best model.

To illustrate, consider the case in which a particular trait T, say X, in which 3.3 percent of the trait's variation is explained by a single QTL. Let Y be another trait such that X is partially causal for Y and the QTL that explains 3.3 percent of X's variation only explains 1.1% of Y's variation in a given population. Further, the coefficient of determination between X and Y is only 0.1 (so ten percent of Y's variation is explained by the variation in X). Clearly, if X and Y were expression or clinical traits, the degree of association between X and Y here would not be striking and, in fact, would most likely be missed using conventional techniques such as agglomerative hierarchical clustering of the data.

Table 1 below gives the Akaike Information Criterion (AIC) for three models in this case (the AIC value is defined as −2 times the loglikelihood added to two times the number of parameters in the model). The AIC is used to select the "best" model from a list of theoretical functions. See, for example, *Akaike Information Criterion Statistics Mathematics and Its Applications*, Japanese Series, Sakamoto et al., D Reidel Pub Co, January 1987. The model with the smallest AIC value represents the model that bests fits the data and therefore has the highest likelihood given the data.

TABLE 1

| LOD scores (X/Y) | AIC for model 306 (independent) | AIC for model 302 (causal) | AIC for model 304 (reactive) |
|---|---|---|---|
| 7.3/2.4 | 13354.5 | 13254.3 | 13276.8 |

From Table 1, it can be seen that causality model 7902 provides the best fit to the data, as would be expected given the hypothetical data. Next, a determination is made as to whether the difference in AIC values is statistically significant. Differences between AIC values essentially represent a likelihood ratio test statistic with one degree of freedom (in this case). These statistics are chi-square distributed when the models are nested, so if this were the case here, then the p-value associated with the difference in AIC values between the causal and reactive model would be 0.000002 (indicating statistical significance). However, the models in the hypothetical case are not nested, and so the standard likelihood ratio test theory does not strictly apply but can be used as an approximate test to determine whether the AIC values are statistically significant.

Permutation testing can also be used to assess the significance of the AIC differences. If the trait values are permuted in a way that maintains the correlation between them, but randomizes them with respect to the genotypes, an assessment can be made as to whether the observed differences are as big as those observed from the actual data. In this present example, 1000 permutations were tested and in no case was the difference between the causal and reactive models as large as it is in Table 1. This example demonstrates the power of the new causality test. It is effectively able to identify a strong causal relationship between two traits that were only moderately associated and weakly linking to a common QTL.

To further highlight the utility consideration of genotypic information (FIG. 1) brings in resolving this causal relationship between these moderately associated traits, the genotypes were randomized at the locus to which the two traits link. This effectively destroys the genetic association between the traits and the locus. The resulting AIC values for each of the models is given in Table 2:

TABLE 2

| LOD scores (X/Y) | AIC for model 306 (independent) | AIC for model 302 (causal) | AIC for model 304 (reactive) |
|---|---|---|---|
| 7.3/2.4 | 13397.9 | 13287.0 | 13287.5 |

Interestingly, the causal and reactive models were significantly better than the independent model, indicating the models were still able to capture the correlation structure between the traits (so randomizing the genotypes does not affect the correlation structure between the two traits), but the AIC values for the causal and reactive models are now statistically equivalent. That is, the causality between these associated traits can no longer be established because the genotypic information was destroyed.

To demonstrate how this procedure can also be used to discriminate between traits related in a causal/reactive way from those related in an independent way (i.e., linked to the same QTL but otherwise independent), a data set for traits Q and Z, where both traits are strongly linked to the same QTL, but are otherwise independent, was tested using the inventive procedure. The results of the analysis are given in Table 3. Here, despite traits Q and Z being very strongly linked to the sane locus, with trait Q significantly more strongly linked to the locus, the independent model fits the data much better than the other two alternatives:

TABLE 3

| LOD scores (Q/Z) | AIC for model 306 (independent) | AIC for model 302 (causal) | AIC for model 304 (reactive) |
|---|---|---|---|
| 37.8/21.5 | 9202.8 | 9288.5 | 9361.1 |

Step 7920. In optional step 7920, a determination is made a to whether the cellular constituents in the candidate causative cellular constituent set are druggable. Hopkins and Groom, 2002, Nature Reviews 1, p. 727 provides one definition of a druggable target. To develop a definition of a druggable genome, Hopkins and Groom identified the molecular targets to rule-of-five compliant compounds. As put forth by Lipinski et al., 1997, Adv. Drug Deliv. Rev. 23, 3, a rule-of-five compliant synthetic compound (e.g., compounds other than those derived from natural products) has less than five hydrogen-bond donors, the molecular mass of the compound is less than 500 Daltons, the lipophilicity is less than 5, and the sum of the nitrogen and oxygen atoms is less than 10. A thorough review of the literature by Hopkins and Groom identified 399 non-redundant molecular targets that have been shown to bind rule-of-five compliant compounds with binding affinities below 10 μM. Next, Hopkins and Groom took the drug-binding domains of the 399 non-redundant molecular targets and determined the families that they represent, a captured by their InterPro domain (Hopkins and Groom, 2002, Nature Reviews 1, p. 727; Apweiler et al., 2001, Nucleic Acids Res. 29, 37). A total of 130 protein families represent the 399 non-redundant molecular targets. These protein families are provided in the online supplemental information for Hopkins and Groom, 2002, Nature Reviews Drug Discovery 1, p. 727 at www.nature.com/reviews/drugdisc and include G-protein coupled receptors, serine/threonine and tyrosine protein kinases, zinc metallopeptidases, urine proteases, nuclear hormone receptors and phosphodiesterases. Thus, in one embodiment of the present invention step 7920 comprises determining whether each cellular constituent in the candidate causative cellular constituent set includes a druggable domain as defined by Hopkins and Groom.

Other methods for defining whether a given cellular constituent includes a druggable domain are available and any such definition can be used in optional step 7920. For example, in a comprehensive review of the accumulated portfolio of the pharmaceutical industry, Drews, 1996, Nature Biotechnol 14, 1516 and Draws and Ryser, 1997, Nature Biotechnol. 15, 1318 identified 483 molecular targets and concluded there could be 5,000-10,000 potential targets on the basis of an estimate of the number of disease related genes. See, Drews, 2000, Science 287, 1960. Thus, in one embodiment of the present invention, the molecular targets identified by Drews are considered the class of cellular constituents that have a druggable domain. In still another embodiment of the present invention, the class of cellular constituents that have a druggable domain are any cellular constituents that are the molecular target of any drug product that has been approved under section 505 of the United States Federal Food, Drug, and Cosmetic Act.

Step 7922. In optional step 7922, the cellular constituents in the candidate causative cellular constituent set are ranked and filtered based on the rank assigned in step 7916 and/or the results of steps 7918 and 7920. A purpose of optional step 7922 is to reduce the number of cellular constituents under consideration as molecular targets of a therapeutic drug discovery program directed at alleviating the trait under study. As such, optional ranking step 7922 serves to prioritize the cellular constituents and/or filter out cellular constituents from the candidate causative cellular constituent set. In some embodiments, for example, the only cellular constituents that are allowed to remain in the candidate causal cellular constituent set are those cellular constituents that (i) are highly ranked in step 7916 (ii), have the null hypothesis of causality accepted in step 7918 for all their associated eQTL that overlap a trait cQTL, and, optionally, (iii) have a druggable domain as determined by step 7920. In some representative embodiments, a high rank means within the top 300, top 200, top 20%, or top 10% of the cellular constituents in the candidate causal cellular constituent set.

Step 7924. The preceding steps describe an analysis of a candidate causal cellular constituent at in order to identify cellular constituents that are causal for a trait of interest. However, the causality test of step 7918 can easily be rewritten to determine whether (i) each eQTL, linked to a trait of interest T, and (ii) a cellular constituent in the candidate causal cellular constituent seat, are correlated conditional on the disease trait in the plurality of organisms. Thus, in addition to determining whether a cellular constituent is causal for a trait, the methods of the present invention can be used to determine whether a cellular constituent is reactive to a trait of interest T. Further, the causality test of step 7918 can easily be rewritten to determine whether (i) the trait of interest T, and (ii) a cellular constituent in the candidate causal cellular constituent et are correlated conditional on the QTL common to both traits. This last test determines whether a QTL common to the trait of interest T and cellular constituent trait drives each of the traits independently, so that the cellular constituent trait is neither causal nor reactive to the trait T of interest. Information on which genes are causal and which genes are reactive for a trait of interest can be used to reconstruct a genetic network using Bayesian analysis.

Section 5.19.5, below, outlines methods that can be used to validate the hypothesis that certain cellular constituents are either causal or reactive to a trait of interest. Further, multivariate analysis can be used to determine whether such cellular constituents act in concert, in the form of a biological pathway, in order to affect the trait under study. In one embodiment in accordance with the present invention, the degree to which each high ranking cellular constituent makes up a candidate pathway group that affect the trait of interest (or are affected by the trait of interest) is tested by fitting a multivariate statistical model to the eQTL of the high ranking cellular constituents. Multivariate statistical models have the capability to consider multiple quantitative traits simultaneously, model epistatic interactions between the QTL and test other interesting variations that test whether a group of cellular constituents belong to the same or related biological pathway. Specific tests can be done to determine if the traits under consideration are actually controlled by the same QTL (pleiotropic effects) or if they are independent.

Importantly, multivariate statistical analysis can be used to simultaneously consider multiple traits. This is of use to determine whether the traits are genetically linked to each other. Accordingly, in such embodiments, the eQTL of high ranking cellular constituents can be subjected to multivariate statistical analysis in order to determine whether the QTL are all genetically linked. Such an analysis can determine that some of the QTL in the cluster found in the QTL interaction map are, in fact, linked whereas other QTL in the cluster are not linked.

Multivariate statistical analysis can also be used to study the same trait from multiple tissues. Multivariate statistical analysis of the same trait from multiple tissues can be used to determine whether genetic linkage varies on a tissue specific basis. Such techniques are of use, for example, in instances where a complex disease has a tissue specific etiology. Exemplary multivariate statistical models that can be used in accordance with the present invention are found in Section 5.6.

5.19.4. Causality Test

This section provides more details on the causality test that is applied in step 7818 of FIG. 78B. Let G be a gene expression trait for some gene g, and let T be a clinical trait. For the correlation between G and T, it is of interest to determine those genetic and environmental components driving the association, and it is of interest to determine whether an assessment can be made in a genetics context as to whether one trait drives the other. That is, does one of the relationships depicted in FIG. 84A hold.

It is not possible to look at these two traits in isolation and determine whether either one of the cases depicted in FIG. 84A holds. In the more classical graphical modeling context, where the aim is to reconstruct a complex network, different graphical structures are assessed and edges are weighted and directed in such structures using mutual information measures that examine all adjacent triplets (say, X, Y, and Z), where these variables represent any combination of QTL, expression trait or clinical trait in the graph where the topology of the graph is constrained a priori to satisfy certain mathematical conditions.

Without the genetic information described herein this network reconstruction problem is difficult because many of the different possibilities that are considered are not distinguishable. For instance, consider the three possible relationships among three traits of interest depicted in FIG. 84B. Cases (i) and (ii) are not distinguishable because they have the same dependency structure. This presents problems for reliable reconstruction of genetic networks given correlation data alone, since in many instances it will simply not be possible to direct edges (directing the edges in such graphs establishes the cause and effect relationships of interest to us in reconstructing pathways associated with disease).

The embodiment of the invention outlined above, and illustrated in FIG. 78, has the significant advantage in that gene expression data and clinical traits ar linked to quantitative trait loci (QTL). The QTL information provides a powerful filter that allows for the rapid restriction of attention from all significantly correlated cellular constituents and trait values to those subsets of cellular constituents and traits that are under the control of a common set of QTL. The triplets described in FIG. 84B then become QTL and traits and it is possible to initially direct an edge between the QTL and a single trait by definition of a QTL, and then test all other traits pair wise as discussed below to determine how the trait pairs are positioned relative to one another. For instance, going back to the case of a clinical trait T linked to a QTL Q, the relationship between Q and T can be immediately fixed as illustrated in FIG. 84C. The relationship in FIG. 84C holds because Q is a QTL for T, and the QTL provides the direction of the relationship (T depends from Q) since Q is causal for T (e.g., variations in the DNA at the QTL location lead to variations in T). To position a given gene expression trait, G, that is correlated with T, all that is required is a test for mutual independence of Q and T given G. That is, if T and Q are independent given G, then the (Q,T,G) triplet has the form depicted in FIG. 84D. However, lack of independence given G indicates one of the alternative possibilities given by FIG. 84E.

The methods discussed below can be applied to determine which of the two structures (FIG. 84D versus FIG. 84E) is supported by the data.

More formally, a determination of whether T is correlated with the genotypes at Q, conditional on G is desired in order to assess if the following property holds:

$P(T,Q|G)=P(T|G)P(Q|G).$

This property is satisfied only if T and Q are conditionally dependent upon G. For formal theoretical support for this conditional dependence property, see Pearl, 1988, *Probabilistic Reasoning In Intelligent Systems: Networks of Plausible Inference*, Revised Second Printing, Morgan Kaufmann Publisher, Inc., San Francisco, Calif., Section 3.1.2. This conditional dependency property is related to the mutual information measure that is typically used in network reconstruction problems:

$$I(T, Q|G) = \sum_{T,Q,G} P(T, Q, G) \log\left(\frac{P(T, Q|G)}{P(T|G)P(Q|G)}\right),$$

where the summation symbol indicates the continuous variables T and G have been discretized to allow for efficient computation over complicated graph structures, as is usually done in network reconstruction problems. The use of mutual information is the reduction in uncertainty about one-variable due to the knowledge of the other variable. See, for example, Duda et al., 2001, *Pattern Classification*, John Wiley & Sam, Inc., New York, p 632.

While the mutual information measure is useful in more general network reconstruction problems, the problem addressed by the instant causality test is significantly more simple than the general case because of the novel requirement that T and G are both linked to Q. This novel requirement leads to a more robust and more powerful test for causality. The purpose of the causality test of the present invention is to position a cellular constituent on the causal or reactive side of a clinical trait of interest, which can be accomplished by testing for independence of T and Q, conditional on G, as discussed above.

In developing a test for independence, a few observations help clarify the specifics of such a test. First, it is assumed a prior that G and T are significantly correlated to Q. That is, these quantitative traits both have QTL at position Q that give rise to significant LOD scores. Second, it is noted that $P(T,Q|G)=P(T|Q,G)P(Q|G),$ so that $P(T,Q|G)=P(T|G)P(Q|G),$ if and only if
 P(T|Q,G)=P(T|G),
 whenever P(Q|G)>0.
These relationships follow from the conditional independence of T and Q given G. Therefore, the term P(Q|G) can be ignored and the focus can center on the single conditional probability. What this last equation implies is that if that portion of the correlation between T and Q that can be explained by the correlation between G and Q is conditioned out, then a determination can be made as to whether the remaining. correlation between T and Q is still significant. If not, then it is expected that a significant QTL for T|Q and G|Q will arise, but that no significant QTL for T|Q, G will arise. By forming the loglikelihood ratio based on these two probability densities, the significance of the resulting LOD score can be used as the significance level for the test of independence.

Before forming the conditional likelihoods based on the conditional probability density functions discussed above, the likelihood for G and T for a single animal in an $F_2$ population are formed, where G and T are taken to be jointly normally distributed, allowing for dependency between G and T. Under the null hypothesis of no correlation between (T,G) and ent at location Q, the likelihood for animal i is:

$$l(\theta_0; t_i, g_i) = \frac{1}{2\pi\sigma_G\sigma_T\sqrt{1-\rho^2}} \exp$$

$$\left\{ -\frac{1}{2(1-\rho^2)} \left[ \frac{(t_i - \mu_T)^2}{\sigma_T^2} - 2\rho\frac{(t_i-\mu_T)(g_i - \mu_G)}{\sigma_T\sigma_G} + \frac{(g_i - \mu_G)^2}{\sigma_G^2} \right] \right\},$$

where $\theta_0 = (\mu_T, \mu_G, \sigma_T, \sigma_G, \rho)$ is the parameter vector for the likelihood, and $\rho$ is the correlation between G and T. Under the alternative hypothesis where G and T are correlated with Q, the likelihood is:

$$l(\theta_A; t_i, g_i \mid Q) = \sum_{j=1}^{3} P(Q_j) \left[ \frac{1}{2\pi\sigma_G\sigma_T\sqrt{1-\rho^2}} \exp\left(-\frac{q_{Q_j}}{2}\right) \right],$$

where
$$q_{Q_j} =$$
$$\left\{ -\frac{1}{1-\rho^2} \left[ \frac{(t_i - \mu_{T_{Q_j}})^2}{\sigma_T^2} - 2\rho\frac{(t_i - \mu_{T_{Q_j}})(g_i - \mu_{G_{Q_j}})}{\sigma_T\sigma_G} + \frac{(g_i - \mu_{G_{Q_j}})^2}{\sigma_G^2} \right] \right\},$$

$$\theta_A = (\mu_{T_{Q_1}}, \mu_{T_{Q_2}}, \mu_{T_{Q_3}}, \mu_{G_{Q_1}}, \mu_{G_{Q_2}}, \mu_{G_{Q_3}}, \sigma_T, \sigma_G, \rho),$$

and $P(Q_j)$ is the probability of genotype Q, at locus Q. Given these likelihoods for the individual animals in an $F_2$ population, the full likelihood over all N animals for the null and alternative hypotheses, respectively, are:

$$L(\theta_0; G, T) = \prod_{i=1}^{N} l(\theta_0; g_i, t_i)$$

and $$L(\theta_A; G, T \mid Q) = \prod_{i=1}^{N} l(\theta_A; g_i, t_i \mid Q).$$

For each likelihood defined above the maximum likelihood estimates for $\theta_0$ and $\theta_A$, $\hat{\theta}_0$ and $\hat{\theta}_A$ are obtained. The likelihood ratio statistic is:

$$LR = -2\ln\left( \frac{L(\hat{\theta}_0; G, T)}{L(\hat{\theta}_A; G, T \mid Q)} \right),$$

which is $\chi^2$ distributed with four degrees of freedom.

With these maximum likelihood estimates in hand for the null and alternative hypotheses, it is possible to compute the conditional likelihoods that are needed to assess conditional independence of T and Q. The form of the conditional likelihood for T) G (the conditional likelihood under the null hypothesis) for a single animal is:

$$l'(\theta_0; t_i \mid g_i) = \frac{1}{\sqrt{2\pi(1-\rho^2)}} \exp\left[ -\frac{(t_i - b)^2}{2\sigma_T^2(1-\rho^2)} \right],$$

where $$b = \mu_T + \rho\frac{\sigma_T}{\sigma_G}(z_i - \mu_G).$$

The corresponding conditional likelihood under the alternative hypothesis is:

$$l'(\theta_A; t_i \mid g_i, Q) = \sum_{j=1}^{3} P(Q_j) \frac{1}{\sqrt{2\pi(1-\rho^2)}} \exp\left[ -\frac{(t_i - b_{Q_j})^2}{2\sigma_T^2(1-\rho^2)} \right],$$

where $$b = \mu_{T_{Q_j}} + \rho\frac{\sigma_T}{\sigma_G}(g_i - \mu_{G_{Q_j}}).$$

The full likelihoods are:

$$L'(\theta_0; T \mid G) = \prod_{i=1}^{N} l'(\theta_0; t_i \mid g_i)$$

and $$L'(\theta_A; T \mid G, Q) = \prod_{i=1}^{N} l'(\theta_A; t_i \mid g_i, Q).$$

Finally, from this, the conditional likelihood ratio test statistic of interest is obtained:

$$LR' = -2\ln\left( \frac{L'(\hat{\theta}_0; T \mid G)}{L'(\hat{\theta}_A; T \mid G, Q)} \right),$$

where $\hat{\theta}_0$ and $\hat{\theta}_A$ are the maximum likelihood estimates obtained from $L_0$ and $L_A$ defined above.

5.19.5. Target Validation

The methods of the present invention can be used to associate a cellular constituent with a complex trait. This section discloses techniques that can be used to validate such cellular constituents identified using the techniques of the present invention. In some embodiments, gene knock-out/knock-in mice or transgenic mice are employed for such validation. In some embodiments, in vivo siRNA is used to validate such genes. See, for example, Cohen et al., 1997, J. Clin. Invest. 99, p. 1906; Xia, et al., 2002, Nature Biotechnology 20, p. 1006; Hannon, 2002, Nature 418, p. 244; Carthew, 2001, Current Opinion in Cell Biology 13, p. 244; Paddison, 2002, Genes & Development 16, p. 948; Paddison & Hannon, 2002, Cancer Cell 2, p. 17; Jang et al., 2002, Proceedings National Academy of Science 99, p. 1984; and Martinez et al., 2002, Proceedings National Academy of Science 99, p. 14849.

In some embodiments, before a putative target cellular constituent is biologically validated in mice, association studies can be carried out in human populations to provide a source of validation in humans. Associating a gene in a human population with a clinical trait, where the gene in mouse 1) was physically co-localized with a cQTL for the corresponding clinical trait in a segregating mouse population, 2) gave rise to a cis-acting QTL with respect to its transcription, and 3) was significantly genetically interacting with the clinical trait QTL, is itself a very powerful validation of a gene's role in the complex trait of interest. See, also, U.S. Provisional Patent Application 60/436,684 filed Dec. 27, 2002. The combined validation in mouse and human provides all that is necessary to move a target forward in a discovery program. Even in cases where the causal gene is not itself druggable, druggable targets driven by the causal gene can be identified by examining those targets that have eQTL that co-localize and are interacting with eQTL for the causative gene. This speaks to the more general use of the combined genetics/gene expression approach to reconstruct genetic networks.

5.20. Drug Discovery Paradigm that Involves the Combination of Genetic, Functional Genomic and Clinical Data Novel techniques for associating genes with complex traits using cross species data have been disclosed in the Sections above. This section describes a novel drug discovery paradigm that ses cross species data to identify potential drug target candidates for drug discovery programs. Further, this section describes techniques for validating these potential drug target candidates. An illustration of a novel paradigm in accordance with one embodiment of the present invention is disclosed in FIG. 69.

Step 6902. The drug discovery paradigm begins with step 6902 where a therapeutic area or disease is selected. The paradigm is particularly useful for associating genes with complex diseases such as those described in Section 5.12, above.

Step 6904. In step 6904, inbred strains that are discordant for the phenotype of interest (e.g., the complex trait) are used to construct genetic crosses that are phenotyped and genotyped. Further, tissues relevant to the disease selected in step 6902 are obtained from the crossed progeny and the levels of a plurality of cellular constituents in these tissues are measured. Representative forms of cellular constituents that can be measured in step 6904 are described in Section 5.1. Step 6904 produces three forms of data for an inbred population. They are phenotypic data, expression data and genotypic data.

Step 6906. In step 6906, a human population, or some other form of outbed population, is identified and relevant tissues from family based samples with disease related phenotypes are collected for expression profiling and for construction of genome-wide genotyping. Step 6906 produces three forms of data for an outbred population. They are phenotypic data, expression data and genotypic data.

Step 6908. In step 6908, the individuals are profiled in order to identify a disease associated pattern. In one approach, in accordance with step 6908, the population observed in step 6904 (or step 6906) is stratified based on a clinical trait that is relevant to the disease selected in step 6902. Then, the upper and lower extremes of this stratified population are considered. Specifically, those genes that are the most differentially expressed in the upper and lower extremes of the stratified population are selected. This set of genes can be considered the most transcriptionally active set of genes for the population falling in the tails of the clinical trait distribution. This set can be termed the "active set". The selection of the active set is not biased by selecting genes based on their ability to discriminate between the clinical trait extremes.

The active set is used to help define the clinical trait under study. Expression vectors for each of the genes in the active set we constructed. Each expression vector includes the expression value of a given gene in the active set across the organisms in the identified population. Then, the expression vectors are subjected to two-dimensional cluster analysis. On the first axis (e.g., the x-axis), the expression vectors for each of the genes in the active set are clustered. To form the clustering on the other axis (e.g., the y-axis), an organism vector is constructed for each of the organisms in the population. Each such organism vector includes the expression value for each of the genes in the active set. The organism vectors are clustered along the y-axis. Thus, the first axis clusters genes that express similarly across the population and the second axis clusters organisms that have similar gene expression values for the active set. Each x,y coordinate in the two-dimensional graph represents a cellular constituent level for a gene in a given organism. In some embodiments, each x,y coordinate in the two-dimensional graph is color coded to indicate the expression level of the gene in the given organism relative to a reference pool. An example of this form of two-dimensional cluster analysis is provided in Section 5.19.

The two-dimensional cluster analysis allows for the determination of subgroups in the population. Clearly such subpopulations will be defined by clusters on the second axis (e.g., y-axis). However, the patterns produced by the clustering on the first axis aid in defining the subpopulations on the second axis. Namely, each subgroup on the second axis should have similar patterns of expression across the active set. In FIG. 59, for example, the y-axis was not clustered based on a clinical trait. Nevertheless, the mice on the y-axis cluster into distinct phenotypic groups. The first set is the low fat pad mass group. The low fat pad mass group is defined by two factors. First, the low fat pad mass group define a cluster on the y-axis. Second, genes in the low fat pad mass group that ware in set 5902 tend to be green-shifted relative to the reference pool whereas genes in set 804 tend to be red-shifted relative to the reference pool. The expression pattern of the genes in the 280 member set along the y-axis serve to validate that the low fat pad mass group is not, in fact, a composite of two or more subgroups. Continuing with this form of analysis, two other groups (high fat pad mass 1 and high fat pad mass 2) are defined on the y-axis and validated by the pattern of expression along the y-axis as summarized in the following table:

| Name | Y-axis | X-axis-gene set 802 | X-axis-gene set 804 |
|---|---|---|---|
| Low FPM | Cluster 5910 | Green | Red |
| High FPM 2 | Cluster 5912 | Green | Red |
| High FPM 1 | Cluster 5914 | Green/red | Green |

Step 6910. In step 6910, the underlying genetics of genes involved in the patterns identified in step 6908 are evaluated. For example, the groups of organisms identified in the analysis above (e.g., low FPM organisms, high FPM 1 organisms, high PPM 1 organisms) can be subjected to independent quantitative genetic analysis. For example, those classified as high PPM group 1 or low FPM, and 2) those classified as high FPM group 2 or low FPM can each independently be subjected to quantitative analysis. In this quantitative analysis, the phenotypic trait associated with the disease selected in step 6902 (e.g., PPM) is analyzed using the subpopulations identified in the two-dimensional cluster analysis rather than the whole population. Several forms of quantitative genetic analysis are possible. First, a clinical trait can be used to derive clinical QTL (cQTL). Second, expression values for the genes can be used to derive eQTL.

Regardless, of whether clinical or expression values serve as quantitative traits, the exact forms of quantitative genetic analysis used in step 6910 will depend on the type of phenotypic data that is available. Inbred populations (or subpopulations) can be profiled using linkage analysis as described in Section 5.13 or any of the techniques described in Chapter 15 of Lynch and Walsh, 1998, *Genetics and Analysis of Quantitative Traits*, Sinauer Associates, Inc., Sunderland, Mass. Outbred populations (or subpopulations) can be profiled using association analysis techniques described in Section 5.14 or any of the techniques described in Chapter 16 of Lynch and Walsh, 1998, *Genetics and Analysis of Quantitative Traits*, Sinauer Associates, Inc., Sunderland, Mass. The purpose of step 6910 is to identify cQTL and eQTL that are associated with the disease selected in step 6902.

Step 6912. In step 6912, the genetics of the disease associated pattern is intersected with the genetics of disease related traits to identify key drivers. Steps 6902 through 6910 serve to identify patterns of expression associated with a clinical trait related to the disease under study. The quantitative genetic analyses identify genetic loci (eQTL and/or cQTL) that control subtypes of the disease. However, such techniques do not, by themselves, lead to identification of the underlying QTL of interest. Genes underlying QTL controlling for a clinical trait can cause variation in the trait through polymorphic transcription due to DNA polymorphisms. Such genes can be identified by combining genetics with gene expression.

In one approach in accordance with step 6912, eQTL that colocalize with cQTL and with the physical location of the gene whose transcription gives rise to the eQTL are identified. In cases where the gene underlying a QTL for a clinical trait controls the variation of that trait through variation in transcription associated with DNA polymorphisms in the gene itself the expression of that gene treated as a quantitative trait should give rise to an eQTL coincident with the cQTL. Depending on the degree of heritability of the clinical and expression traits, and the percentage of variation of the trait explained by the cQTL, it is not expected that the clinical trait values and the expression values will be significantly correlated, even if variation in transcription of the gene causes variation in the clinical trait. However, significant genetic correlation between the clinical trait QTL and gene expression traits is expected in such cases. Therefore, testing for interaction between the clinical trait QTL and the gene expression QTL can identify candidate genes underlying the cQTL for the clinical trait of interest.

Techniques that simultaneously analyze multiple QTLs can be used to identify whether eQTL and cQTL are linked. Such techniques include marker-difference regression (also known as marker regression or joint mapping). See, for example, Kearsey and Hyne, 1994, Theor. Appl. Genet. 89, p. 698; Wu and Li, 1994, Theor. Appl. Genet. 89, p. 535. Such techniques further include interval mapping with marker cofactors. See, for example, Jansen, 1992, Theor. Appl. Genet. 85, p. 252; Jansen, 1993, Genetics 135, p. 205; Zen, 1993, Proc. Natl. Acad. Sci. USA 90, p. 10972; Zeng, 1994, Genetics 136; p. 1457; Stam, 1991, *Proceedings of the Eight Meeting of the Eucarpia Section Biometrics on Plant Breeding*, Brno, Czechoslovakia, pp. 24-32; Jansen, 1995, Theor. App. Gent. 91, p. 33; van Ooijen, 1994, in van Ooijen and Jansen (eds.), *Biometrics in plant breeding: applications of molecular markers*, pp. 205-212, CPRO-DLO, Netherlands; and Utz and Melchinger, 1994, in van Ooijen and Jansen (eds.), *Biometrics in plant breeding: applications of molecular markers*, pp. 195-204, CPRO-DLO, Netherlands. Such techniques further include multiple-trait extensions to composite interval mapping given by Jiang and Zeng. See, for example, Jiang and Zeng, 1995, Genetics 140, p. 1111; and Ronin, et a, 1995, Theor. Appl. Genet. 90, p. 776.

Step 6914. In step 6914, each gene identified in step 6912 is Validated using an association analysis in an independent population. The type of association analyses used in step 6914 can be, for example, any of the various forms of association analyses described in Section 5.14, above. Further, any of the techniques described in Chapter 16 of Lynch and Walsh, 1998, *Genetics and Analysis of Quantitative Traits*, Sinauer Associates, Sunderland, Mass., can be used in step 6914.

Step 6916. In step 6916, each gene identified in step 6912 is validated using advanced crosses, congenic strains or similar modeling systems. Congenics are useful for validations in step 6916. Once a QTL is identified for the trait of interest, the strain whose congenic region covers the QTL region can be identified and studied with respect. to the same phenotype. Further, more complicated genetic models can be constructed using the congenics, based on QTL results from, for example, an F2 cross. For example, suppose two strongly interacting QTL were identified from the F2 cross. The congenic strains covering the two QTL regions could be bred to construct a new congenic strain that had two congenic regions, each covering one of the QTL of interest. These mice could then be studied with respect to the phenotype of interest. The advantage to this sort of construction is that the congenic strains are stable and can be constantly bred to generate progeny that are genetically identical (unlike the F2 populations, where there is no hope of recovering the same genetic background).

Step 6918. In step 6918, synteny (comparative mapping) can be used to provide an informed selection of targets. For example, putative candidates identified (and possibly validated) in one species using the steps described above can be mapped to orthologs in another species using a comparative genetic map between the two species. Then a determination can be made as to whether the region in the second species has been associated with the disease in the second species.

This strategy was employed by Schadt et al., 2003, Nature 422, p. 297 to increase confidence in mouse chromosome QTL tentatively associated with obesity. The mouse loci was homologous to human chromosome 20q12-q13.12, a region that has previously been linked to human obesity-related phenotypes. The human orthologs for the candidates identified in the mouse also reside in the human chromosome 20 region.

Step 6920. Not all genes linked to a disease serve as drugable targets. For example, genes that encode for proteins such as transcription factors may not be ideal targets for a drug discovery program even when their linkage to a disease of interest has been validated. Thus, step 6920 serves to analyze genes that have been linked to a disease of interest to determine if they are suitable targets for drug discovery.

Step 6922. In step 6922, gene targets are further validated by techniques such as gene knock-out/knock-in mice, transgenic mice, or RNAi techniques. FIG. 70 provides a hypothetical example of a validation strategy in accordance with one embodiment of the present invention. In this example, genes Y1 through Y4 are genes that are part of an expression pattern associated with a complex trait of interest. The upper panel plots the lod score curves for the four genes for a particular chromosome, where the cluster of eQTL depicted are coincident with a cQTL for the complex trait. By examining genes that physically reside in the QTL support interval, those genes that have cis-acting eQTL that are significantly genetically interacting with the other eQTL/cQTL are identified. These gene represent the potential causative genes underlying the cQTL/eQTL. Gene X in FIG. 70 highlights one such example. By knocking gene X out using in vivo small interfering RNA (siRNA) methods, the siRNA knock-out animals can be profiled and the genetic signatures of the original genes making up the eQTL cluster examined. Various siRNA knock-out techniques (also referred to as RNA interference or post-transcriptional gene silencing) are disclosed, for example, in Xia, et al., 2002, Nature Biotechnology 20, p. 1006; Hannon, 2002, Nature 418, p. 244; Carthew, 2001, Current Opinion in Cell Biology 13, p. 244; Paddison, 2002, Genes & Development 16, p. 948; Paddison & Hannon, 2002, Cancer Cell 2, p. 17; Jang et al., 2002, Proceedings National Academy of Science 99, p. 1984; Martinez et al., 2002, Proceedings National Academy of Science 99, p. 14849.

The lower panel in FIG. 70 highlights what is expected if gene X were in fact driving the eQTL cluster shown in the upper panel. That is, the disappearance of the eQTL cluster would validate gene X's role as the causal factor underlying the expression pattern associated with the complex trait, and thus, would solidify its role as a key driver for the corresponding complex trait. If the complex trait were a disease like obesity, then validating a gene for the obesity trait directly would require the construction of say, a knock out animal for that gene, which is a lengthy process. However, by defining the complex trait in terms of expression patterns, the candidate gene can be perturbed in more specialized ways and the effects on the expression pattern observed, which can happen in a much shorter time frame.

5.21. Test for Pleiotropy

In some embodiments, a determination is made as to whether the coincidence between an eQTL and a respective cQTL arises through pleiotropy or close linkage between QTL. When a determination is made that the coincidence between an eQTL and a respective cQTL is the result of two closely linked QTL, association between the cellular constituent corresponding to the eQTL and the trait corresponding to the cQTL is not made. In some embodiments, a test for pleiotropy comprises comparing a model for the null hypothesis, indicating the result of pleiotropy, to a model for the alternative hypothesis, indicating two closely linked QTL.

In some embodiments, the model for the null hypothesis is:

$$\begin{pmatrix} y_1 \\ y_2 \end{pmatrix} = \begin{pmatrix} \mu_1 \\ \mu_2 \end{pmatrix} + \begin{pmatrix} \beta_1 \\ \beta_2 \end{pmatrix} Q + \begin{pmatrix} \varepsilon_1 \\ \varepsilon_2 \end{pmatrix},$$

where

Q is a categorical random variable indicating the genotypes at the position of the eQTL and the cQTL in the plurality of organisms;

$$\begin{pmatrix} \varepsilon_1 \\ \varepsilon_2 \end{pmatrix}$$

is distributed as a bivariate normal random variable with mean $$\begin{pmatrix} 0 \\ 0 \end{pmatrix}$$

and covariance matrix $$\begin{pmatrix} \sigma_1^2 & \sigma_1\sigma_2 \\ \sigma_2\sigma_1 & \sigma_2^2 \end{pmatrix};$$

and $\mu_i$ and $\beta_i$ are model parameters.

In some embodiments, the model for the alternative hypothesis is:

$$\begin{pmatrix} y_1 \\ y_2 \end{pmatrix} = \begin{pmatrix} \mu_1 \\ \mu_2 \end{pmatrix} + \begin{pmatrix} \beta_1 & \beta_2 \\ \beta_3 & \beta_4 \end{pmatrix}\begin{pmatrix} Q_1 \\ Q_2 \end{pmatrix} + \begin{pmatrix} \varepsilon_1 \\ \varepsilon_2 \end{pmatrix},$$

where $Q_1$ and $Q_2$ are categorical random variables indicating the genotypes at the position of the eQTL and the cQTL in the plurality of organisms;

$$\begin{pmatrix} \varepsilon_1 \\ \varepsilon_2 \end{pmatrix}$$

is distributed as a bivariate normal random variable with mean $$\begin{pmatrix} 0 \\ 0 \end{pmatrix}$$

and covariance matrix and $$\begin{pmatrix} \sigma_1^2 & \sigma_1\sigma_2 \\ \sigma_2\sigma_1 & \sigma_2^2 \end{pmatrix};$$

and $\mu_i$ and $\beta_i$ are model parameters.

In some embodiments the model for the alternative hypothesis is:

$$\begin{pmatrix} y_1 \\ y_2 \end{pmatrix} = \begin{pmatrix} \mu_1 \\ \mu_2 \end{pmatrix} + \begin{pmatrix} \beta_1 & \beta_2 \\ \beta_3 & \beta_4 \end{pmatrix}\begin{pmatrix} Q_1 \\ Q_2 \end{pmatrix} + \begin{pmatrix} \varepsilon_1 \\ \varepsilon_2 \end{pmatrix},$$

wherein $Q_1$ and $Q_2$ are categorical random variable indicating the genotypes at the position of the eQTL and the cQTL in the plurality of organisms;

$$\begin{pmatrix} \varepsilon_1 \\ \varepsilon_2 \end{pmatrix}$$

is distributed as a bivariate normal random variable with mean $$\begin{pmatrix} 0 \\ 0 \end{pmatrix}$$

and covariance matrix $$\begin{pmatrix} \sigma_1^2 & \sigma_1\sigma_2 \\ \sigma_2\sigma_1 & \sigma_2^2 \end{pmatrix};$$

$\mu_i$ and $\beta_i$ are model parameters; and
one of the conditions (i) through (iv) is valid:
 (i) $\beta_1 \neq 0$, $\beta_4 \neq 0$, $\beta_2 = 0$, and $\beta_3 = 0$;
 (ii) $\beta_1 \neq 0$, $\beta_4 \neq 0$, $\beta_2 \neq 0$, and $\beta_3 = 0$;
 (iii) $\beta_1 \neq 0$, $\beta_4 \neq 0$, $\beta_2 = 0$, and $\beta_3 \neq 0$; and
 (iv) $\beta_1 \neq 0$, $\beta_4 \neq 0$, $\beta_2 \neq 0$, and $\beta_3 \neq 0$.
In some embodiments the loglikelihood for the null hypothesis and the alternative hypothesis are maximized with respect to the model parameters ($\mu_i$, $\beta_j$, and $\sigma_k$) using maximum likelihood analysis. After maximum likelihood estimates are obtained for each model, the likelihood ratio test statistic between the competing models is formed and the test statistic is used to determine whether the model for the alternative hypothesis provides for a statistically significant better fit to the data than the model for the null hypothesis.

6. EXAMPLES

The following examples are presented by way of illustration of the invention and are not limiting.

6.1. Exemplary Sources of Genotype and Pedigree Data

Figure 5:
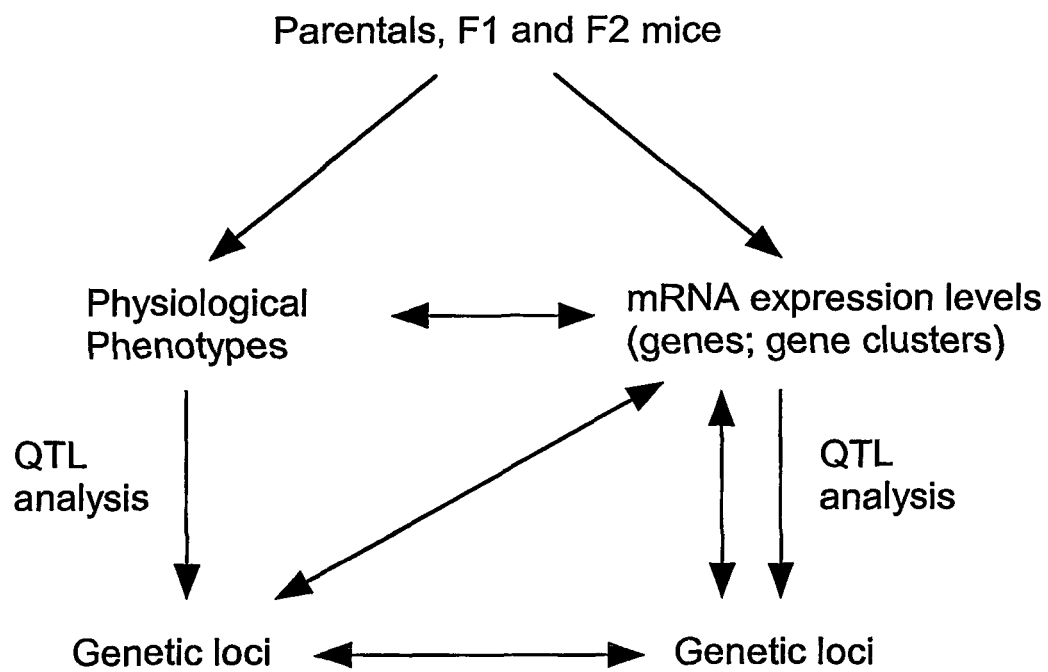
FIG. 5 illustrates genetic crosses used to derive a mouse model for a complex human disease in accordance with one embodiment of the present invention.

Mice.
The methods of the present invention are applicable to any living organism in which genetic variation can be tracked. Therefore, by way of example, genotype and/or pedigree data 68 (FIG. 1) is obtained from experimental crosses or a human population in which genotyping information and relevant clinical trait information is provided. One such experimental design for a mouse model for complex human diseases is given in FIG. 5. In FIG. 5, there are two parental inbred lines that are crossed to obtain an $F_1$ generation. The $F_1$ generation is intercrossed to obtain an F2 generation. At this point, the F2 population is genotyped and physiologic phenotypes for each F2 in the population are determined to yield genotype and pedigree data 68. These same determinations are made for the parents as well as a sampling of the $F_1$ population.

Human Populations.
The present invention is not constrained to model systems, but can be applied directly to human populations. For example, pedigree and other genotype information for the CEPH family is publicly available (Center for Medical Genetics, Marshfield, Wis.), and lymphoblastoid cell lines from individuals in these families can be purchased from the Coriell Institute for Medical Research (Camden, N.J.) and used in the expression profiling experiments of the instant invention. The plant, mouse, and human populations discussed in this Section represent non-limiting examples of genotype and/or pedigree for use in the present invention.

6.2. Identification of Regions that Broadly Control Transcription

The genome-wide consideration of all genes as quantitative traits, representation of individual QTL analysis results in a database, and summarizing the degree of overlap among all genes at all positions where a QTL analysis was run enables the identification of regions that very broadly control transcription. For a given organism, this allows for the identification of regions that potentially control for basal-level transcription levels across most genes that are expressed. An important utility that is provided by the methods of the present invention is the identification of those genes that control biological pathways and/or interactions between biological pathways as well as the separation of these genes from genes that are simply responding to the signals propagated by the potentially small set of genes.

Some approaches see genes that have significantly co-regulated expression patterns over a number of relevant conditions. Many forms of cluster analysis and other pattern detection schemes are used to uncover such patterns. Then, techniques such as multivariate analysis are used to determine whether these co-regulated genes participate in the same biological pathway (e.g., whether these genes genetically interact or control each other). That is, multivariate techniques are used to determine whether such genes are trans acting. However, most strongly genetically controlled genes are actually the least similar, least co-regulated with respect to other genes because their expression patterns are independent of the expression patterns of other genes. Therefore, it is expected that trans acting genes (e.g., genes acting on other genes to affect gene transcription) are harder to detect than cis acting genes. An example of a cis acting gene is a gene in which variation within the gee affects transcription of the gene itself. The methods of the present invention allow for the identification of trans acting genes. The identity of trans acting genes further elucidates control of pathways and disease etiology since they are ostensibly important to the proper functioning of so many pathways.

6.3. Identifying Genes Under Genetic Control In Small Populations

In this example 56 individuals from four CEPH reference families (Dausset, 1990 Genomics 6:575-577) were selected for expression profiling of lymphoblastoid cell lines using a standard 25K human gene oligonucleotide microarray. The 25K human gene oligonucleotide microarray is described in van't Veer et al. Nature 415, 530-536 as well as Hughes et al., 2001, Nat. Biotechnol. 19, 342-347. Briefly, labeled cRNAs were fragmented to an average size of approximately 50-100 nucleotides by heating at 60° C. in the presence of 10 mM $ZnCl_2$, added to hybridization buffer containing 1M NaCl, 0.5% sodium sarcosine, 50 mM MES, pH 6.5, and formamide to a final concentration of 30%, final volume 3 ml at 40° C. The 25K human gene oligonucleotide microarray represents 24,479 biological oligonucleotides plus 1,281 control probes.

The four families, CEPH/Utah pedigrees 1362, 1375, 1377 and 1408, consisted of large sibships along with parents and grandparents. These CEPH families have served as an important scientific resource for polymorphism discovery and human genetic map construction. Hence, extensive genotype data is publicly available for these families.

Lymphoblastoid cell lines from CEPH/Utah pedigree families 1362, 1375, 1377 and 1408 were obtained from Coriell Cell Repositories, Camden, N.J. Other lymphoblastoid cell lines were established from normal donors by immortalization with Epstein-Barr Virus (EBV) as described by Tosatio, *Generation of Epstein-Barr Virus (EBV)-immortalized B cell lines*, Current Protocols in Immunology 1, 7.22.1-7.223, John Wiley & Sons, New York, 1991. Cells were cultured in RPMI 1640 medium containing 15% fetal bovine serum, and penicillin/streptomycin antibiotics (Invitrogen Life Technologies, Carlsbad, Calif.). Cells were maintained in the log phase of cell growth for at least two days and were harvested at densities of $0.4$-$0.9 \times 10e^6$ cell/ml. Total cellular RNA was then purified using an RNeasy Mini kit according to the manufacturer's instructions (Qiagen, Valencia, Calif.). Competitive hybridizations were performed by mixing fluorescently labeled cRNA (5 µg) from each CEPH/Utah lymphoblastoid line with the same amount of cRNA from d reference pool, comprising equal amounts of cRNA from lymphoblastoid lines established from seven unrelated normal blood donors. The human microarray contained 24,479 non-control oligonucleotide probes for human genes. The hybridizations were performed in duplicate with fluor reversal.

Array images were processed to obtain background noise, single channel intensity, and associated measurement error estimates. Expression changes between two samples were quantified as $\log_{10}$ (expression ratio) where the 'expression ratio' was taken to be the ratio between normalized, background-corrected intensity values for the two channels (red and green) for each spot on the array. An error model for the log ratio was applied to quantify the significance of expression changes between two samples. See Roberts et al., 2000, "Signaling and Circuitry of Multiple MAPK Pathways Revealed by a Matrix of Global Gene Expression Profiles," Science 287, 873-880.

Genotype data for the four CEPH families was obtained from the CEPH Genotype database (Murray et al., 1994, Science 265, 2049-2054). A total of 495 autosomal STR polymorphisms were selected for analysis. Polymorphisms were chosen so that genotypes were available for all but three or fewer individuals per pedigree with this condition being true in at least three of the pedigrees. Marker positions were assigned using a Marshfield sex-averaged genetic map (Broman et al., 1998, Am J. Hum. Genet. 63, 861-869). Variance-components analysis (Amos, 1994, Am J. Hum. Genet. 54, 535-543) was used to estimate the heritability of gene expression, as measured by the mean $\log_{10}$ expression ratio, for each of the 2,726 mRNA that were significantly differentially expressed in the founders, and to test whether the heritability was significantly different from zero. Genes were defined as differentially regulated if eight or more founders had a p-value for differential expression less than 0.05. Heritability estimates were obtained by maximizing the likelihood assuming a multivariate normal distribution for the vector of phenotypes for the pedigree. The null hypothesis of no heritability was tested by comparing the full model, which assumes genetic variation, and a reduced model, which assumes no genetic variation, using a likelihood ratio test. The above analyses was repeated allowing for a shared household effect. All analyses were performed using procedures contained in the Sequential Oligogenic Linkage Analysis Routines (SOLAR) package (Almasy and Blangero, Am. J. Hum. Genet. 62, 1198-1211, 1998).

As described above, heritability analysis was performed for gene expression on a subset of 2,726 genes that were significantly differentially regulated within 8 or more of the 16 pedigree founders. Due to the relatively small population size, systematic linkage analysis across all genes was not performed. As indicated in FIG. 6, for the differentially expressed genes, 29% had a detectable genetic component (Type I error<0.05). This result offers a striking glimpse into the genetics of gene expression in humans, with such a large percentage of genes detected with significant heritabilities in such a small sample of "normal" individuals. The group of genes having a detectable genetic component makes good targets for complex human diseases, given the degree of genetic control in these genes is so readily identifiable in this small population. A closer look at many of the genes with most significant heritabilities show that many have already been implicated in human complex diseases: 1) Coagulation Factor XIII, associated with thrombosis (Franco et al., 1999, *Thromb. Haemost*. 81, 676-679), 2) Vitamin D Receptor associated with osteoporosis (Ralston, 2002, *J. Clin Endocrinol Metab* 87, 2460-2466), 3) BCAR1, potentially associated with resistance to breast cancer treatment (Brinkman et al., 2000, J Natl Cancer Inst 92, 112-120), 4) Glycophorin C, associated with red blood cell ovalocytosis and malaria resistance (Mgone et al., 1996, Trans R Soc Trop Med Hyg 90, 228-231), 5) Catenin, expressed in colon cancer (Morin et al., 1997, Science 275, 1787-1790), and 6) Cubilin null mutations have been associated with hereditary megaloblastic anemia (Aminoff et al., 1999, Nat Genet 21, 309-313).

6.4. Genetic Analysis of the Mouse Transcriptome

The following example illustrates how the methods of the present invention uncover significant patterns of gene interactions. In particular, the example demonstrates how QTL that are linked to quantitative traits (e.g., expression statistic sets 304) cluster to specific loci. As defined previously, a QTL is a region of any genome that is responsible for variation of a quantitative trait. A QTL that is linked to a given expression statistic set 304 is referred to as an "expression QTL" or "eQTL". Further, the example illustrates how quantitative trait locus analyses can detect several types of transcript abundance polymorphisms, such as differential transcript decay, differential dosing, differential splicing, and differential transcription rate. As such, this example illustrates the type of information that can be obtain by performing steps 202 through 210 of FIG. 2.

An F2 intercross was constructed from C57BL/6J and DBA/2J strains of mice. All mice were housed under conditions meeting the guidelines of the Association for Accreditation of Laboratory Animal Care. Mice were on a rodent chow diet up to 12 months of age, and then switched to an atherogenic high-fat, high-cholesterol diet for another four months. See, for example, Drake et al., 2001, Physiol Genomics 5, 205-15, which is hereby incorporated by reference in its entirety. Parental and F2 mice were sacrificed at sixteen months of age. At death the livers were immediately removed, flash-frozen in liquid nitrogen and stored at −80° C. Total cellular RNA was purified from 25 mg portions using an Rneasy Mini kit according to the manufacturer's instructions (Qiagen, Valencia, Calif.). Competitive hybridizations were performed by mixing fluorescently labeled cRNA (5 mg) from each of 111 F2 liver samples, 5 DBA/2J liver samples, and 5 C57BL/6J liver samples, with the same amount of cRNA from a reference pool comprised of equal amounts of cRNA from each of the 111 liver samples profiled.

Liver tissues from the 111 F2 mice constructed from two standard inbred strains of mice, C57B/6J and DBA/2J, were profiled using a 25K mouse gene oligonucleotide microarray. The hybridizations were performed in duplicate using fluor reversal. The mouse microarray contained 23,574 non-control oligonucleotide probes for mouse genes and 2,186 control oligos. Full-length mouse sequences were extracted from Unigene clusters, build #91 (Schuler et al., 1996, Science 274, 540-546), and combined with RefSeq mouse sequences from June 2001 (Pruitt and Maglott, 2001, Nucleic Acids Research 29, 137-140), and RIKEN full-length sequences, version fantom 1.01 (Kawai et al., 2001, Nature 409, 685-690, 2001). This collection of full-length sequences was clustered and one representative sequence per cluster was selected, resulting in 18,597 full-length mouse sequences. To complete the array, 3' ESTs were selected from Unigene clusters that did not cluster with any full-length sequence from Unigene, RefSeq, or RIKEN. To further down select ESTs, 3' ESTs that had significant homology to human genes were chosen, resulting in 4,977 3' mouse ESTs with human homology. To select a probe for each gene sequence, a series of filtering steps was used, taking into account repeat sequences, binding energies, base composition, distance from the 3' end, sequence complexity, and potential cross-hybridization interactions (Hughes et. al., 2001, Nat Biotechnol. 19, 342-347). For each gene, every potential 60-nucleotide sequence was examined and the 60-mer best satisfying the criteria was selected and printed on the microarray.

Array images were processed to obtain background noise, single channel intensity, and associated measurement error estimates using the techniques referenced in Hughes, 2000, Cell 102, 109-26. Expression changes between two samples were quantified as $\log_{10}$ (expression ratio) where the 'expression ratio' was taken to be the ratio between normalized, background-corrected intensity values for the two channels (red and green) for each spot on the array. An error model for the log ratio was applied to quantify the significance of expression changes between two samples. This error model is described in Roberts et al., 2000, Science 287, 873-880. This error model for the log ratio was applied to quantify the significance of expression changes between the two samples.

The expression values from these experiments were treated as quantitative traits and carried through a linkage analysis using evenly spaced markers across the autosomal chromosomes, to identify eQTL controlling for transcript abundances in this segregating population (FIG. 2, step 210). For this QTL analysis, a complete linkage map 70 (FIG. 1) for all chromosomes except the Y chromosome in mouse was constructed at an average density of 13 cM using microsatellite markers in the manner described by Drake et al. (J. Orthop. Res. 19, 511-517, 2001). Linkage maps were constructed and QTL analysis was performed using MapMaker QTL (Lincoln, S. E., Daly, M. J. & Lander, E. S., Whitehead Institute for Biomedical Research, Cambridge, Mass.) and QTL Cartographer (Basten, C. A., Weir, B. S. & Zeng, Z. B., Department of Statistics, North Carolina State University, Raleigh, N.C., 1999). Log of the odds ratio (lod) scores were calculated at 2-cM intervals throughout the genome for each of the 23,574 genes represented on the mouse microarray. In addition to standard interval mapping techniques employed to detect loci affecting the gene expression traits of interest, additional analyses were performed to determine whether controlling for genetic background variation using makers outside a putative region of linkage and whether multiple traits considered simultaneously could increase evidence for linkage. Composite interval mapping ("CIM") techniques were employed so that markers unliked with the test position were considered as cofactors in the statistical model for marker-trait association. Given multiple quantitative traits, CIM analysis can be extended to consider multiple traits simultaneously, potentially dramatically increasing the power to detect loci affecting the traits of interest Joint CIM analysis was first described by Jian and Zeng (Genetics 140, 1111-27, 1995) and is currently implemented in the QTL Cartographer software.

Of the 23,574 genes represented on the microarray, 7,861 were detected as significantly differentially expressed (Type I error=0.05) in the parental strains or in at least ten percent of the F2 mice profiled. That is, the expression values for the candidate gene varied across the mouse population. Such behavior is in contrast to the case where a gene is not significantly differentially expressed across a mouse population because, for example, it is always expressed at the same level or is rarely expressed at all. In this experiment, genes that are differentially expressed are of interest for use in constructing expression statistic sets 304 (e.g., FIGS. 3A and 3B).

Each of the 7,861 genes that exhibited differential expression were used to construct a respective expression statistic set 304 (e.g., FIGS. 3A and 3B). That is, each set 304 corresponded to the expression value for one of the 7,861 differentially expressed genes from each of the 111 F2 mice. Each set 304 therefore included 111 expression statistics 308 (FIGS. 3A and 3B) and each of these expression statistics 308 represented the expression value for the same gene from each of the 111 mice. These expression statistics sets 304 as well as a mouse genetic marker map 78 (FIG. 1) were used as input to standard QTL analysis software (FIG. 2, steps 208 and 210). Using such standard QTL analysis techniques, eQTL with a lod score greater than 4.3 (P-value<0.00005) were identified for 2,123 genes. The lod scores over this set ranged from 43 to 80.0 (pvalue<<$10^{-20}$), among the highest lod scores ever reported for a quantitative trait. On average, eQTL with lod scores greater than 4.3 explained twenty-five percent of the transcription variation of the 7,861 corresponding genes observed in the F2 set, with this percentage increasing to nearly 50% for lod scores greater than 7. For any given position, it is expected that no false positive eQTL over the 7,861 differentially expressed genes tested. If the multiple positions tested for each gene is taken into account, it is expected that only 393 false positives at a lod score threshold of 4.3.

In processing all genes with standard interval mapping techniques (without filtering on significant differential expression over the at of mice profiled), 4,339 eQTL over 3,701 genes were detected with lod scores greater than 4.3. When the lod score threshold was dropped to 3.0, 11,021 genes gave rise to at least one eQTL, with a total of 17,415 eQTL over this set of genes. The number of eQTL with lod scores exceeding 7.0 (p-value=$10^3$) jumped by 50% when genes that were not detected as significantly differentially regulated in ten or more mice were considered (no additional genes at this threshold would be expected by chance). This indicates that, while individual tests of hypotheses on the differential regulation of a single gene may not be significant, viewing the behavior of that gene by genotype over 111 animals provides sufficiently more information on the biological activity of that gene. Of the 965 genes with lod scores greater than 7.0, 157 has a maximum log ratio separation among any two mice of less than 0.48 (less than 3.0 fold change), indicating a class of genes whose high lod scores reflect tight transcriptional control (small variance), not large expression differences. Additionally, 153 genes from this same set of 965 were expressed in mice homozygous for one of the parental strains at the genes' location, but not detectably expressed in mice homozygous for the other parental strain.

FIG. 68 plots the percentage of eQTL at different lod score thresholds across 920 evenly-spaced bins, each 2 cM wide, covering the mouse genome. The number of eQTL in each bin was divided by the total number of eQTL plotted. EQTL hot spots are apparent on chromosomes 2, 6, 7, 10, 11 and 17, where for each of these hot spot locations, greater than one percent of the total number of eQTL identified genome wide localize to a 4 cM window. The highly non-uniform nature of this eQTL distribution over the chromosomes is not likely to have happened by chance. In fact, with 460 4 cM windows over the 19 autosomal chromosomes, the probability that greater than one percent of the eQTL would localize to one such window is less than $1.2 \times 10^{-16}$. These eQTL hot spots could represent loci driving key biological processes critical to the system under study, as will be discussed below. At a lod score of 4.3, over eighty percent of the genes have only a single eQTL, with only 10% of the genes having more than two detected eQTL. The view at a lower LDL score threshold represents a slightly more complex picture, given the appearance of many more genes under the control of multiple loci, with greater than 40% of the genes having more than one eQTL and close to 4% of the gene having more than 3 detected eQTL. While a 3.0 lod score does not meet genome-wide significance criteria (Lander & Kruglyak, 1995, Nat. Genet. 11, 241-7) in a single trait setting, and while this significance is even more questionable in a multiple-testing setting where a large number of traits is considered, the pattern of eQTL clustering to specific loci and the relationship between these genes with respect to expression, when taken together, lead to highly significant and interesting patterns that can be associated with phenotypes related to common diseases.

Of the 23,574 genes represented on the mouse array, 18,460 could be reliably mapped to a unique autosomal chromosome location using the Celera Mouse Genome database. Of these 18,460 mapped genes, 3,007 had eQTL with lod score. greater than 4.3, and 784 had eQTL with lod scores greater than 7.0. Approximately 34% of the mapped genes with eQTL exceeding 43 had a physical location coincident with the eQTL position, while 71% of the mapped genes with eQTL exceeding 7.0 had a physical location coincident with its eQTL position. Due to the unreliable nature of QTL positioning in the type of experimental cross used in this experiment, an eQTL and gene were defined as coincident when the physical location of the gene mapped to within 15 cM of its cQTL. By chance, it would be expected that the physical location of genes would coincide with their eQTL positions fewer than 2% of the time. Keeping in mind that the number of mice considered in the QTL analysis is relatively small, leading to reduced power in detecting moderate to small QTL effects, the trend observed here is that eQTL with high lod scores are cis acting in most cases, while moderately significant QTL are transacting in most cases. This is consistent with the expectation that first order effects (DNA variations in a gene that affect transcription of the gene itself) are easier to detect than second order effects (genes acting on other gens to affect transcription).

There are many possible explanations for significant eQTL identified for transcript abundance measurements. While the genetic regulation of transcription explains only a percentage of protein diversity, the extent of biologically meaningful polymorphisms that can be detected in this setting is surprising. In addition, additive and dominance effects in genes whose transcription is polymorphic can be teased apart in experimental crosses such as the one described in this example.

FIG. 7 illustrates a plot of the mean log 10 expression ratios for the Apo-A1 gene (lower panel) and a VCP-like ATPase gene (upper panel) by genotype at markers D9Mit19 (lod score equal to 32.5) and D2Mit50 (lod score equal to 54.3), respectively. Both the Apo-A1 gene and the VCP-like ATPase gene have lod scores exceeding 30.0. The highly significant eQTL are explained by the significant separation of the expression ratios between the genotypes and the tight variance within each genotype group. The QTL effect at the VCP-like ATPase gene is mostly additive, given the differences in expression between the heterozygotes ("0") and DBA homozygotes ("−1"), and between the heterozygotes ("0") and B6 homozygotes ("+1"), are roughly equal. The eQTL effect at the Apo-A1 locus has a large dominance component evidenced by the large expression separation between the DBA homozygotes ("−1") and the heterozygotes ("0"), and the small separation between the B6 homozygotes ("+1") and the heterozygotes ("0"). In summary, the eQTL for Apo-A1 demonstrates strong dominance and the QTL for the VCP-like ATPase demonstrates simple additive effects. Overall, for the 4,339 QTL with LOD greater than 4.3, roughly 20% demonstrated a significant dominance effect (lod associated with dominance effect greater than 3.0).

FIG. 8 highlights a range of gene-centered polymorphisms known to exist between DBA and B6 mouse strains. In each of the examples highlighted, the loci identified by linkage to the transcript abundances of the genes listed were coincident with the physical location of the gene itself. Single nucleotide polymorphisms covered by 60-mar oligonucleotide probes would not be expected to significantly affect transcript abundance measurements among the samples (See Hughes, et al., 2001, *Nat Biotechnol* 19, 342-347), but polymorphisms that lead to changes in transcript half-life, that directly enhance promoter and transcription factor binding sites, or more significant polymorphisms, such as insertions and deletions that could arise by alternative splicing, all provide signatures that are readily detectable by the examination of expression levels in a segregating population.

In particular, FIG. 8 illustrates examples of four types of transcript abundance polymorphisms (differential transcript decay, differential dosing differential splicing, and differential transcription rate) readily detected by eQTL analysis. More details on these observations are provided in Section 6.5 below. The mouse C5 gene has a two base pair deletion in a 5' exon in the DBA strain, which causes a more rapid decay of the transcript in DBA compared to the B6 mouse strain. See, for example, Karp et al., 2000, "Identification of complement factor 5 as a susceptibility locus for experimental allergic asthma," Nat. Immunol 1, 221-226. A lod score of 27.4 centered over the C5 gene on chromosome 2 is readily detected (curve 802). The ALAD gene is present in two copies in the DBA strain and only one copy in the B6 strain. See, for example, Claudio et al., 1997, "A murine model genetic susceptibility to lead bioaccumulation", Fundam Appl Toxicol 35, 84-90. The major QTL (lod score of 9.3) for ALAD transcript abundances is centered over the ALAD gene (curve 804) and represents the differential dosing that occurs between the two strains, due to the different copy numbers. The ST7 gene is differentially spliced at several locations (See Huang et al., 2002, Nucleic Acids Res 30, 186-190), and for a stable splice form at the 3' location of the gene, the probe for this gene fortuitously overlapped the region alternatively spliced out in DBA, but not B6. The differential splicing event is detected by the major QTL (lod score of 20.1) for ST7, which is centered over the ST7 gene (curve 806). Finally, the NNMT gene, important for drag metabolism, is known to be polymorphic with respect to transcription between the DBA and B6 strains. See, for example, Huang et al., 2002, "Putative Alternative Splicing database," Nucleic Acids Research 30, 186-190. This polymorphism is confirmed by a major QTL (lod score of 15.3) for the NNMT gene, centered over the NNMT gene (curve 808).

Identification of cis-acting transcriptional control can serve as a filter for associating polymorphisms in DNA sequence with polymorphisms in transcription. For instance, while the DNA variations noted in FIG. 8 lead to transcriptional polymorphisms, the insulin-like growth factor binding protein complex acid labile chain (Igfals) has five SNPs identified between the B6 and DBA strains, two of which are mis-sense mutations: 1) codon 165 is arginine in DBA and glutamine in B6 and 2) codon 69 is glycine in DBA and serine in B6. Igfals is significantly differentially expressed in 18 of the 111 samples, and has two suggestive linkages on chromosomes 11 (lod 2.72) and 18 (lod=2.5), but is physically mapped to chromosome 17, where no linkage is detected. One can conclude from this that the polymorphisms in the sequence of this gene do not give rise to variation in its transcript levels, unlike those cases highlighted in FIG. 8.

6.5. Types of Polymorphisms that can be Detected Using Expression QTL Analysis Some embodiments of the QTL analysis performed in step 210 (FIG. 2) or step 1910 (FIG. 9) are limited in the sense that the transcription must be polymorphic in the population under study in order for QTL for that transcription to be detected. However, the types of DNA polymorphisms that lead to transcription polymorphisms are extensive, and this example illustrates how QTL analysis on gene expression data is capable of detecting many of these polymorphisms. This example specifically includes (1) identifying QTL for genes that have a higher copy number in one parent than the other (2) identifying QTL associated with differential splicing between two strains (3) identifying QTL associated with a differentially expressed gene between two strains where polymorphisms in the promoter/regulatory regions of the gene explain the differential expression, and (4) identifying QTL for genes that have a nonsense mutation in one parent but not the other. It will be appreciated that, in some embodiments, protein levels are used as quantitative traits in step 210 (FIG. 2) or step 1910 (FIG. 9) rather than transcription levels.

Referring to FIG. 9, the ALAD gene is present in two copies in DBA/2J and a single copy in C57BL/6J, and the gene is known to be expressed in liver. In the F2 generation there are three possible genotypes at the ALAD locus leading to different ALAD copy numbers: 1) homozygous for DBA, giving four total copies of the ALAD gene, 2) heterozygous, giving three total copies of the ALAD gene, and 3) homozygous for C57BL/6J, giving two total copies of the ALAD gene. As illustrated in FIG. 9, the differential expression due to the three different doses is detected in the F2 data. First, the gene is identified as differentially expressed between the parent and F2 strains. Second, a high lod score for ALAD expression that is coincident with the gene's physical location is found using processing steps 202 through 210 of FIG. 2. In particular, an expression statistic set 304 for the ALAD expression level is used as the quantitative trait in a QTL analysis that mouse strains as well as the phenotype data from the DBA/2J, C57BL/61 cross.

Referring to FIG. 10, the Putative Alternative Splicing DB (PALS DB) for murine genes are predicted to be alternatively spliced with very high confidence. Approximately 200 genes had a significant lod score (lod>5.0) in the mouse data set described in Example 6.4 above (liver tissue from 111 F2 mice constructed from two standard inbred strains of mice, C57BW/6J and DBA/23). Probe sequences used on the arrays for each of the 200 genes were mapped to the sequences for those genes. The probes that overlapped the predicted splice sites were identified. Of the 200 genes with significant lod scores, five bad predicted splice sites that overlapped probe sequences. FIG. 10 shows one of these examples. The ST7 gene has a stable splice form in DBA that has an approximate 30 base pair stretch deleted, compared to B6. The lod score curve plot in FIG. 10 demonstrates how the QTL analysis picks up this differential splicing event, since not only is the gene detected to be significantly differentially expressed in the F2 and between the parental strains, but this differential expression leads to a very significant QTL for the ST7 gene that is coincident with the physical location of the ST7 gene. Note that the lod score plot covers the entire genome in this case. In addition, there is a minor QTL on one of the chromosomes that happens to coincide with an enhancer binding protein that is known to be involved in differential splicing. So, not only can splicing events be detected, but the genetic determinants behind the alternative splicing can begin to be understood.

Referring to FIGS. 11 and 12, the nicotinamide N-methyltransferase gene codes for an enzyme that is critical to drug metabolism. Others have shown polymorphisms in the promoter for this gene are responsible for its differential expression between the DBA and B6 mouse strains. Table 4 demonstrates that this differential expression is detected since the expression levels of this gene give rise to a QTL with a lod score of 20.1 that is coincident with the physical location of the gene.

TABLE 4

| Gene Name | Physical Gene Location (Chromosome/ Location) | QTL Locations (Chromosome/ Location) | QTL Peak lod Scores |
|---|---|---|---|
| nicotinamide nucleotide transhydrogenase | 13/64.0 cM | 13/107 cM | 8.7 |
| 9530010C24Rik | Unknown | 6/39.5 cM | 2.2 |
| ectonucleotide pyrophosphatase | 15/30.0 cM | 15/26.3 cM | 10.3 |
| EST AW456442 | 11 | not available | not available |
| 5' nucleotidase | 9 | 6/39.5 | 2.5 |
|  |  | 9/10.0 | 3.1 |
| EST AW540195 | 5/25.0 cM | not available | not available |
| purine-nucleoside phosphorylase | 14/19.5 cM | 9/1.0 cM | 2.4 |
| N-terminal Asn amidase | 16/8.7 cM | 2/79.9 cM | 2.2 |
|  |  | 14/22.0 cM | 3.9 |
| nicotinamide N-methyltransferase | 9/29.0 cM | 9/5.0 cM | 20.1 |
|  |  | 13/88.0 cM | 2.6 |
| aldehyde oxidase 1 | 1/23.2 cM | 16/1.0 cM | 2.1 |

The pathways associated with nicotinate and nicotinamide metabolism are fairly well known. FIG. 11 illustrates these different pathways. FIG. 12 provides a key for the important genes that are found in the pathways illustrated in FIG. 11. Table 4 gives the physical location for these key genes in addition to any QTL for those genes represented on the mouse array that were detected using the expression values of those genes in QTL analysis (FIG. 2, steps 202 through 210). Table 4 shows that several of the genes involved in this pathway have QTL co-localized with the major chromosome 9 nicotinamide N-methyltransferase QTL. In addition, several of the other genes in this pathway are polymorphic with respect to expression (nicotinamide nucleotide transhydrogenase and ectonucleotide pyrophosphatase), with QTL coincident with the physical gene location. Further, several of the other genes in this pathway have QTL co-localizing with these major QTL. The results summarized in Table 4 show that the cross talk going on between genes in the same biochemical pathway are detectable using the combination of genetics and gene expression.

None of the genes described in Table 4 colocalize as clusters in a gene expression cluster map (FIG. 2, step 216). Thus, analysis of a gene expression map would not have tied these genes together. Rather the relationships were discovered by treating the expression level of each respective gene in a plurality of organisms as a quantitative trait in a QTL analysis regimen (FIG. 2, steps 202 through 210).

Referring to FIG. 13, the complement component 5 gene (C5) has a two base pair deletion in axon 6 in the DBA strain, but not in the B6 strain. Others have associated C5 in these two strains with complex diseases, such as asthma and arthritis. The gene is detected as differentially expressed between the two strains because the two base pair deletion in DBA leads to a premature stop codon, which causes the transcripts to be degraded more rapidly. The lod score plot in FIG. 13 covers the genetic signal for the C5 gene over the entire mouse genome. From FIG. 13, it seen that the only significant spike occurs at the chromosome 2 position where the C5 gene physically resides. The lod score in this case is 28, which means that more than 90% of the variation in the C5 gene in this F2 population is explained by the two base pair deletion.

6.6. Colocalization of eQTL for Lipid Metabolism Genes Reveals a QTL Hot Spot that is a Possible Causative Agent for the eQTL In this example, mice from a C57BL/6J×DBA/2J cross were placed on a chow-fed diet through four months of age, and at four months various phenotypic measurements were taken and the mice were then placed on a high-fat diet. At six months of age, the mice were sacrificed and scored with respect to over sixty traits, such as adiposity, retroperitoneal fat pad, body weight, fat pad mass, omental fat pad, perimetrial fat pad, subcutaneous fat pad, and total cholesterol. Each of these phenotypic traits may be used to identify linking QTL using standard QTL analysis. FIG. 14 illustrates the results of one such QTL analysis in a region of mouse chromosome 11 for the phenotypic traits "free fatty acid" (curve 1402) and "triglyceride level" (curve 1404). Curve 1406 is the jointlod score curve. Expression QTL ("eQTL") (not shown in FIG. 14) from approximately 40 genes known to be involved with glucose and lipid metabolism overlap the "free fatty acid" and "triglyceride level" clinical trait QTL ("cQTL"). FIG. 15 highlights five of these genes. Each of these five genes has an eQTL that co-localizes with the "fatty acid" and "triglyceride" cQTL.

One of the genes illustrated in FIG. 15, the peroxisome proliferator activated receptor (PPAR) binding protein, has a very large QTL at this chromosome 11 locus (curve 1502). The PPAR binding protein is known to be a key co-activator for PPAR alpha, which also links to this chromosome 11 locus. FIG. 16 shows a scatter plot that breaks down the mean log ratios for the PPAR binding protein by genotype at the chromosome 11 location across the F2 mouse population (120 F2 mouse livers) that was profiled. Of note in FIG. 16 is the subtle, but consistent expression among the genotypes that would have been completely missed if only the differential expression had been analyzed (i.e., without the use of quantitative expression QTL analysis) because the fold changes range only from only −1.5 to 1.5. However, with the genetics, a very strong signal is measured due to the tightness with which expression groups by genotype. FIG. 17 illustrates what the plot illustrated in FIG. 16 would look like in the random case. FIG. 17 illustrates the expression of PPAR alpha by genotype at the chromosome 15 location where the PPAR alpha gene physically resides. As can be seen by FIG. 17, the expression of PPAR alpha is almost completely random with respect to genotype, although a wider range of expression for the B6 genotype is observed. This may be of some interest because changes in variation are potentially as interesting as changes in mean.

FIG. 18 illustrates how genes known to be involved in lipid metabolism link to the same genetic locus, even though they physically reside at different locations. In FIG. 18, the chromosomal positions of the genes Cyp2a-12, peroxisome proliferator activated receptor binding protein (PPARBP), Atf4, $PPAR_\alpha$, and Abcq8 are shown on mouse genome map 1802. Further, the positions of QTL that correspond to these genes are shown on mouse genome map 1804. Specifically, the eQTL that arise when each of the genes mapped to genome map 1802 is treated as a quantitative trait in a QTL analysis is shown mapped to mouse genome map 1804 of FIG. 18. The gene PPARBP physically resides at an eQTL hot spot positioned on chromosome 11 of genome map 1804. The correspondence of the physical location of PPARBP with this eQTL hot spot implicates this gene as the causative agent for the eQTL at the hotspot. Thus, the data shown in FIG. 8 suggest that PPARBP is in a biological pathway at a point that it is upstream from the genes Cyp2a-12, Atf4, $PPAR_\alpha$, and Abcq8.

6.7. Elucidating Genes and Pathways for Complex Traits

Associating patterns of expression with a clinical trait and dissecting those patterns by associating them with susceptibility loci, represents a potentially powerful way to dissect complex diseases. The present example provides a method for associating a gene with a clinical trait T. In some embodiments, clinical trait T is a complex trait (e.g., complex disease). Section 5.15 describes the characteristics of some complex traits within the scope of the present invention. The method works by interfacing gene expression data with clinical trait data in order to identify potential causative genes for a trait and the associated pattern of response. The steps used in the method are illustrated in FIG. 19 and described in section 5.16, above.

Major loci controlling complex phenotypes like obesity, heart disease and CNS disorders may potentially affect scores of genes, if not hundreds. It is expected that those genes involved in the more downstream aspects of pathways associated with common diseases would have eQTL linked to the major causative loci for those diseases. In addition, there may be heterogeneity among the causative loci for a given disease in a population of interest. When present, this heterogeneity impacts the ability to detect linkages to the causative loci, since the significance of any one locus is diminished when the population is considered as a whole in such a setting. Therefore, the development of techniques that allow for the identification of homogenous subpopulations with respect to causative loci as provided in the present application is a major advance in the elucidation and dissection of genetic basis for complex diseases.

6.7.1. Case Study Using Mouse Data

The steps outlined in FIG. 19 were performed using the mouse system described in Section 6.4. Livers were profiled in mice after the mice had been on a high-fat, atherogenic diet for four months. As described by Drake et al. (J. Orthop Res 19, 511-7, 2001; Physiol Genomics 5, 205-15, 2001), such mice represent the spectrum of disease in a natural population, with many mice developing atherosclerotic lesions and brain lesions, and others having significantly higher fat-pad masses, higher cholesterol levels and larger bone structures than others in the same population. Using the expression data 44 (FIG. 1) to identify patterns that refine the definition of a clinical trait, including identifying subtypes of the clinical trait, and then identifying QTL for these clinical trait (cQTL) subtypes and linking this information with the gene expression traits to elucidate genes and pathways associated with the clinical traits, are the primary motivations for the beginning steps described in FIG. 19. Associating patterns of expression with a clinical trait and dissecting those patterns by associating them with susceptibility loci represents a powerful way to dissect complex diseases.

More than one percent of the eQTL identified genome-wide for the 7,861 genes G that were used in respective QTL analysis (e.g., instances of processing step 1910, FIG. 19) fall within a 10 cM window centered at approximately 100 cM on chromosome 2 in the mouse genome (FIG. 20). There are 867 genes with lod scares over 2.0 linked to this region. The majority of genes inked to the chromosome 2 locus do not physically reside on chromosome 2, and so, are at least partially regulated by one or more loci in the chromosome 2 hot-spot region.

Co-localized with this locus are many cQTL (determined by instances of processing step 1912, FIG. 19) for clinical traits T such as adiposity, fat pad mass, plasma lipid levels and bone density. FIG. 20 shows the lod score curves for four of the obesity-related traits, the peaks of which are almost perfectly coincident with the hundreds of eQTL falling at that locus. The four obesity related traits are (1) subcutaneous fat pad mass (curve 2002 peaking at 105 cM with a lod score=6.25), (2) perimetrial fat pad mass (curve 2004 peaking at 103 cM with a lod score=5.31, (3) omental fat pad mass (curve 2006 peaking at 103 cM with a lod score=3.80), and (4) adiposity (curve 2008 peaking at 105 cM with a lod score=3.69). The joint lod score curve for these four clinical traits is given by line 2010, peaking at 1.05M with a lod score=13.02. The majority of genes linked to this region do not physically reside on chromosome 2, and so are at least partially regulated by one or more loci in the chromosome 2 hot-spot region. For the 423 genes with mapping information, there are only four eQTL with lod scores greater than 3.0 that correspond to genes whose physical locations are within 2 cM of the peak (1916—Yes, 1920, FIG. 19). The lod score curves for these four potential candidate genes that may explain the chromosome 2 eQTL hot spot are represented by lines 2012 in FIG. 20. From highest led score to the lowest, the four candidate genes are (1) RIKEN cDNA 2610042014 (NM_025575) peaking at 103 cM with a lod score=24.43 (curve 2012-4), (2) ATPase, class It, type 9A (NM-015731) peaking at 105 cM with a lod score=6.13 (curve 2012-3), (3) RIKEN cDNA2610100K07 (NM-025996) peaking at 101 cM with a lod score=5.04 (curve 2012-2), and (4) zinc finger protein 64 (NM-009564) peaking at 101 cM with a lod score=3.56 (curve 2012-1). Gene NM_025575 codes for a dolichyl-diphosphooligoaccbharide-protein glycosyltransferase and gene NM_015731 codes for a cation-transporting ATPase; these genes may be considered the primary causative candidates for the linkage activity at the chromosome 2 locus.

The class of genes represented in FIG. 20 (curves 2012), identified by intersecting cQTL data with eQTL data in accordance with FIG. 19, provides convincing evidence that many of the genes co-localized to a single QTL hot spot are associated with the obesity-related traits. Hence, several candidate genes whose physical locations are coincident with their respective eQTL are reasonable candidate genes for further research. It may be that the causative gene is not differentially regulated and so is not detectable with the methods described in this example. However, when these inventive methods are viewed from the standpoint of hypothesis generation, the candidate genes with supporting genetic clusters offers researchers valuable insight into complex traits and suggests meaningful hypothesis for further validation. In this example, the combined gene expression/genetics approach has effectively generated interesting hypotheses by filtering the number of genes that would otherwise need to be considered from 25,000 to three or four reasonable candidates, with hundreds of additional genes forming patterns that represent the reactive changes induced by the causative set, all of which have been identified in a completely objective manner.

6.7.2. Hierarchical Clustering

FIG. 23 represents the results of a two-dimensional hierarchical clustering, with 123 genes along the x-axis and 36 mice along the y-axis, representing the upper and lower $25^{th}$ percentile for the subcutaneous fat pad mass trait over 72 of the 111 F2 mice that were scored with respect to this trait. Two criteria were applied in selecting the 123 genes along the x-axis: 1) genes in this set had to be significantly expressed and differentially expressed in at least 10 mice, and 2) genes in this set had to have expression values that were able to discriminate between the extreme subcutaneous fat pad mass groups (using standard two-sample t test and a significance level of 0.05). To compute the array illustrated in FIG. 23, the $\log_{10}$ (expression ratio) was plotted as red (regions 2320) when the red channel is up-regulated to the green channel and 2) green (regions 2340) when the red channel is down-regulated relative to the green channels. White and gray areas in the array illustrated in FIG. 23 respectfully represent areas in which the $\log_{10}$ (expression ratio) is close to zero and when data from both of the channels for a given prove is unreliable.

All genes depicted in FIG. 23 are either linked to the chromosome 2 locus identified in FIG. 20, or are highly correlated with genes that are linked to the region. The 123 genes used in FIG. 23 are able to discriminate between mice with high fat pad masses and those with low fat pad masses. Arrows 2302 highlight mice that have low fat pad mass, but a high fat pad mass gene signature. Arrow 2304 highlights a single mouse that has high fat pad mass, but a low fat pad mass gene signature.

Interestingly, a group of major urinary protein genes (MUP1, MUP4, and MUP5) are linked to the chromosome 2 locus, in addition to 7 other loci (all with lod scores exceeding 4.0), 4 of which co-localize with adiposity or fat pad mass traits. The MUP genes stand out because they are highly correlated with many other genes known to be involved in obesity-related pathways, including retinoid X receptor (RXR) gamma (R=0.75/P-value<<$1.0E^{-15}$, acyl-Coenzyme A oxidase 1 (R=0.65/P-value=$3.78E^{-15}$), and leptin receptor (R=−0.74/P-value<<$1.0E^{-15}$), in addition to co-localizing with other genes like peroxisome proliferator activated receptor (PPAR) gamma, RXR interacting protein and LPR6, all known to be involved in these pathways. Mutations in the Leptin receptor in mice and man cause hyperphagia and extreme obesity. See, for example, Chen et al., 1996, Cell 84, 491-495; Chua et al., 1996, Science 271, 994-996; Clement et al., 1998, Nature 392, 398-401; Montague et al., 1997, Nature 387, 903-908; Strobel et al., 1998, Nat. Genet. 18, 213-215;

Tsigos et al., 2002, J. Pediatr. Endocrinol Metab. 15, 241-253. RXR is the obligate partner of many nuclear receptors including PPARα and PPARγ that are involved in many aspects of the control of lipid metabolism, glucose tolerance and insulin sensitivity. See Chawla et al., 2001, Science 294, 1866-1870. This demonstrates that the chromosome 2 locus identified in FIG. 20 draws together adiposity, fat pad mass, cholesterol and triglyceride levels and is linked to genes with proven roles in obesity and diabetes. Further, the MUP genes are members of the lipocalin protein family and are known to play a central role in pheromone-binding processes that affect mouse physiology and behavior. See Timm et al., 2001, Protein Science 10, 997-1004. Furthermore, MUP expression levels have been associated with variations in body weight, bone length, and VLDL levels. See, for example, Metcalf et al., 2000, Nature 405, 109-1073; Swift et al., 2001, J. Lipid Res. 42, 218-224; Jiang and Zeng, 1995, Genetics 140, 1111-1127. Arrows 2306 in FIG. 23 indicate the positions of the MUP1, MUP2, and MUP3 genes.

The region supporting the chromosome 2 locus illustrated in FIG. 20 is homologous to human chromosome 20q12-q13.12, a region that has previously been linked to human obesity-related phenotypes. See Borecki et al., 1994, Obesity Research 2, 213-219; Lembertas et al., 1997, J. Clin. Invest 100, 1240-1247. The human homolog for genes NM_025575 (FIG. 20; curve 2012-4) and NM_015731 (FIG. 20, curve 2012-3) also reside in the human chromosome 20 region and have not been completely characterized; they have not been implicated in obesity-related traits before. While other genes such as melanocortin 3 receptor (MC3R) have been suggested as possible candidates for obesity at this locus (Lembertas et al., 1997, J. Clin. Invest 100, 1240-1247), this data suggests the genes NM_025575 (FIG. 20; curve 2012-4) and NM_015731 (FIG. 20, curve 2012-3) may be responsible for the underlying QTL. Unlike MC3R, these two genes are significantly linked to the murine chromosome 2 locus. Further, they are significantly correlated with several of the fat pad mass traits. Further, these two genes are genetically interacting with several of the fat pad mass traits also linked to the chromosome 2 locus. It is observed that expression levels for MC3R are not linked to the chromosome 2 locus illustrated in FIG. 20, and there are no SNPS annotated in the exons or introns of the gene between the C57/BL6 and DBA/2J strains in the most recent build of the Celera RefSNP database. These observations provide evidence and suggests that MC3R may not be the gene underlying chromosome 2 linkage, at least in this particular. system. Of course, it is possible that MC3R is only expressed in the brain, and that polymorphic expression of the MC3R in the brain leads to changes of expression in the liver. Because there are no DNA polymorphisms in this gene between the two strains that lead to codon changes or that likely lead to cis-acting alternative splicing polymorphisms, if it is the causative gene in this case, it would most likely have to be acting through transcriptional regulation.

6.73. Testing for Pleiotropy

In some embodiments, the inventive method disclosed in FIG. 19 is extended. Tests developed by Jiang and Zheng (Genetics 140, 1111-1127, 1995) and implemented by Drake et al. (Physiol. Genomics 5, 205-215, 2001) were applied to assess whether pleiotropy of a common underlying gene rather than close linkage of separate genes were responsible for the colocalized cQTL and eQTL in the chromosome 2 region. As set forth by Jiang and Zang (Genetics 140, 1111-1127, 1995), to test the hypothesis of pleiotropy versus. close linkage for two coincident QTL of interest, the multi-trait composite interval mapping (CIM) (Lynch and Walsh, 1998, *Genetics and Analysis of Quantitative Traits*, Sunderland, Mass.: Sinauer Associates) is reformulated. The hypothesis of interest ($H_0$ and $H_1$) involve the position $p_1$ of the QTL having an effect on trait 1 and position $p_2$ of the QTL having an effect on trait 2 are given by:

$H_0: p_1 = p_2$
$H_1: p_1 \neq p_2$

The alternative hypothesis indicates that the QTL are non-pleiotropic and are located at different map positions. The likelihood for $H_0$ is the same as that given for the multi-trait CIM model. However, the likelihood for the alternative is that developed by Jiang and Zeng (Genetics 140, 1111-1127, 1995). Using the prescription set forth by Jiang and Zeng, calculation of the maximum likelihoods for each hypothesis was carried out using the expectation-conditional maximization (ECM) algorithm. Once the maximum likelihoods under each hypothesis were computed, the log ration of the likelihoods was computed to serve as the test statistic. This log-likelihood ration test statistic is asymptotic to a $\chi^2$ distribution with one degree of freedom.

The test supported the hypothesis of pleiotropy (one allele affecting several traits) in that no significant results for the traits subcutaneous fat pad mass, perimetrial fat pad mass, omental fat pad mass, or adiposity at the 0.05 significance level were found. The results obtained are consistent with pleiotropy of a common underlying gene regulating the clinical and expression traits linked to the chromosome 2 locus. The four genes detailed in FIG. 20 by curves 2012-1 through 2012-4 may be considered as primary causative candidates for all of the linkage activity at the chromosome 2 locus.

The majority of genes linked to the chromosome 2 region are significantly correlated among themselves, and functional patterns emerge from these data that support the hypothesis that these genes are associated with the clinical traits linked to this region. As an example, 186 of the 867 genes linked to this region have been assigned to GO categories (The Gene Ontology Consortium, 2001, Genome Research 11, 1425-1433). Of these, 39 have been assigned to the "ATP binding" molecular function category. With 4,771 genes having GO classifications and lod scores greater than 2.0, the "ATP binding" category occurs in 514 of these genes. Fisher's Exact Test was used to determine if the "ATP binding" category is more represented in the chromosome 2 QTL cluster than would be expected by chance (p-value=0.0000008). Such strong significance indicates that the high occurrence of "ATP binding" in the cluster could not have happened by chance. Further, subsets within the 39 genes are highly correlated with genes known to be associated with obesity related traits. These genes include Leptin receptor (correlation coefficient=3.8E$^{-13}$) and RXR gamma (correlation coefficient 0.78/pvalue=3.8E$^{-13}$).

6.7.4. Determining the Topology of a Biological Pathway That Affects a Complex Trait The processing steps disclosed in FIG. 19 and described in Section 5.16, above, are used to identify the genes associated with a complex trait (e.g., the genes that affect a complex trait). This section describes how the data obtained in Section 5.16, above, can also be used to deduce the topology of a biological pathway that affects a complex trait. In particular, using FIG. 24 as an illustration, cQTL and eQTL data is analyzed in order to deduce the topology of such a biological pathway.

In step 1912, the cQTL for clinical traits 1 through 4 are localized on a representative molecular map 2402 for the population under study. For example, in cases where the population under study is human, representative molecular map 2402 is, for example, a map of the human genome. In some embodiments, molecular map 2402 (FIG. 24) is a marker map, such as one stored as marker data 70 in system 10 (FIG. 1). In some embodiments, molecular map 2402 includes the nucleotide sequence of a portion of the genome (e.g., genomic map) of the population under study.

Step 1912 of FIG. 24 (illustrated as downward arrow in the upper left side of FIG. 24) corresponds to step 1912 of FIG. 19. In step 1912 of FIG. 24, a clinical quantitative trait loci (cQTL) that is linked to a clinical trait T is identified on map 2402 with a QTL analysis that uses the phenotypic statistic set 2102 as the clinical trait T. In some embodiments, these QTL analyses are performed by an embodiment of clinical quantitative trait (cQTL) identification module 2204 (FIG. 22). Referring to FIG. 24, four phenotypic statistics sets 2102 are shown. Each set 2102 corresponds to one of four clinical traits under study. It will be appreciated that any number of clinical traits may be analyzed and that the four traits illustrated in FIG. 24 are merely exemplary. For example, at least 3, 5, 8, 12, 20, 30, or 40 clinical traits could be analyzed using the methods disclosed in FIG. 24.

In one embodiment, the complex trait under study is obesity. In one example of this embodiment, clinical trait 1 is a body mass index (e.g., weight/height), clinical trait 2 is subcutaneous fat pad mass, clinical trait 3 is insulin level in the blood, and clinical trait 4 is leptin levels. Accordingly, cQTL1 is a QTL that is linked to body mass index. cQTL2 is a QTL that is linked to subcutaneous fat pad mass, clinical trait 3 is a QTL that is linked to insulin level in the blood, and cQTL 4 is a QTL that is linked to leptin levels. Further, cQTL1 through cQTL4 are determined using the QTL analysis of step 1912 (FIG. 19) as described in detail in Section 5.16, above.

In addition to the identification of four cQTL in map 2402, which respectively correspond to four clinical traits associated with obesity, FIG. 24 discloses the results of a number of eQTL analyses. The computation of these eQTL analyses will now be described. In FIG. 24, four expression statistics sets 304 (FIG. 3) are illustrated. Each expression statistic set corresponds to a different gene G in the genome of the population under study. As described in detail in previous sections, each expression value in the expression statistic set is a measurement of a cellular constituent corresponding to a particular gene G in an organism in a population of organisms under study. The cellular constituent may be, for example, mRNA levels for the corresponding gene, protein levels for the corresponding gene, or a metabolite level that is directly regulated by the corresponding gene. It will be appreciated that any number of genes may be analyzed and that the four genes illustrated in FIG. 24 are merely exemplary. For example, at least 3, 5, 8, 12, 20, 30, or 40 genes could be analyzed using the methods disclosed in FIG. 24.

Each expression statistic set 304 is used as the quantitative trait in a QTL analysis in accordance with processing step 1910 (FIG. 19). QTL analysis, such as those performed in processing step 1910, are described in detail in Section 5.16, above. A separate QTL analysis is performed for each of the four expression statistics sets 304 illustrated in FIG. 4.

In some embodiments, these QTL analyses are performed by an embodiment of expression quantitative trait loci (eQTL) identification module 2202 (FIG. 22). Each expression statistic set 304 generates eQTL that are linked to the expression statistic set. Expression statistic set 304-Gene1, which is the expression statistic set for gene 1, yields four eQTL (QTL1-1*, eQTL-2, eQTL1-3, and cQTL1-4). These four eQTL map to four different locations on map 2402. It will be appreciated that eQTL will map to various locations on map 2402 and that not all cQTL will colocalize with a cQTL. However, for the ease of illustration of this example, eQTL-1*, eQTL1-2, eQTL1-3, and cQTL1-4 respectively co-localize with cQTL1, cQTL2, cQTL3, and cQTL4. Only one of the eQTL can correspond to the physical location of the gene G that forms the basis of the expression set 304 was used to compute the eQTL. For set 304-Gene1, the eQTL denoted eQTL1-1* maps to the physical location of gene 1 in map 2402. For this reason, eQTL1-1 is marked with an asterisk. For the act 304-Gene4, the eQTL denoted eQTL4-1* maps to the physical location of gene 4.

The physical location of each eQTL for each of genes 1 through 4 is shown in FIG. 4. Analysis of the eQTL and the cQTL allow for the determination of which of the four genes is the furthest upstream in a biological pathway that affects the complex trait T under study. FIG. 4 discloses the eQTL/cQTL relationships that are summarized in Table 5 below.

TABLE 5

| Gene Number | cQTL that colocalize with an eQTL for this Gene | Physical Location of the Gene (expressed in terms of cQTL and eQTL that colocalize to the location on map 2402) |
|---|---|---|
| 1 | cQTL1, cQTL2, cQTL3, cQTL4 | cQTL1/eQTL1-1 |
| 2 | cQTL2, cQTL3, cQTL4 | cQTL2/eQTL2-1 |
| 3 | cQTL3, cQTL4 | cQTL3/eQTL3-1 |
| 4 | cQTL4 | cQTL4/eQTL4-1 |

Referring to FIG. 24, it is seen that cQTL4 colocalizes with an eQTL for each of the four genes under study. In some embodiments, an eQTL and a cQTL are considered colocalized if they fall within about 25 centiMorgans (cM) of each other on map 2402. In some embodiments, an eQTL and cQTL are considered colocalized if they fall within about 10 cM, about 5 cM, about 1 cM, about 0.5 cM, or about 0.1 cM of each other on map 2402. In some embodiments, an eQTL and cQTL are considered colocalized t they fall within about 100 kilobases, 50 kilobase, 25 kilobases, 10 kilobases, 1000 bases, or 500 bases of each other on map 2402. None of the other cQTL colocalize with an eQTL for each of the four genes under study. For example, cQTL2 only colocalizes with an eQTL for two of the genes under study, gene 1 and gene 2. The data shown in FIG. 24 suggests that a gene at position cQTL4 in map 2402 is the further upstream position in a biological pathway. The observation that the eQTL for gene 4 only colocalizes with cQTL4 and none of the other cQTL suggests that the identity of the upstream gene in a biological pathway affecting obesity is, in fact, gene 4.

FIG. 4 further suggests which gene comes after gene 4 in a biological pathway that affects obesity. CQTL3 colocalized with three eQTL, eQTL1-3, eQTL2-2, and eQTL3-1*. These eQTL are respectively linked with gene 1, gene 2, and gene 3. This suggests that there exists a gene that colocalizes with cQTL3 that affects at least two other genes. It is noted that the physical location of gene 3 is cQTL3. Further, the only other eQTL linked to gene 3 that colocalizes with a cQTL on map 2402 is eQTL3-2. But eQTL3-2 colocalizes with cQTL4, a position that has already been determined to colocalize with the most upstream gene in the pathway identified by the data in FIG. 4. Thus, taken together, the data suggests that gene 3 is downstream from gene 4 in a biological pathway that affects obesity. The data further suggests that gene 3 is upstream from genes 1 and 2.

Analysis of the data is completed upon consideration of the eQTL colocalized to cQTL1 and cQTL2. Taken together, the data illustrated in FIG. 24 suggests the following topology for a biological pathway.

Gene 4→Gene 3→Gene 2→Gene 1

In some embodiments, the analysis of data such as that disclosed in FIG. 24 is performed by an embodiment of determination module 2206 (FIG. 22). The biological pathway deduced in this example can be validated using techniques such as multivariate analysis. In addition, the biological pathway deduced in this example can be validated using techniques such as gene knock out studies. Those of skill in the art will recognize numerous other methods for validating the proposed topology for the biological pathway affecting the complex trait, and all such methods are within the scope of the present invention.

While the complex trait analyzed in this hypothetical example is obesity, it will be appreciated that the techniques disclosed in this section can be used to help determine the topology of biological pathways that affect any complex trait of interest. such determines are facilitated by the choosing to analyze clinical traits that are affected or influenced by the complex trait (e.g., complex disease) under study.

The example in this section can be described as a method for determining the topology of a biological pathway that affects a complex trait. The method has the step of (A), identifying one or more expression quantitative trait loci (eQTL) for a gene in a plurality of genes using a first quantitative trait loci (QTL) analysis. This first QTL analysis uses a plurality of expression statistics for the gene as a quantitative trait. Each expression statistic in the plurality of expression statistics represents an expression value for the gene in an organism in a plurality of organisms of a single species. The method further comprises the step of (b), repeating step (a) a first number of times, wherein each repetition of step (a) uses a different gene in the plurality of genes. In some embodiments, step (a) is repeated three or more times. In some embodiments, step (a) is repeated 5 or more times, 8 or more times, 12 or more times, 20 or more times, or 100 or more times. At least some of the genes selected in iterations of step (a) are in the biological pathway that affects a complex trait. An advantage of the present invention is that genes that are not in the biological pathway can be selected in step (a) without failure of the method provided that some of the genes selected in iterations of step (a) are in the pathway.

The method further comprises the step of (c), identifying a clinical quantitative trait loci (cQTL) that is linked to a clinical trait in a plurality of clinical traits using a second QTL analysis. The second QTL analysis uses a plurality of phenotypic values as a quantitative trait. Each phenotypic value in the plurality of phenotypic values represents a phenotypic value for the clinical trait in the plurality of clinical traits in an organism in the plurality of organisms. The method further comprises the step of (d), repeating step (c) a second number of times. Each repetition of step (c) uses a different clinical trait in a plurality of clinical traits. In some embodiments, step (c) is repeated three or more times. In some embodiments, step (c) is repeated five or more times, eight or more times, twelve or more times, twenty or more times, or one hundred or more times. An advantage of the present invention is that clinical traits that are not in fact associated with the complex trait of interest may be selected in instances of step (a) without failure of the method provided that some of the clinical traits selected in iterations of step (c) are in fact indicative of (associated with) the complex trait Finally, the method comprises the step of (e), using (i) the identity of each eQTL, identified in an iteration of step (a), that colocalizes with a cQTL, identified in an iteration of step (c), and (ii) a physical location of each gene in the plurality of genes on a molecular map for the single species, in order to determine the topology of the biological pathway that affects the complex trait. In one embodiment, step (e) is performed by identifying a first eQTL. In general, this first eQTL has the property of colocalizing with a first cQTL identified in step (c). Furthermore, this first eQTL has the property that the gene used to generate the eQTL colocalizes with the physical location of the first cQTL. In the case where each eQTL identified in step (a) colocalizes with more than one cQTL, then preferably an eQTL that colocalizes with the small number of cQTL (among the eQTL identified in step A) is identified. In such instances, the cQTL in the small number of oQTL that actually colocalizes with the gene used to generate the first eQTL is denoted as the first cQTL. Once the first cQTL has been identified, a determination is made a to whether eQTL from other genes in the plurality of genes also colocalize with the first cQTL. When this is the case, the hypothesis is drawn that the gene used to generate the first eQTL is further upstream in a biological pathway affecting a complex trait than each of the genes that generate eQTL colocalizing with the first cQTL. This gene is therefore designated as the first gene. When this is not the case a different first eQTL is identified using the method described above.

The method continues by examining each of the genes that generate eQTL that colocalize with the first cQTL in order to determine their topological order in a biological pathway. This analysis proceeds in the same manner used to identify the first cQTL. For example, a second gene that generates an eQTL that colocalizes with both the first cQTL and a second cQTL is sought. If the physical location of the second gene colocalizes with the second cQTL, then the second gene is considered a downstream candidate in the biological pathway. If the second gene does not colocalize with the second cQTL, then a different second gene is identified or step (E) can recommence. Various checks can be performed on the second gene. First, a determination can be made as to whether eQTL from other genes also colocalize with the second cQTL and, if so, whether they are the same genes that generated cQTL that colocalize with the first cQTL. In cases where the same genes are generating eQTL that colocalize with both the first cQTL and the second cQTL, the suggestion is raised that such genes are downstream members of a biological pathway that starts with the first gene and continues with the second gene. Each of these downstream genes can be further examined using the same techniques used to identify the first and second genes, in order to further describe the topology of the biological pathway that affects a complex trait.

6.7.5. Associating Genes with Traits Using Cross Species Data

The present section provides an example of how the systems and methods of the present invention can be used to associate genes with traits using cross species data. This example builds upon the discovery of the four murine candidate genes identified in Section 6.7.1, above. In Section 6.7.1, four genes were discovered on mouse chromosome number 2 by co-localizing cQTL for the obesity related traits (1) subctaneous fat pad mass (FIG. 20, curve 2002), (2) perimetrial fat pad mass (FIG. 20, curve 2004), (3) omental fat pad mass (FIG. 20, curve 2006), and (4) adiposity (FIG. 20, curve 2008) with four eQTL with lod scores greater than 3.0 that correspond to genes whose physical locations are within the vicinity (e.g., 2 cM) of the four cQTL. The four mouse genes are (1) RIKEN cDNA 2610042014 (NM_025575) (FIG. 20, curve 2012-4), (2) ATPase, class It, type 9A (NM-015731) (FIG. 20, curve 2012-3), (3) RIKEN cDNA2610100K07 (NM-025996) (FIG. 20, curve 2012-2), and (4) zinc finger protein 64 (NM-009564) (FIG. 20, curve 2012-1).

The region of mouse chromosome 2 in which curves 2002 through 2012 are found is homologous to human chromosome region 20q12-q13.12. This region of the human genome has previously been linked to human obesity-related phenotypes. See, for example, Borecki et al., 1994, Obesity Research 2, 213-219 and Lembertas et al., 1997, J. Clin. Investigation 100, 1240-7. The data described in section 6.7.1. strongly suggests that the human genes in human chromosome region 20q12-q13.12 that correspond to the mouse genes are associated with obesity. Therefore, following the methods and systems of the present invention, the human genes that correspond to the four mouse genes identified in Section 6.7.1, above, were characterized. A summary of this characterization is provided in Tables 2 and 3 below. In Table 6, the nucleotide information for the four mouse gene and the four corresponding human genes is provided. In Table 4, the protein products of the four mouse genes and the four corresponding human gene is provided.

TABLE 6

Obesity related genes of the present invention

| Mouse Sequence | Curve Number in FIG. 20 | Mouse Gene Name | Human Sequence | Human Gene Name |
|---|---|---|---|---|
| NM_025575 (SEQ ID NO: 1) | 2012-4 | 2610042014 gene | Corrected form of AL591714 (SEQ ID NO: 2) Coding region only (SEQ ID NO: 3) | Not named |
| NM_015731 (SEQ ID NO: 9) | 2012-3 | ATP9A/ KIAA06111 | Obtained by alignment of protein 075110 to human chromosome 20 (SEQ ID NO: 12) | ATP_2A |
| NM_025996 (SEQ ID NO: 13) | 2012-2 | Not named | NM_006809 (SEQ ID NO: 16) | Tomm34, or Tom 34 |
| NM_009564 (SEQ ID NO: 19) | 2012-1 | Zfp64 | NM_018197 (SEQ ID NO: 20) | Zfp64 |

TABLE 4

Obesity relate gene products of the present invention

| Mouse Sequence | Curve Number in FIG. 20 | Mouse Protein Name | Human Sequence | Human Protein Name |
|---|---|---|---|---|
| NP_079851 (SEQ ID NO: 29) Q9CQK0 (SEQ ID NO: 4) Q9CYM5 (SEQ ID NO: 5) Q9CYX5 (SEQ ID NO: 6) Q9DAU8 (SEQ ID NO: 7) Q9CVJ3 (SEQ ID NO: 28) | 2012-4 | Not named | Translated from SEQ ID NO: 2 (SEQ ID NO: 8) | Unknown |
| NP_056546 (SEQ ID NO: 10) | 2012-3 | ATPase 9A, class II | O75110 (SEQ ID NO: 11) | Phospholipid-transporting ATPase IIA |
| NP_080272 (SEQ ID NO: 14) TR_Q9CYG7 (SEQ ID NO: 17) | 2012-2 | Not named | NP_006800 (SEQ ID NO: 15) TR_Q15785 (SEQ ID NO: 18) | translocase of outer mitochondrial membrane 34 |
| NP_033590 (SEQ ID NO: 21) TR_P97365 (SEQ ID NO: 22) TR_Q99KE8 (SEQ ID NO: 23) TR_Q9CWR3 (SEQ ID NO: 24) | 2012-1 | Zinc finger protein 64 | NP_060667 (SEQ ID NO: 25) TR_Q9NPA5 (SEQ ID NO: 26) TR_Q9NTS7 (SEQ ID NO: 27) | zinc finger protein 64 homolog (mouse) |

6.7.5.1. NM_025575/NP_079851

The nucleotide sequence for the *Mus musculus* gene NM_025575 (FIG. 20, curve 2012-4) is provided in FIG. 27 (SEQ ID NO: 1). There is no human gene given in LocusLink for this mouse sequence (step 2504—No, FIG. 25). A BlastN search (step 2506, FIG. 25) indicates that AL591714.1 is the best candidate human mRNA for the mouse sequence NM_025575 (expectation value of 0.0). The human protein product of AL591714.1 is CAC39448.1. A BlastP search using the translated amino acid sequence of the mouse sequence NM_025575 (N_079851) identifies the human protein CAC39448.1 as the second best hit (expectation score $9e^{-16}$) (step 2508, FIG. 25). A pairwise BlastP search between the human protein CAC39448 and the mouse protein, NP079851, and a translated Blast search of the human RNA nucleotide database sequences against NP_079851 indicates the presence of a frame-shift in the mRNA database sequence AL_591714. In the BlastP search, only the first 42 amino acids of NP_079851 and CAC39448 match. A TblastN search of the human AL591714.1 mRNA with the query mouse protein, NP_079851, covers the entire length of the mouse protein, but in two fragments. Taken together this data indicates that a frameshift occurs at position 241 of AL591714.1. Therefore, the correct sequence for the mRNA that encodes for a protein that is a human analog of the mouse sequence NM_025575 is illustrated in FIG. 28 (SEQ ID NO: 2). This corrected sequence removes two nucleotides that are present in the AL_91714 database sequence. In particular, the portion of SEQ ID NO: 2 that codes for the human protein that corresponds to ti Rouse protein NP_079851 is from 115 nts to 569 nts of SEQ ID NO: 3. This sequence is shown FIG. 29 (SEQ ID NO: 3). A BlastX search of SEQ ID NO: 3 against mouse proteins yields the protein NP_079851 as the best match, establishing that SEQ ID NO: 3 is the best homolog for the mouse protein NP_079851.

There are five complete entries in the TrEMBL database (Bairoch and Apweiler, 2000, "The SWISS-PROT protein sequence database and its supplement TrEMBL in 2000,"

Nucleic Acids Res. 28, 45-48) for the *Mus musculus* amino acid sequence that corresponds to the 2610042O14Rik gene (SEQ ID NO: 1). The TrEMBL accession numbers for these five proteins are Q9CQK0 (FIG. 30A, SEQ ID NO: 4), Q9CYM5 (FIG. 30B, SEQ ID NO: 5), Q9CYX5 (FIG. 30C, SEQ ID NO: 6), Q9DAU8 (FIG. 30D, SEQ ID NO: 7), and Q9CVJ3 (FIG. 30E, SEQ ID NO: 28). The human amino acid sequence that corresponds to the corrected form of accession number AL591714 (SEQ ID NO: 2) is provided in FIG. 31 (SEQ ID NO: 8). A BlastP search with SEQ ID NO: 8 against the mouse protein database gives the mouse protein NP_079851 as the best match (stop 2514, FIG. 25), establishing that SEQ ID NO: 8 is the human analog of the mouse protein. NP_079851. The sequence for the mouse protein NP_079851 is provided in FIG. 30F (SEQ ID NO: 29).

6.7.5.2. NM_015731/NP_056546

The nucleotide sequence for the *Mus musculus* gene NM_015731 (FIG. 20, curve 2012-3) is provided in FIG. 32 (SEQ ID NO: 9). The mouse gene is characterized as ATP9A in Genbank LocusLink. An alternate gene symbol used for this gene is KIAA06111.

There are two records in the human relationships field of the LocusLink record (FIG. 33). Both of these records lead to the same LocusLink record. The cytogenic location of the gene in the human LocusLink record is 20q113:11-13.2. There are several nucleotide and protein sequences associated with human chromosome position 20q13:11-13.2 (FIG. 34). A BLAST search of the mouse refseq protein against the two human ATP9A proteins in the LocusLink record (namely, BAA31589 and AAH16044) was performed. No significant homology was found between the mouse refseq protein (NP_056546) and human AAH16044. Homology was found between the mouse refseq protein (NP_056546) and human BAA31586 (not shown). A BlastN search using the four human sequences in the LocusLink record for ATP9A (FIG. 34, AB014511.1, AK025559, AK026513, and BC016044) against the mouse refseq sequence indicates that only AB014511.1 is similar to NM_015731. The other three sequences are not similar to NM_015731.

The amino acid sequence that corresponds to the *Mus musculus* gene NM_015731 is NP_056546. NP_056546 is provided in FIG. 35 (SEQ ID NO: 10). A BlastP search using the mouse refseq protein (NP_056546) gives the human protein O75110 as the best candidate ortholog, which is provided in FIG. 36 (SEQ ID NO: 11).

A BlastN search of the human nucleotide database with the mouse RefSeq mRNA was performed. This search identified the AB014511.1 sequence identified in the LocusLink record described above. AB014511.1 corresponds to the human protein BAA31568, thus confirming that this protein is the ortholog of the *Mus musculus* gene NM_015731. However, this is only a partial mRNA sequence.

The best possible mRNA sequence for the protein 075110 can only be obtained by genomic alignment of the protein against the human genomic sequence (NCBI assembly, build 30, June 2002). The human chromosome map location of the protein BAA31586, which comes from LocusLink (FIG. 34), and 075110, which come from the alignment of the mouse protein NP_056546 (SEQ ID NO: 10) against the human genome NCBI assembly, are both at position 20q13.2. In summary, the protein O85110 (SEQ ID NO: 11) is the best human ortholog for the mouse protein NP_056546 (SEQ ID NO: 10). However, its full mRNA is not available. The best existing mRNA sequence corresponding to the mouse protein is AB014511.1 (whose protein product is BAA31568). AB014511.1 is a partial mRNA sequence. The full mRNA sequence for the protein O75110 may be inferred from a genomic alignment of the protein against the human genome assembly. The inferred mRNA sequence is given in FIG. 37 as (SEQ ID NO: 12).

6.7.5.3. NM_02596/NP_080272

The nucleotide sequence for the *Mus musculus* gene NM_025996 (FIG. 20, curve 2012-2) is provided in FIG. 38 (SEQ ID NO: 13). The LocusLink record for NM_025996 is provided in FIGS. 39A and 39B. The LocusLink record indicates that the mouse protein that corresponds to NM_025996 (SEQ YD NO: 13) is NP_1080272. NP_080272 is provided in FIG. 40 (SEQ ID NO: 14).

A BlastP search of human proteins using the mouse protein NP_080272 (SEQ ID NO: 14) yields the human protein NP_006800 as the best hit. The human protein NP_006800 is provided in FIG. 41 (SEQ ID NO: 15). NP_006800 is also implied by LocusLink (FIG. 38B). A BlastN search of human nucleotide sequences with the mouse refseq mRNA (NM_080272, SEQ ID NO: 14) gives the human refseq, NM_006809.2 (FIG. 42, SEQ ID NO: 16) as the best hit. This human refseq sequence is also implied in the human-homology relationship information in LocusLink (FIG. 38B).

A BlastP search of mouse proteins with the human protein NP_006800 (SEQ ID NO: 15) yields the mouse protein NP_080272 (SEQ ID NO: 14) as the best hit. A BlastN search of mouse nucleotide sequences with the human mRNA NM_006809 (SEQ ID NO: 16) yields the mouse mRNA, NM_25996 (SEQ ID NO: 13) as the best hit. Therefore, based on LocusLink relationships, and BlastP and BlastN searches performed in accordance with FIG. 25, the human orthologs for the mouse sequences NM_025996 (SEQ ID NO: 13)/NP_080272 (SEQ ID NO: 14) are NM_006809 (SEQ ID NO: 16) and NP_006800 (SEQ ID NO: 15).

In addition to the NP_080272 (SEQ ID NO: 14) entry for the *Mus musculus* protein sequence; the TrEMBL database includes the entry TR_Q9CYG7 that corresponds to the *Mus musculus* nucleotide sequence NM_025996 (SEQ ID NO: 9). The *Mus musculus* protein sequence TR_Q9CYG7 is provided in FIG. 43 (SEQ ID NO: 17). In addition to the NP_006800 (SEQ ID NO: 15) entry, the TrEMBL database includes the human protein TR_Q15785 that corresponds to the human nucleotide sequence NM_006809 (SEQ ID NO: 16). The entry TR_Q15785 is provided in FIG. 44 (SEQ ID NO: 18).

6.7.5.4. NM_009564/NP_033590

The nucleotide sequence for the *Mus musculus* gene NM_009564 (FIG. 20, curve 2012-1) is provided in FIG. 45 (SEQ ID NO: 19). The human nucleotide sequence that corresponds to NM_009564 is NM_018197.1. NM_018197.1 is provided in FIG. 46 (SEQ ID NO: 20). The *Mus musculus* amino acid sequence that corresponds to the *Mus musculus* gene NM_009564 is NP_033590. NP_033590 is provided in FIG. 47 (SEQ ID NO: 21). In addition to the NP_033590 entry, the TrEMBL database includes three amino acid sequences that correspond to the *Mus musculus* gene NM_009564. They are TR_P97365 (FIG. 48, SEQ ID NO: 22), TR_Q99KE8 (FIG. 49, SEQ ID NO: 23), and TR_Q9CWR3 (FIG. 50, SEQ ID NO: 24).

The amino acid sequence that corresponds to the human nucleotide sequence NM_018197 (SEQ ID NO: 20) is NP_060667. NP_060667 is provided in FIG. 51 (SEQ ID NO: 25). The human protein NP_060667 (SEQ ID NO: 25)

and the mRNA NM_018197 (SEQ ID NO: 20) are indicated as the human homologs to the mouse sequences NM_009564 (SEQ ID NO: 19)/NP_033590 (SEQ ID NO: 21) by Locus-Link. Furthermore, a BlastP search of human proteins with the mouse protein NP_033590 (SEQ ID NO: 21) yields the human protein NP_060667 (SEQ ID NO: 25) as the best hit. Further, a BlastP search of mouse proteins with the human protein NP_060667 (SEQ ID NO: 25) yields the mouse protein NP_033590 (SEQ ID NO: 21) as the best mouse sequence. A BlastN search of human nucleotides with mouse NM_009564 (SEQ ID NO: 19) yields NM_018197 (SEQ ID NO: 20) as the best hit. Again, a BlastN search of human nucleotides with human NM_018197 (SEQ ID NO: 20) gives the mouse sequence NM_009564 (SEQ ID NO: 19) as the best hit. Therefore, from the Blast results and the Locus-Link homology information, NM_018197 (SEQ ID NO: 20) and NP_009564 (SEQ ID NO: 19) are the human orthologs of the mouse sequences NM_009564 (SEQ ID NO: 19)/NP_033590 (SEQ ID NO: 21).

In addition to the NP_060667 (SEQ ID NO: 25) entry, the TrEMBL database includes the entry TR_Q9NPA5 and TR_Q9NTS7 that correspond to the human nucleotide sequence NM_018197 (SEQ ID NO: 20). The human amino acid sequence TR_Q9NPA5 is provided in FIG. 52 (SEQ ID NO: 26). The human amino acid sequence TR_Q9NTS7 is provided in FIG. 53 (SEQ ID NO: 27).

6.8. Target Validation Using Cross-Species Data

The utility of the cross species approach described in Section 5.19 for elucidating complex diseases and directly identifying targets for complex diseases is demonstrated by examining the pattern of eQTL linking to one of the major obesity loci identified in the BXD cross described by Schadt et al. (Nature, 2003, 422, pp. 297-302). In this cross, F2 mice were constructed from two standard inbred strains, C57BL/6J and DBA/2J. FIGS. 86A-86D depict cQTL for several clinical traits in the BXD cross (FIG. 86A, plasma insulin levels; FIG. 86B, epidemial fat pad mass; FIG. 86C, plasma leptin levels; FIG. 86D, HDL levels) located on murine chromosome 13. The lod-score curves for these traits support two cQTL at genetic positions 85 cM and 110 cM on mouse chromosome 13.

Liver tissues from 111 F2 mice constructed from strains C57BL/6J and DBA/2J were profiled using a mouse gene oligonucleotide array. The expression values from these experiments were treated as quantitative traits and carried through a linkage analysis using evenly spaced markers across the autosomal chromosomes. Of the 23,574 genes represented on the microarray, 7,861 were detected as significantly differentially expressed (type I error=0.05) in the parental strains or in at least ten percent of the F2 mice profiled. Using standard interval mapping techniques, quantitative trait loci (QTL) with logs of the odds ratio (LOD) scores greater than 4.3 (P-value<0.00005) were identified for 2,123 genes, with a maximum LOD score of 80.0.

FIG. 87 highlights a subset of the genes whose expression in the liver of the BXD animals is controlled by the chromosome 13 cQTL given in FIG. 86 (i.e., these genes have eQTL at either the 85 cM cQTL or 110 cM cQTL given in FIG. 86). These genes were identified in one of two ways: (1) the gene had an eQTL at or new the 85 cM and 110 cM locations and the eQTL was cis-acting (C330026N13Rik or 1810058I14Rik) or (2) the gene had an eQTL at either 85 cM or 110 cM of mouse chromosome 13, but the gene was physically located on a chromosome other than 13, and was a druggable target (CCKar, Foxc2, LepR, DPP IV, LIPE, CPT1a, CB2R, Orexin, CTE1, and RXR9). Here, the definition of a druggable target set forth in Hopkins and Groom, 2002, Nature Reviews 1, 727, was used. By cis-acting, it is meant that the gene physically resides at the eQTL location for the gene. Those genes that are selected under the second criterion were tested for causality with respect to any of the four clinical traits depicted in FIG. 86 using the techniques disclosed in Section 5.19.4. Of these genes, four tested causal (CCKAR, FOXC2, DPP4, LEPR). These four genes were subsequently mapped to orthologous genes in the human genome using standard techniques to determine if any of these genes were coincident with linkages for obesity-related traits in an Icelandic population for which phenotypic information was available for several generations.

The above referenced Icelandic population consisted of large extended times in the Icelandic population. The body mass indices (BMI) in these families were assessed, and linkage analysis was carried out by considering obesity and thinness as qualitative traits (defined as BMI>34 for obesity and BMI<21 for thinness). Gender based differences were considered and observed to contribute to lod scores for obesity overall. The obesity and thinness traits were used in a standard linkage analysis in order to identify genetic loci controlling far each trait. When obesity for females only was considered, a significant locus was identified on human chromosome 4. Only 1 of the 4 genes, cholecystokinin type A receptor (CCKAR; FIG. 88, SEQ ID NO: 30), Ulrich et al., 1993, Biochem. Biophys. Res. Commum. 193, 204-211 fell within a one lod-score drop of this obesity locus. Here, the term one lod-score drop means that portion of a locus that is within one lod score unit of the maximum lod score value of the locus. For example, if a locus has a maximum lod score of 8, that portion of the locus centered around this maximum value that has a lod score value in excess of 7 is considered to be within a one lod-score drop. FIG. 89 highlights a lod score curve on human chromosome 4 for percent body fat in females in the Icelandic population. As shown in FIG. 89, contained within a l lod score drop of the peak of this lod score are 29 genes, including the gene CCKAR.

As a result of the intersection between CCKAR and the chromosome 4 locus from females in the Icelandic population, the gene was resequenced in 752 subjects in the Icelandic population. The 752 subjects were made up of 282 females with percent body fat in the upper 15th percentile in the Icelandic population, 208 females with BMIs over 40 (morbidly obese), and then 282 females older than 40 years of age and with BMIs less than 20 (considered thin). The CCKAR gene was resequenced in these individuals to identify single nucleotide polymorphisms (SNPs) that could be used in an association test to determine if any given SNP or constellation of SNPs were associated with obesity.

FIG. 89 highlights that there were 55 common SNPs (minor allele frequency greater than two percent) found in the CCKAR gene. Haplotypes for these SNPs were constructed using standard techniques, and then each haplotype was tested for association to percent body fat and to thinness phenotypes. FIGS. 90 and 91 highlight the results of the association tests.

Table 9002 of FIG. 90 highlights statistics for two related haplotypes that are strongly associated with percent body fat in females. Each row of Table 9002 represents the statistics for one of the two respective haplotypes. For the first haplotype, the statistics are based on sampling a total of 281 afflicted (N aft, obese) and 282 controls (N_ctrl). For the second haplotype, the statistics are based on a sampling of a total of 281 afflicted and 279 controls. As can be seen by the statistics in Table 9002, the frequency of these haplotypes in the obese population (N_aff) compared to the frequency of these same haplotypes in the thin population (control; N_ctrl) is significantly different three percent in the thin population (Ctrl_freq) and eleven percent in the obese population (Aff_frq). After correcting for multiple testing, the p-value (P_cor) for this association is 0.002, which is considered a very significant association in this setting A different sat of haplotypes was also identified in the CCKAR gene that was significantly associated with thinness (see FIG. 91). Bach row of Table 9102 represents the statistics for one of the two respective haplotypes. For the first haplotype, the statistics are based on sampling a total of 282 afflicted (N_aff; thin) and 421 controls (N_ctrl). For the second haplotype, the statistics are based on a sampling of a total of 282 afflicted and 421 controls. In combination, the two haplotypes in the thin (control) population for which statistics are provided in Table 9102 of FIG. 91 were seen in seventeen percent of the subjects, while these same two haplotypes were only seen in four percent of the subjects in the obese population (p-value corrected for multiple testing equal to 0.02).

This section provides an example of the second cross-species approach outlined in Section 5.19. In this example, a locus for obesity was identified on human chromosome 4. Further, the ortholog of a gene that falls within this locus, CCKAR, was found to be causal for a trait in mice that corresponds to human obesity. This cross species information makes CCKAR a top target, and the results of this testing are significant in that DNA variations in the CCKAR gene in a cohort of obese and thin individuals were seen to significantly associate with obesity and thinness.

6.9. Concluding Remarks

Quantitative trait analyses on gene expression data have been described for the most comprehensive analysis of the genetics of gene expression described to date in mouse and humans. The present invention delineates the type of information that may be obtained by intersecting two important sources of biological information, gene expression data from microarray experiments and DNA variation data in segregating populations. The identification of eQTL for genes expressed in a representative tissues provides insight into the genetic networks that constitute the complexity of living systems. The genes with very significant eQTL in the mouse or significant heritabilities in human provide a list of interesting targets for many complex phenotypes, given the strong degree of genetic control observed in what can be considered naturally segregating population. The several hundred genes with lod scores exceeding 20 in mouse that are described above represent a new class of quantitative traits, with linkage significance not commonly seen before in mammalian systems.

As detailed herein, the potential to provide clustering information in the genetics dimension to help elucidate gene function in complex systems is a powerful tool. The causal nature of genetics allows for the anchoring of multiple gene under the common control of a single or multiple loci, as shown in FIG. 20, thereby providing roots for the graphs that can more completely depict the complicated network of genes interactions at play in complex phenotypes. Genes that are highly correlated with respect to expression will usually have linkage regions in common. Genes that are not highly correlated, but under the control of a common locus, will be appropriately clustered together in a linkage analysis, thereby allowing identification of gene interactions in a novel way.

The class of genes discussed in relation to FIG. 59 and FIG. 20 above provides objective evidence that many of the genes co-localized to a single QTL hot spot are associated with the obesity-related traits. The patterns of expression serve to refine the obesity phenotype and allow for the enrichment of subpopulations that are homogeneous with respect to the underlying causes of obesity in the population. Identifying such subpopulations has significant consequences for drug discovery, since each subpopulation may be more effectively treated by a compound that targets a pathway specifically associated with the disease in that subpopulation. An optimal strategy for the treatment of a given common disease may be a panel of drugs targeting more homogeneous subpopulations that have been objectively identified using the combination of gene expression, genetics, and clinical data.

Several candidate genes for the chromosome 2 FPM QTL (Section 5.19) whose physical locations are coincident with their respective eQTL we reasonable candidate genes for further research. When these methods of the present invention are viewed from the standpoint of hypothesis generation, the candidate genes with supporting genetic clusters offer researchers possible insights into the complex traits and suggest meaningful hypotheses for further validation. In this example, the combined gene expression/genetics approach has effectively generated interesting hypotheses by filtering the number of genes that would otherwise need to be considered from 25,000, to 3 or 4 reasonable candidates, with hundreds of additional genes forming patterns that represent the reactive changes induced by the causative gene set, all of which have been identified in a completely objective manner.

For the last century genetics has been used to identify regions in the genome "causing" variation in a given trait. For the past decade gene expression has been used to identify those genes that are co-regulated over some number of conditions, presenting patterns of expression that help elucidate those genes involved in complex traits. The two combined approaches have the power to refine the definition of complex phenotypes, identify subtypes within a given phenotype, and uncover pathways associated with the phenotype in an unprecedented manner. The potential exists to impact the more significant rate-limiting steps in the drug discovery process: Objectively classifying individuals according to disease subtypes and identifying the drivers of the pathways, the causal factors, underlying those disease subtypes. In the past, dissecting complex traits using genetics has met with limited success, and up to now, gene expression has appeared as an indirect marker for complex traits, so that others have settled for functional uncertainty by restricting attention to the use of DNA makers in identifying the causal factors for complex traits. We have demonstrated that the combination of gene expression and genetics data has the potential to overcome these barriers. The addition of gene expression data can be used to refine the disease phenotype, directly implicate pathways and genes comprising those pathways associated with the disease phenotype, and identify the key drives of the pathways underlying the disease phenotype. Key pathway drivers can potentially be identified even in cases where these drivers are not expressed in the tissues profiled, since such key genes may be expressed in one tissue, yet drive patterns of expressions in different tissues. In such cases, transcript abundance's of those genes comprising the expression patterns in the profiled tissues will be genetically linked to the physical location of the gene driving their expression.

The large-scale consideration of molecular phenotypes as quantitative traits is not tied to microarray data, but can be applied to any form of molecular phenotyping data, where the main aim is to consider large classes of phenotypes simultaneously in the context of genetics to elucidate genes and pathways for complex diseases. Problems of multiple testing, pattern recognition, more advanced multivariate statistical genetics techniques and more efficient data-integration schemes will need to be vigorously pursued to derive the most from this type of data. However, for now, the identification of genes under genetic control, along with the loci that exhibit that control, provide a first step in reaching the ultimate goal of piecing together genetic networks for use in dissecting the etiology of complex traits.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a computer readable storage medium. For instance, the computer program product could contain the program modules shown in FIG. 1. These program modules may be stored on a CD-ROM, magnetic disk storage product, or any other computer readable data or program storage product. The software modules in the computer program product may also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of identifying a molecular target for a second trait in a second species, the method comprising:
   (a) identifying a first gene in a segregating population that is causal for a first trait exhibited by all or a portion of said segregating population, wherein each member of said segregating population is a member of a first species and wherein said second trait in said second species corresponds to said first trait in said first species, comprising:
      (i) identifying a test gene in said first species that has at least one abundance quantitative trait locus (eQTL) coincident with a respective clinical quantitative trait locus (cQTL) for said first trait; and
      (ii) testing, for one or more respective eQTL in said at least one eQTL, whether the genetic variation of said eQTL across said segregating population and the variation of the first trait across said segregating population are correlated conditional on an abundance pattern of the test gene across said segregating population,
   wherein, when the genetic variation of (1) said one or more respective eQTL tested in step (ii) and (2) the variation of the first trait across said segregating population are correlated conditional on an abundance pattern of the test gene across said segregating population, said test gene is identified as said first gene;
   (b) obtaining a biological sample from members of said second species and mapping said first gene in said first species to a corresponding locus in the genome of the second species; and
   (c) determining whether a marker or a haplotype in said corresponding locus in the genome of the second species associates with said second trait, wherein, when said marker or said haplotype associates with said second trait in said second species, said locus is identified as said molecular target for said second trait,
   wherein steps (a) and (b) are performed by a suitably programmed computer having a computer program comprising a clustering module for clustering eQTL data from a plurality of eQTL analysis to form a eQTL locus interaction map and an analysis module for analyzing said eQTL interaction map to identify a locus in the genome of the second species that is associated with the second trait that corresponds to the first trait exhibited by the first species.

2. The method of claim 1 wherein said marker or said haplotype is in a second gene in said corresponding locus and said second gene is identified as said molecular target.

3. The method of claim 2 wherein said first gene and said second gene are orthologous.

4. The method of claim 1 wherein said second species is mammalian.

5. The method of claim 1 wherein said second species is human.

6. The method of claim 1 wherein said second trait is asthma, ataxia telangiectasia, bipolar disorder, cancer, common late-onset Alzheimer's disease, diabetes, heart disease, hereditary early-onset Alzheimer's disease, hereditary nonpolyposis colon cancer, hypertension, infection, maturity-onset diabetes of the young, mellitus, migraine, nonalcoholic fatty liver, nonalcoholic steatohepatitis, non-insulin-dependent diabetes mellitus, obesity, polycystic kidney disease, psoriases, schizophrenia, or xeroderma pigmentosum.

7. The method of claim 1 wherein said molecular target is a gene.

8. The method of claim 1 wherein said molecular target is an exon, an intron, or a regulatory element of a gene.

9. The method of claim 1 wherein said marker is a single nucleotide polymorphism, a microsatellite marker, a restriction fragment length polymorphism, a short tandem repeat, a DNA methylation marker, a sequence length polymorphism, a random amplified polymorphic DNA, an amplified fragment length polymorphisms, or a simple sequence repeat.

10. A method of identifying a molecular target for a second trait in a second species, the method comprising:
   (a) identifying a first gene in biological samples obtained from a segregating population that is causal for a first trait exhibited by all or a portion of said segregating population, wherein each member of said segregating population is a member of a first species and wherein said second trait in said second species corresponds to said first trait in said first species, comprising:
      (i) identifying a test gene in said first species that has at least one abundance quantitative trait locus (eQTL)

coincident with a respective clinical quantitative trait locus (cQTL) for said first trait; and (ii) testing, for one or more respective eQTL in said at least one eQTL, whether the genetic variation of said eQTL across said segregating population and the variation of the first trait across said segregating population are correlated conditional on an abundance pattern of the test gene across said segregating population, wherein, when the genetic variation of (1) said one or more respective eQTL tested in step (ii) and (2) the variation of the first trail across said segregating population are correlated conditional on an abundance pattern of the test gene across said segregating population, said test gene is identified as said first gene;

(b) identifying in a biological sample obtained from members of said second species a locus in the genome of the second species that is (1) linked to said second trait and (2) maps to the position in the genome of said first species where said first gene resides; and (c) determining whether a marker or a haplotype in said corresponding locus in the genome of the second species associates with said second trait, wherein, when said marker or said haplotype associates with said second trait in said second species, said locus is identified as said molecular target for said second trait, wherein steps (a) and (b) are performed by a suitably programmed computer having a computer program comprising a clustering module for clustering eQTL data from a plurality of eQTL analysis to form a eQTL locus interaction map and an analysis module for analyzing said eQTL interaction map to identify a locus in the genome of the second species that is linked with the second trait that corresponds to the first trait exhibited by the first species.

11. The method of claim 10 wherein said marker or said haplotype is in a second gene in said corresponding locus and said second gene is identified as said molecular target.

12. The method of claim 11 wherein said first gene and said second gene are orthologous.

13. The method of claim 10 wherein said second species is mammalian.

14. The method of claim 10 wherein said second species is human.

15. The method of claim 10 wherein said second trait is asthma, ataxia telangiectasia, bipolar disorder, cancer, common late-onset Alzheimer's disease, diabetes, heart disease, hereditary early-onset Alzheimer's disease, hereditary nonpolyposis colon cancer, hypertension, infection, maturity-onset diabetes of the young, mellitus, migraine, nonalcoholic fatty liver, nonalcoholic steatohepatitis, non-insulin-dependent diabetes mellitus, obesity, polycystic kidney disease, psoriases, schizophrenia, or xeroderma pigmentosum.

16. The method of claim 10 wherein said molecular target is a gene.

17. The method of claim 10 wherein said molecular target is an exon, an intron, or a regulatory element of a gene.

18. The method of claim 10 wherein said marker is a single nucleotide polymorphism, a microsatellite marker, a restriction fragment length polymorphism, a short tandem repeat, a DNA methylation marker, a sequence length polymorphism, a random amplified polymorphic DNA, an amplified fragment length polymorphisms, or a simple sequence repeat.

19. A method of identifying a molecular target for a second trait in a second species, the method comprising:

(a) identifying a first gene in a segregating population that is causal for a first trait exhibited by all or a portion of said segregating population, wherein each member of said segregating population is a member of a first species and wherein said second trait in said second species corresponds to said first trait in said first species, comprising:

(i) identifying a test gene in said first species that has at least one abundance quantitative trait locus (eQTL) coincident with a respective clinical quantitative trait locus (cQTL) for said first trait; and (ii) testing, for one or more respective cQTL in said at least one eQTL, whether the genetic variation of said eQTL across said segregating population and the variation of the first trait across said segregating population are correlated conditional on an abundance pattern of the test gene across said segregating population, wherein, when the genetic variation of (1) said one or more respective eQTL tested in step (ii) and (2) the variation of the first trait across said segregating population are correlated conditional on an abundance pattern of the test ene across said segregating population, said test gene is identified as said first gene; and (b) obtaining biological samples from members of a second species and (c) identifying a second gene in the genome of the second species that is orthologous to said first gene and in which (i) the variation of the abundance of the second gene across biological samples taken from a plurality of members of said second species and (ii) the variation of the second trait across said plurality of members of said second species are associated, wherein said second gene is identified as said molecular target for said second trait, wherein steps (a) and (c) are performed by a suitably programmed computer having a computer program comprising a clustering module for clustering eQTL data from a plurality of eQTL analysis to form an eQTL locus interaction map and an analysis module for analyzing said eQTL interaction map to identify a gene in the genome of the second species that is orthologous to said first gene.

20. The method of claim 19, the method further comprising: validating said second gene by determining whether a marker or a haplotype in said second gene associates with said second trait, wherein, when said marker or said haplotype associates with said second trait in said second species, said second gene is validated.

21. The method of claim 19 wherein said second species is mammalian.

22. The method of claim 19 wherein said second species is human.

23. The method of claim 19 wherein said second trait is asthma, ataxia telangiectasia, bipolar disorder, cancer, common late-onset Alzheimer's disease, diabetes, heart disease, hereditary early-onset Alzheimer's disease, hereditary nonpolyposis colon cancer, hypertension, infection, maturity-onset diabetes of the young, mellitus, migraine, nonalcoholic fatty liver, nonalcoholic steatohepatitis, non-insulin-dependent diabetes mellitus, obesity, polycystic kidney disease, psoriases, schizophrenia, or xeroderma pigmentosum.

24. The method of claim 20 wherein said marker is a single nucleotide polymorphism, a microsatellite marker, a restriction fragment length polymorphism, a short tandem repeat, a DNA methylation marker, a sequence length polymorphism, a random amplified polymorphic DNA, an amplified fragment length polymorphisms, or a simple sequence repeat.

* * * * *

UNITED STATES PATENT AND TRADEMARK OFFICE
CERTIFICATE OF CORRECTION

PATENT NO. : 8,843,356 B2
APPLICATION NO. : 10/540405
DATED : September 23, 2014
INVENTOR(S) : E. E. Schadt et al.

Page 1 of 1

It is certified that error appears in the above-identified patent and that said Letters Patent is hereby corrected as shown below:

In the Claims

| COLUMN | LINE | ERROR |
|---|---|---|
| 294 (Claim 19, | 22 line 26) | "test ene" should read --test gene-- |

Signed and Sealed this
Twenty-fourth Day of February, 2015

Michelle K. Lee
*Deputy Director of the United States Patent and Trademark Office*